(12) United States Patent
Moinet et al.

(10) Patent No.: US 7,220,765 B2
(45) Date of Patent: May 22, 2007

(54) DERIVATIVES OF 2-ARYLIMINO-2,3-DIHYDROTHIAZOLES, THEIR PREPARATION PROCESSES AND THEIR THERAPEUTIC USE

(75) Inventors: Christophe Moinet, Montreal (CA); Carole Sackur, Paris (FR); Christophe Thurieau, Paris (FR)

(73) Assignee: Societe de Conseils de Recherches et d'Applications Scientifiques (SCRAS) (FR)

( * ) Notice: Subject to any disclaimer, the term of this patent is extended or adjusted under 35 U.S.C. 154(b) by 143 days.

(21) Appl. No.: 10/615,481

(22) Filed: Jul. 8, 2003

(65) Prior Publication Data

US 2007/0043095 A1    Feb. 22, 2007

Related U.S. Application Data

(63) Continuation-in-part of application No. 10/031,429, filed as application No. PCT/FR02/00093 on Jan. 11, 2002, now Pat. No. 6,727,269.

(30) Foreign Application Priority Data

Jul. 22, 1999  (FR)  .................................. 99 09496
Jan. 12, 2001  (FR)  .................................. 01 00396

(51) Int. Cl.
*A61K 31/426*    (2006.01)
*C07D 277/18*    (2006.01)

(52) U.S. Cl. ...................... 514/370; 548/195
(58) Field of Classification Search ................ 548/194, 548/195; 514/370
See application file for complete search history.

(56) References Cited

U.S. PATENT DOCUMENTS 4,346,088 A * 8/1982 Lang et al. ............. 514/211.15
4,421,757 A * 12/1983 Lang et al. ................. 514/331

FOREIGN PATENT DOCUMENTS

| EP | 0023964 | 2/1981 |
| FR | 1347371 | 1/1963 |
| WO | 9700868 | 1/1997 |
| WO | 0107424 | 2/2001 |

OTHER PUBLICATIONS

XP-002136746 Synthesis . . . Activities, Mohsen et al.

* cited by examiner

*Primary Examiner*—Kamal A. Saeed
*Assistant Examiner*—Nyeemah Grazier
(74) *Attorney, Agent, or Firm*—Charles A. Muserlian

(57) ABSTRACT

The present invention is drawn to compounds of the formula

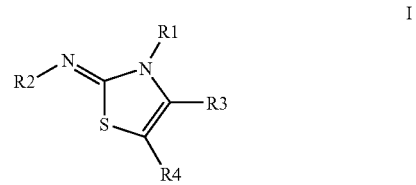

in racemic and enantiomeric form or all combinations of these forms wherein the various substituents are as defined in the application which compounds have a good affinity for certain subtypes of somatostatin receptors and have useful pharmacological properties.

4 Claims, No Drawings

DERIVATIVES OF 2-ARYLIMINO-2,3-DIHYDROTHIAZOLES, THEIR PREPARATION PROCESSES AND THEIR THERAPEUTIC USE

This application is a Continuation-in-Part of U.S. patent application Ser. No. 10/031,429, now U.S. Pat. No. 6,727,269, filed Jan. 15, 2002 which is a 371 of PCT/FR02/00093, filed on Jan. 11, 2002.

A subject of the present Application is new derivatives of 2-arylimino-2,3-dihydrothiazoles and their preparation processes. These products have a good affinity with certain sub-types of somatostatin receptors and therefore have useful pharmacological properties. The invention also relates to these same products as medicaments, the pharmaceutical compositions containing them and their use for the preparation of a medicament intended to treat pathological states or diseases in which one (or more) somatostatin receptors are involved.

Somatostatin (SST) is a cyclic tetradecapeptide which was isolated for the first time from the hypothalamus as a substance which inhibits the growth hormone (Brazeau P. et al., *Science* 1973, 179, 77–79). It also operates as a neurotransmitter in the brain (Reisine T. et al., *Neuroscience* 1995, 67, 777–790; Reisine T. et al., *Endocrinology* 1995, 16, 427–442). Molecular cloning has allowed it to be shown that the bioactivity of somatostatin depends directly on a family of five receptors linked to the membrane.

The heterogeneity of the biological functions of somatostatin has lead to studies which try to identify the structure-activity relationships of peptide analogues on somatostatin receptors, which has led to the discovery of 5 sub-types of receptors (Yamada et al., *Proc. Natl. Acad. Sci. U.S.A.*, 89, 251–255, 1992; Raynor, K. et al, Mol. Pharmacol., 44, 385–392, 1993). The functional roles of these receptors are currently being actively studied. The affinities with different sub-types of somatostatin receptors have been associated with the treatment of the following disorders/diseases. Activation of sub-types 2 and 5 has been associated with suppression of the growth hormone (GH) and more particularly with that of adenomas secreting GH (acromegalia) and those secreting hormone TSH. Activation of sub-type 2 but not sub-type 5 has been associated with the treatment of adenomas secreting prolactin. Other indications associated with the activation of sub-types of somatostatin receptors are the recurrence of stenosis, inhibition of the secretion of insulin and/or of glucagon and in particular diabetes mellitus, hyperlipidemia, insensibility to insulin, Syndrome X, angiopathy, proliferative retinopathy, dawn phenomenon and nephropathy; inhibition of the secretion of gastric acid and in particular peptic ulcers, enterocutaneous and pancreaticocutaneous fistulae, irritable colon syndrome, dumping syndrome, aqueous diarrhoea syndrome, diarrhoea associated with ADS, diarrhoea induced by chemotherapy, acute or chronic pancreatitis and secretory gastrointestinal tumours; the treatment of cancer such as hepatomas; the inhibition of angiogenesis, the treatment of inflamatory disorders such as arthritis; chronic rejection of allografts; angioplasty; the prevention of bleeding of grafted vessels and gastrointestinal-bleeding. The agonists of somatostatin can also be used to reduce the weight of a patient.

Among the pathological disorders associated with somatostatin (Moreau J. P. et al., Life Sciences 1987, 40, 419; Harris A. G. et al., *The European Journal of Medicine*, 1993, 2, 97–105), there can be mentioned for example: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, hyperthyroidism, gigantism, endocrinic gastroenteropancreatic tumours including carcinoid syndrome, VIPoma, insulinoma, nesidioblastoma, hyperinsulinemia, glucagonoma, gastrinoma and Zollin-gr-Ellison's syndrome, GRFoma as well as acute bleeding of oesophageal veins, gastroesophageal reflux, gastroduodenal reflux, pancreatitis, enterocutaneous and pancreatic fistulae but also diarrhoea, refractory diarrhoea of acquired immune deficiency syndrome, chronic secretary diarrhoea, diarrhoea associated with irritable bowel syndrome, disorders linked with gastrin releasing peptide, secondary pathologies with intestinal grafts, portal hypertension as well as haemorrhages of the veins in patients with cirrhosis, gastro-intestinal haemorrhage, haemorrhage of the gastroduodenal ulcer, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumours, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of H pylori, psoriasis, as well as The Applicant found that the compounds of general formula (I) described hereafter have an affinity and a selectivity for the somatostatin receptors. As somatostatin and its peptide analogues often have a poor bioavailability by oral route and a low selectivity (Robinson, C., Drugs of the Future, 1994, 19, 992; Reubi, J. C. et al., TIPS, 1995, 16, 110), said compounds, non-peptide agonists or antagonists of somatostatin, can be advantageously used to treat pathological states or illnesses as presented above and in which one (or more) somatostatin receptors are involved. Preferably, said compounds can be used for the treatment of acromegalia, hypophyseal adenomas or endocrine gastroenteropancreatic tumours including carcinoid syndrome.

The compounds of the present invention correspond to general formula (I)

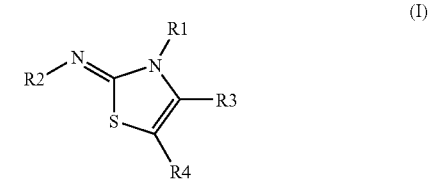

in racemic, enantiomeric form or all combinations of these forms, in which:

R1 represents an amino($C_7$–$C_7$)alkyl, aminoalkylarylalkyl, aminoalkylcycloalkylalkyl, ($C_1$–$C_{15}$)alkyl, ($C_3$–$C_7$)cycloalkyl, ($C_1$–$C_6$)alkyl($C_3$–$C_6$)cycloalkyl, ($C_3$–$C_6$)cycloalkylalkyl, cyclohexenylalkyl, alkenyl, alkynyl, carbocyclic aryl radical containing at least two rings of which at least one is not aromatic, carbocyclic or heterocyclic aralkyl radical optionally substituted on the aryl group, bis-arylalkyl, alkoxyalkyl, furannylalkyl or tetrahydrofurannylalkyl, dialkylaminoalkyl, N-acetoamidoalkyl, cyanoalkyl, alkylthioalkyl, arylhydroxyalkyl, aralkoxyalkyl, morpholinoalkyl, pyrrolidinoalkyl, piperidinoalkyl, N-alkylpyrrolidinoalkyl, N-alkylpiperazinylalkyl or oxypyrrolidinoalkyl radical, or R1 represents one of the radicals represented below:

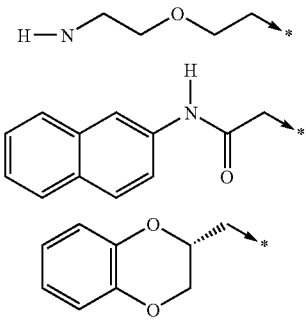

or also R1 represents a —C(R11)(R12)-CO-R10 radical;

R2 represents an optionally substituted carbocyclic or heterocyclic aryl radical, or R2 represents one of the radicals represented below:

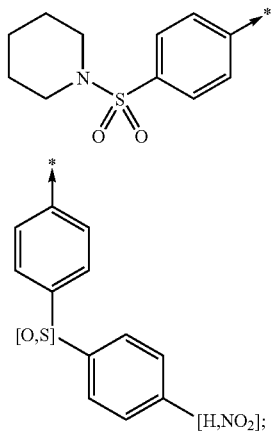

R3 represents an alkyl, adamantyl, optionally substituted carbocyclic or heterocyclic aryl radical, carbocyclic or heterocyclic aralkyl optionally substituted on the aryl group, or R3 represents one of the radicals represented below:

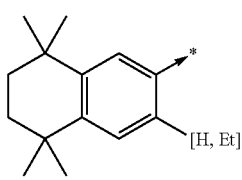

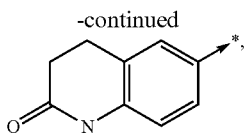

or also R3 represents a —CO-R5 radical;

R4 represents H, alkyl, carbocyclic or heterocyclic aralkyl optionally situated on the aryl radical;

or then the

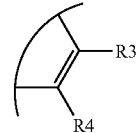

radical represents a radical of general formula

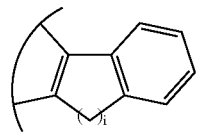

in which i represents an integer from 1 to 3;

R5 represents the N(R6)(R7) radical;

R6 represents a $(C_1-C_{16})$alkyl, cycloalkylalkyl, hydroxyalkyl, aryloxyalkyl radical, carbocyclic or heterocyclic aralkyl radical optionally substituted on the aryl group, aralkoxyalkykl, arylhydroxyalkyl, alkoxyalkyl, alkylthioalkyl, alkenyl, alkynyl, cyclohexenyl, cyclohexenylalkyl, alkylthiohydroxyalkyl, cyanoalkyl, N-acetamidoalkyl radical, bis-arylalkyl radical optionally substituted on the aryl groups, di-arylalkyl radical optionally substituted on the aryl groups, morpholinoalkyl, pyrrolidinoalkyl, piperidinoalkyl, N-alkylpyrrolidinoalkyl, oxopyrrolidinoalkyl, tetrahydrofurannylalkyl, N-benzylpyrrolidinoalkyl, N-alkylpiperazinylalkyl, N-benzylpiperazinylalkyl, N-benzylpiperidinylalkyl or N-alkoxycarbonylpiperidinyl radical, or R6 represents a $(C_3-C_8)$cycloalkyl radical optionally substituted by a radical chosen from the group comprising the hydroxy radical and an alkyl radical, or R6 represents one of the radicals represented below:

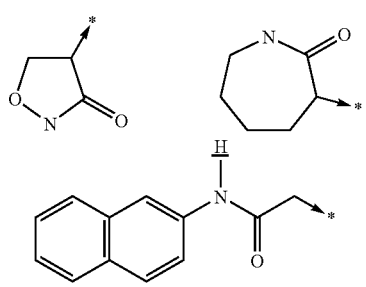

-continued

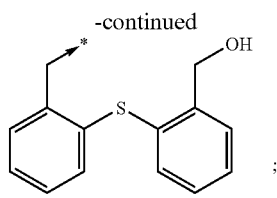

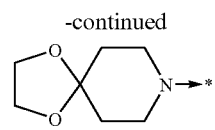

R7 represents H or an alkyl, hydroxyalkyl, mono- or di-aminoalkyl or aralkyl radical; or the —N(R6)(R7) radical represents the radical of the following general formula:

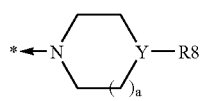

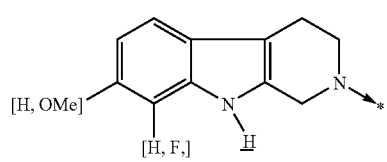

in which:

R8 represents H, alkyl, hydroxyalkyl, optionally substituted carbocyclic or heterocyclic aryl, aralkyl optionally substituted on the aryl group, alkenyl, alkoxyalkyl, cycloalkyl, cycloalkylalkyl, bis-arylalkyl, piperidinyl, pyrrolidinyl, hydroxy, arylalkenyl, or R8 represents —X—(CH$_2$)$_b$-R9;

R9 represents H or an alkyl, alkoxy, aryloxy, optionally substituted carbocyclic or heterocyclic aryl, morpholinyl, pyrrolidinyl, alkylamino or N,N'-(alkyl)(aryl)amino radical;

X represents CO, CO—NH or SO$_2$;

Y represents CH or N;

a represents 1 or 2;

b represents an integer from 0 to 6;

or the N(R6)(R7) radical represents a radical of general formula

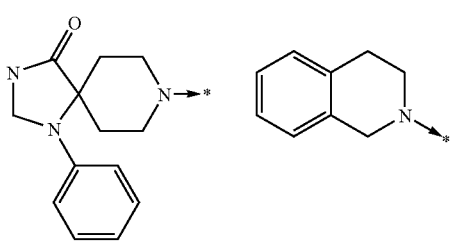

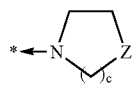

in which:

Z represents CH, O or S;

c represents an integer from 0 to 4;

or the N(R6)(R7) radical represents one of the radicals represented below:

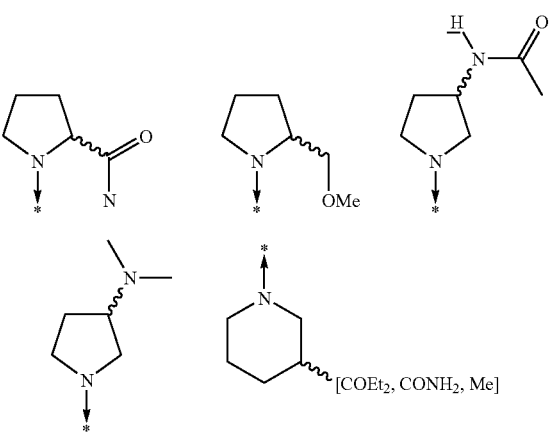

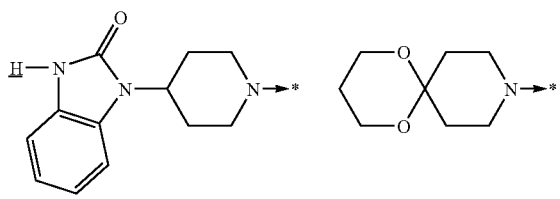

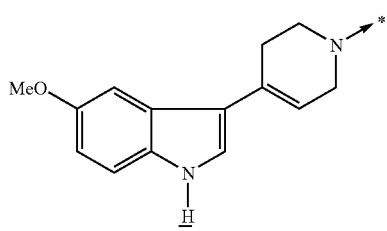

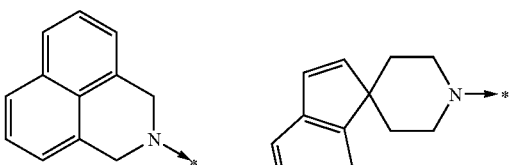

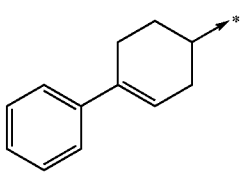

-continued

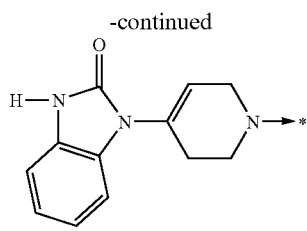

R10 represents an amino($C_2$–$C_7$)alkylamino, ((aminoalkyl)aryl)alkylamino, (aminoalkyl)cycloalkyl)alkylamino, piperazinyl, homopiperazinyl radical, or R10 represents the radical represented below:

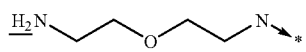

R11 represents H;

R12 represents H or an alkyl, ($C_3$–$C_7$)cycloalkyl, optionally substituted carbocyclic or heterocyclic aralkyl, propargyl, allyl, hydroxyalkyl, alkylthioalkyl, arylalkylalkoxyalkyl, arylalkylthioalkoxyalkyl radical;

or the compounds of the invention are salts of the compounds of general formula (I).

When the compounds of general formula (I) contain the R1, R2, R3, R4, R6, R8, R9 or R12 radicals including a substituted aryl radical or an aralkyl substituted on the aryl group, said aryl or aralkyl radicals are preferably such that:

For R1, when the aryl group is substituted, it can be from 1 to 5 times (other than the bond which, links it with the remainder of the molecule) by radicals chosen independently from the group comprising a halogen atom and an alkyl, alkoxy, alkylthio, haloalkyl, haloalkoxy, aryl, aralkoxy or $SO_2NH_2$ radical. Two substituents can, if appropriate, be linked together and form a ring, for example by representing together a methylenedioxy or propylene radical.

For R2, when the aryl group is substituted, it can be from 1 to 5 times (other than the bond which links it with the remainder of the molecule). The aryl radical can be substituted by radicals chosen independently from the group comprising a halogen atom and an alkyl, alkoxy, alkylthio, haloalkyl, alkenyl, haloalkoxy, nitro, cyano, azido, $SO_2N$, mono- or di-alkylamino, aminoalkyl, aralkoxy, or aryl radical. Two substituents can, if appropriate, be linked together and form a ring, for example by representing together a methylenedioxy, ethylenedioxy or propylene radical.

For R3, when the aryl group or groups (originating from an aryl or aralkyl radical) are substituted, they can be, according to the case, from 1 to 5 times (other than the bond which links them with the remainder of the molecule). The carbocyclic aryl or aralkyl radicals can be substituted from 1 to 5 times on the aryl ring by radicals chosen independently from the group comprising a halogen atom and an alkyl, hydroxy, alkoxy, haloalkyl, haloalkoxy, nitro, cyano, azido, mono- or di-alkylamino, pyrrolidinyl, morpholinyl, aralkoxy or aryl radical. Two substituents can, if appropriate, be linked together and form a ring, for example by representing together an alkylenedioxy radical containing 1 to 3 carbon atoms. The heterocyclic aryl or aralkyl radicals of R3 can be substituted 1 to 2 times on the ring by radicals chosen independently from the group comprising a halogen atom and an alkyl radical.

For R4, when the aryl group is substituted, it can be from 1 to 5 times (other than the bond which links it with the remainder of the molecule). The aryl radical can be substituted by the radicals chosen independently from the group comprising a halogen atom and an alkyl or alkoxy radical.

For R6, when the aryl group or groups are substituted, they can be from 1 to 5 times (other than the bond which links them with the remainder of the molecule). The optional substituents on the aryl groups are chosen independently from the group comprising a halogen atom and an alkyl, alkoxy, alkylthio, haloalkyl, haloalkoxy, aryl, aryloxy or $SO_2NH_2$ radical.

For R8, when the aryl croup or groups are substituted, they can be from 1 to 5 times (other than the bond which links them with the remainder of the molecule). The optional substituents on the aryl groups are chosen independently from the group comprising a halogen atom and an alkyl, haloalkyl, alkoxy, hydroxy, cyano, nitro or alkylthio radical.

For R9, when the carbocyclic or heterocyclic aryl radical is substituted, it can be from 1 to 5 times (other than the bond which links it with the remainder of the molecule). The optional substituents on the aryl group are chosen independently from the group comprising a halogen atom and an alkyl, haloalkyl, alkoxy, haloalkoxy, alkylthio, carbocyclic aryl, hydroxy, cyano or nitro radical.

For R12, when the carbocyclic or heterocyclic aryl radical is substituted, it can be from 1 to 5 times (other than the bond which links it with the remainder of the molecule). The optional substituents on the aryl group are chosen independently from the group comprising a halogen atom and an alkyl alkoxy, carbocyclic aryl, aralkoxy, hydroxy, cyano or nitro radical.

By alkyl, unless specified otherwise, is meant a linear or branched alkyl radical containing 1 to 6 carbon atoms. By cycloalkyl, unless specified otherwise, is meant a monocyclic carbon system containing 3 to 7 carbon atoms. By alkenyl, unless specified otherwise, is meant a linear or branched alkyl radical containing 1 to 6 carbon atoms and having at least one unsaturation (double bond). By alkynyl, unless specified otherwise, is meant a linear or branched alkyl radical containing 1 to 6 carbon atoms and having at least one double unsaturation (triple bond). By carbocyclic or heterocyclic aryl, is meant a carbocyclic or heterocyclic system containing at least one aromatic ring, a system being referred to as heterocyclic when at least one of the rings which comprise it contains a heteroatom (O, N or S). By haloalkyl, is meant an alkyl radical of which at least one of the hydrogen atoms (and optionally all) is replaced by a halogen atom.

By alkylthio, alkoxy, haloalkyl, haloalkoxy, aminoalkyl, alkenyl, alkynyl and aralkyl radicals, is meant respectively the alkylthio, alkoxy, haloalkyl, haloalkoxy, aminoalkyl, alkenyl, alkynyl and aralkyl radicals the alkyl radical of which has the meaning indicated previously.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By cycloalkyl, is meant in particular the cyclopropanyl, cyclobutanyl, cyclopentanyl, cyclohexyl and cycloheptanyl radicals. By carbocyclic or heterocyclic aryl, is meant, in particular the phenyl, naphthyl, pyridinyl, furannyl, thiophenyl, indanyl, indolyl, imidazolyl, benzofurannyl, benzothiophehyl, phthalimidyl radicals. By carbocyclic or heterocyclic aralkyl, is meant in particular the benzyl, phenylethyl, phenylpropyl, phenylbutyl, indolylalkyl, phthalimidoalkyl, naphthylalkyl, furannylalkyl, thiophenylalkyl, benzothiophenylalkyl, pyridinylalkyl and imidazolylalkyl radicals.

When an arrow emanates from a chemical structure, said arrow indicates the point of attachment. For exemple:

represents the benzyl radical.

Preferably, the compounds of general formula (I) are such that:

R1 represents —C(R11)(R12)-CO-R10 or one of the following radicals:

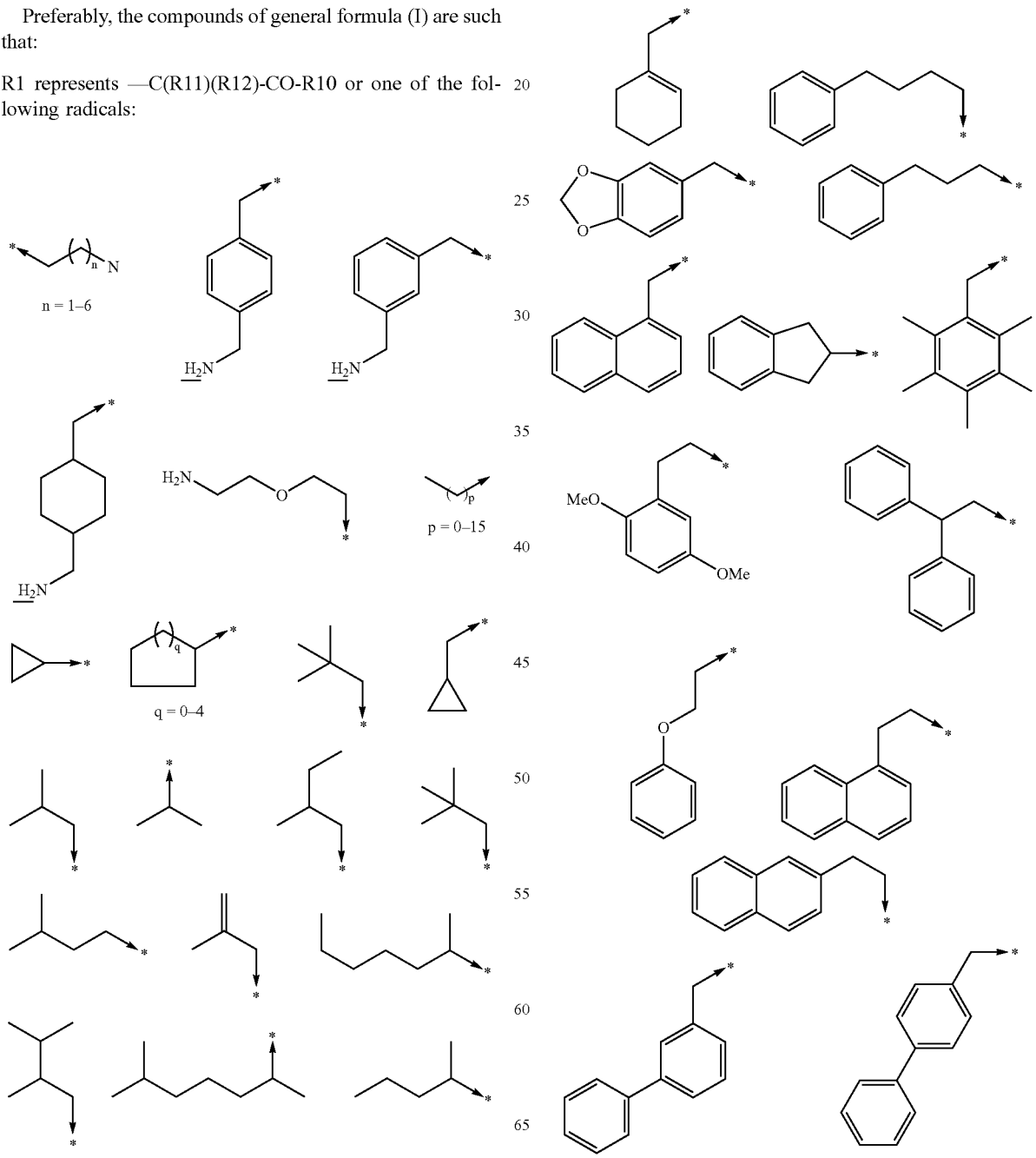

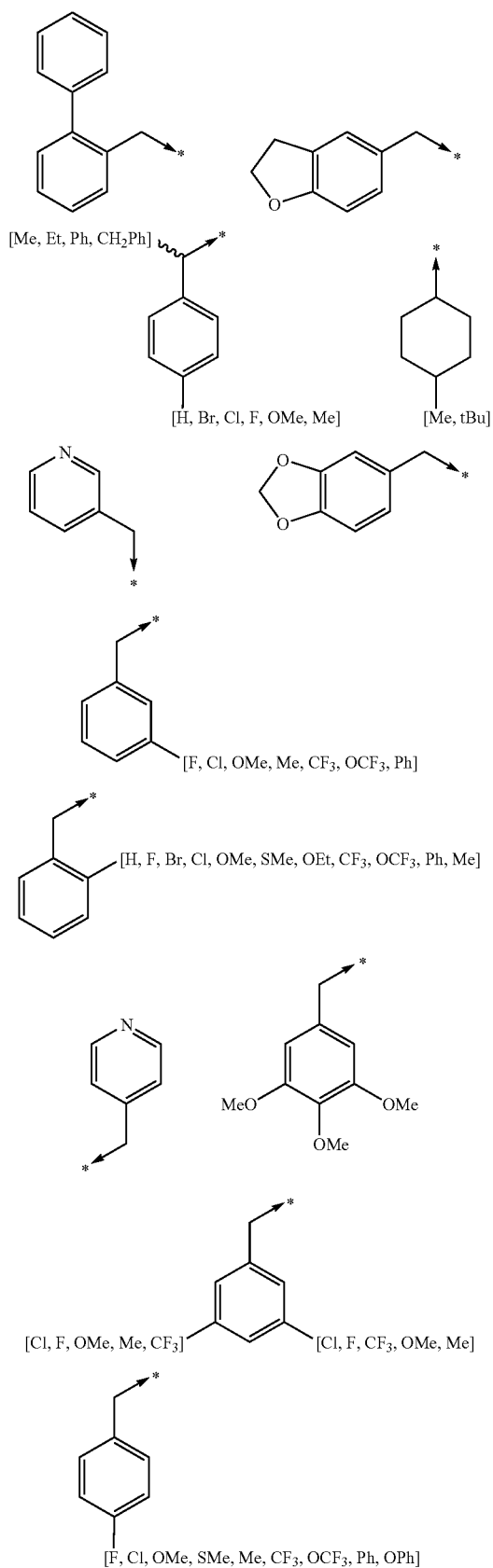
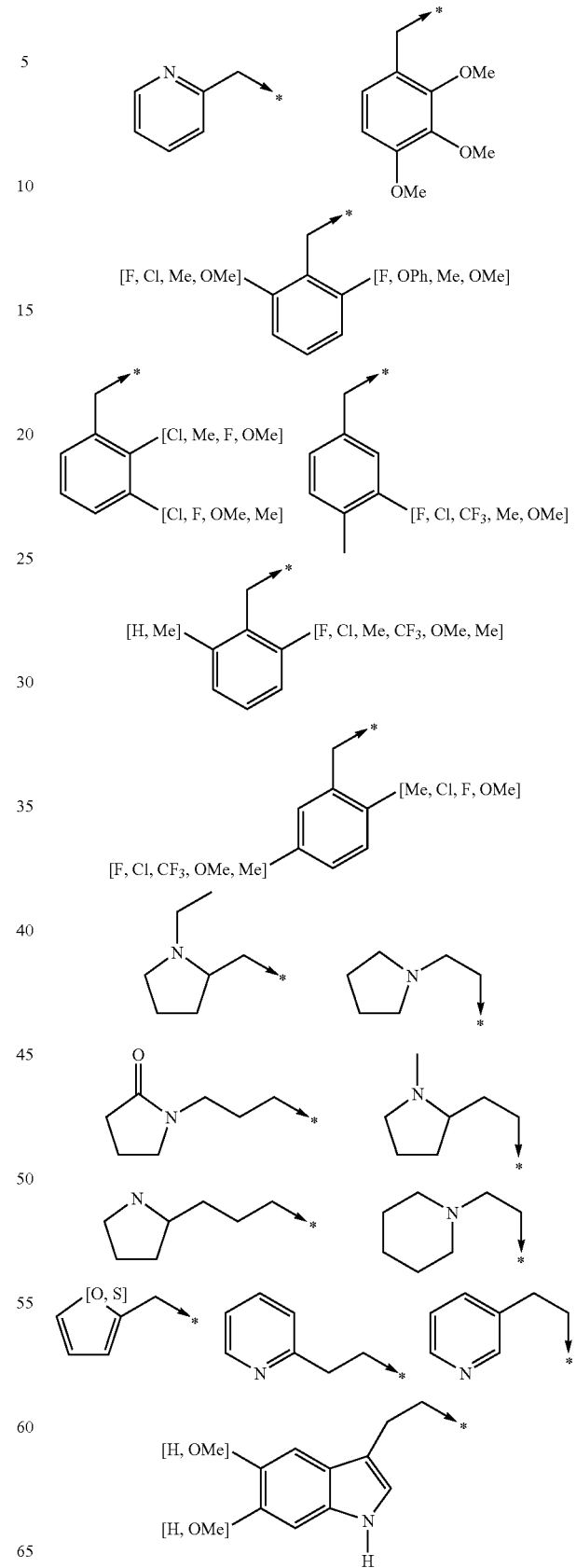

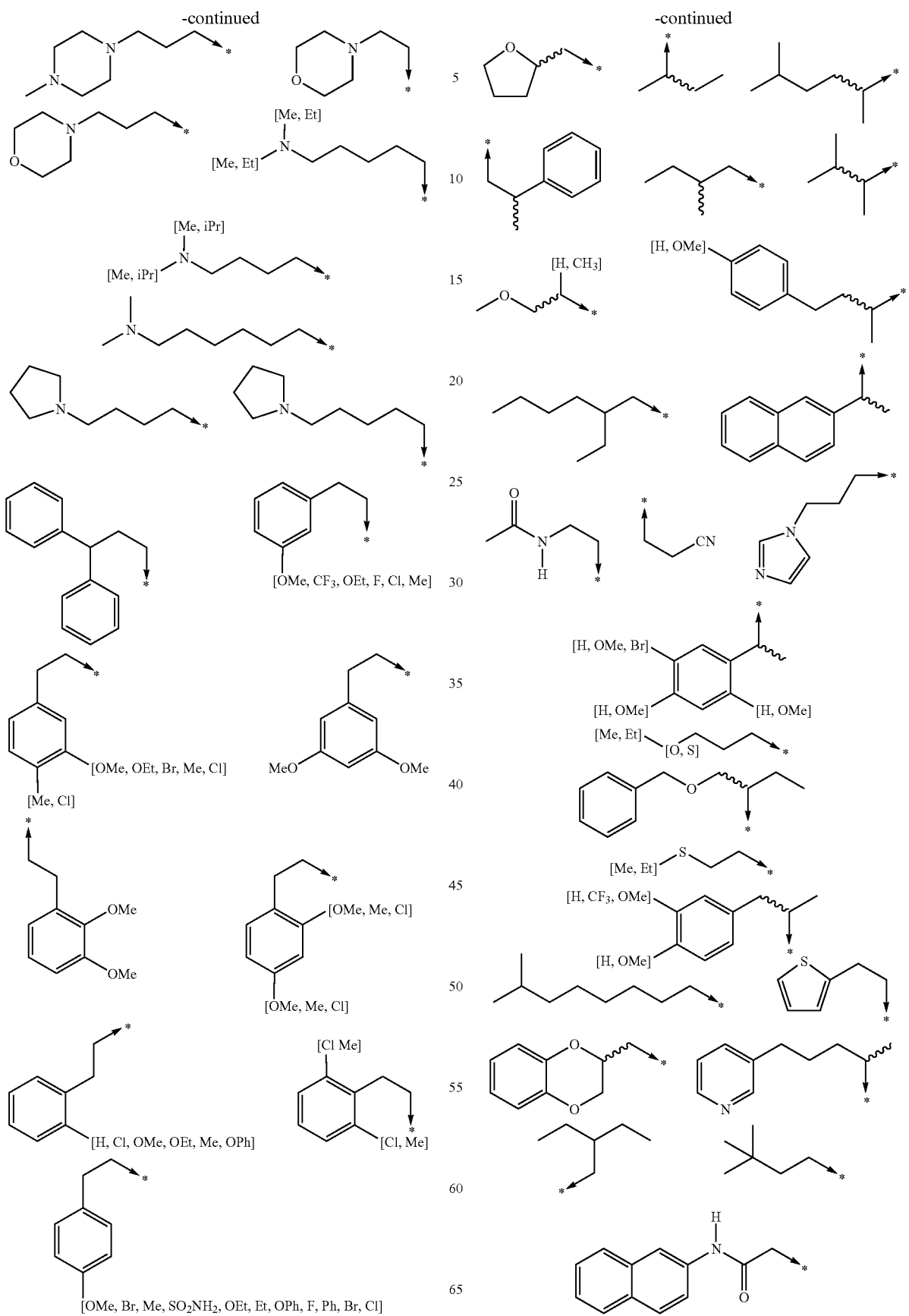

-continued
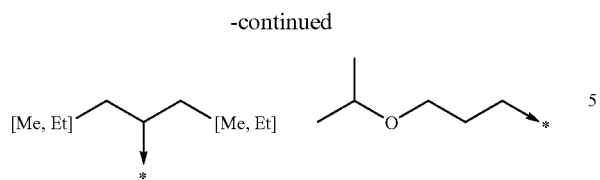
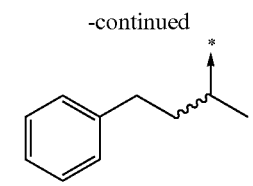
R2 represents one of the following radicals:
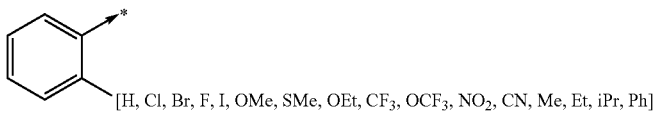
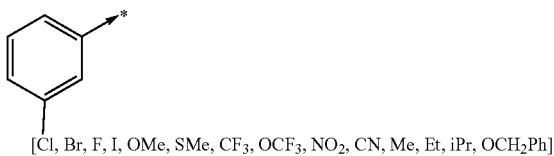
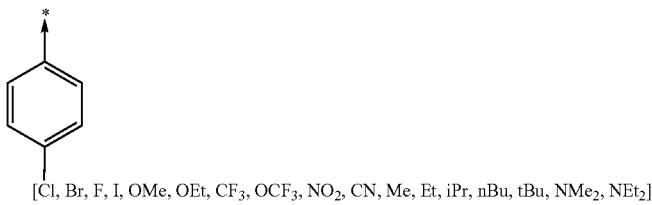
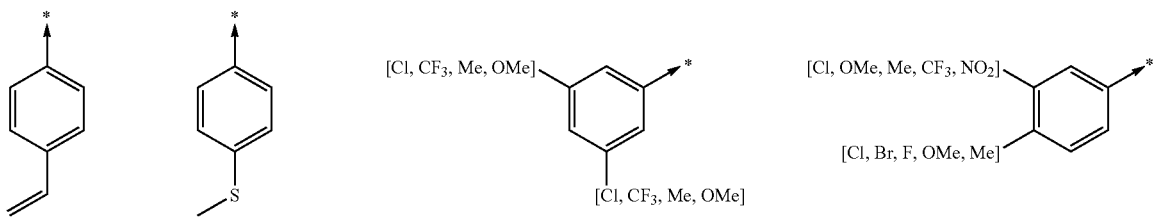
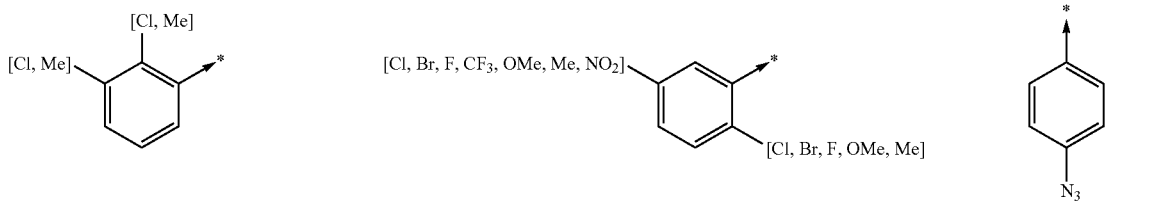
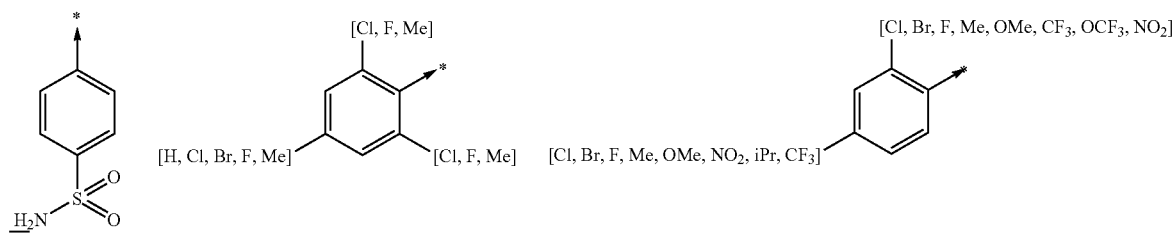

-continued
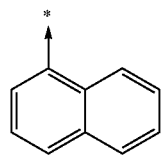 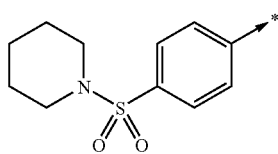 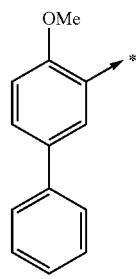 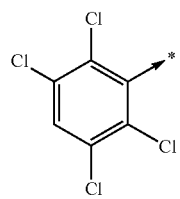 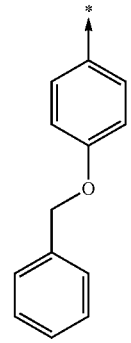
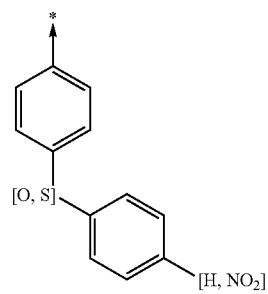 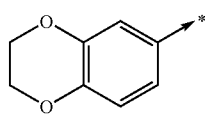 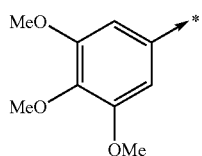 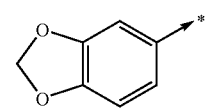
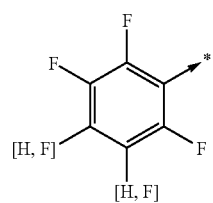 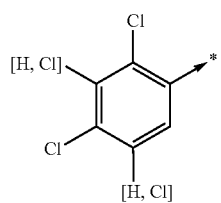 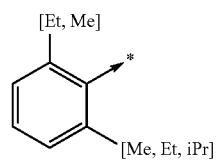 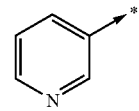
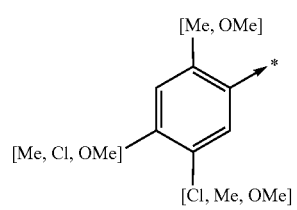 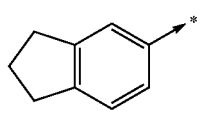 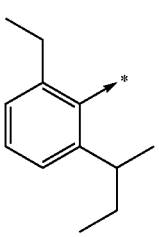 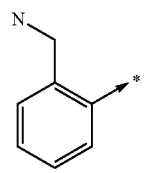
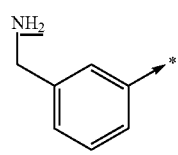 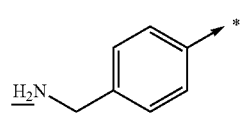 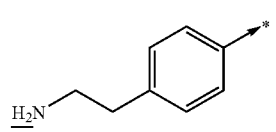

R3 represents CO-R5 or one of the following radicals:
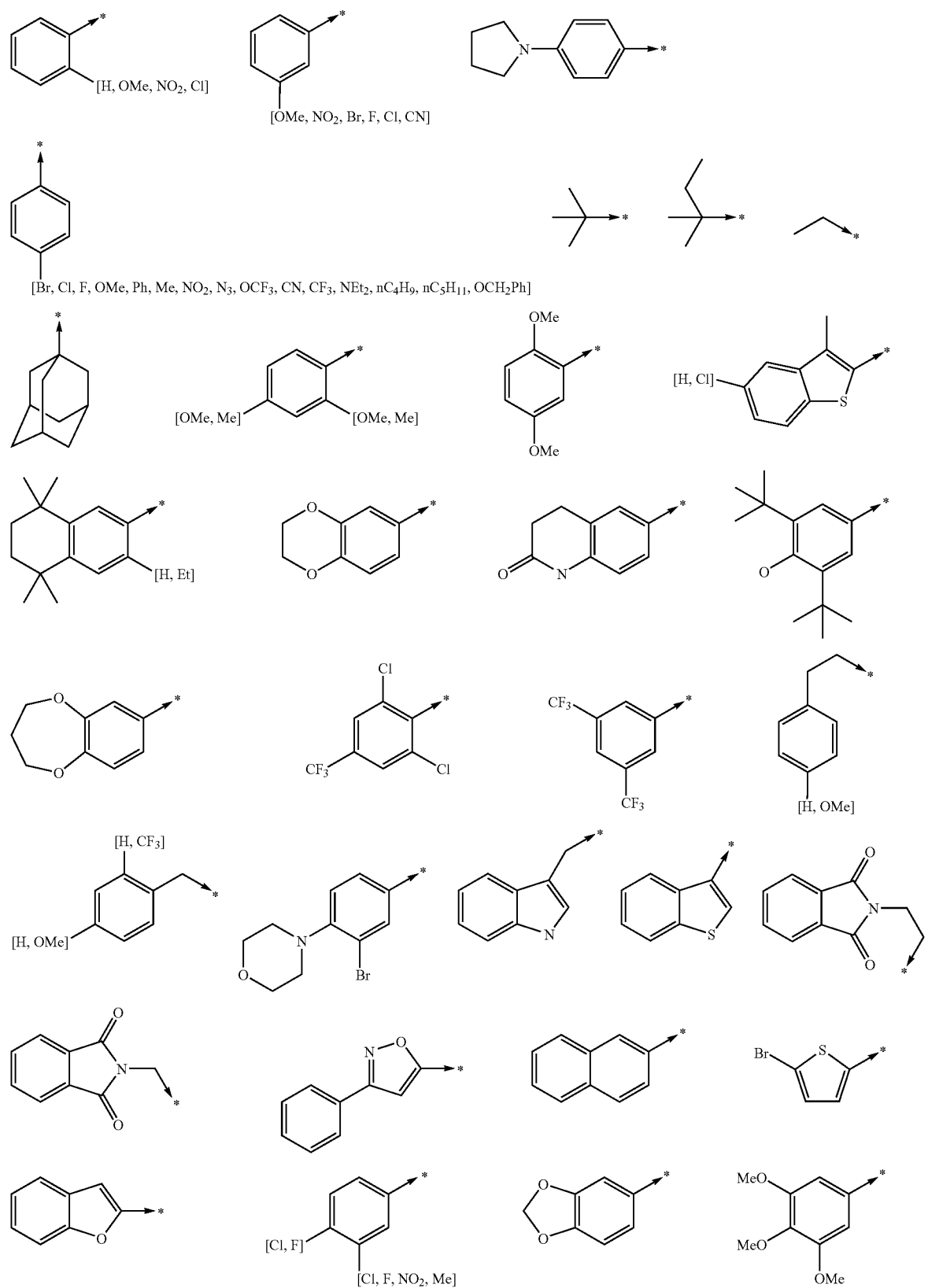

-continued

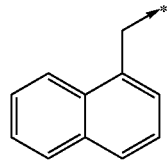 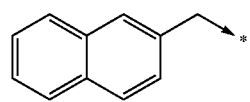

R4 represents H, alkyl, carbocyclic or heterocyclic aralkyl optionally substituted on the aryl radical;

or then the

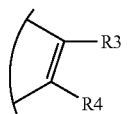

radical represents a radical of general formula

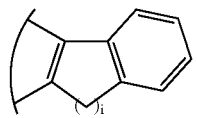

in which i represents an integer from 1 to 3;

R5 represents one of the following radicals:

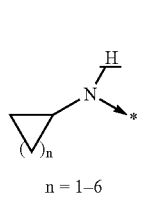

n = 1–6

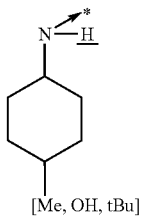

[Me, OH, tBu]

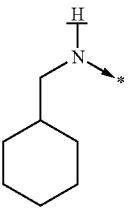

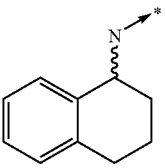

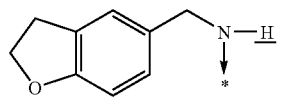

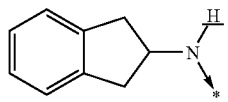

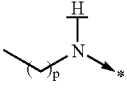

p = 0–15

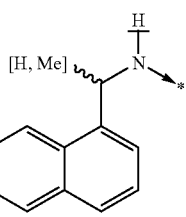

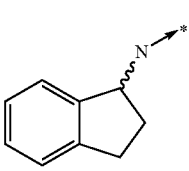

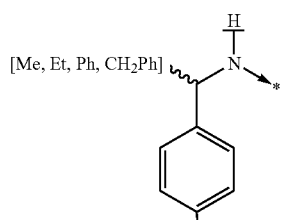

[Me, Et, Ph, CH$_2$Ph]

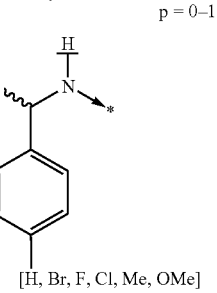

[H, Br, F, Cl, Me, OMe]

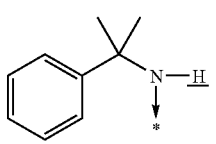

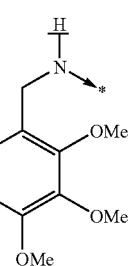

OMe
OMe
OMe

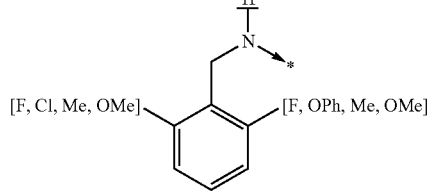

[F, Cl, Me, OMe]      [F, OPh, Me, OMe]

[F, Cl, Me, OMe,]

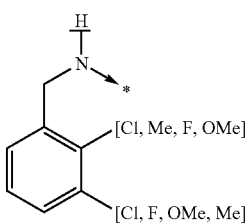

[Cl, Me, F, OMe]

[Cl, F, OMe, Me]

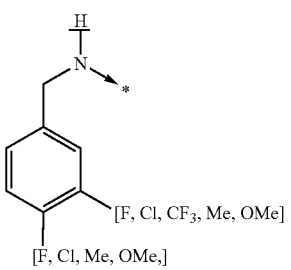

[F, Cl, CF$_3$, Me, OMe]

-continued
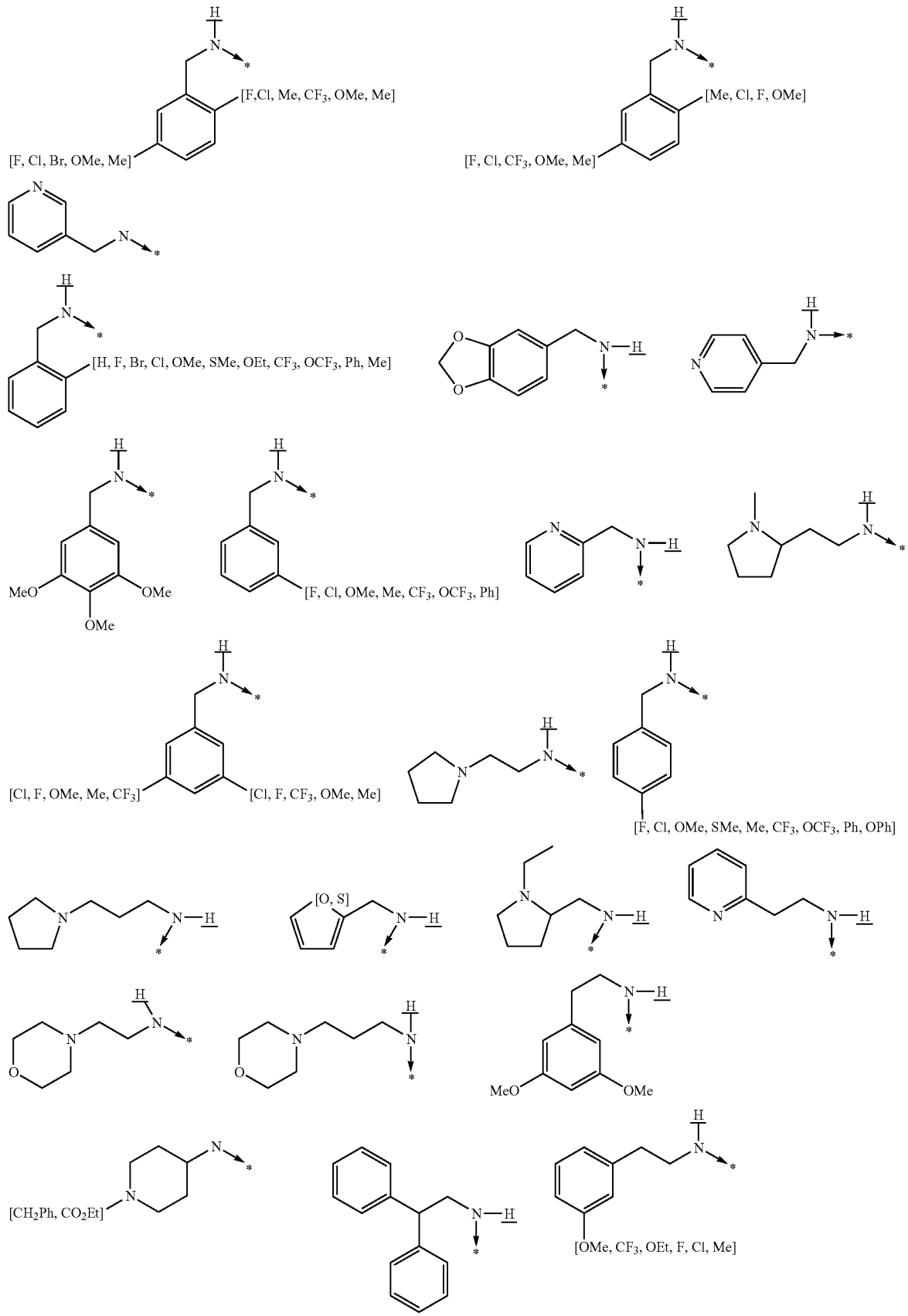

-continued
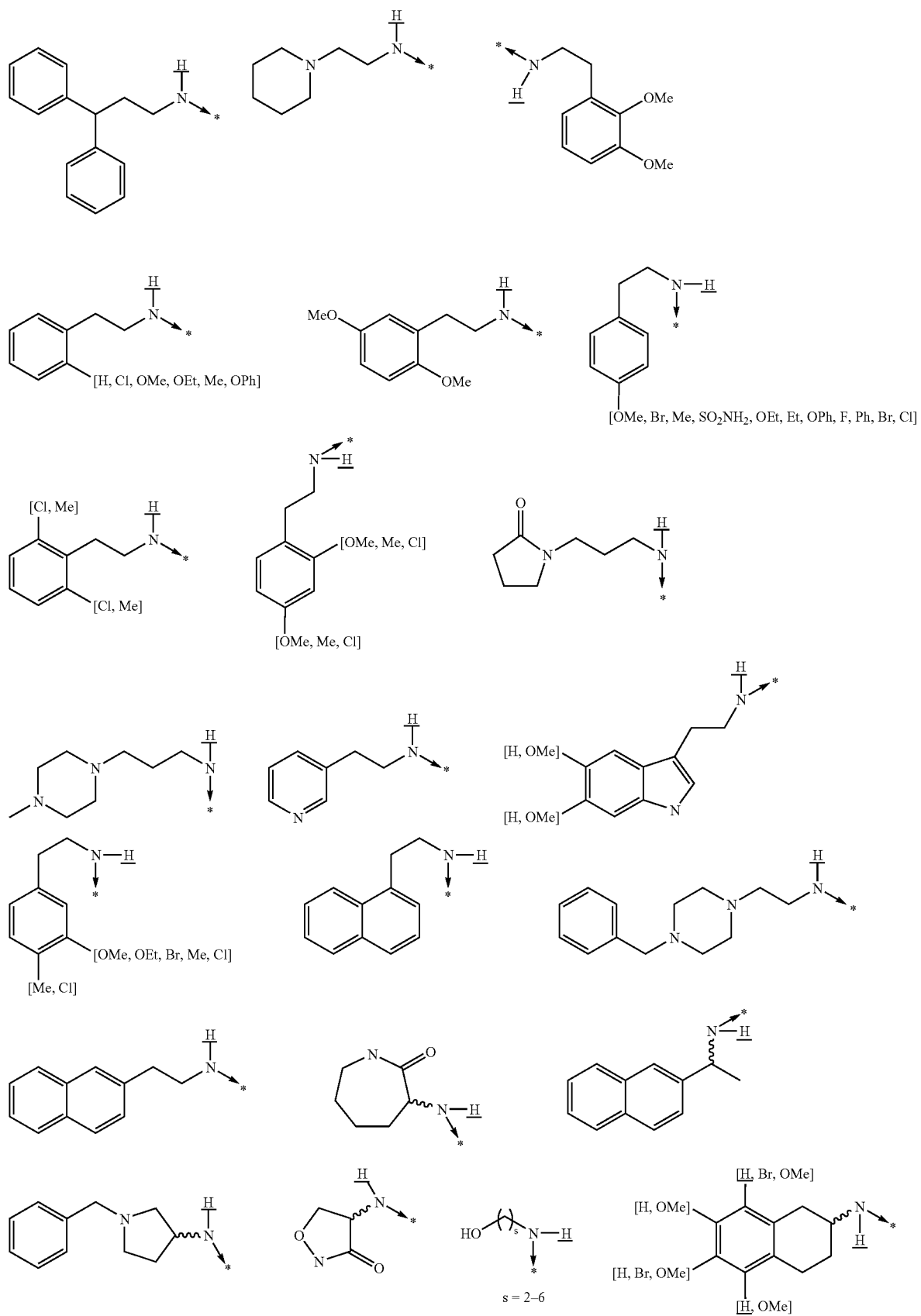

-continued
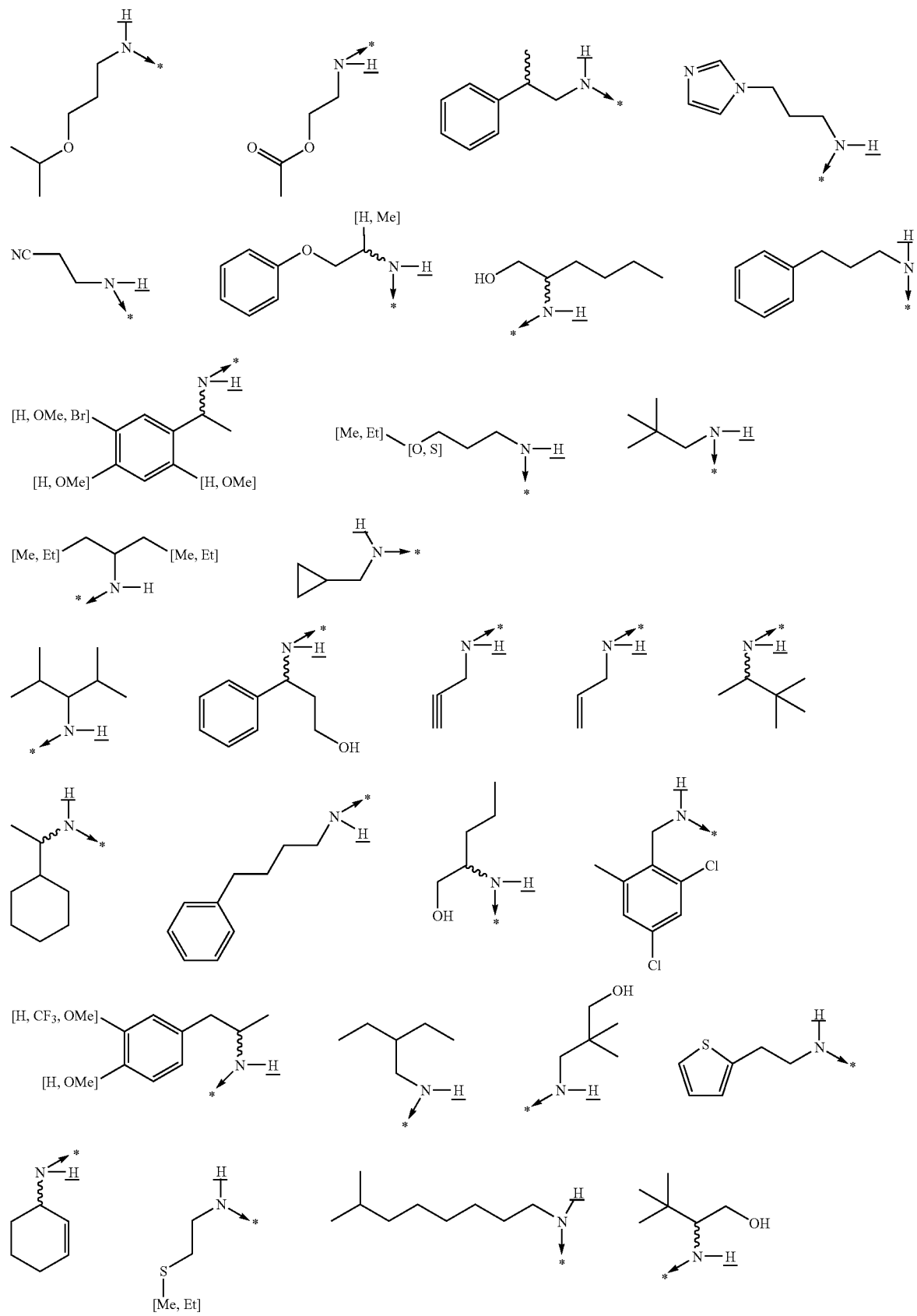

-continued
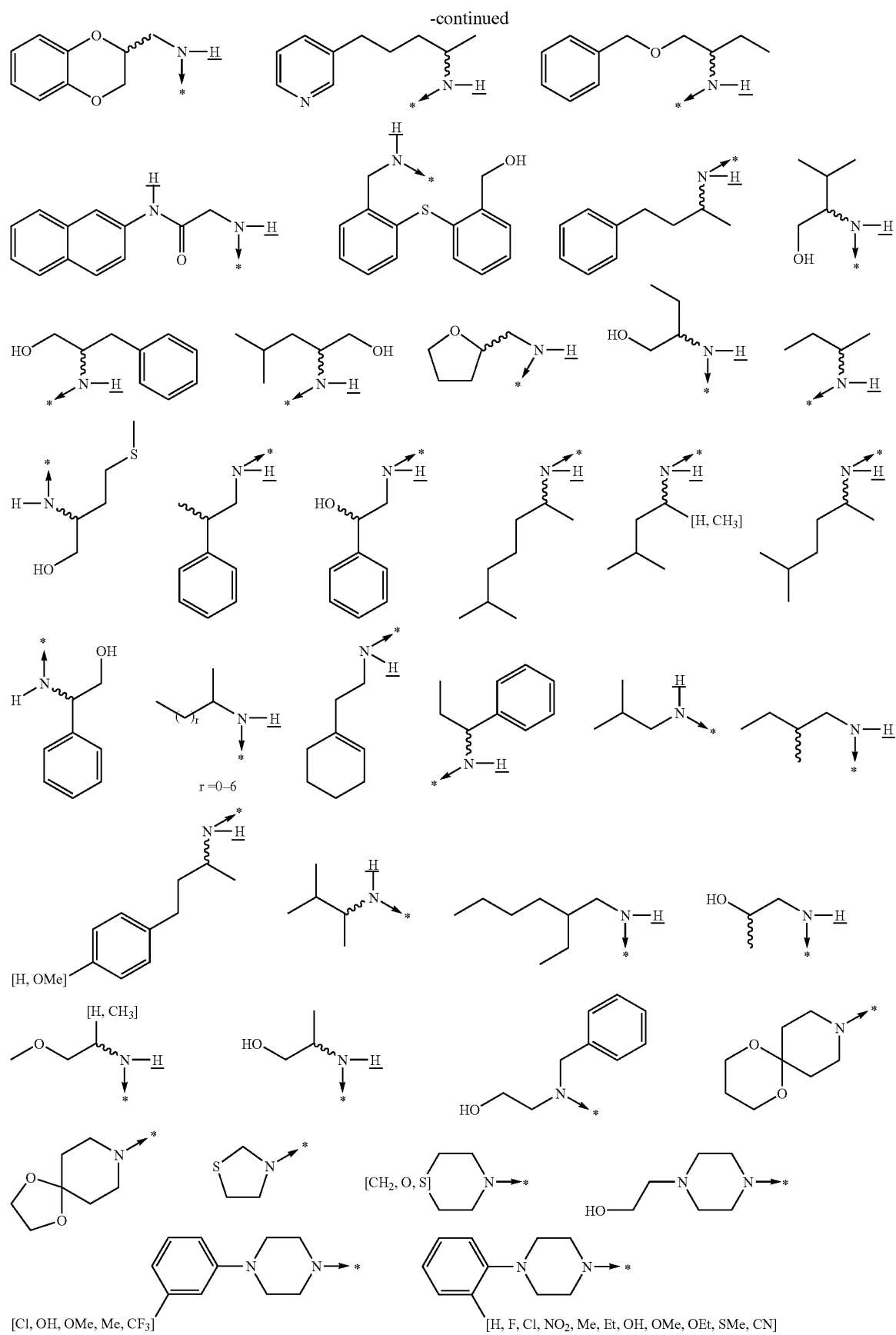

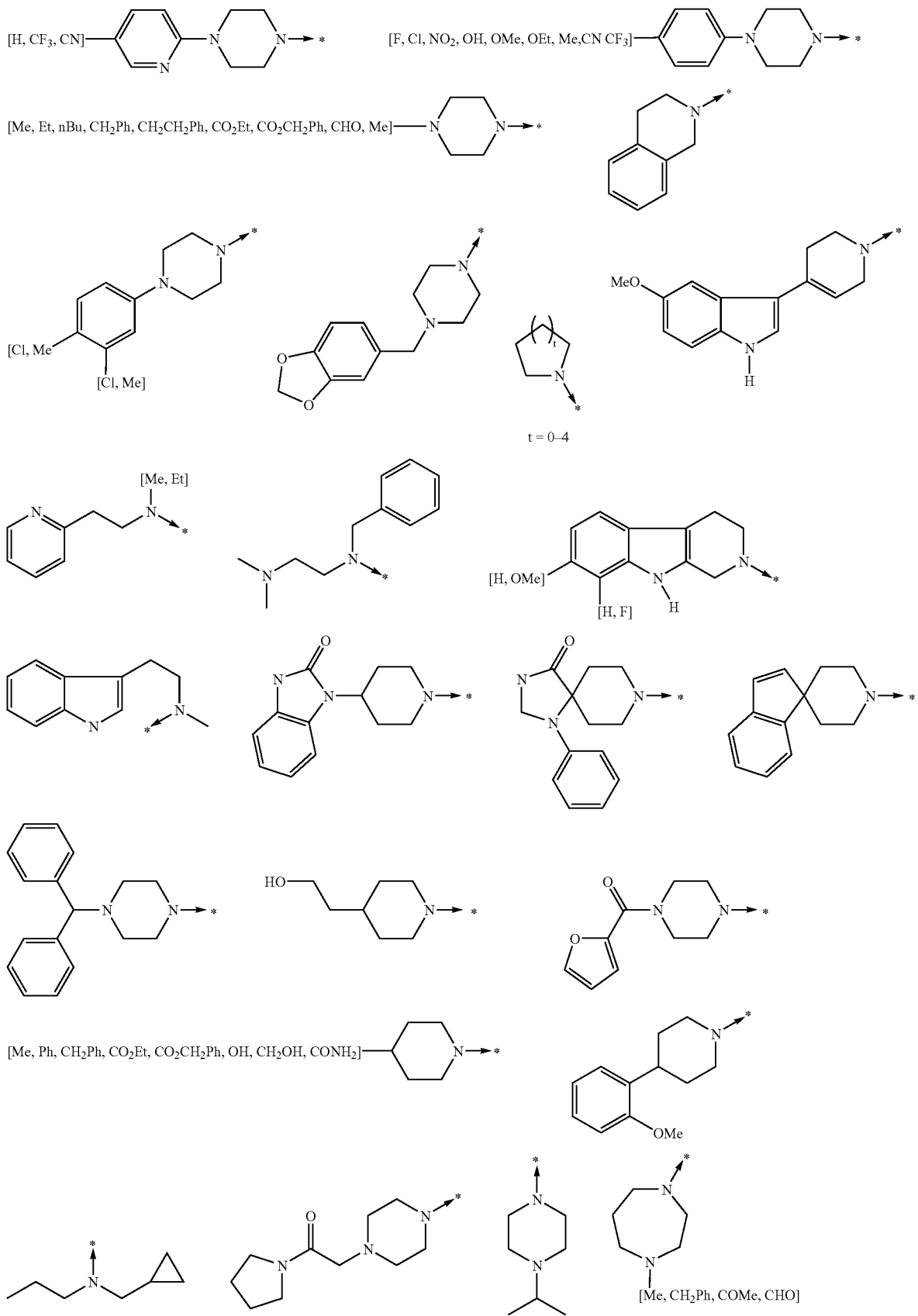

-continued
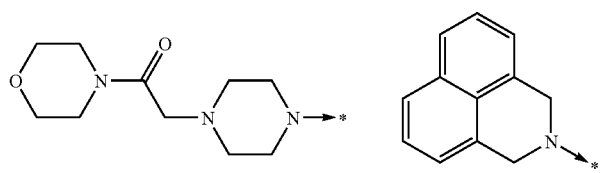
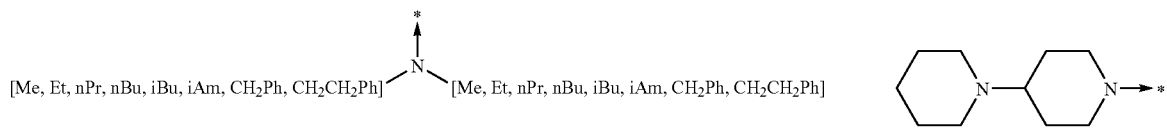
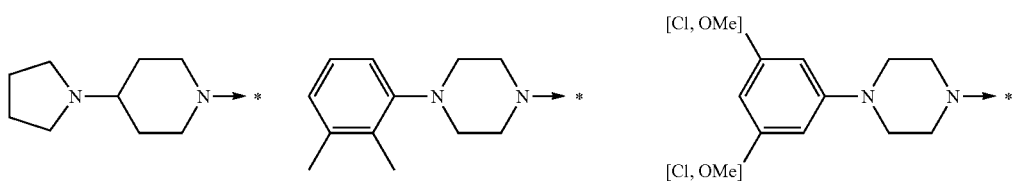
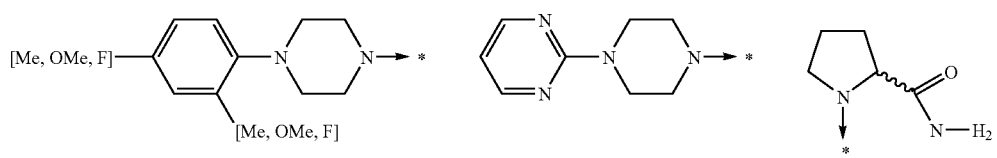
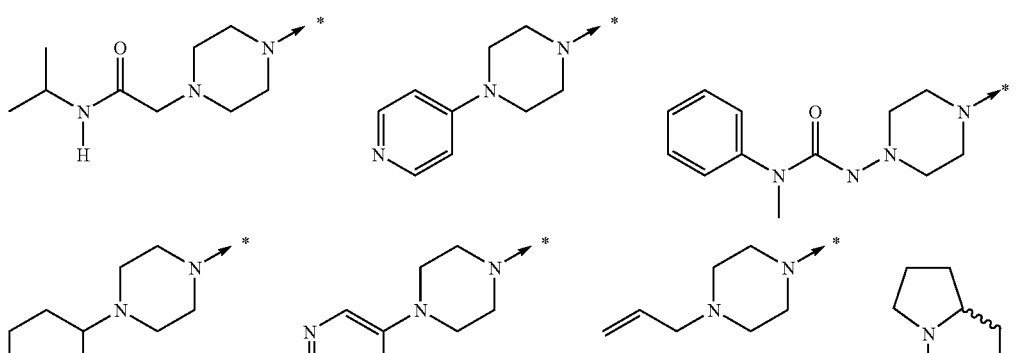
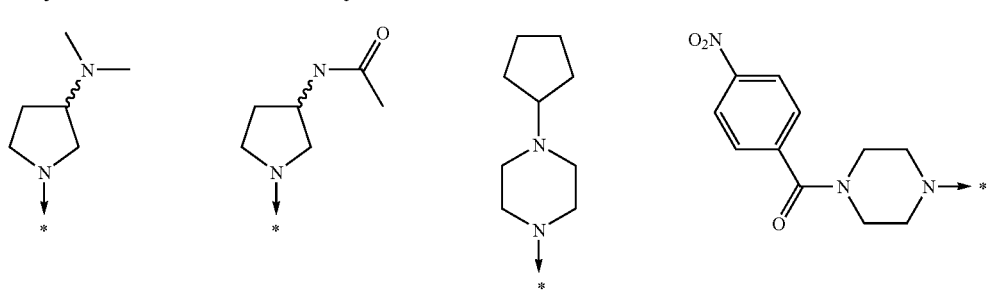
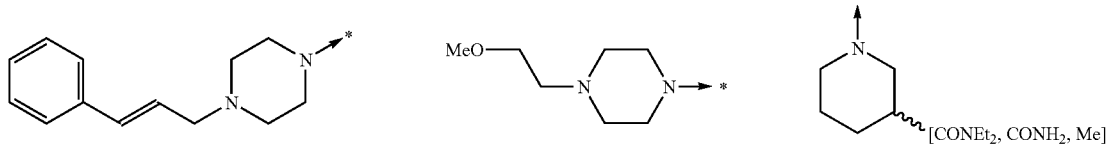

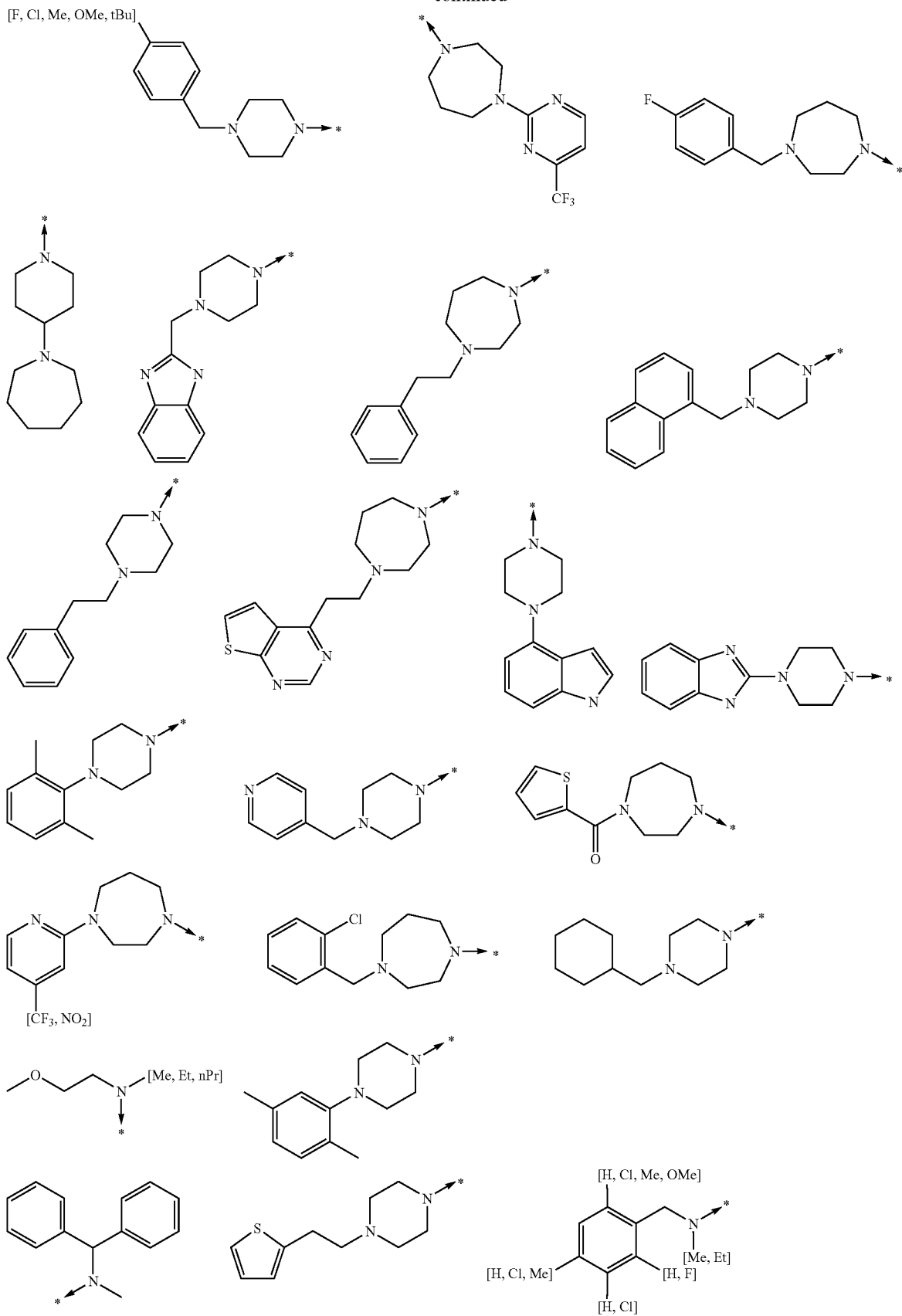

-continued
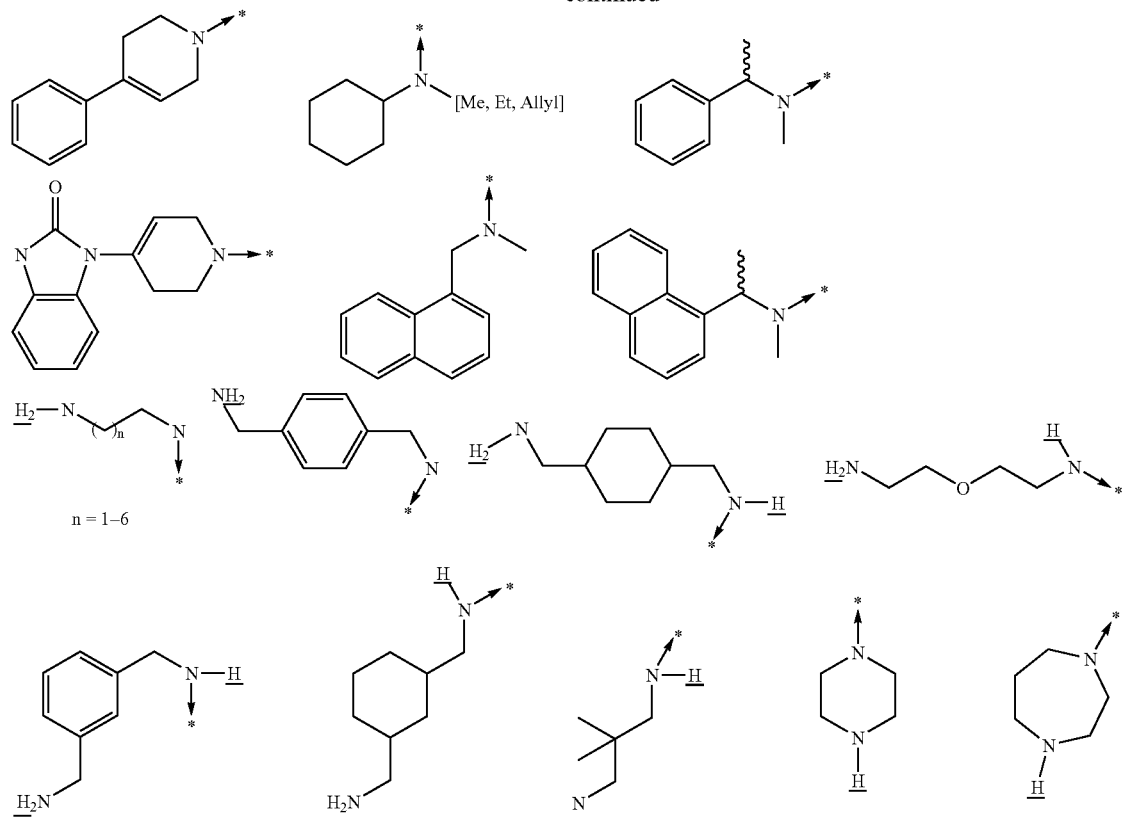
R10 represents one of the following radicals:
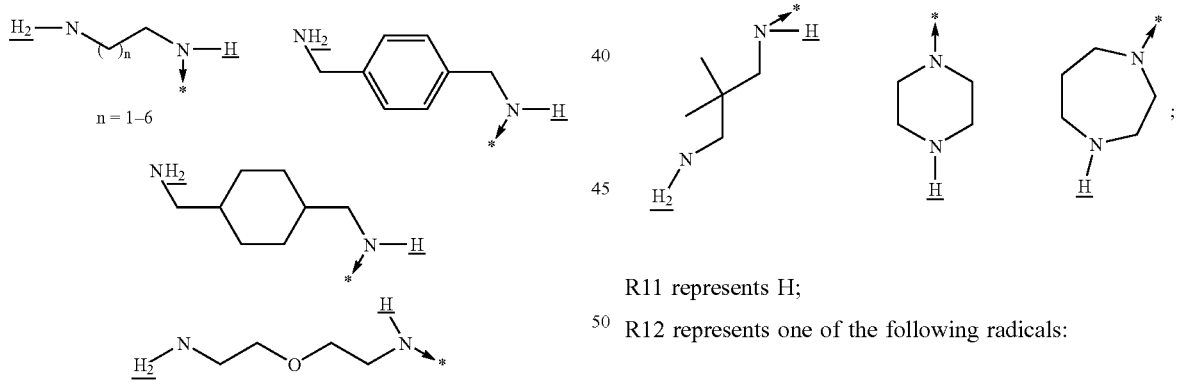
-continued
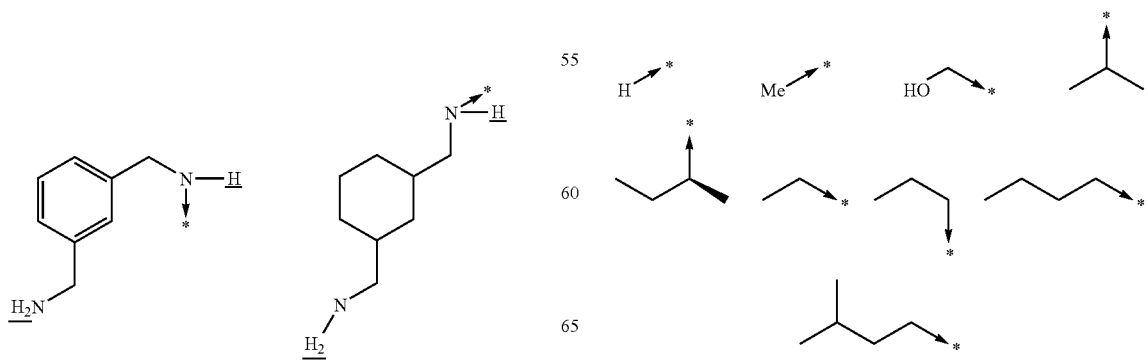
R11 represents H;
R12 represents one of the following radicals:

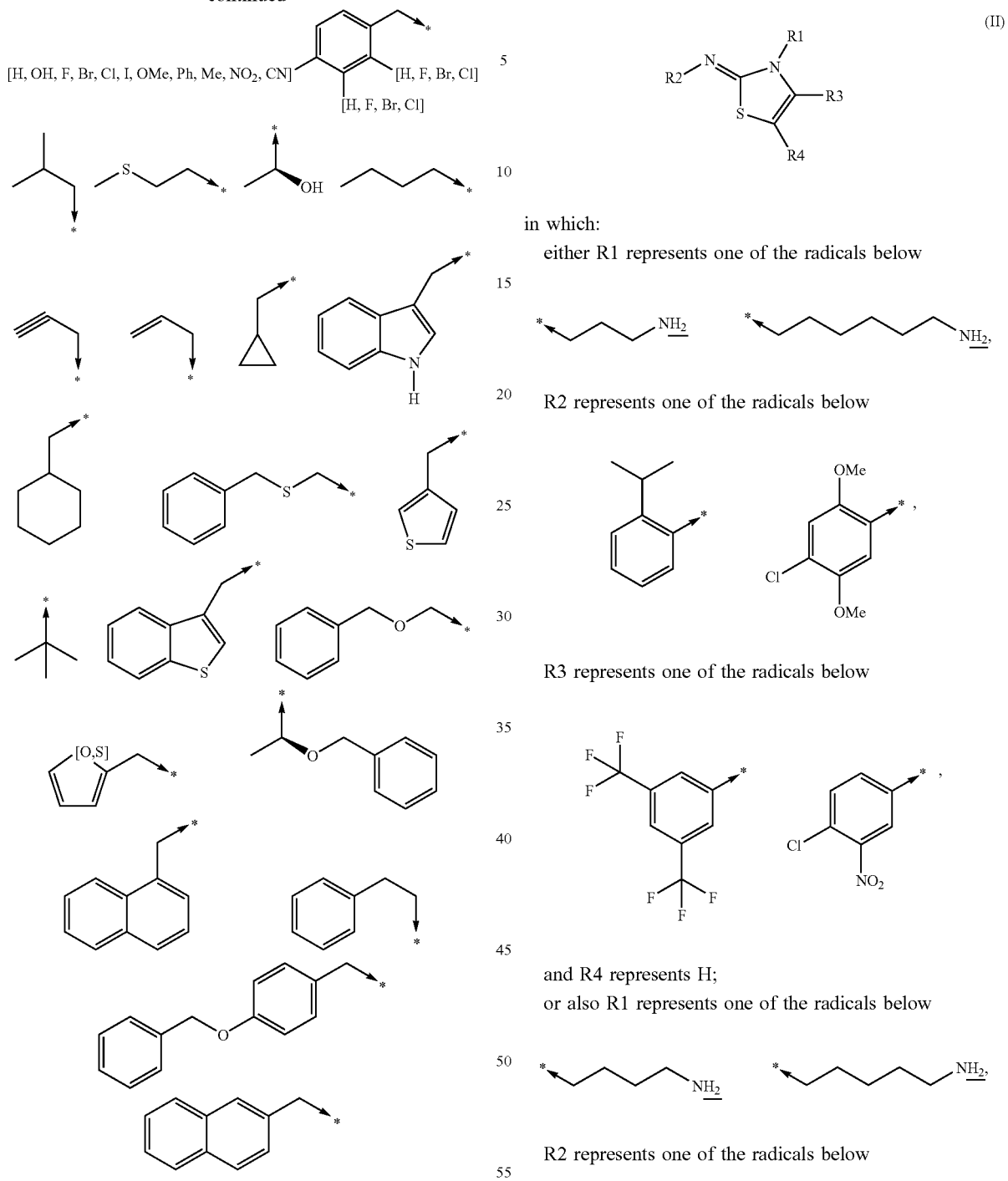

it being understood that for R4, when the aryl group is substituted, it can be from 1 to 5 times (other than the bond which links it with the remainder of the molecule) by radicals chosen independently from the group comprising a halogen atom and an alkyl or alkoxy radical.

The compounds of the invention are preferably such that R4 represents H.

More preferentially, the compounds according to the invention correspond to general formula (II)

in which:
either R1 represents one of the radicals below

R2 represents one of the radicals below

R3 represents one of the radicals below and R4 represents H;
or also R1 represents one of the radicals below R2 represents one of the radicals below R3 represents COR5,
R4 represents H,
and R5 represents one of the radicals below

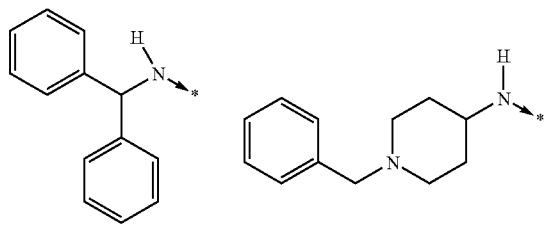

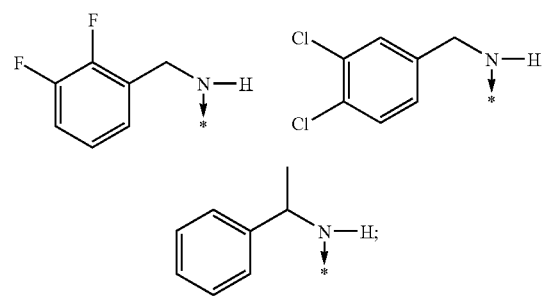

or finally R1 represents the —C(R11)(R12)-CO-R10 radical in which

R10 represents the radical

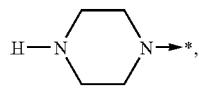

R11 represents H
and R12 represents the radical

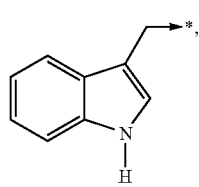

R2 represents the radical

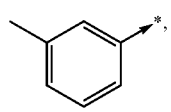

R3 represents the radical

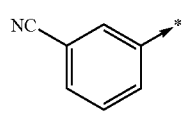

and R4 represents H.

The invention also relates to a compound characterized in that it corresponds: to formula

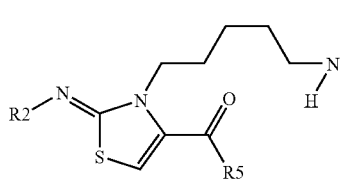

(i)

in which:
R2 represents the

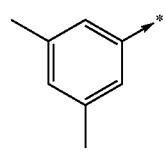

radical and R5 represents the

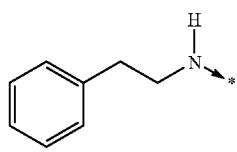

radical,
R2 represents the

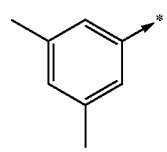

radical and R5 represents the

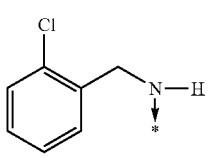

radical,
R2 represents the

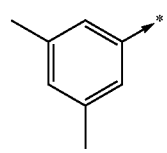

radical and R5 represents the

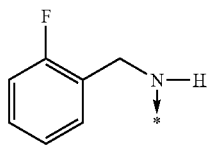
radical,
R2 represents the
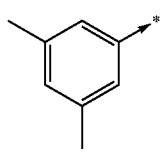
radical and R5 represents the
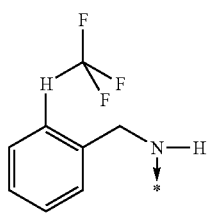
radical,
R2 represents the
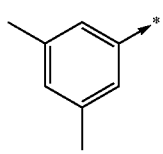
radical and R5 represents the
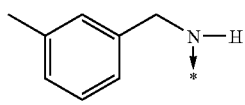
radical,
R2 represents the
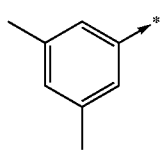
radical and R5 represents the
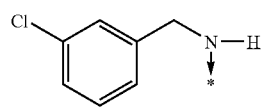
radical,
R2 represents the
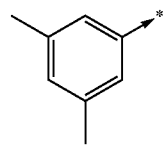
radical and R5 represents the
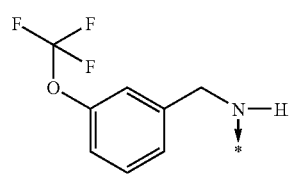
radical,
R2 represents the
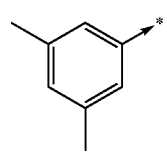
radical and R5 represents the
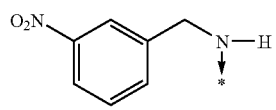
radical,
R2 represents the
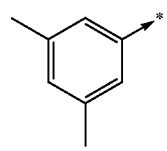
radical and R5 represents the

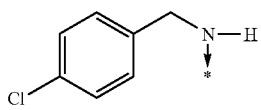
radical,
R2 represents the
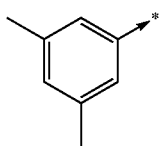
radical and R5 represents the
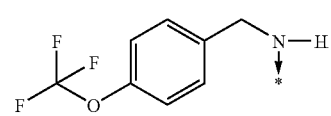
R2 represents the
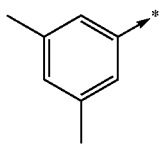
radical and R5 represents the
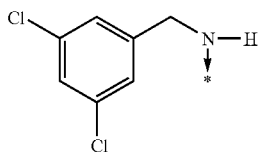
radical,
R2 represents the
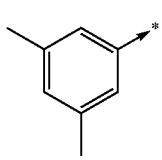
radical and R5 represents the
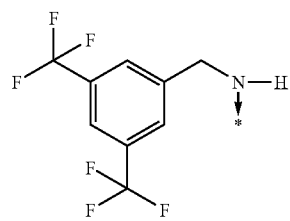
radical,
R2 represents the
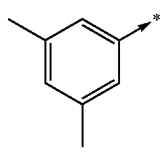
radical and R5 represents the
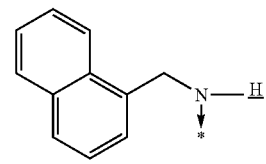
radical,
R2 represents the
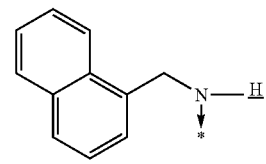
radical and R5 represents the
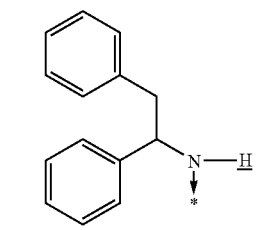
radical, R2 represents the
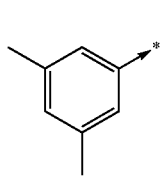
radical and R5 represents the
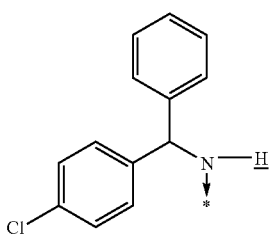
radical,
R2 represents the
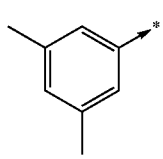
radical and R5 represents the
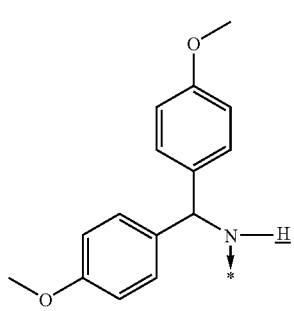
radical,
R2 represents the
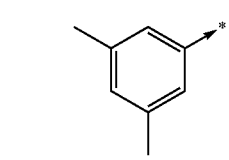
radical and R5 represents the
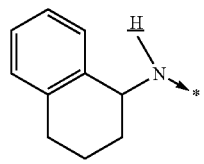
radical,
R2 represents the
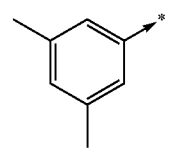
radical and R5 represents the
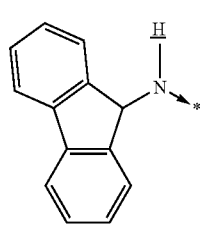
radical,
R2 represents the
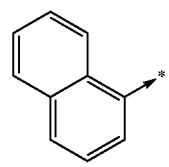
radical and R5 represents the
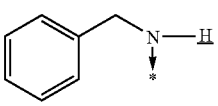
radical,
R2 represents the
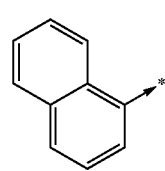
radical and R5 represents the

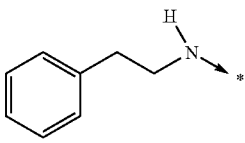
radical,
R2 represents the
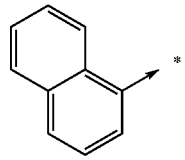
radical and R5 represents the
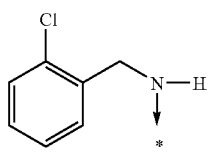
radical,
R2 represents the
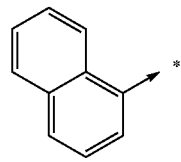
radical and R5 represents the
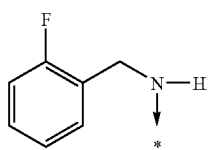
radical,
R2 represents the
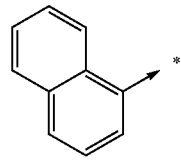
radical and R5 represents the
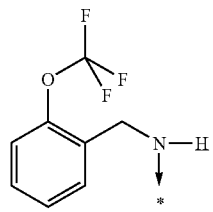
radical,
R2 represents the
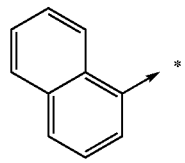
radical and R5 represents the
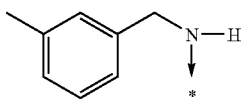
radical,
R2 represents the
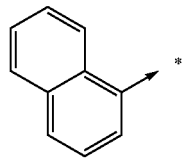
radical and R5 represents the
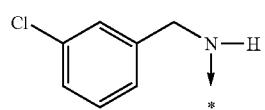
radical,
R2 represents the
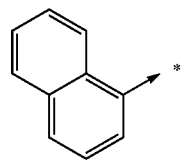
radical and R5 represents the

51
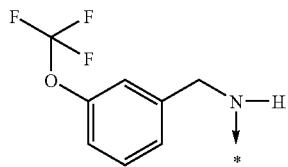
radical,
    R2 represents the
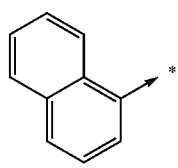
radical and R5 represents the
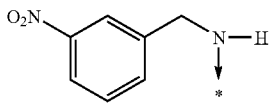
radical,
    R2 represents the
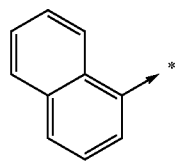
radical and R5 represents the
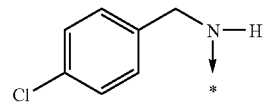
radical,
    R2 represents the
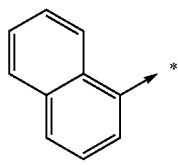
radical and R5 represents the
52
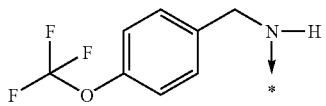
radical,
    R2 represents the
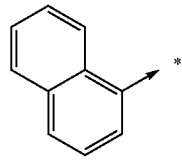
radical and R5 represents the
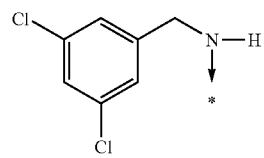
radical,
    R2 represents the
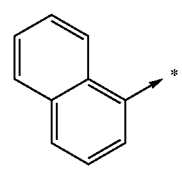
radical and R5 represents the
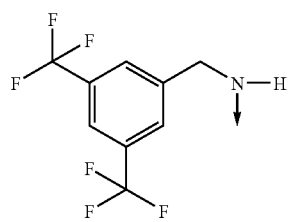
radical,
    R2 represents the
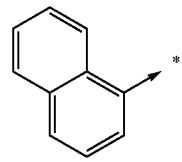
radical and R5 represents the

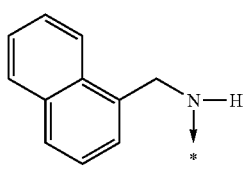
radical,
R2 represents the
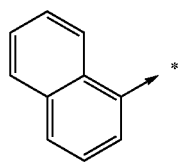
radical and R5 represents the
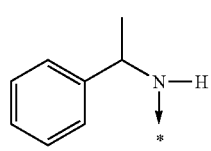
radical,
R2 represents the
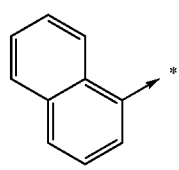
radical and R5 represents the
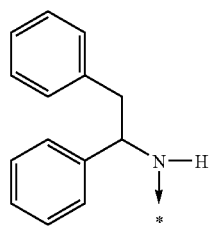
radical,
R2 represents the
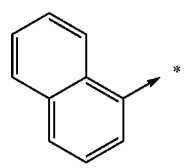
radical and R5 represents the
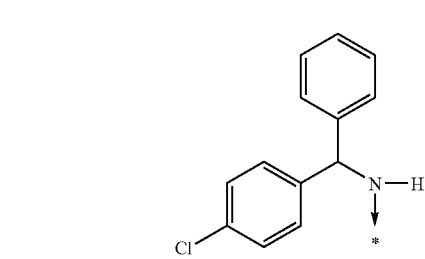
radical,
R2 represents the
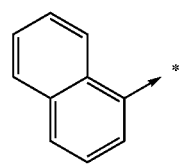
radical and R5 represents the
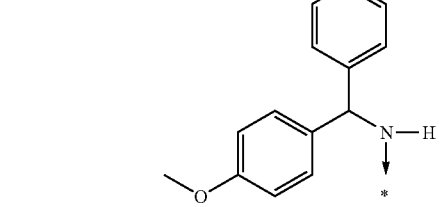
radical.
R2 represents the
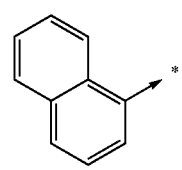
radical and R5 represents the

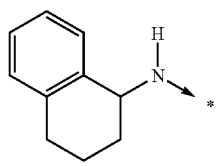
radical, or finally
R2 represents the
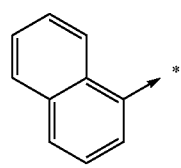
radical and R5 represents the
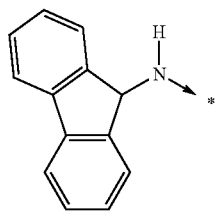
radical;
to formula
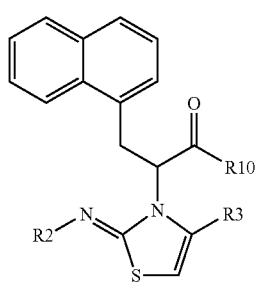
in which:
R10 represents
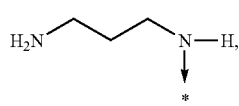
R2 represents
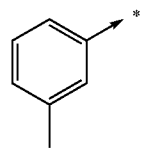
and R3 represents
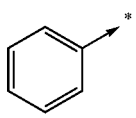,
R10 represents
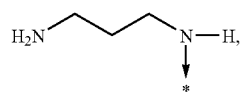
R2 represents
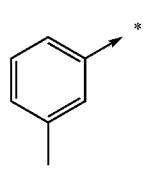
and R3 represents
(ii)
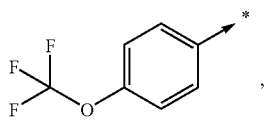,
R10 represents
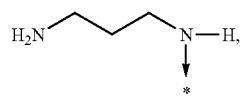
R2 represents
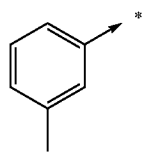
and R3 represents R10 represents
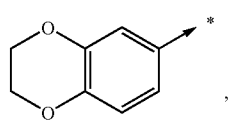
R2 represents
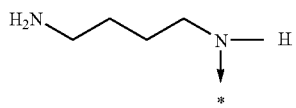
and R3 represents
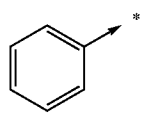
R10 represents
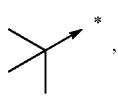,
R2 represents
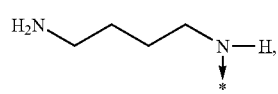
and R3 represents
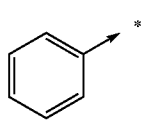
R10 represents
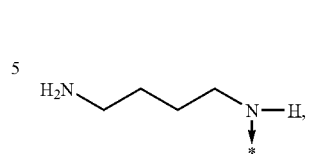
R2 represents
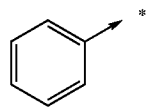
and R3 represents
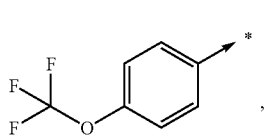,
R10 represents
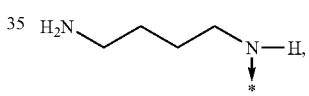
R2 represents
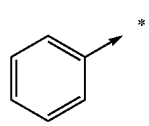
and R3 represents
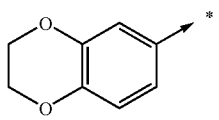,
R10 represents
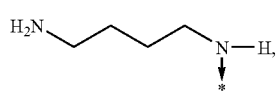

R2 represents
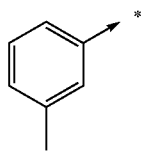
and R3 represents
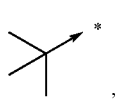,
R10 represents
R2 represents
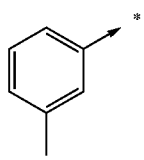
and R3 represents
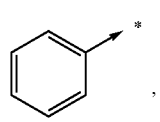,
R10 represents
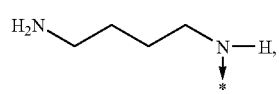
R2 represents
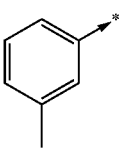
and R3 represents
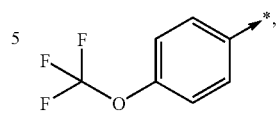,
R10 represents
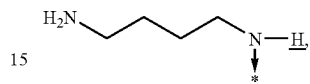
R2 represents
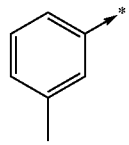
and R3 represents
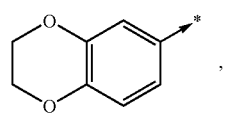,
R10 represents
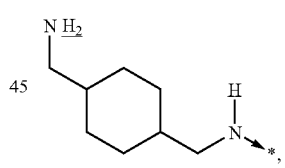
R2 represents
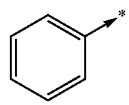
and R3 represents
, R10 represents
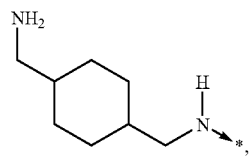
R2 represents
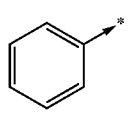
and R3 represents
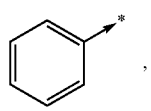,
R10 represents
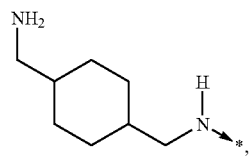
R2 represents
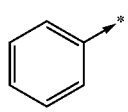
and R3 represents
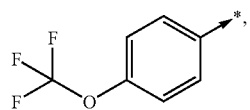
R10 represents
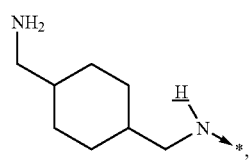
R2 represents
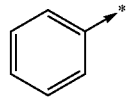
and R3 represents
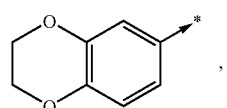,
R10 represents
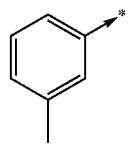,
R2 represents
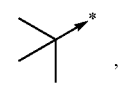
and R3 represents
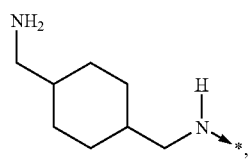,
R10 represents
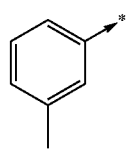,
R2 represents
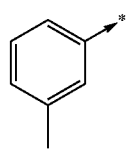

and R3 represents
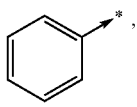
R10 represents
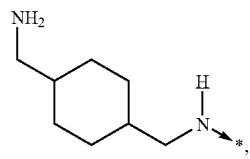
R2 represents
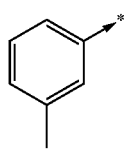
and R3 represents
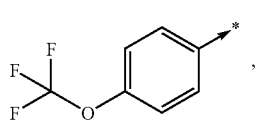
R10 represents
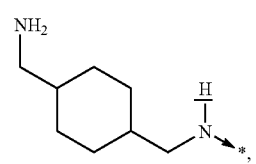
and R2 represents
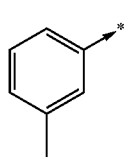
and R3 represents
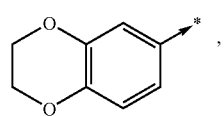
R10 represents
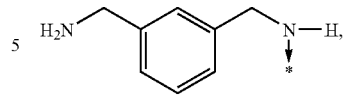
R2 represents
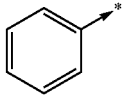
and R3 represents
R10 represents
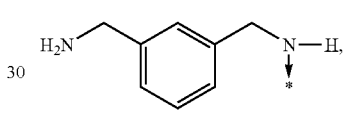
, R2 represents
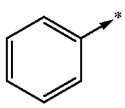
and R3 represents
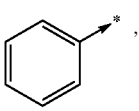
R10 represents
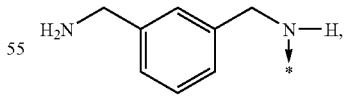
R2 represents
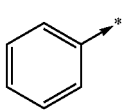

and R3 represents
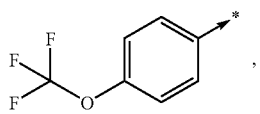
R10 represents
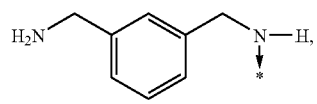
R2 represents
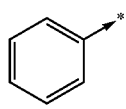
and R3 represents
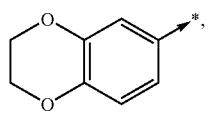
R10 represents
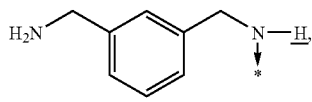
R2 represents
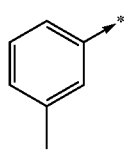
and R3 represents
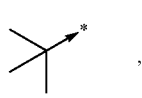
R10 represents
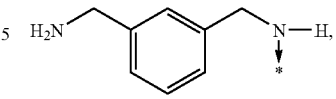
R2 represents
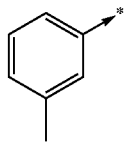
and R3 represent
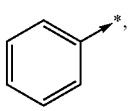
R10 represents
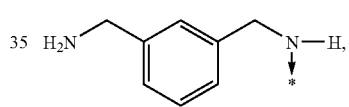
R2 represents
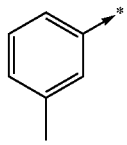
and R3 represents
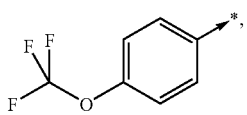
R10 represents
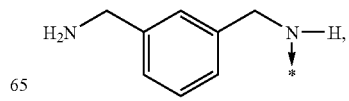

R2 represents
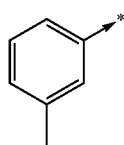
and R3 represents
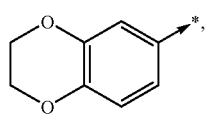
R10 represents
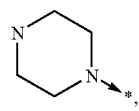
R2 represents
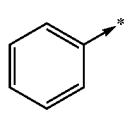
and R3 represents
R10 represents
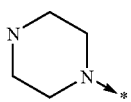
R2 represents
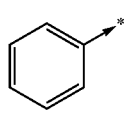
and R3 represents
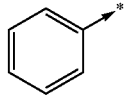
R10 represents
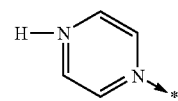
R2 represents
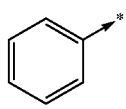
and R3 represents
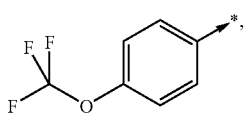
R10 represents
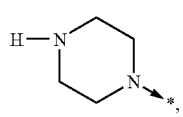
R2 represents
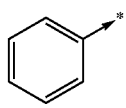
and R3 represents
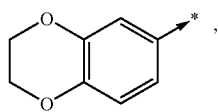

R10 represents
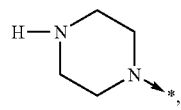
R2 represents
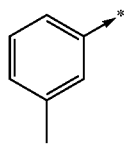
and R3 represents
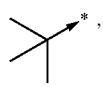
R10 represents
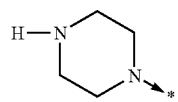
R2 represents
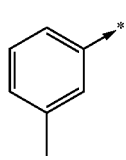
and R3 represents
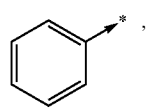
R10 represents
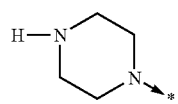
R2 represents
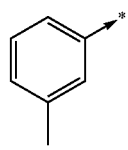
and R3 represents
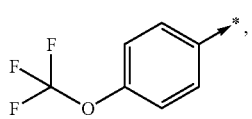
R10 represents
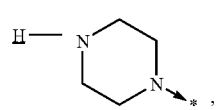
R2 represents
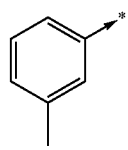
and R3 represents
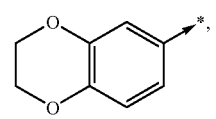
to formula
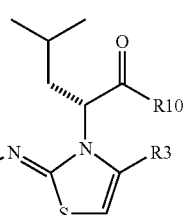
(iii)
in which:

R10 represents
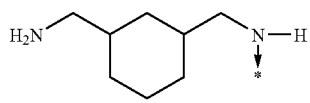
R2 represents
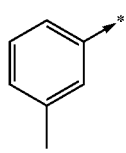
and R3 represents
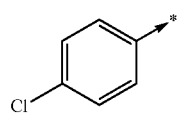
R10 represents
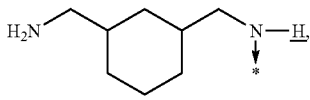
R2 represents
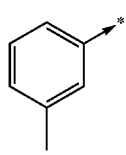
and R3 represents
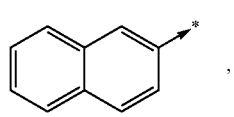
R10 represents
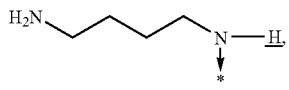
R2 represents
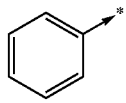
and R3 represents
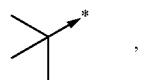,
R10 represents
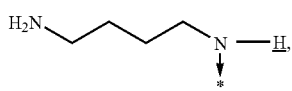
R2 represents
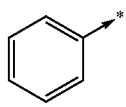
and R3 represents
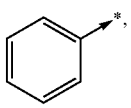,
R10 represents
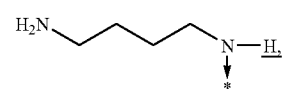
R2 represents
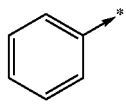
and R3 represents
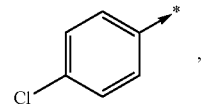, 73
R10 represents
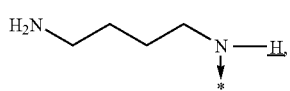
R2 represents
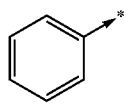
and R3 represents
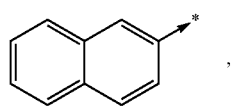
R10 represents
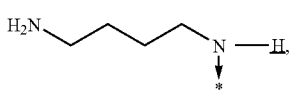
R2 represents
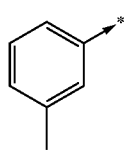
and R3 represents
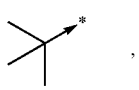
R10 represents
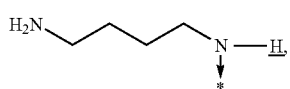
74
R2 represents
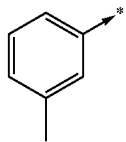
and R3 represents
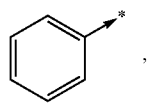
R10 represents
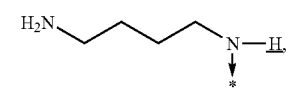
R2 represents
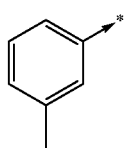
and R3 represents
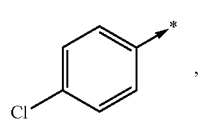
or finally
R10 represents
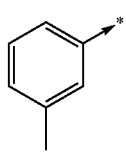
R2 represents and R3 represents
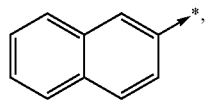
to formula
(iv)
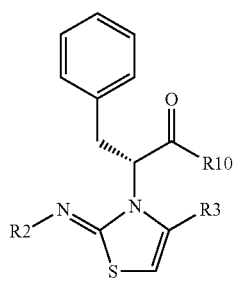
in which:
R10 represents
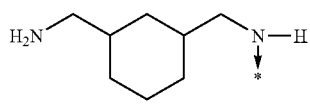
R2 represents
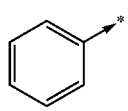
and R3 represents
,
R10 represents
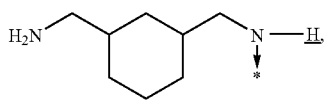
R2 represents
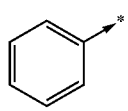
and R3 represents
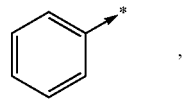,
R10 represents
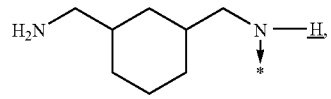
R2 represents
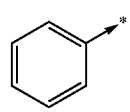
and R3 represents
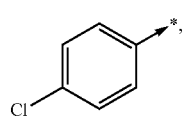,
R10 represents
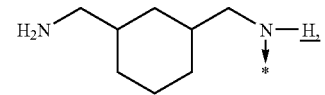
R2 represents
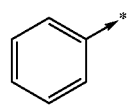
and R3 represents
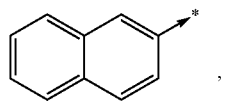,
R10 represents
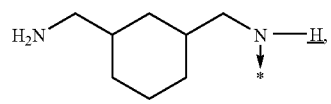

R2 represents
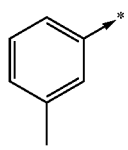
and R3 represents
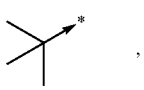,
R10 represents
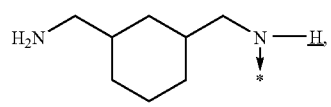
R2 represents
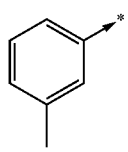
and R3 represents
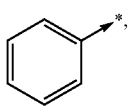,
R10 represents
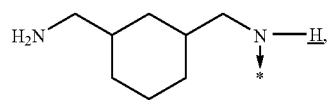
R2 represents
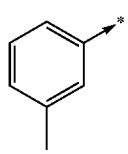
and R3 represents
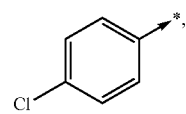,
R10 represents
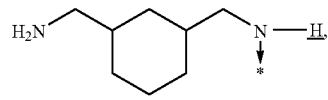
R2 represents
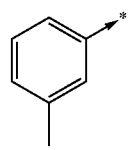
and R3 represents
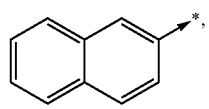,
R10 represents
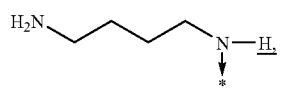
R2 represents
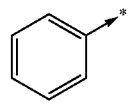
and R3 represents
,
R10 represents
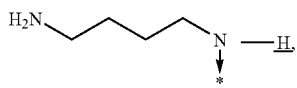

R2 represents
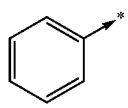
and R3 represents
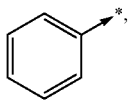
R10 represents
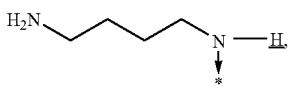
R2 represents
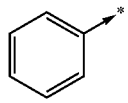
and R3 represents
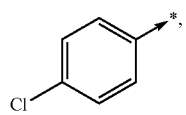
R10 represents
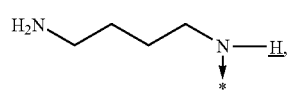
R2 represents
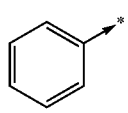
and R3 represents
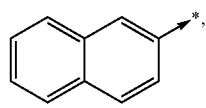
R10 represents
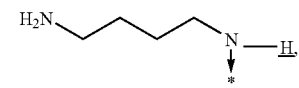
R2 represents
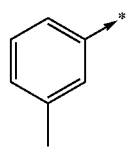
and R3 represents
R10 represents
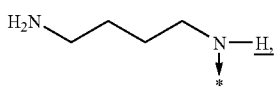
R2 represents
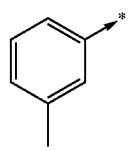
and R3 represents
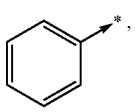

R10 represents
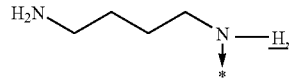
R2 represents
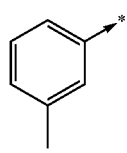
and R3 represents
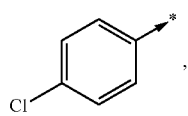,
or finally
R10 represents
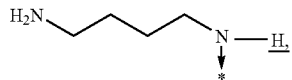
R2 represents
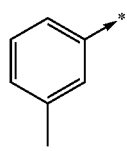
and R3 represents
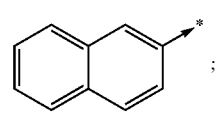;
to formula
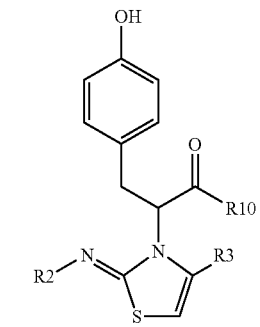 (Y)
in which:
R10 represents
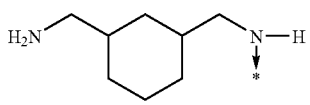
R2 represents
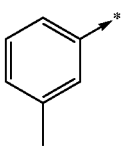
and R3 represents
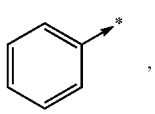,
R10 represents
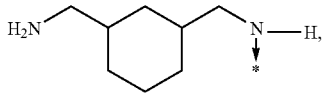
R2 represents
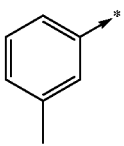

and R3 represents
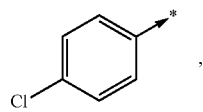
R10 represents
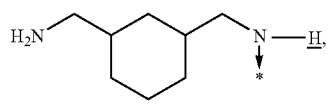
R2 represents
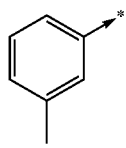
and R3 represents
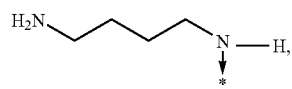
R10 represents
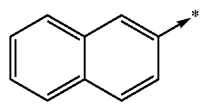
R2 represents
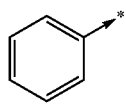
and R3 represents
R10 represents
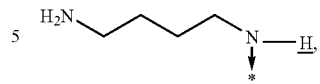
R2 represents
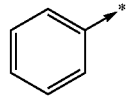
and R3 represents
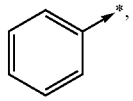
R10 represents
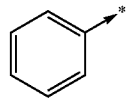
R2 represents
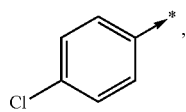
and R3 represents
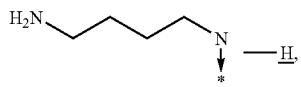
R10 represents R2 represents
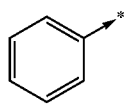
and R3 represents
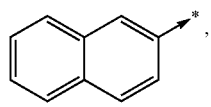
R10 represents
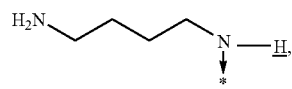
R2 represents
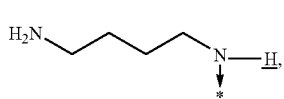
and R3 represents
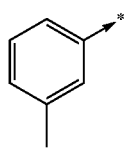
R10 represents
R2 represents
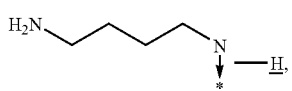
and R3 represents
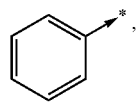,
R10 represents
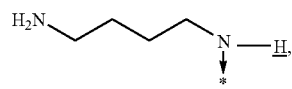
R2 represents
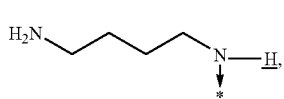
and R3 represents
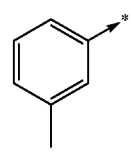,
or finally
R10 represents
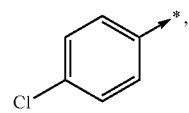
R2 represents
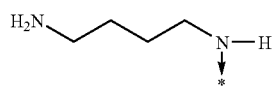
and R3 represents
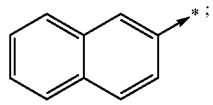;
in formula (vi)

[Structure: benzyl-O-CH2-CH(C(=O)R10)-N in thiazole ring with R2-N= at C2 and R3 at C4, S in ring]

in which:

R10 represents

[Structure: H2N-CH2-cyclohexane-CH2-N(H)-* ]

R2 represents

[phenyl-*]

and R3 represents

[tert-butyl-*],

R10 represents

[H2N-CH2-cyclohexane-CH2-N(H)-*]

R2 represents

[phenyl-*]

and R3 represents

[phenyl-*]

R10 represents

[H2N-CH2-cyclohexane-CH2-N(H)-*]

R2 represents

[phenyl-*]

and R3 represents

[4-chlorophenyl-*],

R10 represents

[H2N-CH2-cyclohexane-CH2-N(H)-*]

R2 represents

[phenyl-*]

and R3 represents

[2-naphthyl-*],

R10 represents
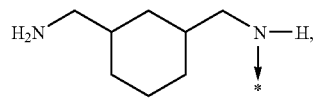
R2 represents
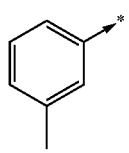
and R3 represents
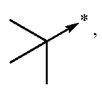,
R10 represents
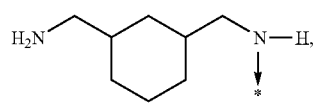
R2 represents
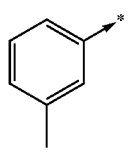
and R3 represents
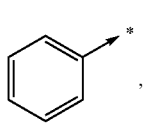,
R10 represents
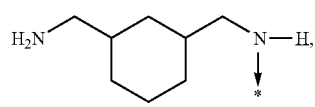
R2 represents
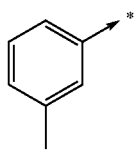
and R3 represents
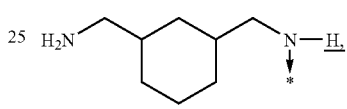,
R10 represents
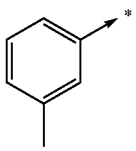
R2 represents
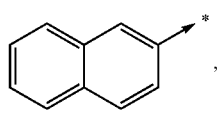
and R3 represents
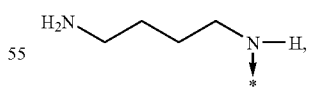,
R10 represents
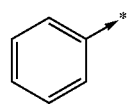
R2 represents and R3 represents
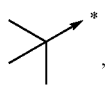,
R10 represents
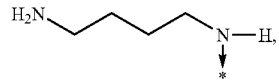
R2 represents
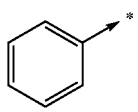
and R3 represents
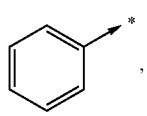,
R10 represents
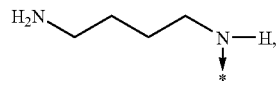
R2 represents
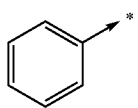
and R3 represents
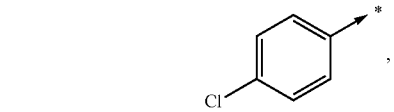,
R10 represents
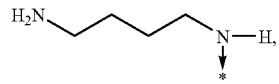
R2 represents
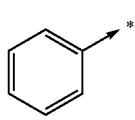
and R3 represents
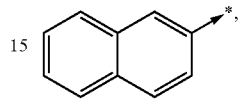,
R10 represents
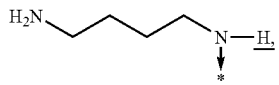
R2 represents
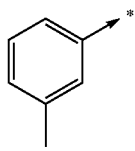
and R3 represents
,
R10 represents
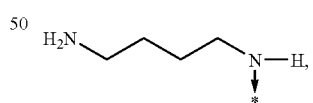
R2 represents
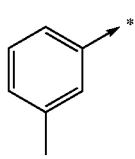

and R3 represents
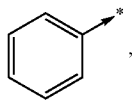,
R10 represents
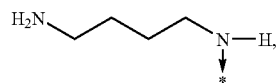
R2 represents
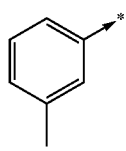
and R3 represents
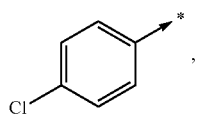,
or finally
R10 represents
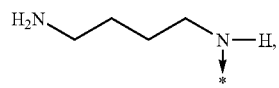
R2 represents
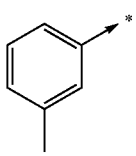
and R3 represents
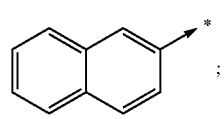;
to formula
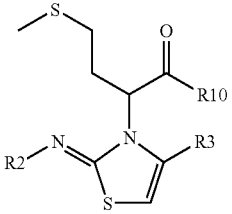 (vii)
in which:
R10 represents
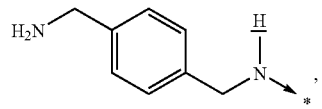,
R2 represents
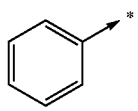
and R3 represents
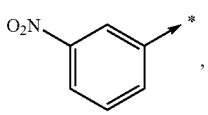,
R10 represents
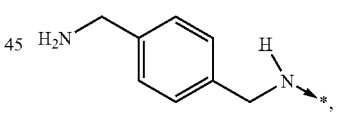,
R2 represents
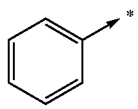
and R3 represents
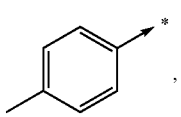, R10 represents
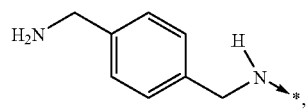
R2 represents
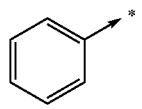
and R3 represents
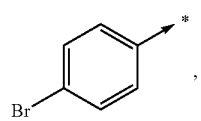
R10 represents
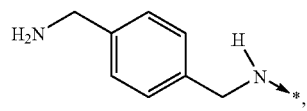
R2 represents
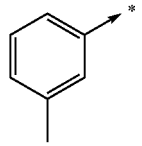
and R3 represents
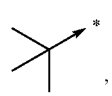
R10 represents
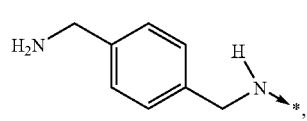
R2 represents
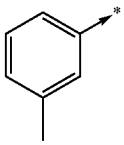
and R3 represents
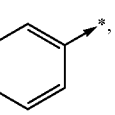
R10 represents
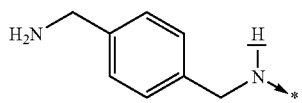
R2 represents
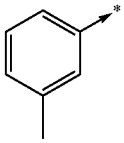
and R3 represents
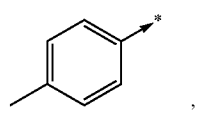
R10 represents
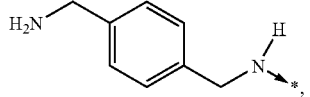
R2 represents
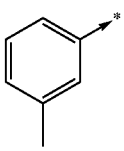

and R3 represents
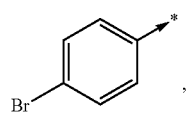
to formula
in which R10 represents
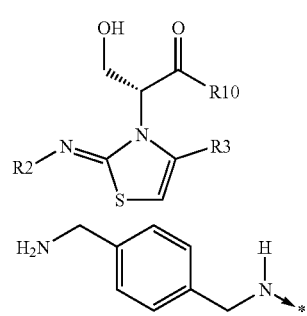
R2 represents
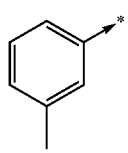
and R3 represents
to formula
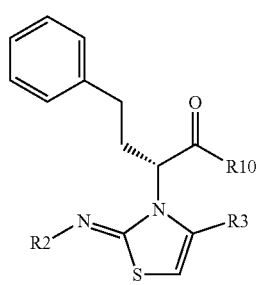
in which:
R10 represents
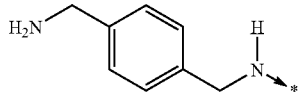
R2 represents
(viii)
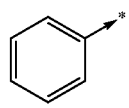
and R3 represents
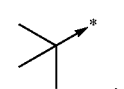
R10 represents
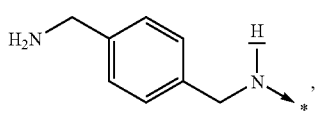
R2 represents
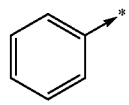
and R3 represents
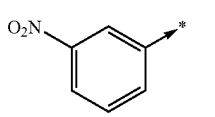
R10 represents
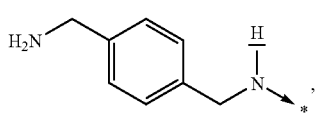

R2 represents
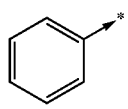
and R3 represents
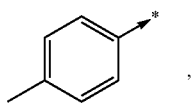,
R10 represents
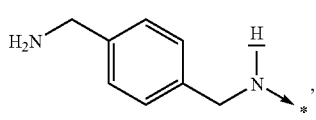,
R2 represents
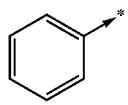
and R3 represents
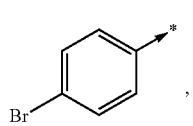,
R10 represents
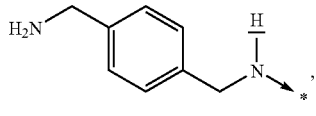,
R2 represents
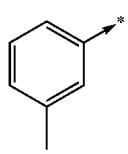
and R3 represents
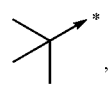,
R10 represents
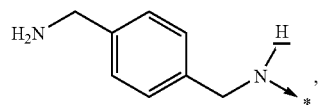,
R2 represents
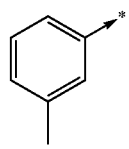
and R3 represents
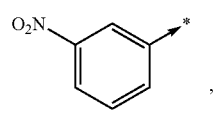,
R10 represents
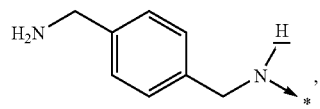,
R2 represents
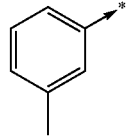
and R3 represents
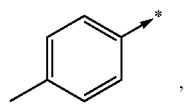,
or finally

101
R10 represents
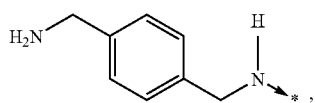
R2 represents
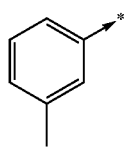
and R3 represents
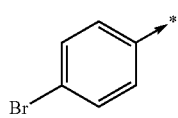
to formula
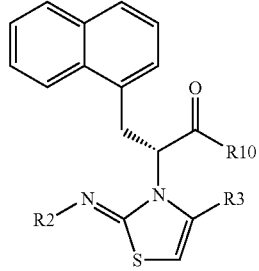
(X)
in which:
R10 represents
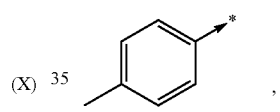
R2 represents
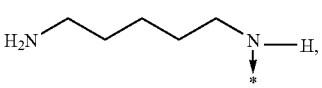
102
and R3 represents
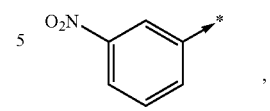
R10 represents
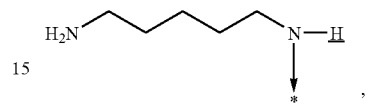
R2 represents
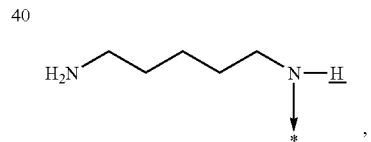
and R3 represents
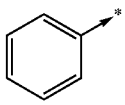
R10 represents
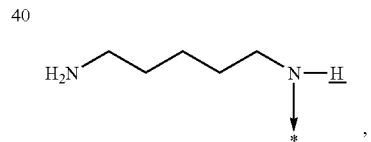
R2 represents
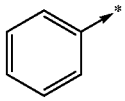
and R3 represents
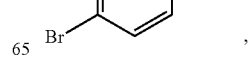

103
R10 represents
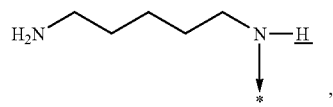
R2 represents
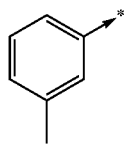
and R3 represents
R10 represents
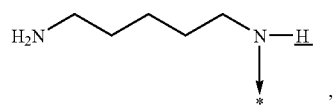
R2 represents
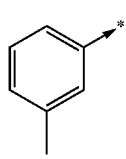
and R3 represents
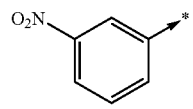
R10 represents
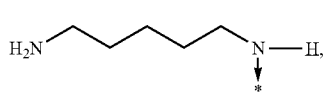
104
R2 represents
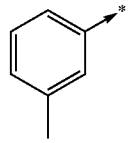
and R3 represents
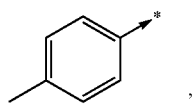
R10 represents
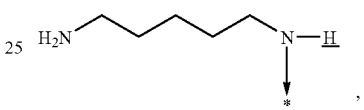
R2 represents
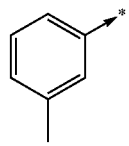
and R3 represents
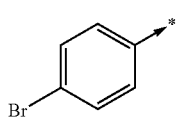
R10 represents
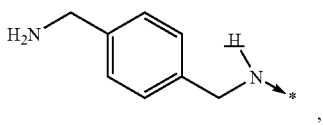
R2 represents
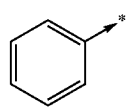

and R3 represents
R10 represents
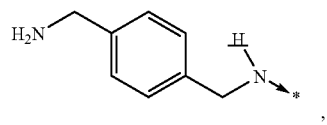,
R2 represents
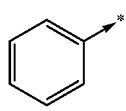
and R3 represents
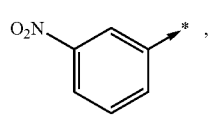,
R10 represents
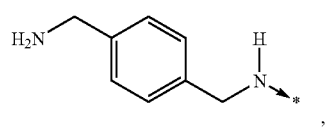,
R2 represents
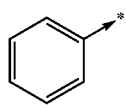
and R3 represents
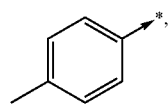,
R10 represents
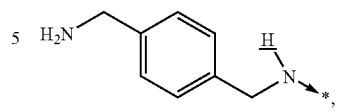
R2 represents
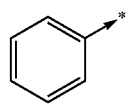
and R3 represents
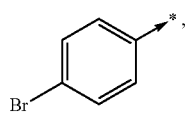,
R10 represents
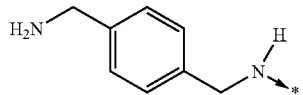
R2 represents
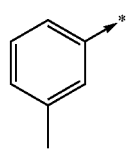
and R3 represents
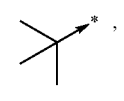,
R10 represents
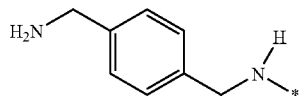

R2 represents
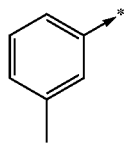
and R3 represents
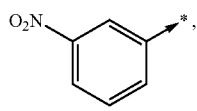
R10 represents
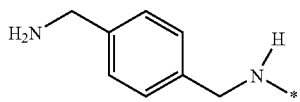
R2 represents
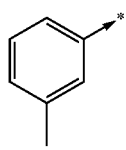
and R3 represents
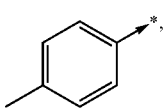
R10 represents
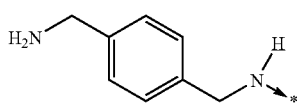
R2 represents
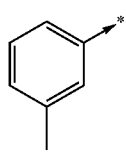
and R3 represents
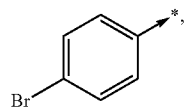
to formula
(xi)
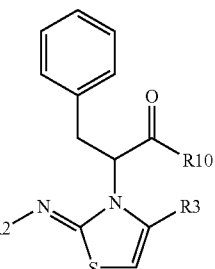
in which:
R10 represents
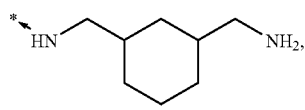
R2 represents
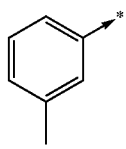
and R3 represents
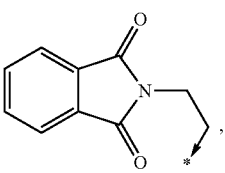
R10 represents
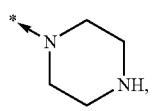

R2 represents
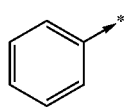
and R3 represents
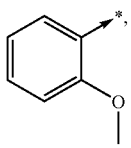,
R10 represents
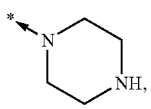
R2 represents
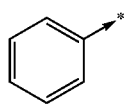
and R3 represents
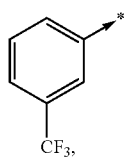
R10 represents
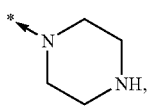
R2 represents
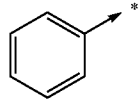
and R3 represents
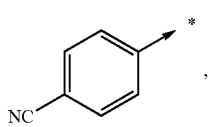,
R10 represents
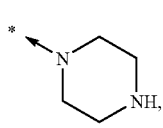
R2 represents
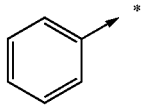
and R3 represents
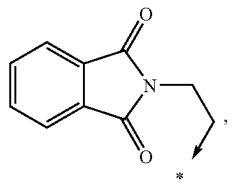,
R10 represents
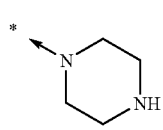
R2 represents
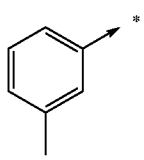

and R3 represents
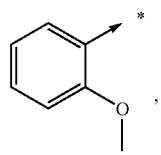,
R10 represents
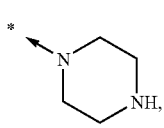
R2 represents
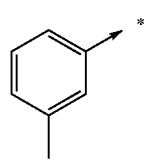
and R3 represents
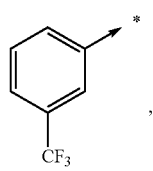,
R10 represents
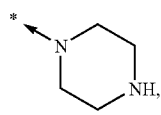
R2 represents
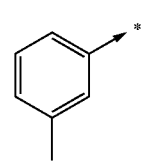
and R3 represents
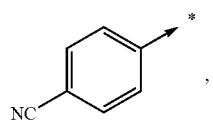,
or finally
R10 represents
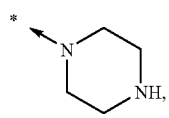
R2 represents
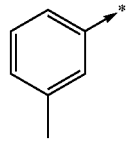
and R3 represents
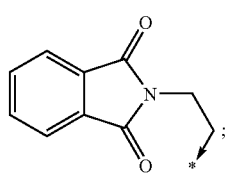;
in formula
(xii)
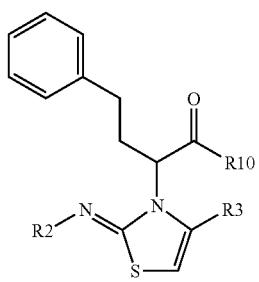
in which:
R10 represents
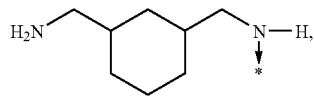

113
R2 represents
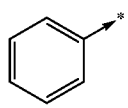
and R3 represents
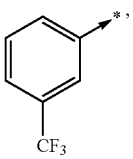
R10 represents
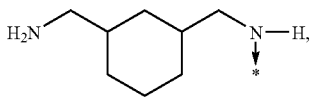
R2 represents
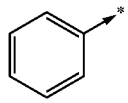
and R3 represents
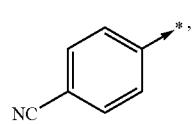
R10 represents
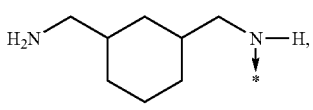
114
R2 represents
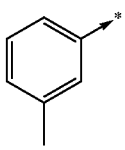
and R3 represents
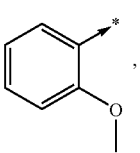
R10 represents
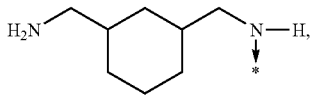
R2 represents
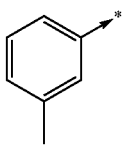
and R3 represents
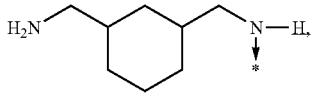
R10 represents
R2 represents and R3 represents
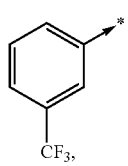
R10 represents
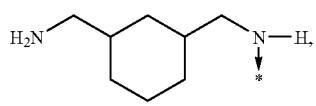
R2 represents
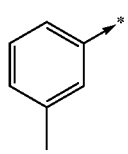
and R3 represents
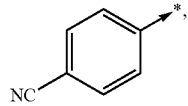
R10 represents
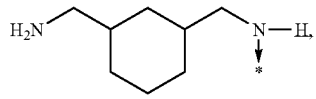
R2 represents
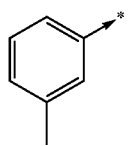
and R3 represents
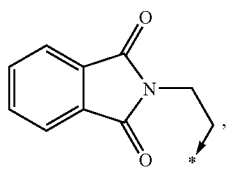
R10 represents
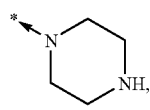
R2 represents
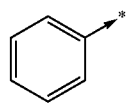
and R3 represents
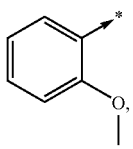
R10 represents
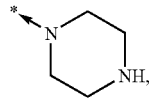
R2 represents
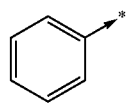
and R3 represents
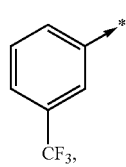

R10 represents
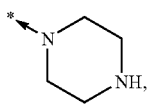
R2 represents
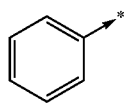
and R3 represents
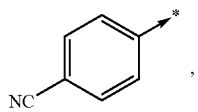,
R10 represents
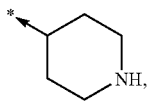
R2 represents
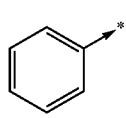
and R3 represents
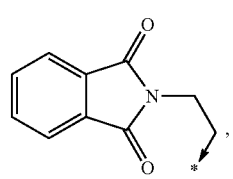,
R10 represents
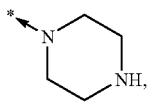
R2 represents
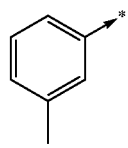
and R3 represents
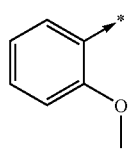
R10 represents
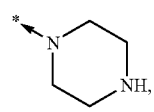
R2 represents
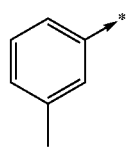
and R3 represents
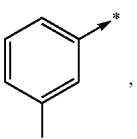,
R10 represents
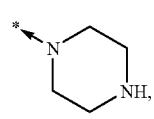

R2 represents
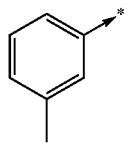
and R3 represents
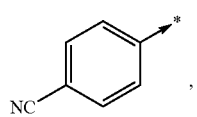,
or finally
R10 represents
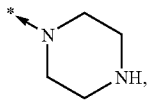
R2 represents
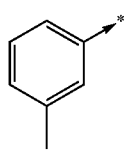
and R3 represents
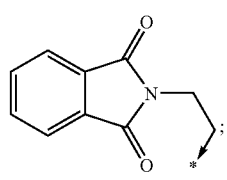;
to formula
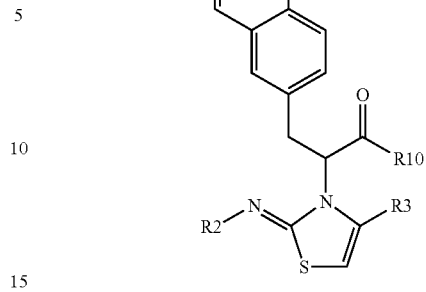 (xiii)
R10 represents
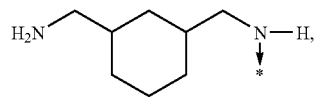
R2 represents
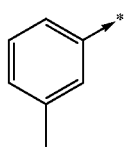
and R3 represents
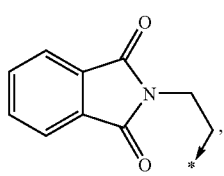,
R10 represents
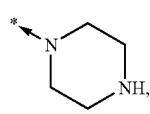
R2 represents
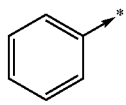

121
and R3 represents
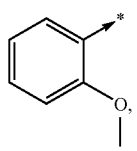
R10 represents
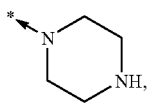
R2 represents
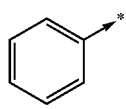
and R3 represents
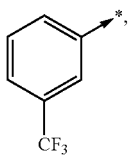
R10 represents
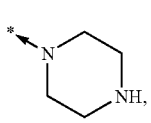
R2 represents
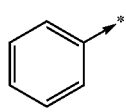
and R3 represents
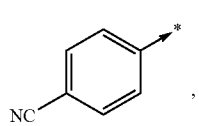
122
R10 represents
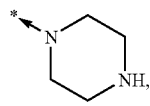
R2 represents
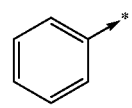
and R3 represents
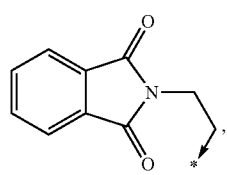
R10 represents
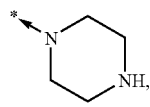
R2 represents
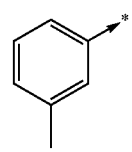
and R3 represents
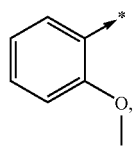
R10 represents
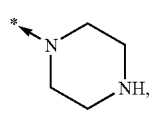

R2 represents
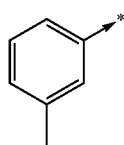
and R3 represents
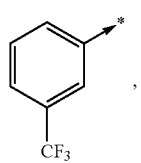,
R10 represents
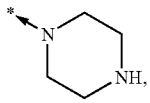
R2 represents
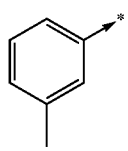
and R3 represents
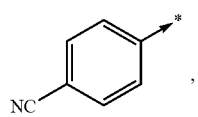,
or finally
R10 represents
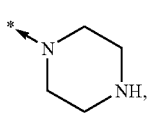
R2 represents
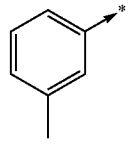
and R3 represents
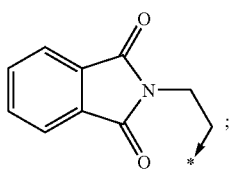;
to formula
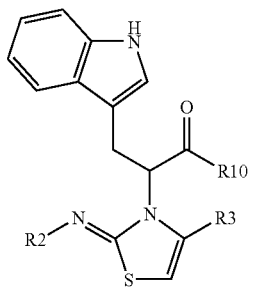 (xiv)
in which:
R10 represents
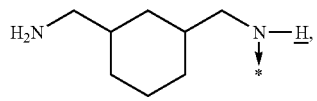
R2 represents
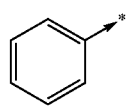
and R3 represents
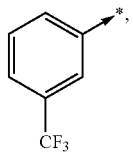,

125
R10 represents
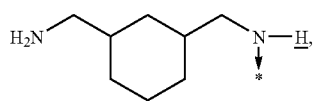
R2 represents
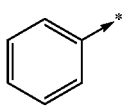
and R3 represents
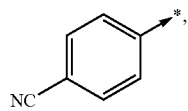
R10 represents
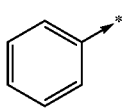
R2 represents
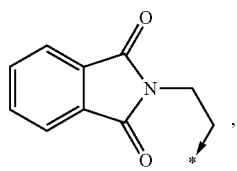
and R3 represents
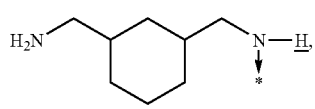
R10 represents
126
R2 represents
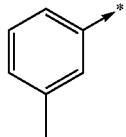
and R3 represents
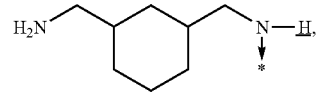
R10 represents
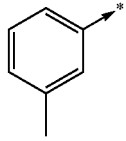
R2 represents
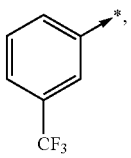
and R3 represents
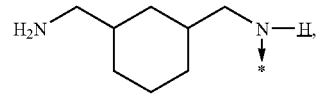
R10 represents
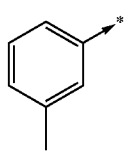
R2 represents and R3 represents
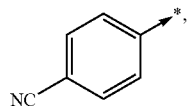
R10 represents
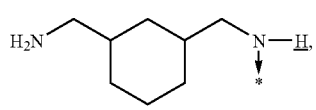
R2 represents
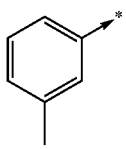
and R3 represents
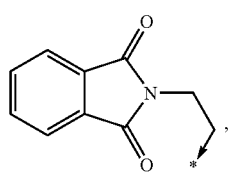
R10 represents
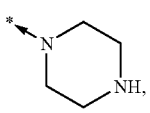
R2 represents
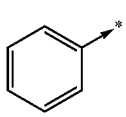
and R3 represents
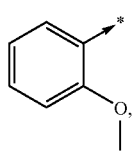
R10 represents
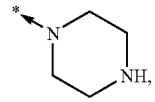
R2 represents
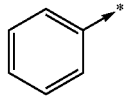
and R3 represents
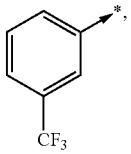
R10 represents
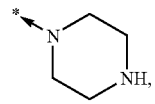
R2 represents
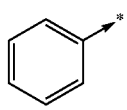
and R3 represents
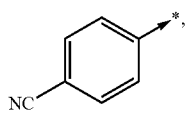
R10 represents
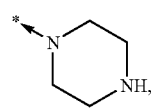

R2 represents
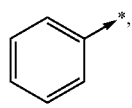
and R3 represents
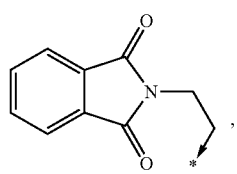
R10 represents
R2 represents
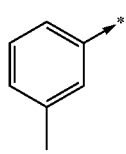
and R3 represents
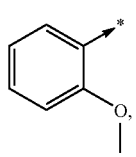
R10 represents
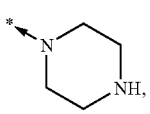
R2 represents
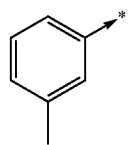
and R3 represents
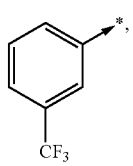
R10 represents
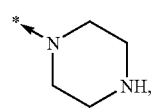
R2 represents
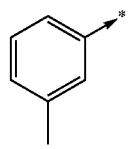
and R3 represents
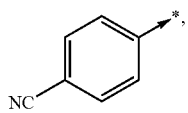
or finally
R10 represents
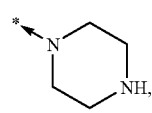

R2 represents
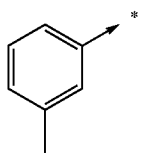
and R3 represents
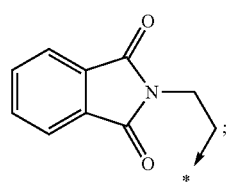
or finally to formula
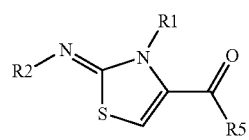
(XV)
in which:
R1 represents
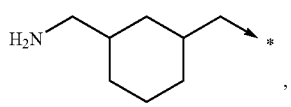
R2 represents
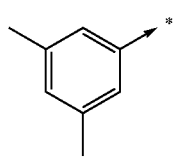
and R5 represents
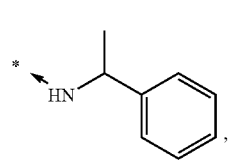
R1 represents
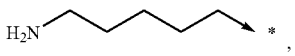
R2 represents
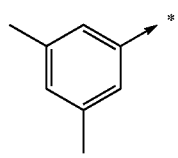
R5 represents
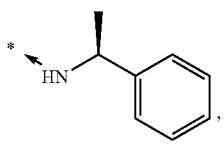
R1 represents
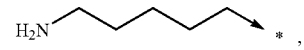
R2 represents
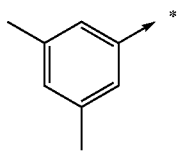
and R5 represents
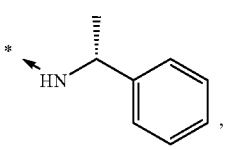
R1 represents
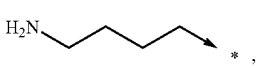

R2 represents
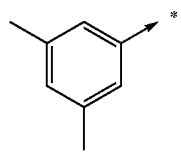
and R5 represents
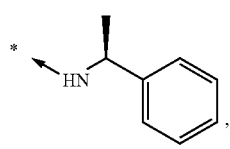
R1 represents
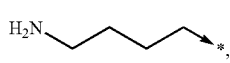
R2 represents
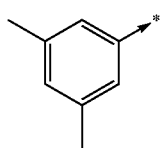
and R5 represents
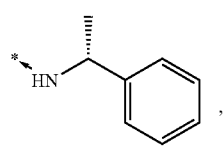
R1 represents
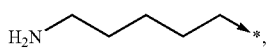
R2 represents
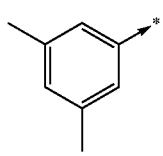
and R5 represents
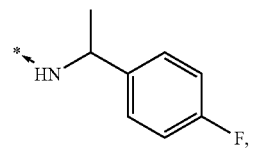
R1 represents
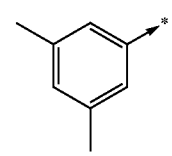
R2 represents
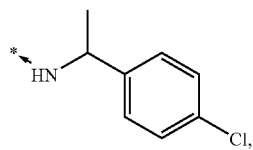
and R5 represents
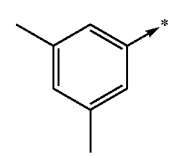
R1 represents
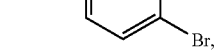
R2 represents
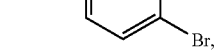
and R5 represents
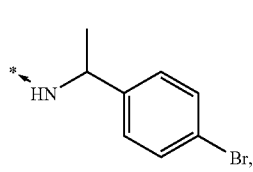

R1 represents
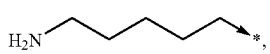
R2 represents
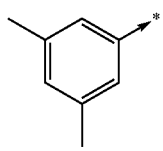
and R5 represents
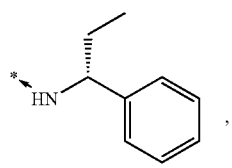
or finally
R1 represents
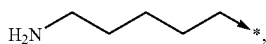
R2 represents
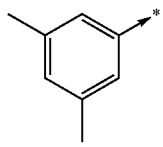
and R5 represents
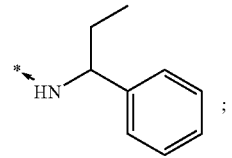
or a salt of one of these compounds.
Even more preferentially, the invention relates to a compound characterized in that it corresponds to the formula
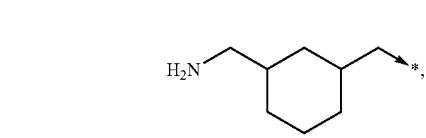
(XV)
in which:
R1 represents
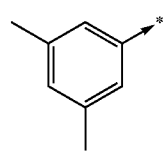
R2 represents
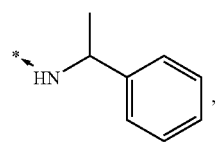
and R5 represents
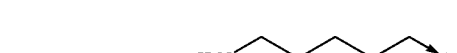
R1 represents
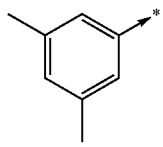
R2 represents
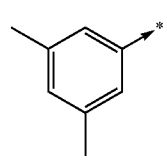
and R5 represents
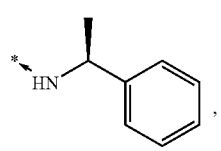

R1 represents
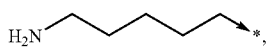
R2 represents
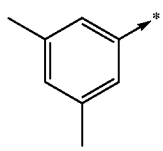
and R5 represents
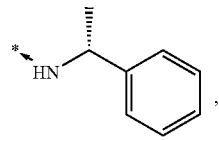
R1 represents
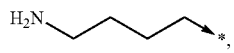
R2 represents
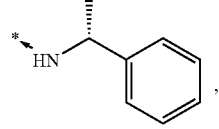
and R5 represents
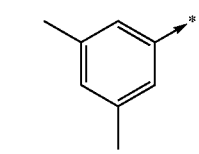
R1 represents
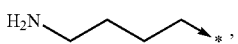
R2 represents
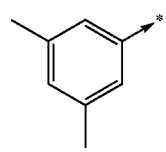
and R5 represents
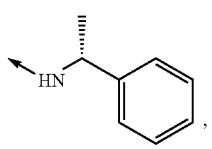
R1 represents
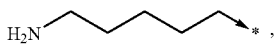
R2 represents
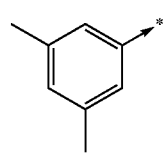
and R5 represents
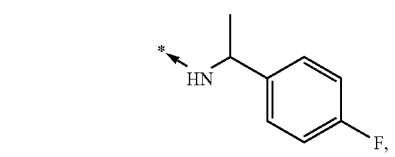
R1 represents
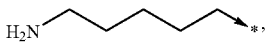
R2 represents
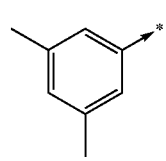

and R5 represents

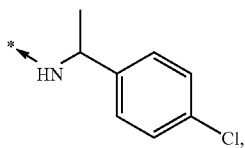

R1 represents

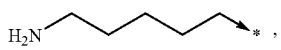

R2 represents

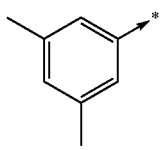

and R5 represents

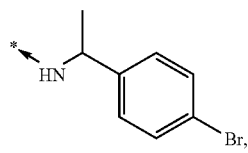

R1 represents

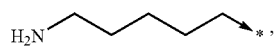

R2 represents

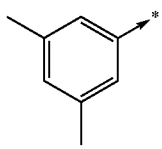

and R5 represents

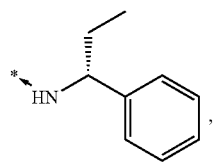

or finally

R1 represents

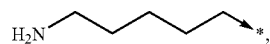

R2 represents

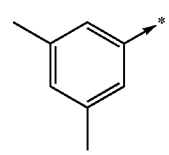

and R5 represents

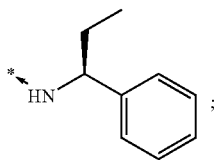

or a salt of one of these compounds.

In other words, the compounds described in Examples 1642 to 1654, 1656 to 1680, 2468 to 2502, 2525 to 2550, 2556 to 2582, 2605 to 2611, 2614, 2623 to 2630, 2632 to 2646, 2670 to 2678, 2680 to 2694, 2702 to 2710, 2712 to 2726 and 2827 to 2836 or a salt of one of these compounds will be preferred. The compounds of Examples 2827 to 2836 or their salts will be even more particularly preferred.

Moreover, the invention relates to preparation processes on a solid support for the compounds of general formula (I) described previously (also applicable to the corresponding compounds of general formula (II)).

According to the invention, the compounds of general formula (I)a

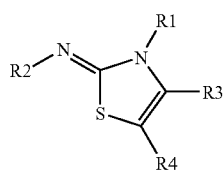

(I)A in which:

R1 represents a —CH$_2$-A1-NH$_2$ radical, in which A1 represents a —(CH$_2$)$_n$—, —(CH$_2$)$_n$—O—(CH$_2$)$_p$—, aralkylene or cycloalkylalkylene radical, n and p represent integers from 1 to 6;

R2 and R4 represent the same radicals as in general formula (I);

and R3 represents the same radicals as in general formula (I), with the exception of the —CO-R5 radicals;

can be prepared for example according to a process characterized in that it comprises the following successive stages:

1) treatment, in an aprotic solvent such as dichloromethane or dimethylformamide, of a p-nitrophenylcarbonate Wang resin with a large excess of R1-NH₂ symmetrical diamine;

2) treatment, in an aprotic solvent such as dichloromethane or dimethylformamide, of the resin isolated after stage 1) with an aromatic isothiocyanate of general formula R2-N=C=S in which the R2 radical has the same meaning as in general formula (I)a;

3) treatment, in an aprotic solvent such as dioxane or dimethylformamide, of the resin obtained in Stage 2) with the compound of general formula (III)

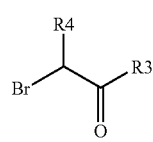

(III)

in which the R3 and R4 radicals have the same meaning as in general formula (I)a;

4) cleavage of the resin under acid conditions;

5) treatment under basic conditions of the product obtained after Stage 4).

The preparation of the p-nitrophenylcarbonate Wang resin is described further on in the part entitled "PREPARATION OF THE COMPOUNDS OF THE INVENTION".

Preferably, for the above process, in order to have the large excess in Stage 1), of the order of 10 to 20 equivalents of diamine R1-NH₂ will be used Stage 1) is preferably carried out at ambient temperature. Stage 3) is carried out at a temperature greater than ambient temperature, for example at a temperature comprised between 60 and 90° C., using of the order of 2 to 5 equivalents of the compound of general formula (III). In Stage 4), the acid conditions can for example be created by using a dichloromethane/trifluroacetic acid mixture at 50%, said acid conditions being preferably maintained for a duration of the order of 1 to 2 hours. In Stage 5), the basic conditions can for example be created by using a saturated solution of sodium hydrogen carbonate or by elution on a basic alumina cartridge.

According to a variant of the invention, the compounds of general formula (I)b

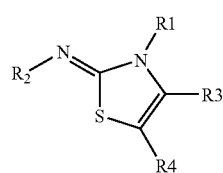

(I)b in which:

R1 represents the same radicals as in general formula (1), with the exception of the —CH₂-A1-NH₂ type radicals, in which A1 represents a —(CH₂)$_n$—, —(CH₂)$_n$—O —(CH₂)$_p$—, aralkylene or cycloalkylalkylene radical, n and p representing integers from 1 to 6, and also with the exception of the —C(R11)(R12)-CO-R10 radicals;

R2 represents an aminoalkylphenyl radical;

R3 represents the same radicals as in general formula (I), with the exception of the —CO-R5 radicals;

can be prepared for example according to a process characterized in that it comprises the following successive stages:

1) treatment, in an aprotic solvent such as dichloromethane or dimethylformamide, of a Wang resin p-nitrophenylcarbonate with an excess of aminoalkylaniline of general formula R2-NH₂ in which the R2 radical has the same meaning as in general formula (I)b;

2) treatment, in an aprotic solvent such as dichloromethane or dimethylformamide, of the resin isolated after Stage 1) with an isothiocyanate of general formula R1-N=C=S in which the R1 radical has the same meaning as in general formula (I)b;

3) treatment, in an aprotic solvent such as dioxane or dimethylformamide, of the resin obtained in Stage 2) with the compound of general formula (III)

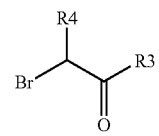

(III)

in which the R3 and R4 radicals have the same meaning as in general formula (I)b;

4) cleavage of the resin under acid conditions;

5) treatment under basic conditions of the product obtained after Stage 4).

Preferably, for the above process, in order to have the excess in Stage 1), of the order of 5 to 10 equivalents of aminoalkylaniline will be used. Stage 1) is preferably carried out at ambient temperature. Stage 3) is carried out at a temperature greater than ambient temperature, for example at a temperature comprised between 60 and 90° C., using of the order of 2 to 5 equivalents of the compound of general formula (III). In Stage 4), the acid conditions can for example be created by using a dichloromethane/trifluoroacetic acid mixture at 50%, said acid conditions being preferably maintained for a duration of the order of 1 to 2 hours. In Stage 5), the basic conditions can for example be created by using a saturated solution of sodium hydrogen carbonate or by elution on a basic alumina cartridge.

According to another variant of the invention, the compounds of general formula (I)c (I)c in which:

R1 represents a —CH$_2$-A1-NH$_2$ radical, in which A1 represents a —(CH$_2$)$_n$—, —(CH$_2$)$_n$—O—(CH$_2$)$_p$—, aralkylene or cycloalkylalkylene radical, n and p representing integers from 1 to 6;

R2 represents the same radicals as in general formula (I);

R3 represents a —CO-R5 radical;

and R4 and R5 represent the same radicals as in general formula (I);

can be prepared according to a process characterized in that it comprises the following successive stages:

1) treatment, in an aprotic solvent such as dichloromethane or dimethylformamide, of a Wang resin p-nitrophenylcarbonate with a large excess of symmetrical diamine of general formula R1-NH$_2$ in which the R1 radical has the same meaning as in general formula (I)c;

2) treatment, in an aprotic solvent such as dichloromethane or dimethylformamide, of the resin isolated after Stage 1) with an aromatic isothiocyanate of general formula R2-N=C=S in which the R2 radical has the same meaning as in general formula (I)c;

3) treatment, in an aprotic solvent such as dioxane or dimethylformamide, of the resin obtained in Stage 2) with the acid of general formula (IV)

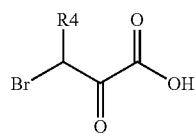

(IV)

in which the R4 radical has the same meaning as in general formula (I)c;

4) peptide coupling;

5) cleavage of the resin under acid conditions;

6) treatment under basic conditions of the product obtained after Stage 5).

Preferably, for the above process, in order to have the large excess in Stage 1) of the order of 10 to 20 equivalents of symmetrical diamine will be used. Stage 1) is preferably carried out at ambient temperature. Stage 3) is carried out at, a temperature greater than ambient temperature, for example at a temperature comprised between 60 and 90° C., using of the order of 2 to 5 equivalents of the acid of general formula (IV). The peptide coupling of Stage 4) is carried out for example in DMF with coupling agents such as for example dicyclohexylcarbodiimide (DCC), diisopropylcarbodiimide (DIC), a DIC/N-hydroxybenzotriazole (HOBt) mixture, benzotriazolyloxytris(dimethylamino)phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU) and aminated compounds. Preferably, the coupling agents are used in proportions of 4 to 5 equivalents, as with the aminated compounds, and the reaction will take place at a temperature of the order of ambient temperature for a duration of the order of 1 to 24 hours. In Stage 5), the acid conditions can for example be created by using a dichloromethane/trifluoroacetic acid mixture at 50%, said acid conditions being preferably maintained for a duration of the order of 1 to 2 hours. In Stage 6), the basic conditions can for example be created by using a saturated solution of sodium hydrogen carbonate or by elution on a basic alumina cartridge.

According to yet another variant, the compounds of general formula (I)d

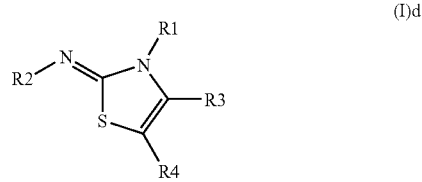

(I)d in which:

R1 represents the same radicals as in general formula (I), with the exception of the —CH$_2$-A1-NH$_2$ type radicals, in which A1 represents a —(CH$_2$)$_n$—, —(CH$_2$)$_n$—O—(CH$_2$)$_p$—, aralkylene or cycloalkylalkylene radical, n and p represent integers from 1 to 6, and also with the exception of the —C(R11)(R12)-CO-R10 radicals;

R2 represents an aminoalkylphenyl radical;

R3 represents a —CO-R5 radical;

and R4 and R5 represent the same radicals as in general formula (I);

can be prepared according to a process characterized in that it comprises the following successive stages:

1) treatment, in an aprotic solvent such as dichloromethane or dimethylformamide, of a Wang resin p-nitrophenylcarbonate with an excess of aminoalkylaniline of general formula R2-NH$_2$ in which the R2 radical has the same meaning as in general formula (I)d;

2) treatment, in an aprotic solvent such as dichloromethane or dimethylformamide, of the resin isolated after Stage 1) with an isothiocyanate of general formula R1-N=C=S in which the R1 radical has the same meaning as in general formula (I)d;

3) treatment, in an aprotic solvent such as dioxane or dimethylformamide, of the resin obtained in Stage 2) with the acid of general formula (IV)

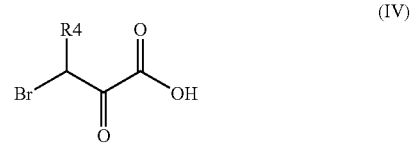

(IV)

in which the R4 radical has the same meaning as in general formula (I)d;

4) peptide coupling;

5) cleavage of the resin under acid conditions;

6) treatment under basic conditions of the product obtained after Stage 5).

Preferably, for the above process, in order to have the excess in Stage 1), of the order of 5 to 10 equivalents of aminoalkylaniline will be used. Stage 1) is preferably carried out at ambient temperature. Stage 3) is carried out at a temperature greater than ambient temperature, for example at a temperature comprised between 60 and 90° C., using of the order of 2 to 5 equivalents of the acid of general formula (IV). The peptide coupling of Stage 4) is carried out for example in DMF with coupling agents such as for example dicyclohexylcarbodiimide (DCC), diisopropylcarbodiimide (DIC), a DIC/N-hydroxybenzotriazole (HOBt) mixture, benzotriazolyloxytris(dim ethylamino) phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU) and aminated compounds. Preferably, the coupling agents are used in proportions of 4 to 5 equivalents, as with the aminated compounds, and the reaction will take place at a temperature of the order of ambient temperature for a duration of the order of 1 to 24 hours. In Stage 5), the acid conditions can for example be created by using a dichloromethane/trifluoroacetic acid mixture at 50%, said acid conditions being preferably maintained for a duration of the order of 1 to 2 hours. In Stage 6), the basic conditions can for example be created by using a saturated solution of sodium hydrogen carbonate or by elution on a basic alumina cartridge.

According to another variant the compounds of general formula (I)e

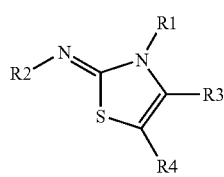
(I)e in which:

R1 represents the same radicals as in general formula (I), with the exception of the —CH$_2$-A1-NH$_2$ type radicals, in which A1 represents a —(CH$_2$)$_n$—, —(CH$_2$)$_n$—O—(CH$_2$)$_p$—, aralkylene or cycloalkylalkylene radical, n and p representing integers from 1 to 6, and also with the exception of the —C(R11)(R12)CO-R10 radicals;

R2 represents the same radicals as in general formula (I);

R3 represents a —CO-R5 radical;

R4 represents H;

R5 represents an —NH—CH$_2$-A1-NH$_2$ radical, in which A1 represents a linear or branched alkylene radical containing 1 to 6 carbon atoms, —(CH$_2$)$_n$—O—(CH$_2$)$_p$—, aralkylene or cycloalkylalkylene, n and p representing integers from 1 to 6, or also R5 represents the N(R6)(R7) radical corresponding to the following general formula:

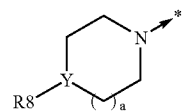

in which:

R8 represents H;

Y represents N;

a represents 1 or 2;

can be prepared by a process characterized in that it comprises the following successive stages:

1) treatment, in an aprotic solvent such as dichloromethane or dimethylformamide, of a Wang resin p-nitrophenylcarbonate with a large excess of symmetrical diamine of general formula R5-H;

2) peptide coupling with the acid of general formula (IV) on the resin obtained in Stage 1)

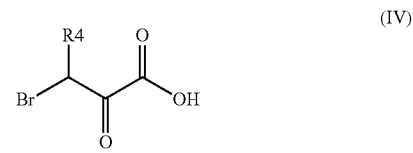
(IV)

in which the R4 radical has the same meaning as in general formula (I)e;

3) reaction of the primary amine of general formula R1-NH$_2$ with the isothiocyanate of general formula R2-NCS in a solvent such as dimethylformamide or dioxane, R1 and R2 having the same meanings as in general formula (I)e;

4) addition of the thiourea obtained in Stage 3) to the resin obtained in Stage 2) and heating the mixture;

5) cleavage of the resin under acid conditions;

6) treatment under basic conditions of the product obtained after Stage 5).

Preferably, for the above process, in order to have the large excess in Stage 1), of the order of 10 to 20 equivalents of diamine R5-H will be used. Stage 1) is preferably carried out at ambient temperature. The peptide coupling of Stage 2) is carried out in DMF with a coupling agent such as for example the DIC/N-hydroxybenzotriazole (HOBt) mixture. Preferably, the reaction of Stage 3) is carried out in a solvent such as dimethylformamide or dioxane. During the addition of Stage 4), 2 to 5 equivalents of thiourea will preferably be used per equivalent of resin; preferably also, heating will be carried out at a temperature greater than ambient temperature, for example at a temperature from 40 to 100° C. (in particular at a temperature of approximately 80° C.) and for a duration of 2 to 24 hours. In Stage 5), the acid conditions can for example be created by using a dichloromethane/trifluoroacetic acid mixture at 50%, said acid conditions being preferably maintained for a duration of the order of 1 to 2 hours. In Stage 6), the basic conditions can for example be created by using a saturated solution of sodium hydrogen carbonate or by elution on a basic alumina cartridge.

According to yet another variant, the compounds of general formula (I)f

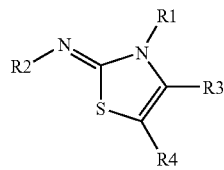 (I)f in which:

R1 represents a —C(R11)(R12)-CO-R10 radical;

R2, R3 and R4 represent the same radicals as in general formula (I);

R10 represents an amino($C_2$–$C_7$)alkylamino, ((aminoalkyl)aryl)alkylamino, ((aminoalkyl)cycloalkyl)alkylamino, piperazinyl, homopiperazinyl radical, or R10 represents the radical represented below:

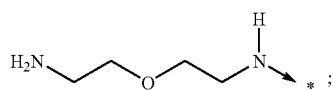

R11 represents H;

R12 represents H or an alkyl, ($C_3$–$C_7$)cycloalkyl, optionally substituted carbocyclic or heterocyclic aralkyl, propargyl, allyl, hydroxyalkyl, alkylthioalkyl, arylalkyl alkoxyalkyl, arylalkylthioalkoxyalkyl radical;

can be prepared by a process characterized in that it comprises the following successive stages:

1) treatment, in an aprotic solvent such as dichloromethane or dimethylformamide, of a Wang resin p-nitrophenylcarbonate with a large excess of symmetrical diamine of general formula R10-H in which R10 has the same meaning as in general formula (I)f;

2) peptide coupling of the resin obtained in Stage 1) with an amino acid of general formula HOOC—C(R11)(R12)-NH-Fmoc in which R11 and R12 have the same meaning as in general formula (I)f;

3) cleavage of the Fmoc group from the resin obtained in Stage 2);

4) reaction of the resin obtained in Stage 3) with an isothiocyanate of general formula R2-NCS in which R2 has the same meaning as in general formula (I)f;

5) cleavage of the resin under acid conditions;

6) treatment under basic conditions of the product obtained after Stage 5).

Preferably, for the above process, in order to have the large excess in Stage 1), of the order of 10 to 20 equivalents of diamine R10-H will be used. Stage 1) is preferably carried out at ambient temperature. The peptide coupling of Stage 2) is carried out for example in DMF with coupling agents such as for example dicyclohexylcarbodiimide (DCC), diisopropylcarbodiimide (DIC), a DIC/N-hydroxybenzotriazole (HOBt) mixture, benzotriazolyloxytris(dimethylamino)phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU). Preferably, the reaction of Stage 2) is carried out at ambient temperature and for a duration of 1 to 24 hours. The deprotection of Stage 3) can be carried out, for example, by a mixture of DMF containing 20% piperidine. Stage 4) will preferably be carried out in a solvent such as dimethylformamide or dichloromethane, the isothiocyanate preferably being added in a proportion of 5 to 10 equivalents per equivalent of the resin obtained in Stage 3). In Stage 5), the acid conditions can for example be created by using a dichloromethane/trifluoroacetic acid mixture at 50% said acid conditions being preferably maintained for a duration of the order of 1 to 2 hours. In Stage 6), the basic conditions can for example be created by using a saturated solution of sodium hydrogen carbonate or by elution on a basic alumina cartridge.

A subject of the invention is also, as medicaments, the compounds of general formulae (I) and (II) described previously or their pharmaceutically acceptable salts. It also relates to pharmaceutical compositions containing said compounds or their pharmaceutically acceptable salts, and their use for the preparation of a medicament intended to treat pathological states or diseases in which one (or more) of the somatostatin receptors are involved.

In particular, the compounds of general formulae (I) and (II) described previously or their pharmaceutically acceptable salts can be used for the preparation of a medicament intended to treat pathological states or diseases chosen from the group comprising the following pathological states or diseases: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, syndrome X, dawn phenomenon, angiopathy, angioplasty, hyperthyroidism, gigantism, endocrinic gastroenteropancreatic tumours including carcinoid syndrome, VIPoma, insulinoma, nesidioblastoma, hyperinsulinemia, glucagonoma, gastrinoma and Zollinsger-Ellison's syndrome, GRFoma as well as acute bleeding of the esophageal veins, ulcers, gastroesophageal reflux, gastroduodenal reflux, pancreatitis, enterocutaneous and pancreatic fistulae but also diarrhoea, refractory diarrhoea's of acquired immunodeficiency syndrome, chronic secretary diarrhoea, diarrhoea associated with irritable bowel syndrome, diarrhoea's induced by chemotherapy, disorders linked with gastrin releasing peptide, secondary pathologies with intestinal grafts, portal hypertension as well as haemorrhages of the veins in patients, with cirrhosis, gastro-intestinal haemorrhage, haemorrhage of the gastroduodenal ulcer, bleeding of grafted vessels, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and in other therapeutic fields such as, for example, cephaleas including cephalea associated with hypophyseal tumours, pain, inflammatory disorders such as arthritis, panic attacks, chemotherapy, cicatrization of wounds, renal insufficiency resulting from delayed development, hyperlipidemia, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of H pylori, psoriasis, chronic rejection of allografts as well as Alzheimer's disease and finally osteoporisis.

Preferably, the compounds of general formulae (I) and (II) described previously or their pharmaceutically acceptable salts can be used for the preparation of a medicament intended to treat the pathological states or diseases chosen from the group comprising the following pathological states, or diseases: acromegalia, hypophyseal adenomas or endocrinic gastroenteropancreatic tumors including carcinoid syndrome, and gastrointestinal bleeding.

By pharmaceutically acceptable salt is meant in particular addition salts of inorganic acids such as hydrochloride, sulphate, phosphate, diphosphate, hydrobromide and nitrate, or of organic acids, such as acetate, maleate, fumarate, tartrate, succinate, citrate, lactate, methanesulphonate, p-toluenesulphonate, pamoate, oxalate and stearate. The salts formed from bases such as sodium or potassium hydroxide also fall within the scope of the present invention, when they can be used. For other examples of pharmaceutically acceptable salts, reference can be made to "Pharmaceutical salts", J. Pharm. Sci. 66:1 (1977).

The pharmaceutical composition can be in the form of a solid, for example powders, granules, tablets, capsules, liposomes or suppositories. Appropriate solid supports can be for example calcium phosphate, magnesium stearate, talc, sugars, lactose, dextrin, starch, gelatin, cellulose, methyl cellulose, sodium carboxymethyl cellulose, polyvinylpyrrolidine and wax. The suspensions contain in particular suspensions of sustained release microparticles loaded with active ingredient (in particular microparticles of polylactide-co-glycolide or PLGA—cf. for example the patents U.S. Pat. No. 3,773,919, EP 52 510 or EP 58 481 or the Patent Application PCT WO 98/47489), which allow the administration of a determined daily dose over a period of several days to several weeks.

The pharmaceutical compositions containing a compound of the invention can also be presented in the form of a liquid, for example, solutions, emulsions, suspensions or syrups. Appropriate liquid supports can be, for example, water, organic solvents such as glycerol or glycols, as well as their mixtures, in varying proportions, in water.

The administration of a medicament according to the invention can be carried out by topical, oral, parenteral route, by intramuscular injection, etc.

The administration dose envisaged for a medicament according to the invention is comprised between 0.1 mg and 10 g according to the type of active compound used.

These compounds can be prepared according to the methods described below.

Preparation of the Compounds of the Invention

I) Preparation of α-bromoketones

First Method

This method is inspired by the protocols described in the following publications: Macholan, L.; Skursky, L. *Chem. Listy* 1955, 49, 1385–1388; Bestman, H. J.; Seng, F. *Chem. Ber.* 1963, 96, 465–469; Jones, R. G.; Kornfeld, E. C.; McLaughlin, K. C. *J. Am. Chem. Soc.* 1950, 72, 4526–4529; Nimgirawath, S.; Ritchie, E.; Taylor, W. C. *Aust. J. Chem.* 1973, 26, 183–193).

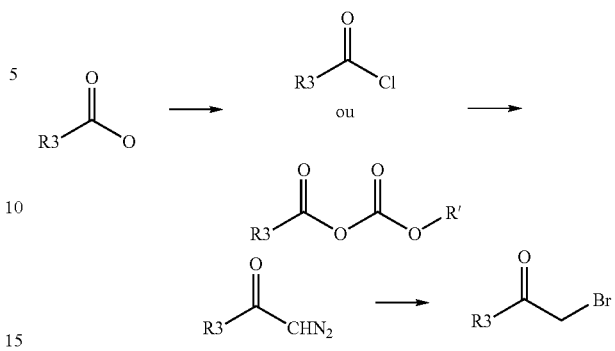

A carboxylic acid is firstly converted to an acid by using oxalyl or thionyl chloride, or by activating it in the form of an anhydride using an alkyl chloroformate (for example isobutyl chloroformate, cf. Krantz, A.; Copp, L. J. *Biochemistry* 1991, 30, 4678–4687; or ethyl chloroformate, cf. Podlech, J.; Seebach, D. *Liebigs Ann.* 1995, 1217–1228) in the presence of a base (triethylamine or N-methylmorpholine).

The activated carboxyl group is then converted to diazoketone using diazomethane in an ethereal solution or a commercial solution of trimethylsilyldiazomethane (Aoyama, T.; Shiori, T. *Chem. Pharm. Bull.* 1981, 29, 3249–3255) in an aprotic solvent such as diethyl ether, tetrahydrofuran (THF) or acetonitrile.

The bromination is then carried out using a bromination agent such as hydrobromic acid in acetic acid, aqueous hydrobromic acid in diethyl ether or dichloromethane.

Preparation 1

2-(4-bromo-3-oxobutyl)-1H-isoindole-1,3 (2H)-dione ($C_{12}H_{10}BrNO_3$, MM=296.12)

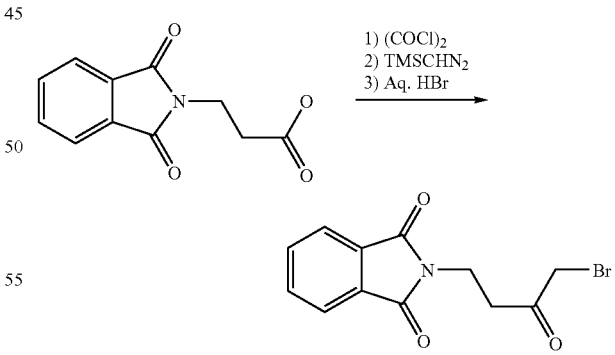

Oxalyl chloride (5.8 ml; 66.7 mmol) is added to Pht-β-Ala-OH (9.96 g; 44.5 mmol) dissolved in dichloromethane (120 ml) and 3 drops of dimethylformamide (DMF). The mixture is agitated for 3 hours at ambient temperature. After elimination of the solvent, the white solid is taken up in a 1:1 mixture of anhydrous tetrahydrofuran and acetonitrile (200 ml) then 49 ml of a 2M solution of (trimethylsilyl) diazomethane in hexane (97.9 mmol) is added dropwise at 0° C.

The solvents are eliminated after agitation overnight at 0° C. The pale yellow solid is then dissolved in dichloromethane (60 ml) and 12 ml of aqueous hydrobromic acid (48%) is added dropwise at 0° C. The mixture is agitated until the temperature reaches 15° C. and 50 ml of a saturated solution of sodium bicarbonate is added. The organic phase is washed with salt water then dried over sodium sulphate. Crystallization from diethyl ether allows a white solid to be obtained (11.39 g; yield=86%).

NMR $^1$H (DMSO D6, 100 MHz, δ): 7.83 (s, 4H); 4.36 (s, 2H, CH$_2$Br); 3.8 (t, 2H, J=7.1 Hz, NCH$_2$); 2.98 (t, 2H, J=6.9 Hz, CH$_2$CO).

Preparations 2–11

The following compounds were prepared in a similar fashion to the procedure described in Preparation 1:

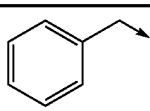

| Prep. | R3 | Yield (%) |
|---|---|---|
| 2* |  | 78 |
| 3* |  | 60 |
| 4* | 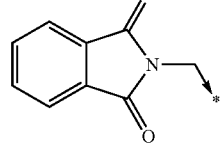 | 10 |
| 5* | 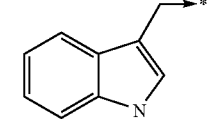 | 69 |
| 6* | 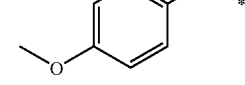 | 41 |
| 7 | 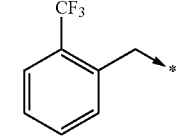 | 67 |
| 8 | 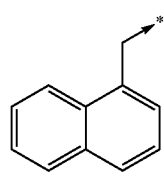 | 51 |// CF3 substituted benzyl
| 9 | 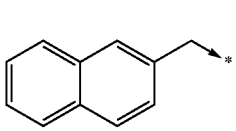 | 38 |
| 10 | 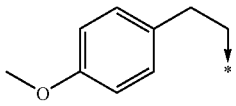 | 22 |
| 11 | 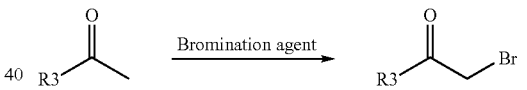 | 67 |

*Compounds already described in the literature.

Second Method

The starting product is an arylmethylketone or a heteroarylmethylketone.

R3—C(=O)—CH$_3$ →(Bromination agent)→ R3—C(=O)—CH$_2$Br

The starting arylmethylketone or heteroarylmethylketone is converted to the corresponding α-bromoketone by using different brominating agents:

CuBr$_2$ (King, L. C.; Ostrum, G. K. *J. Org. Chem.* 1964, 29, 3459–3461) heated in ethyl acetate or dioxane;

N-bromosuccinimide in CCl$_4$ or aqueous acetonitrile (Morton, H. E.; Leanna, M. R. *Tetrahedron Lett.* 1993, 34, 4481–4484);

bromine in glacial acetic acid or sulphuric acid;

phenyltrimethylammonium tribromide (Sanchez, J. P.; Parcell, R. P. *J. Heterocyclic Chem,* 1988, 25, 469–474) at 20–80° C. in an aprotic solvent such as THF or tetrabutylammonium tribromide (Kajigaeshi, S.; Kakinami, T.; Okamoto, T.; Fujisaki, *S. Bull Chem. Soc. Jpn.* 1987, 60, 1159–1160) in a dichloromethane/methanol mixture at ambient temperature;

brominating agent on a polymer support such as perbromide on an Amberlyst A-26 resin, poly(perbromide of vinylpyridinium hydrobromide) (Frechet, J. M. J.; Farrall, M. J. *J. Macromol. Sci. Chem.* 1977, 507–514) in a protic solvent such as methanol at approximately 20–35° C. for approximately 2–10 hours.

Preparation 12

1-(1-benzofuran-2-yl)-2-bromo-1-ethanone (C$_{10}$H$_7$BrO$_2$, MM=239.06)

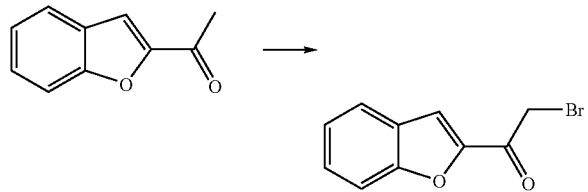

A polymer of perbromide of pyridine hydrobromide (8.75 g; 17.5 mmol; 1.4 equivalent) is added to a solution of (benzofuran-2-yl)methylketone (2 g; 12.5 mmol) in methanol (40 ml). The resulting mixture is agitated at ambient temperature for 7 hours and the reaction is stopped by filtration. The methanol is eliminated under reduced pressure and an additional addition of diethyl ether allows crystallization of the expected product (3.6 g; yield=60%).

NMR $^1$H (DMSO D6, 100 MHz, δ): 8.09 (s, 1H); 7.98 (d, 1H, J=6.6 Hz); 7.75 (d, 1H, J=8.4 Hz); 7.58 (t, 1H, J=8.4 Hz); 7.4 (t, 1H, J=7 Hz); 4.83 (s, 2H, CH$_2$Br).

Preparations 8–12

The following compounds were prepared in a similar fashion to the procedure described in Preparation 12:

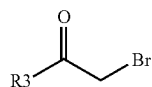

| Prep. | R3 | Duration of reaction (hrs) | Yield (%) |
|---|---|---|---|
| 13* | (3-benzothiophenyl) | 8 | 78 |
| 14* | (4-butylphenyl) | 2 | 62 |
| 15* | (5-bromo-2-thienyl) | 10 | 56 |
| 16* | (3,4,5-trimethoxyphenyl) | 2 | 53 |
| 17* | (4-benzyloxyphenyl) | 3 | 95 |
| 18 | (3,4-difluorophenyl) | 8 | 27 |

*Compound already described in the literature.

II) Synthesis of 2-arylimino-2,3-dihydrothiazoles via synthesis on solid phase

Preparation of Wang Resin p-nitrophenylcarbonate

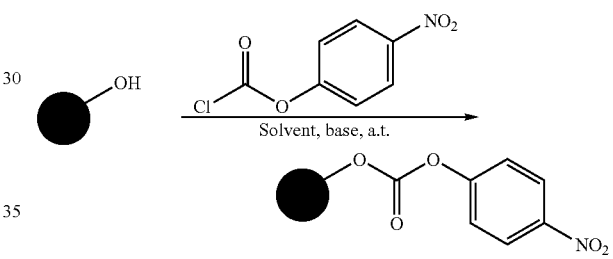

This resin was prepared from Wang resin, acquired from Bachem or Novabiochem with a load greater than 0.89 mmol/g, by a well described general procedure (cf. Bunin, B. A. *The Combinatorial Index*, Academic Press, 1998, p. 62–63; Dressman, B. A.; Spangle, L. A.; Kaldor, S. W. *Tetrahedron Lett.* 1996, 37, 937–940; Hauske, J. R.; Dorff, P. *Tetrahedron Lett.* 1995, 36, 1589–1592; Cao, J.; Cuny, G. D.; Hauske, J. R. *Molecular Diversity* 1998, 3, 173–179): N-methylmorpholine or pyridine as base and 4-nitrophenylchloroformate are successively added to a Wang resin pre-swollen in dichloromethane (DCM) or tetrahydrofuran (THE) at ambient temperature. The mixture is agitated overnight. The resin is then washed successively with THF, diethyl ether and DCM then dried overnight under reduced pressure at 50° C.

Method A

Preparation of Monoprotected Symmetrical Diamines

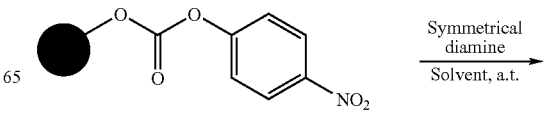

-continued

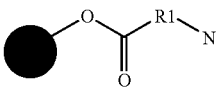

General procedure: as already described in the literature (Dixit, D. M.; Leznoff, C. C. *J. C. S. Chem. Comm.* 1977, 798–799; Dixit, D. M.; Leznoff, C. C. *Israel J. Chem.* 1978, 17, 248–252; Kaljuste K.; Unden, A. *Tetrahedron Lett.* 1995, 36, 9211–9214; Munson, M. C.; Cook, A. W.; Josey, J. A.; Rao, C. *Tetrahedron Lett.* 1998, 39, 7223–7226), a Wang resin p-nitrophenylcarbonate is treated with a large excess of symmetrical diamine (10–20 equivalents), in an aprotic solvent such as DCM or DMF, in order to produce a monoprotected diamine resin after agitation overnight.

Preparation of Thiourea Resins

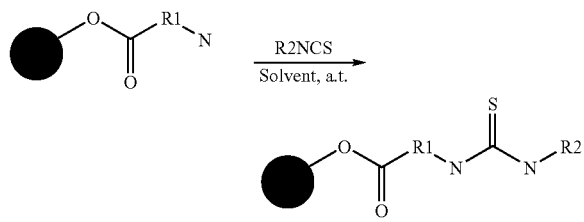

General procedure: aromatic and heteroaromatic isothiocyanates (5–10 equivalents) are added (Smith, J.; Liras, J. L.; Schneider, S. E.; Anslyn, E. V. *J. Org. Chem.* 1996, 61, 8811–8818) to monoprotected symmetrical diamines in a solvent such as DCM or DMF agitated overnight at ambient temperature. Washed successively with DMF and DCM, the thiourea resin is isolated then dried overnight under reduced pressure at 50° C.

Preparation 19

(phenylaminothioyl)ethyl Wang resin carbamate

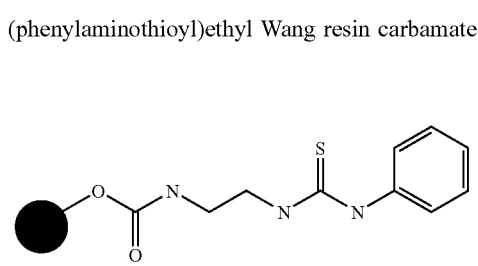

Phenylisothiocyanate (1 ml; 8.5 mmol; 5 eq.) is added to an ethylene diamine Wang resin N-carbamate (2 g; 1.72 mmol; 0.86 mmol/g) swollen in DCM (50 ml). After agitation overnight at ambient temperature, the resin is washed successively with DMF (5×20 ml) and DCM (5×20 ml). The success of the coupling is monitored using the Kaiser ninhydrin test (Kaiser, E.; Colescott, R. L.; Bossinger, C. D.; Cook, P. I. *Anal. Biochem.* 1970, 34, 595–598). A pale yellow resin (1.79 g) is obtained with a load of 0.648 mmol/g calculated from the elemental analysis of sulphur.

Synthesis of 2-arylimino-2,3-dihydrothiazoles

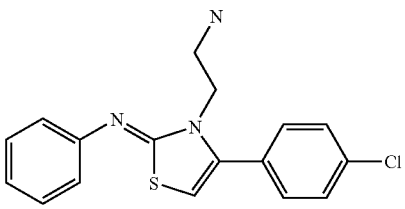

1) Solvent, 80° C.
2) Cleavage stage
3) Basic treatment

General procedure: regioselective cyclization stage (Korohoda, M. J.; Bojarska, A. B. *Polish J. Chem.* 1984, 58, 447–453; Ragab, F. A.; Hussein, M. M.; Hanna, M. M.; Hassan, G. S.; Kenawy, S. A. *Egypt. J. Pharm. Sci.* 1993, 34, 387–400; Hassan, H. Y.; El-Koussi, N. A.; Farghaly, Z. S. *Chem. Pharm. Bull.* 1998, 46, 863–866) takes place in aprotic solvents such as dioxane or DMF at 80° C. for 2–3 hours between the thiourea resin and the α-bromoketone (2–5 equivalents). The resin is then washed successively with DMF, methanol and DCM then dried under reduced pressure. The 2-arylimino-2,3-dihydrothiazole resin is cleaved under acid conditions (DCM/trifluoroacetic acid at 50%) for 1–2 hours then rinsed with DCM. The solvent is evaporated off and the free base is isolated after treatment under basic conditions (saturated solution of sodium hydrogen carbonate), extraction with DCM or elution with methanol in a basic alumina cartridge (500 mg, Interchim).

EXAMPLE 1

N-[3-(2-aminoethyl)-4-(4-chlorophenyl)-1,3-thiazol-2(3H)-ylidene]aniline ($C_{17}H_{16}ClN_3S$, MM=29.86)

2-bromo-4'-chloroacetophenone (30.2 mg; 129 µmol; 2 eq.) dissolved in DMF (1 ml) is added to a thiourea resin prepared above (100 mg; 64.8 µmol; load of 0.648 mmol/g). The mixture is agitated for 2 hours at 80° C. The resin is then successively washed with DMF (3×2 ml), methanol (3×2 ml) and DCM (3×2 ml). The release stage, carried out in 1 ml of a mixture of DCM/trifluoroacetic acid at 50%, produces an oil after one hour 30 minutes of agitation which is eluted with methanol in a basic alumina cartridge (500 mg, Interchim). The free base is isolated in a quantitative fashion (21.3 mg) in the form of a yellow oil having a purity measured by UV spectrophotometry of 98% at 220 nm.

NMR ¹H (DMSO D6, 100 MHz) δ: 7.55 (s, 5H); 7.3 (d, 2H, J=7.1 Hz); 6.99 (d, 2H, J=7.1 Hz); 6.21 (s, 1H, H azole); 3.74 (t, 2H, J=6.2 Hz, NCH$_2$); 3.32 (broad s, 2H, NH$_2$); 2.72 (t, 2H, J=6.2 Hz, NCH$_2$). SM/LC: m/z=330 (M+H)$^+$.

A series of 2-arylimino-2,3-dihydrothiazoles was synthesized according to method A using our robotic system (ACT MOS 496):

R1 groups:

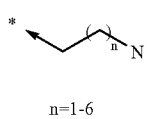
n=1-6

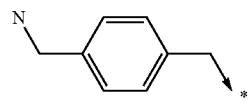

-continued

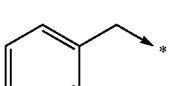

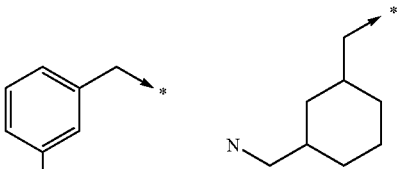

R2 groups:

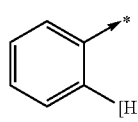
[H, Cl, Br, F, I, OMe, SMe, OEt, CF$_3$, OCF$_3$, NO$_2$, CN, Me, Et, iPr, Ph]

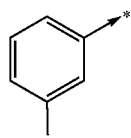
[Cl, Br, F, I, OMe, SMe, CF$_3$, OCF$_3$, NO$_2$, CN, Me, Et, iPr, OCH$_2$Ph]

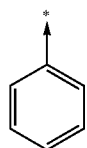
[Cl, Br, F, I, OMe, OEt, CF$_3$, OCF$_3$, NO$_2$, CN, Me, Et, iPr, nBu, tBu, NMe$_2$, NEt$_2$]

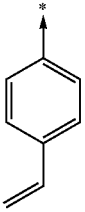

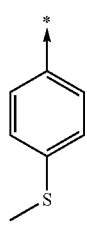

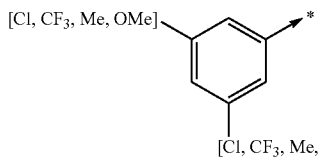
[Cl, CF$_3$, Me, OMe]
[Cl, CF$_3$, Me, OMe]

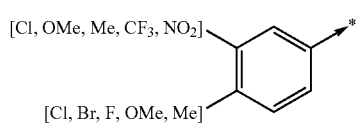
[Cl, OMe, Me, CF$_3$, NO$_2$]
[Cl, Br, F, OMe, Me]

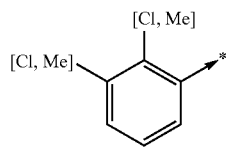
[Cl, Me]   [Cl, Me]

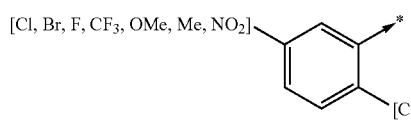
[Cl, Br, F, CF$_3$, OMe, Me, NO$_2$]
[Cl, Br, F, OMe, Me]

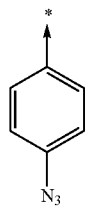

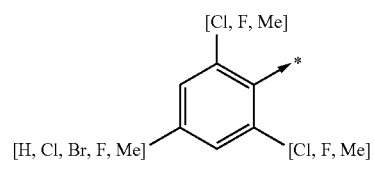
[Cl, F, Me]
[H, Cl, Br, F, Me]   [Cl, F, Me]

-continued
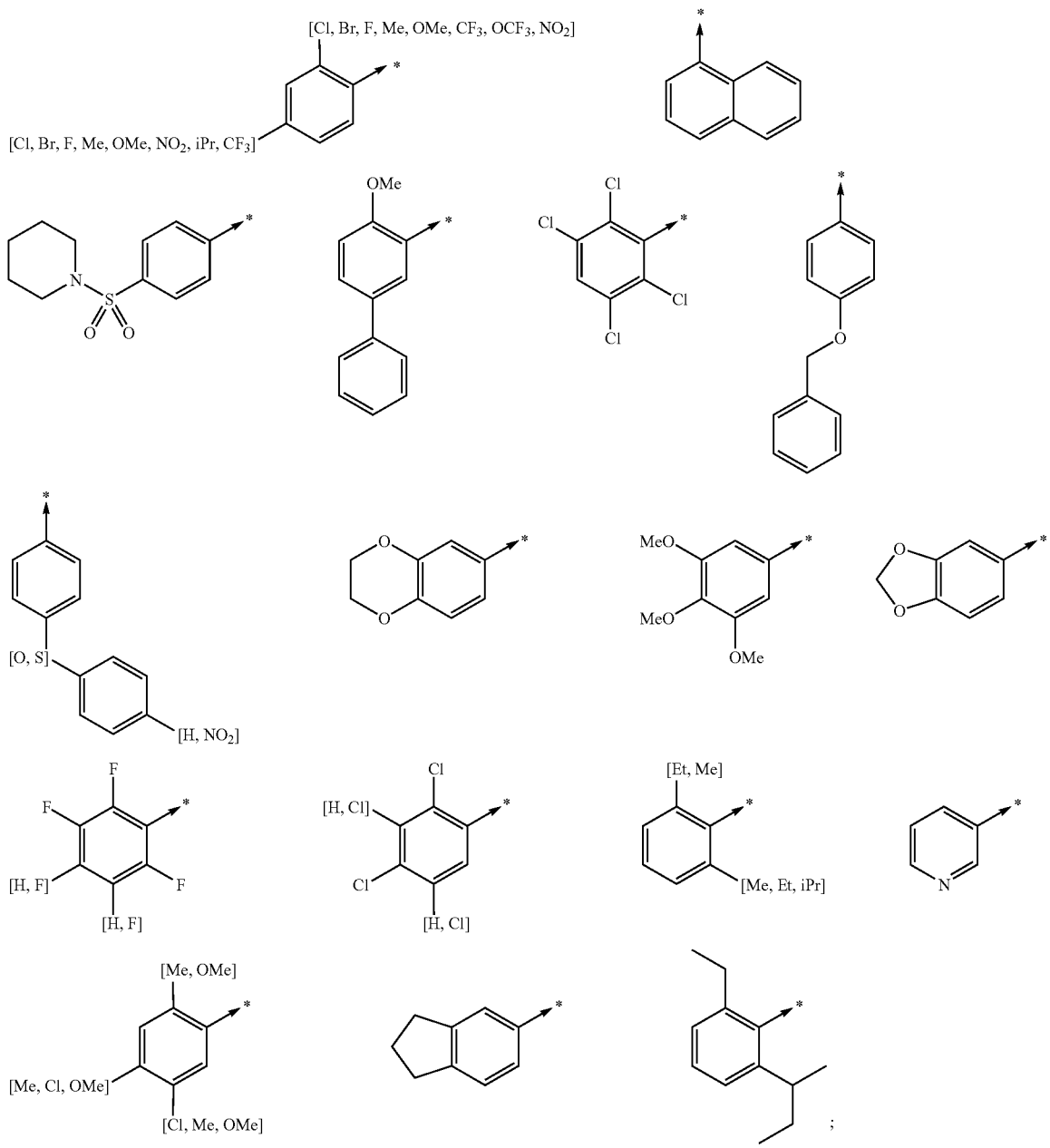
R3 groups:
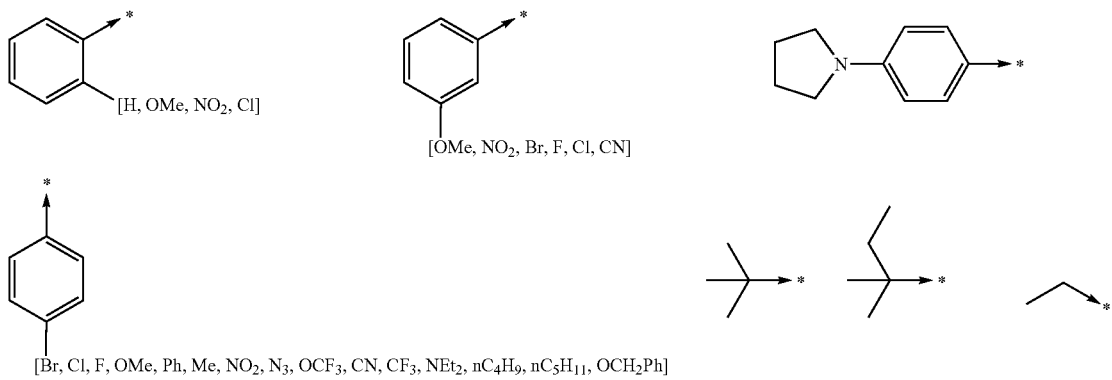

-continued
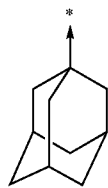 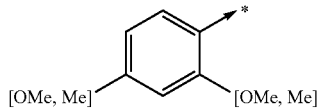 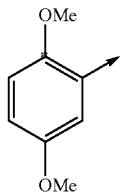 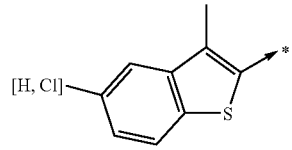
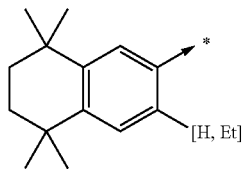 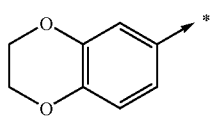 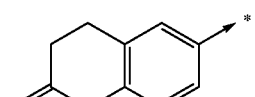 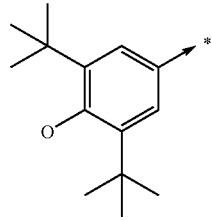
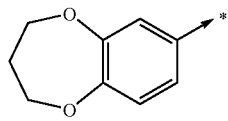 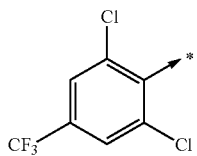 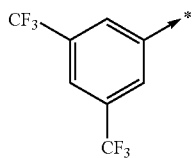 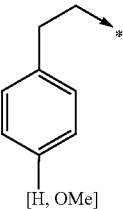
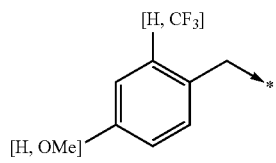 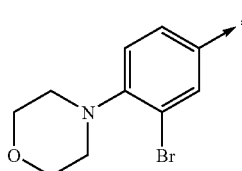 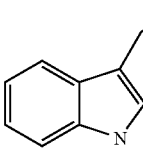 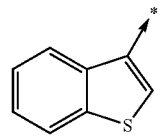
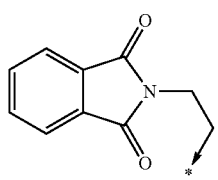 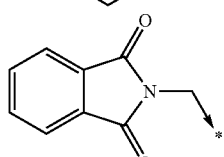 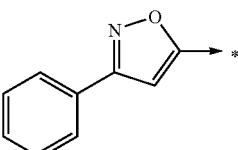 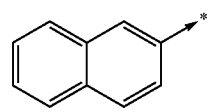
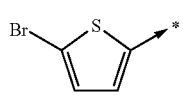 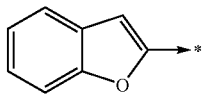 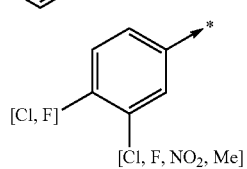 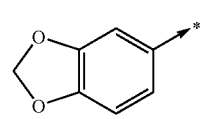
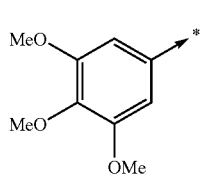 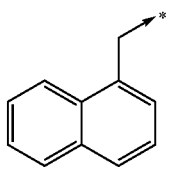 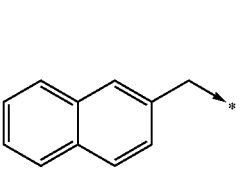

R4 represents H, alkyl, carbocyclic or heterocyclic aralkyl optionally situated on the aryl radical;

or then the

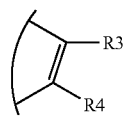

radical represents a radical of general formula

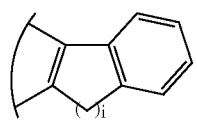

in which i represents an integer from 1 to 3;

it being understood that for R4, when the aryl group is substituted, it can be 1 to 5 times (other than the bond which links it to the remainder of the molecule) by radicals chosen independently from the group composed of a halogen atom and an alkyl or alkoxy radical.

Method B

Preparation of Wang Resin Carbamates from aminoalkylanilines

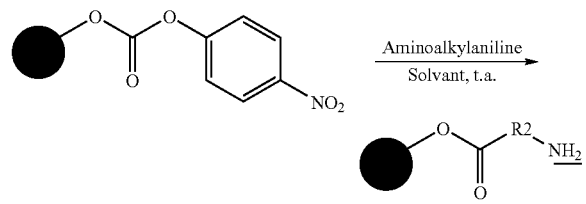

General procedure: as already described (Hulme, C.; Peng, J.; Morton, G.; Salvino, J. M.; Herpin, T.; Labaudiniere, R. Tetrahedron Lett. 1998, 39, 7227–7230), a p-nitrophenylcarbonate Wang resin is treated with an excess of aminoalkylaniline (5–10 eq.) in DCM or DMF and agitated at ambient temperature overnight. The resin is washed successively with DMF, methanol and DCM then dried overnight under reduced pressure at 50° C.

Preparation 20

4-aminophenylethyl Wang Resin Carbamate

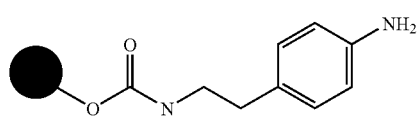

A solution of 2-(4-aminophenyl)ethylamine (2.48 g; 17.3 mmol; 5 eq.) in 30 ml of anhydrous DMF is added to a Wang resin p-nitrophenylcarbonate (4.05 g; 3.47 mmol; load of 0.857 mmol/g) pre-swollen in 50 ml of anhydrous DMF. The mixture is agitated at ambient temperature overnight and filtered. The resin is washed successively with DMF (10×30 ml), methanol (5×30 ml) and DCM (5×30 ml). 3.7 g of yellow resin (load of 0.8 mmol/g calculated from the elemental analysis of the nitrogen), giving a positive Kaiser ninhydrin test, is isolated after drying overnight under reduced pressure at 50° C.

Preparation of Thiourea Resins with aliphatic isothiocyanates

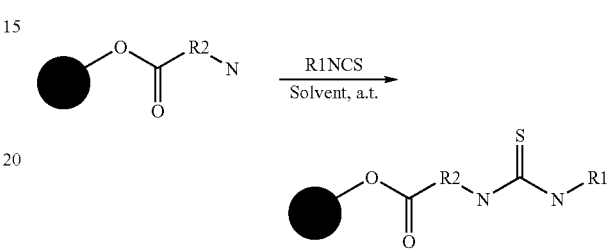

General procedure: aliphatic isothiocyanates (5–10 equivalents) are added to an aminoalkylaniline resin in a solvent such as DCM or DMF and agitation is carried out overnight at ambient temperature. After washing Successively with DMF and DCM, the thiourea resin is isolated and dried overnight under reduced pressure at 50° C.

Preparation 21

4-{([(phenylethylamino)carbothioyi]amino}-phenylethyl Wang resin carbamate

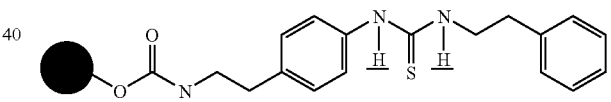

10 ml of anhydrous DMF and phenylethylisothiocyanate (624 μl, 4 mmol, 10 eq.) are added under an argon atmosphere to the resin described previously (0.5 g; 0.4 mmol; load of 0.8 mmol/g). The reaction medium is agitated overnight at ambient temperature and produces a negative Kaiser ninhydrin test. The resin is then washed successively with DMF (5×20 ml) and DCM (5×20 ml). Drying under reduced pressure at 50° C. produces 488 mg of resin with a load of 0.629 mmol/g calculated from elemental analysis of the sulphur.

Synthesis of 2-arylimino-2,3-dihydrothiazoles

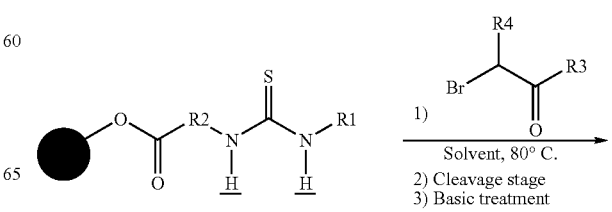

-continued

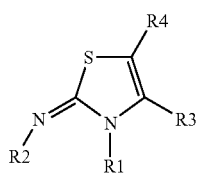

General procedure: the cyclization stage takes place in aprotic solvents such as dioxane or DMF at 80° C. for 2 hours between the thiourea resin and the α-bromoketone (2–5 equivalents). The resin is then washed successively with DMF, methanol and DCM then dried under reduced pressure. The iminothiazole resin is cleaved by treatment under acid conditions (DCM/trifluoroacetic acid at 50%) for 1–2 hours then rinsed with DCM. The solvent is evaporated off and the free base isolated after extraction under basic conditions (saturated solution of sodium hydrogen carbonate), extraction with DCM or elution with methanol in a basic alumina cartridge (500 mg, Interchim).

EXAMPLE 2

4-(2-aminoethyl)-N-[4-(4-chlorophenyl)-3-phenethyl-1,3-thiazol-2(3H)-ylidene]aniline ($C_{25}H_{24}ClN_3S$, MM=434.01)

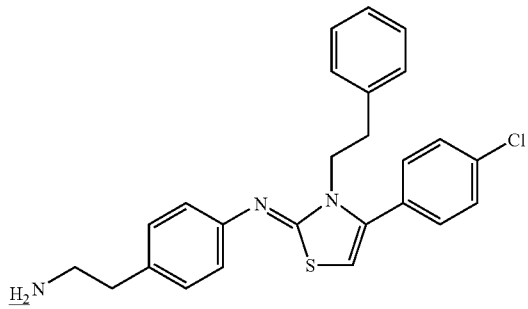

100 mg (62.9 μmol, load of 0.629 mmol/g) of thiourea resin and 2-bromo-4'-chloroacetophenone (30 mg; 125.8 μmol; 2 eq.) are dissolved in 1 ml of DMF and heated to 80° C. for 2 hours. The resin is then washed successively with DMF (5×1 ml), methanol (5×1 ml) and DCM (5×1 ml). The resin is agitated in 1 ml of a DCM/trifluoroacetic acid mixture at 50% for one hour and 30 minutes at ambient temperature. The resin is rinsed with DCM (5×1 ml) and the filtrate evaporated under reduced pressure. The residue, dissolved in methanol, is eluted in a basic alumina cartridge (500 mg, Interchim) in order to quantitatively produce (27.3 mg) the expected product in the form of a solid (UV purity: 97% at 220 nm).

NMR $^1$H (DMSO D6, 100 MHz) δ: 7.9 (broad s, 2H, $\underline{NH_2}$); 7.53 (d, 2H, J=8.5 Hz); 7.32–7.15 (m, 7H); 7.08–6.9 (m, 4H); 6.37 (s, 1H, H azole); 4.07 (m, 2H; N$CH_2$); 3.03 (m, 2H, N$CH_2$); 2.88 (m, 4H). MS/LC: m/z=435 (M+H)$^+$.

A series of 2-arylimino-2,3-dihydrothiazoles was synthesized according to method B with our robotic system (ACT MOS 496):

R1 groups

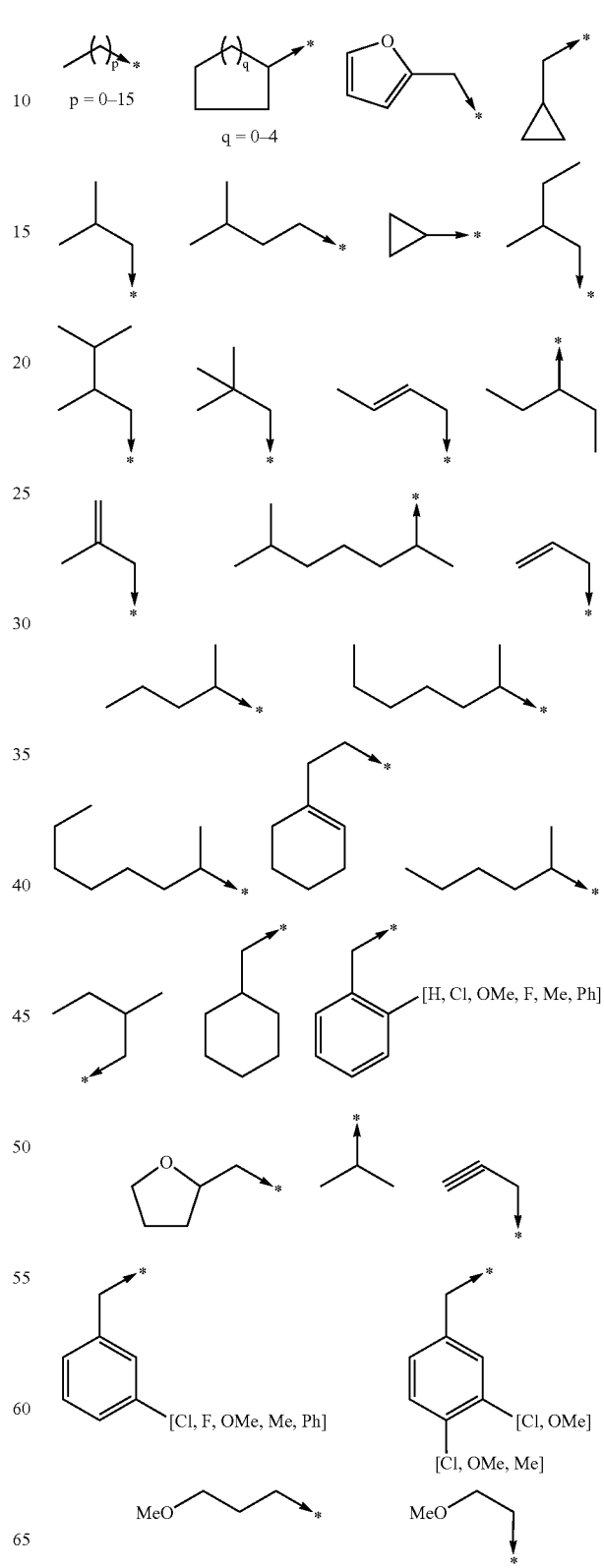

-continued

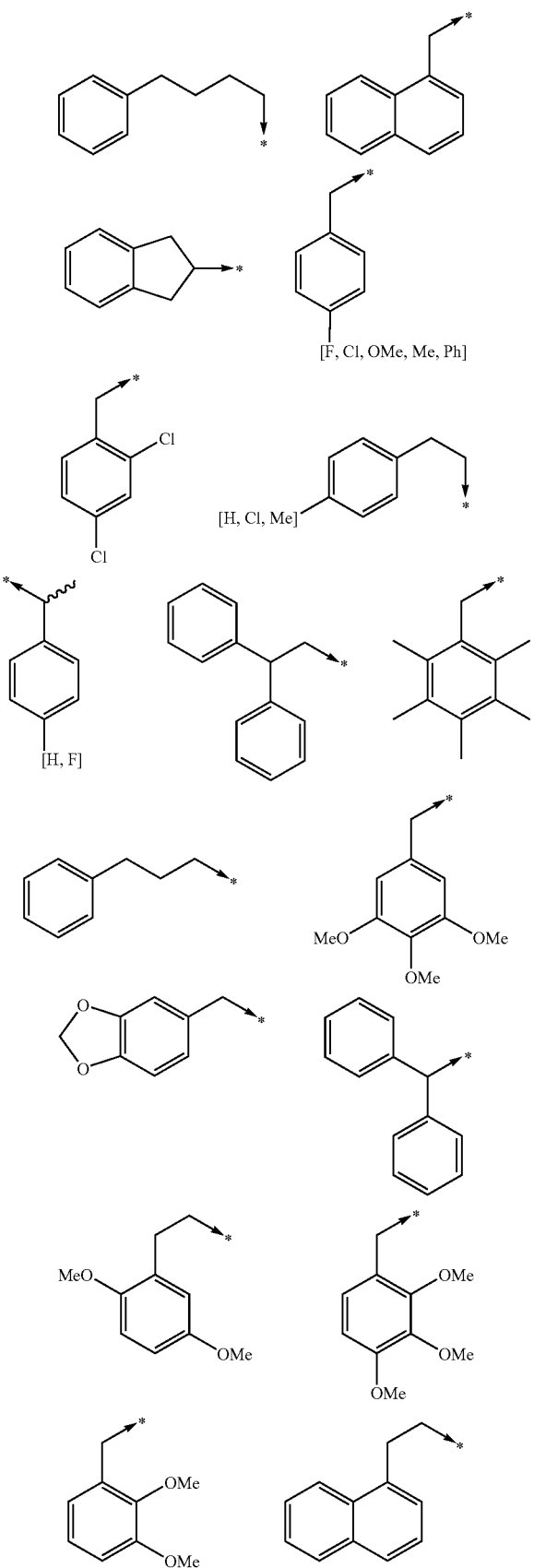

-continued

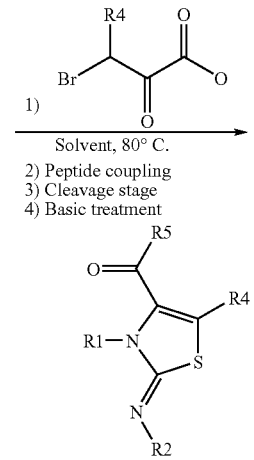

Method C

Synthesis of
2-arylimino-1,3-thiazole-4(3H)-carboxamides

General procedure: a regioselective cyclization stage using α-bromopyruvic acid (2–5 eq.) is carried out starting from the thiourea resin prepared in the method A in aprotic solvents such as dioxane or DMF at 80° C. for 2–3 hours. The resin is then washed successively with DMF, methanol and DCM then dried under reduced pressure. The peptide coupling (Knorr, R.; Trzeciak, A.; Bannwarth, W.; Gillessen, D. *Tetrahedron Lett.* 989, 30, 1927–1930) takes place in DMF at ambient temperature for 1–24 hours with different standard coupling agents (4–5 eq.) such as dicyclohexylcarbodiimide (DCC), diisopropylcarbodiimide (DIC), a DIC/N-hydroxybenzotriazole (HOBt) mixture, benzotriazolyloxytris(dimethylamino)phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU) and aminated compounds (4–5 eq.). The 2-arylimino-1,3-thiazole-4 (3H)-carboxamide resin is cleaved by treatment under acid conditions (DCM/trifluoroacetic acid at 50%) for 1–2 hours then rinsed with DCM. The solvent is evaporated off and the free base is isolated after treatment under basic conditions (saturated solution of sodium hydrogen carbonate), extraction is carried out with DCM or elution with methanol in a basic alumina cartridge (500 mg, Interchim).

EXAMPLE 3

3-(4-aminobutyl)-N-benzhydryl-2-[(4-bromophenyl)imino]-1,3-thiazole-4(3H)-carboxamide ($C_{27}H_{27}BrN_4OS$, MM=535.51)

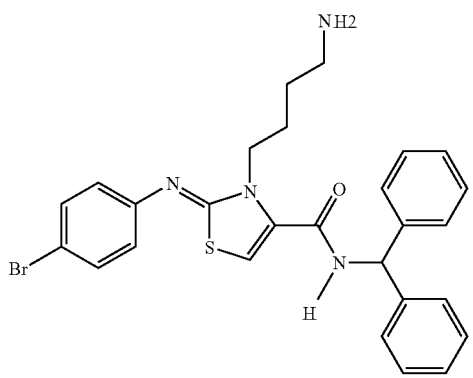

50 mg (27.5 µmol, load of 0.55 mmol/g) of carboxylic acid resin is activated for 15 minutes with 14.8 mg (0.11 mmol, 4 eq.) of N-hydroxybenzotriazole and 35.3 mg (0.11 mmol, 4 eq.) of TBTU in 800 µl of anhydrous DMF. 20.7 mg (0.11 mmol, 4 eq.) of aminodiphenylmethane dissolved in 200 µl of anhydrous DMF is then added and the resin is filtered after agitation overnight at ambient temperature. A sequential washing with DMF (5×1 ml), methanol (5×1 ml) and DCM (5×1 ml) produces a resin which is treated for one hour and 30 minutes under acid conditions (DCM/trifluoroacetic acid at 50%). The resin is rinsed with DCM (5×1 ml) and the filtrate evaporated under reduced pressure. The residue, taken up in methanol, is eluted in a basic alumina cartridge (500 mg, Interchim) in order to produce a pale yellow solid (8.2 mg; yield of 55.7%; UV purity of 94% at 220 nm).

NMR $^1$H (DMSO D6, 100 MHz, δ): 9.6 (d; 1H; J=8.6 Hz; NH); 7.49 (d; 2H; J=8.6 Hz); 7.35 (s; 10H); 6.92 (s; 1H; H azole); 6.91 (d; 2H; J=8.5 Hz); 6.27 (d; 1H; J=8.5 Hz; NHCH); 4.02 (m; 2H; NCH$_2$); 3.45 (broad m; 2H+2H; NH$_2$ and NCH$_2$); 1.55–1.24 (broad m; 4H). MS/LC: m/z=535 (M+H).

A series of 2-arylimino-1,3-thiazole-4(3H)-carboxamides was synthesized according to method C using our robotic system (ACT MOS 496):

R1 and R2 groups already described in method A;

R3=—CO-R5;

R4=H;

R5 groups

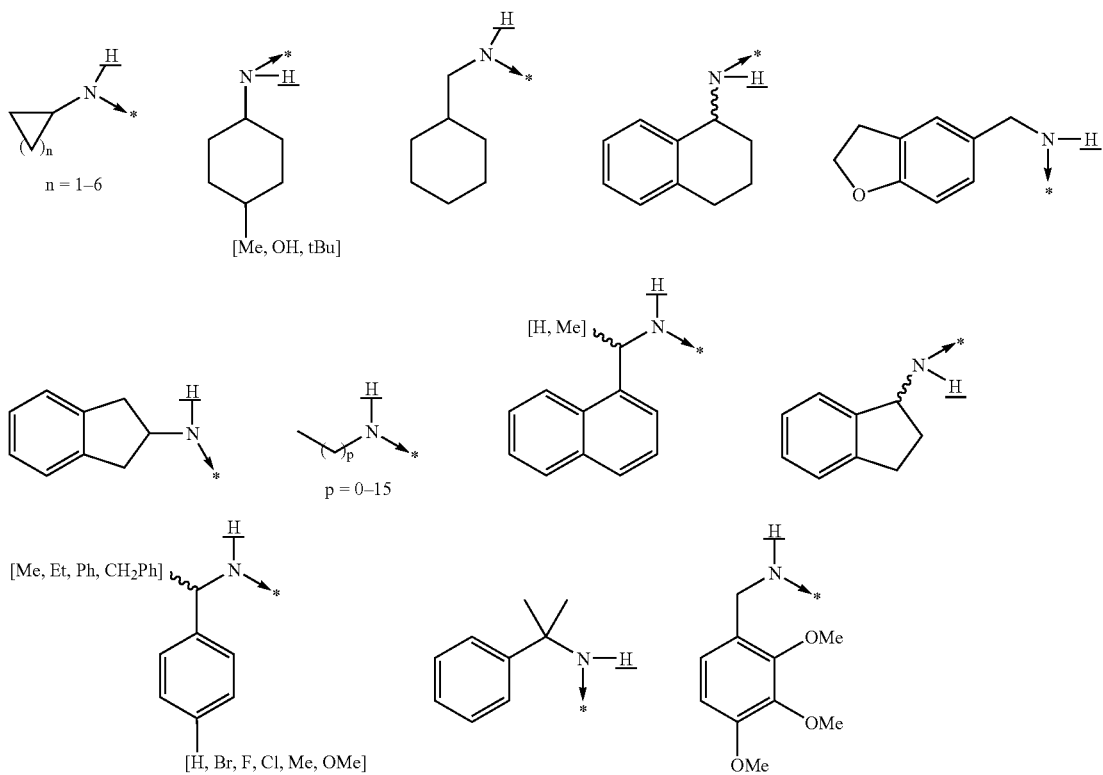

-continued
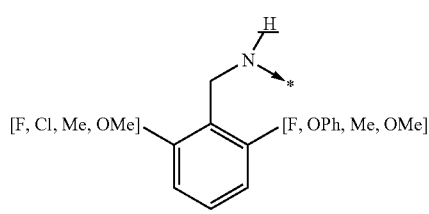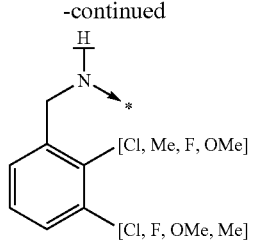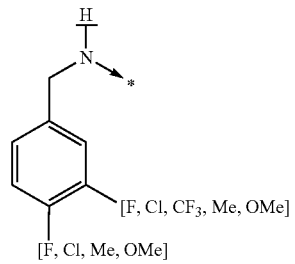
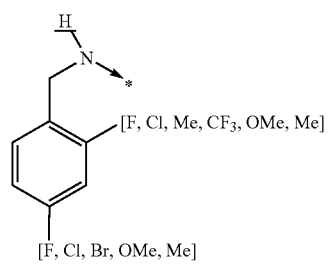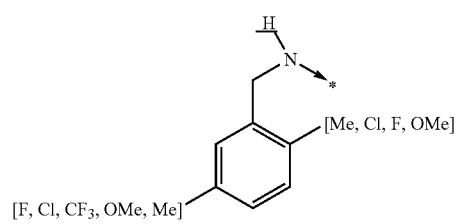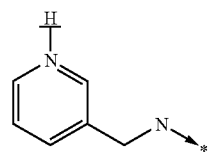
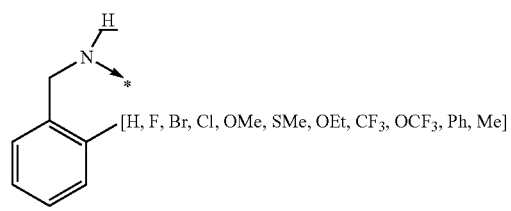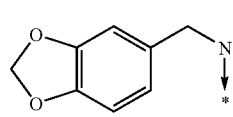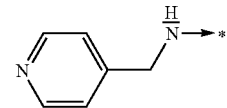
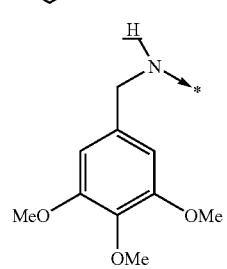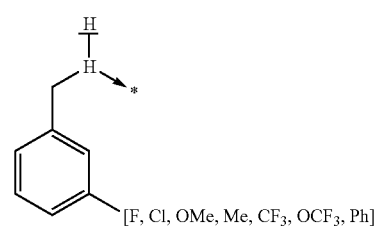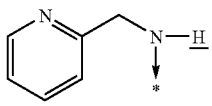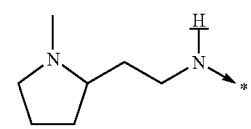
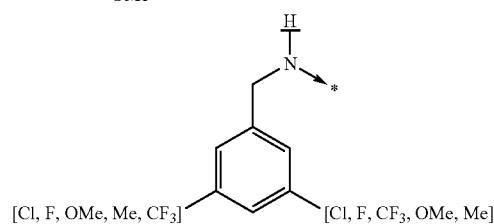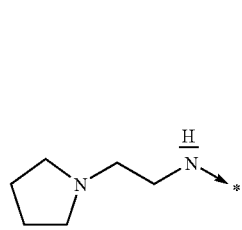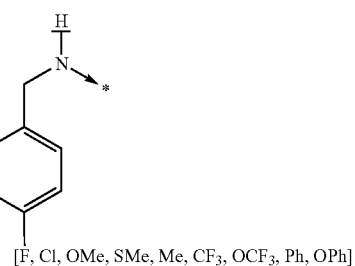
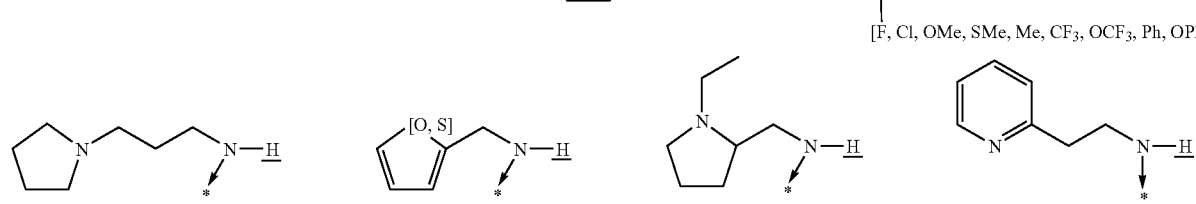
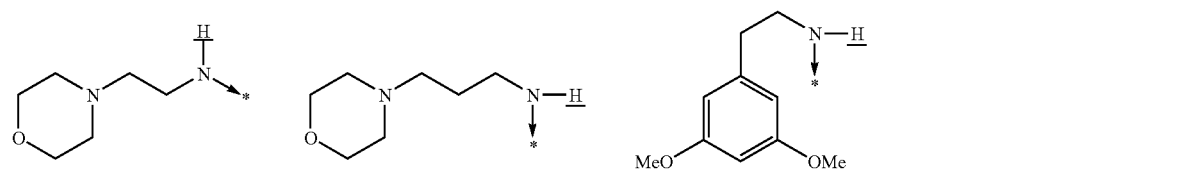

-continued
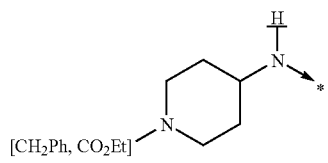
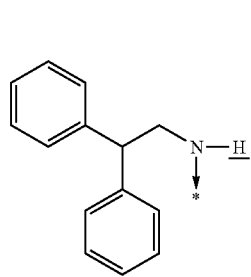
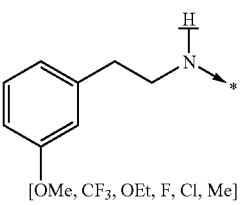
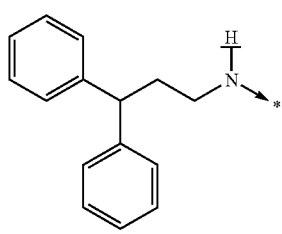
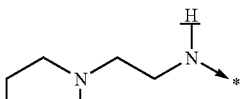
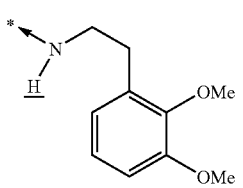
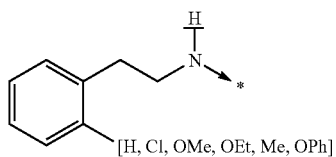
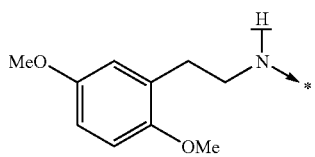
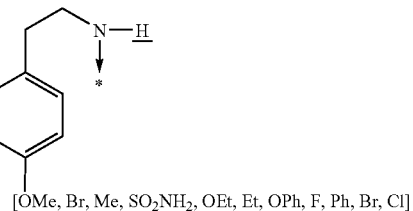
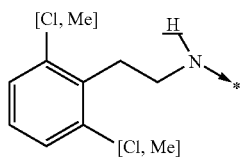
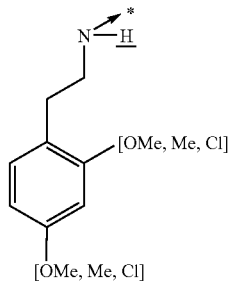
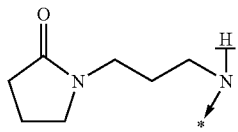
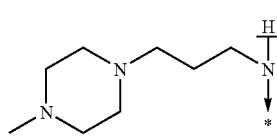
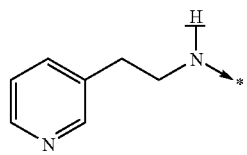
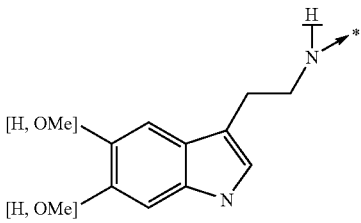
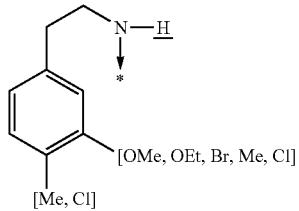
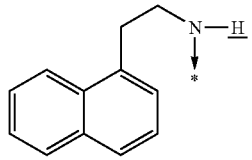
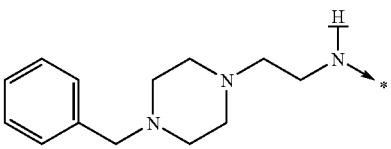
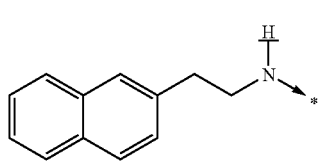
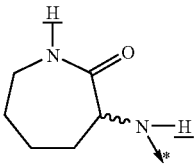
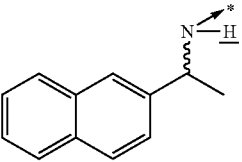

-continued
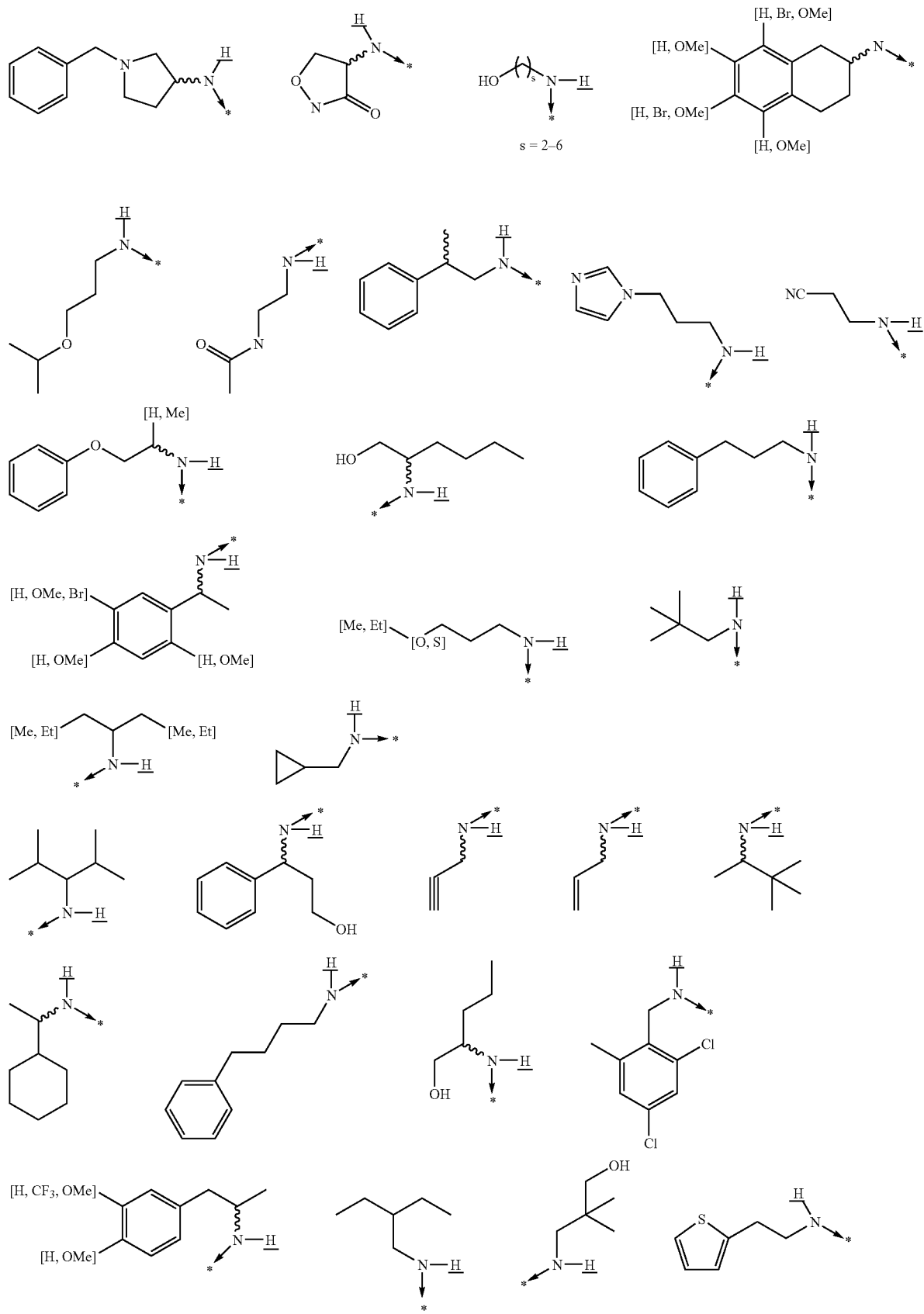

-continued
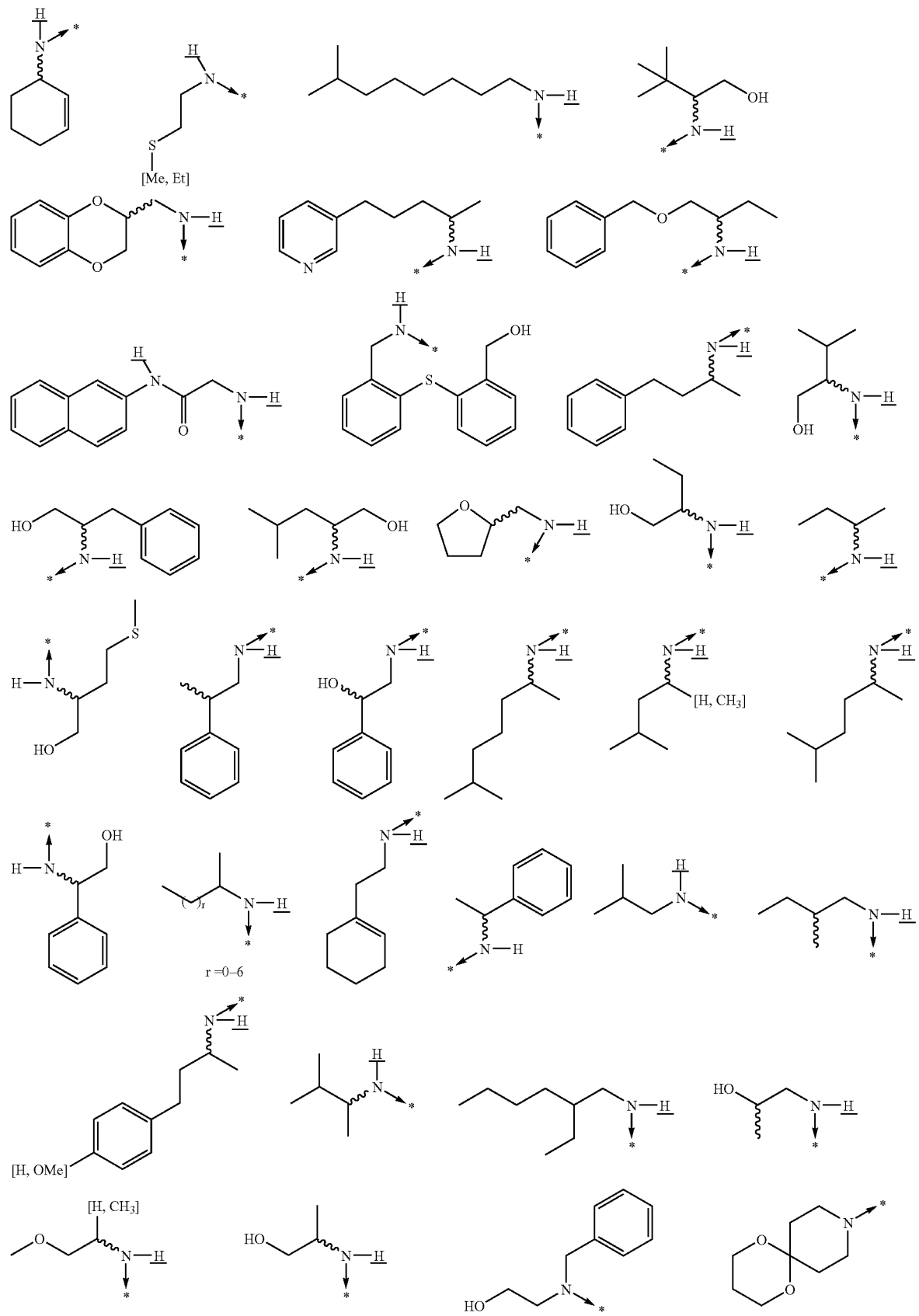

-continued
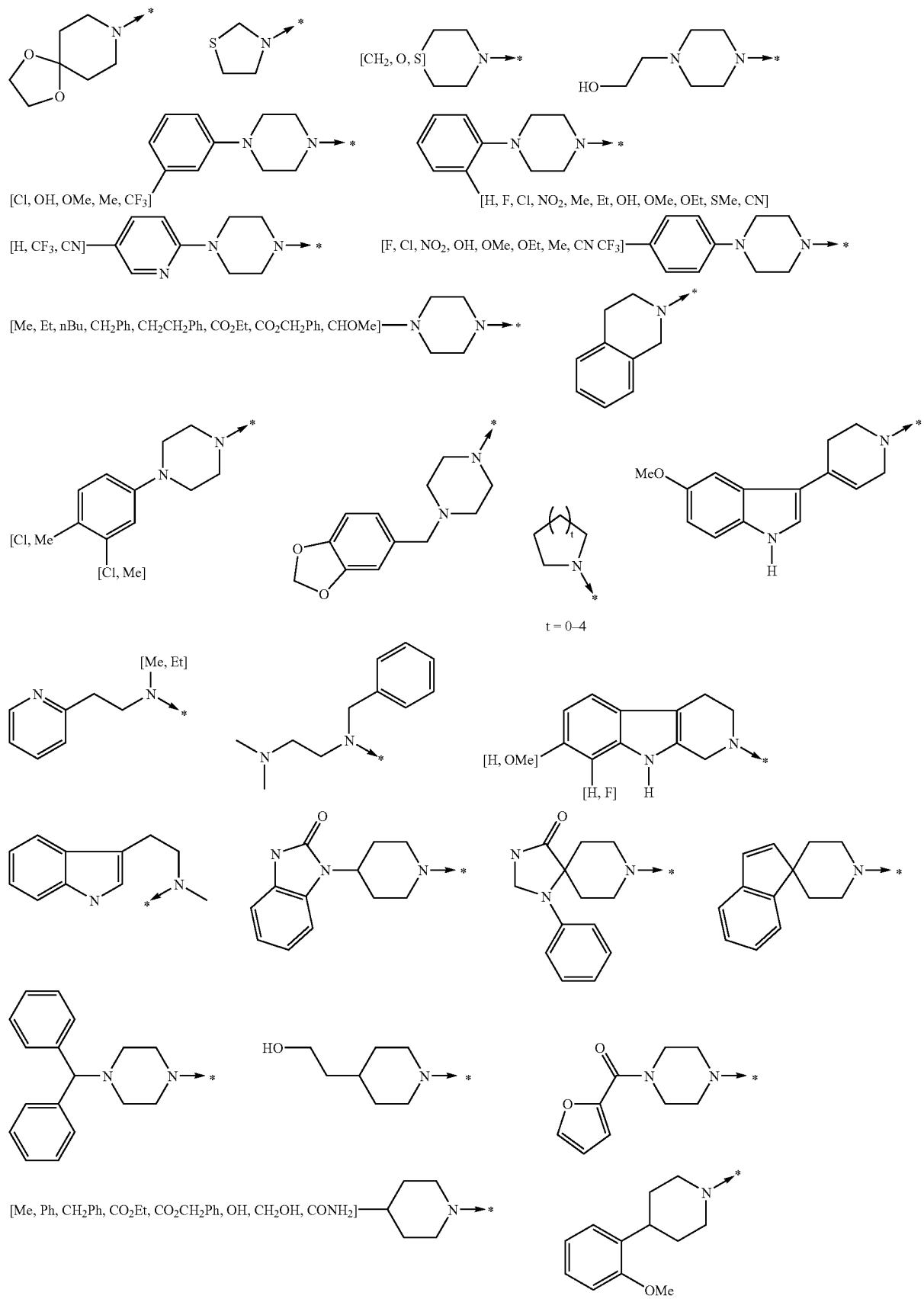

-continued
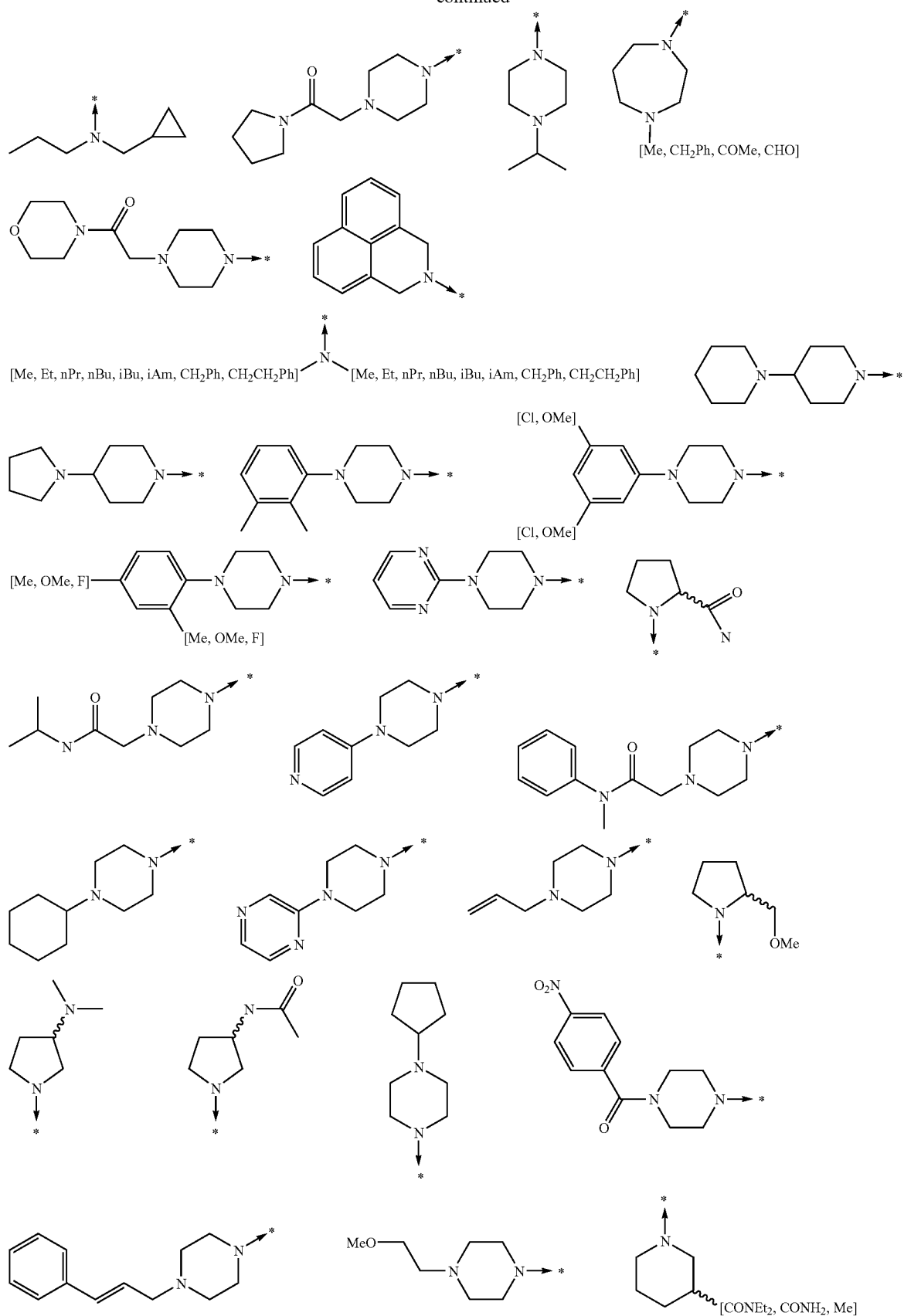

-continued
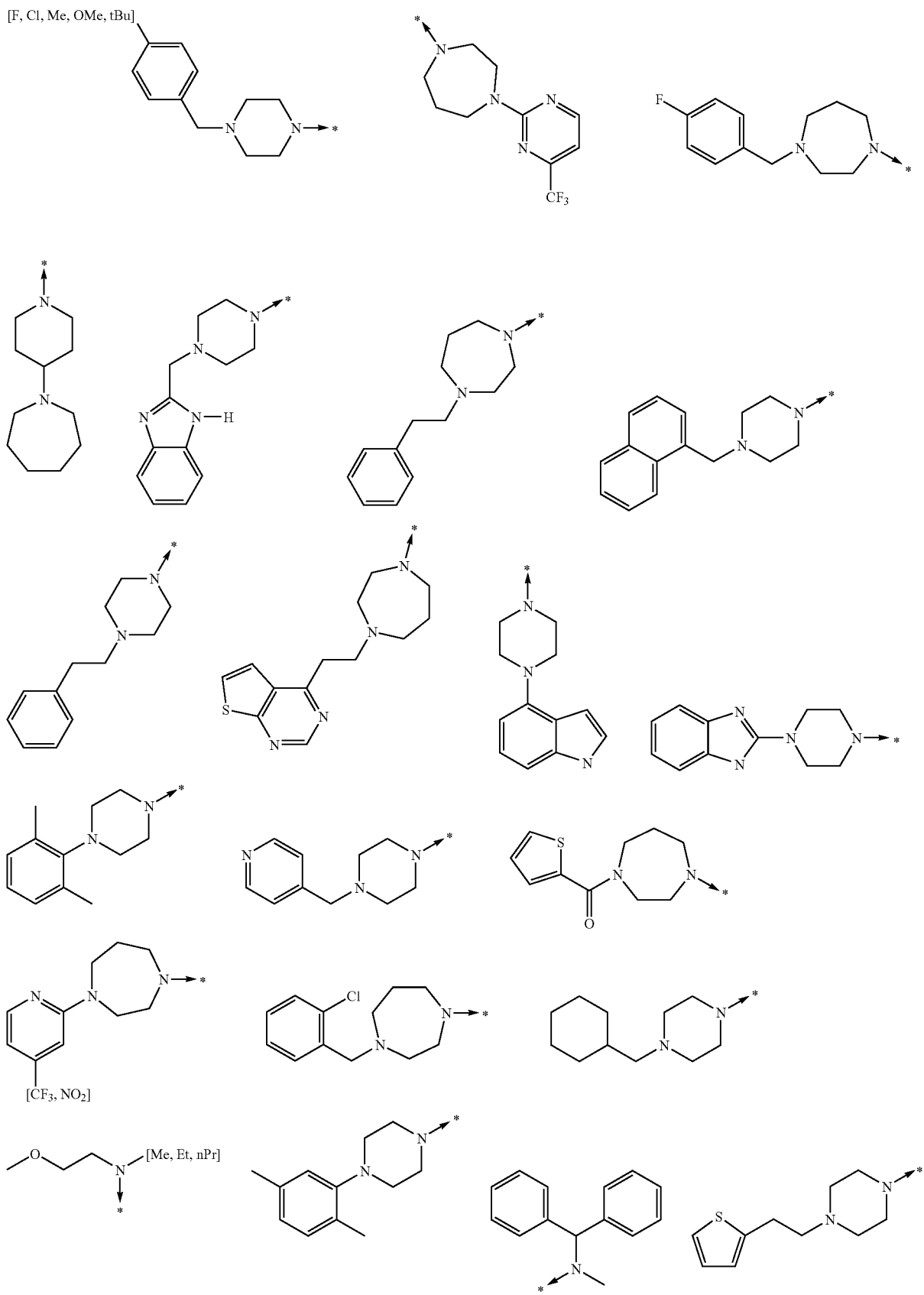

-continued

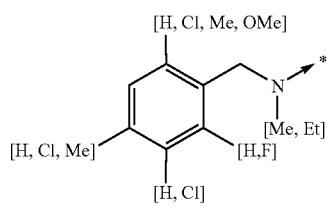

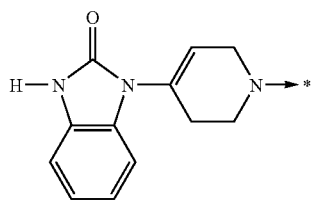

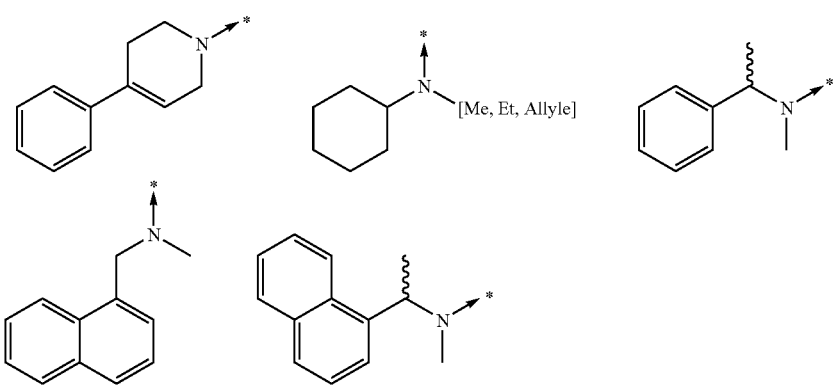

Method D

Synthesis of 2-arylimino-1,3-thiazole-4(3H)-carboxamides

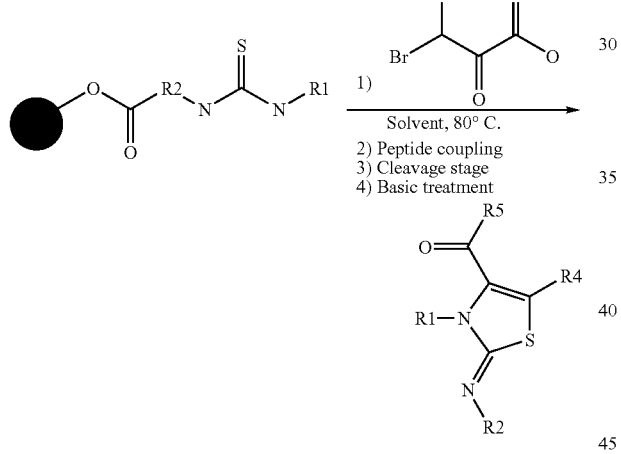

General procedure: a regioselective cyclization stage using α-bromopyruvic acid (2–5 eq.) is carried out starting from the thiourea resin prepared in method B in aprotic solvents such as dioxane or DMF at 80° C. for 2–3 hours. The resin is then successively washed with DMF, methanol and DCM then dried under reduced pressure. The peptide coupling (Knorr, R.; Trzeciak, A.; Bannwarth, W.; Gillessen, D. *Tetrahedron Lett.* 1989, 30, 1927–1930) takes place in DMF at ambient temperature for 1–24 hours with different standard coupling agents (4–5 eq.) such as dicyclohexylcarbodiimide (DCC), diisopropylcarbodiimide (DIC), a DIC/N-hydroxybenzotriazole (HOBt) mixture, benzotriazolyloxytris(dimethylamino)phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU) and aminated compounds (4–5 eq.). The 2-arylimino-1,3-thiazole-4(3H)-carboxamide resin is cleaved by treatment under acid conditions (DCM/trifluoroacetic acid at 50%) for 1–2 hours then rinsed with DCM. The solvent is evaporated off and the free base is isolated after treatment under basic conditions (saturated solution of sodium hydrogen carbonate) followed by an extraction with DCM or elution with methanol in a basic alumina cartridge (500 mg, Interchim).

EXAMPLE 4

(2Z)-2-{[4-(2-aminoethyl)phenyl]inlino}-N-(4-chlorobenzyl)-3-(2-phenylethyl)-2,3-dihydro-1,3-thiazole-4-carboxamide ($C_{27}H_{27}ClN_4OS$, MM=491.05)

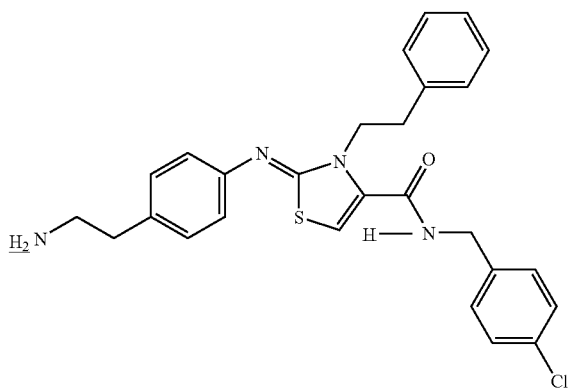

Phenylethylisothiocyanate (310 mg; 1.9 mmol; 10 eq.) in 3 ml of dimethylformamide is added to 200 mg (190 μmol, load of 0.946 mmol/g) of aminated resin (see Preparation 20). Agitation overnight at ambient temperature produces a negative Kaiser ninhydrin test. The resin is then successively washed with DMF (5×3 ml) and DCM (5×3 ml) then dried under vacuum for one hour before adding bromopyruvic acid (63.4 mg; 380 μmol; 2 eq.) diluted beforehand in 3 ml of dimethylformamide. The mixture is agitated for 2.5 hours at 80° C. The resin is filtered and washed with DMF (5×3 ml), methanol (3×3 ml) then DCM (5×3 ml). The carboxylic acid resin is preactivated for 1 hour with 244 mg (0.76 mmol; 4 eq.) of TBTU diluted in 2 ml of anhydrous DMF. 110 mg (0.76 mmol; 4 eq.) of 4-chlorobenzylamine dissolved in 1 ml of anhydrous DMF is then added and the resin is filtered after agitation overnight at ambient temperature. Sequential washing with DMF (5×3 ml), methanol (3×3 ml)

and DCM (3×3 ml) produces a resin which is treated for one hour and 30 minutes under acid conditions (DCM/trifluoroacetic acid at 50%). The resin is rinsed with DCM (5×1 ml) and the filtrate evaporated under reduced pressure. The residue, taken up in DCM, is neutralized with a saturated solution of sodium hydrogen carbonate in order to produce after evaporation a solid (38.2 mg; yield of 41%; UV purity of 90% at 210 nm). NMR $^1$H (DMSO D6, 400 MHz, δ): 9.1 (m, 1H); 7.39 (d, 2H, J=8.4 Hz); 7.33 (d, 2H, J=8.4 Hz); 7.25 (q, 2H, J=6.8 Hz); 7.19 (q, 1H, J=7.2 Hz); 7.11 (m, 4H); 6.8 (d, 2H, J=8 Hz); 6.75 (s, 1H, H azole); 4.34 (d, 2H, J=6 Hz); 4.27 (t, 2H, J=6.8 Hz); 3.14 (m, 1H); 2.89 (t, 2H, J=6.8 Hz); 2.73 (t, 1H, J=7.2 Hz); 2.62 (m, 2H). MS/LC: m/z=491.24 (M+H)$^+$.

A series of 2-arylimino-1,3-thiazole-4(3H)-carboxamides was synthesized according to method D using our robotic system (ACT MOS 496):

R1 and R2 groups already described in method B
R3=—CO-R5
R4=H
R5 groups already described in method C.

Method E

Preparation of Monoprotected Diamine Resin Functionalized with α-bromopyruvic Acid

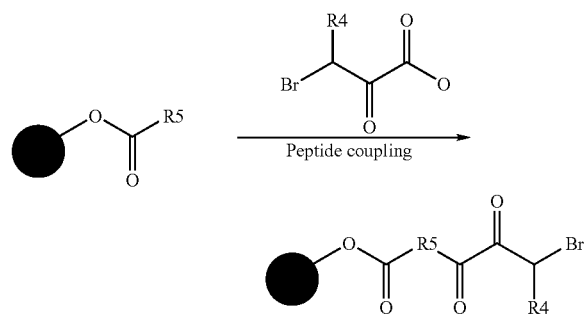

General procedure: the monoprotected symmetrical primary or secondary diamine resin (the preparation of which is already described in method A) is functionalized by peptide coupling with α-bromopyruvic acid (10 eq.), DIC (10 eq.) and HOBt (10 eq.) in a solvent such as DMF at ambient temperature. The resin is washed successively with DMF then with DCM after 2 to 24 hours of agitation before being dried under vacuum. The negative Kaiser ninhydrin test indicates a complete functionalization.

Preparation 22

N-carbamate of 2-[(3-bromo-2-oxopropanoyl)amino]ethyl Wang resin

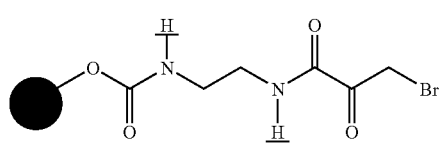

HOBt (0.93 g, 6.88 mmol) and α-bromopyruvic acid (1.18 g, 6.88 mmol) are dissolved in 28 ml of DMF (0.5 M). DIC (1.07 ml; 6.88 mmol) is then added by syringe to activate the acid. The mixture is agitated for approximately 15 minutes at ambient temperature before adding it to the ethylene diamine Wang resin N-carbamate (0.8 g; 0.688 mmol; load rate 0.86 mmol/g). After agitation for 3 hours at ambient temperature, the Kaiser ninhydrin test being negative, the resin is filtered and washed successively with DMF (5×20 ml) then with DCM (5×20 ml) before being dried under vacuum. An ochre resin (0.812 g) is obtained with a load rate of 0.525 mmol/g calculated from elemental analysis of the bromine.

Synthesis of
2-arylimino-1,3-thiazole-4(3H)-carboxamides

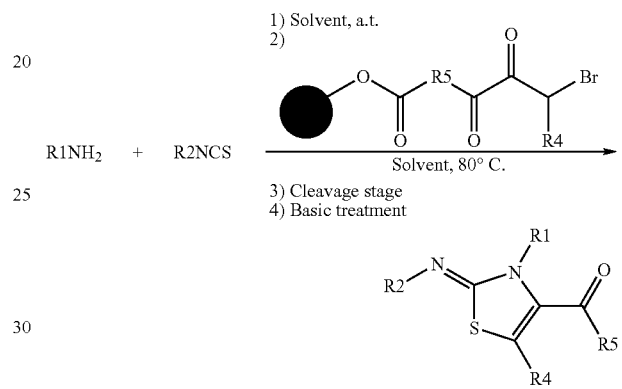

General procedure: formation of the thiourea is carried out in a solvent such as DMF or dioxane by mixing an equimolar quantity of primary amine and aromatic or heteroaromatic isothiocyanate. After agitation for 2 to 24 hours at ambient temperature, the thiourea (2 to 5 eq.) is added to the functionalized resin then heated at 80° C. for 2 to 4 hours. The 2-arylimino-1,3-thiazole-4(3H)-carboxamide resin is cleaved by treatment under acid conditions (DCM/trifluoroacetic acid at 50%) for 1–2 hours then rinsing with DCM. The solvent is evaporated off and the free base isolated after treatment under basic conditions (saturated solution of sodium hydrogen carbonate), extraction with DCM or elution with methanol in a basic alumina cartridge (500 mg, Interchim).

EXAMPLE 5

(2Z)-N-(2-aminoethyl)-3-[2-(3,4-dimethoxyphenyl)ethyl]-2-(phenylimino)-2,3-dihydro-1,3-thiazole-4-carboxamide ($C_{22}H_{26}N_4O_3S$, MM=426.54)

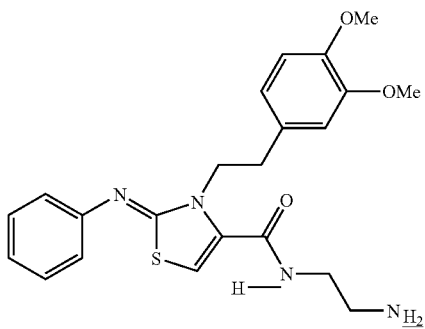

18 μl (105 μmol; 2 eq.) of β-(3,4-dimethoxyphenyl)ethylamine and 12.6 μl (105 μmol; 2 eq.) of phenylisothiocyanate are agitated in 1 ml of DMF for 18 hours. The thiourea is added to 100 mg (52.5 μmol; load rate of 0.525 mmol/g) of resin (Preparation 22) and the mixture heated at 80° C. for 3 hours. The resin is then filtered then washed successively with DMF (5×1 ml), methanol (5×1 ml) then DCM (5×1 ml). The resin is dried under vacuum before adding 1 ml of a 50% DCM/TFA mixture. Agitation is carried out for 1.5 hours at ambient temperature, the resin is filtered and rinsed with DCM. The residue recovered after evaporation is then eluted with methanol in a basic alumina cartridge in order to isolate 22.2 mg (quantitative yield; UV purity of 93.4% at 230 nm) of a brown solid corresponding to the free amine.

NMR $^1$H (DMSO D6, 100 MHz, δ): 8.42 (m, 1H, NH); 7.32 (t, 2H, J=7.1 Hz); 7.08–6.63 (m, 6H); 5.76 (s, 1H, H azole); 4.31 (t, 2H, J=6.6 Hz); 3.72 (s, 6H, OCH$_3$); 3.32 (broad s, 2H); 3.17 (m, 2H); 2.89 (m, 2H); 2.62 (m, 2H). MS/LC: m/z=427.17 (M+H)$^+$.

A series of 2-arylimino-1,3-thiazole-4(3H)-carboxamides was synthesized according to method E using our robotic system (ACT MOS 496):

R1 groups:

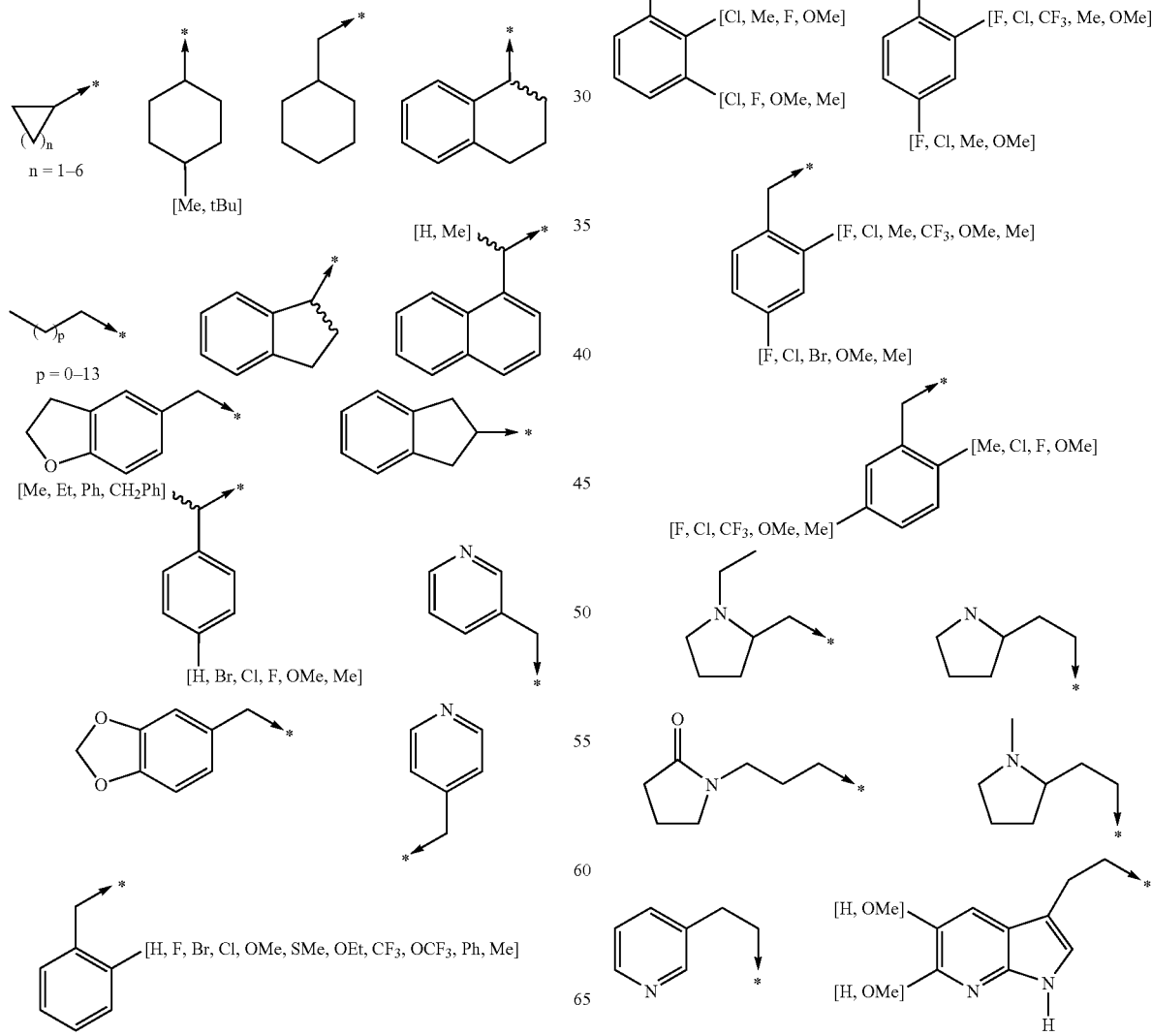

191
-continued
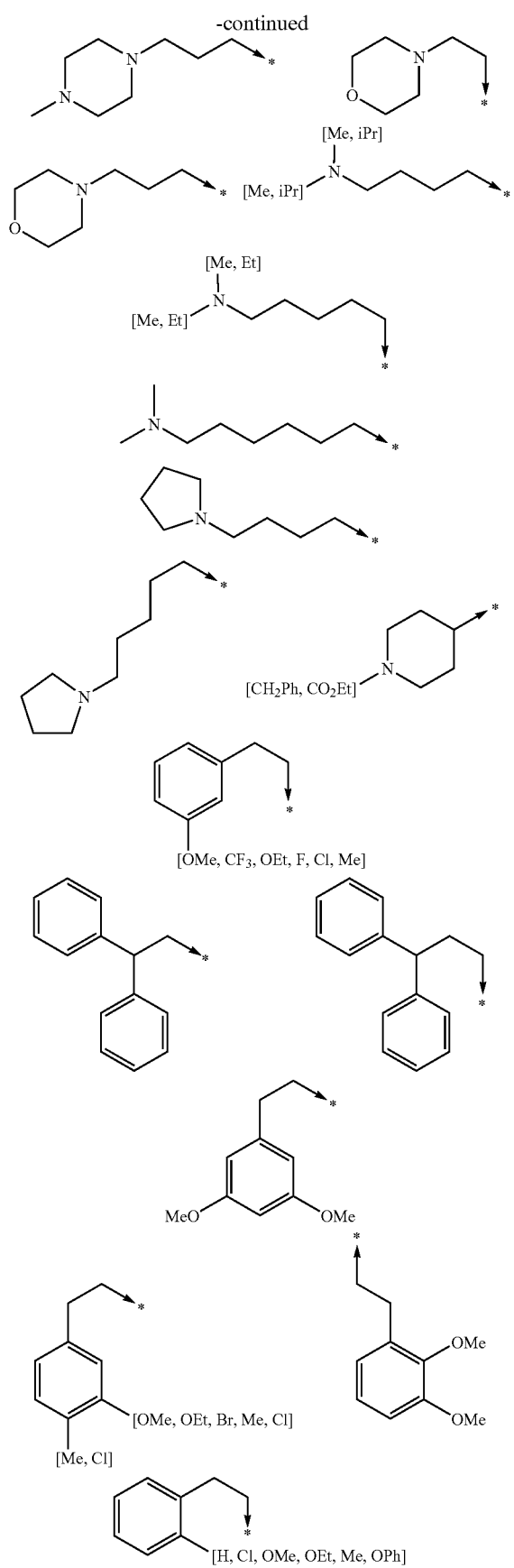
192
-continued
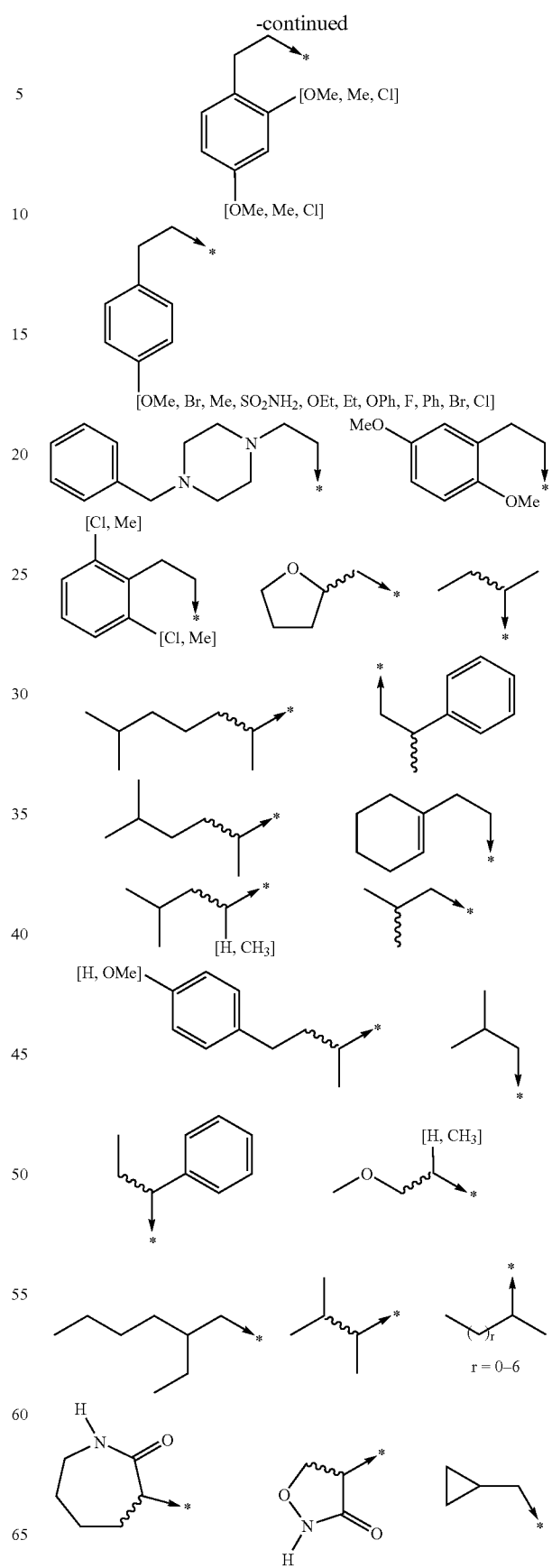

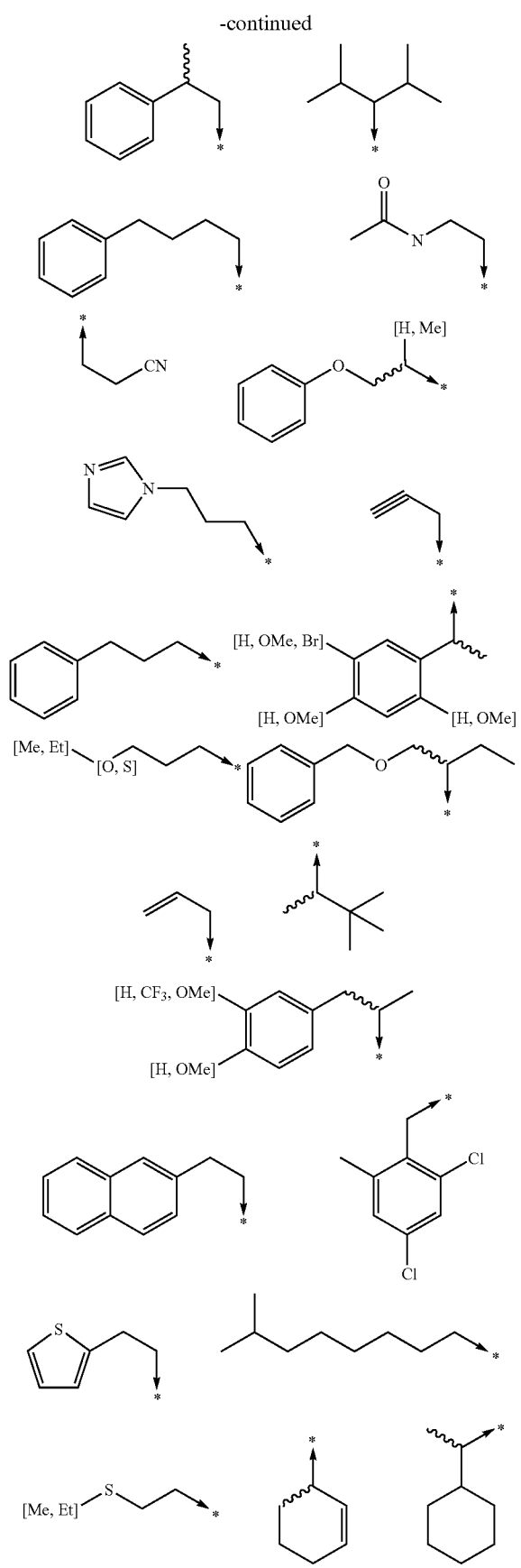
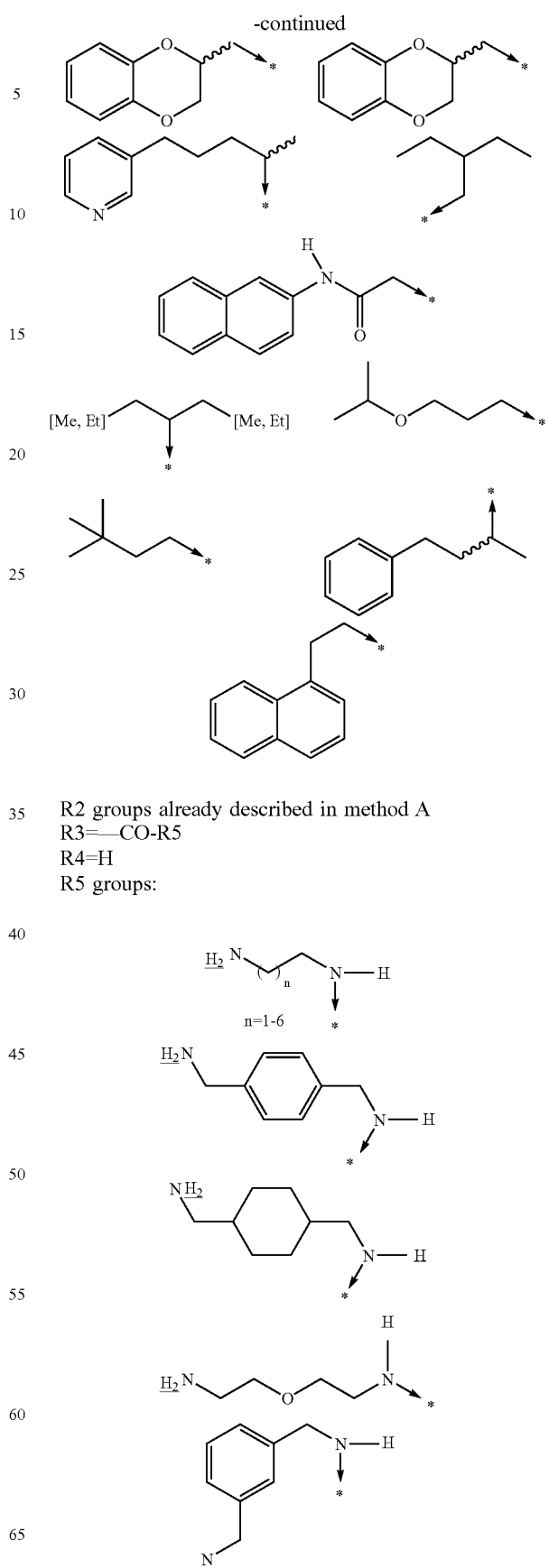
R2 groups already described in method A
R3=—CO-R5
R4=H
R5 groups:

-continued

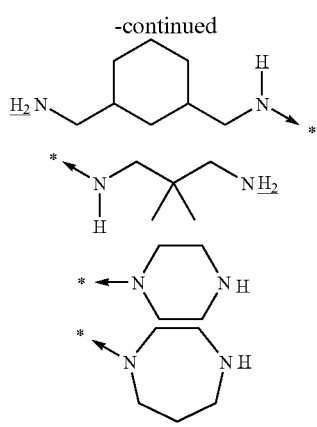

Method F

Preparation of monoprotected diamine resins functionalized with N-protected amino acids (Fmoc)

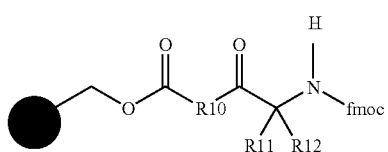

General procedure: the peptide coupling of the monoprotected diamine resins with N-Fmoc amino acids (4 to 10 eq.) which are commercially available (Bunin, B. A. *The Combinatorial Index, Academic Press*, 1998, p. 77–82) is carried out in DMF at ambient temperature for 1 to 24 hours with different standard coupling agents (4 to 10 eq.) such as dicyclohexylcarbodiimide (DCC), diisopropylcarbodiimide (DIC), a DIC/N-hydroxybenzotriazole (HOBt) mixture, benzotriazolyloxytris(dimethylamino) phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU). The resin is then washed successively with DMF and DCM. The coupling sequence can be repeated (once or twice) until the Kaiser ninhydrin test is negative.

Preparation 23

4-[({[(9H-fluoren-9-ylmethoxy)carbonyl]amino}acetyl)amino]butyl N-carbamate

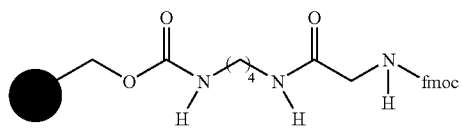

Fmoc-Gly-OH acid (2.36 g, 7.94 mmol) is activated with HOBt (1.07% g, 7.94 mmol) and DIC (1.25 ml, 7.94 mmol) in 22 ml of DMF for 5 minutes before adding the mixture to butylamine Wang resin N-carbamate (1 g, load rate of 0.794 mmol/g) preswollen in 10 ml of DMF. After agitation for 18 hours at ambient temperature, the resin is washed successively with DMF (5×20 ml) then with DCM (5×20 ml) before being dried under vacuum. 1.27 g of pale yellow resin is thus obtained presenting a negative Kaiser ninhydrin test.

Preparation of the thiourea resins

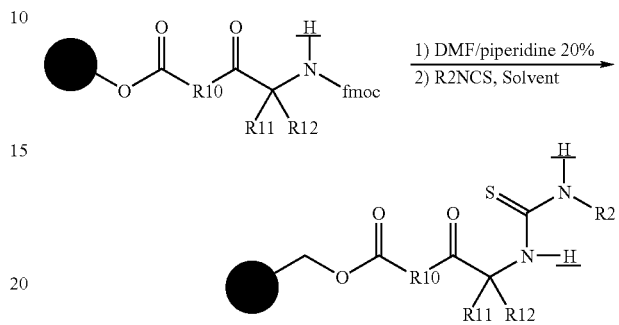

General procedure: a resin described above is deprotected with a 20% DMF/piperidine mixture. After agitation for one hour at ambient temperature, the resin is filtered and washed successively with DMF then with DCM. The deprotection/washing sequence is repeated a second time and the resin is dried under vacuum. The latter is preswollen in a solvent such as DMF or DCM then an aromatic or heteroaromatic isothiocyanate (5 to 10 eq.) is added. The mixture is agitated for 2 to 24 hours at ambient temperature before the resin is filtered and washed successively with DMF then with DCM. The resin is then dried under vacuum and a negative Kaiser ninhydrin test confirms that the substitution reaction is complete.

Preparation 24

4-[({[(1-naphthylamino)carbothioyl]amino}acetyl)amino]butyl Wang resin N-carbamate

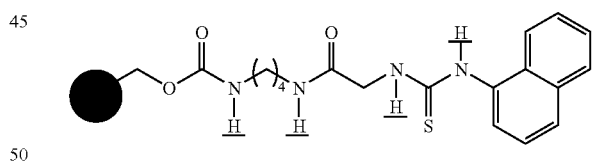

1.27 g of the above resin (see Preparation 23) is deprotected with 14 ml of DMF/piperidine at 20%. The mixture is agitated for one hour at ambient temperature. The resin is then filtered then washed with DMF (5×30 ml) then with DCM (5×30 ml). The deprotection/washing sequence is repeated once before the resin is dried under vacuum. 0.781 g of pale yellow resin was thus obtained with a load rate of 0.758 mmol/g calculated after elemental analysis of the sulphur. 416 mg (2.2 mmol, 10 eq.) of 1-naphthylisothiocyanate diluted in 6 ml of DMF is added to 0.3 g (0.22 mmol) of this thiourea resin. The mixture is agitated for 18 hours at ambient temperature. The resin is filtered then washed successively with DMF (5×20 ml) then with DCM (5×20 ml). 310 mg of a pale yellow resin is isolated after drying under vacuum with a load rate of 0.66 mmol/g calculated after elemental analysis of the nitrogen.

Synthesis of 2-arylimino-2,3-dihydrothiazoles

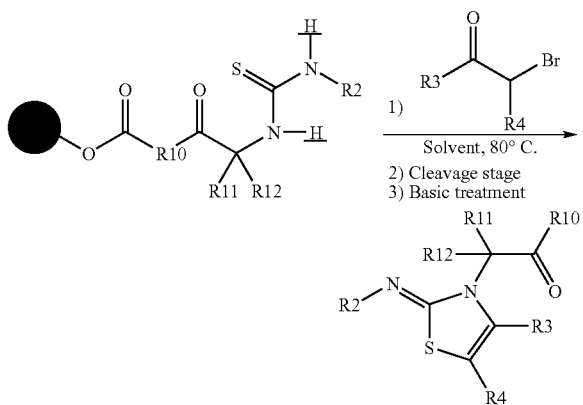

General procedure: the regioselective cyclization stage is carried out in aprotic solvents such as dioxane, DMF or N-methylpyrrolidinone at 80° C. for 2 to 3 hours between the thiourea resin and the α-bromoketone (2 to 5 eq.). The resin is then washed successively with DMF, methanol and DCM then dried under reduced pressure. The 2-arylimino-2,3-dihydrothiazole resin is cleaved under acid conditions (DCM/trifluoroacetic acid at 50%) for 1 to 2 hours then rinsed with DCM. The solvent is evaporated off and the free base isolated after treatment under basic conditions (saturated solution of sodium hydrogen carbonate) followed by an extraction with DCM or elution with methanol in a basic alumina cartridge (500 mg, Interchim).

EXAMPLE 6

N-(4-aminobutyl)-2-((2Z)-4-(4-chlorophenyl)-2-(1-naphthylimino)-1,3-thiazol-3(2H)-yl)acetamide ($C_{25}H_{25}ClN_4OS$, MM=465.02)

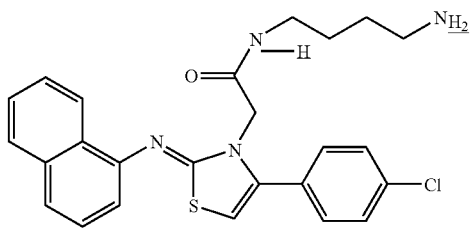

80 mg (52.8 μmol, load rate of 0.66 mmol/g) of thiourea resin (Preparation 24) and 25.1 mg (105.6 mmol, 2 eq.) of 2-bromo-4'-chloroacetophenone are diluted in 1 ml of DMF. The mixture is heated at 80° C. for 2 hours. The resin is filtered then washed with DMF (5×1 ml), methanol (5×1 ml) then DCM (5×1 ml) before being dried under vacuum. 1 ml of a 50% DCM/TFA mixture is added followed by agitation for 1 hour 30 minutes. The resin is filtered and rinsed with DCM. The filtrate is evaporated then rediluted in methanol for elution on basic alumina. 20.6 mg (yield of 84%; UV purity of 94.2% at 220 nm) of yellow solid is thus isolated after evaporation corresponding to the free base.

NMR $^1$H (DMSO D6, 100 MHz, δ): 8.36 (t, 1H, J=4.7 Hz, NH); 8.12 (dd, 1H, J=2.1 and 7.3 Hz); 7.87 (dd, 1H, J=2.7 and 6.3 Hz); 7.63–7.34 (m, 8H); 7.13 (dd, 1H, J=1.6 and 6.7 Hz); 6.33 (s, 1H, H azole); 4.44 (broad s, 2H); 3.14 (m, 2H); 2.7 (m, 2H); 1.5 (m, 4H). MS/LC: m/z=465.21 (M+H)$^+$.

A series of 2-arylimino-2,3-dihydrothiazoles was synthesized according to method F using our robotic system (ACT MOS 496):

R1=—C(R11R12)-CO-R10

R2, R3 and R4 groups already described in method A

R10 groups:

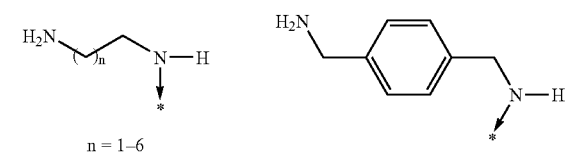

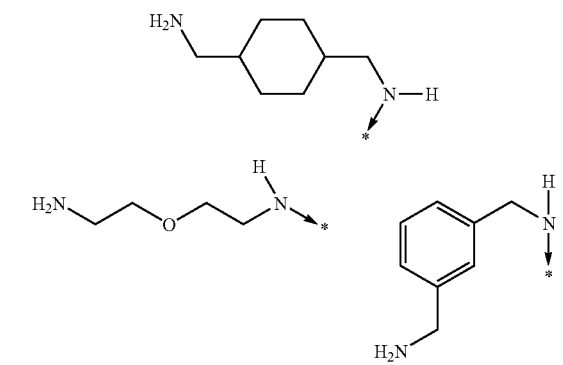

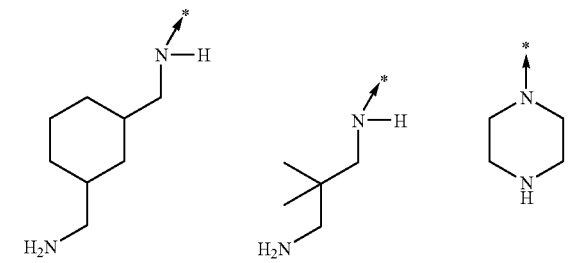

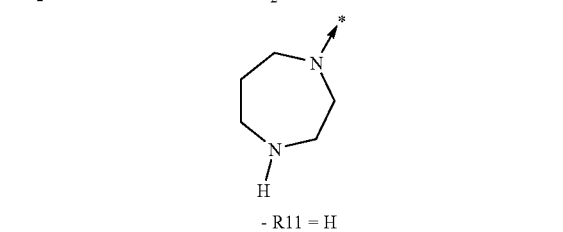

- R11 = H

-R12 groups:

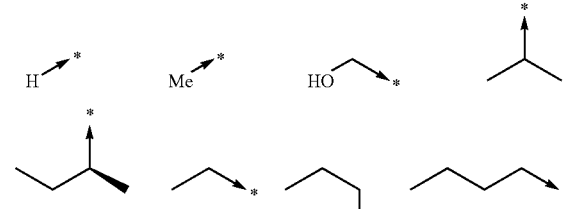

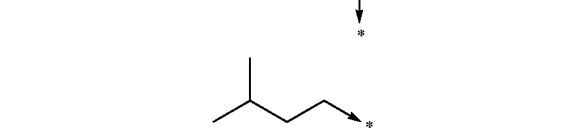

-continued

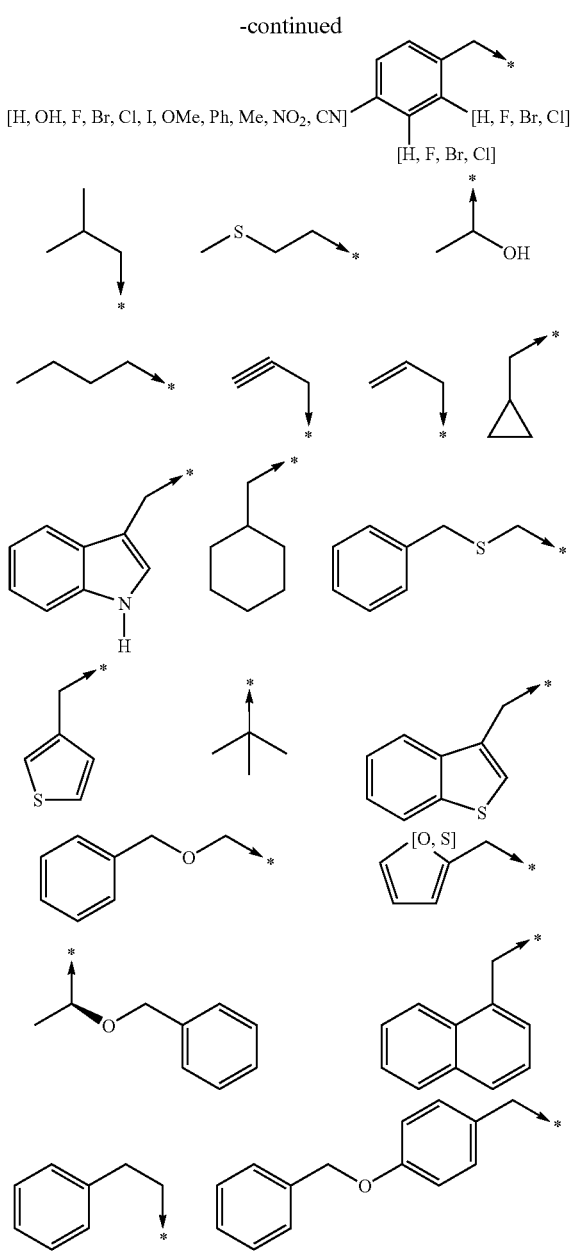

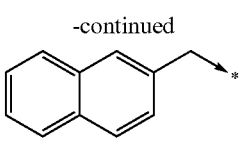

EXAMPLES

Examples obtained according to methods A, B, C, D, E and F described above are shown below in the tables. These examples are shown to illustrate the above processes and must not in any circumstances be considered as limiting the scope of the invention.

The compounds obtained have been characterized by their retention times (rt) and by mass spectrometry $(M+H)^+$.

The chromatograms are obtained from a high performance liquid chromatography device (Hewlett-Packard 1100) equipped with a scanning UV detector. The following conditions were used to measure the retention times by high performance liquid chromatography, it being understood that the extraction wavelength of each of the chromatograms is 220 nm:

| t (min.) | A (%) | B (%) |
|---|---|---|
| 0 | 90 | 10 |
| 6 | 15 | 85 |
| 8 | 15 | 85 |

Eluent A: water + 0.02% trifluoroacetic acid; eluent B: acetonitrile.
Flow rate: 1 ml/min; volume injected: 5 µl; temperature: 40° C.
Column: Uptisphere 3 µm ODS, 50 × 4.6 mm i.d. (Interchim)

The mass spectra are obtained from a single quadrupole mass spectrometer equipped with an electrospray source (Micromass, Platform II).

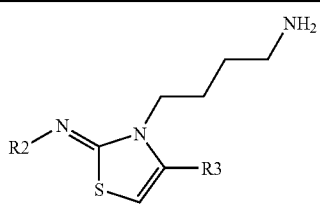

| Ex. | R2 | R3 | Purity (%) | rt (min.) | $[M + H]^+$ |
|---|---|---|---|---|---|
| 7 | (phenyl) | (tert-butyl) | 91.2 | 3.09 | 304.2 |

-continued
| # | 201 | 202 | | | |
|---|---|---|---|---|---|
| 8 | 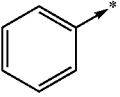 | 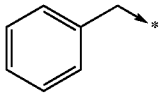 | 93.1 | 3.38 | 338.2 |
| 9 | 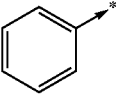 | 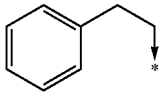 | 94 | 3.56 | 352.2 |
| 10 | 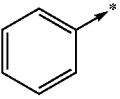 | 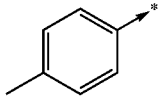 | 93.3 | 3.42 | 338.2 |
| 11 | 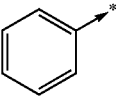 | 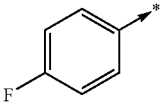 | 96.6 | 3.25 | 342.2 |
| 12 | 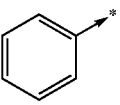 | 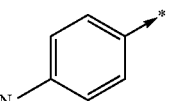 | 96.4 | 3.46 | 365.2 |
| 13 | 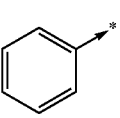 |  | 91.9 | 3.86 | 393.2 |
| 14 | 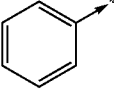 | 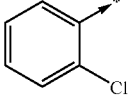 | 96.4 | 3.44 | 358.2 |
| 15 | 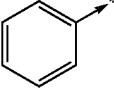 | 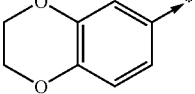 | 95.6 | 3.34 | 382.2 |
| 16 | 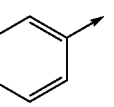 | 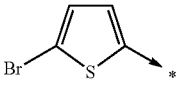 | 94.5 | 3.7 | 408 |
| 17 | 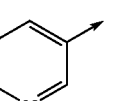 | 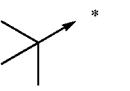 | 54.43 | 2.9 | 305.2 |
| 18 | 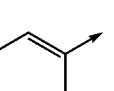 | 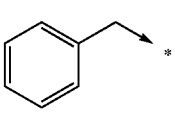 | 50.4 | 3.14 | 339.2 |
| 19 | 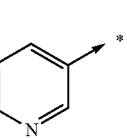 | 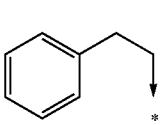 | 48.9 | 3.38 | 535.2 |

-continued
| | | | | | |
|---|---|---|---|---|---|
| 20 | 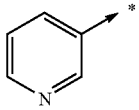 | 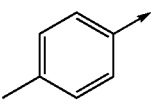 | 39.3 | 3.26 | 339.2 |
| 21 | 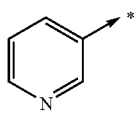 | 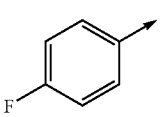 | 49.5 | 3.06 | 343.2 |
| 22 | 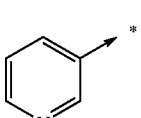 | 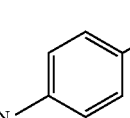 | 42.3 | 3.29 | 366.2 |
| 23 | 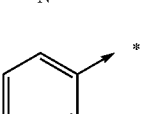 | 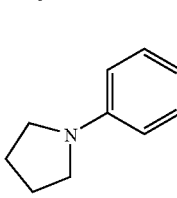 | 43.4 | 3.7 | 394.3 |
| 24 | 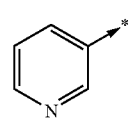 | 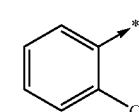 | 56.7 | 3.16 | 359.2 |
| 25 | 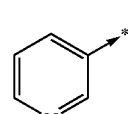 | 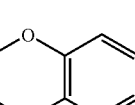 | 45.3 | 3.09 | 383.2 |
| 26 | 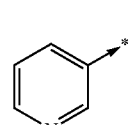 | 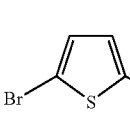 | 45.7 | 3.3 | 409 |
| 27 | 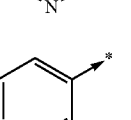 |  | 96.8 | 3.41 | 332.3 |
| 28 | 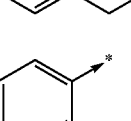 | 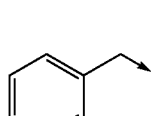 | 92.8 | 3.7 | 366.3 |
| 29 | 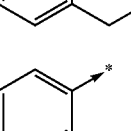 | 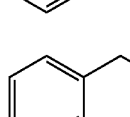 | 90.6 | 3.84 | 380.3 |
| 30 | 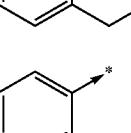 | 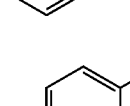 | 93.7 | 3.76 | 366.3 |
| 31 | 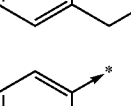 | 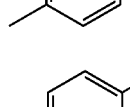 | 94.4 | 3.63 | 370.2 |

| | | | | | |
|---|---|---|---|---|---|
| 32 | 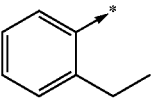 | 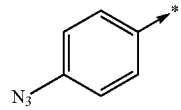 | 89.1 | 3.82 | 393.2 |
| 33 | 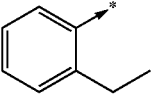 | 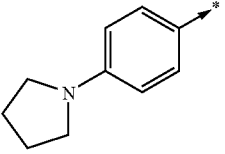 | 90.1 | 4.12 | 410.2 |
| 34 | 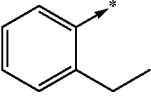 | 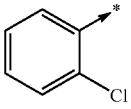 | 96.7 | 3.83 | 386.2 |
| 35 | 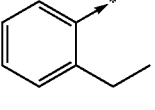 | 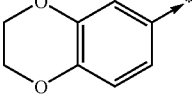 | 95.8 | 3.67 | 410.2 |
| 36 | 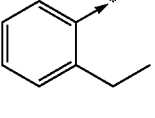 | 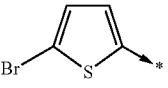 | 93.4 | 4.17 | 436.1 |
| 37 | 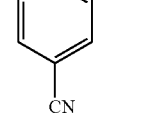 | 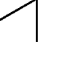 | 88.4 | 3.64 | 329.25 |
| 38 | 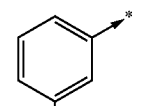 | 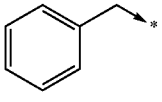 | 91.8 | 4.03 | 363.2 |
| 39 | 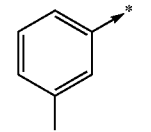 | 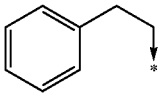 | 88.6 | 4.15 | 377.2 |
| 40 | 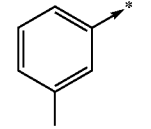 | 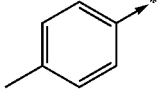 | 94.1 | 4.22 | 363.2 |
| 41 | 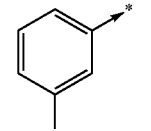 | 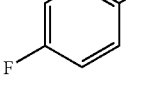 | 95.2 | 4.1 | 376.2 |

| | 207 | 208 | | | |
|---|---|---|---|---|---|
| 42 | 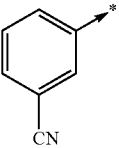 | 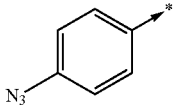 | 92.8 | 4.35 | 390.2 |
| 43 | 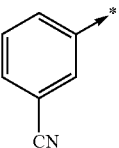 | 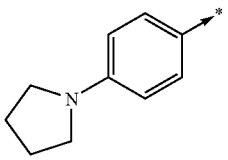 | 94.1 | 4.54 | 418.2 |
| 44 | 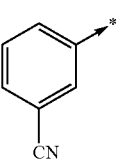 | 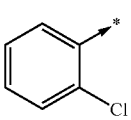 | 95 | 4.34 | 383.1 |
| 45 | 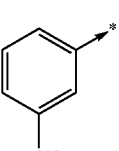 | 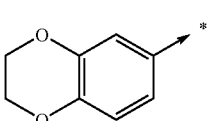 | 95.1 | 4.06 | 407.2 |
| 46 | 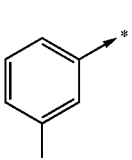 | 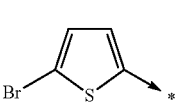 | 93 | 4.7 | 433.1 |
| 47 | 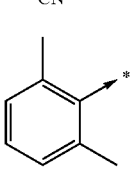 | 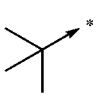 | 96.4 | 3.32 | 332.3 |
| 48 | 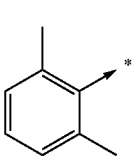 | 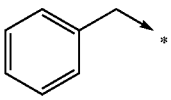 | 92.9 | 3.62 | 366.3 |
| 49 | 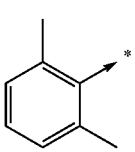 | 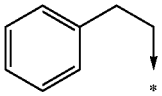 | 95.6 | 3.76 | 380.3 |
| 50 | 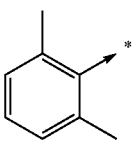 | 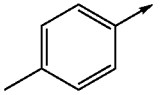 | 95.6 | 3.64 | 366.33 |
| 51 | 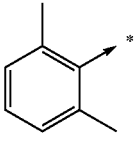 |  | 96 | 3.51 | 370.2 |

-continued
| | 209 | 210 | | | |
|---|---|---|---|---|---|
| 52 | 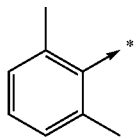 | 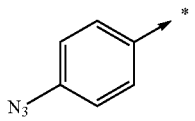 | 87 | 3.69 | 390.2 |
| 53 | 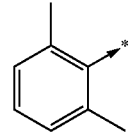 | 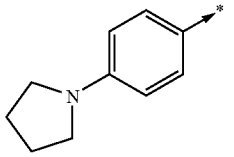 | 80.9 | 4.04 | 421.3 |
| 54 | 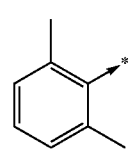 | 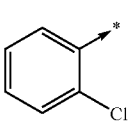 | 97.1 | 3.7 | 436.1 |
| 55 | 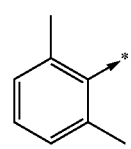 | 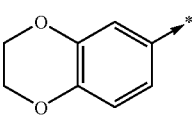 | 94.6 | 3.59 | 410.2 |
| 56 | 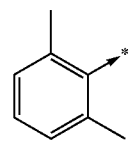 | 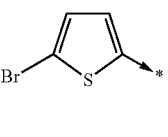 | 95.6 | 3.92 | 436.1 |
| 57 | 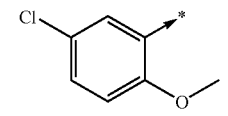 | 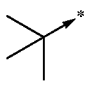 | 82.1 | 3.66 | 368.2 |
| 58 | 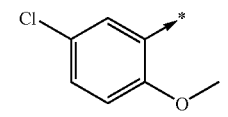 | 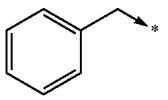 | 90.7 | 3.94 | 402.2 |
| 59 | 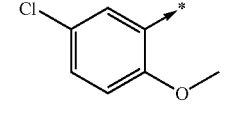 |  | 85.5 | 4.06 | 416.2 |
| 60 | 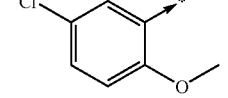 | 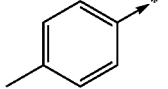 | 94.4 | 4.09 | 402.2 |
| 61 | 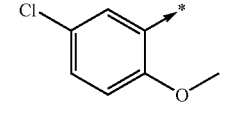 | 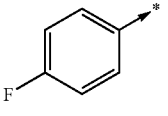 | 95.1 | 3.99 | 406.2 |
| 62 | 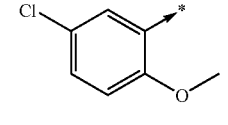 | 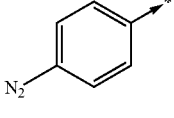 | 93.6 | 4.21 | 429.2 |

| | 211 | 212 | | | |
|---|---|---|---|---|---|
| 63 | 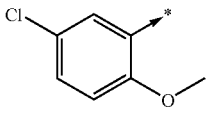 | 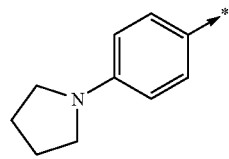 | 93.6 | 4.39 | 457.2 |
| 64 | 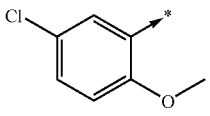 | 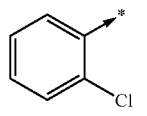 | 96 | 4.22 | 422.1 |
| 65 | 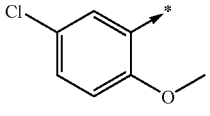 | 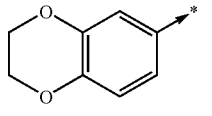 | 91.6 | 3.96 | 446.2 |
| 66 | 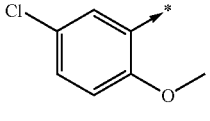 | 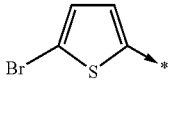 | 94.5 | 4.65 | 472 |
| 67 | 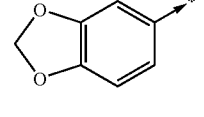 | 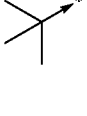 | 97 | 3.07 | 348.2 |
| 68 | 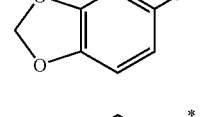 | 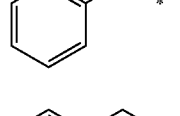 | 93.6 | 3.36 | 382.2 |
| 69 | 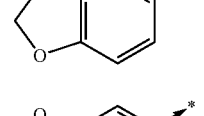 | 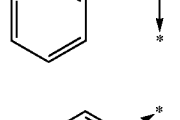 | 93.4 | 3.54 | 396.2 |
| 70 | 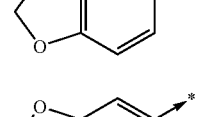 | 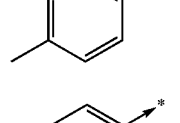 | 94.7 | 3.41 | 382.1 |
| 71 | 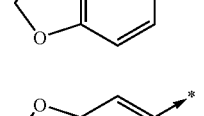 | 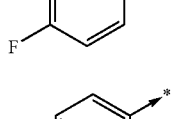 | 96.3 | 3.24 | 386.2 |
| 72 | 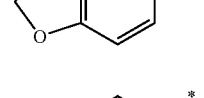 | 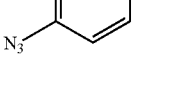 | 94.5 | 3.44 | 409.1 |
| 73 | 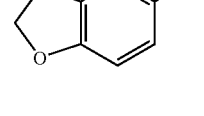 | 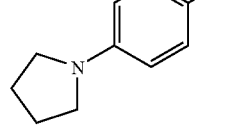 | 93.4 | 3.83 | 437.2 |
| 74 |  | 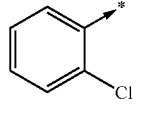 | 95.4 | 3.41 | 402.1 |

-continued
| | | | | | |
|---|---|---|---|---|---|
| 75 |  | 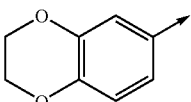 | 95.7 | 3.32 | 426.2 |
| 76 | 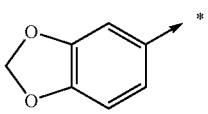 |  | 92.4 | 3.64 | 452.2 |
| 77 |  | 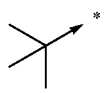 | 98.1 | 3.66 | 324.2 |
| 78 | 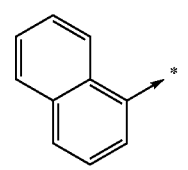 |  | 91.2 | 3.98 | 388.2 |
| 79 | 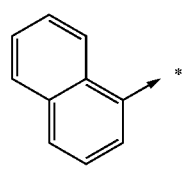 | 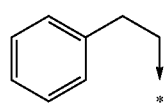 | 81.9 | 4.09 | 402.2 |
| 80 | 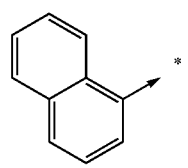 |  | 96.1 | 4.12 | 388.2 |
| 81 | 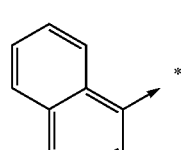 | 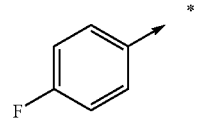 | 96.1 | 4.03 | 392.2 |
| 82 | 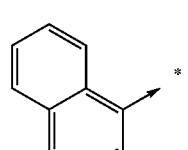 | 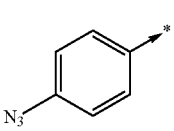 | 94.2 | 4.24 | 415.2 |
| 83 | 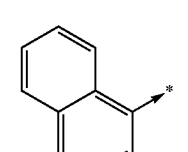 | 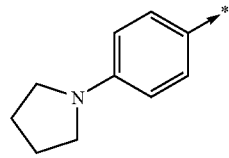 | 93.3 | 4.39 | 443.3 |
| 84 | 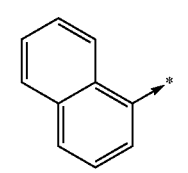 | 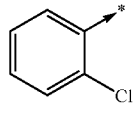 | 96.3 | 4.28 | 408.1 |

-continued
| Ex. | | | Purity (%) | rt (min.) | [M + H]⁺ |
|---|---|---|---|---|---|
| 85 | 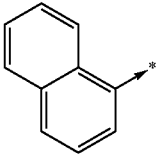 | 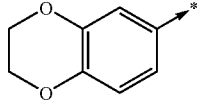 | 94.2 | 4.0 | 432.2 |
| 86 | 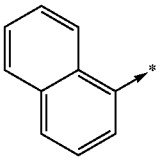 | 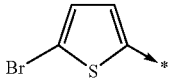 | 95.6 | 4.7 | 458.1 |
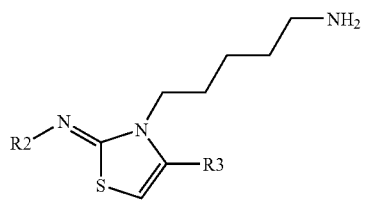
| Ex. | R2 | R3 | Purity (%) | rt (min.) | [M + H]⁺ |
|---|---|---|---|---|---|
| 87 | 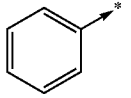 | 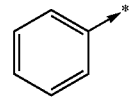 | 97 | 3.35 | 338.2 |
| 88 | 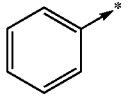 | 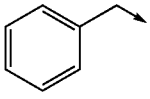 | 94 | 3.51 | 352.3 |
| 89 | 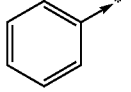 | 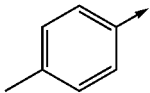 | 94 | 3.58 | 352.3 |
| 90 | 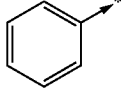 | 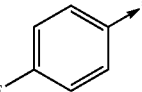 | 97 | 3.42 | 356.2 |
| 91 | 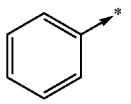 | 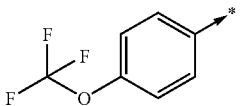 | 86 | 4.01 | 422.2 |
| 92 | 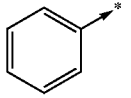 | 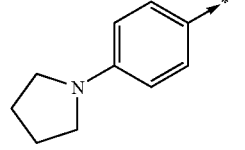 | 96 | 3.99 | 407.3 |
| 93 | 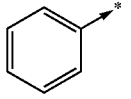 | 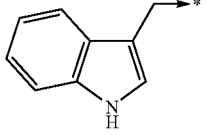 | 7 | 3.65 | 391.3 |

-continued

| | 217 | | 218 | | |
|---|---|---|---|---|---|
| 94 | phenyl* | benzofuran-2-yl* | 92 | 4.11 | 378.2 |
| 95 | phenyl* | N-(2-*)ethyl-phthalimide | 95 | 3.43 | 435.2 |
| 96 | phenyl* | 5-bromo-thiophen-2-yl* | 97 | 3.91 | 422.1 |
| 97 | pyridin-3-yl* | phenyl* | 43 | 3.19 | 339.2 |
| 98 | pyridin-3-yl* | benzyl* | 32 | 3.33 | 353.2 |
| 99 | pyridin-3-yl* | 4-methylphenyl* | 39 | 3.45 | 353.2 |
| 100 | pyridin-3-yl* | 4-fluorophenyl* | 39 | 3.28 | 357.2 |
| 101 | pyridin-3-yl* | 4-(trifluoromethoxy)phenyl* | 42 | 3.8 | 423.2 |
| 102 | pyridin-3-yl* | 4-(pyrrolidin-1-yl)phenyl* | 41 | 3.89 | 408.2 |
| 103 | pyridin-3-yl* | (1H-indol-3-yl)methyl* | 14 | 3.43 | 392.2 |
| 104 | pyridin-3-yl* | benzofuran-2-yl* | 39 | 3.62 | 379.2 |

-continued
| | | | | | |
|---|---|---|---|---|---|
| 105 | 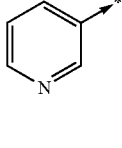 | 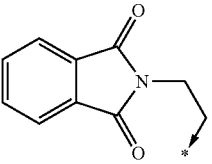 | 28 | 3.2 | 436.2 |
| 106 | 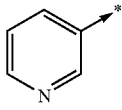 | 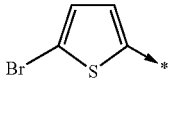 | 35 | 3.56 | 423.1 |
| 107 | 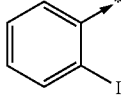 | 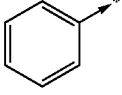 | 95 | 4.65 | 464.1 |
| 108 | 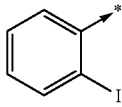 | 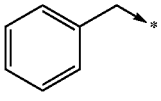 | 89 | 4.64 | 478.2 |
| 109 | 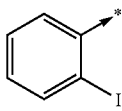 | 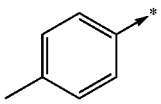 | 82 | 4.88 | 478.1 |
| 110 | 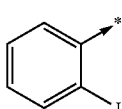 | 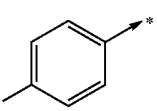 | 92 | 4.76 | 482.1 |
| 111 | 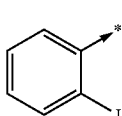 | 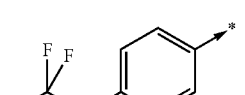 | 90 | 5.41 | 548.1 |
| 112 | 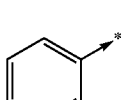 | 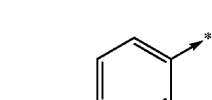 | 86 | 5.13 | 533.2 |
| 113 | 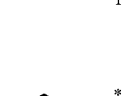 | 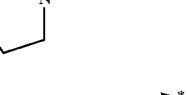 | 9 | 4.5 | 517.1 |
| 114 | 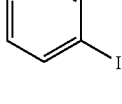 | 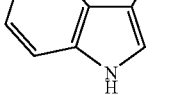 | 95 | 5.49 | 504.1 |
| 115 | 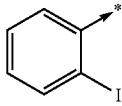 | 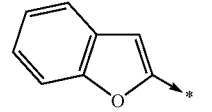 | 80 | 4.4 | 561.1 |

-continued
| | 221 | 222 | | | |
|---|---|---|---|---|---|
| 116 | 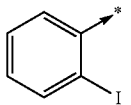 | 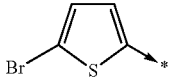 | 89 | 5.4 | 548.0 |
| 117 | 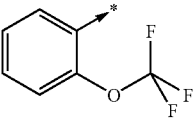 | 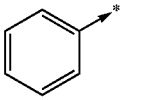 | 96 | 4.85 | 422.2 |
| 118 | 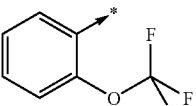 | 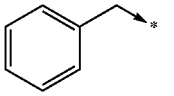 | 91 | 4.86 | 436.2 |
| 119 | 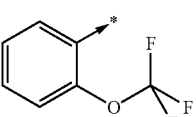 | 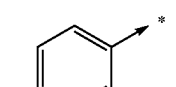 | 88 | 5.08 | 436.2 |
| 120 | 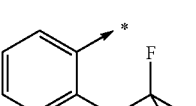 | 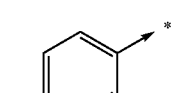 | 95 | 4.96 | 440.2 |
| 121 | 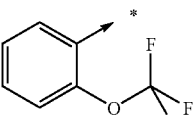 | 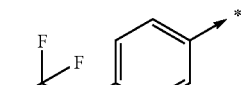 | 81 | 5.56 | 506.2 |
| 122 | 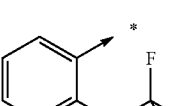 | 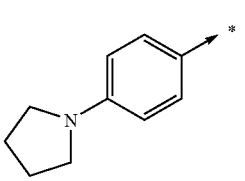 | 83 | 5.34 | 491.2 |
| 123 | 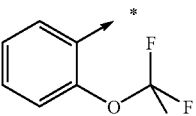 | 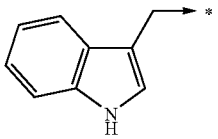 | 3 | 4.7 | 475.3 |
| 124 | 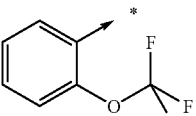 | 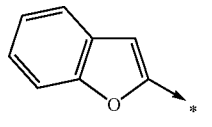 | 91 | 5.59 | 462.2 |
| 125 | 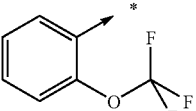 | 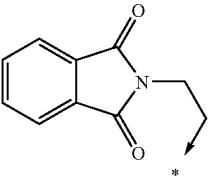 | 92 | 4.61 | 519.2 |

| # | R1 | R2 | Yield | RT | MS |
|---|---|---|---|---|---|
| 126 | 2-(trifluoromethoxy)phenyl | 5-bromothiophen-2-yl | 92 | 5.52 | 506.1 |
| 127 | 2,6-dimethylphenyl | phenyl | 98 | 3.63 | 366.3 |
| 128 | 2,6-dimethylphenyl | benzyl | 97 | 3.76 | 380.3 |
| 129 | 2,6-dimethylphenyl | 4-methylphenyl | 98 | 3.82 | 380.3 |
| 130 | 2,6-dimethylphenyl | 4-fluorophenyl | 98 | 3.67 | 384.2 |
| 131 | 2,6-dimethylphenyl | 4-(trifluoromethoxy)phenyl | 97 | 4.16 | 450.2 |
| 132 | 2,6-dimethylphenyl | 4-(pyrrolidin-1-yl)phenyl | 96 | 4.2 | 435.3 |
| 133 | 2,6-dimethylphenyl | (1H-indol-3-yl)methyl | 21 | 3.9 | 419.3 |
| 134 | 2,6-dimethylphenyl | benzofuran-2-yl | 88 | 4.28 | 406.2 |
| 135 | 2,6-dimethylphenyl | 2-(1,3-dioxoisoindolin-2-yl)ethyl | 97 | 3.68 | 463.3 |

-continued

| # | 225 | 226 | | | |
|---|---|---|---|---|---|
| 136 | 2,6-dimethylphenyl | 5-bromothien-2-yl | 82 | 4.09 | 450.1 |
| 137 | 4-sulfamoylphenyl | phenyl | 93 | 3.44 | 417.2 |
| 138 | 4-sulfamoylphenyl | benzyl | 94 | 3.5 | 431.2 |
| 139 | 4-sulfamoylphenyl | 4-methylphenyl | 95 | 3.71 | 431.2 |
| 140 | 4-sulfamoylphenyl | 4-fluorophenyl | 95 | 3.58 | 435.2 |
| 141 | 4-sulfamoylphenyl | 4-(trifluoromethoxy)phenyl | 94 | 4.27 | 501.2 |
| 142 | 4-sulfamoylphenyl | 4-(pyrrolidin-1-yl)phenyl | 93 | 4.05 | 486.6 |
| 143 | 4-sulfamoylphenyl | benzofuran-2-yl | 94 | 4.28 | 457.2 |
| 144 | 4-sulfamoylphenyl | 2-(1,3-dioxoisoindolin-2-yl)ethyl | 92 | 3.39 | 514.2 |
| 145 | 4-sulfamoylphenyl | 5-bromothien-2-yl | 85 | 4.16 | 501.1 |

-continued

| # | 227 | 228 | | | |
|---|---|---|---|---|---|
| 146 | benzo[1,3]dioxol-5-yl* | phenyl* | 97 | 3.36 | 382.2 |
| 147 | benzo[1,3]dioxol-5-yl* | benzyl* | 94 | 3.53 | 396.2 |
| 148 | benzo[1,3]dioxol-5-yl* | 4-methylphenyl* | 97 | 3.6 | 396.2 |
| 149 | benzo[1,3]dioxol-5-yl* | 4-fluorophenyl* | 97 | 3.43 | 400.2 |
| 150 | benzo[1,3]dioxol-5-yl* | 4-(trifluoromethoxy)phenyl* | 97 | 3.95 | 466.2 |
| 151 | benzo[1,3]dioxol-5-yl* | 4-(pyrrolidin-1-yl)phenyl* | 95 | 4.01 | 451.3 |
| 152 | benzo[1,3]dioxol-5-yl* | (1H-indol-3-yl)methyl* | 15 | 3.57 | 435.2 |
| 153 | benzo[1,3]dioxol-5-yl* | benzofuran-2-yl* | 94 | 4.0 | 422.2 |
| 154 | benzo[1,3]dioxol-5-yl* | 2-(1,3-dioxoisoindolin-2-yl)ethyl* | 95 | 3.45 | 479.3 |
| 155 | benzo[1,3]dioxol-5-yl* | 5-bromothiophen-2-yl* | 95 | 3.84 | 466.1 |
| 156 | naphthalen-1-yl* | phenyl* | 96 | 4.11 | 388.2 |

-continued

| | | | | | |
|---|---|---|---|---|---|
| 157 | naphthalen-1-yl | benzyl | 90 | 4.14 | 402.2 |
| 158 | naphthalen-1-yl | 4-methylphenyl | 96 | 4.31 | 402.2 |
| 159 | naphthalen-1-yl | 4-fluorophenyl | 96 | 4.21 | 406.2 |
| 160 | naphthalen-1-yl | 4-(trifluoromethoxy)phenyl | 97 | 4.83 | 472.3 |
| 161 | naphthalen-1-yl | 4-(pyrrolidin-1-yl)phenyl | 95 | 4.57 | 457.3 |
| 162 | naphthalen-1-yl | benzofuran-2-yl | 96 | 5.12 | 428.2 |
| 163 | naphthalen-1-yl | 2-(phthalimido)ethyl | 88 | 4.01 | 485.3 |
| 164 | naphthalen-1-yl | 5-bromothiophen-2-yl | 97 | 4.91 | 472.1 |

-continued
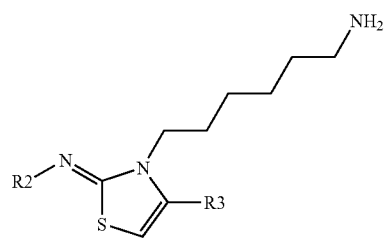
| Ex. | R2 | R3 | Purity (%) | rt (min.) | [M + H]+ |
|---|---|---|---|---|---|
| 165 | phenyl | tert-butyl | 93 | 3.52 | 332.3 |
| 166 | phenyl | 3-fluorophenyl | 99 | 3.76 | 370.3 |
| 167 | phenyl | 4-azidophenyl | 97 | 3.9 | 393.3 |
| 168 | phenyl | 4-(trifluoromethoxy)phenyl | 98 | 4.25 | 436.2 |
| 169 | phenyl | 4-chloro-3-nitrophenyl | 98 | 4.14 | 431.2 |
| 170 | phenyl | 3,5-bis(trifluoromethyl)phenyl | 99 | 4.79 | 488.2 |
| 171 | phenyl | 2,3-dihydro-1,4-benzodioxin-6-yl | 98 | 3.74 | 410.2 |
| 172 | phenyl | adamantyl | 98 | 4.28 | 410.3 |
| 173 | phenyl | benzofuran-2-yl | 98 | 4.38 | 392.2 |

-continued

| | | | | | |
|---|---|---|---|---|---|
| 174 | phenyl* | 5-chloro-3-methylbenzothiophen-2-yl* | 98 | 4.73 | 456.2 |
| 175 | 2-isopropylphenyl* | tert-butyl* | 98 | 4.06 | 374.3 |
| 176 | 2-isopropylphenyl* | 3-fluorophenyl* | 98 | 4.37 | 412.3 |
| 177 | 2-isopropylphenyl* | 4-azidophenyl* | 97 | 4.46 | 435.3 |
| 178 | 2-isopropylphenyl* | 4-(trifluoromethoxy)phenyl* | 98 | 4.8 | 478.3 |
| 179 | 2-isopropylphenyl* | 4-chloro-3-nitrophenyl* | 99 | 4.78 | 473.3 |
| 180 | 2-isopropylphenyl* | 3,5-bis(trifluoromethyl)phenyl* | 94 | 5.43 | 530.3 |
| 181 | 2-isopropylphenyl* | 2,3-dihydrobenzo[1,4]dioxin-6-yl* | 97 | 4.27 | 452.3 |
| 182 | 2-isopropylphenyl* | adamantyl* | 85 | 4.73 | 452.4 |

-continued
| | | | | | |
|---|---|---|---|---|---|
| 183 | 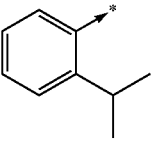 | 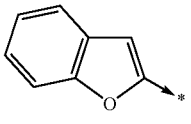 | 98 | 5.07 | 434.3 |
| 184 | 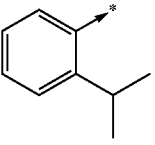 | 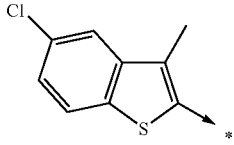 | 93 | 5.33 | 498.3 |
| 185 | 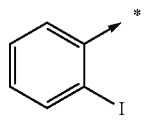 |  | 98 | 4.61 | 458.2 |
| 186 | 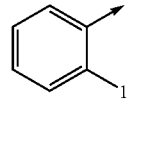 | 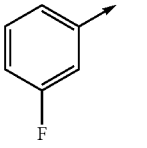 | 97 | 5.23 | 496.1 |
| 187 | 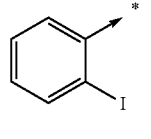 | 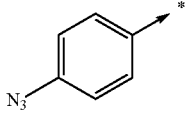 | 96 | 5.34 | 519.1 |
| 188 | 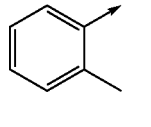 | 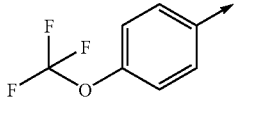 | 97 | 5.72 | 562.1 |
| 189 | 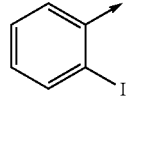 | 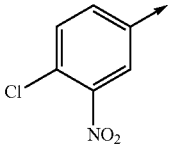 | 98 | 5.57 | 557.1 |
| 190 | 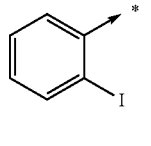 | 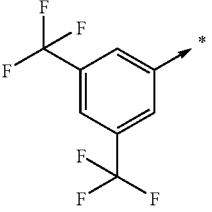 | 96 | 6.16 | 614.1 |
| 191 | 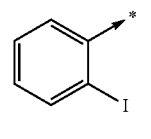 | 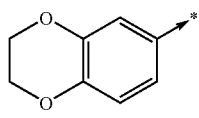 | 96 | 4.97 | 536.1 |
| 192 | 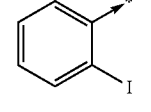 |  | 85 | 5.67 | 536.2 |

-continued
| | | | | | |
|---|---|---|---|---|---|
| 193 | 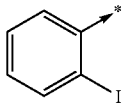 | 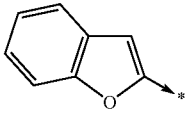 | 96 | 5.86 | 518.1 |
| 194 | 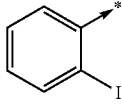 | 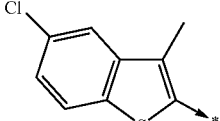 | 97 | 6.32 | 582.1 |
| 195 | 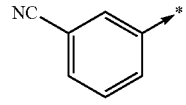 | 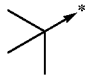 | 96 | 4.16 | 357.3 |
| 196 | 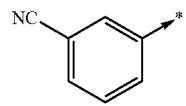 | 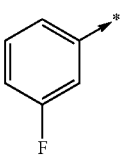 | 98 | 4.74 | 395.2 |
| 197 | 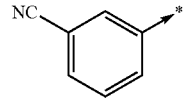 | 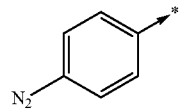 | 97 | 4.86 | 418.2 |
| 198 | 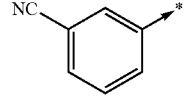 | 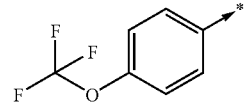 | 98 | 5.26 | 461.2 |
| 199 | 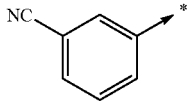 | 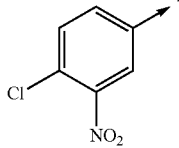 | 98 | 5.12 | 456.2 |
| 200 | 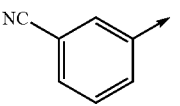 | 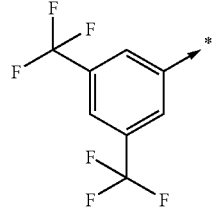 | 97 | 5.72 | 513.2 |
| 201 | 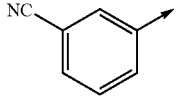 | 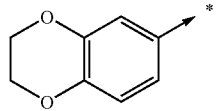 | 96 | 4.51 | 435.2 |
| 202 | 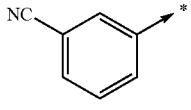 | 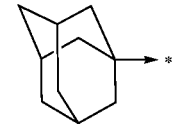 | 98 | 5.18 | 435.3 |

-continued
| | | | | | |
|---|---|---|---|---|---|
| 203 | 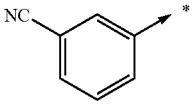 | 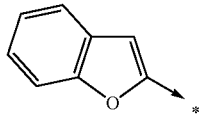 | 95 | 5.37 | 417.2 |
| 204 | 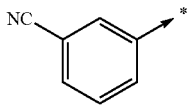 | 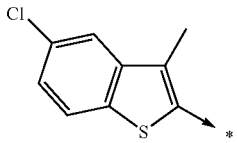 | 95 | 5.84 | 481.2 |
| 205 | 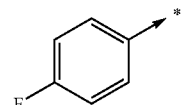 |  | 96 | 3.63 | 350.3 |
| 206 | 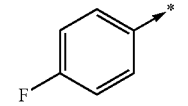 | 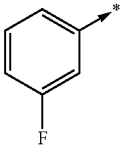 | 98 | 3.95 | 388.2 |
| 207 | 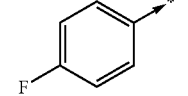 | 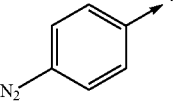 | 95 | 4.07 | 411.2 |
| 208 | 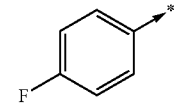 | 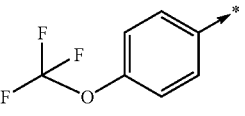 | 98 | 4.44 | 454.2 |
| 209 | 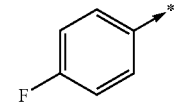 | 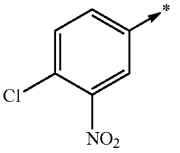 | 97 | 4.38 | 449.2 |
| 210 | 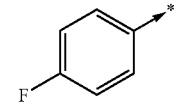 | 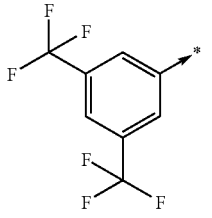 | 89 | 5.03 | 506.2 |
| 211 | 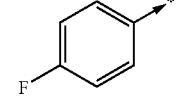 | 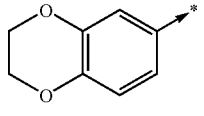 | 96 | 3.87 | 428.2 |
| 212 | 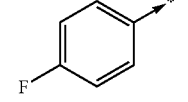 |  | 97 | 4.4 | 428.3 |

-continued
| | | | | | |
|---|---|---|---|---|---|
| 213 | 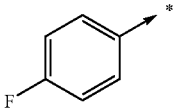 | 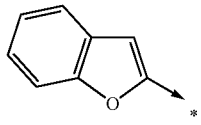 | 96 | 4.63 | 410.2 |
| 214 | 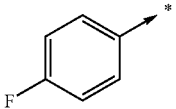 | 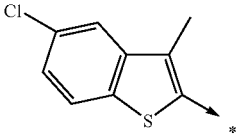 | 96 | 4.96 | 474.2 |
| 215 | 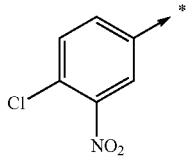 | 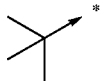 | 94 | 5.38 | 411.2 |
| 216 | 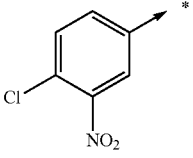 | 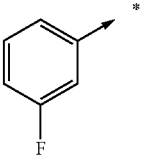 | 98 | 5.63 | 449.2 |
| 217 | 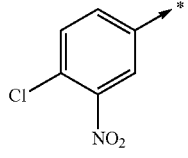 | 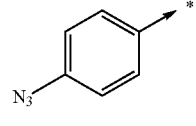 | 96 | 5.77 | 472.2 |
| 218 | 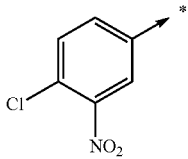 | 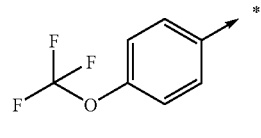 | 98 | 6.04 | 515.2 |
| 219 | 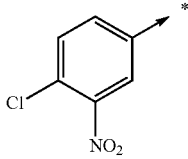 | 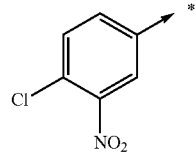 | 98 | 5.74 | 510.1 |
| 220 | 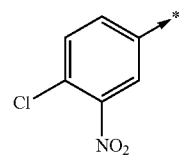 | 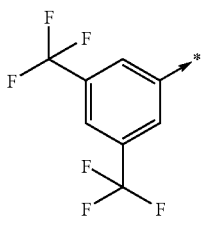 | 91 | 6.29 | 567.2 |
| 221 | 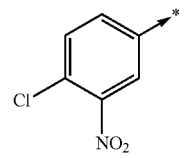 | 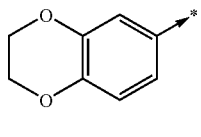 | 98 | 5.53 | 489.2 |

-continued
| | | | | | |
|---|---|---|---|---|---|
| 222 | 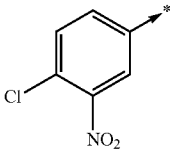 | 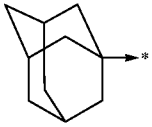 | 96 | 6.38 | 489.3 |
| 223 | 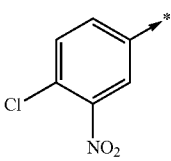 | 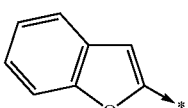 | 97 | 6.0 | 471.2 |
| 224 | 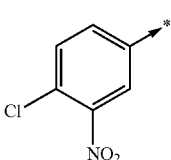 | 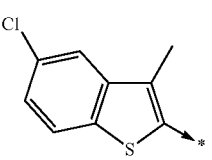 | 98 | 6.49 | 535.1 |
| 225 | 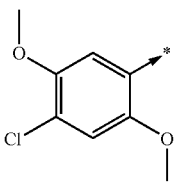 | 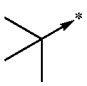 | 98 | 3.99 | 426.3 |
| 226 | 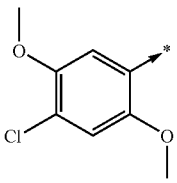 | 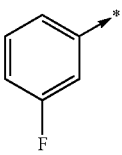 | 98 | 4.34 | 464.2 |
| 227 | 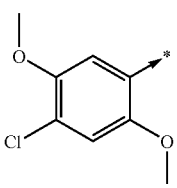 | 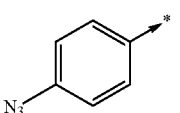 | 96 | 4.43 | 487.3 |
| 228 | 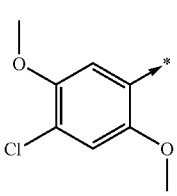 | 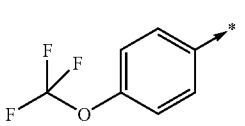 | 97 | 4.78 | 530.2 |
| 229 | 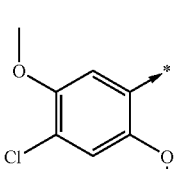 | 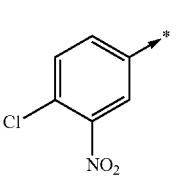 | 98 | 4.76 | 525.2 |

-continued
| | | | | | |
|---|---|---|---|---|---|
| 230 | 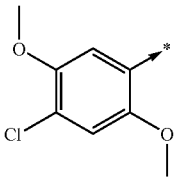 | 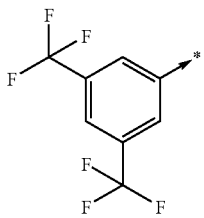 | 96 | 5.36 | 582.2 |
| 231 | 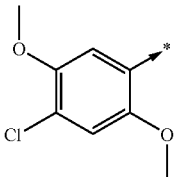 | 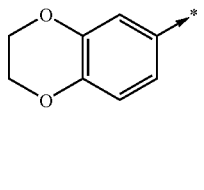 | 95 | 4.23 | 504.3 |
| 232 | 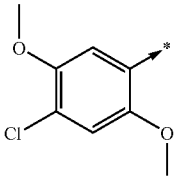 | 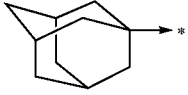 | 97 | 4.7 | 504.3 |
| 233 | 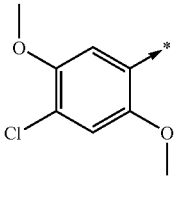 | 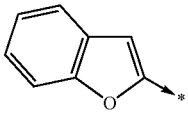 | 98 | 4.99 | 486.2 |
| 234 | 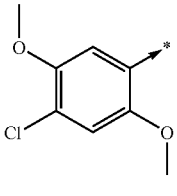 | 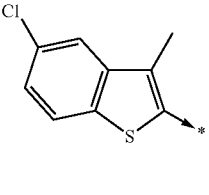 | 97 | 5.3 | 550.2 |
| 235 | 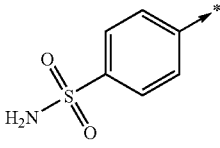 | 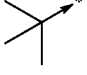 | 96 | 3.44 | 411.2 |
| 236 | 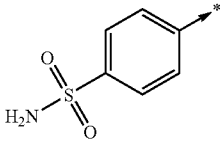 | 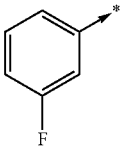 | 95 | 3.94 | 449.2 |
| 237 | 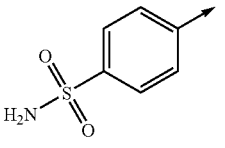 | 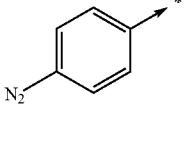 | 96 | 4.11 | 472.3 |

-continued
| | | | Purity (%) | rt (min.) | [M + H]+ |
|---|---|---|---|---|---|
| 238 | 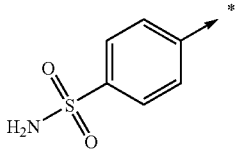 | 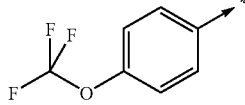 | 95 | 4.52 | 515.2 |
| 239 | 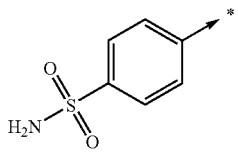 | 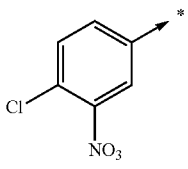 | 95 | 4.39 | 510.2 |
| 240 | 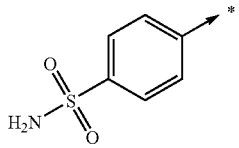 | 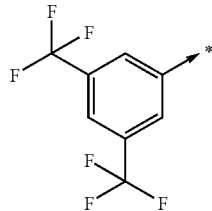 | 94 | 5.01 | 567.2 |
| 241 | 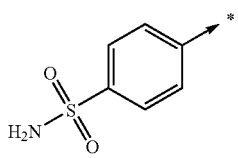 | 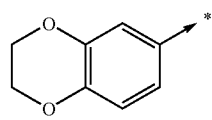 | 96 | 3.74 | 489.2 |
| 242 | 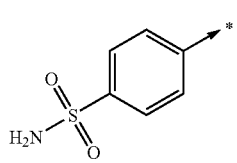 | 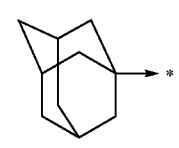 | 96 | 4.41 | 489.3 |
| 243 | 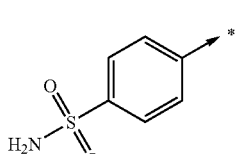 | 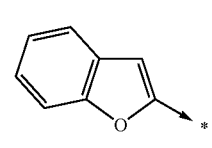 | 96 | 4.56 | 471.2 |
| 244 | 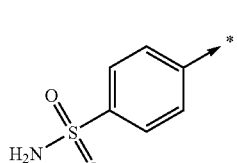 | 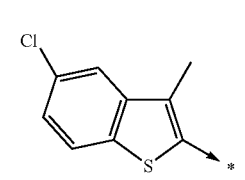 | 97 | 5.01 | 535.2 |
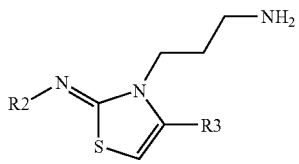
| Ex. | R2 | R3 | Purity (%) | rt (min.) | [M + H]+ |
|---|---|---|---|---|---|
| 245 | 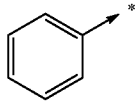 | 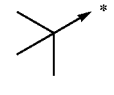 | 98.1 | 3.2 | 290.2 |

-continued
| | | | | | |
|---|---|---|---|---|---|
| 246 | 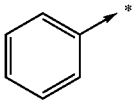 | 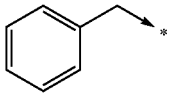 | 96.9 | 3.78 | 324.2 |
| 247 | 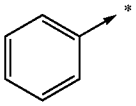 | 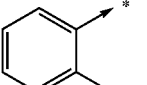 | 69.3 | 3.88 | 355.2 |
| 248 | 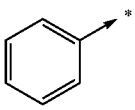 | 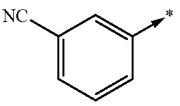 | 99.3 | 3.79 | 335.2 |
| 249 | 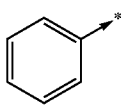 | 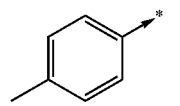 | 99.4 | 3.86 | 324.2 |
| 250 | 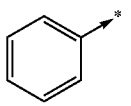 | 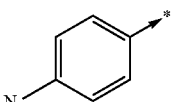 | 98 | 3.97 | 351.2 |
| 251 | 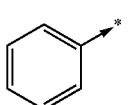 | 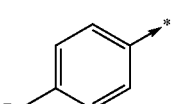 | 98.7 | 4.14 | 388.1 |
| 252 | 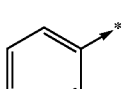 | 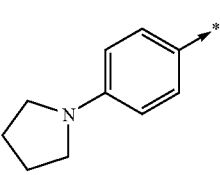 | 93.5 | 4.24 | 379.3 |
| 253 | 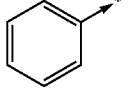 | 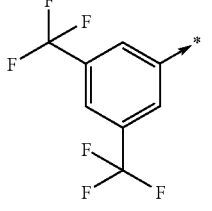 | 82.4 | 5.16 | 446.2 |
| 254 | 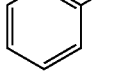 | 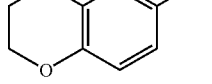 | 98.8 | 3.7 | 368.2 |
| 255 | 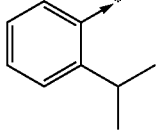 |  | 98.5 | 3.9 | 332.3 |
| 256 | 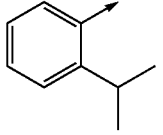 | 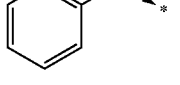 | 92.3 | 4.4 | 366.3 |

-continued
| | | | | | |
|---|---|---|---|---|---|
| 257 | 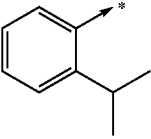 | 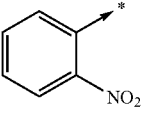 | 82.3 | 4.55 | 397.2 |
| 258 | 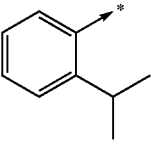 | 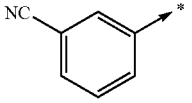 | 98.4 | 4.48 | 377.3 |
| 259 | 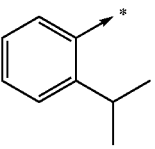 | 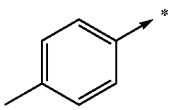 | 97.3 | 4.49 | 366.3 |
| 260 | 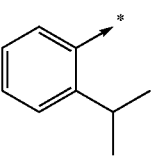 | 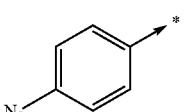 | 95.4 | 4.59 | 393.3 |
| 261 | 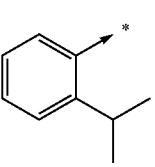 | 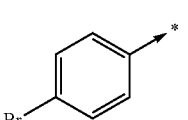 | 98.7 | 4.77 | 430.2 |
| 262 | 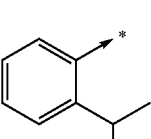 | 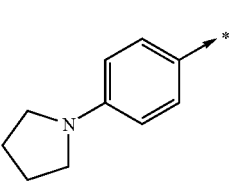 | 90.9 | 4.76 | 421.3 |
| 263 | 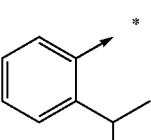 | 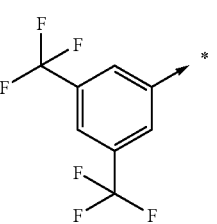 | 98.7 | 5.72 | 488.2 |
| 264 | 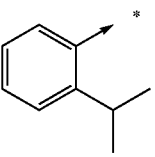 | 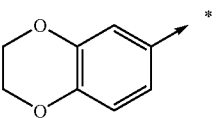 | 97.7 | 4.33 | 410.3 |
| 265 | 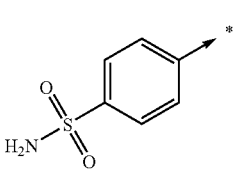 | 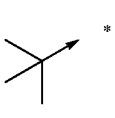 | 98.5 | 3.42 | 369.2 |

-continued
| | 253 | 254 | | | |
|---|---|---|---|---|---|
| 266 | 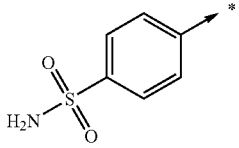 | 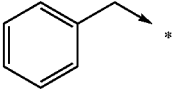 | 94.9 | 3.91 | 403.2 |
| 267 | 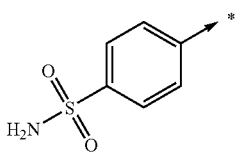 | 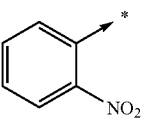 | 98.1 | 3.81 | 434.2 |
| 268 | 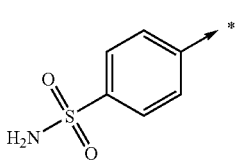 | 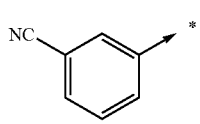 | 97.9 | 3.78 | 414.1 |
| 269 | 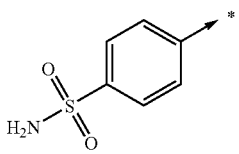 | 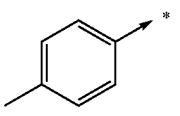 | 98.1 | 4.06 | 403.2 |
| 270 | 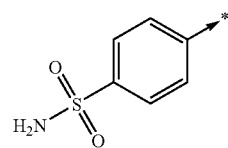 | 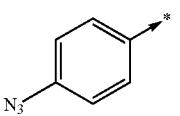 | 96.2 | 4.14 | 430.2 |
| 271 | 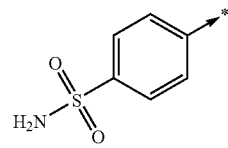 | 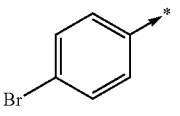 | 98.3 | 4.28 | 467.1 |
| 272 | 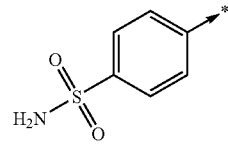 | 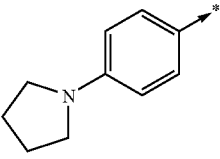 | 96.8 | 4.5 | 458.2 |
| 273 | 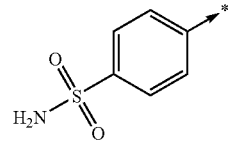 | 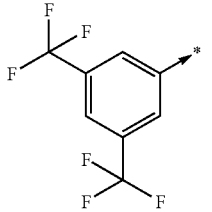 | 98.3 | 4.92 | 525.2 |
| 274 | 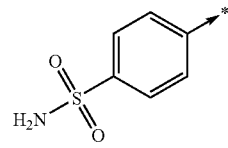 |  | 97.1 | 3.84 | 447.2 |

| | | | | | |
|---|---|---|---|---|---|
| 275 | 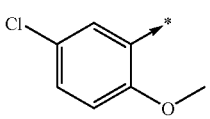 |  | 96.5 | 4.28 | 354.2 |
| 276 | 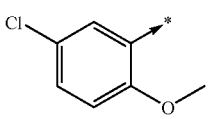 | 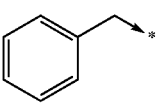 | 93.3 | 5.02 | 388.2 |
| 277 | 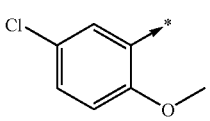 | 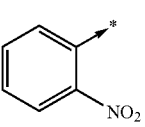 | 68.7 | 4.96 | 419.2 |
| 278 | 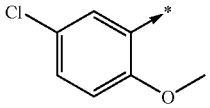 | 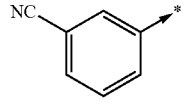 | 97.8 | 4.86 | 399.2 |
| 279 | 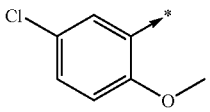 | 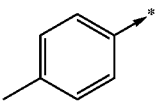 | 96 | 5.13 | 388.2 |
| 280 | 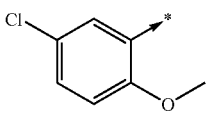 | 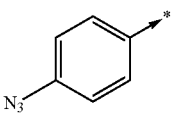 | 96.9 | 5.18 | 415.2 |
| 281 | 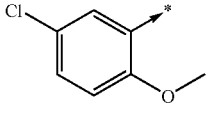 | 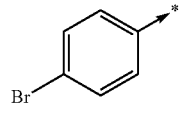 | 98.6 | 5.31 | 452.1 |
| 282 | 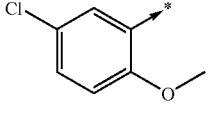 | 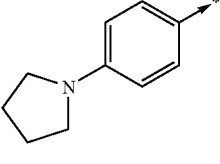 | 89.5 | 5.54 | 443.2 |
| 283 | 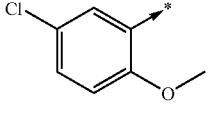 | 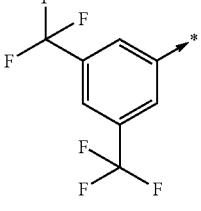 | 65.5 | 5.89 | 510.2 |
| 284 | 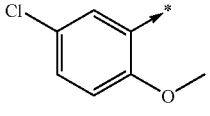 | 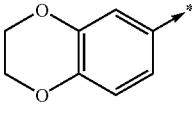 | 97.8 | 4.89 | 432.2 |

-continued
| | | | | | |
|---|---|---|---|---|---|
| 285 | 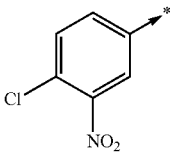 | 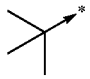 | 93.2 | 5.08 | 369.2 |
| 286 | 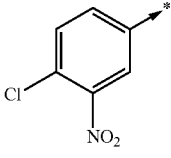 | 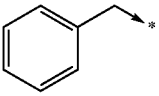 | 94.6 | 5.31 | 403.1 |
| 287 | 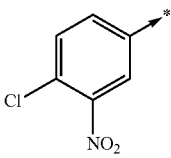 | 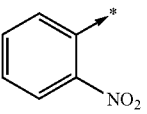 | 97.6 | 5.07 | 434.1 |
| 288 | 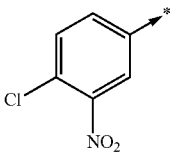 | 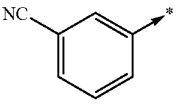 | 99.1 | 5.05 | 414.1 |
| 289 | 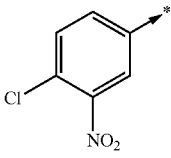 | 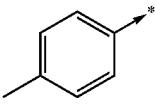 | 99.1 | 5.39 | 403.1 |
| 290 | 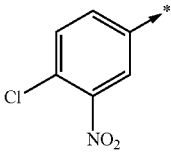 | 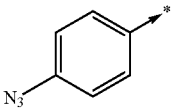 | 98.3 | 5.44 | 430.2 |
| 291 | 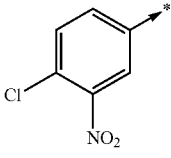 | 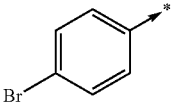 | 99.4 | 5.47 | 467.1 |
| 292 | 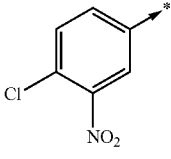 | 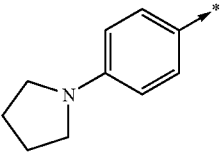 | 97.4 | 5.86 | 458.2 |
| 293 | 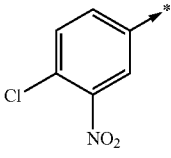 | 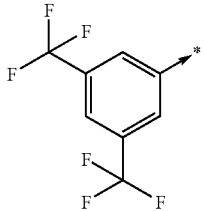 | 99.5 | 5.87 | 525.1 |

-continued
| | | | | | |
|---|---|---|---|---|---|
| 294 | 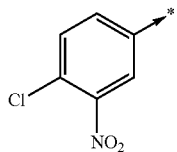 | 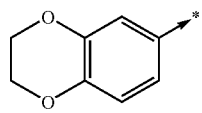 | 98.5 | 5.21 | 447.2 |
| 295 | 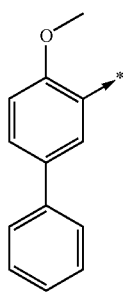 |  | 95.7 | 4.41 | 396.3 |
| 296 | 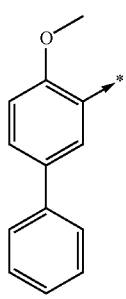 | 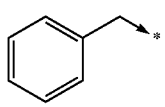 | 92.9 | 5.06 | 430.3 |
| 297 | 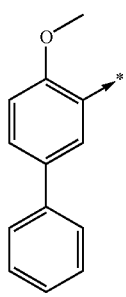 | 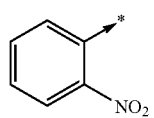 | 54 | 5.19 | 461.2 |
| 298 | 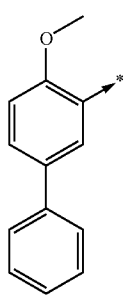 | 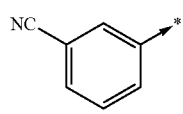 | 91.8 | 5.07 | 441.2 |

-continued
| | | | | | |
|---|---|---|---|---|---|
| 299 | 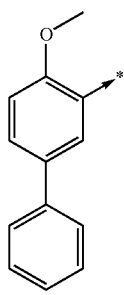 | 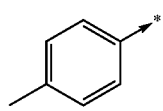 | 95.8 | 5.18 | 430.3 |
| 300 | 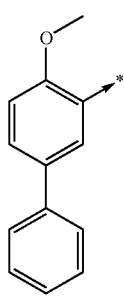 | 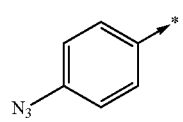 | 96 | 5.28 | 457.3 |
| 301 | 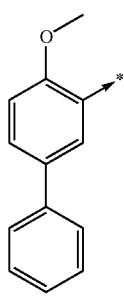 | 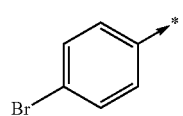 | 96.9 | 5.45 | 494.2 |
| 302 | 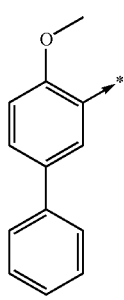 | 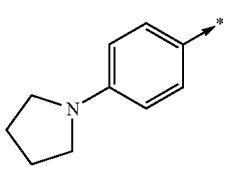 | 87 | 5.49 | 485.3 |
| 303 | 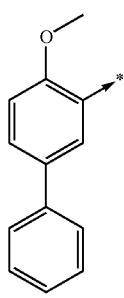 | 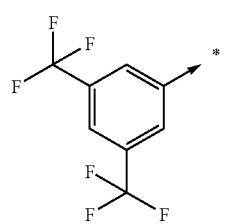 | 35.6 | 6.18 | 552.2 |

-continued
| | | | | | |
|---|---|---|---|---|---|
| 304 | 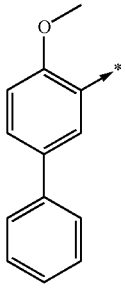 | 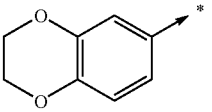 | 96.7 | 4.97 | 474.3 |
| 305 | 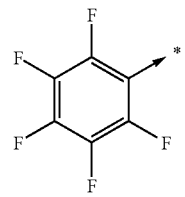 | 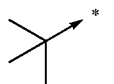 | 83.9 | 5.24 | 380.2 |
| 306 | 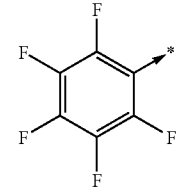 | 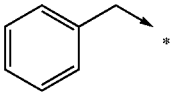 | 92.8 | 5.39 | 414.2 |
| 307 | 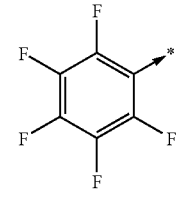 | 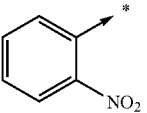 | 92 | 5.14 | 445.2 |
| 308 | 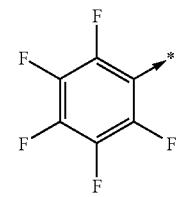 | 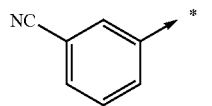 | 97.4 | 5.11 | 425.1 |
| 309 | 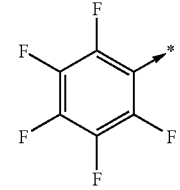 | 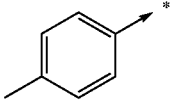 | 98.1 | 5.47 | 414.2 |
| 310 | 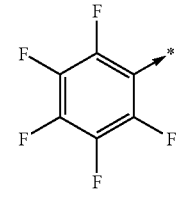 | 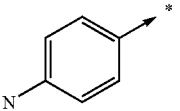 | 97.2 | 5.47 | 441.1 |

| | | | | | |
|---|---|---|---|---|---|
| 311 | 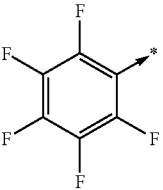 | 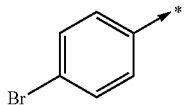 | 97 | 5.52 | 478.1 |
| 312 |  | 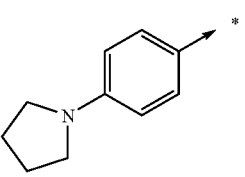 | 93.3 | 5.99 | 469.2 |
| 313 | 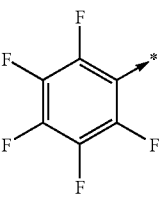 | 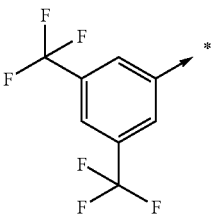 | 98.3 | 5.91 | 536.1 |
| 314 | 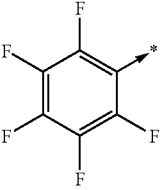 | 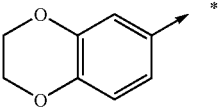 | 96.5 | 5.31 | 458.2 |
| 315 | 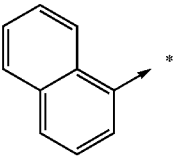 | 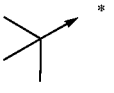 | 98.7 | 4.12 | 340.3 |
| 316 | 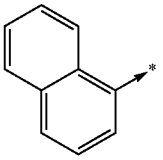 | 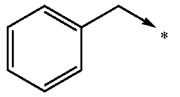 | 93.4 | 4.66 | 374.2 |
| 317 | 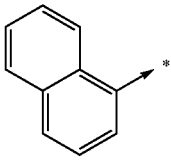 | 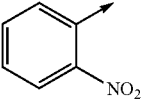 | 98.9 | 4.78 | 405.2 |
| 318 | 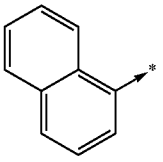 | 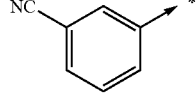 | 97.8 | 4.71 | 385.2 |

-continued
| Ex. | R2 | R3 | Purity (%) | rt (min.) | [M + H]+ |
|---|---|---|---|---|---|
| 319 | 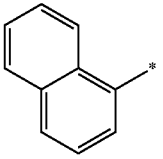 | 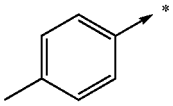 | 98.1 | 4.78 | 374.2 |
| 320 | 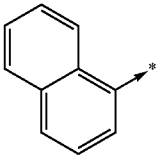 | 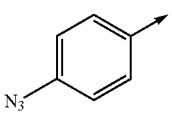 | 97.2 | 4.9 | 401.2 |
| 321 | 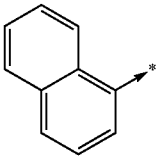 | 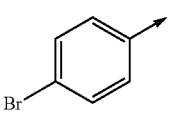 | 98.8 | 5.09 | 438.1 |
| 322 | 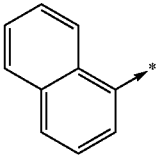 | 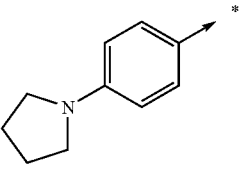 | 95.8 | 5.07 | 429.3 |
| 323 | 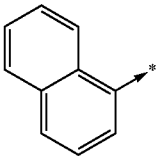 | 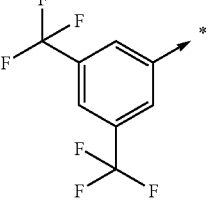 | 98.5 | 5.82 | 496.2 |
| 324 | 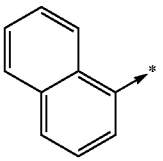 | 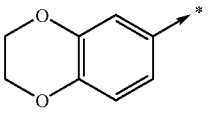 | 97.5 | 4.59 | 418.2 |
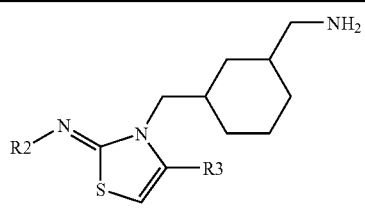
| Ex. | R2 | R3 | Purity (%) | rt (min.) | [M + H]+ |
|---|---|---|---|---|---|
| 325 | 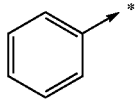 | 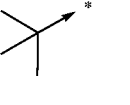 | 93 | 3.71 | 358.2 |
| 326 | 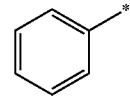 | 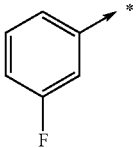 | 68 + 30 | 4.0 + 4.1 | 396.2 |

-continued
| | | | | | |
|---|---|---|---|---|---|
| 327 | 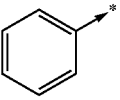 | 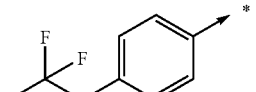 | 69 + 31 | 4.5 + 4.6 | 462.2 |
| 328 | 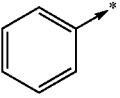 | 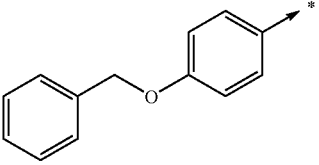 | 66 + 27 | 4.7 + 4.8 | 484.3 |
| 329 | 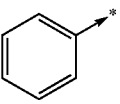 | 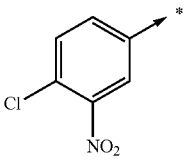 | 67 + 31 | 4.4 + 4.6 | 457.2 |
| 330 | 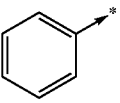 | 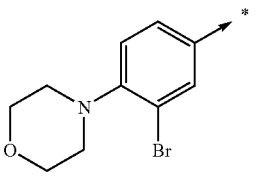 | 67 + 30 | 4.3 + 4.5 | 541.2 |
| 331 | 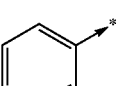 | 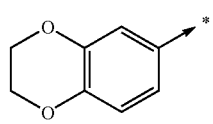 | 62 + 33 | 3.9 + 4.0 | 436.2 |
| 332 |  | 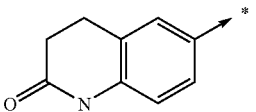 | 64 + 30 | 3.5 + 3.6 | 447.3 |
| 333 | 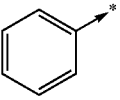 | 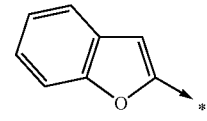 | 65 + 30 | 4.7 + 4.9 | 418.2 |
| 334 | 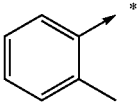 | 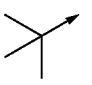 | 68 + 29 | 3.8 + 3.9 | 372.3 |
| 335 | 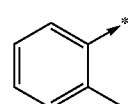 | 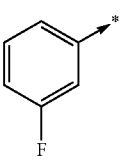 | 69 + 29 | 4.2 + 4.3 | 410.2 |
| 336 | 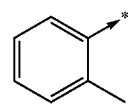 | 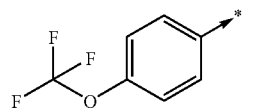 | 68 + 30 | 4.6 + 4.8 | 476.2 |

-continued
| | | | | | |
|---|---|---|---|---|---|
| 337 |  | 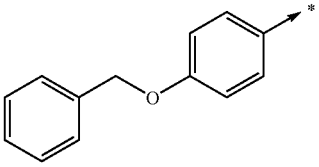 | 61 + 32 | 4.8 + 4.89 | 498.3 |
| 338 |  |  | 66 + 30 | 4.55 + 4.71 | 471.2 |
| 339 |  |  | 68 + 29 | 4.46 + 4.58 | 555.2 |
| 340 | 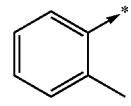 |  | 22 + 11 | 5.13 + 5.22 | 520.4 |
| 341 |  |  | 67 + 24 | 4.09 + 4.14 | 450.3 |
| 342 |  |  | 71 + 23 | 3.7 + 3.74 | 461.3 |
| 343 |  |  | 67 + 31 | 4.82 + 5.02 | 432.2 |
| 344 |  |  | 66 + 31 | 4.14 + 4.39 | 404.3 |
| 345 | 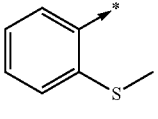 | 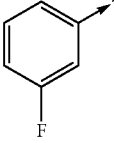 | 65 + 31 | 4.74 + 4.94 | 442.2 |
| 346 | 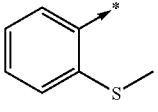 | 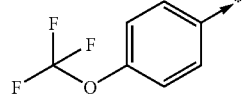 | 65 + 31 | 5.25 + 5.47 | 508.2 |

-continued
| | | | | | |
|---|---|---|---|---|---|
| 347 | 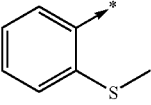 | 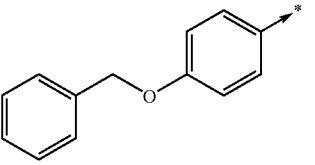 | 62 + 29 | 5.28 + 5.5 | 530.3 |
| 348 | 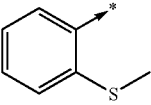 | 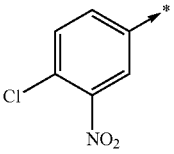 | 65 + 30 | 5.21 + 5.38 | 503.2 |
| 349 | 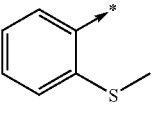 |  | 63 + 30 | 5.03 + 5.24 | 587.2 |
| 350 | 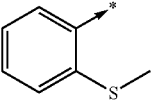 | 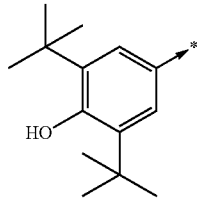 | 64 + 30 | 5.59 + 5.84 | 552.3 |
| 351 | 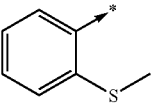 | 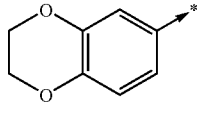 | 58 + 28 | 4.49 + 4.66 | 482.3 |
| 352 | 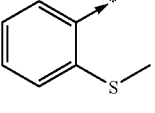 | 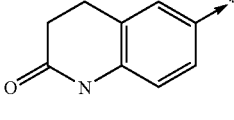 | 64 + 26 | 4.01 + 4.11 | 493.3 |
| 353 | 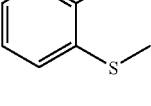 | 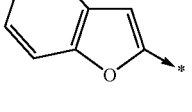 | 65 + 31 | 5.54 + 5.71 | 464.2 |
| 354 | 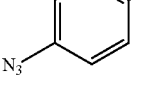 |  | 57 + 24 | 4.08 + 4.19 | 399.3 |
| 355 | 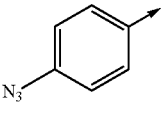 | 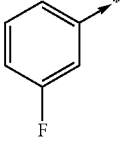 | 62 + 28 | 4.52 + 4.7 | 437.2 |
| 356 | 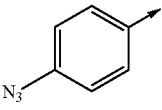 | 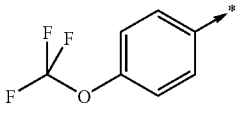 | 62 + 28 | 5 + 5.2 | 503.2 |

| | | | | | |
|---|---|---|---|---|---|
| 357 | 4-azidophenyl | 4-(benzyloxy)phenyl | 58 + 26 | 5.08 + 5.25 | 525.3 |
| 358 | 4-azidophenyl | 4-chloro-3-nitrophenyl | 62 + 29 | 4.98 + 5.19 | 498.2 |
| 359 | 4-azidophenyl | 3-bromo-4-morpholinophenyl | 62 + 29 | 4.82 + 4.99 | 582.2 |
| 360 | 4-azidophenyl | 3,5-di-tert-butyl-4-hydroxyphenyl (2,6-diisopropyl variant) | 62 + 28 | 5.39 + 5.58 | 547.3 |
| 361 | 4-azidophenyl | 2,3-dihydro-1,4-benzodioxin-6-yl | 56 + 26 | 4.37 + 4.49 | 477.3 |
| 362 | 4-azidophenyl | benzofuran-2-yl | 64 + 32 | 5.32 + 5.55 | 459.2 |
| 363 | 4-bromo-2-(trifluoromethyl)phenyl | tert-butyl | 94 | 6.36 | 505.2 |
| 364 | 4-bromo-2-(trifluoromethyl)phenyl | 3-fluorophenyl | 98 | 6.39 | 542.1 |
| 365 | 4-bromo-2-(trifluoromethyl)phenyl | 4-(trifluoromethoxy)phenyl | 25 + 72 | 6.74 + 6.77 | 608.1 |

-continued

| # | R1 | R2 | col4 | col5 | col6 |
|---|----|----|------|------|------|
| 366 | 4-Br, 2-CF3 phenyl | 4-(benzyloxy)phenyl | 92 | 7.07 | 630.2 |
| 367 | 4-Br, 2-CF3 phenyl | 4-Cl, 3-NO2 phenyl | 23 + 73 | 6.38 + 6.42 | 603.1 |
| 368 | 4-Br, 2-CF3 phenyl | 4-morpholino-3-bromo phenyl | 26 + 69 | 6.73 + 6.76 | 687.1 |
| 369 | 4-Br, 2-CF3 phenyl | 3,5-di-tert-butyl-4-hydroxyphenyl | 60 | 7.55 | 652.3 |
| 370 | 4-Br, 2-CF3 phenyl | 2,3-dihydro-1,4-benzodioxin-6-yl | 82 | 6.39 | 582.1 |
| 371 | 4-Br, 2-CF3 phenyl | 2-oxo-1,2,3,4-tetrahydroquinolin-6-yl | 94 | 5.74 | 593.2 |
| 372 | 4-Br, 2-CF3 phenyl | benzofuran-2-yl | 22 + 73 | 6.68 + 6.74 | 564.1 |
| 373 | 3-NO2 phenyl | tert-butyl | 59 + 27 | 4.88 + 5.13 | 403.3 |
| 374 | 3-NO2 phenyl | 3-F phenyl | 67 + 30 | 5.35 + 5.44 | 441.2 |

-continued

| # | R1 | R2 | | | |
|---|---|---|---|---|---|
| 375 | 3-O2N-C6H4- | 4-(OCF3)-C6H4- | 64 + 34 | 5.84 + 5.92 | 507.2 |
| 376 | 3-O2N-C6H4- | 4-(OBn)-C6H4- | 62 + 28 | 6 + 6.13 | 529.3 |
| 377 | 3-O2N-C6H4- | 4-Cl-3-NO2-C6H3- | 97 | 5.58 | 502.2 |
| 378 | 3-O2N-C6H4- | 3-Br-4-morpholino-C6H3- | 65 + 32 | 5.71 + 5.8 | 586.2 |
| 379 | 3-O2N-C6H4- | 3,5-di-tBu-4-OH-C6H2- | 49 + 23 | 6.45 + 6.58 | 551.3 |
| 380 | 3-O2N-C6H4- | 2,3-dihydrobenzo[1,4]dioxin-6-yl | 61 + 26 | 5.18 + 5.3 | 481.2 |
| 381 | 3-O2N-C6H4- | 2-oxo-1,2,3,4-tetrahydroquinolin-6-yl | 45 + 21 | 4.57 + 4.68 | 492.3 |
| 382 | 3-O2N-C6H4- | benzofuran-2-yl | 84 | 5.9 | 463.2 |
| 383 | 3-Cl-4-F-C6H3- | tBu- | 56 + 26 | 4.65 + 4.89 | 410.2 |
| 384 | 3-Cl-4-F-C6H3- | 3-F-C6H4- | 64 + 30 | 5.29 + 5.47 | 448.2 |

| | | | | | |
|---|---|---|---|---|---|
| 385 | 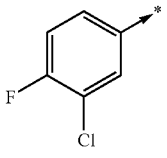 | 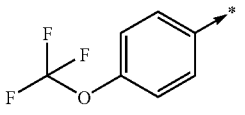 | 65 + 30 | 5.78 + 5.95 | 514.2 |
| 386 | 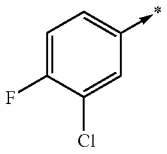 | 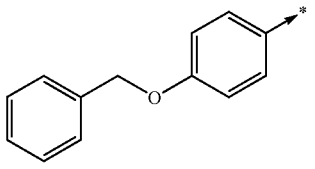 | 63 + 27 | 5.8 + 6.02 | 536.2 |
| 387 | 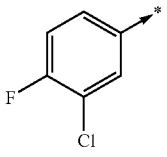 | 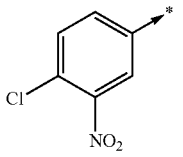 | 65 + 31 | 5.71 + 5.81 | 509.1 |
| 388 | 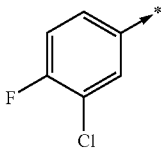 | 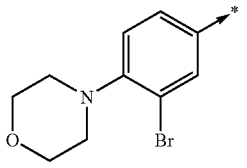 | 62 + 32 | 5.59 + 5.79 | 593.1 |
| 389 | 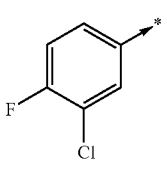 | 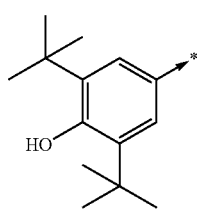 | 30 + 14 | 6.22 + 6.45 | 558.3 |
| 390 | 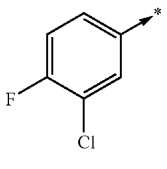 | 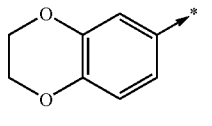 | 57 + 26 | 5.01 + 5.2 | 488.2 |
| 391 | 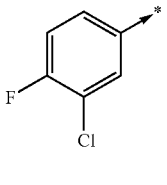 | 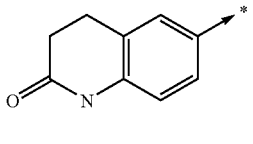 | 54 + 26 | 4.46 + 4.61 | 499.2 |
| 392 | 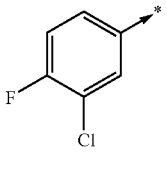 | 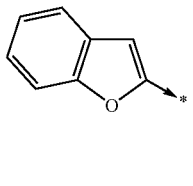 | 27 + 11 | 6.09 + 6.18 | 470.2 |

-continued
| | | | | | |
|---|---|---|---|---|---|
| 393 | 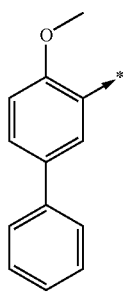 |  | 63 + 29 | 4.53 + 4.6 | 464.3 |
| 394 | 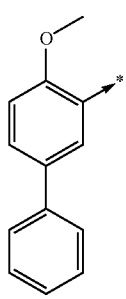 | 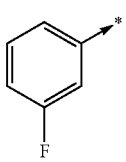 | 65 + 30 | 4.78 + 4.93 | 502.3 |
| 395 | 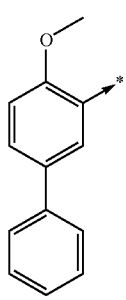 | 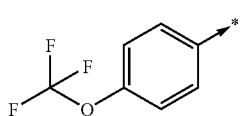 | 61 + 28 | 5.16 + 5.35 | 568.2 |
| 396 | 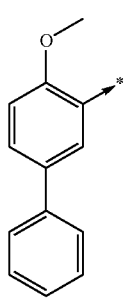 | 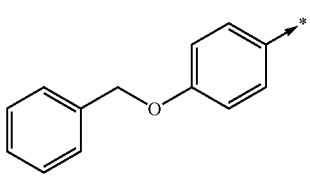 | 59 + 25 | 5.3 + 5.42 | 590.3 |
| 397 | 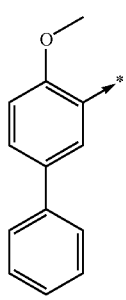 | 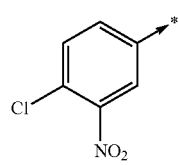 | 60 + 30 | 5.12 + 5.34 | 563.2 |

-continued
| | | | Purity (%) | rt (min.) | [M + H]⁺ |
|---|---|---|---|---|---|
| 398 | | | 63 + 32 | 5.01 + 5.17 | 647.2 |
| 399 | | | 59 + 26 | 5.55 + 5.7 | 612.4 |
| 400 | | | 52 + 14 | 4.35 + 4.4 | 553.3 |
| 401 | | | 61 + 29 | 5.36 + 5.64 | 524.3 |
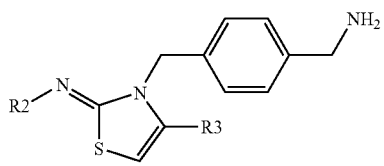
| Ex. | R2 | R3 | Purity (%) | rt (min.) | [M + H]⁺ |
|---|---|---|---|---|---|
| 402 | | | 88.5 | 4.52 | 442.1 |

-continued

| # | R1 | R2 | % | t | m/z |
|---|---|---|---|---|---|
| 403 | 2-isopropylphenyl | 3-fluorophenyl | 94.6 | 4.72 | 432.15 |
| 404 | 2-isopropylphenyl | 4-azidophenyl | 95 | 4.78 | 455.16 |
| 405 | 2-isopropylphenyl | 4-chloro-3-nitrophenyl | 98.6 | 5.19 | 493.12 |
| 406 | 2-isopropylphenyl | 3-bromo-4-morpholinophenyl | 95.8 | 4.99 | 577.11 |
| 407 | 2-isopropylphenyl | 2,3-dihydrobenzo[1,4]dioxin-6-yl | 95.1 | 4.44 | 472.19 |
| 408 | 2-isopropylphenyl | 2-oxo-1,2,3,4-tetrahydroquinolin-6-yl | 96.3 | 4.0 | 483.21 |
| 409 | 2-isopropylphenyl | 5-bromothiophen-2-yl | 94.5 | 5.35 | 498.04 |
| 410 | 2-isopropylphenyl | benzofuran-2-yl | 94.1 | 5.61 | 454.15 |
| 411 | 2-iodophenyl | phenethyl | 83 | 5.43 | 526.03 |
| 412 | 2-iodophenyl | 3-fluorophenyl | 94.9 | 5.4 | 515.97 |

| | | | | | |
|---|---|---|---|---|---|
| 413 | 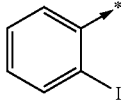 | 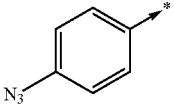 | 93.4 | 5.52 | 539.00 |
| 414 | 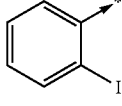 | 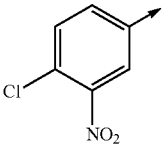 | 97.1 | 5.48 | 576.95 |
| 415 | 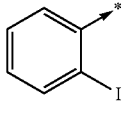 | 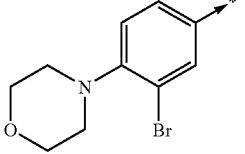 | 92.7 | 5.69 | 660.99 |
| 416 | 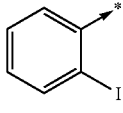 | 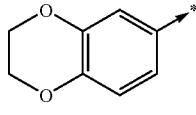 | 92.2 | 5.27 | 555.98 |
| 417 | 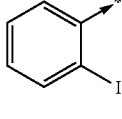 | 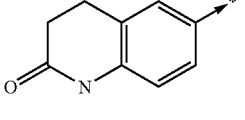 | 92 | 4.7 | 567.00 |
| 418 | 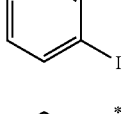 | 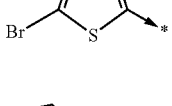 | 89.7 | 5.73 | 581.87 |
| 419 | 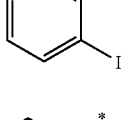 | 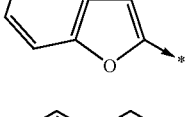 | 87.8 | 5.77 | 538.00 |
| 420 | 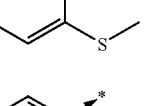 | 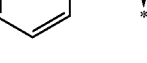 | 84.4 | 4.74 | 446.14 |
| 421 | 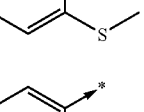 | 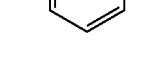 | 92.6 | 4.9 | 436.08 |
| 422 | 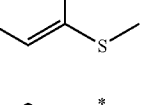 | 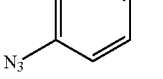 | 91.2 | 5.0 | 459.10 |
| 423 | 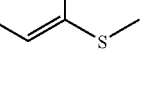 | 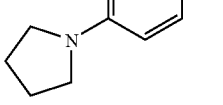 | 72.4 | 5.0 | 487.16 |

-continued
| | | | | | |
|---|---|---|---|---|---|
| 424 | 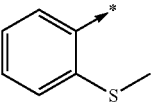 | 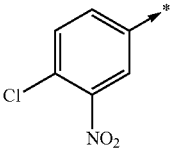 | 94.9 | 5.19 | 497.07 |
| 425 | 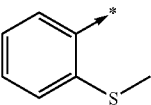 | 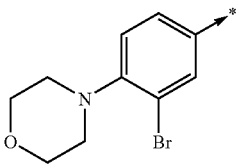 | 91.7 | 5.18 | 581.05 |
| 426 | 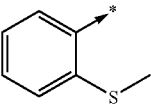 | 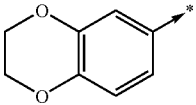 | 91.5 | 4.67 | 476.12 |
| 427 | 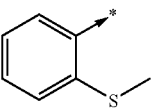 | 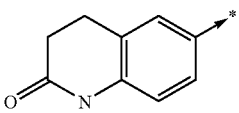 | 89.6 | 4.16 | 487.13 |
| 428 | 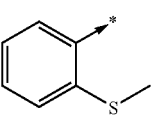 | 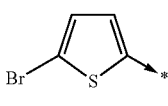 | 91.7 | 5.38 | 501.96 |
| 429 | 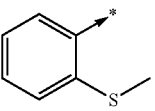 | 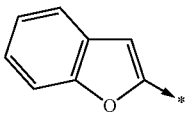 | 89.9 | 5.48 | 458.10 |
| 430 | 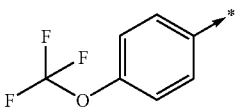 | 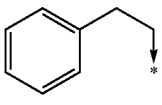 | 87.1 | 5.26 | 484.14 |
| 431 | 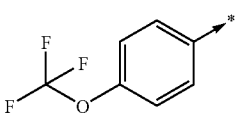 | 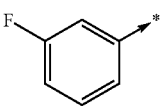 | 95.7 | 5.41 | 474.10 |
| 432 | 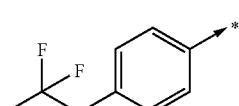 | 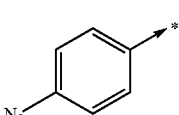 | 94.6 | 5.51 | 497.12 |
| 433 | 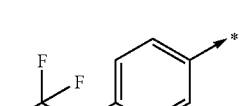 | 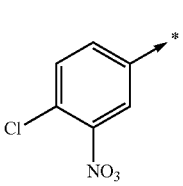 | 97.4 | 5.64 | 535.01 |
| 434 | 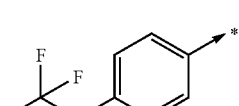 | 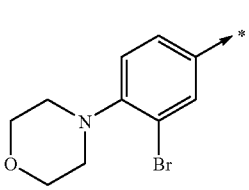 | 96.2 | 5.69 | 619.04 |

| # | | | | | |
|---|---|---|---|---|---|
| 435 | 4-(trifluoromethoxy)phenyl * | 2,3-dihydro-1,4-benzodioxin-6-yl * | 94.4 | 5.21 | 514.10 |
| 436 | 4-(trifluoromethoxy)phenyl * | 2-oxo-1,2,3,4-tetrahydroquinolin-6-yl * | 94.7 | 4.67 | 525.11 |
| 437 | 4-(trifluoromethoxy)phenyl * | 5-bromothiophen-2-yl * | 92.7 | 5.84 | 539.94 |
| 438 | 4-(trifluoromethoxy)phenyl * | benzofuran-2-yl * | 91 | 5.93 | 496.09 |
| 439 | 4-phenoxyphenyl * | phenethyl * | 82.4 | 4.82 | 492.18 |
| 440 | 4-phenoxyphenyl * | 3-fluorophenyl * | 92.2 | 5.03 | 482.14 |
| 441 | 4-phenoxyphenyl * | 4-azidophenyl * | 90.4 | 5.08 | 505.15 |
| 442 | 4-phenoxyphenyl * | 4-(pyrrolidin-1-yl)phenyl * | 33.4 | 5.14 | 533.18 |
| 443 | 4-phenoxyphenyl * | 4-chloro-3-nitrophenyl * | 97.6 | 5.45 | 543.07 |
| 444 | 4-phenoxyphenyl * | 3-bromo-4-morpholinophenyl * | 93.9 | 5.26 | 627.10 |

-continued
| | | | | | |
|---|---|---|---|---|---|
| 445 | 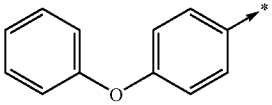 | 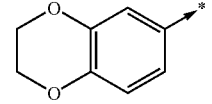 | 93.6 | 4.78 | 522.14 |
| 446 | 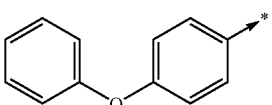 | 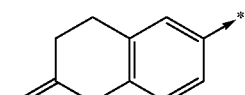 | 94 | 4.34 | 533.15 |
| 447 | 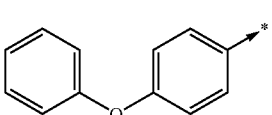 | 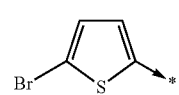 | 91.6 | 5.6 | 547.98 |
| 448 | 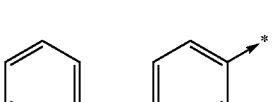 | 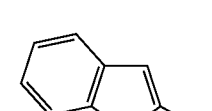 | 92.6 | 5.82 | 504.14 |
| 449 | 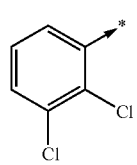 | 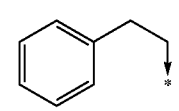 | 84.9 | 5.76 | 468.08 |
| 450 | 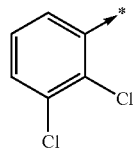 | 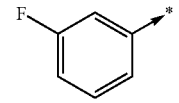 | 95.4 | 5.54 | 458.03 |
| 451 | 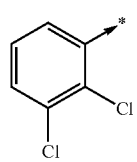 | 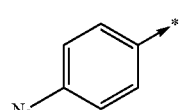 | 93.3 | 5.74 | 481.03 |
| 452 | 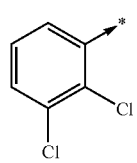 | 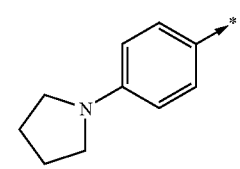 | 85.3 | 6.21 | 509.06 |
| 453 | 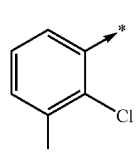 | 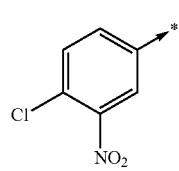 | 97.4 | 5.62 | 518.97 |
| 454 | 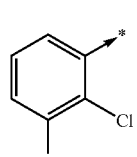 | 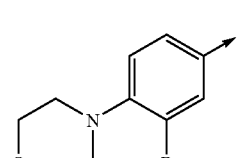 | 92 | 5.91 | 602.90 |

-continued
| | | | | | |
|---|---|---|---|---|---|
| 455 | 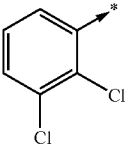 | 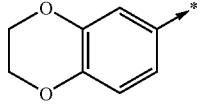 | 91.4 | 5.54 | 498.06 |
| 456 | 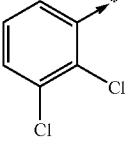 | 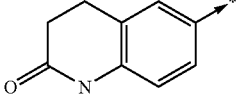 | 91.4 | 4.98 | 509.06 |
| 457 | 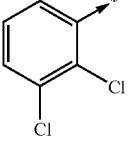 | 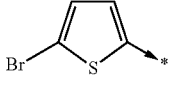 | 88.7 | 5.9 | 523.88 |
| 458 | 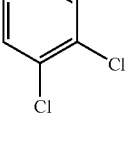 | 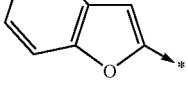 | 88.5 | 5.88 | 480.05 |
| 459 | 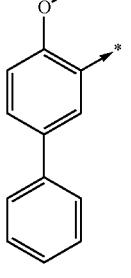 | 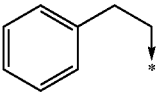 | 88.2 | 4.69 | 506.18 |
| 460 | 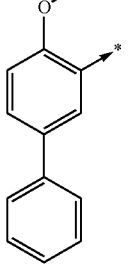 | 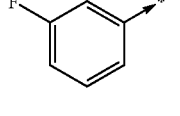 | 93.1 | 4.87 | 496.15 |
| 461 | 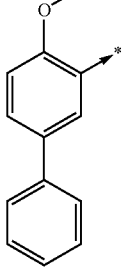 | 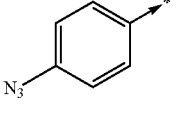 | 91.2 | 4.92 | 519.15 |

-continued
| | | | | | |
|---|---|---|---|---|---|
| 462 | 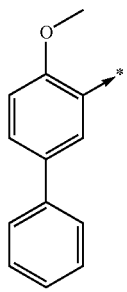 | 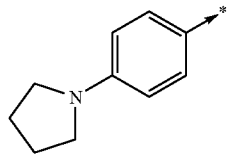 | 26.9 | 5.01 | 547.17 |
| 463 | 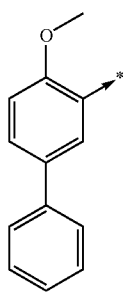 | 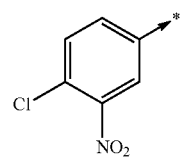 | 93.9 | 5.26 | 557.08 |
| 464 | 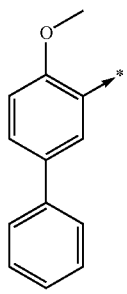 | 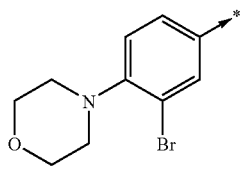 | 93.2 | 5.08 | 641.13 |
| 465 | 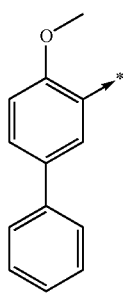 | 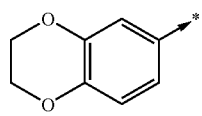 | 95.7 | 4.64 | 536.15 |
| 466 | 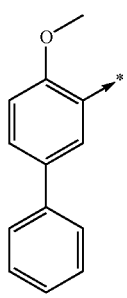 | 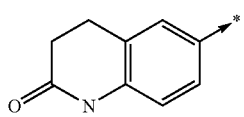 | 95.3 | 4.24 | 547.15 |

-continued

| | 301 | 302 | | | |
|---|---|---|---|---|---|
| 467 | 4-methoxybiphenyl-3-yl | 5-bromothien-2-yl | 92.3 | 5.39 | 562.00 |
| 468 | 4-methoxybiphenyl-3-yl | benzofuran-2-yl | 92 | 5.6 | 518.14 |
| 469 | 4-chloro-2,5-dimethoxyphenyl | phenethyl | 75.3 | 4.59 | 494.13 |
| 470 | 4-chloro-2,5-dimethoxyphenyl | 3-fluorophenyl | 97.1 | 4.73 | 484.11 |
| 471 | 4-chloro-2,5-dimethoxyphenyl | 4-azidophenyl | 95.4 | 4.81 | 507.11 |
| 472 | 4-chloro-2,5-dimethoxyphenyl | 4-(pyrrolidin-1-yl)phenyl | 10.7 | 4.9 | 535.14 |
| 473 | 4-chloro-2,5-dimethoxyphenyl | 4-chloro-3-nitrophenyl | 96.4 | 5.07 | 545.02 |

-continued

| | | | Purity (%) | rt (min.) | [M + H]+ |
|---|---|---|---|---|---|
| 474 | 4-chloro-2,5-dimethoxyphenyl | 4-morpholino-3-bromophenyl | 96.5 | 4.98 | 629.05 |
| 475 | 4-chloro-2,5-dimethoxyphenyl | 2,3-dihydrobenzo[1,4]dioxin-6-yl | 95.2 | 4.5 | 524.08 |
| 476 | 4-chloro-2,5-dimethoxyphenyl | 2-oxo-1,2,3,4-tetrahydroquinolin-6-yl | 96 | 4.06 | 535.09 |
| 477 | 4-chloro-2,5-dimethoxyphenyl | 5-bromothiophen-2-yl | 95.3 | 5.22 | 549.95 |
| 478 | 4-chloro-2,5-dimethoxyphenyl | benzofuran-2-yl | 94.1 | 5.36 | 506.08 |

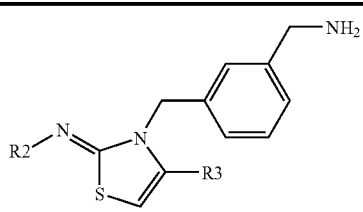

| Ex. | R2 | R3 | Purity (%) | rt (min.) | [M + H]+ |
|---|---|---|---|---|---|
| 479 | 2-cyanophenyl | tert-butyl | 45.6 | 4.95 | 377.14 |
| 480 | 2-cyanophenyl | 2-chlorophenyl | 79 | 5.17 | 431.07 |
| 481 | 2-cyanophenyl | 2-nitropyridin-3-yl | 56.8 | 4.84 | 442.08 |

| 482 | 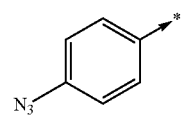 | 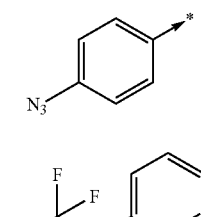 | 79.2 | 5.04 | 415.07 |
| --- | --- | --- | --- | --- | --- |
| 483 | 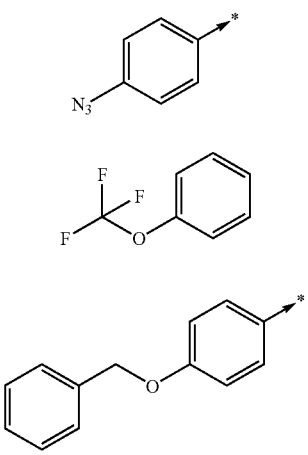 | 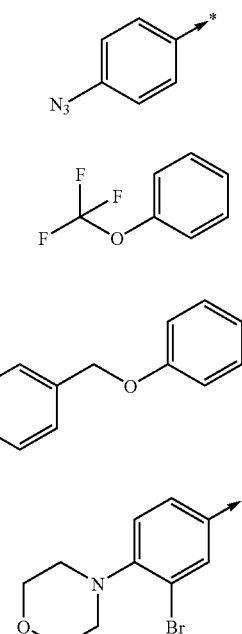 | 78.4 | 5.25 | 438.11 |
| 484 | 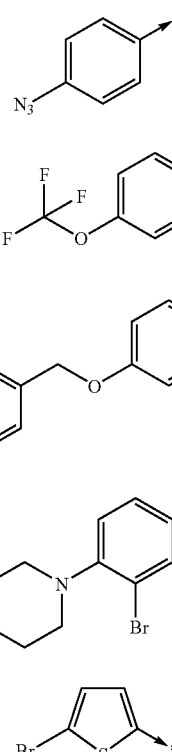 | 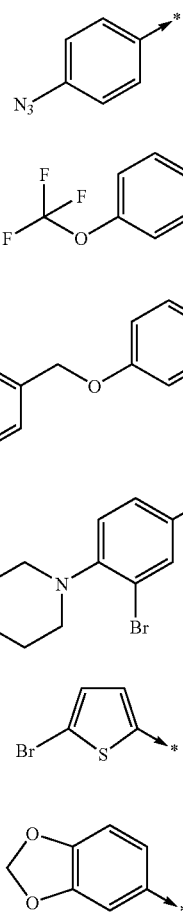 | 82.6 | 5.47 | 481.10 |
| 485 |  | 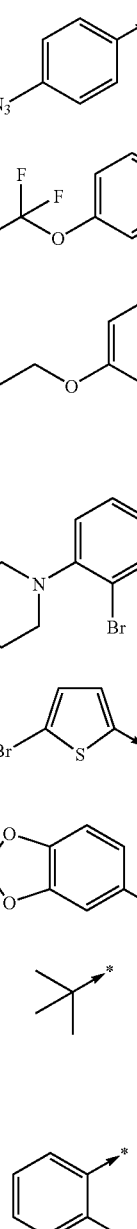 | 72.6 | 5.81 | 503.17 |
| 486 | 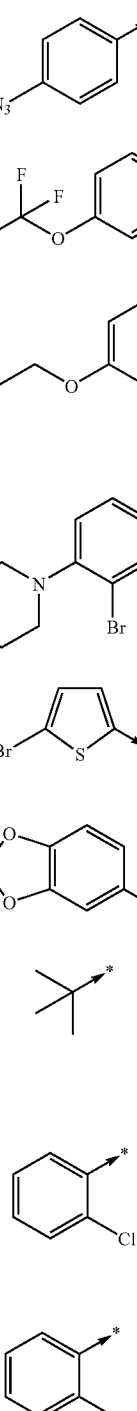 | | 79 | 5.36 | 560.04 |
| 487 | | | 72.1 | 5.34 | 480.98 |
| 488 | | | 76.9 | 5.0 | 441.09 |
| 489 | | | 94.5 | 4.6 | 386.09 |
| 490 | | | 95.4 | 5.34 | 440.04 |
| 491 | | | 95.3 | 5.05 | 451.06 |

-continued
| | | | | | |
|---|---|---|---|---|---|
| 492 | 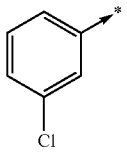 | 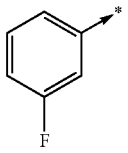 | 95.2 | 5.23 | 424.07 |
| 493 | 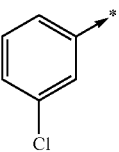 | 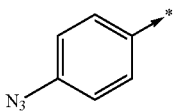 | 93.4 | 5.35 | 447.07 |
| 494 | 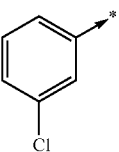 | 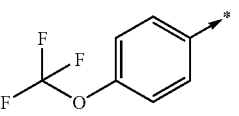 | 96.1 | 5.67 | 490.07 |
| 495 | 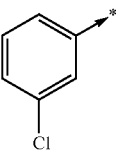 | 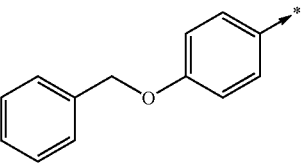 | 88.5 | 5.84 | 512.12 |
| 496 | 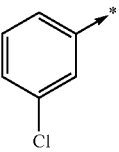 | 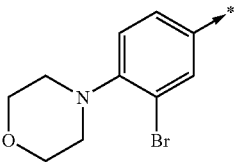 | 92.9 | 5.55 | 569.00 |
| 497 | 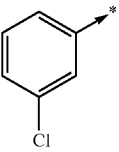 | 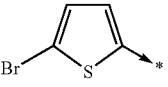 | 92.8 | 5.64 | 489.95 |
| 498 | 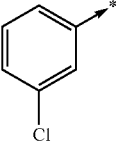 | 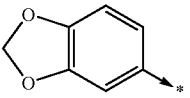 | 92 | 5.03 | 450.08 |
| 499 | 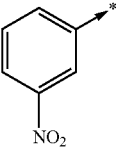 | 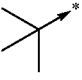 | 96.5 | 4.87 | 397.11 |
| 500 | 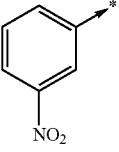 | 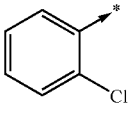 | 96.1 | 5.26 | 451.06 |

-continued

| | | | | | |
|---|---|---|---|---|---|
| 501 | 3-NO2-C6H4-* | 2-NO2-C6H4-* | 96.1 | 4.95 | 462.07 |
| 502 | 3-NO2-C6H4-* | 3-F-C6H4-* | 96.3 | 5.15 | 435.08 |
| 503 | 3-NO2-C6H4-* | 4-N3-C6H4-* | 96.2 | 5.31 | 458.11 |
| 504 | 3-NO2-C6H4-* | 4-(OCF3)-C6H4-* | 96.5 | 5.57 | 501.08 |
| 505 | 3-NO2-C6H4-* | 4-(OBn)-C6H4-* | 89.3 | 5.86 | 523.15 |
| 506 | 3-NO2-C6H4-* | 4-morpholino-3-Br-C6H3-* | 95.8 | 5.46 | 580.03 |
| 507 | 3-NO2-C6H4-* | 5-Br-thien-2-yl-* | 94.2 | 5.45 | 500.96 |
| 508 | 3-NO2-C6H4-* | benzo[1,3]dioxol-5-yl-* | 93.5 | 5.07 | 461.08 |
| 509 | 4-tBu-C6H4-* | tBu-* | 98.5 | 4.29 | 408.18 |

-continued

| | 311 | 312 | | | |
|---|---|---|---|---|---|
| 510 | 4-tert-butylphenyl* | 2-chlorophenyl* | 97.2 | 4.98 | 462.13 |
| 511 | 4-tert-butylphenyl* | 2-nitrophenyl* | 96.4 | 4.81 | 473.19 |
| 512 | 4-tert-butylphenyl* | 3-fluorophenyl* | 96.3 | 4.9 | 446.17 |
| 513 | 4-tert-butylphenyl* | 4-azidophenyl* | 94.7 | 4.93 | 469.19 |
| 514 | 4-tert-butylphenyl* | 4-(trifluoromethoxy)phenyl* | 96.9 | 5.29 | 512.17 |
| 515 | 4-tert-butylphenyl* | 4-(benzyloxy)phenyl* | 90.6 | 5.33 | 534.20 |
| 516 | 4-tert-butylphenyl* | 3-bromo-4-morpholinophenyl* | 96.3 | 5.15 | 591.13 |
| 517 | 4-tert-butylphenyl* | 5-bromothien-2-yl* | 93.5 | 5.47 | 512.04 |
| 518 | 4-tert-butylphenyl* | benzo[1,3]dioxol-5-yl* | 95 | 4.65 | 472.19 |

-continued

| | | | | | |
|---|---|---|---|---|---|
| 519 | 4-(trifluoromethyl)phenyl | tert-butyl | 95.5 | 5.14 | 420.13 |
| 520 | 4-(trifluoromethyl)phenyl | 2-chlorophenyl | 95.6 | 5.63 | 474.07 |
| 521 | 4-(trifluoromethyl)phenyl | 2-nitrophenyl | 93.8 | 5.35 | 485.10 |
| 522 | 4-(trifluoromethyl)phenyl | 3-fluorophenyl | 95.1 | 5.53 | 458.09 |
| 523 | 4-(trifluoromethyl)phenyl | 4-azidophenyl | 94.2 | 5.67 | 481.10 |
| 524 | 4-(trifluoromethyl)phenyl | 4-(trifluoromethoxy)phenyl | 94.6 | 5.9 | 524.09 |
| 525 | 4-(trifluoromethyl)phenyl | 4-(benzyloxy)phenyl | 88.4 | 6.15 | 546.11 |
| 526 | 4-(trifluoromethyl)phenyl | 3-bromo-4-morpholinophenyl | 92.6 | 5.83 | 603.07 |
| 527 | 4-(trifluoromethyl)phenyl | 5-bromothiophen-2-yl | 89.8 | 5.87 | 523.97 |

| # | 315 (Ar1) | 316 (Ar2) | % | t | M |
|---|---|---|---|---|---|
| 528 | 4-CF3-C6H4- | benzo[1,3]dioxol-5-yl | 92.3 | 5.41 | 484.11 |
| 529 | 2,4-dimethylphenyl | tert-butyl | 98.2 | 3.75 | 380.18 |
| 530 | 2,4-dimethylphenyl | 2-Cl-C6H4- | 96.4 | 4.35 | 434.11 |
| 531 | 2,4-dimethylphenyl | 2-NO2-C6H4- | 96.5 | 4.19 | 445.13 |
| 532 | 2,4-dimethylphenyl | 3-F-C6H4- | 95.7 | 4.25 | 418.14 |
| 533 | 2,4-dimethylphenyl | 4-N3-C6H4- | 94.4 | 4.33 | 441.13 |
| 534 | 2,4-dimethylphenyl | 4-OCF3-C6H4- | 95.5 | 4.69 | 484.14 |
| 535 | 2,4-dimethylphenyl | 4-OBn-C6H4- | 89.5 | 4.81 | 506.18 |
| 536 | 2,4-dimethylphenyl | 4-morpholino-3-Br-C6H3- | 95.5 | 4.54 | 563.08 |
| 537 | 2,4-dimethylphenyl | 5-Br-thiophen-2-yl | 92.2 | 4.79 | 484.03 |
| 538 | 2,4-dimethylphenyl | benzo[1,3]dioxol-5-yl | 93.7 | 4.07 | 444.14 |

-continued
| | | | | | |
|---|---|---|---|---|---|
| 539 | 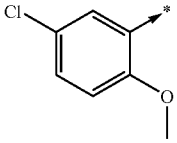 |  | 95.4 | 4.25 | 416.10 |
| 540 | 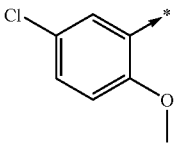 | 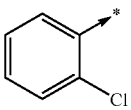 | 95.7 | 5.05 | 470.07 |
| 541 | 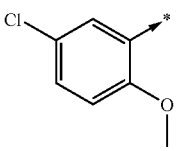 | 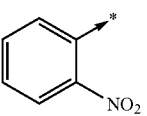 | 95.6 | 4.81 | 481.05 |
| 542 | 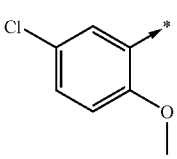 | 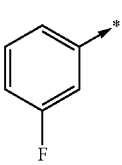 | 95.4 | 4.96 | 454.07 |
| 543 | 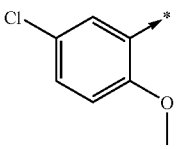 | 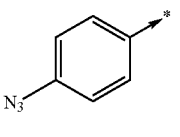 | 94.4 | 5.05 | 477.10 |
| 544 | 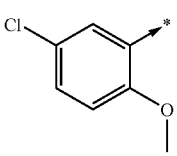 | 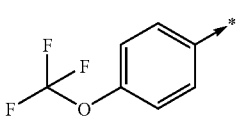 | 95.9 | 5.4 | 520.04 |
| 545 | 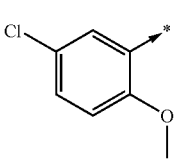 | 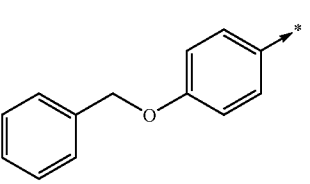 | 89.5 | 5.51 | 542.11 |
| 546 | 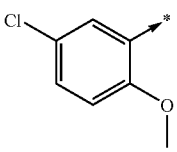 | 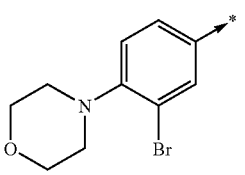 | 94 | 5.26 | 599.02 |
| 547 | 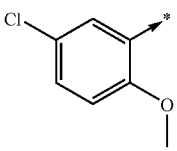 | 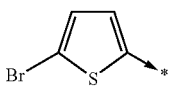 | 92.9 | 5.4 | 519.93 |
| 548 | 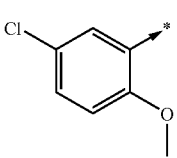 | 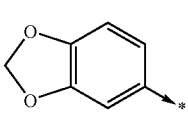 | 92.3 | 4.72 | 480.08 |

-continued

| # | R1 | R2 | % | t | M |
|---|---|---|---|---|---|
| 549 | 2,4,6-tribromophenyl | tert-butyl | 92 | 6.01 | 585.84 |
| 550 | 2,4,6-tribromophenyl | 2-chlorophenyl | 96.7 | 6.18 | 639.79 |
| 551 | 2,4,6-tribromophenyl | 2-nitrophenyl | 95.8 | 5.84 | 650.83 |
| 552 | 2,4,6-tribromophenyl | 3-fluorophenyl | 96 | 6.04 | 623.81 |
| 553 | 2,4,6-tribromophenyl | 4-azidophenyl | 94.7 | 6.22 | 646.85 |
| 554 | 2,4,6-tribromophenyl | 4-(trifluoromethoxy)phenyl | 95 | 6.39 | 689.82 |
| 555 | 2,4,6-tribromophenyl | 4-(benzyloxy)phenyl | 88.8 | 6.7 | 711.88 |
| 556 | 2,4,6-tribromophenyl | 3-bromo-4-morpholinophenyl | 94.9 | 6.4 | 768.76 |
| 557 | 2,4,6-tribromophenyl | 5-bromothien-2-yl | 95 | 6.35 | 689.71 |

-continued
| Ex. | | | Purity (%) | rt (min.) | [M + H]+ |
|---|---|---|---|---|---|
| 558 | Br-substituted (2,4,6-tribromophenyl) | benzo[1,3]dioxol-5-yl | 93.7 | 6.01 | 649.83 |
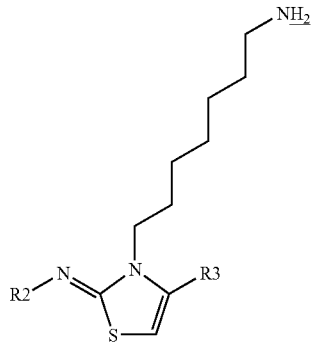
| Ex. | R2 | R3 | Purity (%) | rt (min.) | [M + H]+ |
|---|---|---|---|---|---|
| 559 | 2-methylphenyl | phenethyl | 87.5 | 4.07 | 408.18 |
| 560 | 2-methylphenyl | 4-bromophenyl | 89.6 | 4.15 | 458.09 |
| 561 | 2-methylphenyl | 4-azidophenyl | 89.5 | 4.04 | 421.17 |
| 562 | 2-methylphenyl | 4-(pyrrolidin-1-yl)phenyl | 54.6 | 4.37 | 449.23 |
| 563 | 2-methylphenyl | 3,5-bis(trifluoromethyl)phenyl | 92.7 | 4.85 | 516.14 |
| 564 | 2-methylphenyl | 4-chloro-3-nitrophenyl | 92.5 | 4.27 | 459.14 |
| 565 | 2-methylphenyl | 2,3-dihydrobenzo[1,4]dioxin-6-yl | 94.2 | 3.87 | 438.18 |

-continued
| | | | | | |
|---|---|---|---|---|---|
| 566 |  | 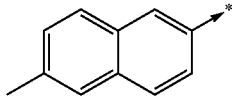 | 92.6 | 4.41 | 444.2 |
| 567 | 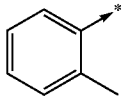 |  | 92.2 | 3.5 | 449.21 |
| 568 | 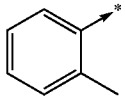 | 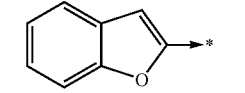 | 92.4 | 4.53 | 420.17 |
| 569 |  | 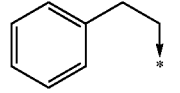 | 86.7 | 4.23 | 422.21 |
| 570 | 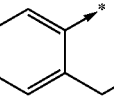 |  | 93.7 | 4.38 | 472.12 |
| 571 | 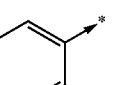 | 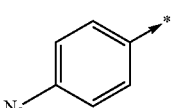 | 88.7 | 4.27 | 435.19 |
| 572 |  | 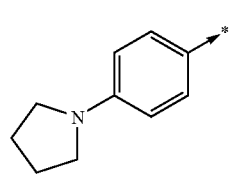 | 64.2 | 4.53 | 463.25 |
| 573 | 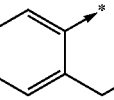 |  | 93.8 | 5.15 | 530.18 |
| 574 | 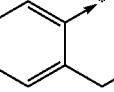 | 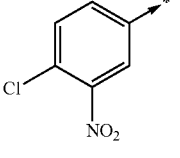 | 93.6 | 4.55 | 473.17 |
| 575 |  | 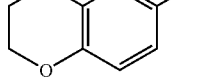 | 86.8 | 4.07 | 452.21 |
| 576 | 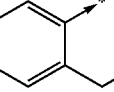 |  | 93.4 | 4.65 | 458.24 |

-continued
| | | | | | |
|---|---|---|---|---|---|
| 577 | 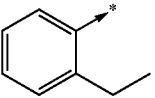 | 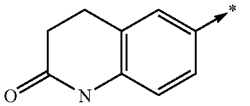 | 91.8 | 3.71 | 463.23 |
| 578 | 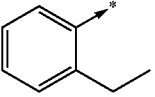 | 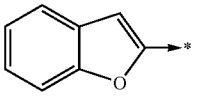 | 91.6 | 4.85 | 434.20 |
| 579 | 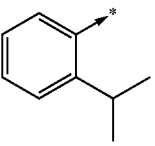 | 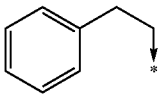 | 83.1 | 4.38 | 436.23 |
| 580 | 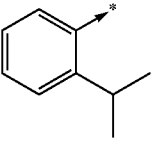 | 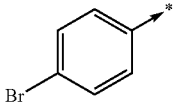 | 92.7 | 4.56 | 486.14 |
| 581 | 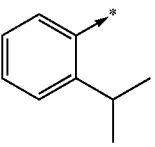 | 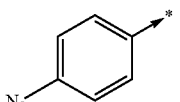 | 88.9 | 4.43 | 449.24 |
| 582 | 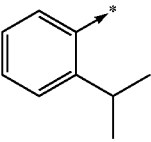 | 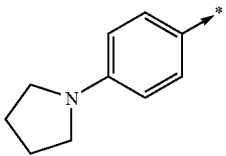 | 80.4 | 4.65 | 477.25 |
| 583 | 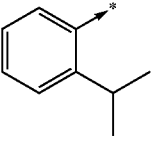 | 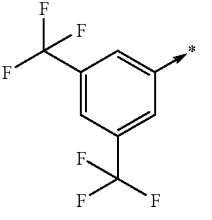 | 93 | 5.34 | 544.19 |
| 584 | 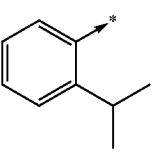 | 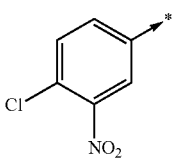 | 94.3 | 4.75 | 487.20 |
| 585 | 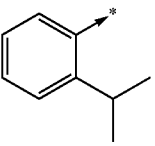 | 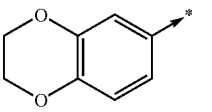 | 93.2 | 4.23 | 466.23 |
| 586 | 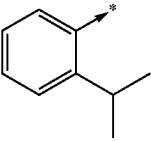 | 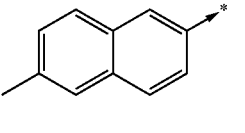 | 94 | 4.82 | 472.28 |

-continued
| | 327 | 328 | | | |
|---|---|---|---|---|---|
| 587 | 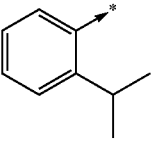 | 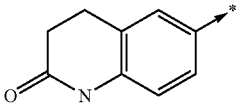 | 92.1 | 3.88 | 477.28 |
| 588 | 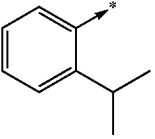 | 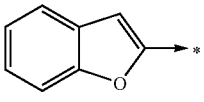 | 91.7 | 5.06 | 448.23 |
| 589 | 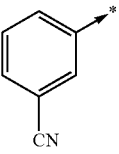 | 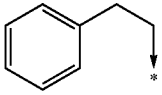 | 83.1 | 4.62 | 419.20 |
| 590 | 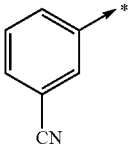 | 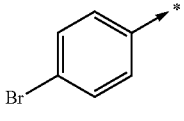 | 93 | 5.06 | 469.09 |
| 591 | 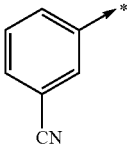 | 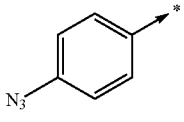 | 88 | 4.89 | 432.18 |
| 592 | 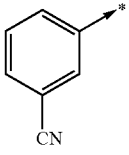 | 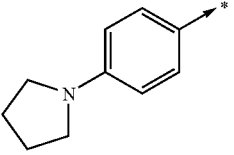 | 88.5 | 5.02 | 460.23 |
| 593 | 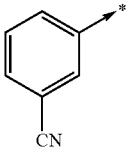 | 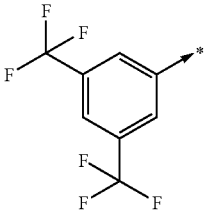 | 93.2 | 5.69 | 527.16 |
| 594 | 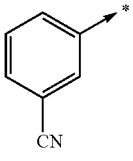 | 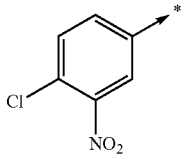 | 91.6 | 5.11 | 470.15 |
| 595 | 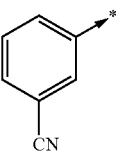 | 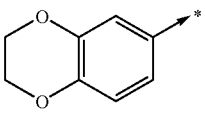 | 90.2 | 4.53 | 449.19 |

-continued

| # | R1 | R2 | % | t | m/z |
|---|---|---|---|---|---|
| 596 | 3-CN-C6H4- | 6-methylnaphthalen-2-yl | 91.9 | 5.4 | 455.19 |
| 597 | 3-CN-C6H4- | 2-oxo-1,2,3,4-tetrahydroquinolin-6-yl | 90.2 | 3.99 | 460.20 |
| 598 | 3-CN-C6H4- | benzofuran-2-yl | 93 | 5.41 | 431.16 |
| 599 | 3-MeO-C6H4- | phenethyl | 86.1 | 4.05 | 424.22 |
| 600 | 3-MeO-C6H4- | 4-Br-C6H4- | 91.8 | 4.17 | 474.12 |
| 601 | 3-MeO-C6H4- | 4-N3-C6H4- | 90.2 | 4.04 | 437.19 |
| 602 | 3-MeO-C6H4- | 4-(pyrrolidin-1-yl)-C6H4- | 86.4 | 4.34 | 465.24 |
| 603 | 3-MeO-C6H4- | 3,5-bis(trifluoromethyl)-C6H3- | 93.5 | 4.91 | 532.19 |
| 604 | 3-MeO-C6H4- | 4-Cl-3-NO2-C6H3- | 93.4 | 4.3 | 475.16 |

| | | | | | |
|---|---|---|---|---|---|
| 605 | 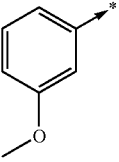 | 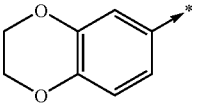 | 87.9 | 3.86 | 454.20 |
| 606 | 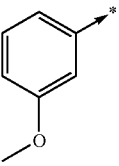 | 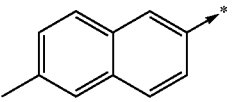 | 91.8 | 4.47 | 460.25 |
| 607 | 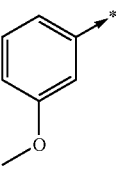 | 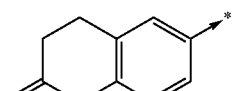 | 90.7 | 3.48 | 465.21 |
| 608 | 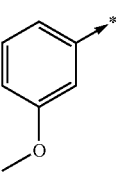 | 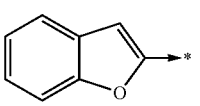 | 92 | 4.55 | 436.19 |
| 609 | 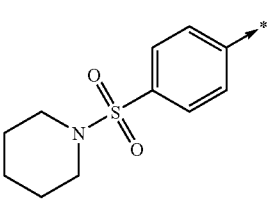 | 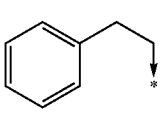 | 85.9 | 5.19 | 541.25 |
| 610 | 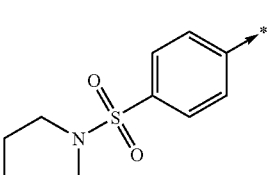 | 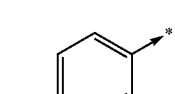 | 92.4 | 5.6 | 591.13 |
| 611 | 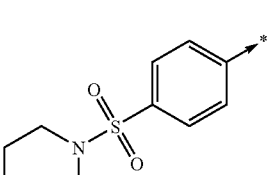 | 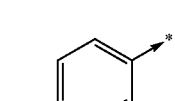 | 89.7 | 5.45 | 554.23 |
| 612 | 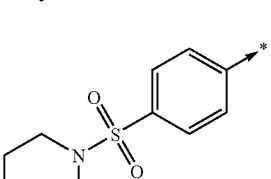 | 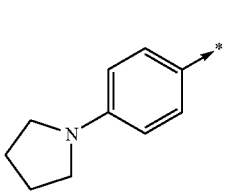 | 88.7 | 5.58 | 582.28 |

-continued
| | 333 | 334 | | | |
|---|---|---|---|---|---|
| 613 | 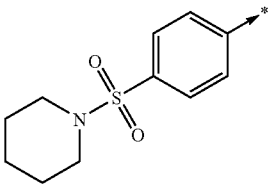 | 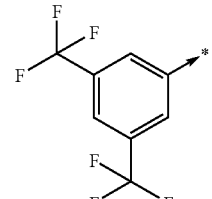 | 93.2 | 6.06 | 649.24 |
| 614 | 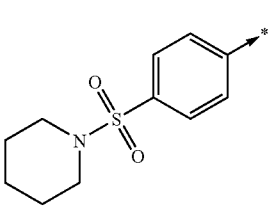 | 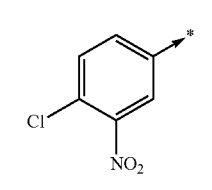 | 94.1 | 5.55 | 592.18 |
| 615 | 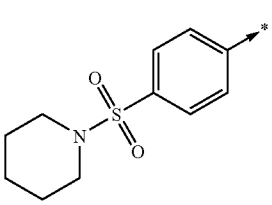 | 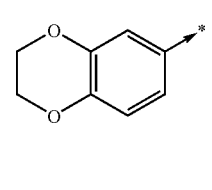 | 90 | 5.09 | 571.23 |
| 616 | 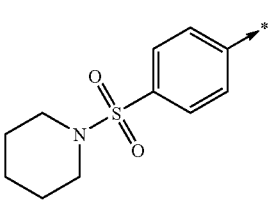 | 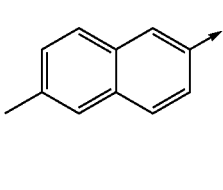 | 93.3 | 5.91 | 577.26 |
| 617 | 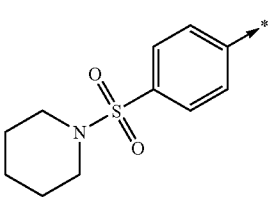 | 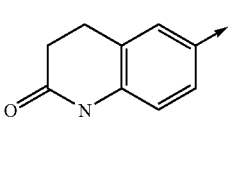 | 91.4 | 4.53 | 582.24 |
| 618 | 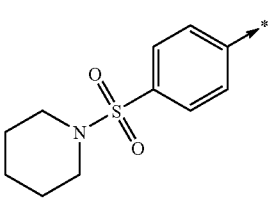 | 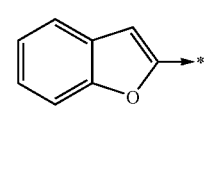 | 92.1 | 5.84 | 553.22 |
| 619 | 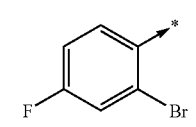 | 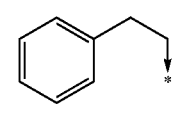 | 76.6 | 5.06 | 490.15 |
| 620 | 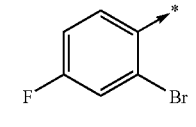 | 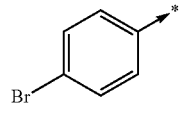 | 91.2 | 5.56 | 539.99 |
| 621 | 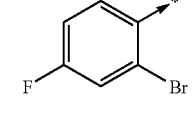 | 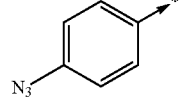 | 86.7 | 5.39 | 503.12 |

-continued
| | | | | | |
|---|---|---|---|---|---|
| 622 | 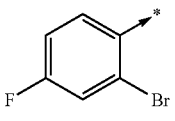 | 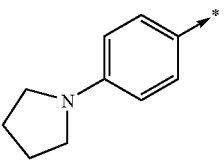 | 81 | 5.47 | 531.15 |
| 623 | 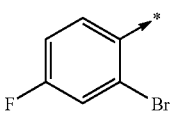 | 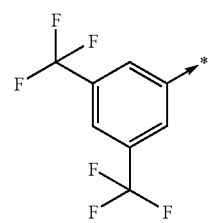 | 92.2 | 6.13 | 598.06 |
| 624 | 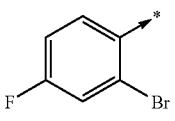 | 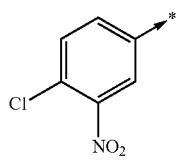 | 84.8 | 5.59 | 541.03 |
| 625 | 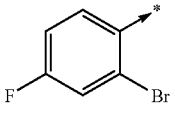 | 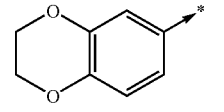 | 88 | 5.04 | 520.11 |
| 626 | 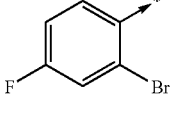 | 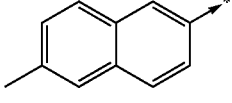 | 91.6 | 5.91 | 526.14 |
| 627 | 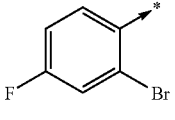 | 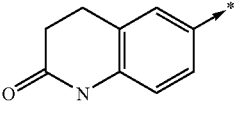 | 89.4 | 4.49 | 531.11 |
| 628 | 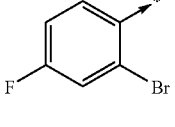 | 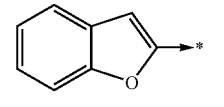 | 90.3 | 5.89 | 502.10 |
| 629 | 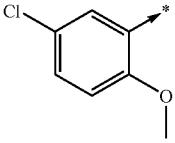 | 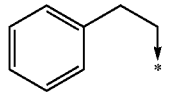 | 83.3 | 4.41 | 458.20 |
| 630 | 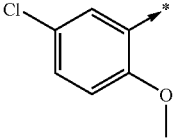 | 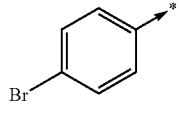 | 91.5 | 4.72 | 508.08 |
| 631 | 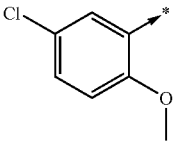 | 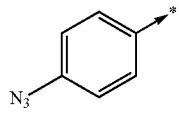 | 87.8 | 4.57 | 471.18 |

-continued
| | | | Purity (%) | rt (min.) | [M + H]+ |
|---|---|---|---|---|---|
| 632 | 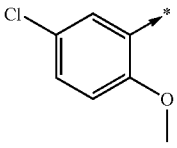 | 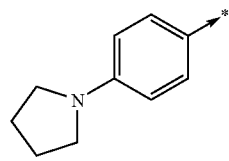 | 57.7 | 4.71 | 499.23 |
| 633 | 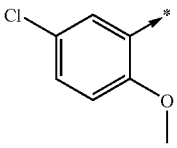 | 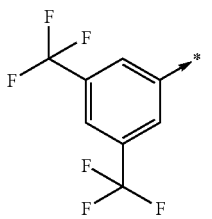 | 92.8 | 5.54 | 566.12 |
| 634 | 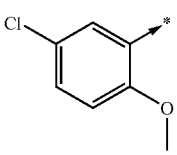 | 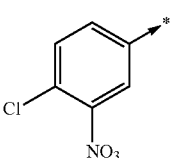 | 93.5 | 4.93 | 509.13 |
| 635 | 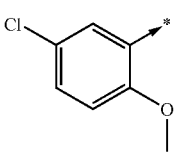 | 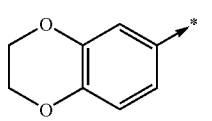 | 89.3 | 4.29 | 488.19 |
| 636 | 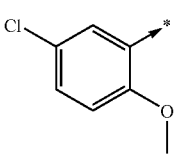 | 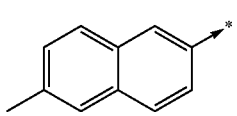 | 93.6 | 4.99 | 494.21 |
| 637 | 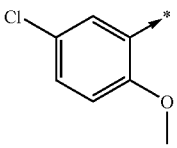 | 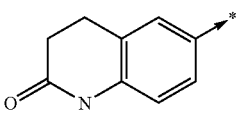 | 91.7 | 3.88 | 499.21 |
| 638 | 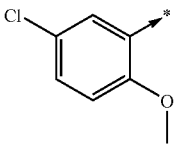 | 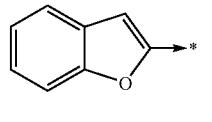 | 91.9 | 5.22 | 470.18 |
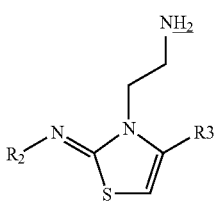
| Ex. | R2 | R3 | Purity (%) | rt (min.) | [M + H]+ |
|---|---|---|---|---|---|
| 639 | 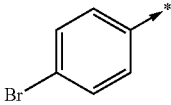 | 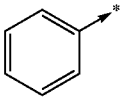 | 95 | 7.28 | 374.10 |

-continued
| | | | | | |
|---|---|---|---|---|---|
| 640 | 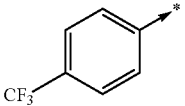 | 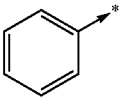 | 87 | 7.62 | 364.24 |
| 641 | 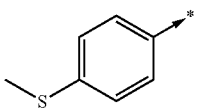 | 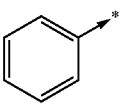 | 84 | 6.75 | 342.23 |
| 642 | 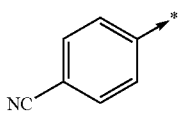 | 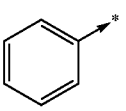 | 79 | 6.6 | 321.24 |
| 643 | 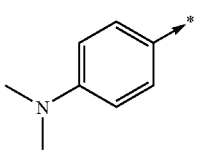 | 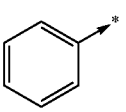 | 81 | 4.96 | 339.29 |
| 644 | 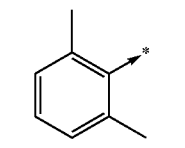 | 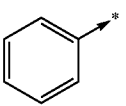 | 82 | 6.44 | 324.28 |
| 645 | 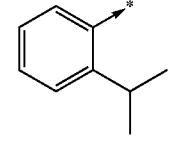 | 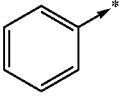 | 83 | 7.16 | 338.30 |
| 646 | 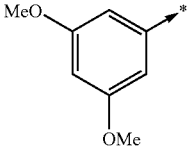 | 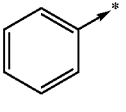 | 59 | 6.6 | 356.25 |
| 647 | 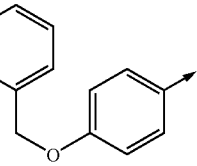 | 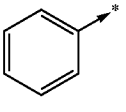 | 86 | 7.28 | 402.23 |
| 648 | 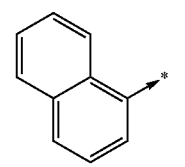 | 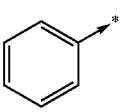 | 84 | 7.29 | 346.26 |
| 649 | 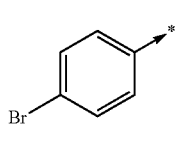 | 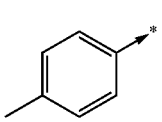 | 85 | 7.66 | 388.1 |
| 650 | 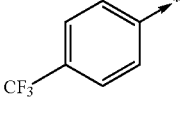 | 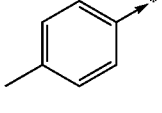 | 84 | 7.96 | 378.21 |

| | | | | | |
|---|---|---|---|---|---|
| 651 | 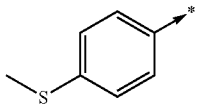 | 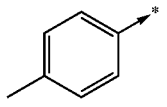 | 85 | 7.14 | 356.23 |
| 652 | 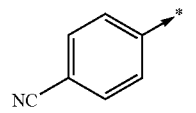 | 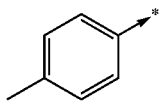 | 73 | 7.02 | 335.26 |
| 653 | 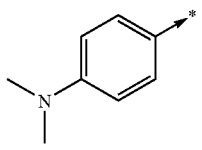 | 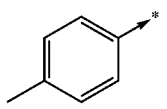 | 76 | 5.37 | 353.29 |
| 654 | 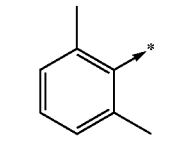 | 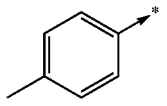 | 83 | 6.84 | 338.30 |
| 655 | 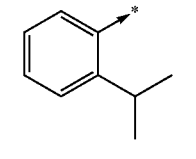 | 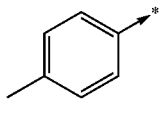 | 81 | 7.51 | 352.29 |
| 656 | 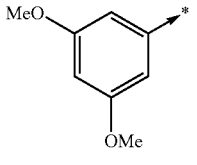 | 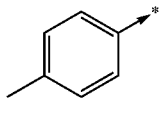 | 75 | 6.99 | 370.27 |
| 657 | 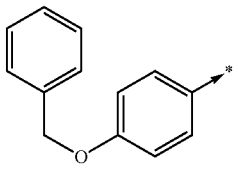 | 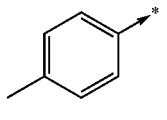 | 77 | 7.6 | 416.26 |
| 658 | 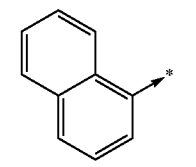 | 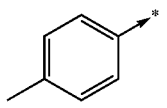 | 80 | 7.65 | 360.25 |
| 659 | 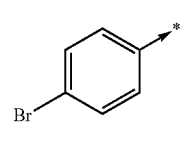 | 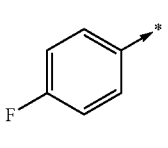 | 87 | 7.37 | 392.10 |
| 660 | 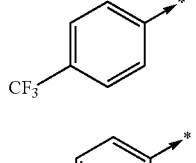 | 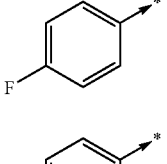 | 71 | 7.7 | 382.16 |
| 661 | 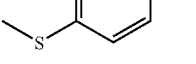 | 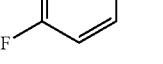 | 63 | 6.9 | 360.21 |

-continued
| | | | | | |
|---|---|---|---|---|---|
| 662 | 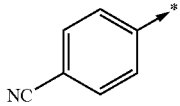 | 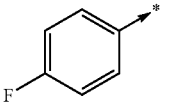 | 59 | 6.7 | 339.23 |
| 663 | 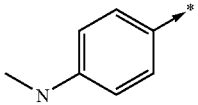 | 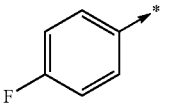 | 80 | 5.06 | 357.26 |
| 664 | 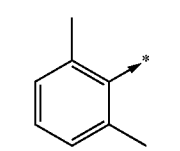 | 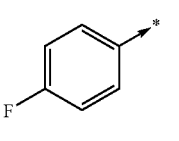 | 63 | 6.61 | 342.26 |
| 665 | 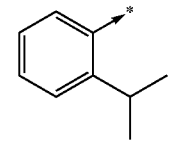 | 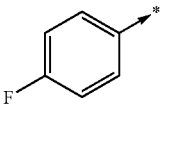 | 82 | 7.28 | 356.25 |
| 666 | 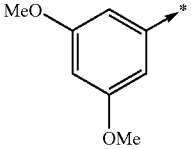 | 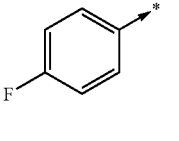 | 39 | 6.74 | 374.22 |
| 667 | 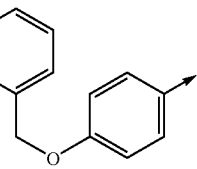 | 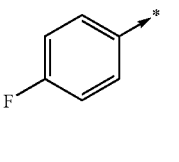 | 85 | 7.42 | 420.24 |
| 668 | 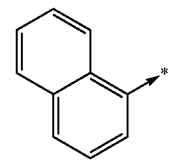 | 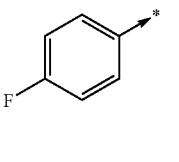 | 81 | 7.39 | 364.26 |
| 669 | 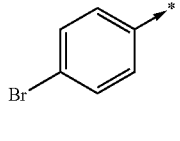 | 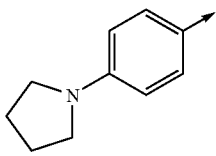 | 93 | 8.28 | 443.2 |
| 670 | 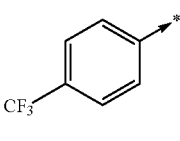 | 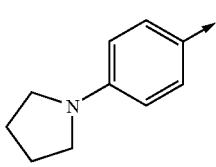 | 88 | 8.61 | 433.2 |
| 671 | 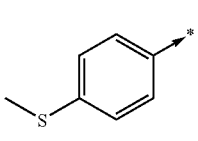 | 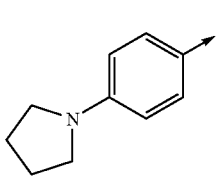 | 88 | 7.7 | 411.2 |

| | | | | | |
|---|---|---|---|---|---|
| 672 | 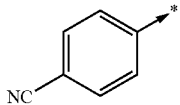 | 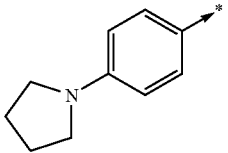 | 80 | 7.76 | 390.26 |
| 673 | 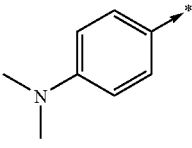 | 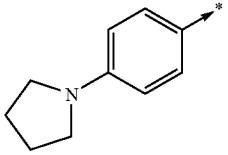 | 85 | 6.08 | 408.3 |
| 674 | 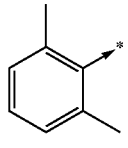 | 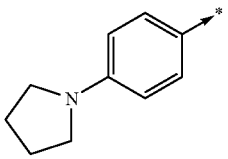 | 89 | 7.36 | 393.3 |
| 675 | 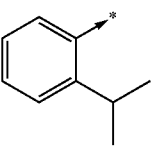 | 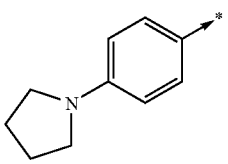 | 84 | 8.03 | 407.3 |
| 676 | 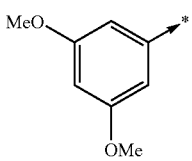 | 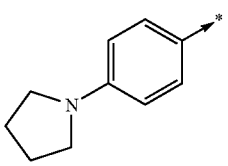 | 81 | 7.59 | 425.3 |
| 677 | 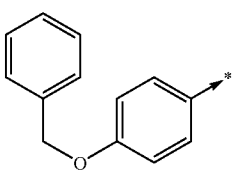 | 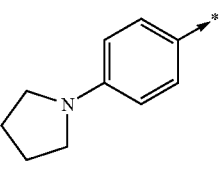 | 83 | 8.03 | 471.3 |
| 678 | 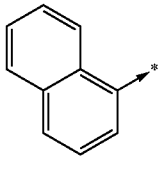 | 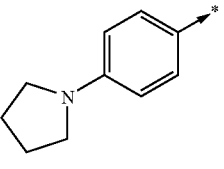 | 91 | 8.24 | 415.2 |
| 679 | 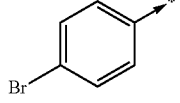 | 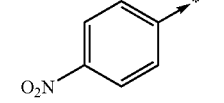 | 78 | 7.41 | 419.09 |
| 680 | 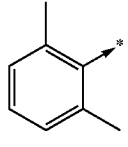 | 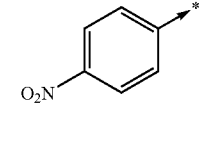 | 75 | 6.98 | 369.23 |

-continued
| | | | | | |
|---|---|---|---|---|---|
| 681 | 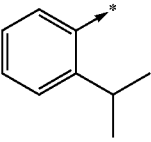 | 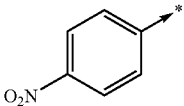 | 81 | 7.51 | 383.23 |
| 682 | 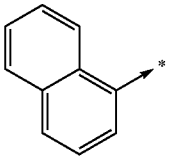 | 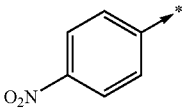 | 85 | 7.46 | 391.20 |
| 683 | 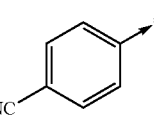 | 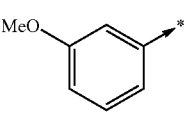 | 74 | 6.79 | 351.21 |
| 684 | 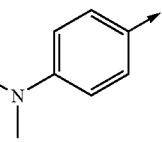 | 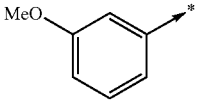 | 81 | 5.18 | 369.26 |
| 685 | 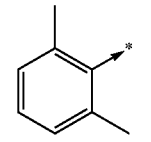 | 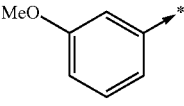 | 76 | 6.73 | 354.26 |
| 686 | 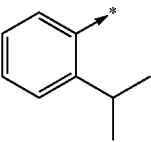 | 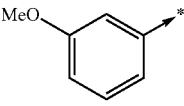 | 87 | 7.39 | 368.27 |
| 687 | 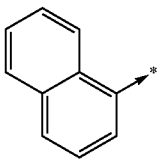 | 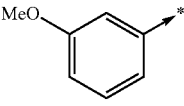 | 80 | 7.48 | 376.22 |
| 688 | 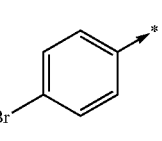 | 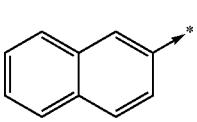 | 83 | 8.14 | 424.11 |
| 689 | 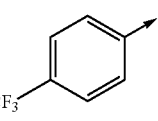 | 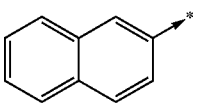 | 83 | 8.37 | 414.14 |
| 690 | 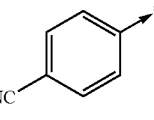 | 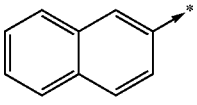 | 78 | 7.48 | 371.21 |
| 691 | 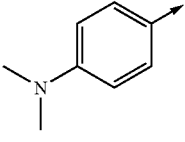 | 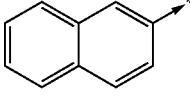 | 85 | 5.88 | 389.24 |

-continued
| | | | | | |
|---|---|---|---|---|---|
| 692 | 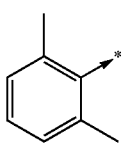 | 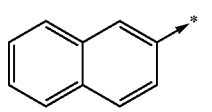 | 79 | 7.53 | 374.24 |
| 693 | 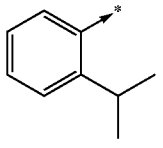 | 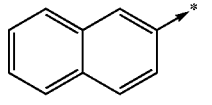 | 83 | 8.1 | 388.23 |
| 694 | 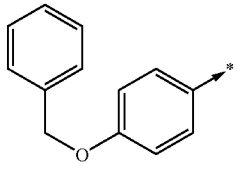 | 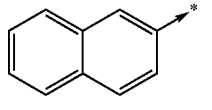 | 77 | 8.18 | 452.23 |
| 695 | 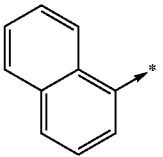 | 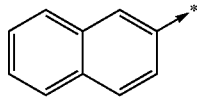 | 81 | 8.14 | 396.20 |
| 696 | 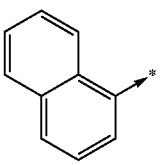 | 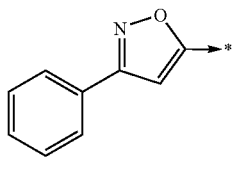 | 76 | 7.94 | 413.16 |
| 697 | 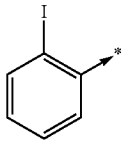 | 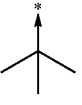 | 86 | 7.41 | 402.01 |
| 698 | 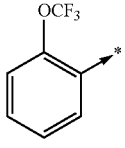 | 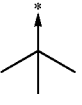 | 93 | 7.57 | 360.16 |
| 699 | 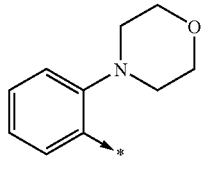 | 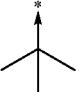 | 74 | 6.32 | 361.23 |
| 700 | 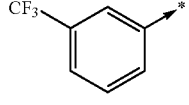 | 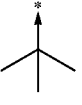 | 88 | 7.75 | 344.19 |
| 701 | 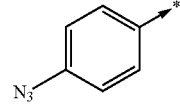 |  | 83 | 6.88 | 317.22 |

-continued
| | | | | | |
|---|---|---|---|---|---|
| 702 | 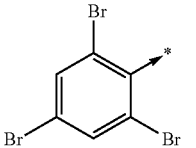 | 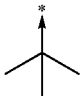 | 93 | 8.33 | 509.9 |
| 703 | 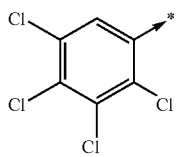 | 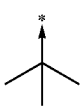 | 90 | 8.69 | 411.99 |
| 704 | 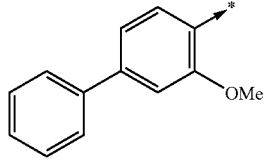 | 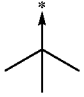 | 72 | 8.16 | 382.21 |
| 705 | 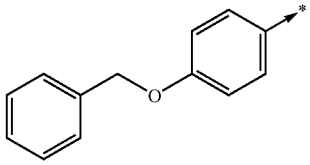 | 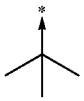 | 81 | 7.27 | 382.2 |
| 706 | 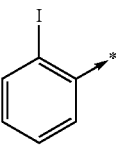 | 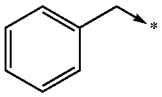 | 82 | 7.7 | 436.05 |
| 707 | 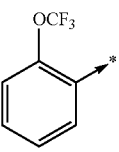 | 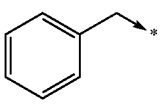 | 91 | 7.85 | 394.16 |
| 708 | 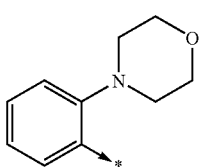 | 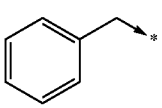 | 80 | 6.59 | 395.19 |
| 709 | 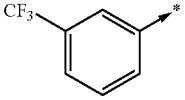 | 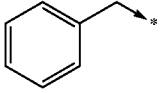 | 87 | 7.99 | 378.16 |
| 710 | 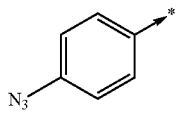 | 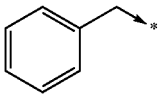 | 83 | 7.3 | 351.2 |
| 711 | 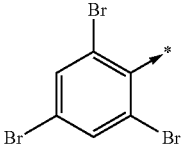 | 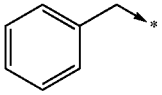 | 89 | 8.58 | 543.85 |

-continued
| | | | | | |
|---|---|---|---|---|---|
| 712 | 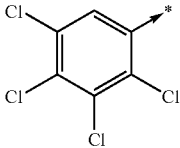 | 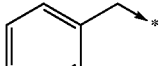 | 89 | 8.9 | 446.01 |
| 713 | 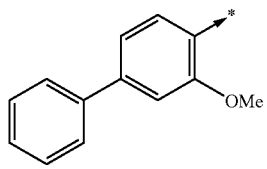 | 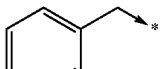 | 72 | 8.35 | 416.19 |
| 714 | 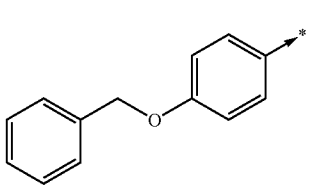 | 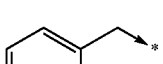 | 82 | 7.62 | 416.19 |
| 715 | 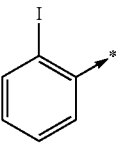 | 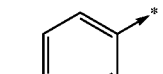 | 85 | 7.84 | 436.05 |
| 716 | 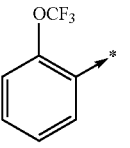 | 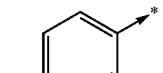 | 88 | 7.97 | 394.14 |
| 717 | 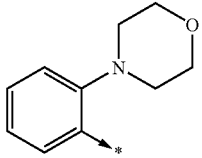 | 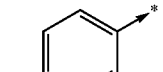 | 75 | 6.82 | 395.21 |
| 718 | 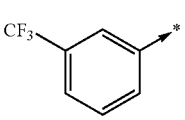 | 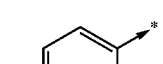 | 88 | 8.13 | 378.13 |
| 719 | 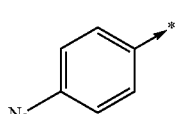 | 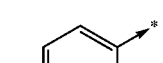 | 78 | 7.5 | 351.2 |
| 720 | 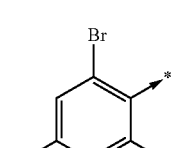 | 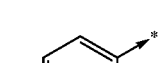 | 91 | 8.65 | 543.86 |
| 721 | 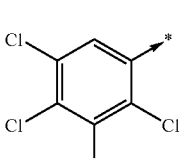 | 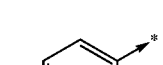 | 89 | 8.97 | 446.0 |

-continued
| | | | | | |
|---|---|---|---|---|---|
| 722 | 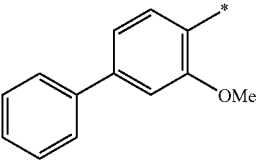 | 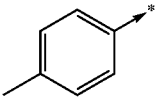 | 75 | 8.55 | 416.19 |
| 723 | 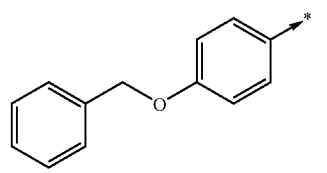 | 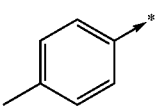 | 83 | 7.84 | 416.19 |
| 724 | 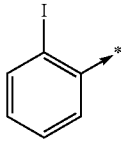 | 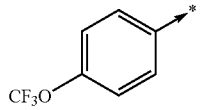 | 90 | 8.24 | 506.01 |
| 725 | 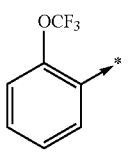 | 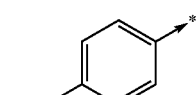 | 88 | 8.37 | 464.1 |
| 726 | 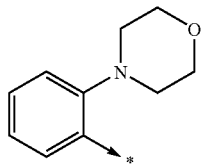 | 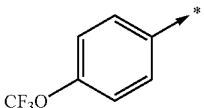 | 76 | 7.43 | 465.17 |
| 727 | 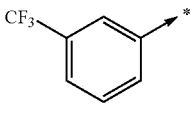 | 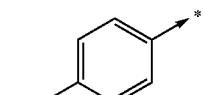 | 86 | 8.52 | 448.1 |
| 728 | 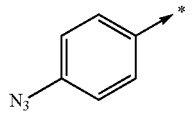 | 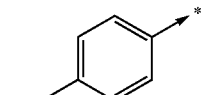 | 84 | 8.11 | 421.11 |
| 729 | 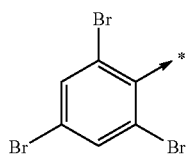 | 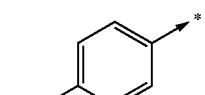 | 89 | 8.97 | 613.8 |
| 730 | 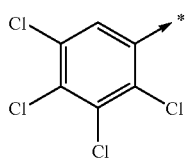 | 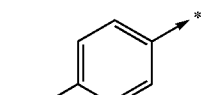 | 90 | 9.24 | 515.94 |

-continued
| | | | | | |
|---|---|---|---|---|---|
| 731 | 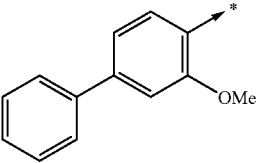 | 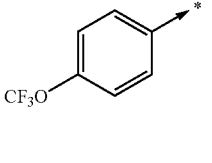 | 74 | 8.94 | 486.17 |
| 732 | 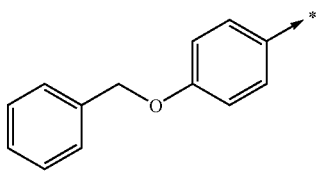 | 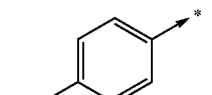 | 81 | 8.51 | 486.16 |
| 733 | 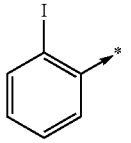 |  | 82 | 8.15 | 584.93 |
| 734 | 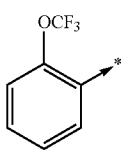 | 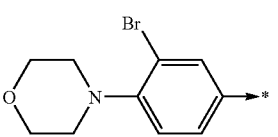 | 81 | 8.26 | 543.05 |
| 735 | 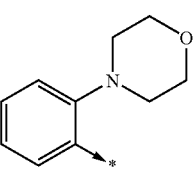 | 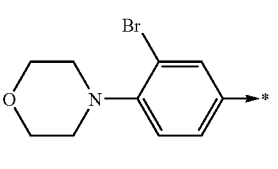 | 69 | 7.31 | 544.1 |
| 736 | 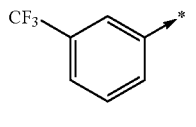 | 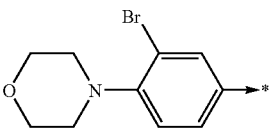 | 80 | 8.43 | 527.07 |
| 737 | 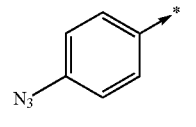 | 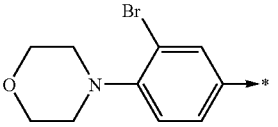 | 82 | 7.99 | 500.1 |
| 738 | 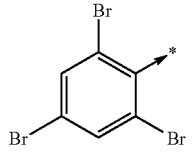 | 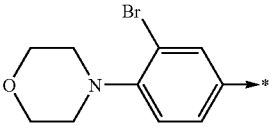 | 88 | 8.92 | 692.79 |
| 739 | 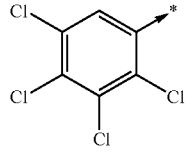 | 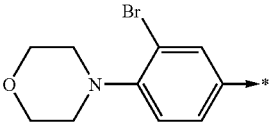 | 85 | 9.23 | 594.87 |

-continued
| | | | | | |
|---|---|---|---|---|---|
| 740 | 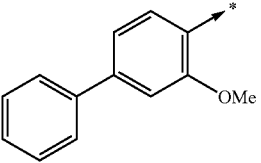 | 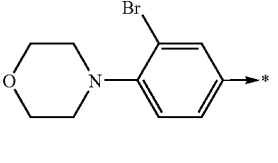 | 71 | 8.84 | 565.1 |
| 741 | 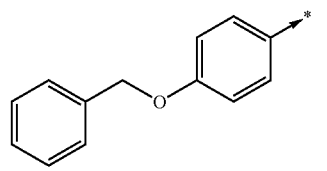 | 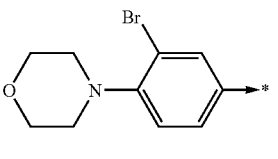 | 79 | 8.36 | 565.08 |
| 742 | 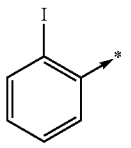 | 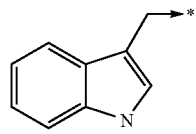 | 82 | 7.77 | 475.06 |
| 743 | 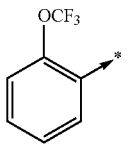 | 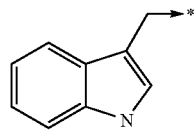 | 81 | 7.91 | 433.13 |
| 744 | 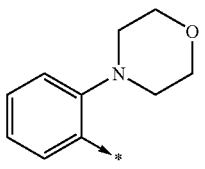 | 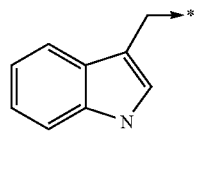 | 86 | 6.72 | 434.21 |
| 745 | 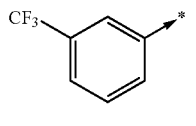 | 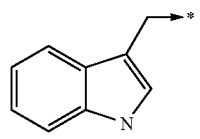 | 82 | 8.03 | 417.15 |
| 746 | 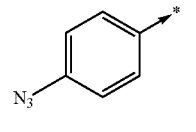 | 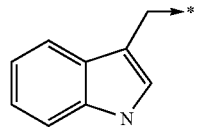 | 74 | 7.32 | 390.17 |
| 747 | 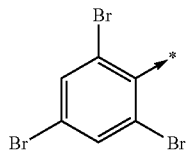 | 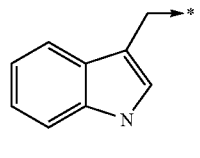 | 86 | 8.61 | 582.85 |
| 748 | 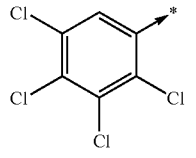 | 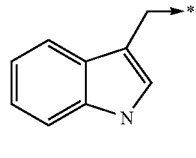 | 76 | 8.94 | 485.01 |

-continued
| | | | | | |
|---|---|---|---|---|---|
| 749 | 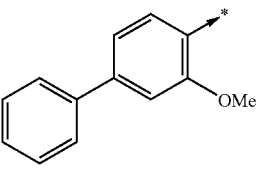 | 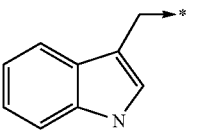 | 73 | 8.33 | 455.19 |
| 750 | 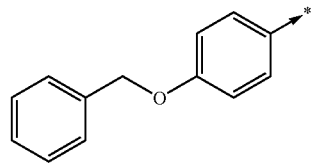 | 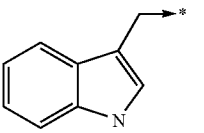 | 84 | 7.59 | 455.2 |
| 751 | 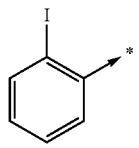 | 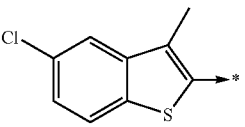 | 67 | 8.82 | 525.96 |
| 752 | 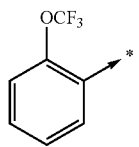 | 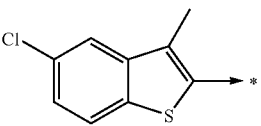 | 75 | 8.93 | 484.08 |
| 753 | 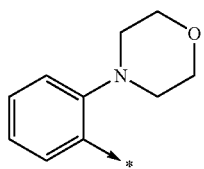 | 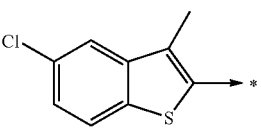 | 68 | 8.08 | 485.14 |
| 754 | 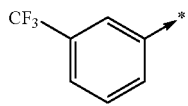 | 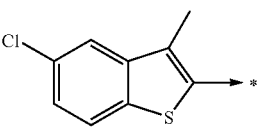 | 75 | 9.08 | 468.06 |
| 755 | 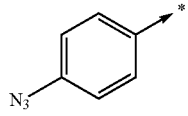 | 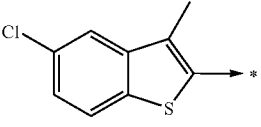 | 78 | 8.77 | 441.06 |
| 756 | 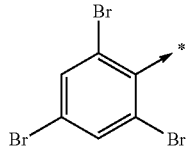 | 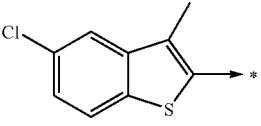 | 81 | 9.56 | 633.79 |
| 757 | 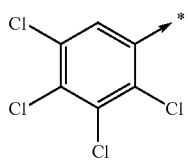 | 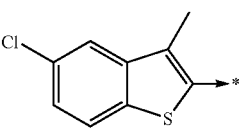 | 81 | 9.77 | 535.91 |

-continued
| Ex. | | | | | |
|---|---|---|---|---|---|
| 758 | 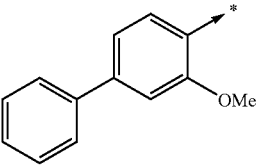 |  | 70 | 9.55 | 506.12 |
| 759 | 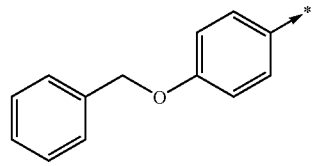 |  | 78 | 9.21 | 506.13 |
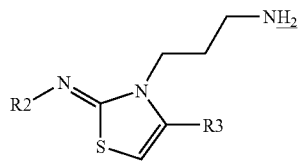
| Ex. | R2 | R3 | Purity (%) | rt (min.) | [M + H]⁺ |
|---|---|---|---|---|---|
| 760 | 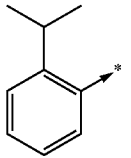 |  | 92.9 | 5.03 | 436.23 |
| 761 | 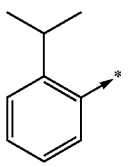 |  | 90.4 | 5.56 | 422.33 |
| 762 | 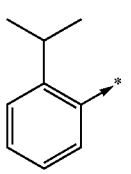 | 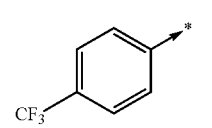 | 94.36 | 4.94 | 420.26 |
| 763 | 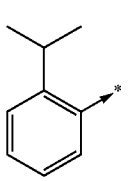 | 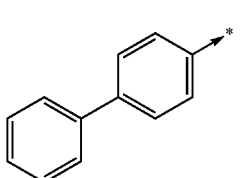 | 88.08 | 5.09 | 428.30 |
| 764 | 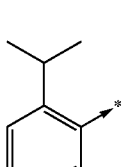 | 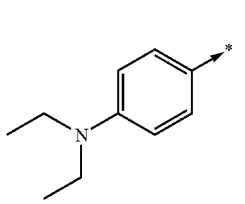 | 77.6 | 4.42 | 423.34 |

-continued
| | | | | | |
|---|---|---|---|---|---|
| 765 | 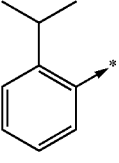 | 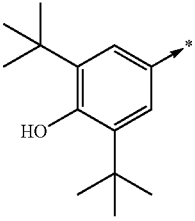 | 92.4 | 5.52 | 480.38 |
| 766 | 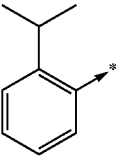 | 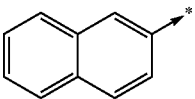 | 84.6 | 4.8 | 402.25 |
| 767 | 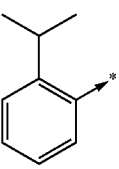 | 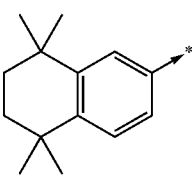 | 89.8 | 5.79 | 462.37 |
| 768 | 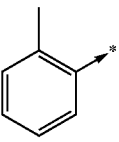 | 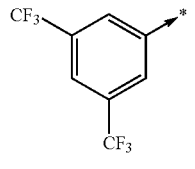 | 91.9 | 5.12 | 460.20 |
| 769 | 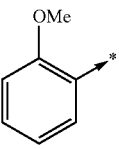 | 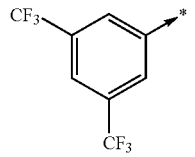 | 91.4 | 5.14 | 476.21 |
| 770 | 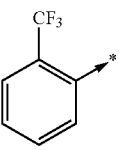 | 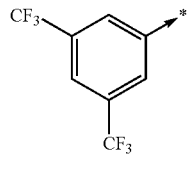 | 94.2 | 5.67 | 514.18 |
| 771 | 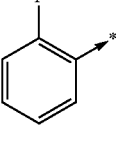 | 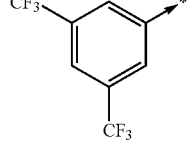 | 93.0 | 5.37 | 464.18 |
| 772 | 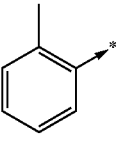 | 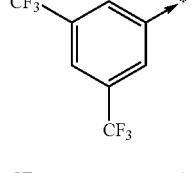 | 94.5 | 5.64 | 572.07 |
| 773 | 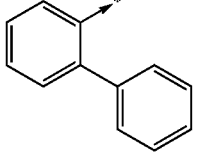 | 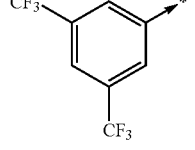 | 87.9 | 5.76 | 522.21 |

-continued
| | | | | | |
|---|---|---|---|---|---|
| 774 | 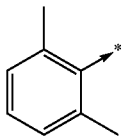 | 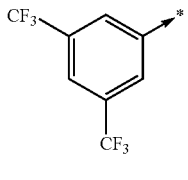 | 91.2 | 5.12 | 474.23 |
| 775 | 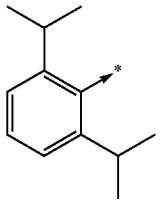 | 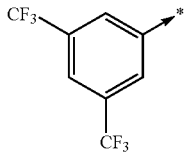 | 78.1 | 5.82 | 530.27 |
| 776 | 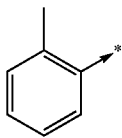 | 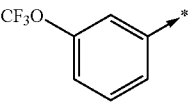 | 88.8 | 4.55 | 408.22 |
| 777 | 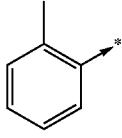 | 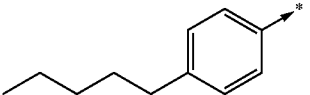 | 90.7 | 5.13 | 394.34 |
| 778 | 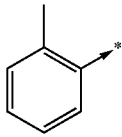 | 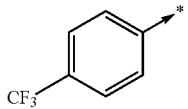 | 92.6 | 4.45 | 392.23 |
| 779 | 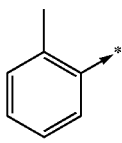 | 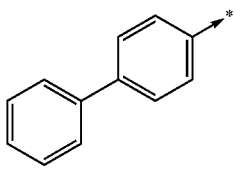 | 88.8 | 4.65 | 400.30 |
| 780 | 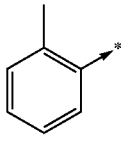 | 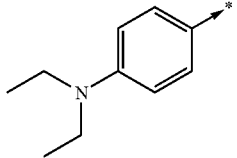 | 76.5 | 3.94 | 395.33 |
| 781 | 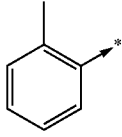 | 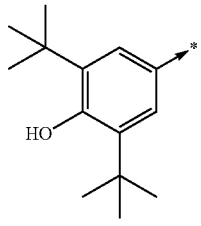 | 90.8 | 5.11 | 452.38 |
| 782 | 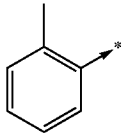 | 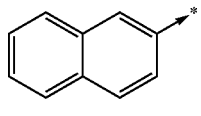 | 87.7 | 4.33 | 374.29 |

-continued
| | | | | | |
|---|---|---|---|---|---|
| 783 | 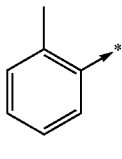 | 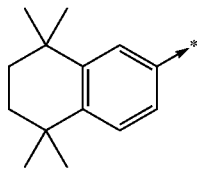 | 91.5 | 5.35 | 434.38 |
| 784 | 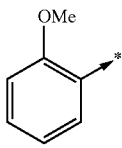 | 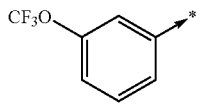 | 92.1 | 4.61 | 424.25 |
| 785 | 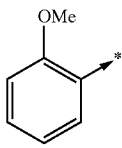 | 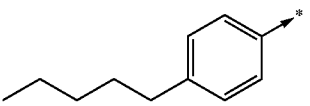 | 89.3 | 5.28 | 410.33 |
| 786 | 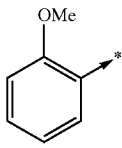 | 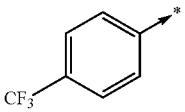 | 95 | 4.49 | 408.22 |
| 787 | 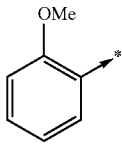 | 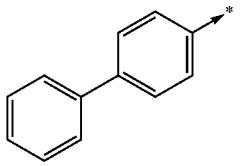 | 82.4 | 4.74 | 416.27 |
| 788 | 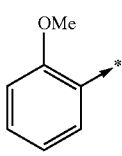 | 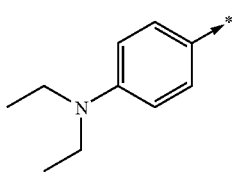 | 73.8 | 3.95 | 411.30 |
| 789 | 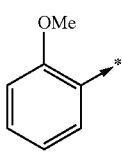 | 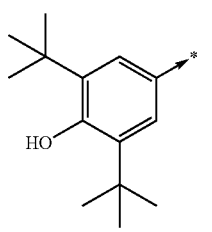 | 92.9 | 5.27 | 468.36 |
| 790 | 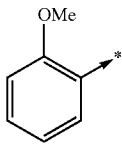 | 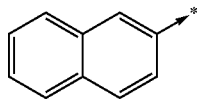 | 84.9 | 4.39 | 390.28 |
| 791 | 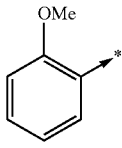 | 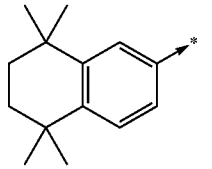 | 91.5 | 5.53 | 450.37 |

-continued
| | | | | | |
|---|---|---|---|---|---|
| 792 | 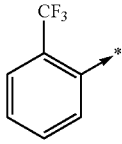 | 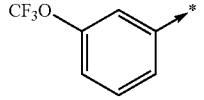 | 90 | 5.5 | 462.19 |
| 793 | 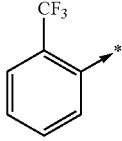 | 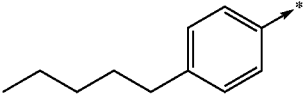 | 93.9 | 6.25 | 448.31 |
| 794 | 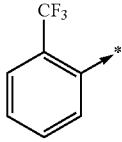 | 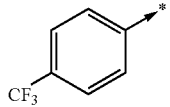 | 94.9 | 5.41 | 446.22 |
| 795 | 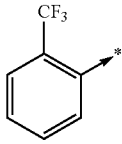 | 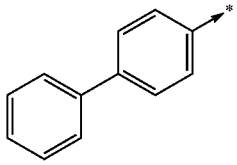 | 93.5 | 5.76 | 454.26 |
| 796 | 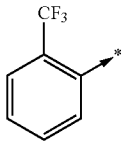 | 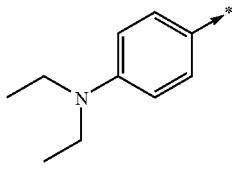 | 89.8 | 4.95 | 449.30 |
| 797 | 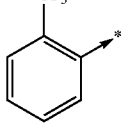 | 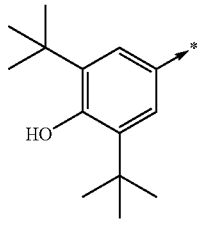 | 92.4 | 6.22 | 506.34 |
| 798 | 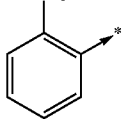 | 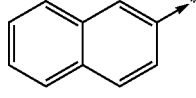 | 93 | 5.52 | 428.245 |
| 799 | 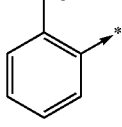 | 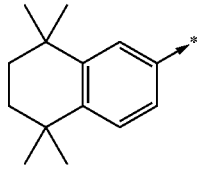 | 92.8 | 6.39 | 488.34 |
| 800 | 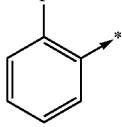 | 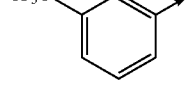 | 87.6 | 5.11 | 412.20 |

-continued
| | | | | | |
|---|---|---|---|---|---|
| 801 | 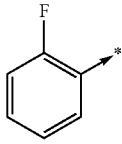 | 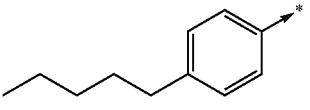 | 92.5 | 5.9 | 398.30 |
| 802 | 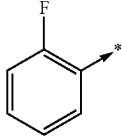 | 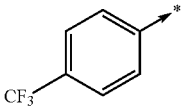 | 93.5 | 5 | 396.20 |
| 803 | 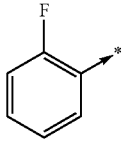 | 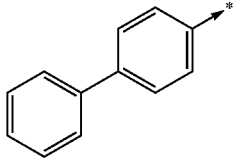 | 92.2 | 5.35 | 404.26 |
| 804 | 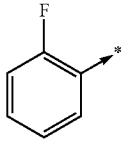 | 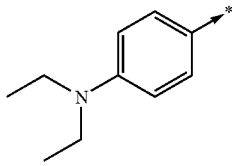 | 90.7 | 4.41 | 399.28 |
| 805 | 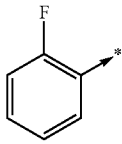 | 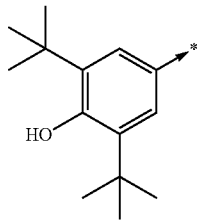 | 94.2 | 5.87 | 456.34 |
| 806 | 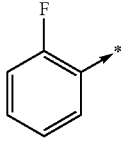 | 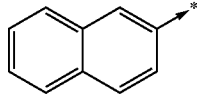 | 89.3 | 5.05 | 378.23 |
| 807 | 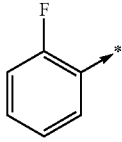 | 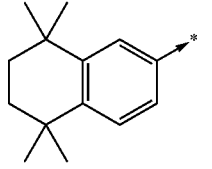 | 90.9 | 6.07 | 438.33 |
| 808 | 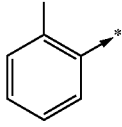 | 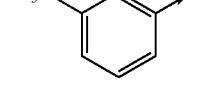 | 88.8 | 5.43 | 520.09 |
| 809 | 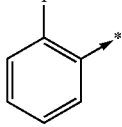 | 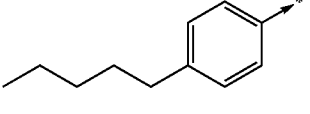 | 94 | 6.19 | 506.19 |

-continued

| | | | | | |
|---|---|---|---|---|---|
| 810 | 2-iodophenyl | 4-(trifluoromethyl)phenyl | 95.9 | 5.33 | 504.12 |
| 811 | 2-iodophenyl | 4-biphenyl | 92.9 | 5.68 | 512.15 |
| 812 | 2-iodophenyl | 4-(diethylamino)phenyl | 88.9 | 4.8 | 507.18 |
| 813 | 2-iodophenyl | 3,5-di-tert-butyl-4-hydroxyphenyl | 92.3 | 6.17 | 564.20 |
| 814 | 2-iodophenyl | 2-naphthyl | 93.9 | 5.41 | 486.14 |
| 815 | 2-iodophenyl | 5,5,8,8-tetramethyl-5,6,7,8-tetrahydronaphthalen-2-yl | 93.5 | 6.35 | 546.18 |
| 816 | 2-biphenyl | 3-(trifluoromethoxy)phenyl | 91.9 | 5.41 | 470.25 |
| 817 | 2-biphenyl | 4-pentylphenyl | 93 | 5.98 | 456.34 |
| 818 | 2-biphenyl | 4-(trifluoromethyl)phenyl | 91.4 | 5.29 | 454.24 |

| | | | | | |
|---|---|---|---|---|---|
| 819 | 2-biphenyl* | 4-biphenyl* | 90.4 | 5.49 | 462.29 |
| 820 | 2-biphenyl* | 4-(N,N-diethylamino)phenyl* | 86.5 | 4.75 | 457.34 |
| 821 | 2-biphenyl* | 3,5-di-tert-butyl-4-hydroxyphenyl* | 90.5 | 5.94 | 514.34 |
| 822 | 2-biphenyl* | 2-naphthyl* | 90.1 | 5.21 | 436.26 |
| 823 | 2-biphenyl* | 5,5,8,8-tetramethyl-5,6,7,8-tetrahydronaphthalen-2-yl* | 89.7 | 6.18 | 496.37 |
| 824 | 2,3-dimethylphenyl* | 3-(trifluoromethoxy)phenyl* | 79.4 | 4.56 | 422.22 |
| 825 | 2,3-dimethylphenyl* | 4-pentylphenyl* | 92.5 | 5.08 | 408.32 |
| 826 | 2,3-dimethylphenyl* | 4-(trifluoromethyl)phenyl* | 93 | 4.45 | 406.23 |
| 827 | 2,3-dimethylphenyl* | 4-biphenyl* | 90.2 | 4.63 | 414.26 |

-continued
| | | | | | |
|---|---|---|---|---|---|
| 828 | 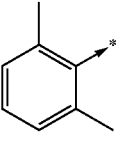 | 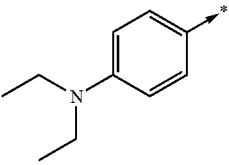 | 76.3 | 4.01 | 409.31 |
| 829 | 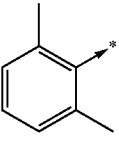 | 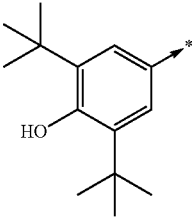 | 94 | 5.08 | 466.36 |
| 830 | 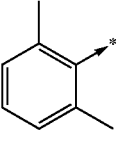 | 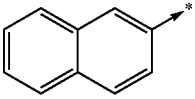 | 90.7 | 4.34 | 388.25 |
| 831 | 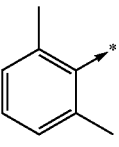 | 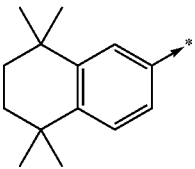 | 92.9 | 5.29 | 448.36 |
| 832 | 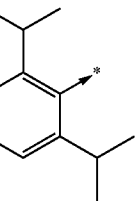 | 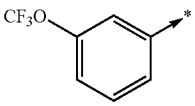 | 56 | 5.3 | 478.29 |
| 833 | 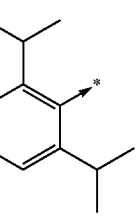 | 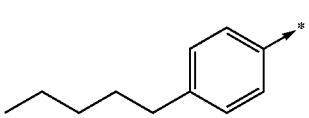 | 83.9 | 5.7 | 464.38 |
| 834 | 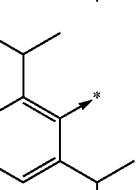 | 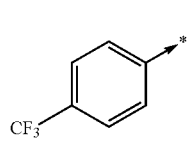 | 82.1 | 5.19 | 462.29 |
| 835 | 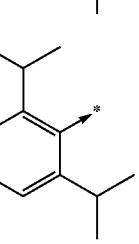 | 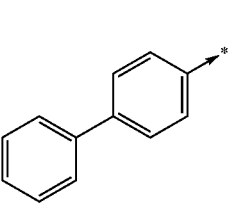 | 80.5 | 5.31 | 470.35 |

-continued
| Ex. | R2 | R3 | Purity (%) | rt (min.) | [M + H]+ |
|---|---|---|---|---|---|
| 836 | 2,6-diisopropylphenyl | 4-(diethylamino)phenyl | 70.6 | 4.8 | 465.39 |
| 837 | 2,6-diisopropylphenyl | 3,5-di-tert-butyl-4-hydroxyphenyl | 82.9 | 5.67 | 522.41 |
| 838 | 2,6-diisopropylphenyl | 2-naphthyl | 81 | 5.07 | 444.33 |
| 839 | 2,6-diisopropylphenyl | 5,5,8,8-tetramethyl-5,6,7,8-tetrahydronaphthalen-2-yl | 83.5 | 5.91 | 504.41 |
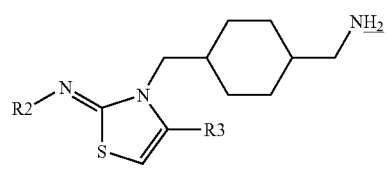
| Ex. | R2 | R3 | Purity (%) | rt (min.) | [M + H]+ |
|---|---|---|---|---|---|
| 840 | phenyl | 2-nitrophenyl | 35 + 64 | 3.68 + 3.78 | 423.2 |
| 841 | phenyl | 2,5-dimethoxyphenyl | 98 | 3.7 | 438.3 |
| 842 | phenyl | 3,4-dichlorophenyl | 35 + 63 | 4.3 + 4.4 | 446.2 |

| | | | | | |
|---|---|---|---|---|---|
| 843 | phenyl* | 2,3-dihydro-1,4-benzodioxin-6-yl* | 97 | 3.71 | 436.3 |
| 844 | phenyl* | 2-oxo-1,2,3,4-tetrahydroquinolin-6-yl* | 32 + 65 | 3.28 + 3.34 | 447.3 |
| 845 | phenyl* | 4-methylphenyl* | 96 | 3.84 | 392.3 |
| 846 | phenyl* | 4-(pyrrolidin-1-yl)phenyl* | 96 | 4.18 | 447.3 |
| 847 | phenyl* | 2-(1,3-dioxoisoindolin-2-yl)ethyl* | 30 + 64 | 3.62 + 3.64 | 475.3 |
| 848 | phenyl* | benzofuran-2-yl* | 36 + 61 | 4.46 + 4.61 | 418.3 |
| 849 | 4-bromo-2-(trifluoromethyl)phenyl* | 2-nitrophenyl* | 96 | 5.89 | 569.1 |
| 850 | 4-bromo-2-(trifluoromethyl)phenyl* | 2,4-dimethoxyphenyl* | 94 | 6.09 | 584.2 |
| 851 | 4-bromo-2-(trifluoromethyl)phenyl* | 3,4-dichlorophenyl* | 57 + 39 | 6.55 + 6.6 | 592.1 |

-continued

| | R1 | R2 | Yield | RT | MS |
|---|---|---|---|---|---|
| 852 | 4-Br-2-CF3-phenyl | 2,3-dihydro-1,4-benzodioxin-6-yl | 96 | 6.16 | 582.2 |
| 853 | 4-Br-2-CF3-phenyl | 2-oxo-1,2,3,4-tetrahydroquinolin-6-yl | 28 + 59 | 5.53 + 5.61 | 593.2 |
| 854 | 4-Br-2-CF3-phenyl | 4-methylphenyl | 95 | 6.35 | 538.2 |
| 855 | 4-Br-2-CF3-phenyl | 4-(pyrrolidin-1-yl)phenyl | 54 + 41 | 6.8 + 6.88 | 593.3 |
| 856 | 4-Br-2-CF3-phenyl | 2-(1,3-dioxoisoindolin-2-yl)ethyl | 94 | 5.96 | 621.2 |
| 857 | 4-Br-2-CF3-phenyl | benzofuran-2-yl | 56 + 39 | 6.46 + 6.55 | 564.2 |
| 858 | 2-ethylphenyl | 2-nitrophenyl | 34 + 63 | 4.09 + 4.2 | 451.3 |
| 859 | 2-ethylphenyl | 2,5-dimethoxyphenyl | 96 | 4.03 | 466.4 |

-continued
| | | | | | |
|---|---|---|---|---|---|
| 860 | 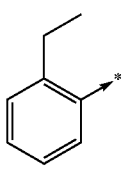 | 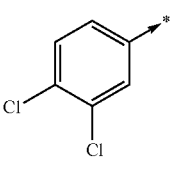 | 33 + 64 | 4.69 + 4.76 | 474.3 |
| 861 | 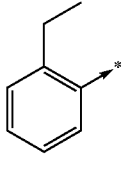 | 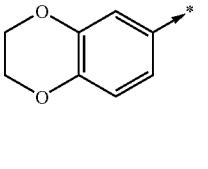 | 27 + 70 | 4.04 + 4.07 | 464.4 |
| 862 | 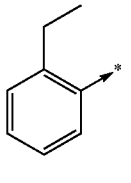 | 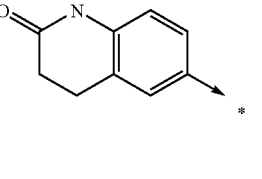 | 33 + 63 | 3.63 + 3.71 | 475.4 |
| 863 | 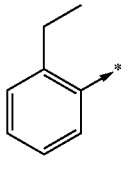 | 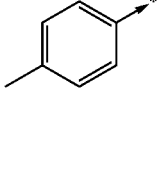 | 95 | 4.18 | 420.4 |
| 864 | 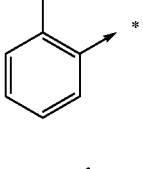 | 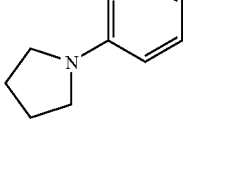 | 89 | 4.46 | 475.4 |
| 865 | 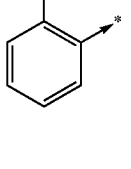 | 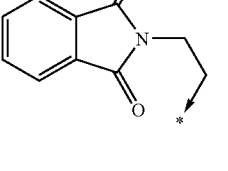 | 22 + 68 | 3.94 + 3.98 | 503.4 |
| 866 | 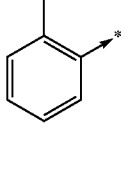 | 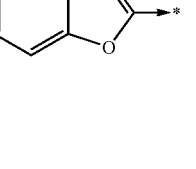 | 35 + 62 | 4.9 + 5.01 | 446.4 |
| 867 | 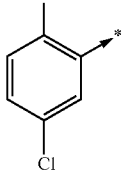 | 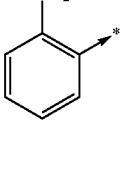 | 35 + 61 | 4.39 + 4.52 | 487.3 |

-continued
| | | | | | |
|---|---|---|---|---|---|
| 868 | 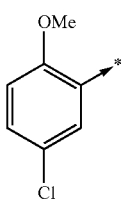 | 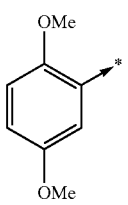 | 33 + 63 | 4.22 + 4.29 | 502.3 |
| 869 | 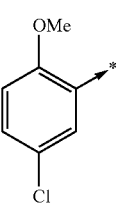 | 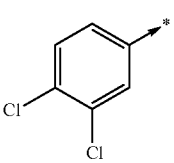 | 35 + 62 | 5.08 + 5.2 | 510.2 |
| 870 | 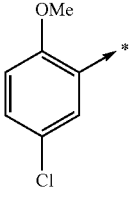 | 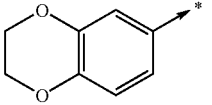 | 31 + 63 | 4.26 + 4.34 | 500.3 |
| 871 | 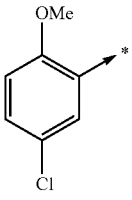 | 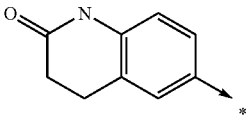 | 33 + 62 | 3.82 + 3.91 | 511.3 |
| 872 | 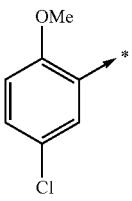 | 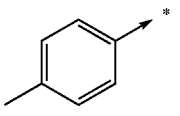 | 31 + 62 | 4.42 + 4.51 | 456.3 |
| 873 | 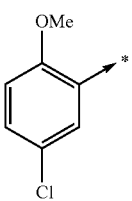 | 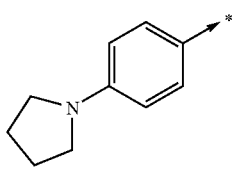 | 29 + 64 | 4.66 + 4.72 | 511.4 |
| 874 | 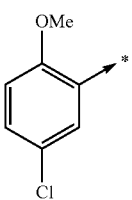 | 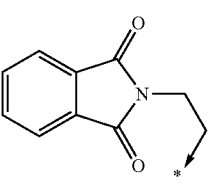 | 33 + 57 | 4.11 + 4.2 | 539.3 |

-continued
| | 391 | 392 | | | |
|---|---|---|---|---|---|
| 875 | 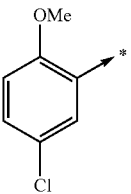 | 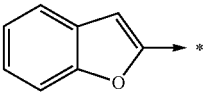 | 35 + 62 | 5.26 + 5.39 | 482.3 |
| 876 | 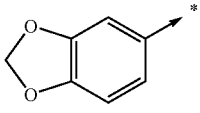 | 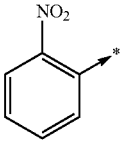 | 32 + 65 | 3.63 + 3.7 | 467.3 |
| 877 | 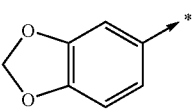 | 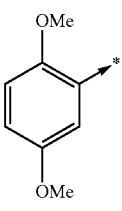 | 97 | 3.69 | 482.4 |
| 878 | 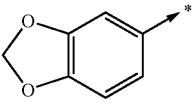 | 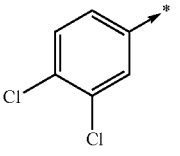 | 35 + 62 | 4.2 + 4.28 | 490.3 |
| 879 | 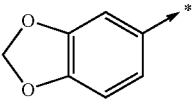 | 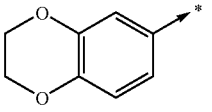 | 94 | 3.69 | 480.3 |
| 880 | 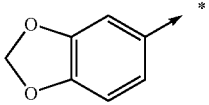 | 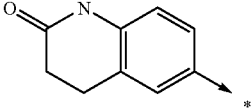 | 28 + 68 | 3.3 + 3.33 | 491.3 |
| 881 | 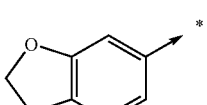 | 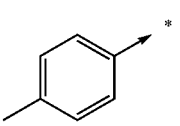 | 96 | 3.8 | 436.3 |
| 882 | 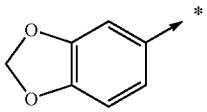 | 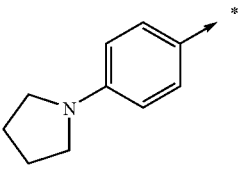 | 96 | 4.18 | 491.4 |
| 883 | 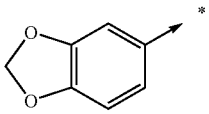 | 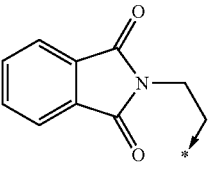 | 94 | 3.63 | 519.3 |
| 884 | 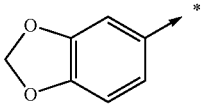 | 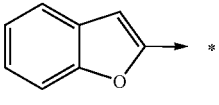 | 36 + 61 | 4.28 + 4.42 | 462.3 |

| | | | | | |
|---|---|---|---|---|---|
| 885 | 2,5-dimethoxy-4-chlorophenyl | 2-nitrophenyl | 36 + 62 | 4.24 + 4.36 | 517.3 |
| 886 | 2,5-dimethoxy-4-chlorophenyl | 2,5-dimethoxyphenyl | 28 + 69 | 4.15 + 4.21 | 532.3 |
| 887 | 2,5-dimethoxy-4-chlorophenyl | 3,4-dichlorophenyl | 35 + 62 | 4.84 + 4.96 | 540.2 |
| 888 | 2,5-dimethoxy-4-chlorophenyl | 2,3-dihydrobenzo[1,4]dioxin-6-yl | 33 + 64 | 4.15 + 4.22 | 530.3 |
| 889 | 2,5-dimethoxy-4-chlorophenyl | 2-oxo-1,2,3,4-tetrahydroquinolin-6-yl | 32 + 63 | 3.76 + 3.84 | 541.3 |
| 890 | 2,5-dimethoxy-4-chlorophenyl | 4-methylphenyl | 32 + 63 | 4.28 + 4.36 | 486.3 |
| 891 | 2,5-dimethoxy-4-chlorophenyl | 4-(pyrrolidin-1-yl)phenyl | 24 + 73 | 4.56 + 4.6 | 541.3 |

-continued

| | | | | | |
|---|---|---|---|---|---|
| 892 | 2,5-dimethoxy-4-chlorophenyl | N-ethyl-phthalimide | 31 + 59 | 4.05 + 4.11 | 569.3 |
| 893 | 2,5-dimethoxy-4-chlorophenyl | benzofuran-2-yl | 35 + 61 | 4.99 + 5.14 | 512.3 |
| 894 | 4-(4-nitrophenylthio)phenyl | 2-nitrophenyl | 33 + 64 | 5.59 + 5.7 | 576.3 |
| 895 | 4-(4-nitrophenylthio)phenyl | 2,5-dimethoxyphenyl | 35 + 61 | 5.29 + 5.39 | 591.3 |
| 896 | 4-(4-nitrophenylthio)phenyl | 3,4-dichlorophenyl | 26 + 71 | 6.32 + 6.35 | 599.2 |
| 897 | 4-(4-nitrophenylthio)phenyl | 2,3-dihydrobenzo[1,4]dioxin-6-yl | 34 + 63 | 5.41 + 5.5 | 589.3 |
| 898 | 4-(4-nitrophenylthio)phenyl | 2-oxo-1,2,3,4-tetrahydroquinolin-6-yl | 35 + 61 | 4.88 + 4.99 | 600.3 |
| 899 | 4-(4-nitrophenylthio)phenyl | 4-methylphenyl | 35 + 62 | 5.63 + 5.72 | 545.3 |
| 900 | 4-(4-nitrophenylthio)phenyl | 4-(pyrrolidin-1-yl)phenyl | 34 + 61 | 5.76 + 5.86 | 600.3 |

-continued

| | | | | | |
|---|---|---|---|---|---|
| 901 | O2N-C6H4-S-C6H4-* | phthalimide-N-CH2CH2-* | 34 + 68 | 5.16 + 5.28 | 628.3 |
| 902 | O2N-C6H4-S-C6H4-* | benzofuran-2-yl-* | 98 | 6.45 | 571.3 |
| 903 | HN=S(=O)2-C6H4-* | 2-NO2-C6H4-* | 35 + 60 | 3.84 + 3.93 | 502.3 |
| 904 | HN=S(=O)2-C6H4-* | 2,5-(OMe)2-C6H3-* | 32 + 62 | 3.72 + 3.79 | 517.3 |
| 905 | HN=S(=O)2-C6H4-* | 3,4-Cl2-C6H3-* | 32 + 62 | 4.59 + 4.68 | 525.2 |
| 906 | HN=S(=O)2-C6H4-* | benzo[1,4]dioxin-6-yl-* | 33 + 61 | 3.75 + 3.82 | 515.3 |
| 907 | HN=S(=O)2-C6H4-* | 2-oxo-1,2,3,4-tetrahydroquinolin-6-yl-* | 29 + 64 | 3.18 + 3.26 | 526.3 |
| 908 | HN=S(=O)2-C6H4-* | 4-Me-C6H4-* | 32 + 59 | 4 + 4.09 | 471.3 |
| 909 | HN=S(=O)2-C6H4-* | 4-(pyrrolidin-1-yl)-C6H4-* | 32 + 60 | 4.28 + 4.38 | 526.3 |

-continued
| Ex. | | | Purity (%) | rt (min.) | [M + H]+ |
|---|---|---|---|---|---|
| 910 | 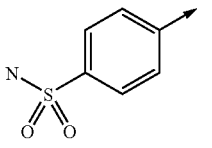 | 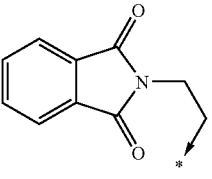 | 34 + 56 | 3.62 + 3.71 | 554.3 |
| 911 | 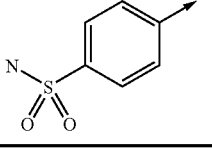 | 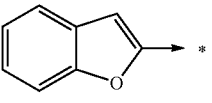 | 31 + 63 | 4.58 + 4.66 | 497.3 |
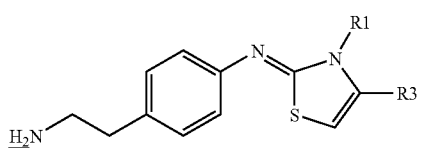
| Ex. | R1 | R3 | Purity (%) | rt (min.) | [M + H]+ |
|---|---|---|---|---|---|
| 912 | 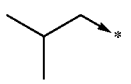 | 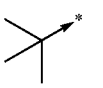 | 6.8 + 91.2 | 3.6 + 3.76 | 332.22 |
| 913 | 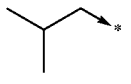 | 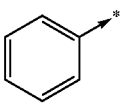 | 88.1 | 3.94 | 352.19 |
| 914 |  | 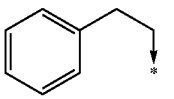 | 89.6 | 4.22 | 380.22 |
| 915 | 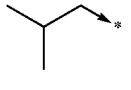 | 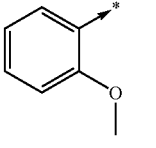 | 61.6 | 3.95 | 382.17 |
| 916 | 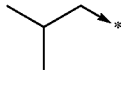 | 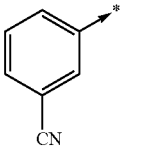 | 83.5 | 3.8 | 377.19 |
| 917 | 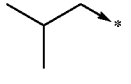 | 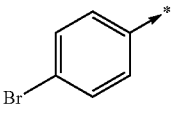 | 84.2 | 4.41 | 430.10 |
| 918 | 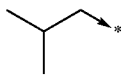 | 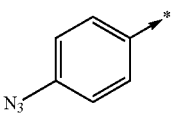 | 70.9 | 4.24 | 393.18 |
| 919 | 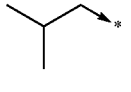 | 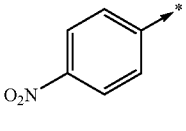 | 84.1 | 4.1 | 397.16 |

-continued

| # | R1 | R2 | % | t | MS |
|---|---|---|---|---|---|
| 920 | isobutyl | 5-bromothien-2-yl | 82.2 | 4.55 | 436.05 |
| 921 | isobutyl | benzofuran-2-yl | 82.8 | 4.66 | 392.17 |
| 922 | phenethyl | tert-butyl | 98 | 4.25 | 380.22 |
| 923 | phenethyl | phenyl | 91.1 | 4.26 | 400.17 |
| 924 | phenethyl | phenethyl | 92.4 | 4.46 | 428.21 |
| 925 | phenethyl | 2-methoxyphenyl | 93.8 | 4.23 | 430.20 |
| 926 | phenethyl | 3-cyanophenyl | 86.4 | 4.14 | 425.17 |
| 927 | phenethyl | 4-bromophenyl | 92.3 | 4.7 | 478.11 |
| 928 | phenethyl | 4-azidophenyl | 82 | 4.56 | 441.18 |
| 929 | phenethyl | 4-nitrophenyl | 90.9 | 4.44 | 445.18 |
| 930 | phenethyl | 5-bromothien-2-yl | 89.8 | 4.9 | 484.07 |
| 931 | phenethyl | benzofuran-2-yl | 86.4 | 5.0 | 440.17 |
| 932 | 3-phenylpropyl | tert-butyl | 97.2 | 4.38 | 394.22 |

-continued
| | 403 | | 404 | | | |
|---|---|---|---|---|---|---|
| 933 | 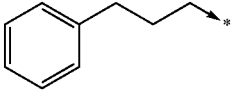 | 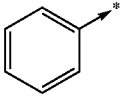 | | 86.3 | 4.48 | 414.18 |
| 934 | 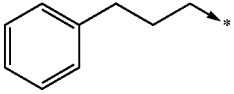 | 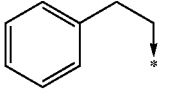 | | 92.6 | 4.68 | 442.22 |
| 935 | 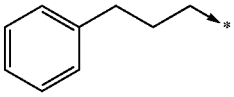 | 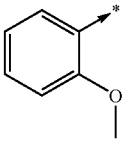 | | 91 | 4.44 | 444.22 |
| 936 | 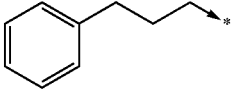 | 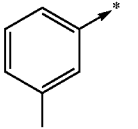 | | 85.9 | 4.34 | 439.18 |
| 937 | 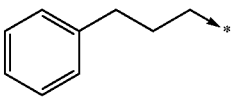 | 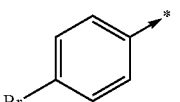 | | 88.2 | 4.86 | 492.12 |
| 938 | 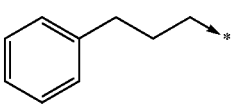 | 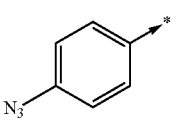 | | 83.6 | 4.71 | 455.2 |
| 939 | 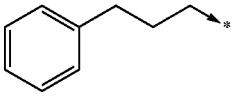 | 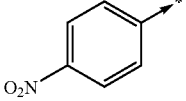 | | 87.8 | 4.59 | 459.19 |
| 940 | 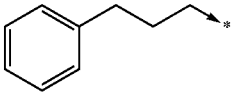 |  | | 89.8 | 5.0 | 498.09 |
| 941 | 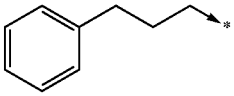 | 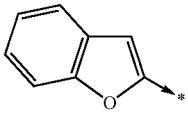 | | 83.9 | 5.14 | 454.20 |
| 942 | 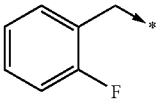 | 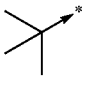 | | 87.7 | 4.26 | 384.17 |
| 943 | 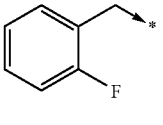 | 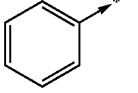 | | 94.7 | 4.5 | 404.15 |
| 944 | 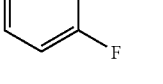 | 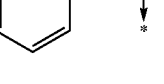 | | 18.6 + 76.4 | 4.2 + 4.64 | 432.18 |

-continued
| | 405 | 406 | | | |
|---|---|---|---|---|---|
| 945 | 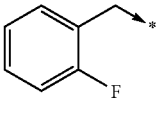 | 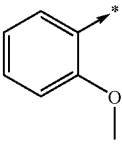 | 95.2 | 4.32 | 434.16 |
| 946 | 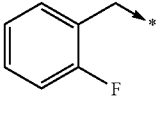 | 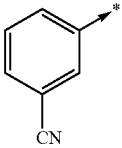 | 92 | 4.46 | 429.15 |
| 947 | 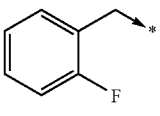 | 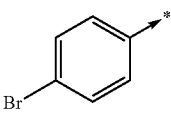 | 94.4 | 5.08 | 482.06 |
| 948 | 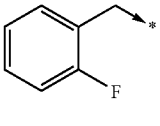 | 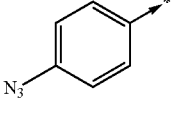 | 93 | 4.86 | 445.16 |
| 949 | 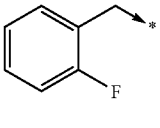 | 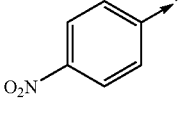 | 94.2 | 4.82 | 449.13 |
| 950 | 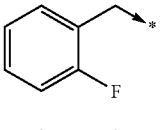 | 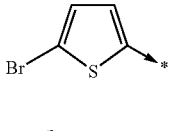 | 93.1 | 5.34 | 488.03 |
| 951 | 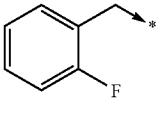 | 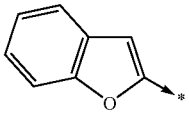 | 93.7 | 5.47 | 444.16 |
| 952 | 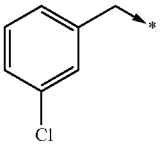 | 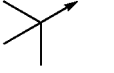 | 91.5 | 4.43 | 400.13 |
| 953 | 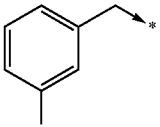 | 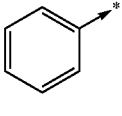 | 95 | 4.82 | 420.12 |
| 954 | 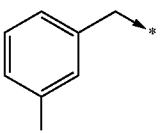 | 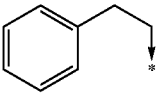 | 14.8 + 81.2 | 4.38 + 4.88 | 448.15 |
| 955 | 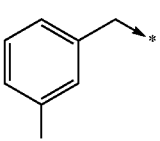 | 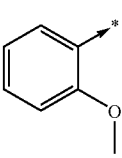 | 95.8 | 4.64 | 450.13 |

-continued
| | 407 | 408 | | | |
|---|---|---|---|---|---|
| 956 | 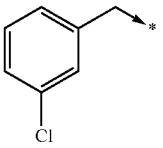 3-Cl-C6H4-CH2-* | 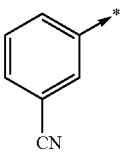 3-CN-C6H4-* | 95 | 4.79 | 445.11 |
| 957 | 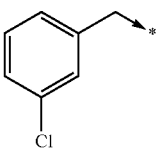 3-Cl-C6H4-CH2-* | 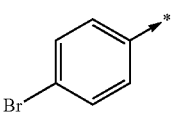 4-Br-C6H4-* | 95.4 | 5.4 | 498.06 |
| 958 | 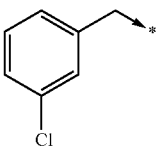 3-Cl-C6H4-CH2-* | 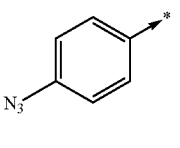 4-N3-C6H4-* | 93.9 | 5.14 | 461.12 |
| 959 | 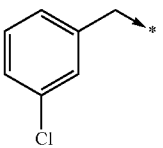 3-Cl-C6H4-CH2-* | 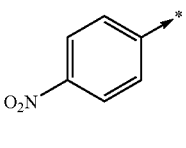 4-O2N-C6H4-* | 94.5 | 5.12 | 465.10 |
| 960 | 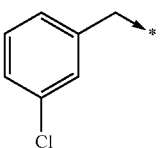 3-Cl-C6H4-CH2-* | 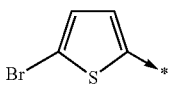 5-Br-thiophene-2-* | 94.6 | 5.62 | 504.00 |
| 961 | 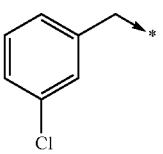 3-Cl-C6H4-CH2-* | 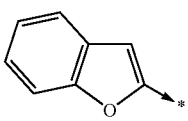 benzofuran-2-* | 96.4 | 5.74 | 460.13 |
| 962 | 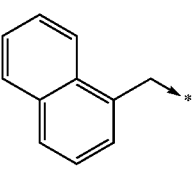 1-naphthyl-CH2-* | 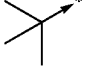 t-Bu-* | 6.5 + 87.5 | 4.2 + 4.54 | 416.19 |
| 963 | 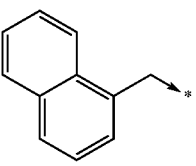 1-naphthyl-CH2-* | 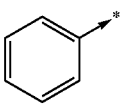 Ph-* | 92.9 | 4.76 | 436.17 |
| 964 | 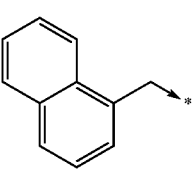 1-naphthyl-CH2-* | 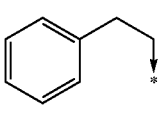 Ph-CH2-CH2-* | 17.3 + 6.2 | 4.5 + 4.9 | 464.21 |

| | | | | | |
|---|---|---|---|---|---|
| 965 | 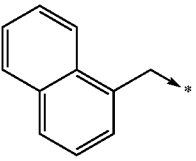 | 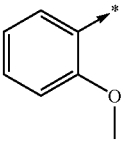 | 92.6 | 4.64 | 466.17 |
| 966 | 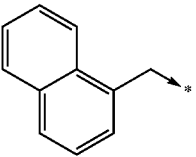 | 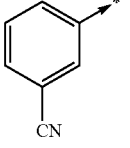 | 89 | 4.76 | 461.16 |
| 967 | 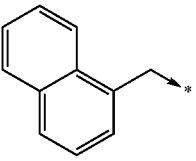 | 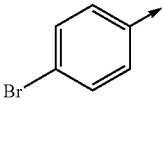 | 94.1 | 5.32 | 514.09 |
| 968 | 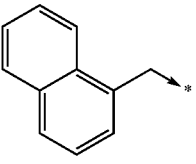 | 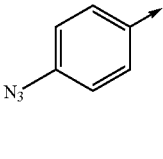 | 92.1 | 5.09 | 477.19 |
| 969 | 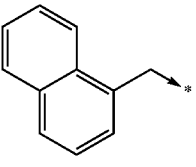 | 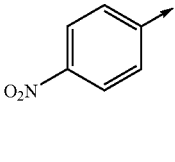 | 90.5 | 5.1 | 481.16 |
| 970 | 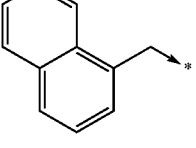 | 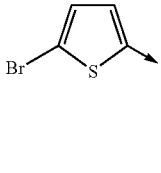 | 92 | 5.56 | 520.02 |
| 971 | 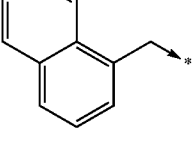 | 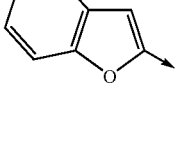 | 93 | 5.72 | 476.17 |
| 972 | 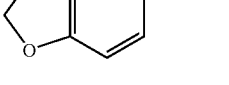 |  | 91.6 | 4 | 410.16 |
| 973 | 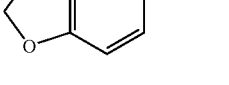 | 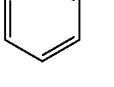 | 89.7 | 4.28 | 430.15 |
| 974 | 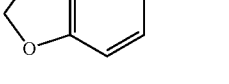 | 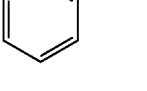 | 83.4 | 4.46 | 458.19 |

| | 411 | 412 | | | |
|---|---|---|---|---|---|
| | | -continued | | | |
| 975 | benzodioxole-CH2-* | 2-methoxyphenyl-* | 96.9 | 4.19 | 460.16 |
| 976 | benzodioxole-CH2-* | 3-cyanophenyl-* | 58.2 | 4.29 | 455.12 |
| 977 | benzodioxole-CH2-* | 4-bromophenyl-* | 81.4 | 4.84 | 508.06 |
| 978 | benzodioxole-CH2-* | 4-azidophenyl-* | 85.8 | 4.64 | 471.15 |
| 979 | benzodioxole-CH2-* | 4-nitrophenyl-* | 46.8 | 4.62 | 475.14 |
| 980 | benzodioxole-CH2-* | 5-bromothiophen-2-yl-* | 77.4 | 5.06 | 514.02 |
| 981 | benzodioxole-CH2-* | benzofuran-2-yl-* | 61.7 | 5.24 | 470.16 |
| 982 | furan-2-yl-CH2-* | tert-butyl-* | 4.8 | 3.54 | 356.15 |
| 983 | furan-2-yl-CH2-* | phenyl-* | 71.4 | 4.1 | 376.14 |
| 984 | furan-2-yl-CH2-* | benzyl-CH2-* | 79 | 4.3 | 404.17 |
| 985 | furan-2-yl-CH2-* | 2-methoxyphenyl-* | 88.3 | 4.0 | 406.13 |

-continued
| Ex. | R1 | R3 | Purity (%) | rt (min.) | [M + H]+ |
|---|---|---|---|---|---|
| 986 |  | 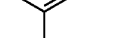 | 12.2 | 5.32 | 401.11 |
| 987 | 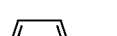 |  | 46.5 | 4.72 | 454.04 |
| 988 |  | 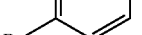 | 56.3 | 4.49 | 417.15 |
| 989 | 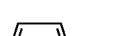 |  | 13.8 | 5.52 | 421.12 |
| 990 | 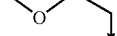 | 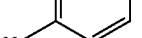 | 35.3 | 4.95 | 460.02 |
| 991 | 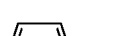 |  | 9.1 | 5.71 | 416.11 |
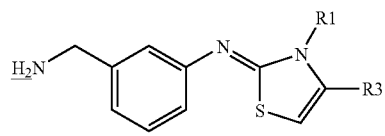
| Ex. | R1 | R3 | Purity (%) | rt (min.) | [M + H]+ |
|---|---|---|---|---|---|
| 992 | | | 95.3 | 3.33 | 367.12 |
| 993 | | | 91.9 | 3.97 | 400.03 |
| 994 | | | 92.5 | 3.64 | 336.17 |
| 995 | | | 83.7 | 3.75 | 363.13 |

-continued

| # | R1 | R2 | % | a | m/z |
|---|---|---|---|---|---|
| 996 | allyl | 3,5-bis(trifluoromethyl)phenyl | 94.7 | 4.88 | 458.11 |
| 997 | allyl | 2-naphthyl | 93.1 | 4.03 | 372.14 |
| 998 | allyl | 2,3-dihydro-1,4-benzodioxin-6-yl | 92.6 | 3.37 | 380.14 |
| 999 | allyl | benzofuran-2-yl | 92.1 | 4.36 | 362.12 |
| 1000 | allyl | phthalimidomethyl | 91 | 3.32 | 405.11 |
| 1001 | isobutyl | 2-nitrophenyl | 87.8 | 3.9 | 397.14 |
| 1002 | isobutyl | 3-bromophenyl | 64.2 | 4.46 | 430.09 |
| 1003 | isobutyl | 4-methylphenyl | 61.6 | 4.18 | 366.23 |
| 1004 | isobutyl | 4-azidophenyl | 45.6 | 4.26 | 393.16 |
| 1005 | isobutyl | 3,5-bis(trifluoromethyl)phenyl | 72.4 | 5.28 | 488.17 |

-continued

| # | R1 | R2 | a | b | c |
|---|---|---|---|---|---|
| 1006 | isopentyl | naphthalen-2-yl | 67 | 4.47 | 402.17 |
| 1007 | isopentyl | 2,3-dihydrobenzo[1,4]dioxin-6-yl | 51.1 | 3.86 | 410.16 |
| 1008 | isopentyl | benzofuran-2-yl | 57.6 | 4.86 | 392.16 |
| 1009 | isopentyl | (1,3-dioxoisoindolin-2-yl)methyl | 75.1 | 3.92 | 435.16 |
| 1010 | 3-methoxypropyl | 2-nitrophenyl | 90.7 | 3.24 | 399.13 |
| 1011 | 3-methoxypropyl | 3-bromophenyl | 79.6 | 3.79 | 432.06 |
| 1012 | 3-methoxypropyl | 4-methylphenyl | 74.5 | 3.55 | 368.16 |
| 1013 | 3-methoxypropyl | 4-azidophenyl | 58.8 | 3.62 | 395.15 |
| 1014 | 3-methoxypropyl | 3,5-bis(trifluoromethyl)phenyl | 81 | 4.65 | 490.15 |
| 1015 | 3-methoxypropyl | naphthalen-2-yl | 86.8 | 3.88 | 404.17 |
| 1016 | 3-methoxypropyl | 2,3-dihydrobenzo[1,4]dioxin-6-yl | 71.4 | 3.3 | 412.13 |

-continued
| | | | | | |
|---|---|---|---|---|---|
| 1017 | 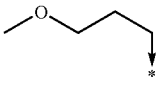 | 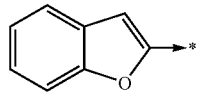 | 73.7 | 4.13 | 394.15 |
| 1018 | 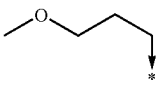 | 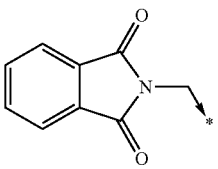 | 80.5 | 3.3 | 437.15 |
| 1019 | 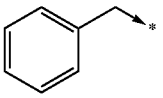 | 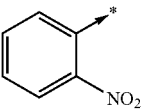 | 94.6 | 4.19 | 417.10 |
| 1020 | 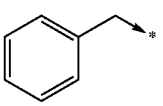 | 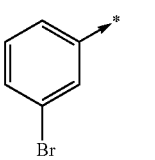 | 94.8 | 4.76 | 450.07 |
| 1021 | 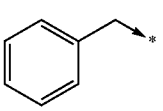 | 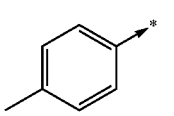 | 92.9 | 4.42 | 386.13 |
| 1022 | 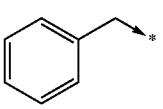 | 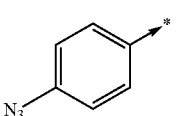 | 88.8 | 4.56 | 413.11 |
| 1023 | 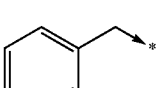 | 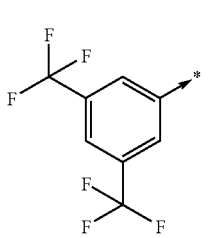 | 94.1 | 5.48 | 508.13 |
| 1024 | 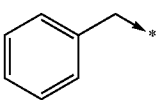 | 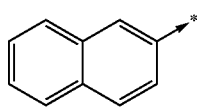 | 93.8 | 4.79 | 422.13 |
| 1025 | 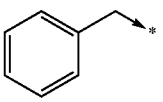 | 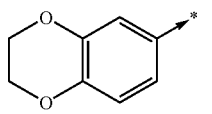 | 92.3 | 4.04 | 430.15 |
| 1026 | 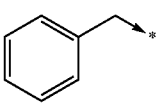 | 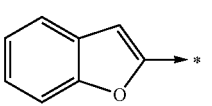 | 90 | 5.08 | 412.10 |
| 1027 | 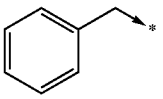 | 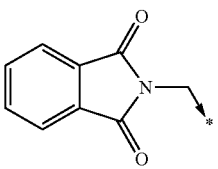 | 93.2 | 3.95 | 455.13 |

-continued
| | 421 | 422 | | | |
|---|---|---|---|---|---|
| 1028 | 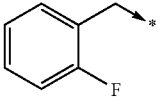 | 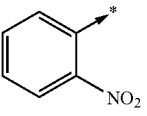 | 92.6 | 4.3 | 435.1 |
| 1029 | 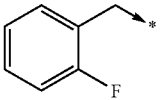 | 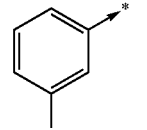 | 92.8 | 4.9 | 470.1 |
| 1030 | 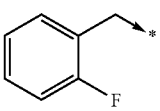 | 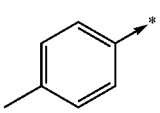 | 89.2 | 4.6 | 404.1 |
| 1031 | 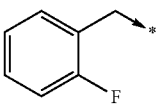 | 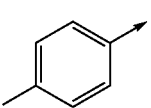 | 89.2 | 4.76 | 431.1 |
| 1032 | 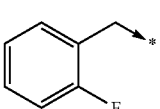 | 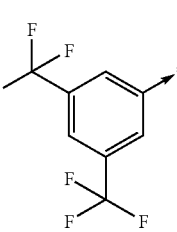 | 94.3 | 5.6 | 526.1 |
| 1033 | 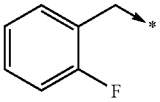 | 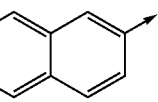 | 93.5 | 5 | 440.2 |
| 1034 | 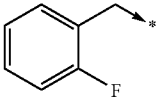 | 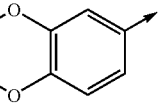 | 92.4 | 4.2 | 448.1 |
| 1035 | 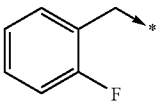 | 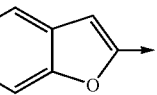 | 87.9 | 5.2 | 430.1 |
| 1036 | 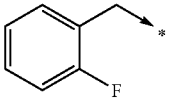 | 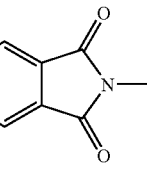 | 93.6 | 4.1 | 473.2 |
| 1037 | 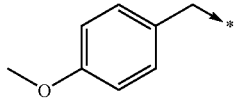 | 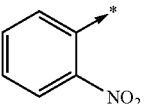 | 80.4 | 4.16 | 447.14 |
| 1038 | 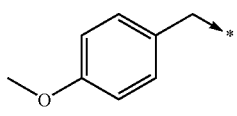 | 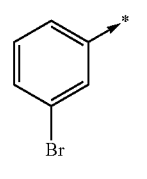 | 72.7 | 4.72 | 480.08 |

-continued
| | 423 | 424 | | | |
|---|---|---|---|---|---|
| 1039 | 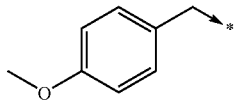 | 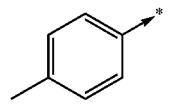 | 77 | 4.39 | 416.14 |
| 1040 | 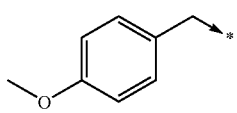 | 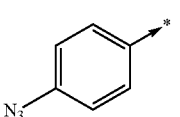 | 59.2 | 4.5 | 443.16 |
| 1041 | 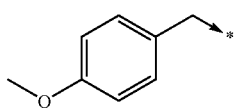 | 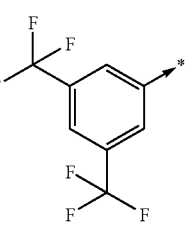 | 16.8 | 5.98 | 538.12 |
| 1042 | 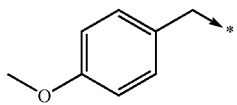 | 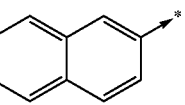 | 59.5 | 4.74 | 452.16 |
| 1043 | 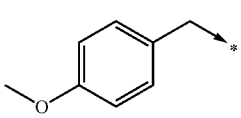 | 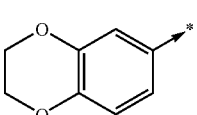 | 74 | 4.02 | 460.16 |
| 1044 | 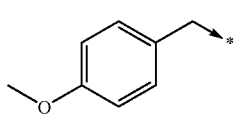 | 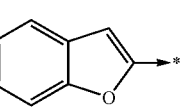 | 26.3 | 5.52 | 442.13 |
| 1045 | 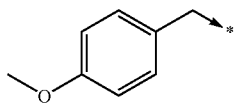 | 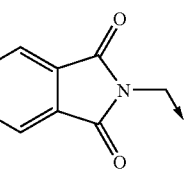 | 91 | 3.82 | 485.17 |
| 1046 | 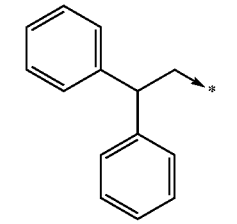 | 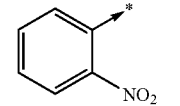 | 89.8 | 5.09 | 507.19 |
| 1047 | 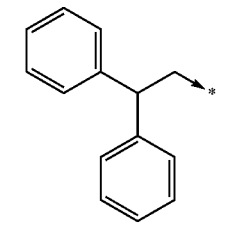 | 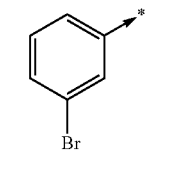 | 84.5 | 5.52 | 540.09 |

-continued
| | | | | | |
|---|---|---|---|---|---|
| 1048 | 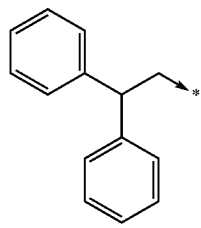 | 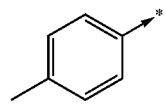 | 86 | 5.06 | 476.21 |
| 1049 | 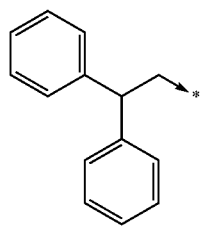 | 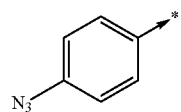 | 75.6 | 5.22 | 503.21 |
| 1050 | 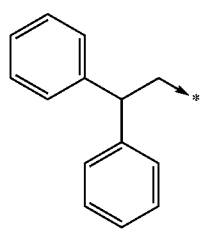 | 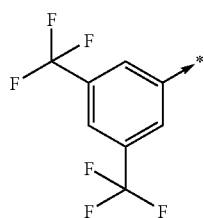 | 90.3 | 6.14 | 598.15 |
| 1051 | 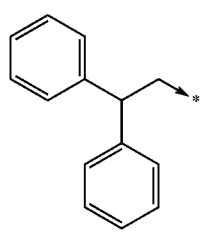 | 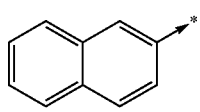 | 85.9 | 5.38 | 512.22 |
| 1052 | 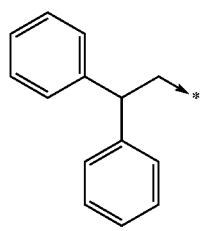 | 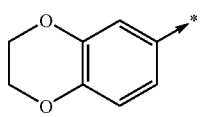 | 81.3 | 4.68 | 520.19 |
| 1053 | 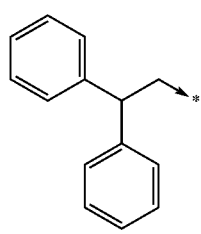 | 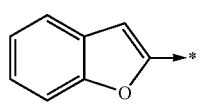 | 83.3 | 5.66 | 502.20 |

-continued

| | 427 | 428 | | | |
|---|---|---|---|---|---|
| 1054 | diphenylmethyl-CH2-* | phthalimide-N-CH2-* | 82 | 4.92 | 545.17 |
| 1055 | 4-methylphenyl-CH2CH2-* | 2-nitrophenyl-* | 93.1 | 4.34 | 445.16 |
| 1056 | 4-methylphenyl-CH2CH2-* | 3-bromophenyl-* | 81.5 | 4.77 | 478.10 |
| 1057 | 4-methylphenyl-CH2CH2-* | 4-methylphenyl-* | 79.9 | 4.46 | 414.17 |
| 1058 | 4-methylphenyl-CH2CH2-* | 4-azidophenyl-* | 70.2 | 4.56 | 441.15 |
| 1059 | 4-methylphenyl-CH2CH2-* | 3,5-bis(trifluoromethyl)phenyl-* | 85.8 | 5.56 | 536.11 |
| 1060 | 4-methylphenyl-CH2CH2-* | 2-naphthyl-* | 84.1 | 4.73 | 450.19 |
| 1061 | 4-methylphenyl-CH2CH2-* | 2,3-dihydrobenzo[1,4]dioxin-6-yl-* | 78.4 | 4.12 | 458.20 |
| 1062 | 4-methylphenyl-CH2CH2-* | benzofuran-2-yl-* | 83.3 | 5.13 | 440.16 |
| 1063 | 4-methylphenyl-CH2CH2-* | phthalimide-N-CH2-* | 83.1 | 4.22 | |

-continued
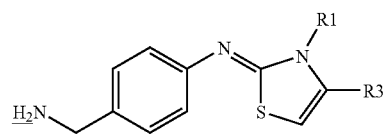
| Ex. | R1 | R3 | Purity (%) | rt (min.) | [M + H]+ |
|---|---|---|---|---|---|
| 1064 | propyl-CH2-* | phenyl-* | 86.6 | 3.52 | 338.12 |
| 1065 | propyl-CH2-* | 2-NO2-phenyl-* | 90.4 | 3.44 | 383.09 |
| 1066 | propyl-CH2-* | 3-OCF3-phenyl-* | 87.3 | 4.25 | 422.10 |
| 1067 | propyl-CH2-* | 4-Br-phenyl-* | 85.9 | 4.04 | 416.04 |
| 1068 | propyl-CH2-* | 4-OBn-phenyl-* | 70.5 | 4.4 | 444.18 |
| 1069 | propyl-CH2-* | 3,5-bis(CF3)-phenyl-* | 80.1 | 4.83 | 474.13 |
| 1070 | propyl-CH2-* | 6-methyl-naphth-2-yl-* | 80.6 | 4.34 | 402.16 |
| 1071 | propyl-CH2-* | benzofuran-2-yl-* | 80.8 | 4.37 | 378.14 |
| 1072 | propyl-CH2-* | 5-Cl-3-methyl-benzothiophen-2-yl-* | 86.5 | 4.77 | 442.06 |

-continued

| | | | | | |
|---|---|---|---|---|---|
| 1073 | butyl group | 3-phenylisoxazol-5-yl | 83.4 | 4.72 | 405.12 |
| 1074 | 2-methoxyethyl | phenyl | 90.5 | 3.02 | 340.15 |
| 1075 | 2-methoxyethyl | 2-nitrophenyl | 93.5 | 2.98 | 385.10 |
| 1076 | 2-methoxyethyl | 3-(trifluoromethoxy)phenyl | 91.7 | 3.9 | 424.12 |
| 1077 | 2-methoxyethyl | 4-bromophenyl | 90.8 | 3.62 | 418.04 |
| 1078 | 2-methoxyethyl | 4-(benzyloxy)phenyl | 80.8 | 4.09 | 446.18 |
| 1079 | 2-methoxyethyl | 3,5-bis(trifluoromethyl)phenyl | 88.1 | 4.6 | 476.12 |
| 1080 | 2-methoxyethyl | 6-methylnaphthalen-2-yl | 91.5 | 3.98 | 404.16 |
| 1081 | 2-methoxyethyl | benzofuran-2-yl | 89.2 | 3.87 | 380.13 |
| 1082 | 2-methoxyethyl | 5-chloro-3-methylbenzo[b]thiophen-2-yl | 87.3 | 4.36 | 444.10 |

-continued
| | | | | | |
|---|---|---|---|---|---|
| 1083 | 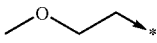 | 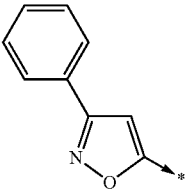 | 90.6 | 4.24 | 407.13 |
| 1084 | 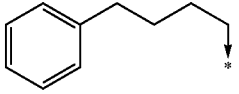 | 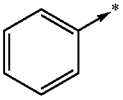 | 86.4 | 4.24 | 414.15 |
| 1085 | 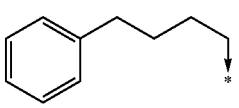 | 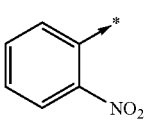 | 91.8 | 4.21 | 459.17 |
| 1086 | 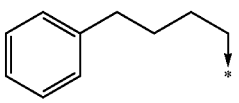 | 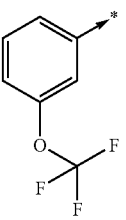 | 88.2 | 4.89 | 498.19 |
| 1087 | 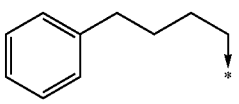 | 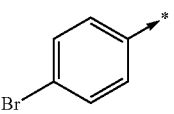 | 85.8 | 4.71 | 492.12 |
| 1088 | 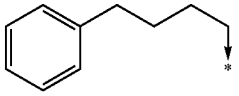 | 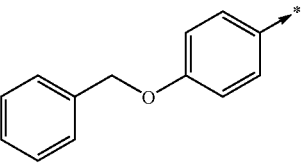 | 76.1 | 4.9 | 520.21 |
| 1089 | 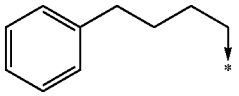 | 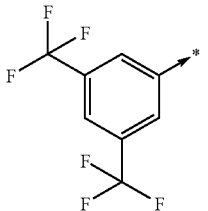 | 83.3 | 5.45 | 550.17 |
| 1090 | 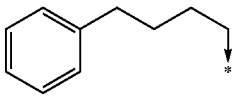 | 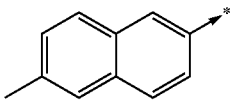 | 84.9 | 4.9 | 478.24 |
| 1091 | 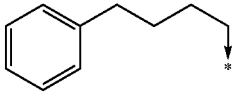 | 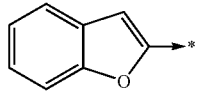 | 86.1 | 5.08 | 454.19 |
| 1092 | 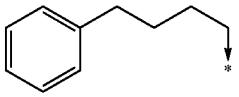 | 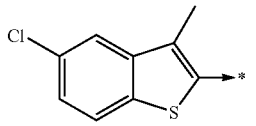 | 78 | 5.38 | 518.14 |

-continued

| | | | | | |
|---|---|---|---|---|---|
| 1093 | phenyl-(CH2)3-CH2-* | 3-phenylisoxazol-5-yl-* | 84.5 | 5.38 | 481.21 |
| 1094 | PhCH(CH3)-* | phenyl-* | 37.5 | 3.36 | 386.14 |
| 1095 | PhCH(CH3)-* | 2-NO2-phenyl-* | 57.1 | 3.35 | 431.14 |
| 1096 | PhCH(CH3)-* | 3-(OCF3)-phenyl-* | 44 | 3.78 | 470.17 |
| 1097 | PhCH(CH3)-* | 4-Br-phenyl-* | 42 | 3.62 | 464.09 |
| 1098 | PhCH(CH3)-* | 4-(OBn)-phenyl-* | 38.8 | 4.14 | 492.21 |
| 1099 | PhCH(CH3)-* | 3,5-bis(CF3)-phenyl-* | 45.2 | 3.98 | 522.14 |
| 1100 | PhCH(CH3)-* | 6-methylnaphth-2-yl-* | 33.4 | 3.99 | 450.20 |
| 1101 | PhCH(CH3)-* | benzofuran-2-yl-* | 44.7 | 3.68 | 426.14 |

-continued
| | | | | | |
|---|---|---|---|---|---|
| 1102 | 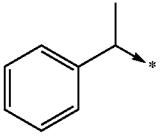 | 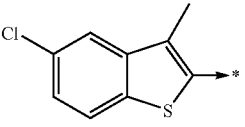 | 33.4 | 4.08 | 490.12 |
| 1103 | 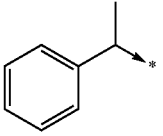 | 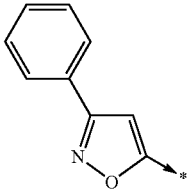 | 42.4 | 3.67 | 453.17 |
| 1104 | 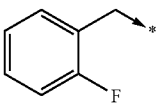 | 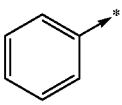 | 92.6 | 4.23 | 390.14 |
| 1105 | 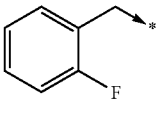 | 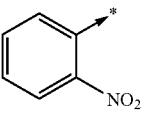 | 91.9 | 4.1 | 439.1 |
| 1106 | 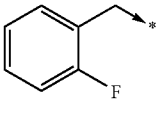 | 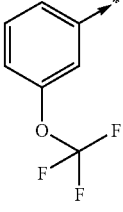 | 92.1 | 5 | 474.13 |
| 1107 | 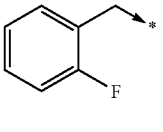 | 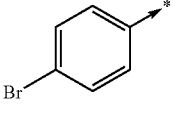 | 93 | 4.85 | 468.04 |
| 1108 | 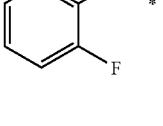 | 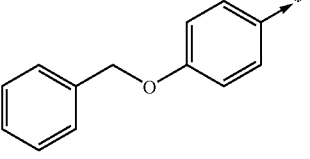 | 86.5 | 5.04 | 496.18 |
| 1109 | 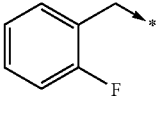 | 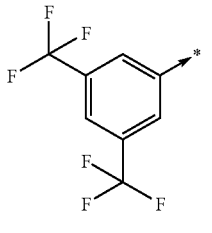 | 92.8 | 5.5 | 526.13 |
| 1110 | 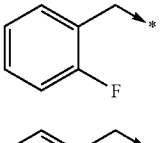 | 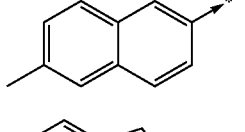 | 92.8 | 5.1 | 454.17 |
| 1111 | 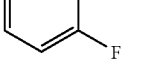 | 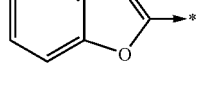 | 92 | 5.1 | 430.10 |

-continued

| # | R1 | R2 | a | b | c |
|---|---|---|---|---|---|
| 1112 | 2-F-C6H4-CH2- | 5-Cl-3-methyl-benzothiophen-2-yl | 92.8 | 5.48 | 494.08 |
| 1113 | 2-F-C6H4-CH2- | 3-phenyl-isoxazol-5-yl | 92.8 | 5.1 | 457.18 |
| 1114 | 3-Cl-C6H4-CH2- | phenyl | 93.8 | 4.6 | 406.10 |
| 1115 | 3-Cl-C6H4-CH2- | 2-NO2-C6H4- | 93.6 | 4.5 | 451.03 |
| 1116 | 3-Cl-C6H4-CH2- | 3-OCF3-C6H4- | 93.1 | 5.2 | 490.10 |
| 1117 | 3-Cl-C6H4-CH2- | 4-Br-C6H4- | 94.5 | 5.1 | 483.99 |
| 1118 | 3-Cl-C6H4-CH2- | 4-(benzyloxy)-C6H4- | 89.54 | 5.29 | 512.13 |
| 1119 | 3-Cl-C6H4-CH2- | 3,5-bis(CF3)-C6H3- | 95.2 | 5.6 | 542.1 |
| 1120 | 3-Cl-C6H4-CH2- | 6-methyl-naphthalen-2-yl | 92.8 | 5.38 | 470.15 |

-continued

| # | R1 | R2 | % | t | MW |
|---|---|---|---|---|---|
| 1121 | 3-chlorophenyl-CH2-* | benzofuran-2-yl-* | 93.4 | 5.3 | 445.94 |
| 1122 | 3-chlorophenyl-CH2-* | 5-chloro-3-methylbenzothiophen-2-yl-* | 94.7 | 5.7 | 510.05 |
| 1123 | 3-chlorophenyl-CH2-* | 3-phenylisoxazol-5-yl-* | 94.3 | 5.3 | 473.04 |
| 1124 | 4-methylphenyl-CH2CH2-* | phenyl-* | 89.5 | 4.06 | 400.12 |
| 1125 | 4-methylphenyl-CH2CH2-* | 2-nitrophenyl-* | 92.1 | 4.13 | 445.13 |
| 1126 | 4-methylphenyl-CH2CH2-* | 3-(trifluoromethoxy)phenyl-* | 88.9 | 4.81 | 484.15 |
| 1127 | 4-methylphenyl-CH2CH2-* | 4-bromophenyl-* | 88.8 | 4.56 | 478.09 |
| 1128 | 4-methylphenyl-CH2CH2-* | 4-benzyloxyphenyl-* | 82.4 | 4.76 | 506.20 |
| 1129 | 4-methylphenyl-CH2CH2-* | 3,5-bis(trifluoromethyl)phenyl-* | 88.6 | 5.36 | 536.12 |

-continued
| | | | | | |
|---|---|---|---|---|---|
| 1130 | 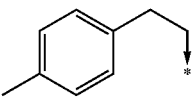 | 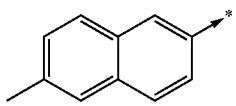 | 85.7 | 4.78 | 464.18 |
| 1131 | 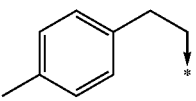 | 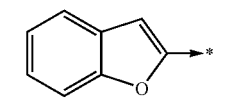 | 84 | 4.94 | 440.15 |
| 1132 | 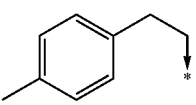 | 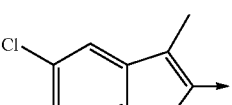 | 64.3 | 5.38 | 504.10 |
| 1133 | 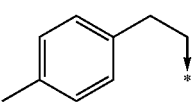 | 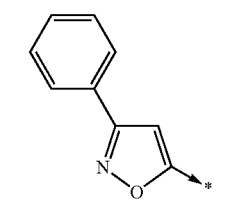 | 88.4 | 5.16 | 467.17 |
| 1134 | 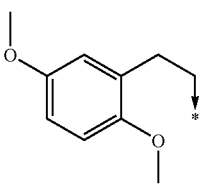 | 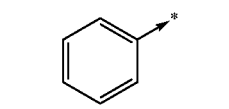 | 82.7 | 3.76 | 446.16 |
| 1135 | 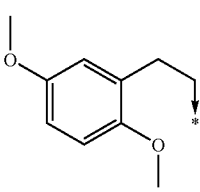 | 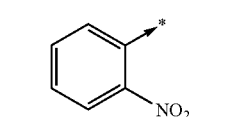 | 89 | 3.77 | 491.14 |
| 1136 | 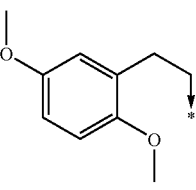 | 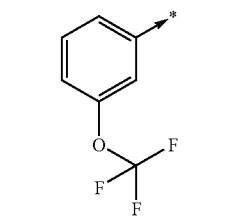 | 87.1 | 4.4 | 530.13 |
| 1137 | 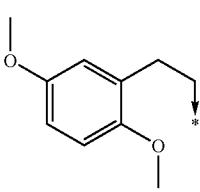 | 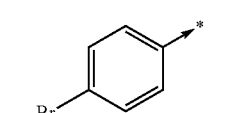 | 84.6 | 4.21 | 524.08 |
| 1138 | 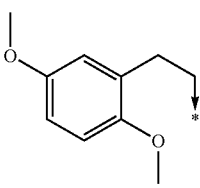 | 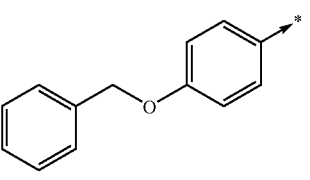 | 76 | 4.52 | 552.19 |

-continued
| | | | | | |
|---|---|---|---|---|---|
| 1139 | (2,5-dimethoxyphenethyl) | 3,5-bis(trifluoromethyl)phenyl | 85.6 | 4.98 | 582.12 |
| 1140 | (2,5-dimethoxyphenethyl) | 6-methylnaphthalen-2-yl | 83.1 | 4.44 | 510.21 |
| 1141 | (2,5-dimethoxyphenethyl) | benzofuran-2-yl | 88.3 | 4.6 | 486.19 |
| 1142 | (2,5-dimethoxyphenethyl) | 5-chloro-3-methylbenzo[b]thiophen-2-yl | 1.5 | 5.07 | 550.12 |
| 1143 | (2,5-dimethoxyphenethyl) | 3-phenylisoxazol-5-yl | 84 | 4.75 | 513.16 |
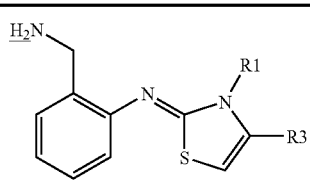
| Ex. | R1 | R3 | Purity (%) | rt (min.) | [M + H]+ |
|---|---|---|---|---|---|
| 1144 | but-3-yn-1-yl | tert-butyl | 75 | 4.48 | 300.16 |
| 1145 | but-3-yn-1-yl | phenethyl | 82 | 4.89 | 348.16 |
| 1146 | prop-2-yn-1-yl | 2-chlorophenyl | 86.7 | 4.72 | 354.09 |

-continued
| | | | | | |
|---|---|---|---|---|---|
| 1147 | 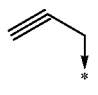 | 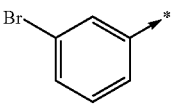 | 89 | 4.96 | 398.01 |
| 1148 | 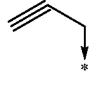 | 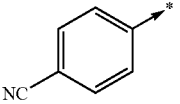 | 87 | 4.37 | 345.18 |
| 1149 | 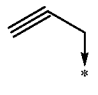 | 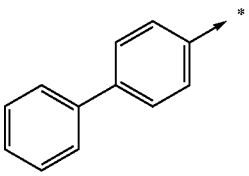 | 90 | 5.4 | 396.1 |
| 1150 | 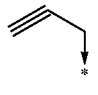 | 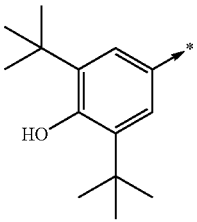 | 89 | 5.9 | 448.2 |
| 1151 | 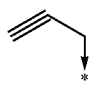 | 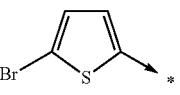 | 85 | 5 | 404 |
| 1152 | 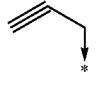 | 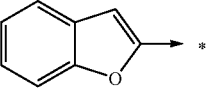 | 85 | 4.96 | 360.10 |
| 1153 | 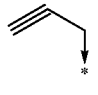 | 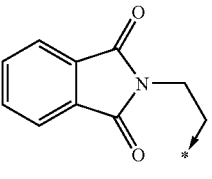 | 91 | 4.39 | 417.14 |
| 1154 | 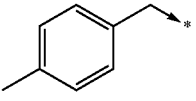 | 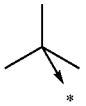 | 95 | 5.14 | 366.21 |
| 1155 | 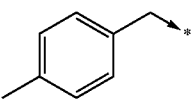 | 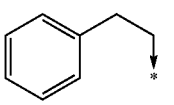 | 92 | 5.52 | 414.17 |
| 1156 | 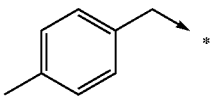 | 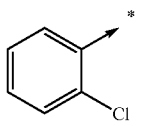 | 95 | 5.37 | 420.13 |
| 1157 | 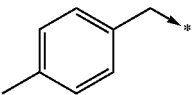 | 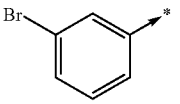 | 93 | 5.6 | 464.08 |

-continued

| | | | | | |
|---|---|---|---|---|---|
| 1158 | 4-methylphenyl-CH2-* | 4-NC-phenyl-* | 94 | 5 | 411.2 |
| 1159 | 4-methylphenyl-CH2-* | 4-biphenyl-* | 91 | 6.04 | 462.19 |
| 1160 | 4-methylphenyl-CH2-* | 3,5-di-tert-butyl-4-hydroxyphenyl-* | 91.5 | 6.4 | 514.2 |
| 1161 | 4-methylphenyl-CH2-* | 5-bromo-thien-2-yl-* | 92.6 | 5.7 | 470.1 |
| 1162 | 4-methylphenyl-CH2-* | benzofuran-2-yl-* | 93.8 | 5.6 | 426.14 |
| 1163 | 4-methylphenyl-CH2-* | phthalimido-ethyl-* | 91.4 | 5.02 | 483.21 |
| 1164 | 2,4-dichlorophenyl-CH2-* | tert-butyl-* | 96.3 | 5.55 | 420.10 |
| 1165 | 2,4-dichlorophenyl-CH2-* | phenyl-CH2CH2-* | 78.2 | 5.81 | 468.10 |
| 1166 | 2,4-dichlorophenyl-CH2-* | 2-chlorophenyl-* | 96.7 | 5.6 | 474.06 |
| 1167 | 2,4-dichlorophenyl-CH2-* | 3-bromophenyl-* | 96.9 | 5.8 | 517.97 |

-continued

| # | R1 | R2 | % | RT | MS |
|---|---|---|---|---|---|
| 1168 | 2,4-dichlorobenzyl | 4-cyanophenyl | 94.2 | 5.18 | 465.06 |
| 1169 | 2,4-dichlorobenzyl | 4-biphenyl | 94 | 6.25 | 516.10 |
| 1170 | 2,4-dichlorobenzyl | 3,5-di-tert-butyl-4-hydroxyphenyl | 96.4 | 6.52 | 568.2 |
| 1171 | 2,4-dichlorobenzyl | 5-bromothiophen-2-yl | 94.6 | 5.9 | 524.0 |
| 1172 | 2,4-dichlorobenzyl | benzofuran-2-yl | 94.9 | 5.81 | 480.07 |
| 1173 | 2,4-dichlorobenzyl | 2-(phthalimido)ethyl | 91.9 | 5.25 | 537.09 |
| 1174 | 3,4-dimethoxyphenethyl | benzofuran-2-yl | 77.4 | 5.24 | 486.16 |
| 1175 | naphthalen-1-ylmethyl | tert-butyl | 96.8 | 5.36 | 402.15 |
| 1176 | naphthalen-1-ylmethyl | phenethyl | 92.4 | 5.66 | 450.19 |

-continued
| | | | | | |
|---|---|---|---|---|---|
| 1177 | 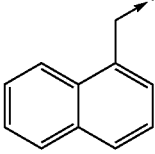 | 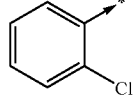 | 93.3 | 5.48 | 456.12 |
| 1178 | 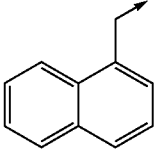 | 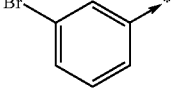 | 93.3 | 5.7 | 500.08 |
| 1179 | 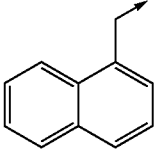 | 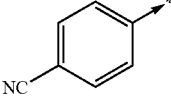 | 90.7 | 5.12 | 447.15 |
| 1180 | 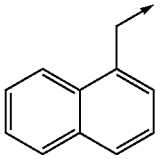 | 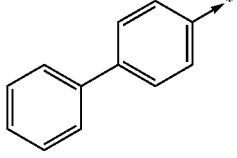 | 91.9 | 6.12 | 498.21 |
| 1181 | 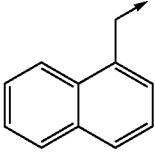 | 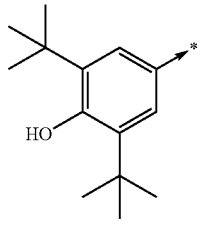 | 95.1 | 6.5 | 550.3 |
| 1182 | 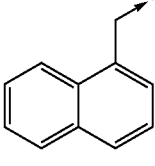 | 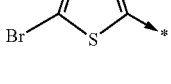 | 92.8 | 5.7 | 506.0 |
| 1183 | 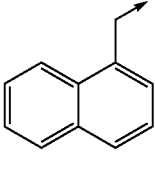 | 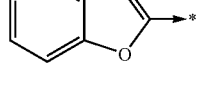 | 94.9 | 5.74 | 462.15 |
| 1184 | 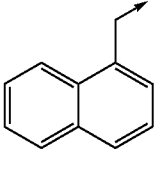 | 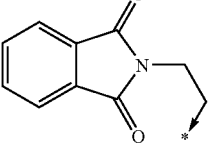 | 91.4 | 5.13 | 519.17 |
| 1185 | 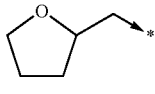 |  | 73.6 | 3.52 | 346.19 |

-continued

| | | | | | |
|---|---|---|---|---|---|
| 1186 | tetrahydrofuran-2-ylmethyl | phenethyl | 71.5 | 4.5 | 394.17 |
| 1187 | tetrahydrofuran-2-ylmethyl | 2-chlorophenyl | 82.2 | 4.58 | 400.10 |
| 1188 | tetrahydrofuran-2-ylmethyl | 3-bromophenyl | 78.6 | 4.86 | 444.09 |
| 1189 | tetrahydrofuran-2-ylmethyl | biphenyl-4-yl | 70.5 | 5.3 | 442.17 |
| 1190 | tetrahydrofuran-2-ylmethyl | benzofuran-2-yl | 76.8 | 5 | 406.13 |
| 1191 | tetrahydrofuran-2-ylmethyl | 2-(1,3-dioxoisoindolin-2-yl)ethyl | 80.5 | 4.1 | 463.19 |

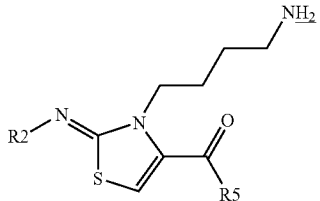

| Ex. | R2 | R5 | Purity (%) | rt (min.) | [M + H]+ |
|---|---|---|---|---|---|
| 1192 | phenyl | cyclohexylamino | 28.3 | 3.61 | 373.15 |
| 1193 | phenyl | 2-(pyridin-2-yl)ethylamino | 64.3 | 2.55 | 396.15 |
| 1194 | phenyl | benzo[d][1,3]dioxol-5-ylmethylamino | 66.8 | 3.58 | 425.13 |
| 1195 | phenyl | thiophen-2-ylmethylamino | 51.9 | 3.47 | 387.07 |

-continued
| | | | | | |
|---|---|---|---|---|---|
| 1196 | 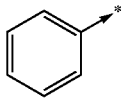 | 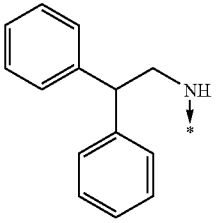 | 75.8 | 4.43 | 471.21 |
| 1197 | 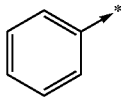 | 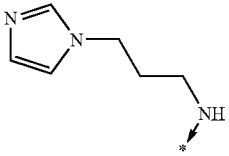 | 66.4 | 2.38 | 399.15 |
| 1198 | 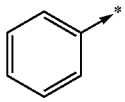 | 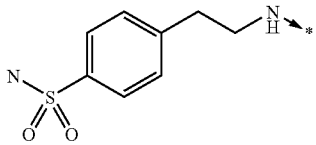 | 42.6 | 3.11 | 474.14 |
| 1199 | 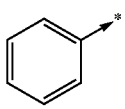 | 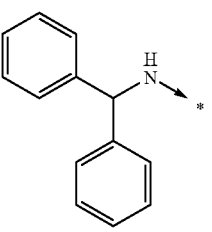 | 45.3 | 4.39 | 457.18 |
| 1200 | 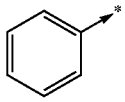 | 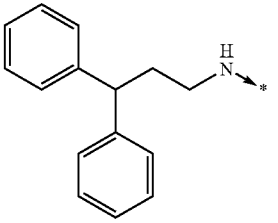 | 64 | 4.62 | 485.21 |
| 1201 | 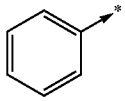 | 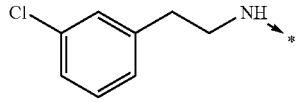 | 55.1 | 4.09 | 429.12 |
| 1202 | 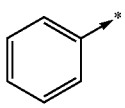 | 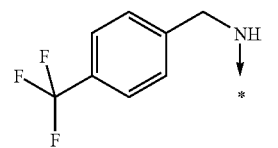 | 75 | 4.22 | 449.13 |
| 1203 | 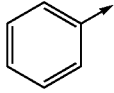 | 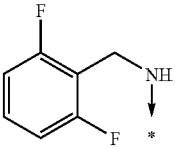 | 67.9 | 3.64 | 417.11 |
| 1204 | 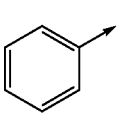 | 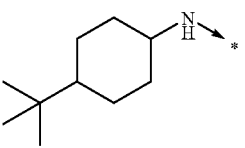 | 31.7 + 17.3 | 4.65 + 4.8 | 429.24 |

-continued

| | | | | | |
|---|---|---|---|---|---|
| 1205 | phenyl* | indan-2-yl-NH-* | 41.8 | 3.86 | 407.14 |
| 1206 | phenyl* | 2-(2-phenoxyphenyl)ethyl-NH-* | 67.8 | 4.58 | 487.20 |
| 1207 | 2-isopropylphenyl* | cyclohexyl-NH-* | 33.2 | 4.31 | 415.20 |
| 1208 | 2-isopropylphenyl* | 2-(pyridin-2-yl)ethyl-NH-* | 60.9 | 3.29 | 438.21 |
| 1209 | 2-isopropylphenyl* | benzo[1,3]dioxol-5-ylmethyl-NH-* | 58 | 4.29 | 467.18 |
| 1210 | 2-isopropylphenyl* | thiophen-2-ylmethyl-NH-* | 51.9 | 4.21 | 429.15 |
| 1211 | 2-isopropylphenyl* | 2,2-diphenylethyl-NH-* | 70 | 5.03 | 513.24 |
| 1212 | 2-isopropylphenyl* | 3-(imidazol-1-yl)propyl-NH-* | 22.9 | 3.17 | 441.19 |

-continued

| | | | | | |
|---|---|---|---|---|---|
| 1213 | isopropylphenyl* | 4-(2-aminoethyl)benzenesulfonamide-N | 71.8 | 3.81 | 516.16 |
| 1214 | isopropylphenyl* | diphenylmethylamine* | 35.4 | 5.03 | 499.23 |
| 1215 | isopropylphenyl* | 3,3-diphenylpropylamine* | 64 | 5.18 | 527.25 |
| 1216 | isopropylphenyl* | 3-chlorophenethylamine* | 68.2 | 4.71 | 471.19 |
| 1217 | isopropylphenyl* | 4-(trifluoromethyl)benzylamine* | 76.5 | 4.84 | 491.18 |
| 1218 | isopropylphenyl* | 2,6-difluorobenzylamine* | 67.6 | 4.35 | 459.16 |
| 1219 | isopropylphenyl* | 4-tert-butylcyclohexylamine* | 28.7 + 14.2 | 5.27 + 5.4 | 471.30 |
| 1220 | isopropylphenyl* | 2-aminoindane* | 66.9 | 4.52 | 449.21 |

-continued

| | | | | | |
|---|---|---|---|---|---|
| 1221 | 2-isopropylphenyl-* | 2-phenoxyphenethylamine-* | 64.1 | 5.17 | 529.21 |
| 1222 | 1-naphthyl-* | cyclohexyl-NH-* | 49.7 | 4.55 | 423.19 |
| 1223 | 1-naphthyl-* | 2-(pyridin-2-yl)ethylamine-* | 78.8 | 3.41 | 446.17 |
| 1224 | 1-naphthyl-* | benzo[d][1,3]dioxol-5-ylmethylamine-* | 76.2 | 4.48 | 475.15 |
| 1225 | 1-naphthyl-* | thiophen-2-ylmethylamine-* | 68.3 | 4.42 | 437.12 |
| 1226 | 1-naphthyl-* | 2,2-diphenylethylamine-* | 79.6 | 5.24 | 521.17 |
| 1227 | 1-naphthyl-* | 3-(1H-imidazol-1-yl)propylamine-* | 49.1 | 3.29 | 449.20 |
| 1228 | 1-naphthyl-* | 4-(sulfamoyl)phenethylamine-* | 72.2 | 4 | 524.15 |

-continued

| | | | | | |
|---|---|---|---|---|---|
| 1229 | naphthalen-1-yl* | Ph₂CH-NH-* | 69.7 | 5.22 | 507.20 |
| 1230 | naphthalen-1-yl* | Ph₂CH-CH₂-NH-* | 75 | 5.42 | 535.20 |
| 1231 | naphthalen-1-yl* | 3-Cl-C₆H₄-CH₂CH₂-NH-* | 78 | 4.93 | 479.13 |
| 1232 | naphthalen-1-yl* | 4-CF₃-C₆H₄-CH₂-NH-* | 79.1 | 5.04 | 499.16 |
| 1233 | naphthalen-1-yl* | 2,6-F₂-C₆H₃-CH₂-NH-* | 82.6 | 4.56 | 467.13 |
| 1234 | naphthalen-1-yl* | 4-tBu-cyclohexyl-NH-* | 45 + 24.6 | 5.53 + 5.7 | 479.26 |
| 1235 | naphthalen-1-yl* | indan-2-yl-NH-* | 77 | 4.75 | 457.18 |
| 1236 | naphthalen-1-yl* | 2-PhO-C₆H₄-CH₂CH₂-NH-* | 70.4 | 5.41 | 537.18 |
| 1237 | 4-Cl-C₆H₄-* | cyclohexyl-NH-* | 47.7 | 4.38 | 407.12 |

| | | | | | |
|---|---|---|---|---|---|
| 1238 | 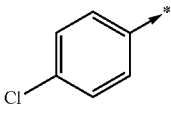 | 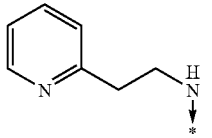 | 71.3 | 3.27 | 430.12 |
| 1239 | 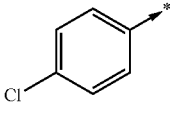 | 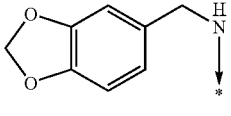 | 70.2 | 4.35 | 459.10 |
| 1240 | 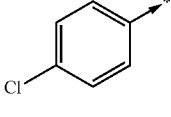 | 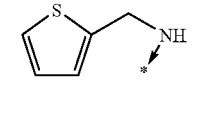 | 68.1 | 4.27 | 421.06 |
| 1241 | 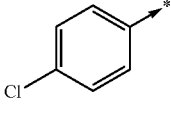 | 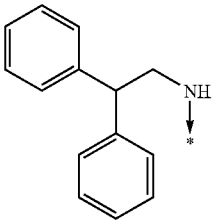 | 78.8 | 5.13 | 505.13 |
| 1242 | 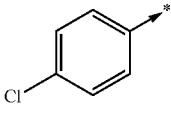 | 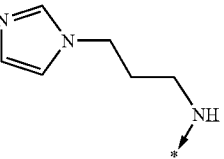 | 24 | 3.17 | 433.11 |
| 1243 | 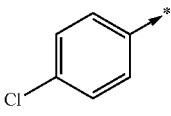 | 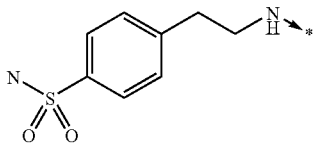 | 74.2 | 3.86 | 508.08 |
| 1244 | 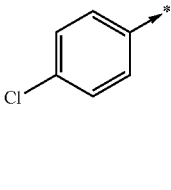 | 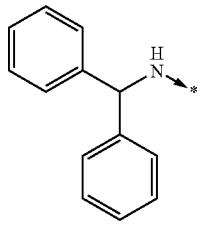 | 43 | 5.16 | 491.08 |
| 1245 | 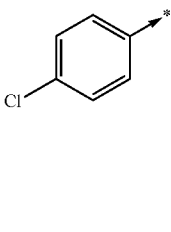 | 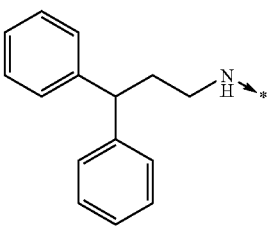 | 71.8 | 5.38 | 519.12 |
| 1246 | 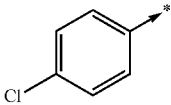 | 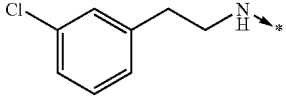 | 69.9 | 4.85 | 463.05 |

-continued
| | | | | | |
|---|---|---|---|---|---|
| 1247 | 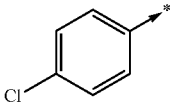 | 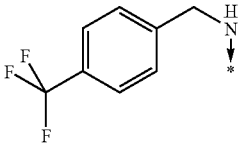 | 79.2 | 4.96 | 483.10 |
| 1248 | 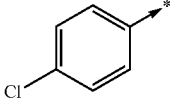 | 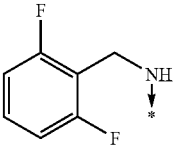 | 77.9 | 4.45 | 451.07 |
| 1249 | 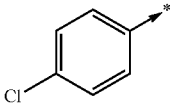 | 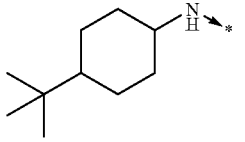 | 42.6 + 23.5 | 5.42 + 5.6 | 463.20 |
| 1250 | 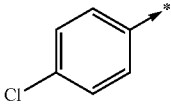 | 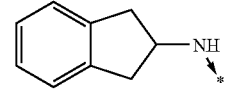 | 70 | 4.65 | 441.11 |
| 1251 | 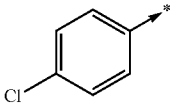 | 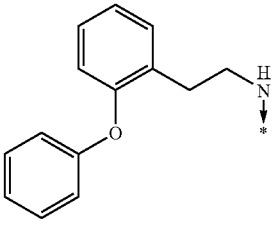 | 72 | 5.36 | 521.12 |
| 1252 |  | 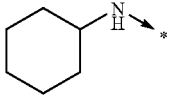 | 28.2 | 4.96 | 441.14 |
| 1253 | 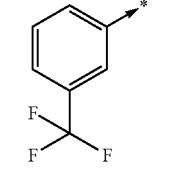 | 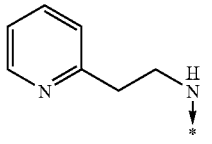 | 65.8 | 3.69 | 464.14 |
| 1254 | 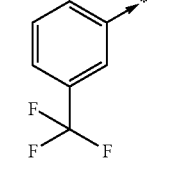 | 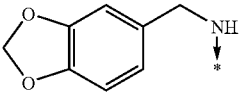 | 51 | 4.86 | 493.14 |
| 1255 | 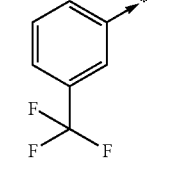 | 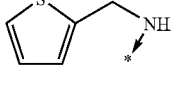 | 64.5 | 4.79 | 455.08 |

-continued
| | | | | | |
|---|---|---|---|---|---|
| 1256 |  | 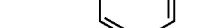 | 72.2 | 5.55 | 539.16 |
| 1257 |  |  | 27.2 | 3.59 | 467.16 |
| 1258 |  |  | 38.6 | 4.38 | 542.12 |
| 1259 | 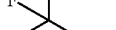 |  | 49.4 | 5.53 | 525.16 |
| 1260 |  |  | 60.6 | 5.73 | 553.20 |
| 1261 |  |  | 67.7 | 5.27 | 497.13 |
| 1262 |  |  | 80.8 | 5.34 | 517.12 |
| 1263 |  |  | 78 | 4.92 | 485.13 |

-continued
| Ex. | R2 | R5 | Purity (%) | rt (min.) | [M + H]⁺ |
|---|---|---|---|---|---|
| 1264 | 3-CF₃-phenyl | 4-tert-butylcyclohexyl-NH- | 28.5 + 14.4 | 5.87 + 6.0 | 497.26 |
| 1265 | 3-CF₃-phenyl | indan-2-yl-NH- | 60.5 | 5.13 | 475.16 |
| 1266 | 3-CF₃-phenyl | 2-(2-phenoxyphenyl)ethyl-NH- | 65.7 | 5.73 | 555.14 |
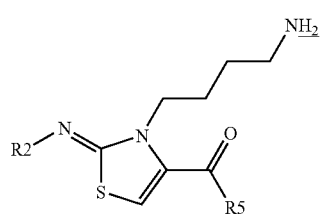
| Ex. | R2 | R5 | Purity (%) | rt (min.) | [M + H]⁺ |
|---|---|---|---|---|---|
| 1267 | phenyl | 2-(2-methoxyphenyl)ethyl-NH- | 60 | 3.86 | 439.18 |
| 1268 | phenyl | 1-benzylpiperidin-4-yl-NH- | 88.1 | 2.89 | 478.24 |
| 1269 | phenyl | 3,3-dimethylbutyl-NH- | 89.1 | 3.83 | 389.20 |
| 1270 | phenyl | pyridin-4-ylmethyl-NH- | 94.3 | 2.41 | 396.14 |
| 1271 | phenyl | 2-morpholinoethyl-NH- | 94 | 2.33 | 418.20 |

| | | | | | |
|---|---|---|---|---|---|
| 1272 | phenyl* | *NH-CH2-(2-thio-phenyl)-phenyl-CH2-O | 80.3 | 4.05 | 533.17 |
| 1273 | phenyl* | Ph2CH-CH2-NH-* | 93 | 4.33 | 485.23 |
| 1274 | phenyl* | Ph2CH-NH-* | 90.5 | 4.27 | 471.22 |
| 1275 | phenyl* | Ph-CH2CH2CH2-NH-* | 82.4 | 3.94 | 423.20 |
| 1276 | phenyl* | 4-Br-C6H4-CH2CH2-NH-* | 92.8 | 4.07 | 487.10 |
| 1277 | phenyl* | 3-CF3-C6H4-CH2-NH-* | 92.3 | 4.09 | 463.16 |
| 1278 | phenyl* | 2-oxo-pyrrolidin-1-yl-CH2CH2CH2-NH-* | 90.6 | 2.9 | 430.20 |
| 1279 | phenyl* | 2,3-diF-C6H3-CH2-NH-* | 94.7 | 3.69 | 431.14 |
| 1280 | phenyl* | biphenyl-4-yl-CH2-N-* | 90.6 | 4.37 | 471.21 |

-continued

| | | | | | |
|---|---|---|---|---|---|
| 1281 | phenyl* | 4-phenoxyphenethyl-NH-* | 86.4 | 4.51 | 501.20 |
| 1282 | phenyl* | 3,4-dichlorobenzyl-NH-* | 93.1 | 4.16 | 463.09 |
| 1283 | 4-chloro-2-(trifluoromethyl)phenyl* | 2-(2-methoxyphenyl)ethyl-NH-* | 63.6 | 5.58 | 541.11 |
| 1284 | 4-chloro-2-(trifluoromethyl)phenyl* | 1-benzylpiperidin-4-yl-NH-* | 82.4 | 4.23 | 580.17 |
| 1285 | 4-chloro-2-(trifluoromethyl)phenyl* | 3,3-dimethylbutyl-NH-* | 87.6 | 5.63 | 491.16 |
| 1286 | 4-chloro-2-(trifluoromethyl)phenyl* | pyridin-4-ylmethyl-NH-* | 91.5 | 4.03 | 498.13 |
| 1287 | 4-chloro-2-(trifluoromethyl)phenyl* | 2-morpholinoethyl-NH-* | 89.5 | 3.91 | 520.13 |
| 1288 | 4-chloro-2-(trifluoromethyl)phenyl* | 2-((2-(methoxymethyl)phenyl)thio)benzyl-NH-* | 82.2 | 5.61 | 635.14 |

-continued
| | | | | | |
|---|---|---|---|---|---|
| 1289 | 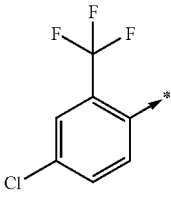 | 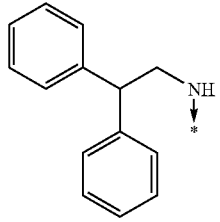 | 92.3 | 5.9 | 587.14 |
| 1290 | 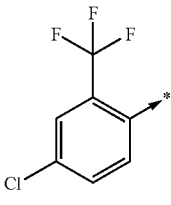 | 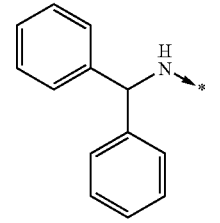 | 89.9 | 5.86 | 573.11 |
| 1291 | 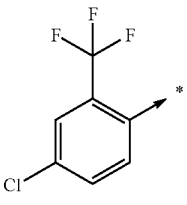 | 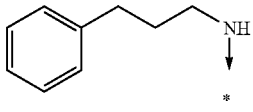 | 90 | 5.66 | 525.14 |
| 1292 | 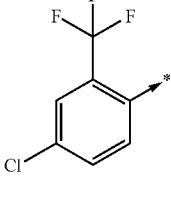 | 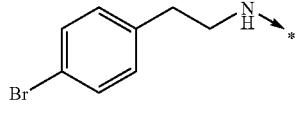 | 90.9 | 5.73 | 589.02 |
| 1293 | 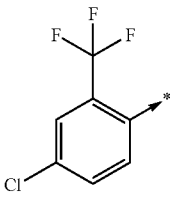 | 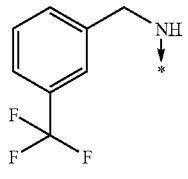 | 91.2 | 5.69 | 565.07 |
| 1294 | 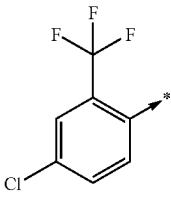 | 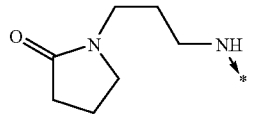 | 89.4 | 4.72 | 532.13 |
| 1295 | 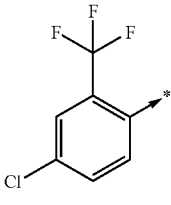 | 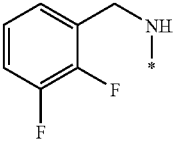 | 93.3 | 5.44 | 533.08 |

-continued
| | | | | | |
|---|---|---|---|---|---|
| 1296 | 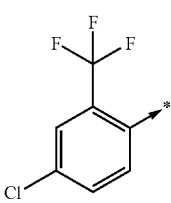 | 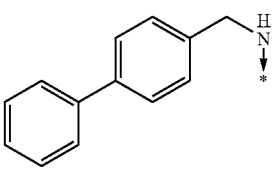 | 93.1 | 5.95 | 573.11 |
| 1297 | 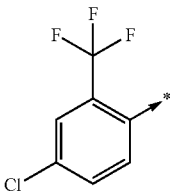 | 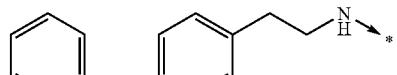 | 90.1 | 6.06 | 603.16 |
| 1298 | 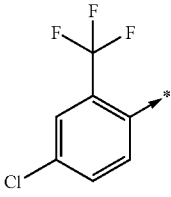 | 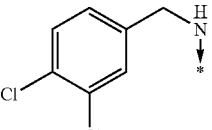 | 90.3 | 5.79 | 565.00 |
| 1299 | 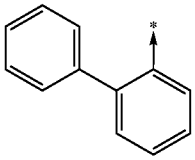 | 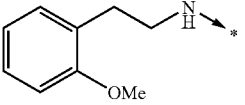 | 63.6 | 4.65 | 515.20 |
| 1300 | 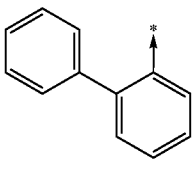 | 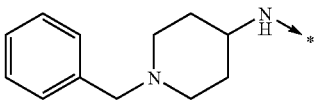 | 82.9 | 3.63 | 554.24 |
| 1301 | 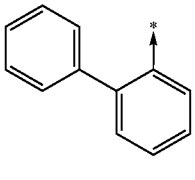 | 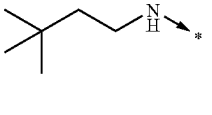 | 85.9 | 4.67 | 465.23 |
| 1302 | 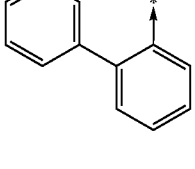 | 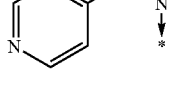 | 85.4 | 3.41 | 472.20 |
| 1303 | 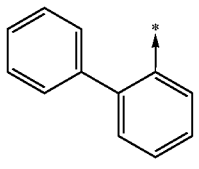 | 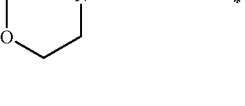 | 83.7 | 3.31 | 494.23 |

-continued

| | | | | | |
|---|---|---|---|---|---|
| 1304 | biphenyl | NH-CH2-(2-thio-phenyl)-CH2-O | 84.2 | 4.79 | 609.20 |
| 1305 | biphenyl | Ph2CH-CH2-NH-* | 86.5 | 5.11 | 561.20 |
| 1306 | biphenyl | Ph2CH-NH-* | 84.2 | 5.11 | 547.19 |
| 1307 | biphenyl | Ph-CH2CH2CH2-NH-* | 84.8 | 4.75 | 499.23 |
| 1308 | biphenyl | 3-CF3-C6H4-CH2-NH-* | 89 | 4.89 | 539.15 |
| 1309 | biphenyl | 2-oxopyrrolidin-1-yl-(CH2)3-NH-* | 85.9 | 3.76 | 506.23 |
| 1310 | biphenyl | 2,3-difluoro-C6H3-CH2-NH-* | 88.5 | 4.59 | 507.17 |
| 1311 | biphenyl | 4-phenyl-C6H4-CH2-NH-* | 87.8 | 5.16 | 547.20 |

-continued
| | | | | | |
|---|---|---|---|---|---|
| 1312 | 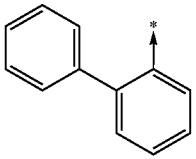 | 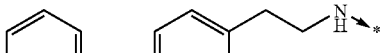 | 1.5 | 5.6 | 577.22 |
| 1313 | 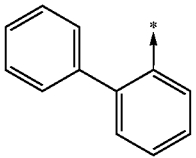 | 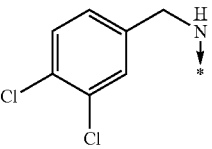 | 89.7 | 4.99 | 539.10 |
| 1314 | 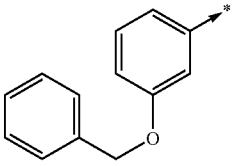 | 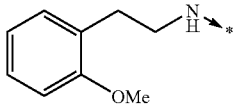 | 65.3 | 4.81 | 545.20 |
| 1315 | 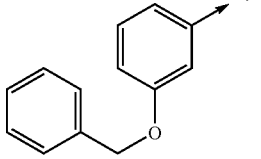 | 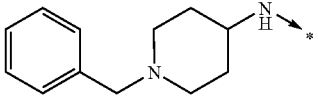 | 86.7 | 3.82 | 584.25 |
| 1316 | 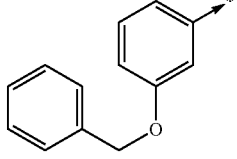 | 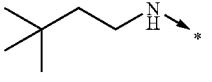 | 87.6 | 4.81 | 495.24 |
| 1317 | 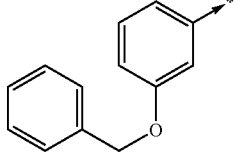 | 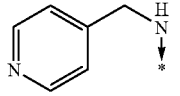 | 91 | 3.63 | 502.20 |
| 1318 | 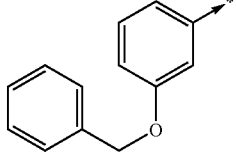 | 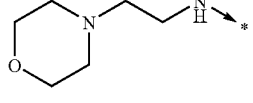 | 90.2 | 3.54 | 524.24 |
| 1319 | 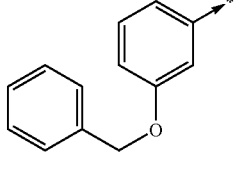 | 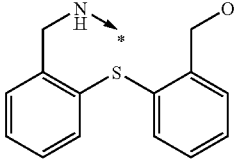 | 85.4 | 4.91 | 639.22 |

-continued
| | | | | | |
|---|---|---|---|---|---|
| 1320 | 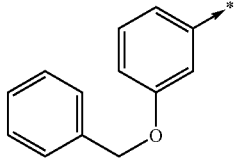 | 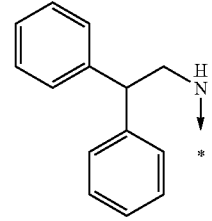 | 85.7 | 5.21 | 591.23 |
| 1321 | 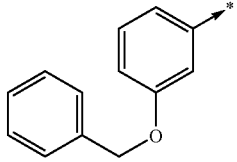 | 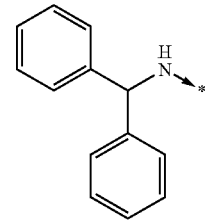 | 90 | 5.19 | 577.22 |
| 1322 | 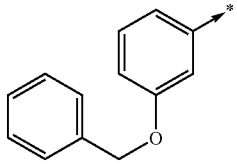 | 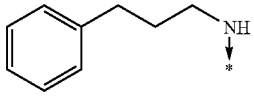 | 87.9 | 4.87 | 529.22 |
| 1323 | 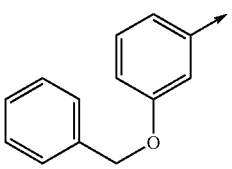 | 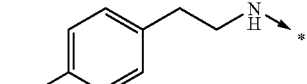 | 86.4 | 5 | 593.12 |
| 1324 | 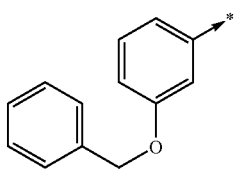 | 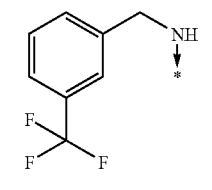 | 87.5 | 5.01 | 569.16 |
| 1325 | 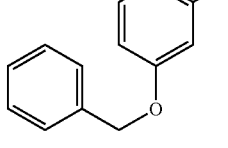 | 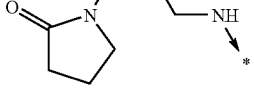 | 89.7 | 4 | 536.23 |
| 1326 | 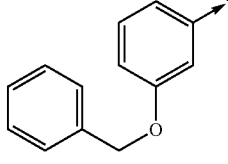 | 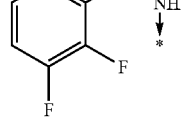 | 89.6 | 4.73 | 537.18 |
| 1327 | 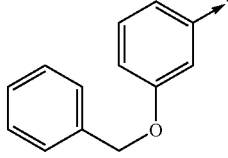 | 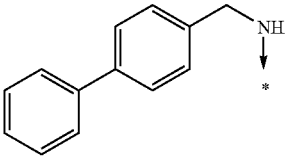 | 89.6 | 5.24 | 577.24 |

-continued

| # | R1 | R2 | a | b | c |
|---|---|---|---|---|---|
| 1328 | 3-(benzyloxy)phenyl* | 4-phenoxyphenethyl-NH-* | 86.7 | 5.33 | 607.24 |
| 1329 | 3-(benzyloxy)phenyl* | 3,4-dichlorobenzyl-NH-* | 90.6 | 5.1 | 569.10 |
| 1330 | 3,5-dimethylphenyl* | 2-methoxyphenethyl-NH-* | 62.1 | 4.17 | 467.23 |
| 1331 | 3,5-dimethylphenyl* | 1-benzylpiperidin-4-yl-NH-* | 92.8 | 3.23 | 506.28 |
| 1332 | 3,5-dimethylphenyl* | 3,3-dimethylbutyl-NH-* | 81.3 | 4.14 | 417.24 |
| 1333 | 3,5-dimethylphenyl* | pyridin-4-ylmethyl-NH-* | 91.9 | 2.95 | 424.19 |
| 1334 | 3,5-dimethylphenyl* | 2-morpholinoethyl-NH-* | 91.8 | 2.87 | 446.24 |
| 1335 | 3,5-dimethylphenyl* | 2,2'-thiobis(benzyl) derivative | 78.7 | 4.31 | 561.19 |
| 1336 | 3,5-dimethylphenyl* | 2,2-diphenylethyl-NH-* | 89.5 | 4.58 | 513.25 |

-continued

| | 491 | 492 | | | |
|---|---|---|---|---|---|
| 1337 | 3,5-dimethylphenyl | diphenylmethyl-NH-* | 91.3 | 4.54 | 499.24 |
| 1338 | 3,5-dimethylphenyl | PhCH2CH2CH2-NH-* | 80.3 | 4.24 | 451.23 |
| 1339 | 3,5-dimethylphenyl | 4-Br-C6H4-CH2CH2-NH-* | 77.6 | 4.37 | 515.12 |
| 1340 | 3,5-dimethylphenyl | 3-CF3-C6H4-CH2-NH-* | 85.7 | 4.37 | 491.18 |
| 1341 | 3,5-dimethylphenyl | 2-oxopyrrolidin-1-yl-propyl-NH-* | 92.3 | 3.34 | 458.25 |
| 1342 | 3,5-dimethylphenyl | 2,3-difluorobenzyl-NH-* | 90.8 | 4.05 | 459.19 |
| 1343 | 3,5-dimethylphenyl | 4-biphenylmethyl-NH-* | 79.9 | 4.63 | 499.25 |
| 1344 | 3,5-dimethylphenyl | 4-phenoxyphenethyl-NH-* | 76.6 | 4.75 | 529.24 |
| 1345 | 3,5-dimethylphenyl | 3,4-dichlorobenzyl-NH-* | 91.9 | 4.45 | 491.13 |

-continued
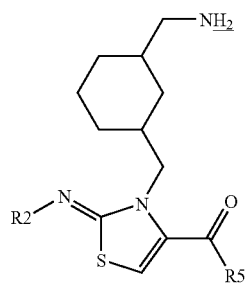
| Ex. | R2 | R5 | Purity (%) | rt (min.) | [M + H]+ |
|---|---|---|---|---|---|
| 1346 | 2-F-C6H4- | pyrrolidin-1-yl- | 56.9 + 24.5 | 4.07 + 4.2 | 417.23 |
| 1347 | 2-F-C6H4- | 4-(4-F-phenyl)piperazin-1-yl- | 64.6 + 24.4 | 4.98 + 5.1 | 526.30 |
| 1348 | 2-F-C6H4- | N-(2-cyanoethyl)-N-methylamino- | 62.4 + 25.1 | 3.96 + 4.1 | 430.25 |
| 1349 | 2-F-C6H4- | 2-(diisopropylamino)ethylamino- | 80.5 | 3.44 | 490.37 |
| 1350 | 2-F-C6H4- | (naphthalen-1-ylmethyl)amino- | 65.4 + 27.8 | 4.9 + 5.0 | 503.31 |
| 1351 | 2-F-C6H4- | 4-(2,4-dimethylphenyl)piperazin-1-yl- | 64.5 + 25.5 | 5.6 + 5.7 | 536.35 |
| 1352 | 2-F-C6H4- | 4-(pyridin-4-yl)piperazin-1-yl- | 86.8 | 3.3 | 509.30 |

-continued

| # | R1 | R2 | col4 | col5 | col6 |
|---|---|---|---|---|---|
| 1353 | 2-F-phenyl* | 2-(OCF3)-benzyl-NH-* | 64.1 + 29.8 | 5.02 + 5.1 | 537.26 |
| 1354 | 2-F-phenyl* | 4-phenyl-phenethyl-NH-* | 60.8 + 32.2 | 5.37 + 5.5 | 543.32 |
| 1355 | 2-F-phenyl* | 4-phenoxy-benzyl-NH-* | 59.6 + 31.5 | 5.24 + 5.3 | 545.30 |
| 1356 | 2-F-phenyl* | 2,3-(OMe)2-phenethyl-NH-* | 61.6 + 24.8 | 4.69 + 4.8 | 527.31 |
| 1357 | 2-F-phenyl* | 4-phenethyl-piperazin-1-yl-* | 88.7 | 3.8 | 536.36 |
| 1358 | 2-F-phenyl* | 4-(cyclohexylmethyl)-piperazin-1-yl-* | 87.5 | 3.8 | 528.38 |
| 1359 | 2-F-phenyl* | cyclopropylmethyl-NH-* | 58 + 25.2 | 4.12 + 4.3 | 417.27 |
| 1360 | 2-F-phenyl* | 2-phenyl-benzyl-NH-* | 68.1 + 24.5 | 5.22 + 5.3 | 529.31 |

-continued

| # | R1 | R2 | A | B | C |
|---|----|----|---|---|---|
| 1361 | 2-fluorophenyl | N-(2,6-dichlorophenethyl)amino | 64.8 + 23.1 | 5.12 + 5.2 | 535.19 |
| 1362 | 3,5-bis(trifluoromethyl)phenyl | pyrrolidin-1-yl | 61.9 + 21.6 | 5.46 + 5.5 | 535.23 |
| 1363 | 3,5-bis(trifluoromethyl)phenyl | 4-(4-fluorophenyl)piperazin-1-yl | 90.4 | 6.06 | 644.33 |
| 1364 | 3,5-bis(trifluoromethyl)phenyl | N-methyl-N-(2-cyanoethyl)amino | 89.7 | 5.31 | 548.24 |
| 1365 | 3,5-bis(trifluoromethyl)phenyl | (diisopropylaminomethyl)amino | 84.3 | 4.5 | 608.34 |
| 1366 | 3,5-bis(trifluoromethyl)phenyl | (naphthalen-1-ylmethyl)amino | 95.2 | 6.06 | 621.27 |
| 1367 | 3,5-bis(trifluoromethyl)phenyl | 4-(2,4-dimethylphenyl)piperazin-1-yl | 90.9 | 6.6 | 654.4 |

-continued
| | | | | | |
|---|---|---|---|---|---|
| 1368 | 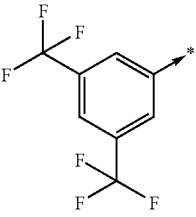 | 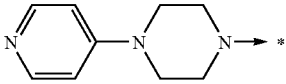 | 84.2 | 4.41 | 627.29 |
| 1369 | 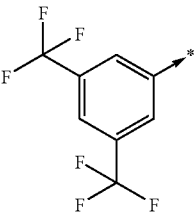 | 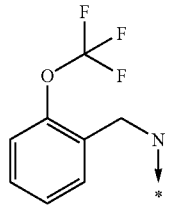 | 92.8 | 6.12 | 655.27 |
| 1370 | 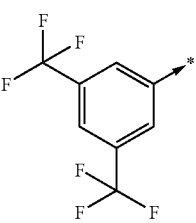 | 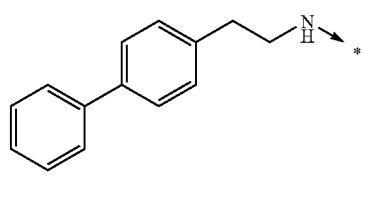 | 91.9 | 6.4 | 661.33 |
| 1371 | 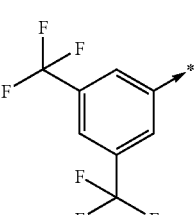 | 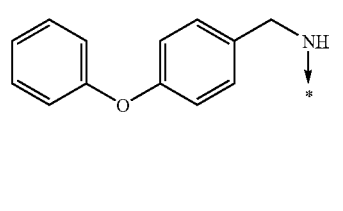 | 93.2 | 6.3 | 663.32 |
| 1372 | 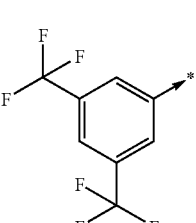 | 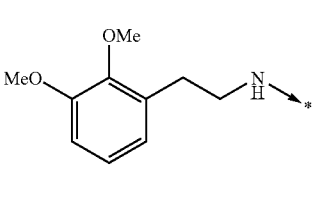 | 87.3 | 5.9 | 645.32 |
| 1373 | 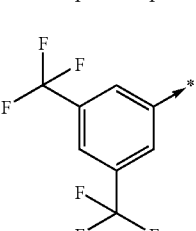 | 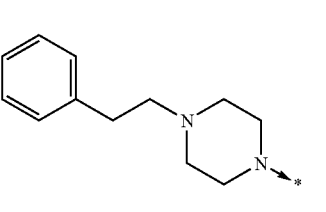 | 87.5 | 4.7 | 654.4 |
| 1374 | 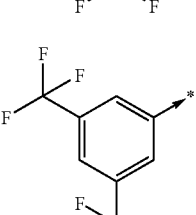 | 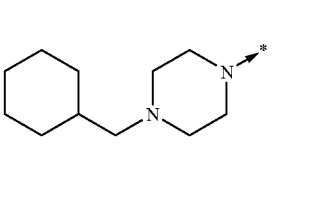 | 84.8 | 4.7 | 646.38 |

| | 501 | 502 | | | |
|---|---|---|---|---|---|
| 1375 | 3,5-bis(trifluoromethyl)phenyl-* | cyclopropylmethyl-NH-* | 71.8 | 5.53 | 535.23 |
| 1376 | 3,5-bis(trifluoromethyl)phenyl-* | 2-biphenyl-CH2-NH-* | 94.2 | 6.28 | 647.32 |
| 1377 | 3,5-bis(trifluoromethyl)phenyl-* | 2,6-dichlorophenyl-CH2CH2-NH-* | 91.6 | 6.25 | 653.22 |
| 1378 | 4-isopropylphenyl-* | pyrrolidin-1-yl-* | 63 + 26.1 | 3.98 + 4.2 | 441.30 |
| 1379 | 4-isopropylphenyl-* | 4-(4-fluorophenyl)piperazin-1-yl-* | 64.5 + 28 | 4.8 + 5.0 | 550.36 |
| 1380 | 4-isopropylphenyl-* | NC-CH2CH2-N(CH3)-* | 65.1 + 26.9 | 3.93 + 4.1 | 454.30 |
| 1381 | 4-isopropylphenyl-* | (iPr)2N-CH2CH2-NH-* | 56.6 + 30.1 | 3.54 + 3.6 | 514.40 |
| 1382 | 4-isopropylphenyl-* | naphthalen-1-yl-CH2-NH-* | 64.8 + 30.3 | 4.64 + 4.9 | 527.34 |

-continued

| | 503 | 504 | | | |
|---|---|---|---|---|---|
| 1383 | 4-isopropylphenyl | 2,4-dimethylphenyl piperazine | 64.3 + 28.3 | 5.33 + 5.6 | 560.39 |
| 1384 | 4-isopropylphenyl | 4-pyridyl piperazine | 64.5 + 24.8 | 3.5 + 3.6 | 533.35 |
| 1385 | 4-isopropylphenyl | 2-(trifluoromethoxy)benzyl-NH | 62.9 + 27.5 | 4.77 + 5.0 | 561.29 |
| 1386 | 4-isopropylphenyl | 4-biphenyl-ethyl-NH | 48.5 + 20.8 | 5.08 + 5.3 | 567.36 |
| 1387 | 4-isopropylphenyl | 4-phenoxybenzyl-NH | 61.2 + 27.5 | 4.98 + 5.2 | 569.33 |
| 1388 | 4-isopropylphenyl | 2,3-dimethoxyphenethyl-NH | 58.4 + 22.7 | 4.5 + 4.7 | 551.36 |
| 1389 | 4-isopropylphenyl | 4-phenethylpiperazine | 65.1 + 26.4 | 3.92 + 4.0 | 560.38 |
| 1390 | 4-isopropylphenyl | 4-(cyclohexylmethyl)piperazine | 63.6 + 26.1 | 3.92 + 4.1 | 552.43 |
| 1391 | 4-isopropylphenyl | cyclopropylmethyl-NH | 64 + 27.3 | 4.01 + 4.2 | 441.30 |

-continued

| # | R1 | R2 | col1 | col2 | MW |
|---|---|---|---|---|---|
| 1392 | 4-isopropylphenyl | 2-phenylbenzyl-NH- | 66.2 + 28.9 | 4.96 + 5.2 | 553.35 |
| 1393 | 4-isopropylphenyl | 2,6-dichlorophenethyl-NH- | 62.8 + 26.6 | 4.84 + 5.0 | 559.23 |
| 1394 | 3-methylthiophenyl | pyrrolidin-1-yl | 59.4 + 26.3 | 3.95 + 4.1 | 445.26 |
| 1395 | 3-methylthiophenyl | 4-(4-fluorophenyl)piperazin-1-yl | 63.7 + 28.7 | 4.89 + 5.1 | 554.28 |
| 1396 | 3-methylthiophenyl | N-methyl-2-cyanoethylamino | 62 + 27.9 | 3.9 + 4.1 | 458.27 |
| 1397 | 3-methylthiophenyl | 2-(diisopropylamino)ethyl-NH- | 58.9 + 28.7 | 3.48 + 3.5 | 518.35 |
| 1398 | 3-methylthiophenyl | (naphthalen-1-ylmethyl)-NH- | 62.9 + 29.3 | 4.75 + 5.0 | 531.28 |
| 1399 | 3-methylthiophenyl | 4-(2,4-dimethylphenyl)piperazin-1-yl | 63.2 + 28.4 | 5.46 + 5.7 | 564.32 |
| 1400 | 3-methylthiophenyl | 4-(pyridin-4-yl)piperazin-1-yl | 58.3 + 30.4 | 3.39 + 3.5 | 537.30 |

-continued
| | | | | | |
|---|---|---|---|---|---|
| 1401 | 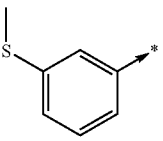 | 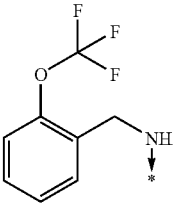 | 61.8 + 28.3 | 4.88 + 5.0 | 565.23 |
| 1402 | 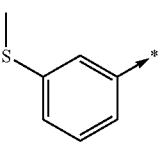 | 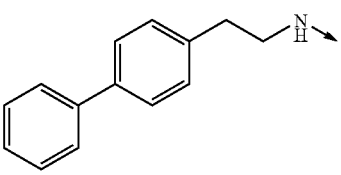 | 61.5 + 27.9 | 5.2 + 5.4 | 571.28 |
| 1403 | 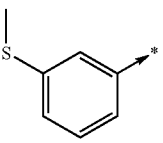 | 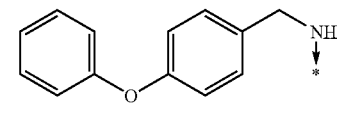 | 62.2 + 29.5 | 5.09 + 5.3 | 573.28 |
| 1404 | 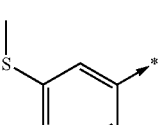 | 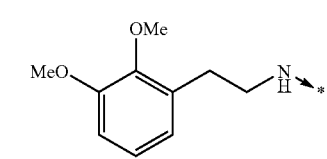 | 60.6 + 26.7 | 4.54 + 4.7 | 555.30 |
| 1405 | 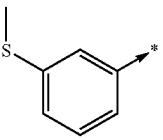 | 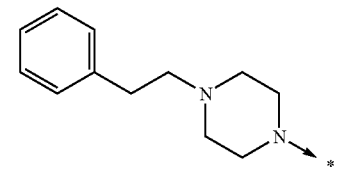 | 59.2 + 31.8 | 3.86 + 4.0 | 564.32 |
| 1406 | 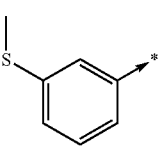 | 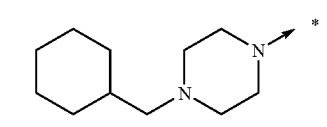 | 59.3 + 31.2 | 3.86 + 4.0 | 556.37 |
| 1407 | 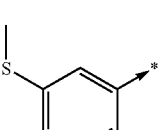 | 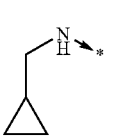 | 49.3 + 21.7 | 4 + 4.2 | 445.26 |
| 1408 | 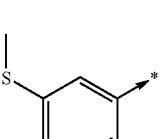 | 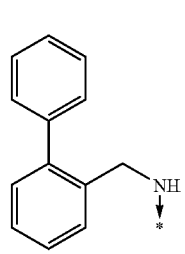 | 64.4 + 29.7 | 5.07 + 5.3 | 557.28 |

-continued
| | | | | | |
|---|---|---|---|---|---|
| 1409 | 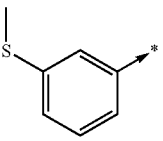 | 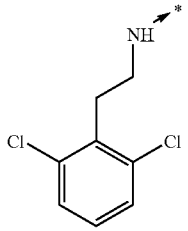 | 61.7 + 27.9 | 4.96 + 5.1 | 563.20 |
| 1410 | 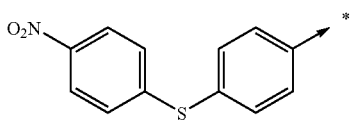 | 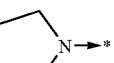 | 62.4 + 25.4 | 5.24 + 5.4 | 552.27 |
| 1411 | 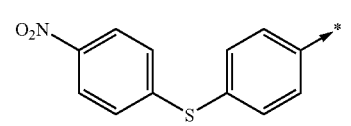 | 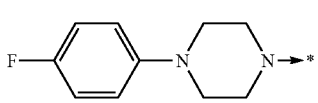 | 63.6 + 28.1 | 5.91 + 6.0 | 661.33 |
| 1412 | 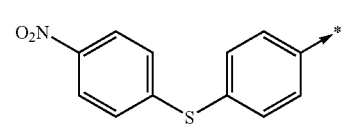 | 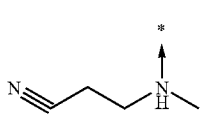 | 60.5 + 30.2 | 5.14 + 5.2 | 565.25 |
| 1413 | 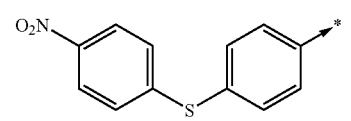 | 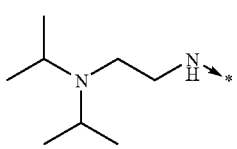 | 87.2 | 4.43 | 625.36 |
| 1414 | 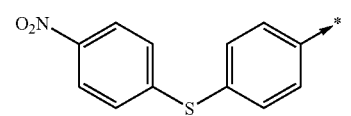 | 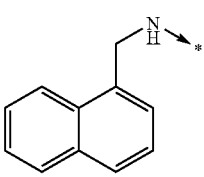 | 60.9 + 31.9 | 5.88 + 6.0 | 638.30 |
| 1415 | 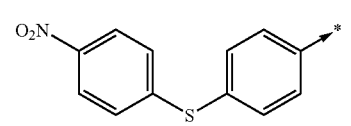 | 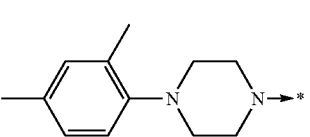 | 61.1 + 31.2 | 6.47 + 6.6 | 671.37 |
| 1416 | 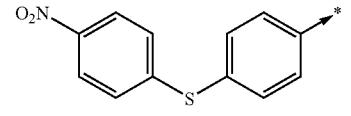 | 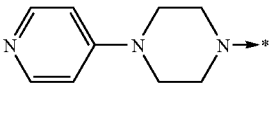 | 89.3 | 4.34 | 644.35 |
| 1417 | 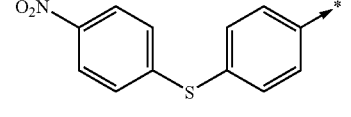 | 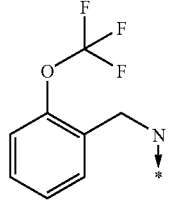 | 66.6 + 25.7 | 5.96 + 6.0 | 672.28 |
| 1418 | 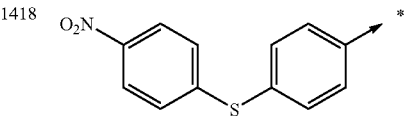 | 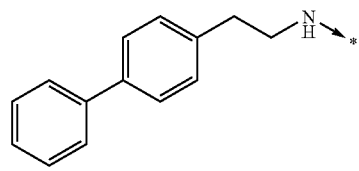 | 65.1 + 25.4 | 6.25 + 6.3 | 678.35 |

-continued
| | | | | | |
|---|---|---|---|---|---|
| 1419 | O₂N-C₆H₄-S-C₆H₄-* | Ph-O-C₆H₄-CH₂-NH-* | 63 + 27.5 | 6.13 + 6.2 | 680.32 |
| 1420 | O₂N-C₆H₄-S-C₆H₄-* | (MeO)(OMe)C₆H₃-CH₂CH₂-NH-* | 54.7 + 29.8 | 5.75 + 5.8 | 662.33 |
| 1421 | O₂N-C₆H₄-S-C₆H₄-* | Ph-CH₂CH₂-piperazine-* | 91.7 | 4.71 | 671.38 |
| 1422 | O₂N-C₆H₄-S-C₆H₄-* | cyclohexyl-CH₂-piperazine-* | 89.3 | 4.72 | 663.41 |
| 1423 | O₂N-C₆H₄-S-C₆H₄-* | cyclopropyl-CH₂-NH-* | 49 + 23.9 | 5.34 + 5.4 | 552.26 |
| 1424 | O₂N-C₆H₄-S-C₆H₄-* | biphenyl-CH₂-NH-* | 64.1 + 27.2 | 6.18 + 6.2 | 664.34 |
| 1425 | O₂N-C₆H₄-S-C₆H₄-* | 2,6-Cl₂-C₆H₃-CH₂CH₂-NH-* | 62.3 + 27.3 | 6.13 + 6.2 | 670.25 |
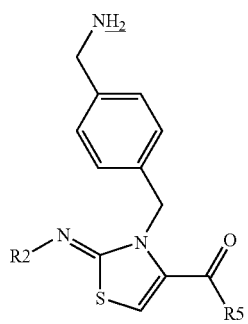
| Ex. | R2 | R5 | Purity (%) | rt (min.) | [M + H]⁺ |
|---|---|---|---|---|---|

-continued
| | | | | | |
|---|---|---|---|---|---|
| 1426 | 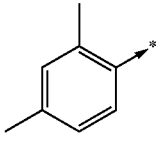 | 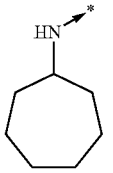 | 78.4 | 4.58 | 463.27 |
| 1427 | 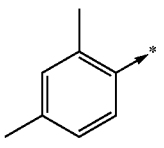 | 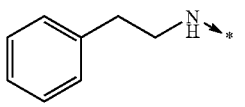 | 53.4 | 4.48 | 471.23 |
| 1428 | 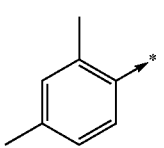 | 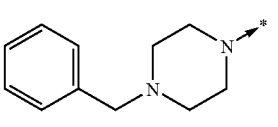 | 86.2 | 3.67 | 526.29 |
| 1429 | 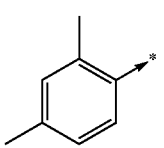 | 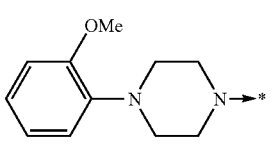 | 86 | 4.58 | 542.25 |
| 1430 | 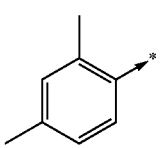 | 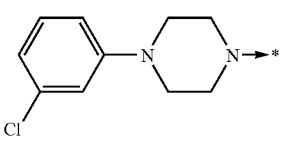 | 84.9 | 4.98 | 546.21 |
| 1431 | 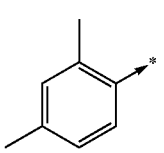 | 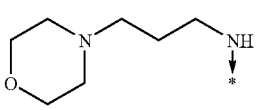 | 42.9 | 3.26 | 494.27 |
| 1432 | 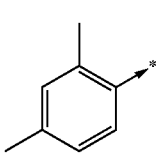 | 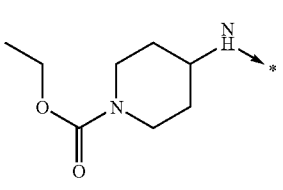 | 84.4 | 4.14 | 522.26 |
| 1433 | 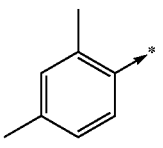 | 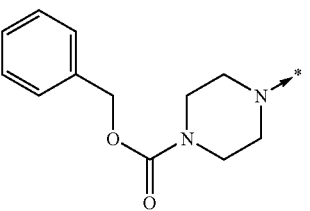 | 83.2 | 4.72 | 570.25 |
| 1434 | 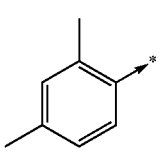 | 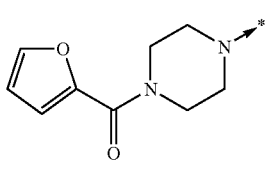 | 87.1 | 4.04 | 530.22 |

-continued
| | | | | | |
|---|---|---|---|---|---|
| 1435 | 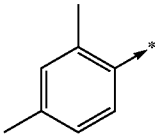 | 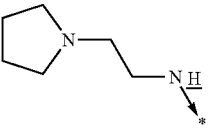 | 45.6 | 3.16 | 464.25 |
| 1436 | 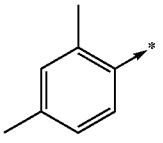 | 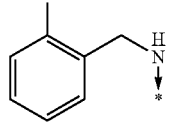 | 85.6 | 4.4 | 475.20 |
| 1437 | 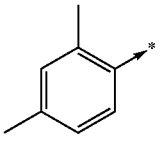 | 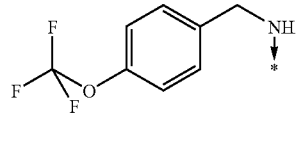 | 84.2 | 4.96 | 541.18 |
| 1438 | 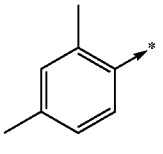 | 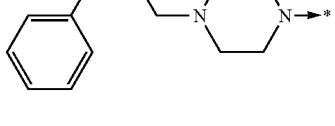 | 87.2 | 3.88 | 554.28 |
| 1439 | 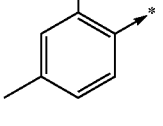 | 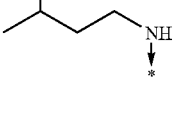 | 84.5 | 4.39 | 437.23 |
| 1440 | 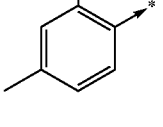 | 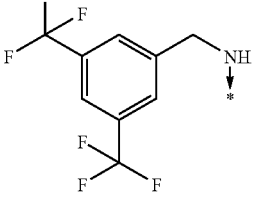 | 33.8 | 5.34 | 593.17 |
| 1441 | 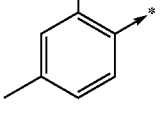 | 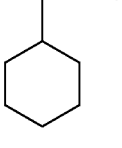 | 9.5 | 4.7 | 463.24 |
| 1442 | 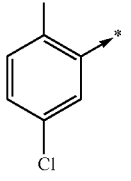 | 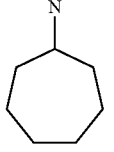 | 78.8 | 5.11 | 499.20 |
| 1443 | 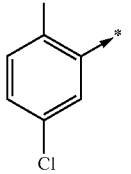 | 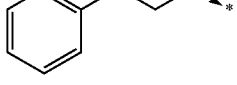 | 46.9 | 4.98 | 507.17 |

| | | | | | |
|---|---|---|---|---|---|
| 1444 | 2-OMe, 5-Cl phenyl* | 4-benzylpiperazin-1-yl* | 87.9 | 3.88 | 562.19 |
| 1445 | 2-OMe, 5-Cl phenyl* | 4-(2-methoxyphenyl)piperazin-1-yl* | 85.6 | 4.95 | 578.19 |
| 1446 | 2-OMe, 5-Cl phenyl* | 4-(3-chlorophenyl)piperazin-1-yl* | 84.9 | 5.3 | 582.14 |
| 1447 | 2-OMe, 5-Cl phenyl* | 3-morpholinopropylamino* | 49 | 3.45 | 530.19 |
| 1448 | 2-OMe, 5-Cl phenyl* | 1-(ethoxycarbonyl)piperidin-4-ylamino* | 81.4 | 4.62 | 558.18 |
| 1449 | 2-OMe, 5-Cl phenyl* | 4-(benzyloxycarbonyl)piperazin-1-yl* | 83 | 5.06 | 606.20 |
| 1450 | 2-OMe, 5-Cl phenyl* | 4-(furan-2-carbonyl)piperazin-1-yl* | 84.9 | 4.42 | 566.15 |

| | | | | | |
|---|---|---|---|---|---|
| 1451 | OMe, Cl (phenyl) | pyrrolidine-CH2CH2-NH-* | 40.7 | 3.5 | 500.19 |
| 1452 | OMe, Cl (phenyl) | 2-F-benzyl-NH-* | 85.1 | 4.87 | 511.13 |
| 1453 | OMe, Cl (phenyl) | 4-OCF3-benzyl-NH-* | 87.4 | 5.33 | 577.13 |
| 1454 | OMe, Cl (phenyl) | Ph-CH2CH2-piperazine-* | 85.6 | 4.08 | 590.24 |
| 1455 | OMe, Cl (phenyl) | isopentyl-NH-* | 54.9 | 4.92 | 473.21 |
| 1456 | OMe, Cl (phenyl) | 3,5-bis(CF3)-benzyl-NH-* | 43 | 5.66 | 629.13 |
| 1457 | OMe, Cl (phenyl) | cyclohexylmethyl-NH-* | 17.2 | 5.2 | 499.20 |

-continued

| | 521 | 522 | | | |
|---|---|---|---|---|---|
| 1458 | benzodioxole-* | cycloheptyl-NH-* | 77.6 | 4.3 | 479.20 |
| 1459 | benzodioxole-* | PhCH2CH2-NH-* | 55.3 | 4.2 | 487.18 |
| 1460 | benzodioxole-* | 4-benzylpiperazin-1-yl-* | 85.2 | 3.32 | 542.22 |
| 1461 | benzodioxole-* | 4-(2-methoxyphenyl)piperazin-1-yl-* | 87 | 4.22 | 558.19 |
| 1462 | benzodioxole-* | 4-(3-chlorophenyl)piperazin-1-yl-* | 85.9 | 4.64 | 562.14 |
| 1463 | benzodioxole-* | 3-morpholinopropyl-NH-* | 82.9 | 2.74 | 510.23 |
| 1464 | benzodioxole-* | 1-(ethoxycarbonyl)piperidin-4-yl-NH-* | 81.6 | 3.84 | 538.20 |
| 1465 | benzodioxole-* | 4-(benzyloxycarbonyl)piperazin-1-yl-* | 84.1 | 4.41 | 586.21 |
| 1466 | benzodioxole-* | 4-(furan-2-carbonyl)piperazin-1-yl-* | 85.5 | 3.65 | 546.16 |
| 1467 | benzodioxole-* | 2-(pyrrolidin-1-yl)ethyl-NH-* | 49.3 | 2.8 | 480.20 |

-continued

| # | R1 | R2 | % | RT | MS |
|---|---|---|---|---|---|
| 1468 | benzo[1,3]dioxol-5-yl* | 2-fluorobenzyl-NH-* | 81.7 | 4.11 | 491.15 |
| 1469 | benzo[1,3]dioxol-5-yl* | 4-(trifluoromethoxy)benzyl-NH-* | 83.7 | 4.71 | 557.14 |
| 1470 | benzo[1,3]dioxol-5-yl* | 4-(3-phenylpropyl)piperazin-1-yl-* | 82.2 | 3.59 | 570.24 |
| 1471 | benzo[1,3]dioxol-5-yl* | isopentyl-NH-* | 66.1 | 4.11 | 453.19 |
| 1472 | benzo[1,3]dioxol-5-yl* | 3,5-bis(trifluoromethyl)benzyl-NH-* | 29.5 | 5.12 | 609.14 |
| 1473 | benzo[1,3]dioxol-5-yl* | cyclohexylmethyl-NH-* | 9.9 | 4.44 | 479.20 |
| 1474 | 4-propylphenyl-* | cycloheptyl-NH-* | 82.8 | 5.36 | 491.28 |
| 1475 | 4-propylphenyl-* | phenethyl-NH-* | 58.2 | 5.29 | 499.26 |
| 1476 | 4-propylphenyl-* | 4-benzylpiperazin-1-yl-* | 86.5 | 4.37 | 554.27 |
| 1477 | 4-propylphenyl-* | 4-(2-methoxyphenyl)piperazin-1-yl-* | 86.6 | 5.33 | 570.26 |

-continued
| | | | | | |
|---|---|---|---|---|---|
| 1478 | 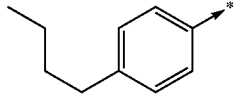 | 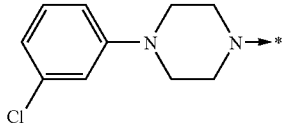 | 84.1 | 5.67 | 574.20 |
| 1479 | 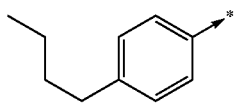 | 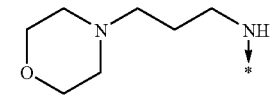 | 70.3 | 3.89 | 522.29 |
| 1480 | 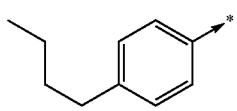 | 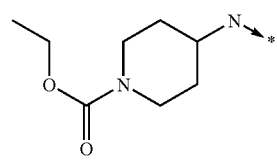 | 84.2 | 4.94 | 550.28 |
| 1481 | 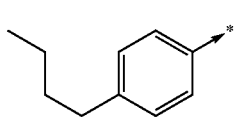 | 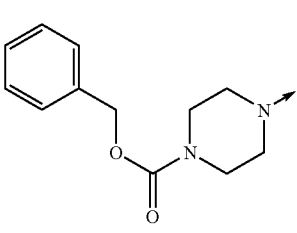 | 84.5 | 5.44 | 598.26 |
| 1482 | 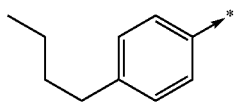 | 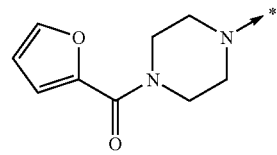 | 86 | 4.84 | 558.24 |
| 1483 | 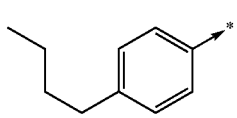 | 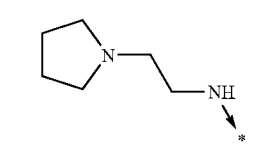 | 50.1 | 3.93 | 492.29 |
| 1484 | 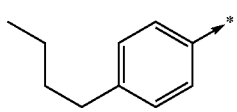 | 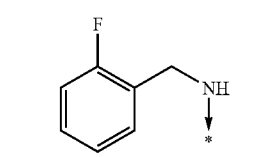 | 82.5 | 5.23 | 503.25 |
| 1485 | 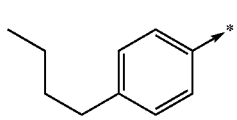 | 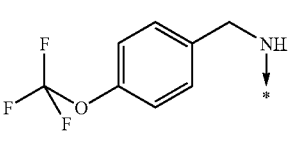 | 79.3 | 5.68 | 569.19 |
| 1486 | 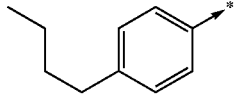 | 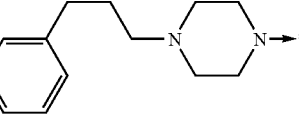 | 87.3 | 4.51 | 582.31 |
| 1487 | 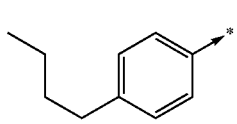 | 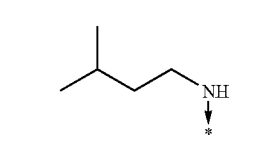 | 79.7 | 5.22 | 465.25 |

-continued
| | | | | | |
|---|---|---|---|---|---|
| 1488 | 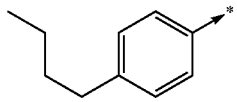 | 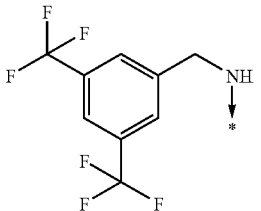 | 26.1 | 6.06 | 621.20 |
| 1489 | 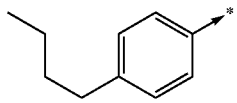 | 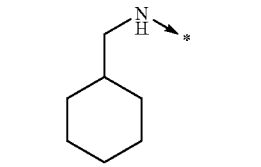 | 16.1 | 5.51 | 491.28 |
| 1490 | 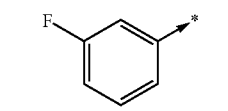 | 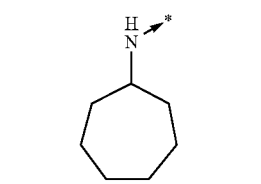 | 77 | 5.02 | 453.22 |
| 1491 | 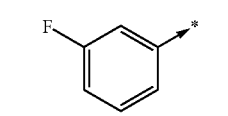 | 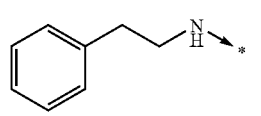 | 48.4 | 4.88 | 461.16 |
| 1492 | 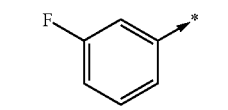 | 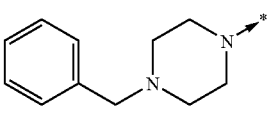 | 83.3 | 3.74 | 516.22 |
| 1493 | 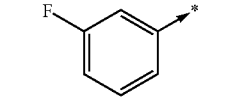 | 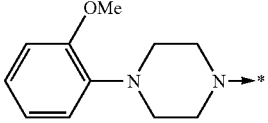 | 84.6 | 4.85 | 532.2 |
| 1494 | 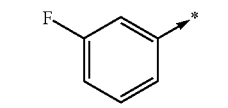 | 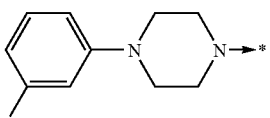 | 84.4 | 5.23 | 536.15 |
| 1495 | 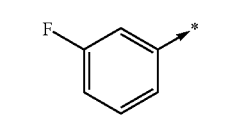 | 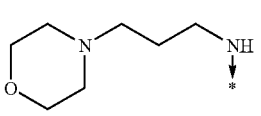 | 69.9 | 3.29 | 484.23 |
| 1496 | 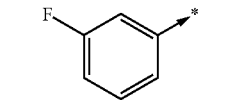 | 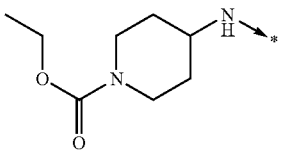 | 79.5 | 4.51 | 512.22 |
| 1497 | 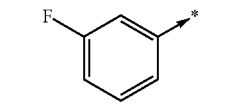 | 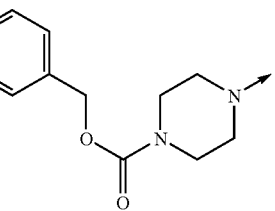 | 81.9 | 4.96 | 560.17 |

-continued
| | R2 | R5 | Purity (%) | rt (min.) | [M + H]+ |
|---|---|---|---|---|---|
| 1498 | 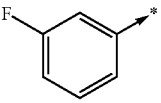 | 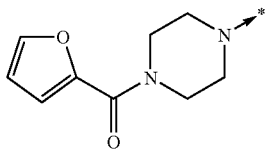 | 85.5 | 4.29 | 520.16 |
| 1499 | 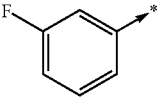 | 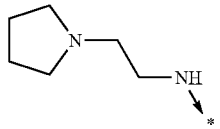 | 67.7 | 3.32 | 454.19 |
| 1500 | 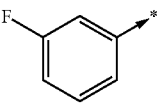 | 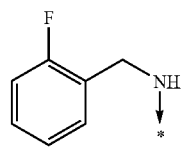 | 82.7 | 4.78 | 465.14 |
| 1501 | 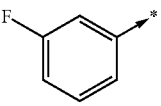 | 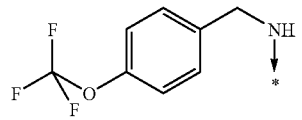 | 82.1 | 5.26 | 531.13 |
| 1502 | 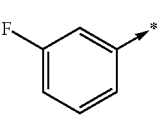 | 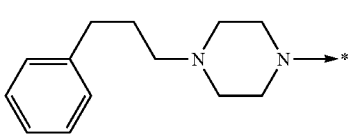 | 84.8 | 3.95 | 544.22 |
| 1503 | 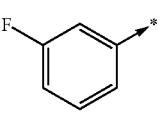 | 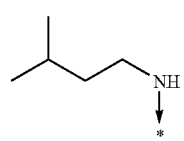 | 77.5 | 4.83 | 427.16 |
| 1504 | 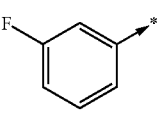 | 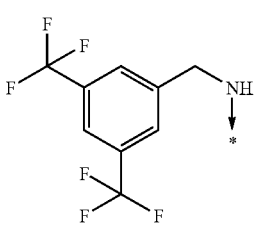 | 24 | 5.6 | 583.11 |
| 1505 | 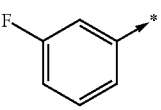 | 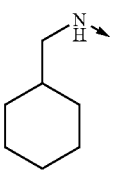 | 17.7 | 5.12 | 453.21 |
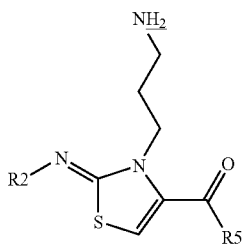
| Ex. | R2 | R5 | Purity (%) | rt (min.) | [M + H]+ |
|---|---|---|---|---|---|

-continued

| | | | | | |
|---|---|---|---|---|---|
| 1506 | (benzyloxy)phenyl | 4-[3-(trifluoromethyl)phenyl]piperazin-1-yl | 89.7 | 5.52 | 596.26 |
| 1507 | (benzyloxy)phenyl | 4-(2-chlorophenyl)piperazin-1-yl | 87.2 | 5.37 | 562.23 |
| 1508 | (benzyloxy)phenyl | 4-(2-oxo-2,3-dihydro-1H-benzimidazol-1-yl)piperidin-1-yl | 77 | 4.62 | 583.26 |
| 1509 | (benzyloxy)phenyl | 4-(2-morpholin-4-yl-2-oxoethyl)piperazin-1-yl | 89.1 | 3.7 | 579.25 |
| 1510 | (benzyloxy)phenyl | 2,3-dihydro-1H-benz[de]isoquinolin-2-yl | 88.6 | 5.32 | 535.23 |
| 1511 | (benzyloxy)phenyl | 4-(2-phenylethyl)-1,4-diazepan-1-yl | 87.6 | 4 | 570.27 |
| 1512 | 3-chloro-4-fluorophenyl | 4-phenylpiperazin-1-yl | 88 | 5.12 | 474.19 |
| 1513 | 3-chloro-4-fluorophenyl | 4-(4-nitrophenyl)piperazin-1-yl | 90.5 | 5.09 | 519.14 |
| 1514 | 3-chloro-4-fluorophenyl | 4-(4-chlorophenyl)-3,6-dihydropyridin-1(2H)-yl | 91.2 | 5.7 | 505.1 |

-continued
| | | | | | |
|---|---|---|---|---|---|
| 1515 |  |  | 88 | 3.74 | 475.17 |
| 1516 |  |  | 86.7 | 5.58 | 487.20 |
| 1517 |  |  | 88.3 | 3.88 | 532.18 |
| 1518 |  |  | 90.4 | 3 | 487.27 |
| 1519 |  |  | 92.8 | 4.86 | 443.21 |
| 1520 |  |  | 87.8 | 3.58 | 478.28 |
| 1521 |  |  | 90.4 | 5.2 | 478.28 |
| 1522 |  |  | 79.8 | 5.37 | 488.26 |
| 1523 |  |  | 90.3 | 5.13 | 523.27 |
| 1524 | | | 81.2 | 5.7 | 509.2 |
| 1525 | | | 91 | 3.88 | 479.26 |

-continued

| Ex. | R2 | R5 | Purity (%) | rt (min.) | [M + H]+ |
|---|---|---|---|---|---|
| 1526 | 4-tert-butylphenyl | 4-benzylpiperidin-1-yl | 91.5 | 5.62 | 491.29 |
| 1527 | 4-tert-butylphenyl | 4-(benzo[1,3]dioxol-5-ylmethyl)piperazin-1-yl | 91.1 | 4.1 | 536.28 |
| 1528 | 4-tert-butylphenyl | 4-(3-trifluoromethylphenyl)piperazin-1-yl | 91.9 | 5.68 | 546.25 |
| 1529 | 4-tert-butylphenyl | 4-(2-chlorophenyl)piperazin-1-yl | 92 | 5.54 | 512.24 |
| 1530 | 4-tert-butylphenyl | 4-(2-morpholin-4-yl-2-oxoethyl)piperazin-1-yl | 91.4 | 3.7 | 529.3 |
| 1531 | 4-tert-butylphenyl | 2,3-dihydro-1H-benz[de]isoquinolin-2-yl | 92.4 | 5.49 | 485.23 |
| 1532 | 4-tert-butylphenyl | 4-phenethyl-[1,4]diazepan-1-yl | 89.4 | 4.2 | 520.28 |

| Ex. | R2 | R5 | Purity (%) | rt (min.) | [M + H]+ |
|---|---|---|---|---|---|
| 1533 | 3-methoxyphenyl | 4-phenylpiperazin-1-yl | 90.1 | 4.56 | 452.20 |

| | | | | | |
|---|---|---|---|---|---|
| 1534 | MeO-phenyl-* | 2,3,4,9-tetrahydro-1H-β-carboline (N-*) | 76.8 | 4.76 | 462.18 |
| 1535 | MeO-phenyl-* | 4-(4-nitrophenyl)piperazin-1-yl-* | 92.5 | 4.58 | 497.22 |
| 1536 | MeO-phenyl-* | 4-(pyridin-2-yl)piperazin-1-yl-* | 93.4 | 3.21 | 453.21 |
| 1537 | MeO-phenyl-* | 4-benzylpiperidin-1-yl-* | 91.2 | 5.04 | 465.22 |
| 1538 | MeO-phenyl-* | 4-(benzo[d][1,3]dioxol-5-ylmethyl)piperazin-1-yl-* | 92.7 | 3.44 | 510.22 |
| 1539 | MeO-phenyl-* | 4-(3-(trifluoromethyl)phenyl)piperazin-1-yl-* | 89.6 | 5.14 | 520.18 |
| 1540 | MeO-phenyl-* | 4-(2-chlorophenyl)piperazin-1-yl-* | 90.2 | 4.93 | 486.17 |
| 1541 | MeO-phenyl-* | 2-(morpholino)-2-oxoethyl-piperazin-1-yl-* | 89.4 | 2.98 | 503.26 |
| 1542 | MeO-phenyl-* | 2,3-dihydro-1H-benz[de]isoquinolin-2-yl-* | 90.9 | 4.84 | 459.18 |
| 1543 | MeO-phenyl-* | 4-phenethyl-1,4-diazepan-1-yl-* | 89.1 | 3.55 | 494.26 |

-continued
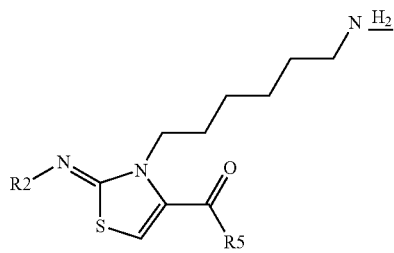
| Ex. | R2 | R5 | Purity (%) | rt (min.) | [M + H]+ |
|---|---|---|---|---|---|
| 1544 | naphthalen-1-yl | isobutylamino | 83.5 | 4.19 | 425.25 |
| 1545 | naphthalen-1-yl | biphenyl-3-ylmethylamino | 78.8 | 5.1 | 535.25 |
| 1546 | 3-nitrophenyl | 2-phenoxyethylamino | 79.7 | 4.67 | 484.23 |
| 1547 | 3-nitrophenyl | 4-(2,6-dimethylphenyl)piperazin-1-yl | 88 | 5.46 | 537.27 |
| 1548 | 3-nitrophenyl | 3,4-dihydroisoquinolin-2(1H)-yl | 87.4 | 4.72 | 480.22 |
| 1549 | 3-nitrophenyl | 1,2,3,4-tetrahydronaphthalen-1-ylamino | 82 | 4.94 | 494.23 |
| 1550 | 3-nitrophenyl | 2-(trifluoromethyl)benzylamino | 89.6 | 4.92 | 522.18 |

-continued
| | | | | | |
|---|---|---|---|---|---|
| 1551 | 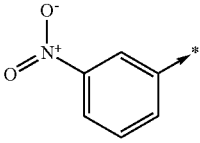 | 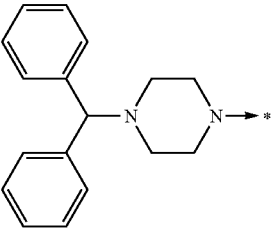 | 86.9 | 5.03 | 599.27 |
| 1552 | 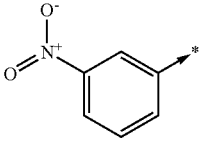 | 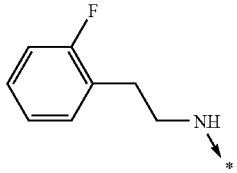 | 84.3 | 4.7 | 486.20 |
| 1553 | 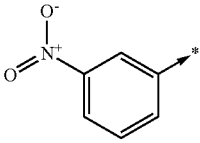 | 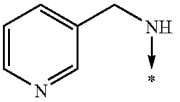 | 82.7 | 3.36 | 455.18 |
| 1554 | 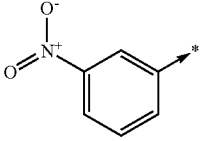 | 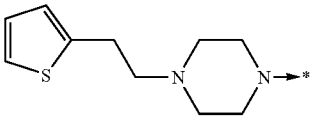 | 82 | 3.68 | 543.20 |
| 1555 | 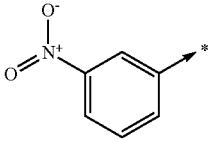 | 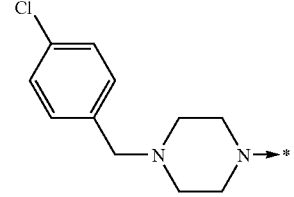 | 86.7 | 3.91 | 557.20 |
| 1556 | 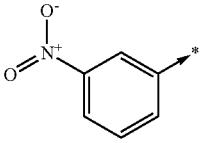 | 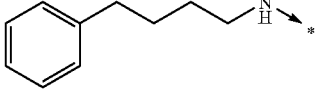 | 80.9 | 5.06 | 496.26 |
| 1557 | 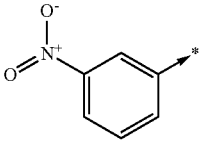 | 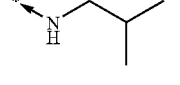 | 83.1 | 4.35 | 420.21 |
| 1558 | 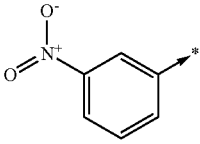 | 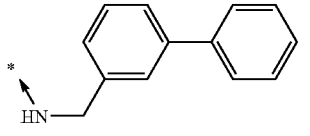 | 87.5 | 5.2 | 530.22 |
| 1559 | 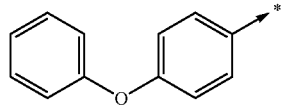 | 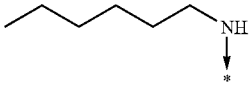 | 76.7 | 4.62 | 495.27 |

-continued
| | | | | | |
|---|---|---|---|---|---|
| 1560 | 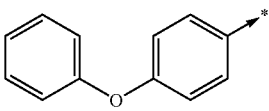 | 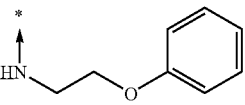 | 80.9 | 4.44 | 531.25 |
| 1561 | 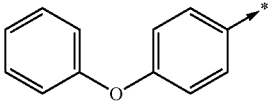 | 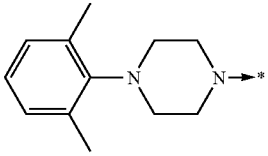 | 85.7 | 5.16 | 584.30 |
| 1562 | 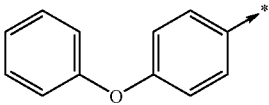 | 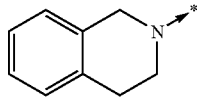 | 85.4 | 4.51 | 527.25 |
| 1563 | 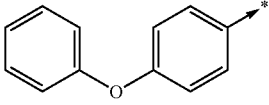 | 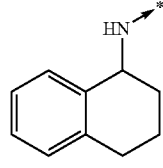 | 82.1 | 4.66 | 541.25 |
| 1564 | 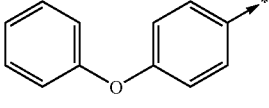 | 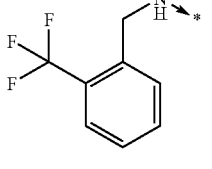 | 87.4 | 4.66 | 569.19 |
| 1565 | 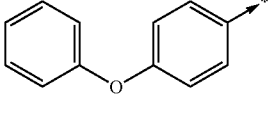 | 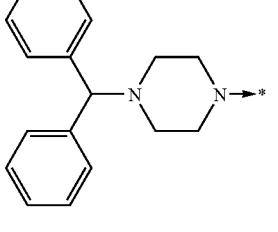 | 82.9 | 5.03 | 646.34 |
| 1566 | 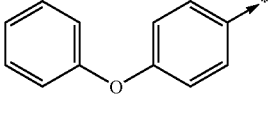 | 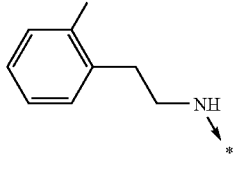 | 82.7 | 4.44 | 533.23 |
| 1567 | 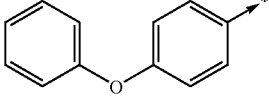 | 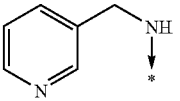 | 85 | 3.46 | 502.24 |
| 1568 | 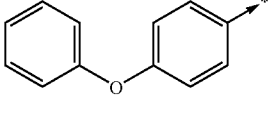 | 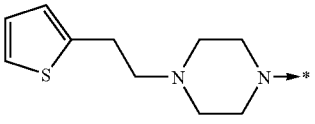 | 81.8 | 3.82 | 590.27 |

-continued

| # | R1 | R2 | % | t | m/z |
|---|---|---|---|---|---|
| 1569 | phenoxyphenyl* | 4-chlorobenzyl-piperazinyl* | 84.5 | 4.03 | 604.26 |
| 1570 | phenoxyphenyl* | 4-phenylbutyl-NH* | 81.9 | 4.74 | 543.27 |
| 1571 | phenoxyphenyl* | isobutyl-NH* | 84.3 | 4.13 | 467.25 |
| 1572 | phenoxyphenyl* | biphenylmethyl-NH* | 77.4 | 4.9 | 577.2 |
| 1573 | 2-methyl-4-(piperidin-1-ylsulfonyl)phenyl* | hexyl-NH* | 77.7 | 5.15 | 550.3 |
| 1574 | 4-(piperidin-1-ylsulfonyl)phenyl* | 2-phenoxyethyl-NH* | 80.7 | 4.9 | 586.24 |
| 1575 | 4-(piperidin-1-ylsulfonyl)phenyl* | 2,6-dimethylphenyl-piperazinyl* | 86.4 | 5.6 | 639.34 |
| 1576 | 4-(piperidin-1-ylsulfonyl)phenyl* | tetrahydroisoquinolin-2-yl* | 86.2 | 4.94 | 582.25 |
| 1577 | 4-(piperidin-1-ylsulfonyl)phenyl* | 1,2,3,4-tetrahydronaphthalen-1-yl-NH* | 82 | 5.17 | 596.28 |
| 1578 | 4-(piperidin-1-ylsulfonyl)phenyl* | 2-(trifluoromethyl)benzyl-NH* | 89.7 | 5.14 | 624.22 |

| | | | | | |
|---|---|---|---|---|---|
| 1579 | [piperidine-SO2-C6H4-*] | [diphenylmethyl-piperazine-*] | 86.1 | 5.22 | 701.35 |
| 1580 | [piperidine-SO2-C6H4-*] | [2-F-C6H4-CH2CH2-NH-*] | 85.1 | 4.92 | 588.23 |
| 1581 | [piperidine-SO2-C6H4-*] | [pyridin-3-yl-CH2-N(*)] | 81.7 | 3.67 | 557.23 |
| 1582 | [piperidine-SO2-C6H4-*] | [thiophen-2-yl-CH2CH2-piperazine-*] | 81 | 3.9 | 645.32 |
| 1583 | [piperidine-SO2-C6H4-*] | [4-Cl-C6H4-CH2-piperazine-*] | 85.2 | 4.12 | 659.31 |
| 1584 | [piperidine-SO2-C6H4-*] | [Ph-(CH2)3-NH-*] | 82.4 | 5.26 | 598.26 |
| 1585 | [piperidine-SO2-C6H4-*] | [isobutyl-NH-*] | 83.6 | 4.62 | 522.25 |
| 1586 | [piperidine-SO2-C6H4-*] | [biphenyl-3-yl-CH2-NH-*] | 85.3 | 5.39 | 632.29 |
| 1587 | [3-Br-C6H4-*] | [n-pentyl-NH-*] | 82.8 | 4.94 | 481.16 |

-continued
| | | | | | |
|---|---|---|---|---|---|
| 1588 | 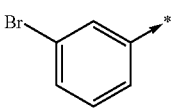 | 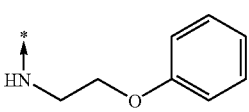 | 84.3 | 4.71 | 517.16 |
| 1589 | 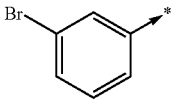 | 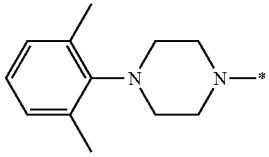 | 89.6 | 5.54 | 570.16 |
| 1590 | 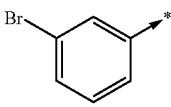 | 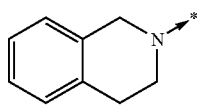 | 87.8 | 4.78 | 513.13 |
| 1591 | 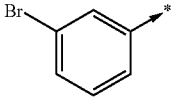 | 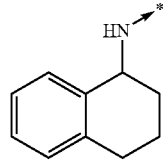 | 85.2 | 4.99 | 527.15 |
| 1592 | 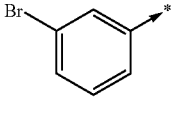 | 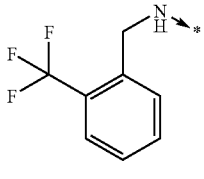 | 90.9 | 4.98 | 555.07 |
| 1593 | 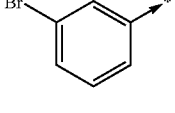 | 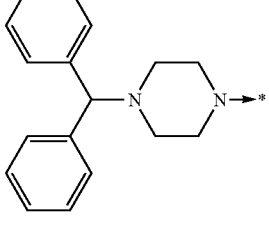 | 88.1 | 5.21 | 632.22 |
| 1594 | 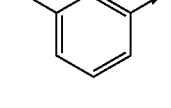 | 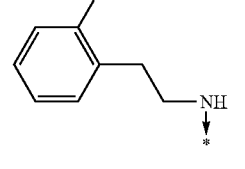 | 86.9 | 4.72 | 519.10 |
| 1595 | 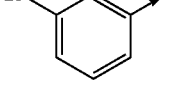 | 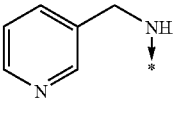 | 87.4 | 3.47 | 488.12 |
| 1596 | 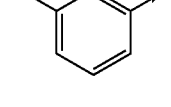 | 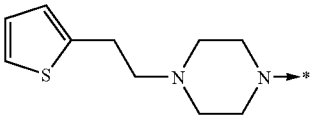 | 82.5 | 3.82 | 576.16 |

-continued
| Ex. | R2 | R5 | Purity (%) | rt (min.) | [M + H]+ |
|---|---|---|---|---|---|
| 1597 | 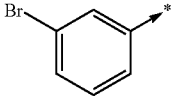 | 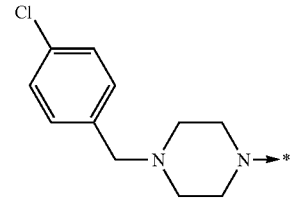 | 86.1 | 4.06 | 590.12 |
| 1598 | 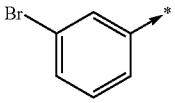 | 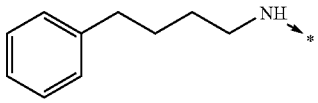 | 85.1 | 5.08 | 529.16 |
| 1599 | 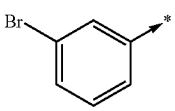 | 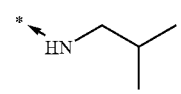 | 84.8 | 4.34 | 453.13 |
| 1600 | 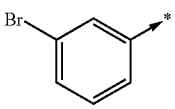 | 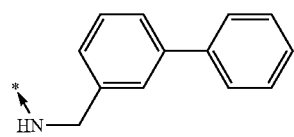 | 74.9 | 5.26 | 563.13 |
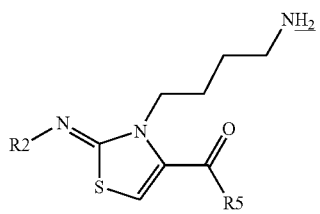
| Ex. | R2 | R5 | Purity (%) | rt (min.) | [M + H]+ |
|---|---|---|---|---|---|
| 1601 | 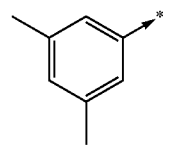 | 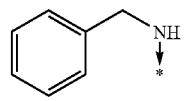 | 88.1 | 3.87 | 409.24 |
| 1602 | 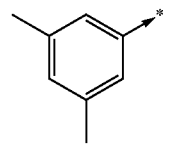 | 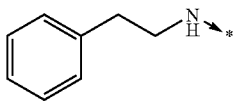 | 90.1 | 4.0 | 423.26 |
| 1603 | 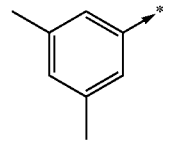 | 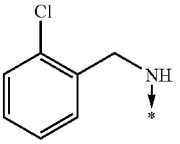 | 60.2 | 4.1 | 443.21 |
| 1604 | 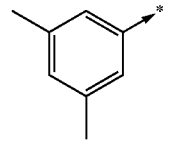 | 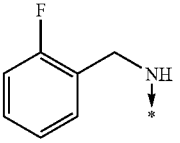 | 91 | 3.9 | 427.24 |

-continued
| | | | | | |
|---|---|---|---|---|---|
| 1605 | 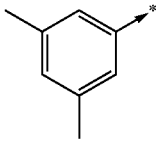 | 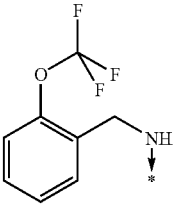 | 57.6 | 4.4 | 493.23 |
| 1606 | 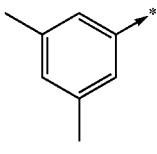 | 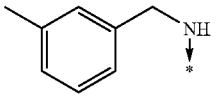 | 48.1 | 4.12 | 423.27 |
| 1607 | 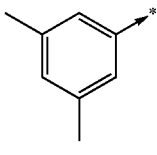 | 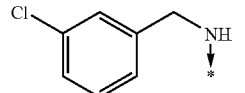 | 45.1 | 4.2 | 443.22 |
| 1608 | 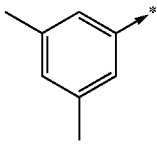 | 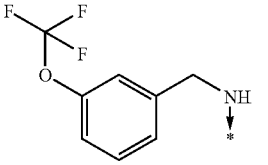 | 60.8 | 4.49 | 493.24 |
| 1609 | 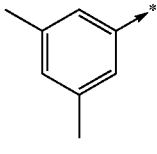 | 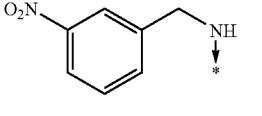 | 54.5 | 3.98 | 454.26 |
| 1610 | 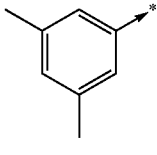 | 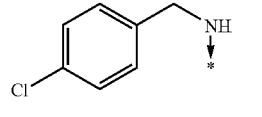 | 84 | 4.19 | 443.23 |
| 1611 | 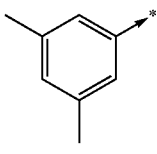 | 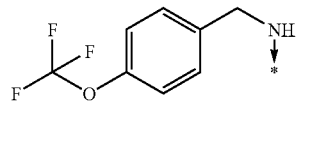 | 92.8 | 4.49 | 493.25 |
| 1612 | 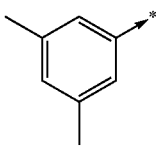 | 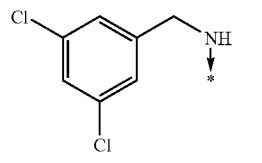 | 86.2 | 4.51 | 477.21 |
| 1613 | 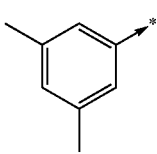 | 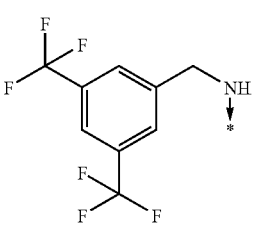 | 84.1 | 4.84 | 545.22 |

-continued
| | | | | | |
|---|---|---|---|---|---|
| 1614 | 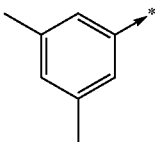 | 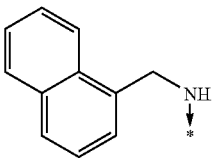 | 77.7 | 4.34 | 459.30 |
| 1615 | 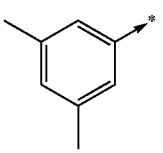 | 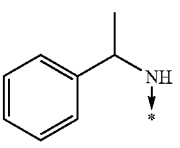 | 90.6 | 3.95 | 423.29 |
| 1616 | 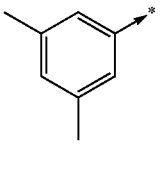 | 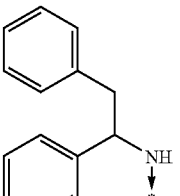 | 91.8 | 4.6 | 499.35 |
| 1617 | 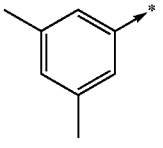 | 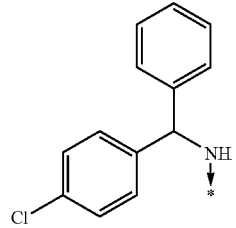 | 91.9 | 4.86 | 519.27 |
| 1618 | 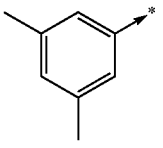 | 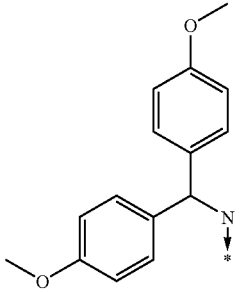 | 62 | 4.6 | 545.3 |
| 1619 | 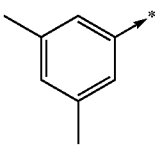 | 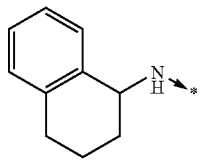 | 91.7 | 4.28 | 449.32 |
| 1620 | 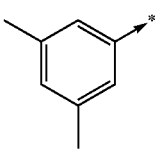 | 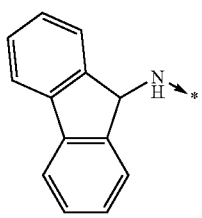 | 63.1 | 4.62 | 483.29 |

-continued
| | | | | | |
|---|---|---|---|---|---|
| 1621 | 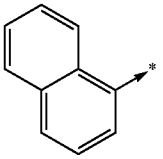 | 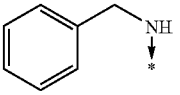 | 83.8 | 4.41 | 431.26 |
| 1622 | 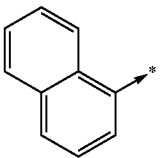 | 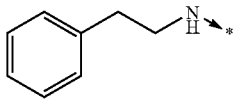 | 64.2 | 4.55 | 445.26 |
| 1623 | 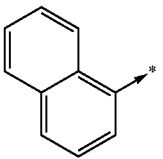 |  | 48.9 | 4.66 | 465.21 |
| 1624 | 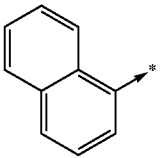 | 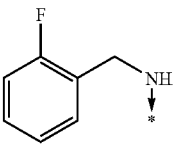 | 89 | 4.46 | 449.27 |
| 1625 | 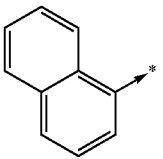 | 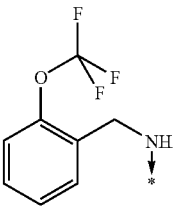 | 56.7 | 4.94 | 515.24 |
| 1626 | 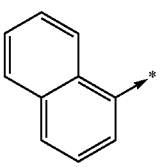 | 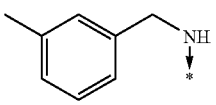 | 78.4 | 4.65 | 445.25 |
| 1627 | 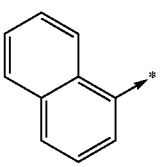 | 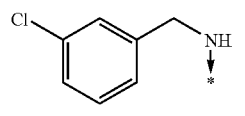 | 44.5 | 4.72 | 465.21 |
| 1628 | 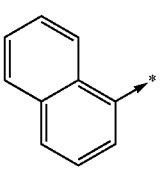 | 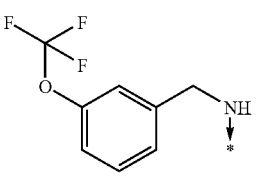 | 84.7 | 5.01 | 515.24 |
| 1629 | 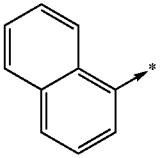 | 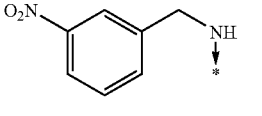 | 73.9 | 4.5 | 476.27 |

-continued
| | | | | | |
|---|---|---|---|---|---|
| 1630 | 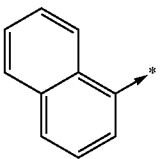 | 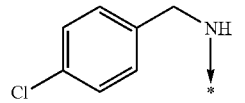 | 76.8 | 4.74 | 465.21 |
| 1631 | 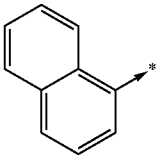 | 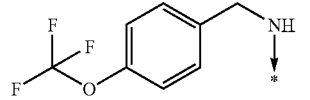 | 88.6 | 5.02 | 515.24 |
| 1632 | 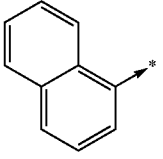 | 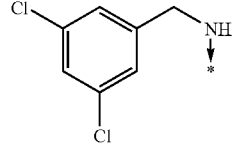 | 90.6 | 5.05 | 499.19 |
| 1633 | 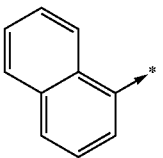 | 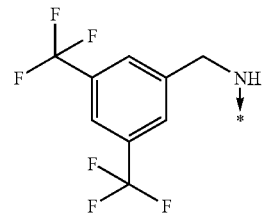 | 89.4 | 5.35 | 567.21 |
| 1634 | 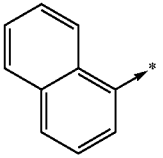 | 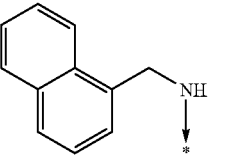 | 80.6 | 4.88 | 481.28 |
| 1635 | 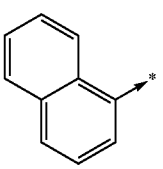 | 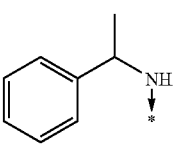 | 90.6 | 4.49 | 445.26 |
| 1636 | 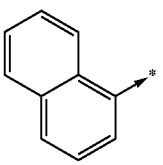 | 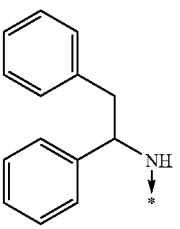 | 91.1 | 5.14 | 521.28 |
| 1637 | 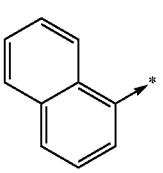 | 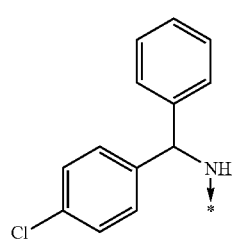 | 91.2 | 5.38 | 541.23 |

-continued
| Ex. | | | Purity (%) | rt (min.) | [M + H]⁺ |
|---|---|---|---|---|---|
| 1638 | naphthalen-1-yl | bis(4-methoxyphenyl)methyl-NH-* | 90 | 5.1 | 567.3 |
| 1639 | naphthalen-1-yl | 1,2,3,4-tetrahydronaphthalen-1-yl-NH-* | 92.9 | 4.84 | 471.28 |
| 1640 | naphthalen-1-yl | 9H-fluoren-9-yl-NH-* | 88.3 | 5.13 | 505.28 |
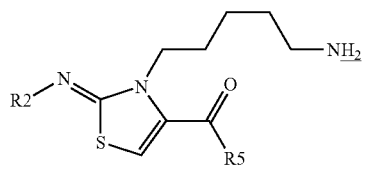
| Ex. | R2 | R5 | Purity (%) | rt (min.) | [M + H]⁺ |
|---|---|---|---|---|---|
| 1641 | 3,5-dimethylphenyl | benzyl-NH-* | 83.5 | 3.86 | 423.29 |
| 1642 | 3,5-dimethylphenyl | phenethyl-NH-* | 81.9 | 4 | 437.30 |
| 1643 | 3,5-dimethylphenyl | 2-chlorobenzyl-NH-* | 81.1 | 4.07 | 457.25 |
| 1644 | 3,5-dimethylphenyl | 2-fluorobenzyl-NH-* | 89.9 | 3.89 | 441.27 |

| | | | | | |
|---|---|---|---|---|---|
| 1645 | 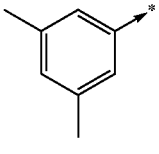 |  | 91.5 | 4.35 | 507.27 |
| 1646 | 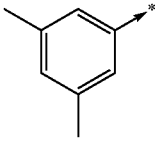 |  | 70.6 | 4.08 | 437.31 |
| 1647 | 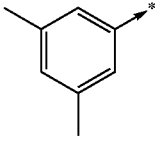 | 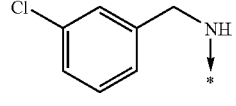 | 73.2 | 4.14 | 457.26 |
| 1648 | 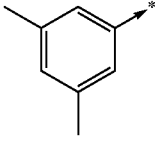 | 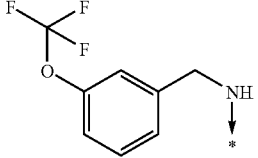 | 91.7 | 4.42 | 507.27 |
| 1649 | 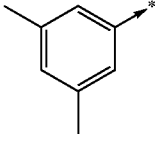 | 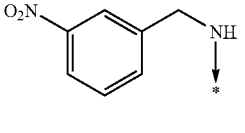 | 61.9 | 3.96 | 468.26 |
| 1650 | 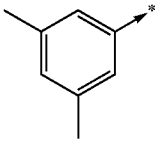 | 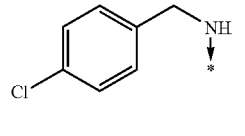 | 82.6 | 41.6 | 457.25 |
| 1651 | 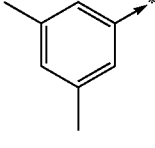 | 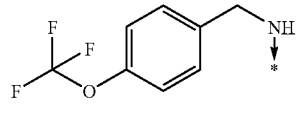 | 78.5 | 4.46 | 507.26 |
| 1652 | 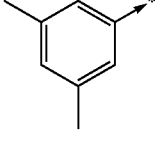 | 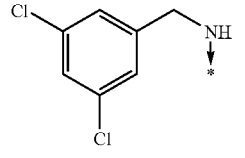 | 80 | 4.46 | 491.21 |
| 1653 | 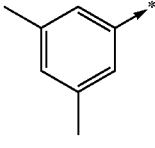 | 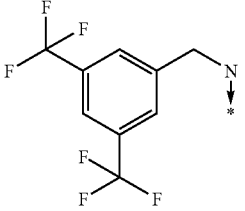 | 80.7 | 4.78 | 559.24 |

-continued

| # | R1 | R2 | % | t | M |
|---|----|----|----|----|----|
| 1654 | 3,5-dimethylphenyl-* | naphthalen-1-ylmethyl-NH-* | 90.3 | 4.28 | 473.33 |
| 1655 | 3,5-dimethylphenyl-* | 1-phenylethyl-NH-* | 91.4 | 3.93 | 437.30 |
| 1656 | 3,5-dimethylphenyl-* | 1,2-diphenylethyl-NH-* | 93.5 | 4.55 | 513.33 |
| 1657 | 3,5-dimethylphenyl-* | (4-chlorophenyl)(phenyl)methyl-NH-* | 92.8 | 4.82 | 533.27 |
| 1658 | 3,5-dimethylphenyl-* | bis(4-methoxyphenyl)methyl-HN-* | 58 | 4.5 | 559.3 |
| 1659 | 3,5-dimethylphenyl-* | 1,2,3,4-tetrahydronaphthalen-1-yl-NH-* | 92.1 | 4.24 | 463.32 |
| 1660 | 3,5-dimethylphenyl-* | 9H-fluoren-9-yl-NH-* | 92.2 | 4.53 | 497.29 |

-continued
| | | | | | |
|---|---|---|---|---|---|
| 1661 |  |  | 36.9 | 4.42 | 445.25 |
| 1662 |  |  | 31 | 4.56 | 459.28 |
| 1663 |  |  | 38.9 | 4.67 | 479.24 |
| 1664 |  |  | 43.4 | 4.47 | 463.27 |
| 1665 |  |  | 47.9 | 4.98 | 529.2 |
| 1666 |  |  | 32.1 | 4.66 | 459.28 |
| 1667 |  |  | 23 | 4.74 | 479.23 |
| 1668 |  |  | 38.1 | 5.02 | 529.25 |
| 1669 |  |  | 35.5 | 4.51 | 490.27 |

-continued

| | | | | | |
|---|---|---|---|---|---|
| 1670 | naphthalen-1-yl | 4-chlorobenzyl-NH-* | 47.1 | 4.74 | 479.23 |
| 1671 | naphthalen-1-yl | 4-(trifluoromethoxy)benzyl-NH-* | 37.1 | 5.04 | 529.25 |
| 1672 | naphthalen-1-yl | 3,5-dichlorobenzyl-NH-* | 60.9 | 5.07 | 513.19 |
| 1673 | naphthalen-1-yl | 3,5-bis(trifluoromethyl)benzyl-NH-* | 82.8 | 5.34 | 581.23 |
| 1674 | naphthalen-1-yl | naphthalen-1-ylmethyl-NH-* | 20.5 | 4.91 | 495.27 |
| 1675 | naphthalen-1-yl | 1-phenylethyl-NH-* | 72 | 4.52 | 459.28 |
| 1676 | naphthalen-1-yl | 1,2-diphenylethyl-NH-* | 91.1 | 5.14 | 535.30 |
| 1677 | naphthalen-1-yl | (4-chlorophenyl)(phenyl)methyl-NH-* | 89.3 | 5.4 | 555.23 |

-continued

| | | | | | |
|---|---|---|---|---|---|
| 1678 | naphthalen-1-yl | bis(4-methoxyphenyl)methyl-N-N* | 52 | 5.1 | 581.3 |
| 1679 | naphthalen-1-yl | 1,2,3,4-tetrahydronaphthalen-1-yl-NH-* | 91.3 | 4.84 | 485.31 |
| 1680 | naphthalen-1-yl | 9H-fluoren-9-yl-NH-* | 71.7 | 5.14 | 519.29 |
| 1681 | biphenyl-2-yl | *-HN-CH2-phenyl | 72.7 | 4.26 | 471.34 |
| 1682 | biphenyl-2-yl | *-HN-CH(CH3)-phenyl | 76.3 | 4.36 | 485.34 |
| 1683 | biphenyl-2-yl | *-HN-CH2-(2-methylphenyl) | 51.6 | 4.47 | 485.33 |
| 1684 | biphenyl-2-yl | *-HN-CH2-(2-methoxyphenyl) | 33.6 | 4.39 | 501.32 |
| 1685 | biphenyl-2-yl | *-HN-CH2-(2-trifluoromethylphenyl) | 79.9 | 4.7 | 539.29 |

-continued

| # | R1 | R2 | % | logP | MW |
|---|---|---|---|---|---|
| 1686 | biphenyl-2-yl | 2-(OCHF2)benzyl-NH- | 76 | 4.77 | 555.28 |
| 1687 | biphenyl-2-yl | 2-F-benzyl-NH- | 53.2 | 4.34 | 489.30 |
| 1688 | biphenyl-2-yl | 2-Cl-benzyl-NH- | 59.2 | 4.51 | 505.27 |
| 1689 | biphenyl-2-yl | 2-Br-benzyl-NH- | 74.7 | 4.57 | 549.21 |
| 1690 | biphenyl-2-yl | biphenyl-2-ylmethyl-NH- | 82 | 4.84 | 547.34 |
| 1691 | biphenyl-2-yl | 3-methylbenzyl-NH- | 68.8 | 4.49 | 485.32 |
| 1692 | biphenyl-2-yl | 3-methoxybenzyl-NH- | 73.4 | 4.25 | 510.37 |
| 1693 | biphenyl-2-yl | 3-(OCF3)benzyl-NH- | 75.0 | 4.83 | 555.27 |
| 1694 | biphenyl-2-yl | 3-F-benzyl-NH- | 44.5 | 4.39 | 489.30 |

-continued
| | | | | | |
|---|---|---|---|---|---|
| 1695 | 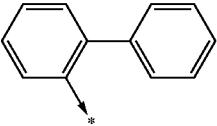 | 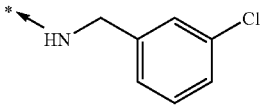 | 42.7 | 4.57 | 505.25 |
| 1696 | 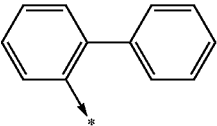 | 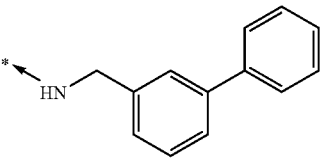 | 79.8 | 4.97 | 547.32 |
| 1697 | 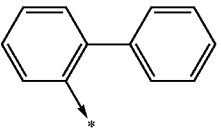 | 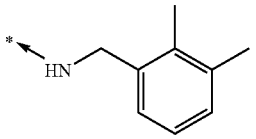 | 78.9 | 4.56 | 499.39 |
| 1698 | 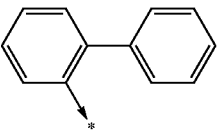 | 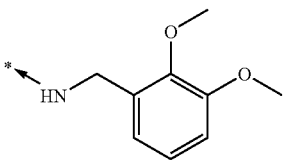 | 70.8 | 4.27 | 531.36 |
| 1699 | 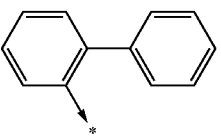 | 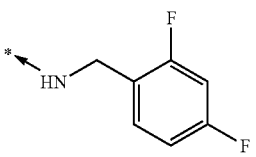 | 77.5 | 4.35 | 507.33 |
| 1700 | 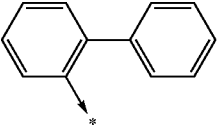 | 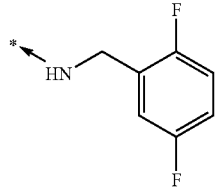 | 78.9 | 4.34 | 507.33 |
| 1701 | 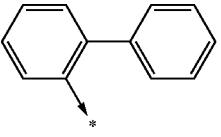 | 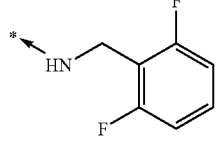 | 75.8 | 4.27 | 507.32 |
| 1702 | 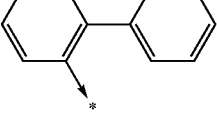 | 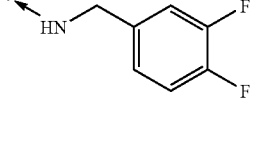 | 74.9 | 4.41 | 507.32 |
| 1703 | 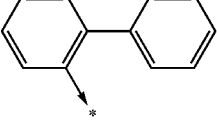 | 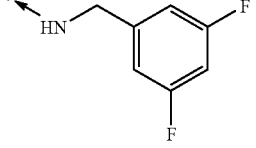 | 75.3 | 4.49 | 507.29 |

-continued

| 1704 | 2-biphenyl | 2,3-dichlorobenzylamine (HN-CH2-C6H3Cl2) | 73.5 | 4.75 | 539.22 |
| 1705 | 2-biphenyl | 1-naphthylmethylamine (HN-CH2-naphthyl) | 82.9 | 4.7 | 521.31 |

Core structure: H2N-CH2-CH2-C6H4-N=C(S-)(N-R1)-C(=O)-R5 (2-aminothiazole with 4-(2-aminoethyl)phenyl imino group)

| Ex. | R1 | R5 | Purity (%) | rt (min.) | [M + H]+ |
|---|---|---|---|---|---|
| 1706 | allyl (CH2-CH=CH2) | 4-phenylpiperazin-1-yl | 87.3 | 3.8 | 448.31 |
| 1707 | allyl | 4-(3-chlorophenyl)piperazin-1-yl | 86.0 | 4.3 | 482.24 |
| 1708 | allyl | N-methyl-N-(2-cyanoethyl)amino | 90.0 | 2.4 | 370.24 |
| 1709 | allyl | 3,3-dimethylbutylamino | 76.6 | 3.88 | 387.26 |
| 1710 | allyl | (pyridin-4-ylmethyl)amino | 53.2 | 3.0 | 394.2 |
| 1711 | allyl | 4-(pyridin-2-yl)piperazin-1-yl | 91.2 | 2.3 | 449.29 |
| 1712 | allyl | (naphth-1-ylmethyl)amino | 87.7 | 4.13 | 443.29 |
| 1713 | allyl | 1,2,3,4-tetrahydroisoquinolin-2-yl | 88.3 | 3.7 | 419.28 |

-continued

| # | R1 | R2 | a | b | c |
|---|---|---|---|---|---|
| 1714 | allyl | benzo[1,3]dioxol-5-ylmethyl-NH- | 70.8 | 3.5 | 437.25 |
| 1715 | allyl | benzhydryl-NH- | 87.0 | 4.4 | 469.30 |
| 1716 | allyl | 4-bromophenethyl-NH- | 82.5 | 4.12 | 485.20 |
| 1717 | allyl | 3-(2-oxopyrrolidin-1-yl)propyl-NH- | 88.1 | 2.59 | 428.29 |
| 1718 | allyl | 4-phenethyl-1,4-diazepan-1-yl- | 88.7 | 2.8 | 490.35 |
| 1719 | allyl | 3,5-bis(trifluoromethyl)benzyl-NH- | 79.0 | 4.68 | 529.23 |
| 1720 | allyl | cyclohexylmethyl-NH- | 78.0 | 3.94 | 399.29 |
| 1721 | 3-methoxypropyl | 4-phenylpiperazin-1-yl- | 87.4 | 3.7 | 480.32 |
| 1722 | 3-methoxypropyl | 4-(3-chlorophenyl)piperazin-1-yl- | 83.1 | 4.14 | 514.28 |
| 1723 | 3-methoxypropyl | (2-cyanoethyl)(methyl)amino- | 89.1 | 2.44 | 402.24 |

-continued

| # | R1 | R2 | % | t | MW |
|---|---|---|---|---|---|
| 1724 | methoxypropyl | 3,3-dimethylbutyl-NH- | 81.5 | 3.73 | 419.3 |
| 1725 | methoxypropyl | (pyridin-4-yl)methyl-N- | 56.1 | 3.0 | 416.2 |
| 1726 | methoxypropyl | 4-(pyridin-2-yl)piperazin-1-yl | 90.1 | 2.3 | 481.33 |
| 1727 | methoxypropyl | (naphthalen-1-yl)methyl-NH- | 87.3 | 3.96 | 475.31 |
| 1728 | methoxypropyl | 2-morpholinoethyl-NH- | 75.2 | 2.9 | 448.3 |
| 1729 | methoxypropyl | 1,2,3,4-tetrahydroisoquinolin-2-yl | 85.7 | 3.61 | 451.29 |
| 1730 | methoxypropyl | (benzo[d][1,3]dioxol-5-yl)methyl-NH- | 74.5 | 3.37 | 469.28 |
| 1731 | methoxypropyl | diphenylmethyl-NH- | 83.7 | 4.22 | 501.32 |
| 1732 | methoxypropyl | 2-(4-bromophenyl)ethyl-NH- | 86.7 | 3.95 | 517.20 |
| 1733 | methoxypropyl | 3-(2-oxopyrrolidin-1-yl)propyl-NH- | 80.6 | 2.61 | 460.32 |
| 1734 | methoxypropyl | 4-phenethyl-1,4-diazepan-1-yl | 80.8 | 2.8 | 522.35 |

-continued

| # | R1 | R2 | % | t | M |
|---|---|---|---|---|---|
| 1735 | methoxypropyl-* | 3,5-bis(trifluoromethyl)benzyl-NH-* | 74.0 | 4.48 | 561.23 |
| 1736 | methoxypropyl-* | cyclohexylmethyl-NH-* | 81.2 | 3.8 | 431.31 |
| 1737 | 4-chlorophenethyl-* | 4-phenylpiperazin-1-yl-* | 87.1 | 4.76 | 546.27 |
| 1738 | 4-chlorophenethyl-* | 4-(3-chlorophenyl)piperazin-1-yl-* | 85.5 | 5.16 | 580.24 |
| 1739 | 4-chlorophenethyl-* | 2-cyanoethyl(methyl)amino-* | 85.5 | 3.72 | 468.24 |
| 1740 | 4-chlorophenethyl-* | 3,3-dimethylbutyl-NH-* | 82.1 | 4.74 | 485.29 |
| 1741 | 4-chlorophenethyl-* | pyridin-4-ylmethyl-NH-* | 80.7 | 3.04 | 492.24 |
| 1742 | 4-chlorophenethyl-* | 4-(pyridin-2-yl)piperazin-1-yl-* | 87.7 | 3.4 | 547.28 |
| 1743 | 4-chlorophenethyl-* | naphthalen-1-ylmethyl-NH-* | 81.9 | 4.96 | 541.23 |
| 1744 | 4-chlorophenethyl-* | 2-morpholinoethyl-NH-* | 55.2 | 2.9 | 514.27 |
| 1745 | 4-chlorophenethyl-* | 3,4-dihydroisoquinolin-2(1H)-yl-* | 87.2 | 4.7 | 517.25 |

| | | | | | |
|---|---|---|---|---|---|
| 1746 | 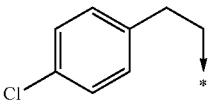 | 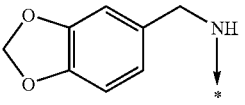 | 73.7 | 4.39 | 535.21 |
| 1747 | 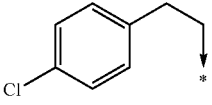 | 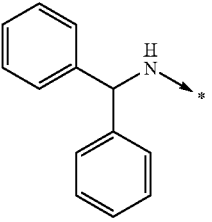 | 84.3 | 5.22 | 567.25 |
| 1748 | 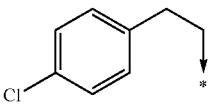 | 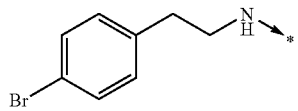 | 74.7 | 4.9 | 583.16 |
| 1749 | 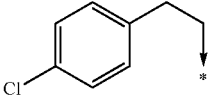 | 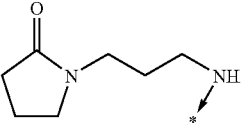 | 76.8 | 3.53 | 526.28 |
| 1750 | 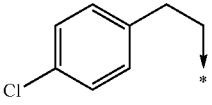 | 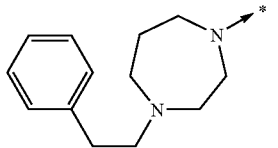 | 84.3 | 3.7 | 588.34 |
| 1751 | 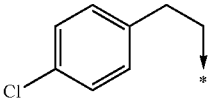 | 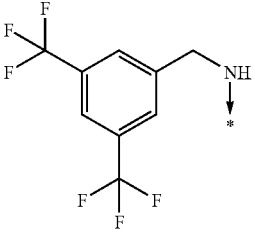 | 74.4 | 5.41 | 627.20 |
| 1752 | 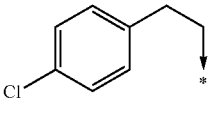 | 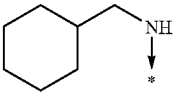 | 80.9 | 4.88 | 497.31 |
| 1753 | 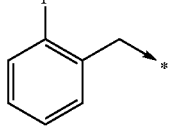 | 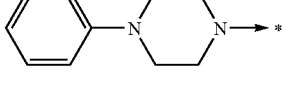 | 83.4 | 4.53 | 516.2 |
| 1754 | 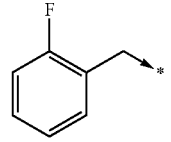 | 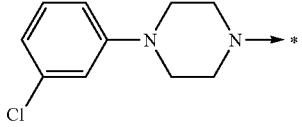 | 83.2 | 4.96 | 550.24 |

-continued

| # | R1 | R2 | a | b | c |
|---|---|---|---|---|---|
| 1755 | 2-F-benzyl | N≡C-CH2CH2-N(H)(CH3)- | 84.1 | 3.39 | 438.25 |
| 1756 | 2-F-benzyl | (CH3)3C-CH2CH2-NH- | 84.7 | 4.71 | 455.28 |
| 1757 | 2-F-benzyl | 4-pyridyl-CH2-NH- | 56.6 | 2.8 | 462.24 |
| 1758 | 2-F-benzyl | 4-(2-pyridyl)piperazin-1-yl | 85.0 | 3.0 | 517.30 |
| 1759 | 2-F-benzyl | 1-naphthyl-CH2-NH- | 84.6 | 4.9 | 511.26 |
| 1760 | 2-F-benzyl | morpholino-CH2CH2-NH- | 82.1 | 2.8 | 484.3 |
| 1761 | 2-F-benzyl | 1,2,3,4-tetrahydroisoquinolin-2-yl | 84.4 | 4.44 | 487.27 |
| 1762 | 2-F-benzyl | 1,3-benzodioxol-5-yl-CH2-NH- | 52.0 | 4.3 | 505.23 |
| 1763 | 2-F-benzyl | (Ph)2CH-NH- | 84.5 | 5.12 | 537.28 |

-continued
| | | | | | |
|---|---|---|---|---|---|
| 1764 | 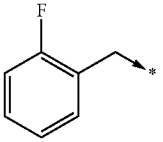 | 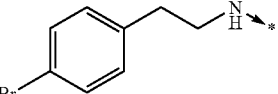 | 81.5 | 4.93 | 553.17 |
| 1765 | 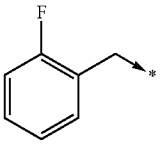 | 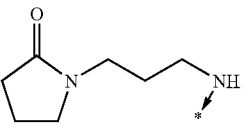 | 80.2 | 3.34 | 496.29 |
| 1766 | 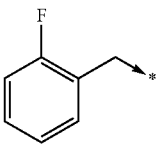 | 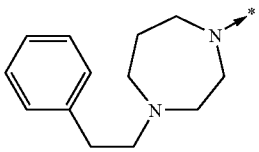 | 85.9 | 3.5 | 558.31 |
| 1767 | 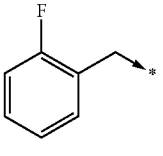 | 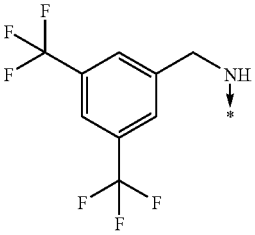 | 53.4 | 5.39 | 597.22 |
| 1768 | 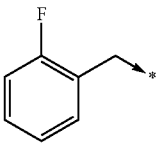 | 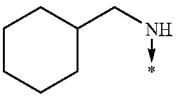 | 81.6 | 4.81 | 467.29 |
| 1769 | 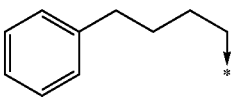 | 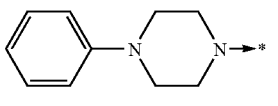 | 83.5 | 3.5 | 540.32 |
| 1770 | 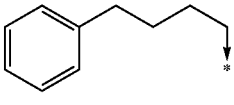 | 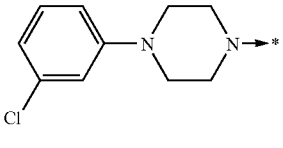 | 82.4 | 5.01 | 574.27 |
| 1771 | 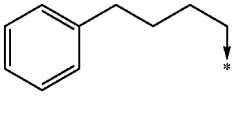 | 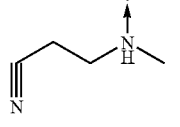 | 80.9 | 3.72 | 462.30 |
| 1772 | 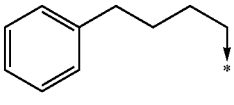 | 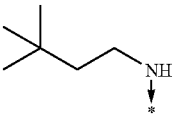 | 77.9 | 4.78 | 479.36 |
| 1773 | 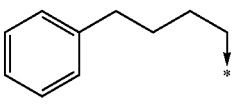 | 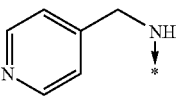 | 79.3 | 3.11 | 486.32 |

-continued

| # | R1 | R2 | a | b | c |
|---|---|---|---|---|---|
| 1774 | PhCH2CH2CH2CH2-* | 2-pyridyl-piperazine-N-* | 85.0 | 3.4 | 541.35 |
| 1775 | PhCH2CH2CH2CH2-* | naphthalen-1-yl-CH2-NH-* | 85.3 | 4.9 | 535.31 |
| 1776 | PhCH2CH2CH2CH2-* | morpholine-N-CH2CH2-NH-* | 74.9 | 3.0 | 508.34 |
| 1777 | PhCH2CH2CH2CH2-* | 1,2,3,4-tetrahydroisoquinolin-2-yl-* | 83.9 | 4.58 | 511.33 |
| 1778 | PhCH2CH2CH2CH2-* | benzo[1,3]dioxol-5-yl-CH2-NH-* | 69.1 | 4.4 | 529.3 |
| 1779 | PhCH2CH2CH2CH2-* | Ph2CH-NH-* | 83.1 | 5.1 | 561.3 |
| 1780 | PhCH2CH2CH2CH2-* | 4-Br-C6H4-CH2CH2-NH-* | 81.8 | 4.9 | 577.23 |
| 1781 | PhCH2CH2CH2CH2-* | 2-oxo-pyrrolidin-1-yl-CH2CH2CH2-NH-* | 83.6 | 3.64 | 520.34 |
| 1782 | PhCH2CH2CH2CH2-* | 4-phenethyl-[1,4]diazepan-1-yl-* | 80.9 | 3.7 | 582.4 |
| 1783 | PhCH2CH2CH2CH2-* | 3,5-bis(trifluoromethyl)benzyl-NH-* | 68.0 | 5.34 | 621.28 |

-continued
| Ex. | R1 | R5 | Purity (%) | rt (min.) | [M + H]+ |
|---|---|---|---|---|---|
| 1784 | 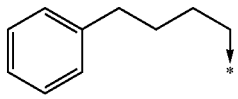 | 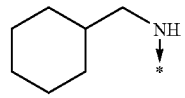 | 76.3 | 4.85 | 491.36 |
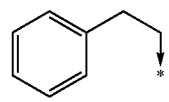
| Ex. | R1 | R5 | Purity (%) | rt (min.) | [M + H]+ |
|---|---|---|---|---|---|
| 1785 | 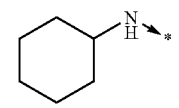 | 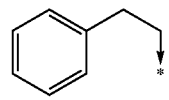 | 77.9 | 4.44 | 435.25 |
| 1786 | 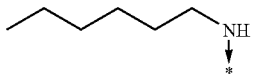 | 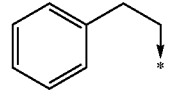 | 78.8 | 4.83 | 437.30 |
| 1787 | 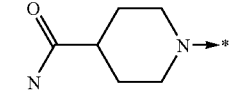 | 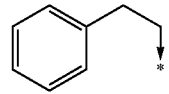 | 79.5 | 3.13 | 464.27 |
| 1788 | 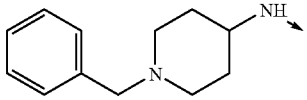 | 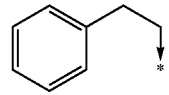 | 80.3 | 3.28 | 526.38 |
| 1789 | 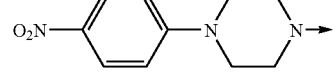 | 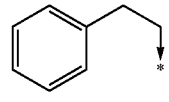 | 86.6 | 4.67 | 543.32 |
| 1790 | 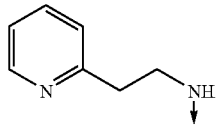 | 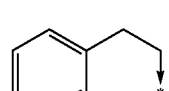 | 74.8 | 2.9 | 458.32 |
| 1791 | 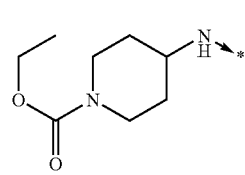 | 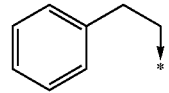 | 81.7 | 3.99 | 508.34 |
| 1792 | 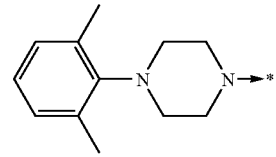 | 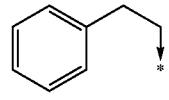 | 86.9 | 5.41 | 526.38 |
| 1793 | 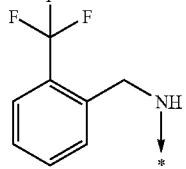 | | 86.4 | 4.85 | 511.27 |

-continued
| | | | | | |
|---|---|---|---|---|---|
| 1794 | 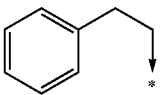 | 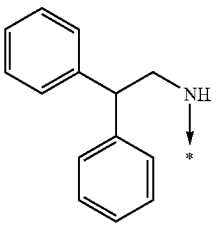 | 82.2 | 5.07 | 533.35 |
| 1795 | 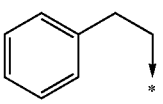 | 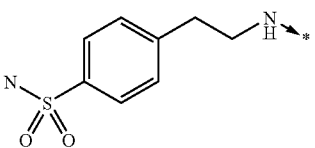 | 83.1 | 3.55 | 536.28 |
| 1796 | 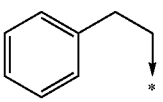 | 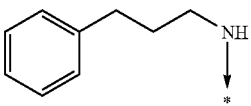 | 82.3 | 4.66 | 471.3 |
| 1797 | 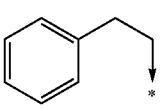 | 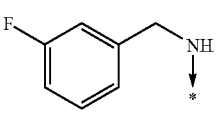 | 86.3 | 4.41 | 461.31 |
| 1798 | 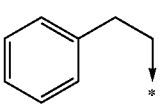 | 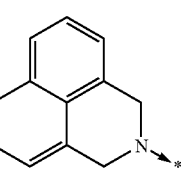 | 85.1 | 4.95 | 505.33 |
| 1799 | 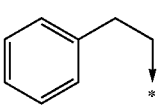 | 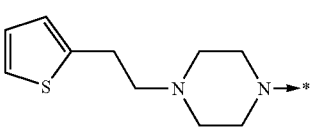 | 76.0 | 3.5 | 532.3 |
| 1800 | 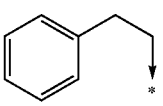 | 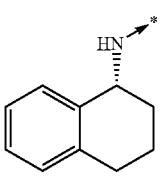 | 81.1 | 4.87 | 483.34 |
| 1801 | 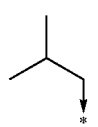 | 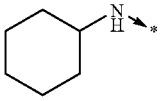 | 68.62 | 3.96 | 387.33 |
| 1802 | 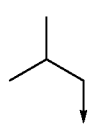 | 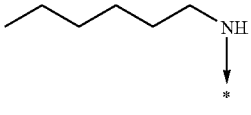 | 73.4 | 4.39 | 389.33 |
| 1803 | 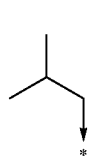 | 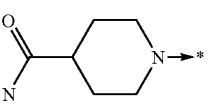 | 81.2 | 2.57 | 416.32 |

-continued
| | | | | | |
|---|---|---|---|---|---|
| 1804 | 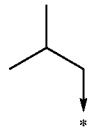 | 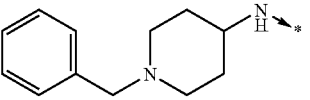 | 79.2 | 2.9 | 478.3 |
| 1805 | 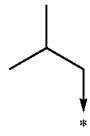 | 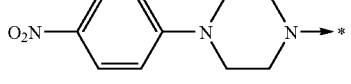 | 83.2 | 4.26 | 495.34 |
| 1806 | 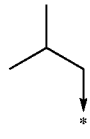 | 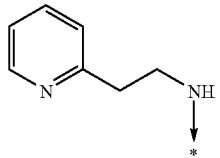 | 70.2 | 2.5 | 410.3 |
| 1807 | 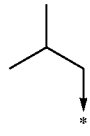 | 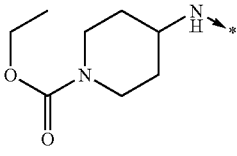 | 73.3 | 3.6 | 460.37 |
| 1808 | 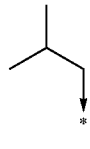 | 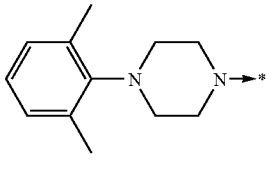 | 75.0 | 5.01 | 478.39 |
| 1809 | 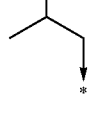 | 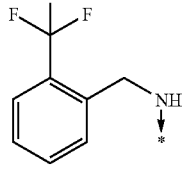 | 70.3 | 4.45 | 463.31 |
| 1810 | 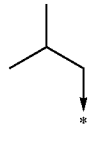 | 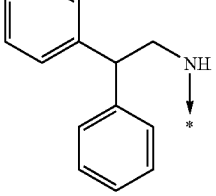 | 83.9 | 4.73 | 485.37 |
| 1811 | 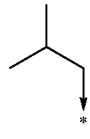 | 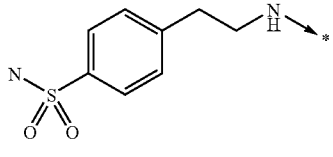 | 76.5 | 3.14 | 488.31 |
| 1812 | 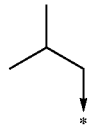 | 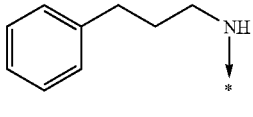 | 79.1 | 4.28 | 423.35 |

-continued

| # | R1 | R2 | % | t | m/z |
|---|---|---|---|---|---|
| 1813 | isobutyl-* | 3-fluorobenzyl-NH-* | 79.2 | 3.99 | 413.29 |
| 1814 | isobutyl-* | 2,3-dihydro-1H-benzo[de]isoquinolin-2-yl-* | 75.5 | 4.55 | 457.33 |
| 1815 | isobutyl-* | 4-(2-(thiophen-2-yl)ethyl)piperazin-1-yl-* | 67.7 | 3.1 | 484.3 |
| 1816 | isobutyl-* | (1S)-1,2,3,4-tetrahydronaphthalen-1-ylamino-* | 62.7 | 4.44 | 435.33 |
| 1817 | naphthalen-1-ylmethyl-* | cyclohexyl-NH-* | 85.7 | 5.02 | 471.33 |
| 1818 | naphthalen-1-ylmethyl-* | pentyl-NH-* | 70.2 | 5.31 | 473.37 |
| 1819 | naphthalen-1-ylmethyl-* | 4-carbamoylpiperidin-1-yl-* | 86.6 | 3.59 | 500.35 |
| 1820 | naphthalen-1-ylmethyl-* | 1-benzylpiperidin-4-ylamino-* | 83.8 | 3.7 | 562.4 |
| 1821 | naphthalen-1-ylmethyl-* | 4-(4-nitrophenyl)piperazin-1-yl-* | 88.5 | 5.04 | 579.32 |

-continued

| | 601 | 602 | | | |
|---|---|---|---|---|---|
| 1822 | naphthalen-1-ylmethyl* | 2-(pyridin-2-yl)ethyl-NH-* | 39.8 | 3.3 | 494.3 |
| 1823 | naphthalen-1-ylmethyl* | ethyl 4-amino-piperidine-1-carboxylate-* | 85.8 | 4.55 | 544.33 |
| 1824 | naphthalen-1-ylmethyl* | 4-(2,6-dimethylphenyl)piperazin-1-yl-* | 86.4 | 5.78 | 562.36 |
| 1825 | naphthalen-1-ylmethyl* | 2-(trifluoromethyl)benzyl-NH-* | 84.3 | 5.27 | 547.25 |
| 1826 | naphthalen-1-ylmethyl* | 2,2-diphenylethyl-NH-* | 69.7 | 5.58 | 569.32 |
| 1827 | naphthalen-1-ylmethyl* | 4-(aminosulfonyl)phenethyl-NH-* | 70.3 | 4.17 | 572.27 |
| 1828 | naphthalen-1-ylmethyl* | 3-phenylpropyl-NH-* | 85.4 | 5.17 | 507.34 |
| 1829 | naphthalen-1-ylmethyl* | 3-fluorobenzyl-NH-* | 82.3 | 4.91 | 497.28 |

|   | 603 | 604 |   |   |
|---|---|---|---|---|
| 1830 | 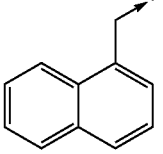 | 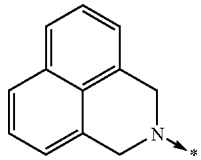 | 82.4 | 5.41 | 541.29 |
| 1831 | 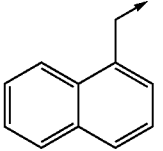 | 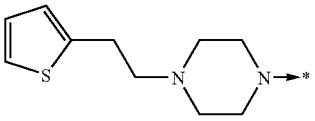 | 79.4 | 3.8 | 568.3 |
| 1832 | 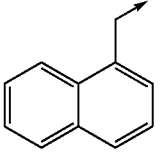 | 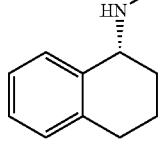 | 86.9 | 5.31 | 519.33 |
| 1833 | 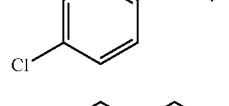 | 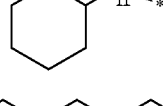 | 86.3 | 4.99 | 455.27 |
| 1834 | 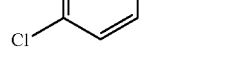 | 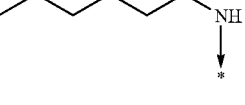 | 84.5 | 5.3 | 457.30 |
| 1835 | 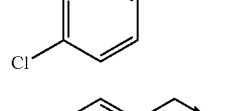 | 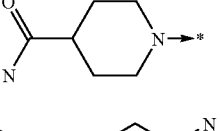 | 88.3 | 3.42 | 484.27 |
| 1836 | 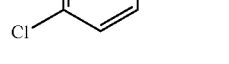 | 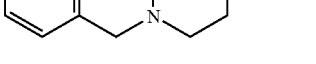 | 83.6 | 3.65 | 546.29 |
| 1837 | 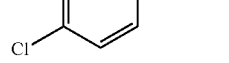 |  | 88.8 | 4.91 | 563.24 |
| 1838 | 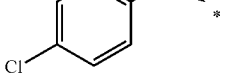 | 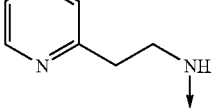 | 65.2 | 3.3 | 478.24 |
| 1839 | 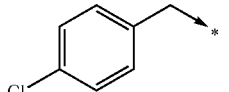 | 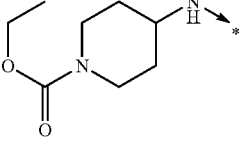 | 87.6 | 4.5 | 528.30 |
| 1840 | 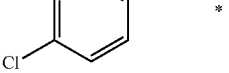 | 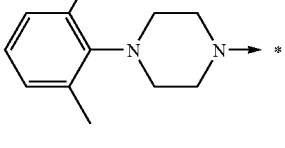 | 90.4 | 5.68 | 546.30 |

-continued

| | | | | | |
|---|---|---|---|---|---|
| 1841 | 4-Cl-C6H4-CH2-* | 2-(CF3)-C6H4-CH2-NH-* | 82.8 | 5.31 | 521.23 |
| 1842 | 4-Cl-C6H4-CH2-* | (Ph)2CH-CH2-NH-* | 68.2 | 5.57 | 553.28 |
| 1843 | 4-Cl-C6H4-CH2-* | 4-(H2N-SO2)-C6H4-CH2CH2-NH-* | 72.4 | 4.11 | 556.21 |
| 1844 | 4-Cl-C6H4-CH2-* | Ph-CH2CH2CH2-NH-* | 83.9 | 5.15 | 491.29 |
| 1845 | 4-Cl-C6H4-CH2-* | 3-F-C6H4-CH2-NH-* | 86.4 | 4.93 | 481.27 |
| 1846 | 4-Cl-C6H4-CH2-* | 2,3-dihydro-1H-benzo[de]isoquinolin-2-yl-* | 86.3 | 5.29 | 525.25 |
| 1847 | 4-Cl-C6H4-CH2-* | 4-(2-(thiophen-2-yl)ethyl)piperazin-1-yl-* | 82.6 | 3.7 | 552.3 |
| 1848 | 4-Cl-C6H4-CH2-* | (1S)-1,2,3,4-tetrahydronaphthalen-1-yl-NH-* | 88.1 | 5.3 | 503.29 |
| 1849 | 2-OMe-C6H4-CH2-* | cyclohexyl-NH-* | 82.9 | 4.25 | 451.32 |

-continued
| | | | | | |
|---|---|---|---|---|---|
| 1850 | 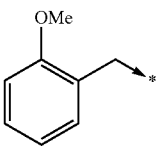 | 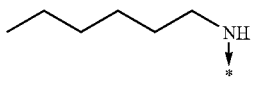 | 82.1 | 4.64 | 453.35 |
| 1851 | 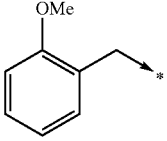 | 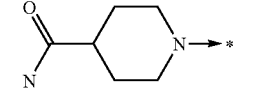 | 85.6 | 2.72 | 480.33 |
| 1852 | 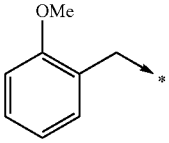 | 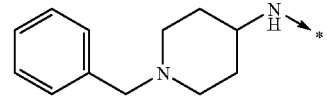 | 82.9 | 3.16 | 542.35 |
| 1853 | 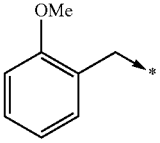 | 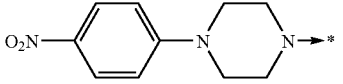 | 87.7 | 4.28 | 559.29 |
| 1854 | 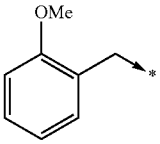 | 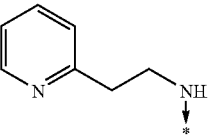 | 75.3 | 2.82 | 474.33 |
| 1855 | 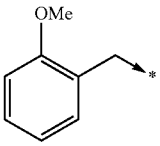 | 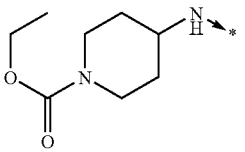 | 84.4 | 3.83 | 524.32 |
| 1856 | 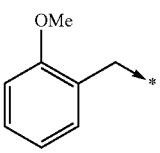 | 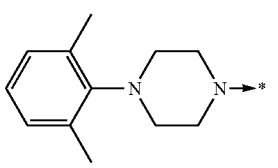 | 87.0 | 5.0 | 542.36 |
| 1857 | 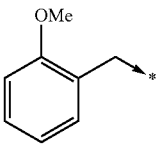 | 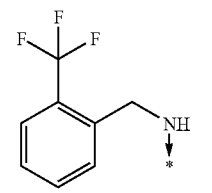 | 82.6 | 4.73 | 527.28 |
| 1858 | 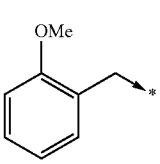 | 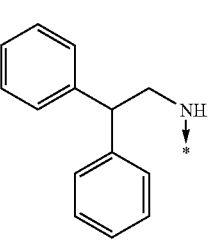 | 65.8 | 5.01 | 549.31 |

| Ex. | R1 | R5 | Purity (%) | rt (min.) | [M + H]+ |
|---|---|---|---|---|---|
| 1859 | 2-OMe-benzyl | 4-(sulfamoyl)phenethylamine | 76.4 | 3.49 | 552.26 |
| 1860 | 2-OMe-benzyl | 3-phenylpropylamine | 80.4 | 4.54 | 487.35 |
| 1861 | 2-OMe-benzyl | 3-fluorobenzylamine | 81.3 | 4.28 | 477.30 |
| 1862 | 2-OMe-benzyl | 2,3-dihydro-1H-benz[de]isoquinoline | 79.9 | 4.59 | 521.29 |
| 1863 | 2-OMe-benzyl | 1-(2-thiophen-2-yl-ethyl)piperazine | 77.5 | 3.2 | 548.3 |
| 1864 | 2-OMe-benzyl | 1,2,3,4-tetrahydronaphthalen-1-ylamine | 86.5 | 4.65 | 499.32 |
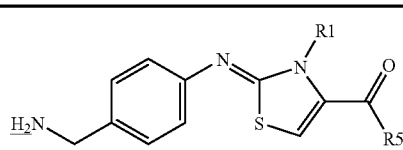
| Ex. | R1 | R5 | Purity (%) | rt (min.) | [M + H]+ |
|---|---|---|---|---|---|
| 1865 | benzyl | cycloheptylamine | 84.7 | 4.94 | 435.29 |
| 1866 | benzyl | phenethylamine | 85.0 | 4.66 | 443.26 |
| 1867 | benzyl | 2,3,4,9-tetrahydro-1H-β-carboline | 26.2 | 4.82 | 494.26 |

-continued

| | 611 | 612 | | | |
|---|---|---|---|---|---|
| 1868 | benzyl-* | 4-(4-fluorophenyl)piperazin-1-yl-* | 88.4 | 4.8 | 502.28 |
| 1869 | benzyl-* | dibenzylamino-* | 83.6 | 5.48 | 519.28 |
| 1870 | benzyl-* | dibutylamino-* | 63.17 | 5.3 | 451.33 |
| 1871 | benzyl-* | 4-(benzo[d][1,3]dioxol-5-ylmethyl)piperazin-1-yl-* | 91.1 | 3.4 | 542.3 |
| 1872 | benzyl-* | (thiophen-2-ylmethyl)amino-* | 35.7 | 4.48 | 435.20 |
| 1873 | benzyl-* | 4-(furan-2-carbonyl)piperazin-1-yl-* | 88.8 | 3.8 | 502.26 |
| 1874 | benzyl-* | (3,3-diphenylpropyl)amino-* | 87.1 | 5.41 | 533.29 |
| 1875 | benzyl-* | (3-(trifluoromethoxy)benzyl)amino-* | 89.5 | 5.14 | 513.22 |
| 1876 | benzyl-* | (2,3-dihydro-1H-inden-2-yl)amino-* | 47.8 | 4.82 | 455.24 |
| 1877 | benzyl-* | (4-phenoxybenzyl)amino-* | 77.1 | 5.32 | 521.24 |

-continued

| # | R1 | R2 | % | a | MW |
|---|---|---|---|---|---|
| 1878 | benzyl-* | 2-phenylbenzyl-NH-* | 81.8 | 5.31 | 505.26 |
| 1879 | benzyl-* | isobutyl-NH-* | 19.7 | 4.37 | 395.24 |
| 1880 | benzyl-* | 2-(3-trifluoromethylphenyl)ethyl-NH-* | 61.4 | 5.14 | 511.22 |
| 1881 | 3-phenylpropyl-* | cycloheptyl-NH-* | 82.7 | 4.95 | 463.31 |
| 1882 | 3-phenylpropyl-* | phenethyl-NH-* | 82.2 | 4.71 | 471.27 |
| 1883 | 3-phenylpropyl-* | 1,2,3,4-tetrahydro-β-carbolin-2-yl-* | 67.2 | 4.84 | 522.26 |
| 1884 | 3-phenylpropyl-* | 4-(4-fluorophenyl)piperazin-1-yl-* | 87.7 | 4.9 | 530.28 |
| 1885 | 3-phenylpropyl-* | dibenzylamino-* | 79.4 | 5.54 | 547.28 |
| 1886 | 3-phenylpropyl-* | dibutylamino-* | 80.8 | 5.3 | 479.34 |
| 1887 | 3-phenylpropyl-* | 4-(benzo[1,3]dioxol-5-ylmethyl)piperazin-1-yl-* | 88.9 | 3.6 | 570.24 |

-continued
| | | | | | |
|---|---|---|---|---|---|
| 1888 | 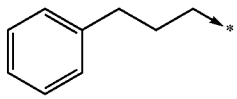 | 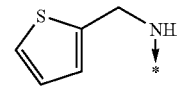 | 30.2 | 4.53 | 463.23 |
| 1889 | 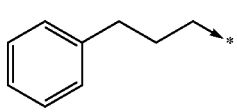 | 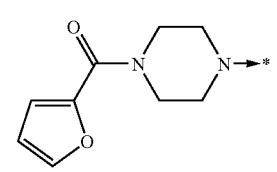 | 88.9 | 3.98 | 530.26 |
| 1890 | 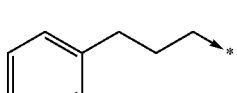 | 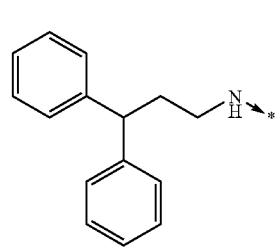 | 84.2 | 5.42 | 561.30 |
| 1891 | 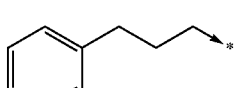 | 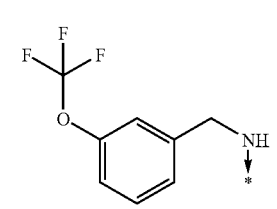 | 75.8 | 5.17 | 541.22 |
| 1892 | 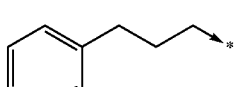 | 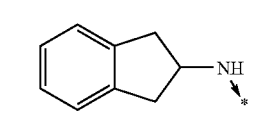 | 85.8 | 4.86 | 483.28 |
| 1893 | 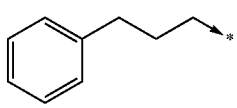 | 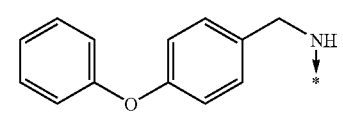 | 71.7 | 5.33 | 549.26 |
| 1894 | 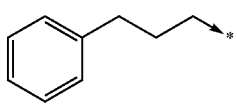 | 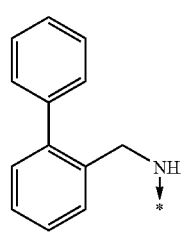 | 86.6 | 5.34 | 533.29 |
| 1895 | 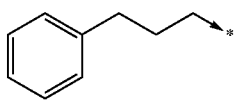 | 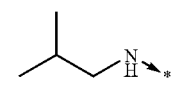 | 54.1 | 4.43 | 423.28 |
| 1896 | 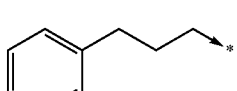 | 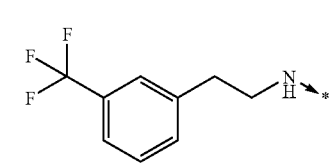 | 47.7 | 5.16 | 539.26 |
| 1897 | 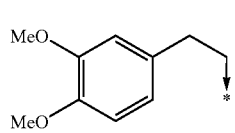 | 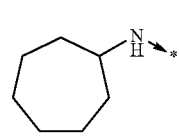 | 74.6 | 4.44 | 509.30 |

-continued
| | | | | | |
|---|---|---|---|---|---|
| 1898 | 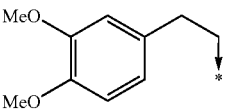 | 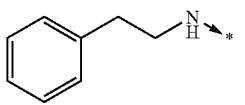 | 77.6 | 4.2 | 517.27 |
| 1899 | 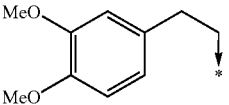 | 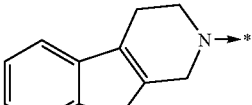 | 38.8 | 4.53 | 568.26 |
| 1900 | 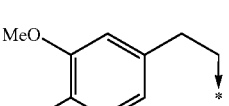 | 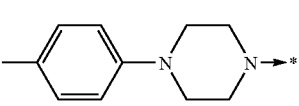 | 80.1 | 4.5 | 576.3 |
| 1901 | 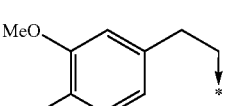 | 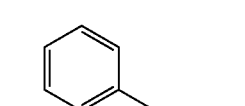 | 72.3 | 5.17 | 593.30 |
| 1902 | 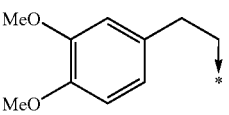 | 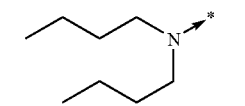 | 77.0 | 4.88 | 525.34 |
| 1903 | 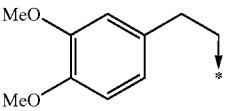 | 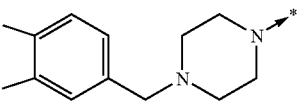 | 80.5 | 3.3 | 616.3 |
| 1904 | 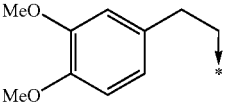 | 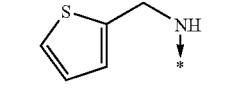 | 34.6 | 4.03 | 509.21 |
| 1905 | 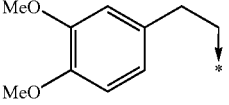 | 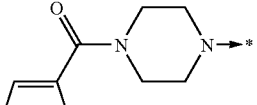 | 81.3 | 3.6 | 576.2 |
| 1906 | 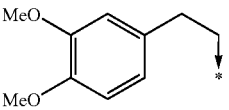 | 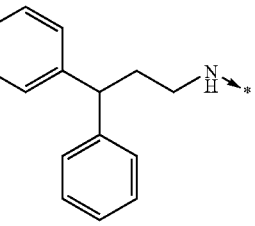 | 77.1 | 5.04 | 607.31 |

-continued

| | | | | | |
|---|---|---|---|---|---|
| 1907 | 3,4-dimethoxyphenethyl | 3-(trifluoromethoxy)benzyl-NH- | 79.6 | 4.76 | 587.24 |
| 1908 | 3,4-dimethoxyphenethyl | indan-2-yl-NH- | 77.8 | 4.38 | 529.28 |
| 1909 | 3,4-dimethoxyphenethyl | 4-phenoxybenzyl-NH- | 78.0 | 4.95 | 595.28 |
| 1910 | 3,4-dimethoxyphenethyl | 2-biphenylmethyl-NH- | 81.1 | 4.88 | 579.29 |
| 1911 | 3,4-dimethoxyphenethyl | isobutyl-NH- | 32.4 | 3.89 | 469.29 |
| 1912 | 3,4-dimethoxyphenethyl | 3-(trifluoromethyl)phenethyl-NH- | 49.3 | 4.7 | 585.26 |
| 1913 | 2,4-dichlorobenzyl | cycloheptyl-NH- | 87.0 | 5.59 | 503.20 |
| 1914 | 2,4-dichlorobenzyl | phenethyl-NH- | 88.5 | 5.3 | 511.15 |
| 1915 | 2,4-dichlorobenzyl | 1,2,3,4-tetrahydro-β-carbolin-2-yl | 69.5 | 5.28 | 562.16 |
| 1916 | 2,4-dichlorobenzyl | 4-(4-fluorophenyl)piperazin-1-yl | 89.4 | 5.3 | 570.1 |

| | 621 | 622 | | | |
|---|---|---|---|---|---|
| 1917 | 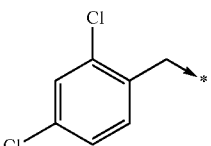 | 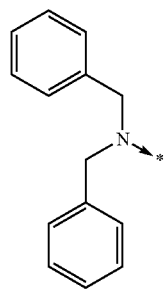 | 79.1 | 5.98 | 587.17 |
| 1918 | 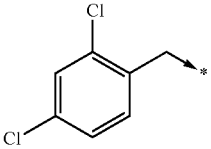 | 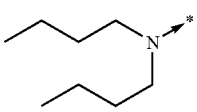 | 82.4 | 5.84 | 519.23 |
| 1919 | 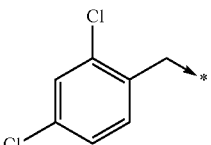 | 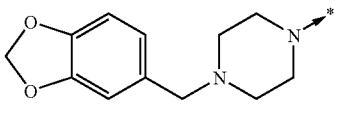 | 89.5 | 3.9 | 610.1 |
| 1920 | 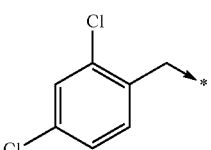 | 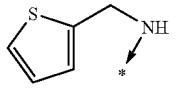 | 27.2 | 5.12 | 503.11 |
| 1921 | 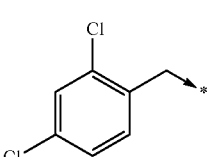 | 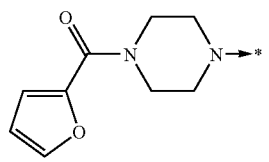 | 88.6 | 4.41 | 570.13 |
| 1922 | 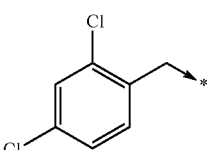 | 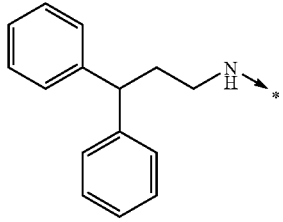 | 86.4 | 5.91 | 601.19 |
| 1923 | 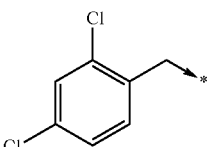 | 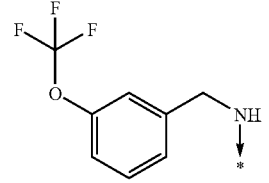 | 84.9 | 5.66 | 581.11 |
| 1924 | 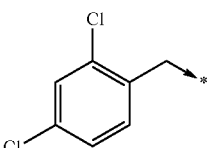 | 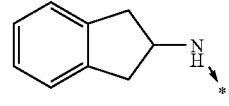 | 86.4 | 5.44 | 523.13 |

-continued
| | | | | | |
|---|---|---|---|---|---|
| 1925 | 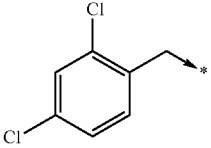 | 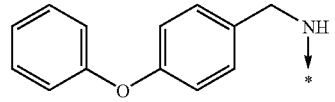 | 61.9 | 5.81 | 589.16 |
| 1926 | 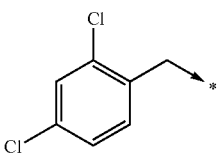 | 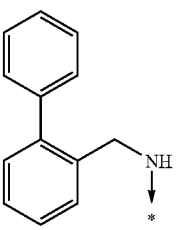 | 84.7 | 5.85 | 573.15 |
| 1927 | 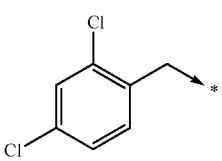 | 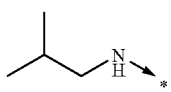 | 36.8 | 5.1 | 463.16 |
| 1928 | 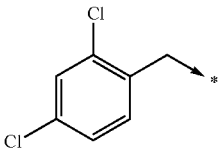 | 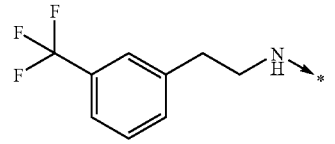 | 76.4 | 5.68 | 579.13 |
| 1929 | 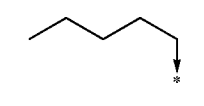 | 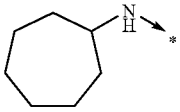 | 79.4 | 4.65 | 415.30 |
| 1930 | 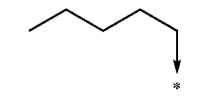 | 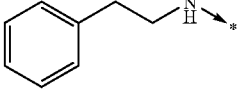 | 84.5 | 4.41 | 423.29 |
| 1931 | 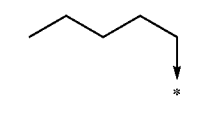 | 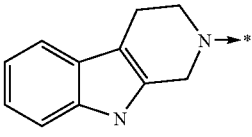 | 44.0 | 4.62 | 474.29 |
| 1932 | 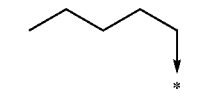 | 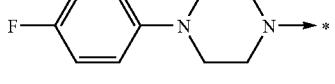 | 86.1 | 4.65 | 482.3 |
| 1933 | 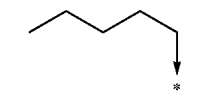 | 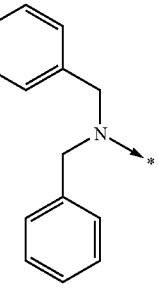 | 78.5 | 5.33 | 499.31 |

-continued
| | | | | | |
|---|---|---|---|---|---|
| 1934 | 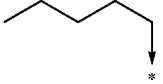 | 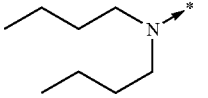 | 79.6 | 5.06 | 431.33 |
| 1935 | 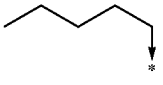 | 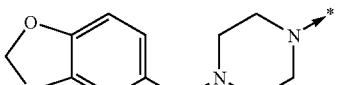 | 84.6 | 3.4 | 522.30 |
| 1936 | 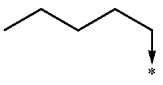 | 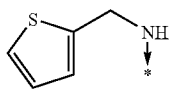 | 54.6 | 4.2 | 415.21 |
| 1937 | 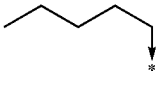 | 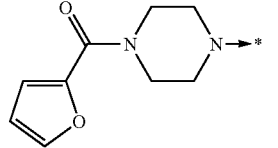 | 85.4 | 3.7 | 482.29 |
| 1938 | 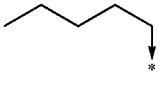 | 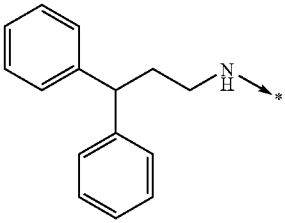 | 83.5 | 5.21 | 513.32 |
| 1939 | 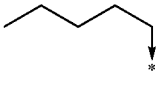 | 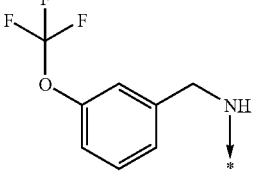 | 85.7 | 4.92 | 493.24 |
| 1940 | 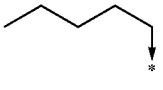 | 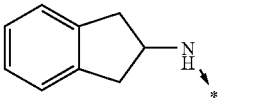 | 83.0 | 4.58 | 435.29 |
| 1941 | 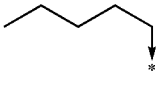 | 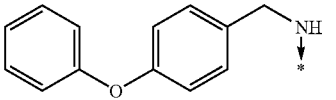 | 75.1 | 5.1 | 501.31 |
| 1942 | 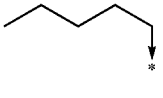 | 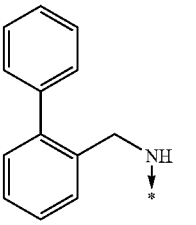 | 88.2 | 5.1 | 485.31 |
| 1943 | 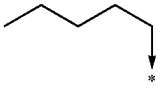 | 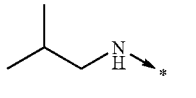 | 76.1 | 4.08 | 375.28 |

-continued
| Ex. | R1 | R5 | Purity (%) | rt (min.) | [M + H]+ |
|---|---|---|---|---|---|
| 1944 | 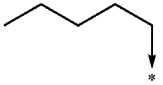 | 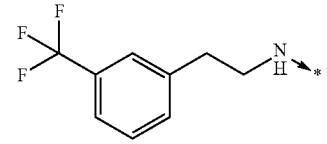 | 81.1 | 4.9 | 491.28 |
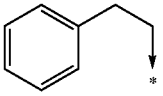
| Ex. | R1 | R5 | Purity (%) | rt (min.) | [M + H]+ |
|---|---|---|---|---|---|
| 1945 | 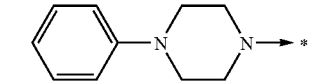 | 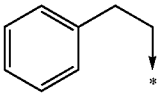 | 84.3 | 4.24 | 512.26 |
| 1946 | 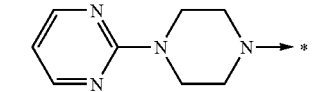 | 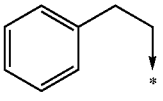 | 85.4 | 3.63 | 514.25 |
| 1947 | 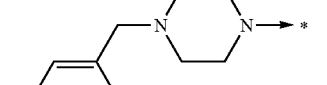 | 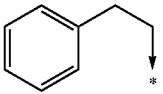 | 86.8 | 3.1 | 526.27 |
| 1948 | 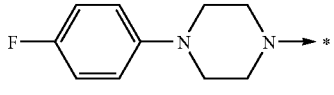 | 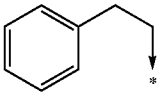 | 87.7 | 4.32 | 530.23 |
| 1949 | 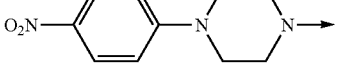 | 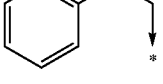 | 87.5 | 4.24 | 557.23 |
| 1950 | 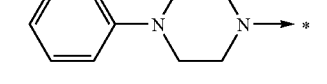 |  | 88.8 | 2.9 | 513.26 |
| 1951 | 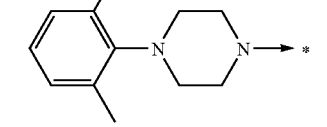 | 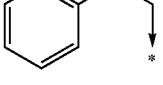 | 84.5 | 4.92 | 540.28 |
| 1952 | 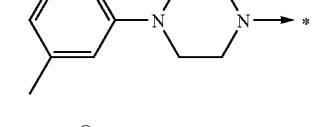 | 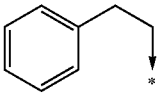 | 87.7 | 4.49 | 526.27 |
| 1953 | 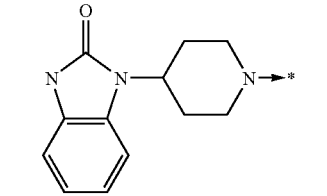 | | 62.5 | 3.66 | 567.26 |

-continued

| | | | | | |
|---|---|---|---|---|---|
| 1954 | PhCH2CH2-* | 4-MeO-C6H4-piperazine-* | 89 | 4.08 | 542.26 |
| 1955 | PhCH2CH2-* | 2-F-C6H4-piperazine-* | 87.7 | 4.38 | 530.24 |
| 1956 | PhCH2CH2-* | 4-pyridyl-piperazine-* | 82.4 | 2.7 | 513.28 |
| 1957 | PhCH2CH2-* | 2-NO2-C6H4-piperazine-* | 87.7 | 4.31 | 557.23 |
| 1958 | PhCH2CH2-* | 2-EtO-C6H4-piperazine-* | 91.0 | 4.44 | 556.27 |
| 1959 | PhCH2CH2-* | 2-pyrazinyl-piperazine-* | 80.7 | 3.44 | 514.25 |
| 1960 | PhCH2CH2-* | spiro[indene-piperidine]-* | 68.6 | 4.67 | 535.24 |
| 1961 | PhCH2CH2CH2-* | phenyl-piperazine-* | 85.3 | 4.32 | 526.27 |
| 1962 | PhCH2CH2CH2-* | 2-pyrimidinyl-piperazine-* | 83.0 | 3.75 | 528.25 |
| 1963 | PhCH2CH2CH2-* | benzyl-piperazine-* | 88.7 | 3.28 | 540.28 |
| 1964 | PhCH2CH2CH2-* | 4-F-C6H4-piperazine-* | 86.8 | 4.37 | 544.25 |
| 1965 | PhCH2CH2CH2-* | 4-NO2-C6H4-piperazine-* | 89.4 | 4.29 | 571.24 |

-continued
| | 631 | 632 | | | |
|---|---|---|---|---|---|
| 1966 |  | 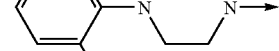 | 86.9 | 3.1 | 527.25 |
| 1967 |  |  | 86.1 | 4.94 | 554.29 |
| 1968 |  | 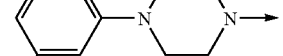 | 87.6 | 4.54 | 540.27 |
| 1969 |  |  | 65.4 | 3.76 | 581.27 |
| 1970 | 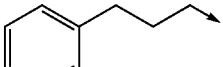 |  | 86.3 | 4.16 | 556.28 |
| 1971 |  | 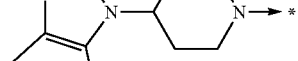 | 86.0 | 4.43 | 544.25 |
| 1972 |  |  | 83.2 | 2.8 | 527.3 |
| 1973 | 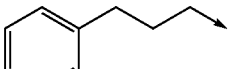 | 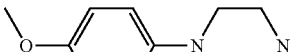 | 84.8 | 4.38 | 571.24 |
| 1974 |  |  | 87.8 | 4.5 | 570.28 |
| 1975 | 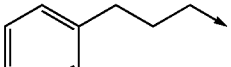 | 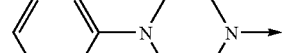 | 80.9 | 3.55 | 528.26 |
| 1976 |  |  | 62.7 | 4.71 | 549.27 |

-continued

| # | R1 | R2 | a | b | c |
|---|---|---|---|---|---|
| 1977 | 4-methylphenethyl | 1-phenylpiperazinyl | 85.7 | 4.41 | 526.29 |
| 1978 | 4-methylphenethyl | 1-(pyrimidin-2-yl)piperazinyl | 84.2 | 3.82 | 528.27 |
| 1979 | 4-methylphenethyl | 1-benzylpiperazinyl | 87.4 | 3.28 | 540.28 |
| 1980 | 4-methylphenethyl | 1-(4-fluorophenyl)piperazinyl | 86.6 | 4.47 | 544.24 |
| 1981 | 4-methylphenethyl | 1-(4-nitrophenyl)piperazinyl | 86.4 | 4.38 | 571.24 |
| 1982 | 4-methylphenethyl | 1-(pyridin-2-yl)piperazinyl | 85.9 | 3.1 | 527.27 |
| 1983 | 4-methylphenethyl | 1-(2,6-dimethylphenyl)piperazinyl | 85.3 | 5.06 | 554.28 |
| 1984 | 4-methylphenethyl | 1-(3-methylphenyl)piperazinyl | 85.3 | 4.66 | 540.28 |
| 1985 | 4-methylphenethyl | 1-(2-oxobenzimidazol-1-yl)piperidinyl | 60.8 | 3.8 | 581.28 |
| 1986 | 4-methylphenethyl | 1-(4-methoxyphenyl)piperazinyl | 86.1 | 4.25 | 556.28 |
| 1987 | 4-methylphenethyl | 1-(2-fluorophenyl)piperazinyl | 86.4 | 4.54 | 544.25 |
| 1988 | 4-methylphenethyl | 1-(pyridin-4-yl)piperazinyl | 75.9 | 2.86 | 527.28 |

-continued

| # | R1 | R2 | % | t | M |
|---|---|---|---|---|---|
| 1989 | 4-Me-C6H4-CH2CH2-* | 2-NO2-C6H4-piperazine-* | 86.5 | 4.46 | 571.24 |
| 1990 | 4-Me-C6H4-CH2CH2-* | 2-OEt-C6H4-piperazine-* | 88.4 | 4.6 | 570.29 |
| 1991 | 4-Me-C6H4-CH2CH2-* | pyrazin-2-yl-piperazine-* | 79.8 | 3.62 | 528.27 |
| 1992 | 4-Me-C6H4-CH2CH2-* | spiro[indene-piperidine]-* | 63.2 | 4.82 | 549.26 |
| 1993 | 2,5-(OMe)2-C6H3-CH2CH2-* | phenyl-piperazine-* | 81.8 | 4.15 | 572.25 |
| 1994 | 2,5-(OMe)2-C6H3-CH2CH2-* | pyrimidin-2-yl-piperazine-* | 81.0 | 3.58 | 574.25 |
| 1995 | 2,5-(OMe)2-C6H3-CH2CH2-* | benzyl-piperazine-* | 83.5 | 3.08 | 586.3 |
| 1996 | 2,5-(OMe)2-C6H3-CH2CH2-* | 4-F-C6H4-piperazine-* | 84.3 | 4.2 | 590.27 |
| 1997 | 2,5-(OMe)2-C6H3-CH2CH2-* | 4-NO2-C6H4-piperazine-* | 85.3 | 4.12 | 617.26 |

-continued
| | | | | | |
|---|---|---|---|---|---|
| 1998 | 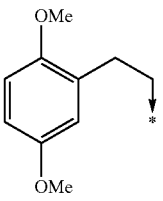 | 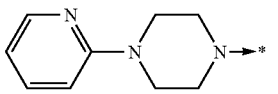 | 86.1 | 2.91 | 573.28 |
| 1999 | 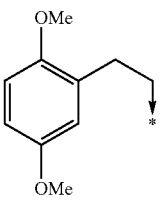 | 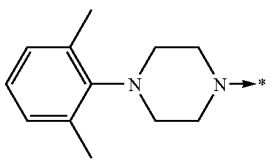 | 85.5 | 4.74 | 600.31 |
| 2000 | 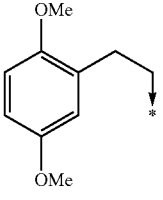 | 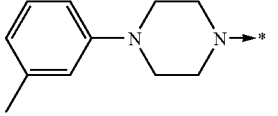 | 87.3 | 4.37 | 586.28 |
| 2001 | 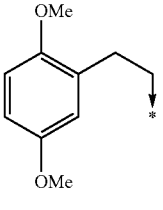 | 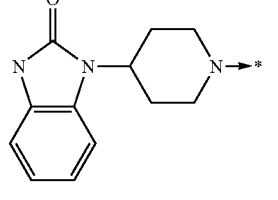 | 68.4 | 3.6 | 627.28 |
| 2002 | 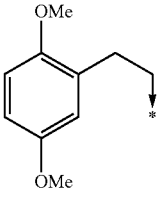 | 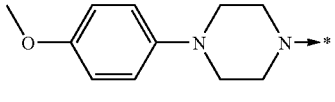 | 85.4 | 3.98 | 602.28 |
| 2003 | 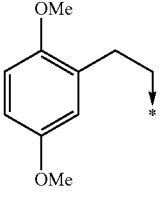 | 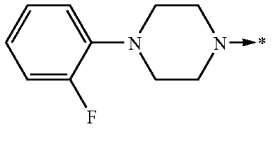 | 83.1 | 4.26 | 590.27 |
| 2004 | 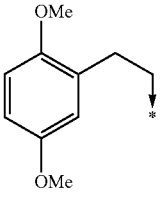 | 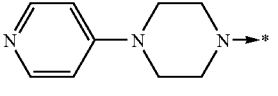 | 84.5 | 2.7 | 573.26 |

-continued

| | | | | | |
|---|---|---|---|---|---|
| 2005 | 2,5-diOMe-benzyl | 2-nitrophenyl piperazine | 85.9 | 4.2 | 617.27 |
| 2006 | 2,5-diOMe-benzyl | 2-ethoxyphenyl piperazine | 86.9 | 4.32 | 616.31 |
| 2007 | 2,5-diOMe-benzyl | 2-pyrazinyl piperazine | 81.2 | 3.4 | 574.24 |
| 2008 | 2,5-diOMe-benzyl | spiro[indene-piperidine] | 69.0 | 4.54 | 595.29 |
| 2009 | biphenyl-2-ylmethyl | 4-phenylpiperazine | 82.1 | 4.72 | 574.25 |
| 2010 | biphenyl-2-ylmethyl | 2-pyrimidinyl piperazine | 80.1 | 4.15 | 576.27 |
| 2011 | biphenyl-2-ylmethyl | 4-benzylpiperazine | 83.9 | 3.53 | 588.27 |

-continued
| | | | | | |
|---|---|---|---|---|---|
| 2012 | 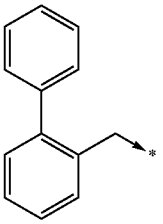 | 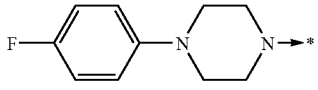 | 80.8 | 4.78 | 592.26 |
| 2013 | 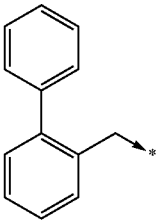 | 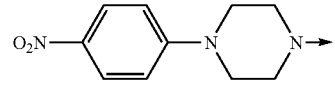 | 83.0 | 4.68 | 619.26 |
| 2014 | 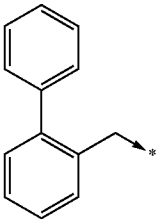 | 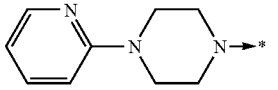 | 85.6 | 3.35 | 575.25 |
| 2015 | 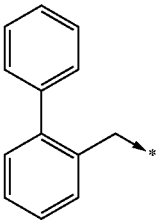 | 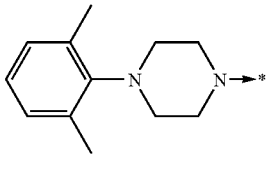 | 82.9 | 5.41 | 602.30 |
| 2016 | 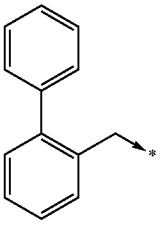 | 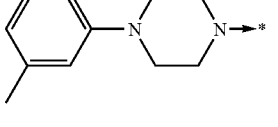 | 81.9 | 4.96 | 588.26 |
| 2017 | 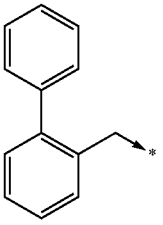 | 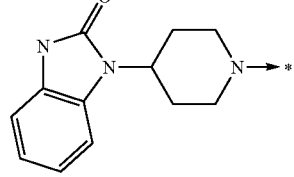 | 58.6 | 4.09 | 629.29 |

-continued
| | | | | | |
|---|---|---|---|---|---|
| 2018 | 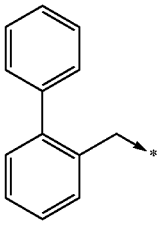 | 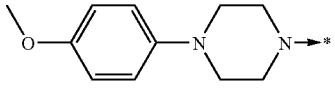 | 81.7 | 4.53 | 604.27 |
| 2019 | 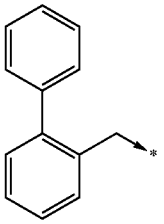 | 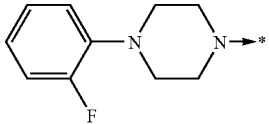 | 81.4 | 4.84 | 592.26 |
| 2020 | 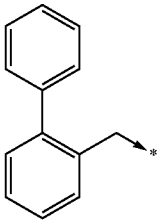 | 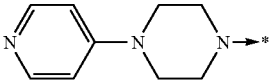 | 78.7 | 3.06 | 575.31 |
| 2021 | 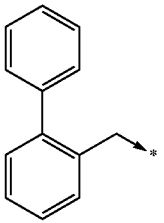 | 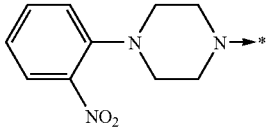 | 83.9 | 4.74 | 619.25 |
| 2022 | 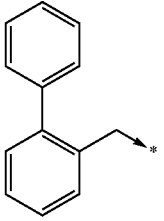 | 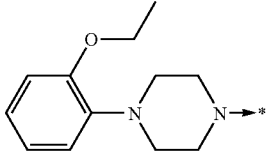 | 82.6 | 4.89 | 618.29 |
| 2023 | 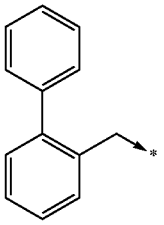 | 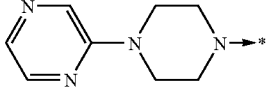 | 79.5 | 3.9 | 576.27 |

-continued
| | | | | | |
|---|---|---|---|---|---|
| 2024 | 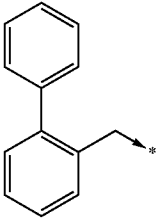 | 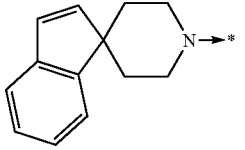 | 64.2 | 5.15 | 597.27 |
| 2025 | 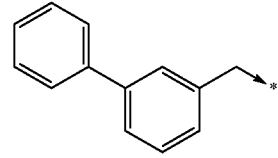 | 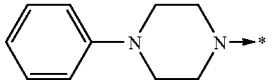 | 88.8 | 4.94 | 574.23 |
| 2026 | 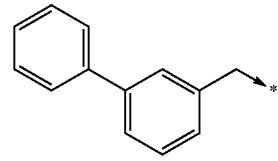 | 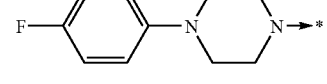 | 88.4 | 4.96 | 592.25 |
| 2027 | 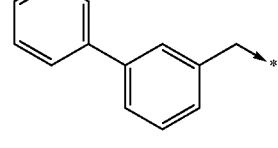 | 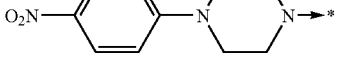 | 87.7 | 4.86 | 619.24 |
| 2028 | 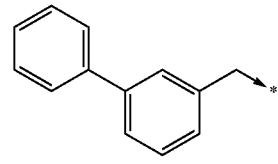 | 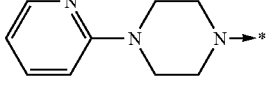 | 89.7 | 3.61 | 575.2 |
| 2029 | 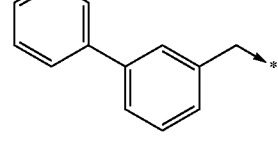 | 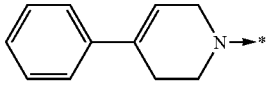 | 70.4 | 5.13 | 571.25 |
| 2030 | 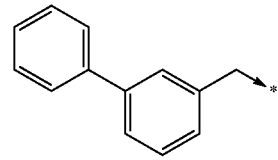 | 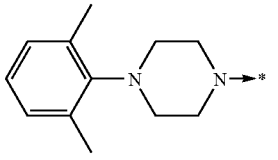 | 88.0 | 5.58 | 602.28 |
| 2031 | 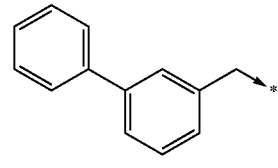 | 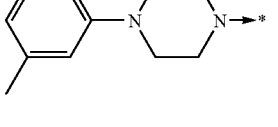 | 87.8 | 5.15 | 588.26 |

| | | | | | |
|---|---|---|---|---|---|
| 2032 | 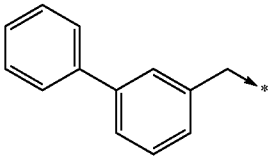 | 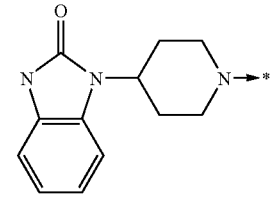 | 76.5 | 4.24 | 629.28 |
| 2033 | 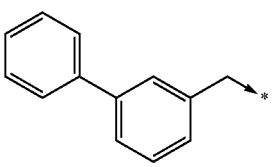 | 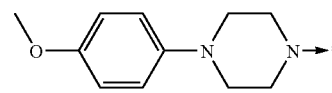 | 88.8 | 4.7 | 604.27 |
| 2034 | 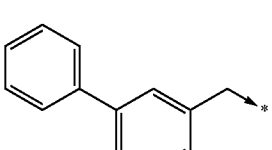 | 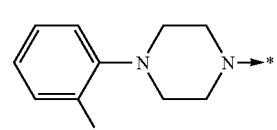 | 88.3 | 5.04 | 592.25 |
| 2035 | 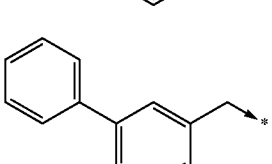 | 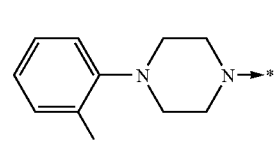 | 89.5 | 4.96 | 619.24 |
| 2036 | 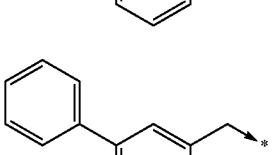 | 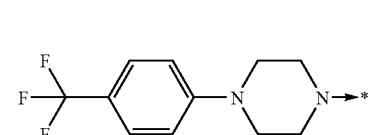 | 87.5 | 5.41 | 642.26 |
| 2037 | 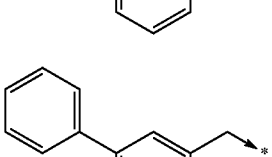 | 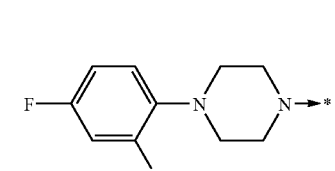 | 88.9 | 5.12 | 610.24 |
| 2038 | 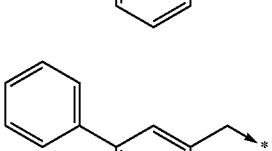 | 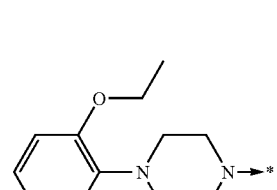 | 89.4 | 5.07 | 618.27 |
| 2039 | 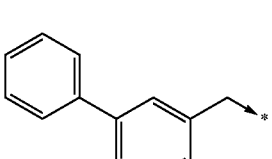 | 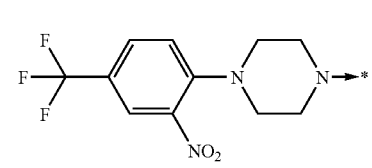 | 88.7 | 5.42 | 687.24 |
| 2040 | 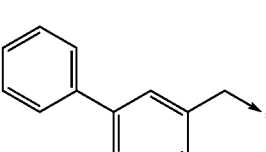 | 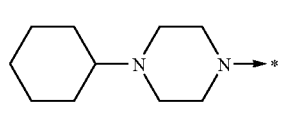 | 87.7 | 3.68 | 580.30 |

| | | | | | |
|---|---|---|---|---|---|
| 2041 | 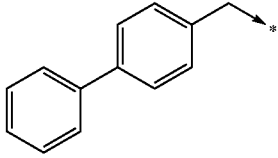 | 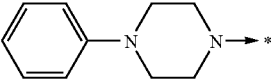 | 85.2 | 4.89 | 574.23 |
| 2042 | 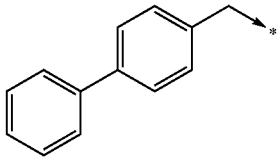 | 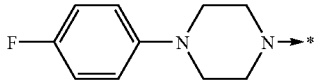 | 84.4 | 4.9 | 592.25 |
| 2043 | 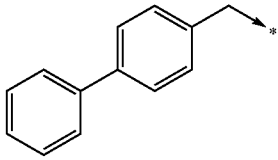 | 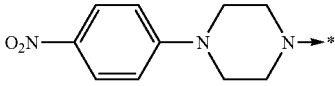 | 84.7 | 4.78 | 619.23 |
| 2044 | 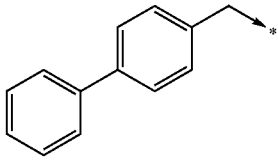 | 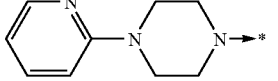 | 89.0 | 3.58 | 575.25 |
| 2045 | 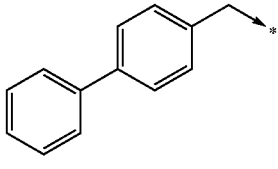 | 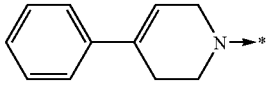 | 61.5 | 5.16 | 571.22 |
| 2046 | 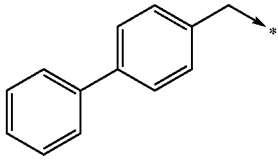 | 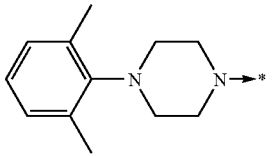 | 83.2 | 5.57 | 602.28 |
| 2047 | 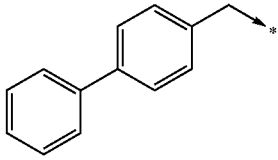 | 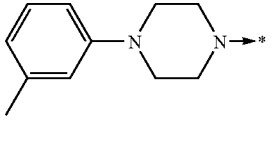 | 84.4 | 5.1 | 588.25 |
| 2048 | 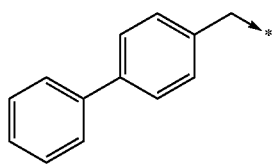 | 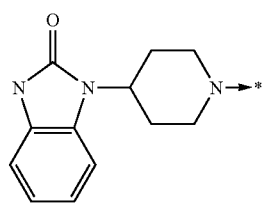 | 73.2 | 4.25 | 629.27 |
| 2049 | 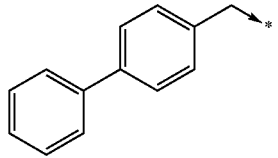 | 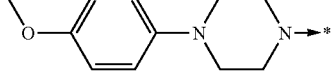 | 85.5 | 4.64 | 604.26 |

-continued
| | | | | | |
|---|---|---|---|---|---|
| 2050 | 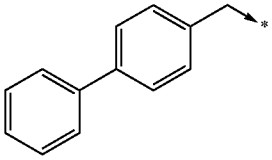 | 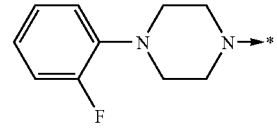 | 85.6 | 4.99 | 592.2 |
| 2051 | 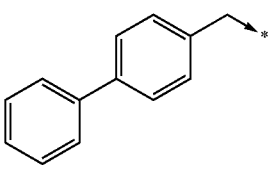 | 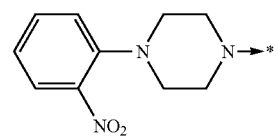 | 85.7 | 4.93 | 619.24 |
| 2052 | 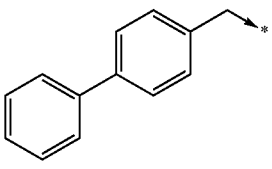 | 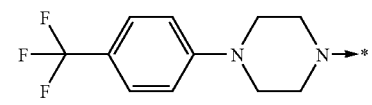 | 86.2 | 5.34 | 642.25 |
| 2053 | 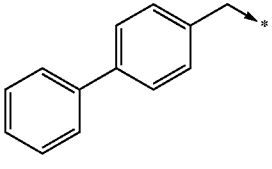 | 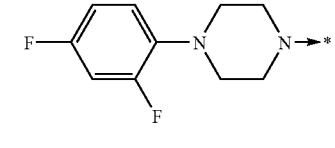 | 85.1 | 5.06 | 610.23 |
| 2054 | 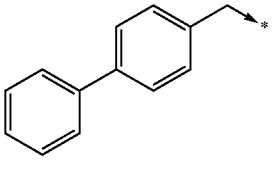 | 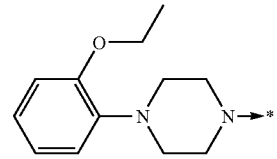 | 84.6 | 5.06 | 618.27 |
| 2055 | 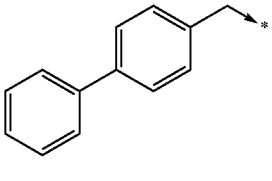 | 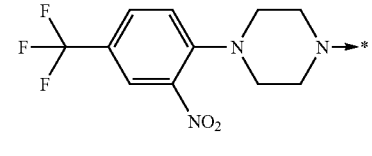 | 85.4 | 5.37 | 687.23 |
| 2056 | 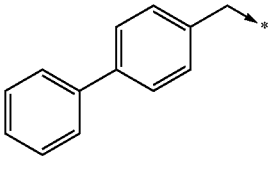 | 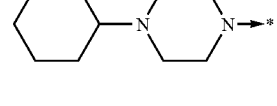 | 85.8 | 3.68 | 580.30 |
| 2057 | 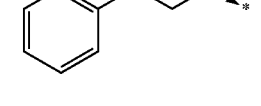 | 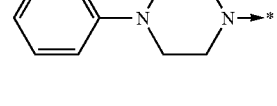 | 68.0 | 4.37 | 528.26 |
| 2058 | 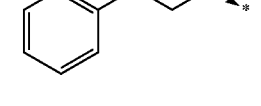 | 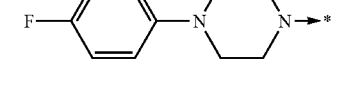 | 86.3 | 4.41 | 546.22 |
| 2059 | 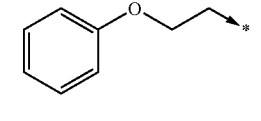 | 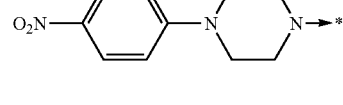 | 88.1 | 4.32 | 573.19 |

-continued

| # | R1 | R2 | a | b | c |
|---|---|---|---|---|---|
| 2060 | phenoxyethyl | 2-pyridyl piperazine | 86.1 | 3 | 529.25 |
| 2061 | phenoxyethyl | 4-phenyl-tetrahydropyridine | 67.2 | 4.56 | 525.25 |
| 2062 | phenoxyethyl | 2,6-dimethylphenyl piperazine | 91.2 | 4.98 | 556.26 |
| 2063 | phenoxyethyl | 3-methylphenyl piperazine | 87.8 | 4.56 | 542.26 |
| 2064 | phenoxyethyl | 1-(2-oxo-2,3-dihydro-1H-benzimidazol-1-yl)piperidine | 75.6 | 3.73 | 583.23 |
| 2065 | phenoxyethyl | 4-methoxyphenyl piperazine | 88.7 | 4.16 | 558.23 |
| 2066 | phenoxyethyl | 2-fluorophenyl piperazine | 88.4 | 4.46 | 546.22 |
| 2067 | phenoxyethyl | 2-nitrophenyl piperazine | 87.4 | 4.4 | 573.20 |
| 2068 | phenoxyethyl | 4-trifluoromethylphenyl piperazine | 87.7 | 4.88 | 596.21 |
| 2069 | phenoxyethyl | 2,4-difluorophenyl piperazine | 87.9 | 4.56 | 564.21 |
| 2070 | phenoxyethyl | 2-ethoxyphenyl piperazine | 87.5 | 4.51 | 572.26 |

| | | | | | |
|---|---|---|---|---|---|
| 2071 | phenoxyethyl-* | 4-(trifluoromethyl)-2-nitrophenyl piperazinyl-* | 88.8 | 4.91 | 641.20 |
| 2072 | phenoxyethyl-* | cyclohexyl piperazinyl-* | 86.2 | 3.08 | 534.27 |
| 2073 | 1-naphthylethyl-* | phenyl piperazinyl-* | 71.7 | 4.78 | 562.25 |
| 2074 | 1-naphthylethyl-* | 4-fluorophenyl piperazinyl-* | 82.1 | 4.8 | 580.23 |
| 2075 | 1-naphthylethyl-* | 4-nitrophenyl piperazinyl-* | 82.6 | 4.68 | 607.23 |
| 2076 | 1-naphthylethyl-* | 2-pyridyl piperazinyl-* | 79.5 | 3.4 | 563.21 |
| 2077 | 1-naphthylethyl-* | 4-phenyl-1,2,3,6-tetrahydropyridinyl-* | 67.5 | 4.92 | 559.23 |
| 2078 | 1-naphthylethyl-* | 2,6-dimethylphenyl piperazinyl-* | 83.0 | 5.39 | 590.27 |
| 2079 | 1-naphthylethyl-* | 3-methylphenyl piperazinyl-* | 82.5 | 4.98 | 576.26 |

-continued

| # | R1 | R2 | a | b | c |
|---|---|---|---|---|---|
| 2080 | naphthalen-1-ylmethyl-CH2-* | 4-(2-oxo-2,3-dihydro-1H-benzimidazol-1-yl)piperidin-1-yl-* | 42.5 | 4.1 | 617.23 |
| 2081 | naphthalen-1-ylmethyl-CH2-* | 4-(4-methoxyphenyl)piperazin-1-yl-* | 86.9 | 4.58 | 592.26 |
| 2082 | naphthalen-1-ylmethyl-CH2-* | 4-(2-fluorophenyl)piperazin-1-yl-* | 82.5 | 4.88 | 580.23 |
| 2083 | naphthalen-1-ylmethyl-CH2-* | 4-(2-nitrophenyl)piperazin-1-yl-* | 81.4 | 4.77 | 607.23 |
| 2084 | naphthalen-1-ylmethyl-CH2-* | 4-(4-trifluoromethylphenyl)piperazin-1-yl-* | 82.3 | 5.24 | 630.26 |
| 2085 | naphthalen-1-ylmethyl-CH2-* | 4-(2,4-difluorophenyl)piperazin-1-yl-* | 83.5 | 4.97 | 598.20 |
| 2086 | naphthalen-1-ylmethyl-CH2-* | 4-(2-ethoxyphenyl)piperazin-1-yl-* | 81.6 | 4.93 | 606.28 |
| 2087 | naphthalen-1-ylmethyl-CH2-* | 4-(2-nitro-4-trifluoromethylphenyl)piperazin-1-yl-* | 82.7 | 5.25 | 675.23 |
| 2088 | naphthalen-1-ylmethyl-CH2-* | 4-cyclohexylpiperazin-1-yl-* | 84.4 | 3.4 | 568.26 |

-continued

| # | R1 | R2 | a | b | c |
|---|---|---|---|---|---|
| 2089 | naphthalen-2-yl-ethyl | 4-phenyl-piperazin-1-yl | 67.0 | 4.64 | 562.24 |
| 2090 | naphthalen-2-yl-ethyl | 4-(4-fluorophenyl)-piperazin-1-yl | 83.0 | 4.66 | 580.23 |
| 2091 | naphthalen-2-yl-ethyl | 4-(4-nitrophenyl)-piperazin-1-yl | 83.6 | 4.54 | 607.22 |
| 2092 | naphthalen-2-yl-ethyl | 4-(pyridin-2-yl)-piperazin-1-yl | 82.5 | 3.3 | 563.25 |
| 2093 | naphthalen-2-yl-ethyl | 4-phenyl-3,6-dihydro-2H-pyridin-1-yl | 84.2 | 4.8 | 559.22 |
| 2094 | naphthalen-2-yl-ethyl | 4-(2,6-dimethylphenyl)-piperazin-1-yl | 86.2 | 5.21 | 590.29 |
| 2095 | naphthalen-2-yl-ethyl | 4-(3-methylphenyl)-piperazin-1-yl | 83.2 | 4.82 | 576.28 |
| 2096 | naphthalen-2-yl-ethyl | 4-(2-oxo-2,3-dihydro-1H-benzimidazol-1-yl)-piperidin-1-yl | 62.8 | 3.99 | 617.26 |
| 2097 | naphthalen-2-yl-ethyl | 4-(4-methoxyphenyl)-piperazin-1-yl | 86.0 | 4.44 | 592.2 |
| 2098 | naphthalen-2-yl-ethyl | 4-(2-fluorophenyl)-piperazin-1-yl | 85.8 | 4.72 | 580.25 |
| 2099 | naphthalen-2-yl-ethyl | 4-(2-nitrophenyl)-piperazin-1-yl | 84.0 | 4.62 | 607.23 |
| 2100 | naphthalen-2-yl-ethyl | 4-(4-trifluoromethylphenyl)-piperazin-1-yl | 83.4 | 5.09 | 630.26 |

-continued
| Ex. | | | Purity (%) | rt (min.) | [M + H]+ |
|---|---|---|---|---|---|
| 2101 | 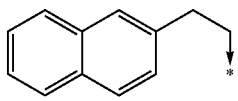 | 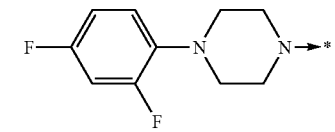 | 84.8 | 4.8 | 598.21 |
| 2102 | 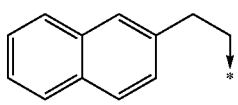 | 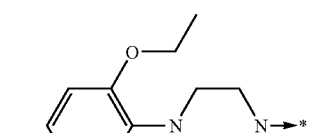 | 83.7 | 4.78 | 606.29 |
| 2103 | 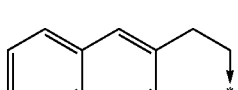 | 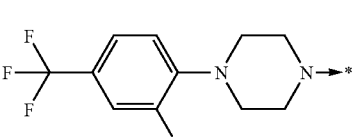 | 83.6 | 5.1 | 675.24 |
| 2104 | 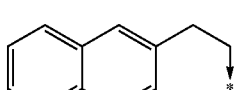 | 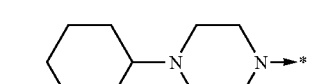 | 5.6 | 3.05 | 568.28 |
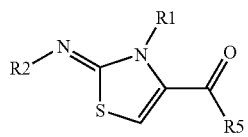
| Ex. | R5 | R2 | R1 | Purity (%) | rt (min.) | [M + H]+ |
|---|---|---|---|---|---|---|
| 2105 | 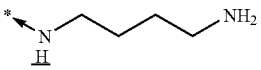 | 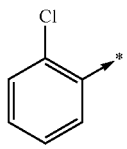 | 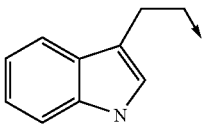 | 81.5 | 4.9 | 468.27 |
| 2106 | 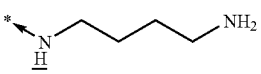 | 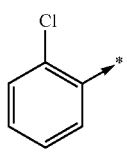 | 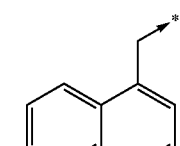 | 81.4 | 5.01 | 465.28 |
| 2107 | 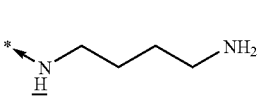 | 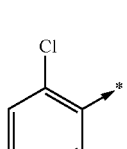 | 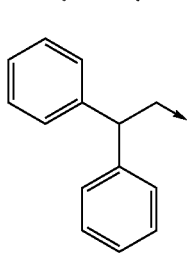 | 77.3 | 5.34 | 505.31 |
| 2108 | 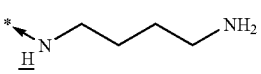 | 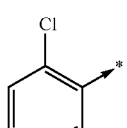 | 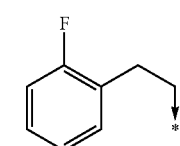 | 73.5 | 4.7 | 447.29 |

-continued

| | | | | | | |
|---|---|---|---|---|---|---|
| 2109 | *−NH−(CH2)4−NH2 | 2-Cl-C6H4−* | 4-(OCF3)-C6H4-CH2−* | 70.5 | 5.28 | 499.26 |
| 2110 | *−NH−(CH2)4−NH2 | 2-Cl-C6H4−* | 4-Ph-C6H4-CH2−* | 73.9 | 5.38 | 491.30 |
| 2111 | *−NH−(CH2)4−NH2 | 2-Cl-C6H4−* | 2,5-(OMe)2-C6H3-CH2CH2−* | 72.0 | 4.5 | 489.31 |
| 2112 | *−NH−(CH2)4−NH2 | 2-Cl-C6H4−* | 4-(PhO)-C6H4-CH2CH2−* | 73.0 | 5.5 | 521.29 |
| 2113 | *−NH−(CH2)4−NH2 | 2-Cl-C6H4−* | isobutyl−* | 90.0 | 4.23 | 381.29 |
| 2114 | *−NH−(CH2)4−NH2 | 2-Cl-C6H4−* | 3,5-(Me)2-C6H3-CH2−* | 76.1 | 5.02 | 443.30 |
| 2115 | *−NH−(CH2)4−NH2 | C6H5−* | indol-3-yl-CH2CH2−* | 56.9 | 4.2 | 434.32 |
| 2116 | *−NH−(CH2)4−NH2 | C6H5−* | naphth-1-yl-CH2−* | 79.8 | 4.29 | 431.31 |
| 2117 | *−NH−(CH2)4−NH2 | C6H5−* | Ph2CH-CH2−* | 79.1 | 4.45 | 471.35 |

| | | | | | | |
|---|---|---|---|---|---|---|
| 2118 | *−N(H)−(CH2)4−NH2 | phenyl* | 2-fluorophenethyl | 70.2 | 3.56 | 413.29 |
| 2119 | *−N(H)−(CH2)4−NH2 | phenyl* | 4-(trifluoromethoxy)benzyl | 72.4 | 4.68 | 465.27 |
| 2120 | *−N(H)−(CH2)4−NH2 | phenyl* | 4-biphenylmethyl | 78.3 | 4.66 | 457.33 |
| 2121 | *−N(H)−(CH2)4−NH2 | phenyl* | 2,5-dimethoxyphenethyl | 90.1 | 3.41 | 455.33 |
| 2122 | *−N(H)−(CH2)4−NH2 | phenyl* | 4-phenoxyphenethyl | 82.2 | 4.38 | 487.36 |
| 2123 | *−N(H)−(CH2)4−NH2 | phenyl* | isobutyl | 68.8 | 2.99 | 347.34 |
| 2124 | *−N(H)−(CH2)4−NH2 | phenyl* | 3,5-dimethylbenzyl | 75.2 | 4.13 | 409.33 |
| 2125 | *−N(H)−(CH2)4−NH2 | 4-sulfamoylphenyl* | 3-(indol-3-yl)ethyl | 56.9 | 4.01 | 513.30 |
| 2126 | *−N(H)−(CH2)4−NH2 | 4-sulfamoylphenyl* | 1-naphthylmethyl | 70.1 | 3.88 | 510.29 |

-continued

| # | | | | | | |
|---|---|---|---|---|---|---|
| 2127 | butane-1,4-diamine (NH) | 4-sulfamoylphenyl (H2) | 2,2-diphenylethyl | 77.8 | 4.16 | 550.29 |
| 2128 | butane-1,4-diamine (NH) | 4-sulfamoylphenyl (H2) | 2-(2-fluorophenyl)ethyl | 67.7 | 3.49 | 492.28 |
| 2129 | butane-1,4-diamine (NH) | 4-sulfamoylphenyl (H2) | (biphenyl-4-yl)methyl | 71 | 4.27 | 536.28 |
| 2130 | butane-1,4-diamine (NH) | 4-sulfamoylphenyl (H2) | 2-(2,5-dimethoxyphenyl)ethyl | 71.4 | 3.38 | 534.30 |
| 2131 | butane-1,4-diamine (NH) | 4-sulfamoylphenyl (H2) | 2-(4-phenoxyphenyl)ethyl | 67.7 | 4.29 | 566.30 |
| 2132 | butane-1,4-diamine (NH) | 4-sulfamoylphenyl (H2) | isobutyl | 54.5 | 2.98 | 426.29 |
| 2133 | butane-1,4-diamine (NH) | 4-sulfamoylphenyl (H2) | (3,5-dimethylphenyl)methyl | 70.1 | 3.85 | 488.31 |
| 2134 | butane-1,4-diamine (NH) | 3,5-dimethylphenyl | 2-(1H-indol-3-yl)ethyl | 57.1 | 4.5 | 462.36 |
| 2135 | butane-1,4-diamine (NH) | 3,5-dimethylphenyl | (naphthalen-1-yl)methyl | 83.2 | 4.61 | 459.35 |

-continued

| # | R1 | R2 | R3 | % | t | MW |
|---|----|----|----|---|---|----|
| 2136 | *−NH−(CH₂)₄−NH₂ | 3,5-dimethylphenyl | CH(Ph)₂CH₂−* | 91.6 | 4.72 | 499.40 |
| 2137 | *−NH−(CH₂)₄−NH₂ | 3,5-dimethylphenyl | 2-F-C₆H₄-CH₂CH₂−* | 80.7 | 3.94 | 441.32 |
| 2138 | *−NH−(CH₂)₄−NH₂ | 3,5-dimethylphenyl | 4-OCF₃-C₆H₄-CH₂−* | 73.9 | 4.99 | 493.32 |
| 2139 | *−NH−(CH₂)₄−NH₂ | 3,5-dimethylphenyl | 4-biphenyl-CH₂−* | 77.5 | 4.95 | 485.37 |
| 2140 | *−NH−(CH₂)₄−NH₂ | 3,5-dimethylphenyl | 2,5-(OMe)₂-C₆H₃-CH₂CH₂−* | 77.4 | 3.79 | 483.36 |
| 2141 | *−NH−(CH₂)₄−NH₂ | 3,5-dimethylphenyl | 4-PhO-C₆H₄-CH₂CH₂−* | 66.1 | 4.62 | 515.38 |
| 2142 | *−NH−(CH₂)₄−NH₂ | 3,5-dimethylphenyl | isobutyl−* | 70.1 | 3.49 | 375.33 |
| 2143 | *−NH−(CH₂)₄−NH₂ | 3,5-dimethylphenyl | 3,5-dimethylphenyl-CH₂−* | 74.1 | 4.46 | 437.35 |
| 2144 | *−NH−CH₂-(m-C₆H₄)-CH₂−NH₂ | 2-Cl-C₆H₄−* | indol-3-yl-CH₂CH₂−* | 93.8 | 5.14 | 516.28 |

-continued

| # | | | | | | |
|---|---|---|---|---|---|---|
| 2145 | *NH-CH2-C6H4-CH2-NH2 (meta) | 2-Cl-C6H4-* | naphthalen-1-ylmethyl-* | 90.0 | 5.27 | 513.28 |
| 2146 | *NH-CH2-C6H4-CH2-NH2 (meta) | 2-Cl-C6H4-* | 2,2-diphenylethyl-* | 81.4 | 5.58 | 553.30 |
| 2147 | *NH-CH2-C6H4-CH2-NH2 (meta) | 2-Cl-C6H4-* | 2-(2-fluorophenyl)ethyl-* | 78.6 | 5.02 | 495.27 |
| 2148 | *NH-CH2-C6H4-CH2-NH2 (meta) | 2-Cl-C6H4-* | 4-(trifluoromethoxy)benzyl-* | 81.4 | 5.51 | 547.21 |
| 2149 | *NH-CH2-C6H4-CH2-NH2 (meta) | 2-Cl-C6H4-* | biphenyl-4-ylmethyl-* | 85.5 | 5.62 | 539.29 |
| 2150 | *NH-CH2-C6H4-CH2-NH2 (meta) | 2-Cl-C6H4-* | 2-(2,5-dimethoxyphenyl)ethyl-* | 78.9 | 4.86 | 537.28 |
| 2151 | *NH-CH2-C6H4-CH2-NH2 (meta) | 2-Cl-C6H4-* | 2-(4-phenoxyphenyl)ethyl-* | 83.2 | 5.76 | 569.28 |
| 2152 | *NH-CH2-C6H4-CH2-NH2 (meta) | 2-Cl-C6H4-* | isobutyl-* | 90.5 | 4.62 | 429.28 |
| 2153 | *NH-CH2-C6H4-CH2-NH2 (meta) | 2-Cl-C6H4-* | 3,5-dimethylbenzyl-* | 91.8 | 5.31 | 491.31 |

| | | | | | | |
|---|---|---|---|---|---|---|
| | | | -continued | | | |
| 2154 | *−N(H)−CH2−C6H4−CH2NH2 (meta) | Ph−* | indol-3-yl-ethyl−* | 60.4 | 4.47 | 462.33 |
| 2155 | *−N(H)−CH2−C6H4−CH2NH2 (meta) | Ph−* | naphthalen-1-ylmethyl−* | 83.6 | 4.62 | 479.31 |
| 2156 | *−N(H)−CH2−C6H4−CH2NH2 (meta) | Ph−* | 2,2-diphenylethyl−* | 79.1 | 4.72 | 519.34 |
| 2157 | *−N(H)−CH2−C6H4−CH2NH2 (meta) | Ph−* | 2-(2-fluorophenyl)ethyl−* | 72.6 | 3.96 | 461.31 |
| 2158 | *−N(H)−CH2−C6H4−CH2NH2 (meta) | Ph−* | 4-(trifluoromethoxy)benzyl−* | 75.7 | 5.0 | 513.27 |
| 2159 | *−N(H)−CH2−C6H4−CH2NH2 (meta) | Ph−* | biphenyl-4-ylmethyl−* | 79.3 | 4.99 | 505.34 |
| 2160 | *−N(H)−CH2−C6H4−CH2NH2 (meta) | Ph−* | 2-(2,5-dimethoxyphenyl)ethyl−* | 89.6 | 3.72 | 503.34 |
| 2161 | *−N(H)−CH2−C6H4−CH2NH2 (meta) | Ph−* | 2-(4-phenoxyphenyl)ethyl−* | 89.6 | 4.7 | 535.32 |
| 2162 | *−N(H)−CH2−C6H4−CH2NH2 (meta) | Ph−* | isobutyl−* | 73.5 | 3.38 | 395.32 |
| 2163 | *−N(H)−CH2−C6H4−CH2NH2 (meta) | Ph−* | 3,5-dimethylbenzyl−* | 80.1 | 4.5 | 457.32 |

-continued

| # | R1 | R2 | R3 | a | b | c |
|---|---|---|---|---|---|---|
| 2164 | 3-(aminomethyl)benzylamine | 4-sulfonamidophenyl | tryptamine (indol-3-yl-ethyl) | 58.8 | 4.24 | 561.29 |
| 2165 | 3-(aminomethyl)benzylamine | 4-sulfonamidophenyl | naphthalen-1-ylmethyl | 77.9 | 4.16 | 558.27 |
| 2166 | 3-(aminomethyl)benzylamine | 4-sulfonamidophenyl | 2,2-diphenylethyl | 85.5 | 4.42 | 598.29 |
| 2167 | 3-(aminomethyl)benzylamine | 4-sulfonamidophenyl | 2-fluorophenethyl | 82.8 | 3.87 | 540.27 |
| 2168 | 3-(aminomethyl)benzylamine | 4-sulfonamidophenyl | 4-(trifluoromethoxy)benzyl | 1.54 | 4.52 | 592.25 |
| 2169 | 3-(aminomethyl)benzylamine | 4-sulfonamidophenyl | biphenyl-4-ylmethyl | 56.0 | 4.54 | 584.25 |
| 2170 | 3-(aminomethyl)benzylamine | 4-sulfonamidophenyl | 2-(2,5-dimethoxyphenyl)ethyl | 82.5 | 3.76 | 582.30 |
| 2171 | 3-(aminomethyl)benzylamine | 4-sulfonamidophenyl | 2-(4-phenoxyphenyl)ethyl | 71.8 | 4.58 | 614.31 |
| 2172 | 3-(aminomethyl)benzylamine | 4-sulfonamidophenyl | isobutyl | 71.9 | 3.43 | 474.30 |

| | | | | | | |
|---|---|---|---|---|---|---|
| 2173 | *~N(H)-CH2-C6H4-CH2-NH2 (m) | 4-SO2NH-C6H4-* | 3,5-dimethylbenzyl-* | 80.9 | 4.16 | 536.28 |
| 2174 | *~N(H)-CH2-C6H4-CH2-NH2 (m) | 3,5-dimethylphenyl-* | indol-3-yl-ethyl-* | 61.9 | 4.76 | 510.36 |
| 2175 | *~N(H)-CH2-C6H4-CH2-NH2 (m) | 3,5-dimethylphenyl-* | naphthalen-1-ylmethyl-* | 83.1 | 4.93 | 507.35 |
| 2176 | *~N(H)-CH2-C6H4-CH2-NH2 (m) | 3,5-dimethylphenyl-* | 2,2-diphenylethyl-* | 92.0 | 4.99 | 547.36 |
| 2177 | *~N(H)-CH2-C6H4-CH2-NH2 (m) | 3,5-dimethylphenyl-* | 2-fluorophenethyl-* | 88.3 | 4.27 | 489.35 |
| 2178 | *~N(H)-CH2-C6H4-CH2-NH2 (m) | 3,5-dimethylphenyl-* | 4-trifluoromethoxybenzyl-* | 86.3 | 5.41 | 541.29 |
| 2179 | *~N(H)-CH2-C6H4-CH2-NH2 (m) | 3,5-dimethylphenyl-* | biphenyl-4-ylmethyl-* | 79.7 | 5.36 | 533.36 |
| 2180 | *~N(H)-CH2-C6H4-CH2-NH2 (m) | 3,5-dimethylphenyl-* | 2,5-dimethoxyphenethyl-* | 82.5 | 4.13 | 531.35 |
| 2181 | *~N(H)-CH2-C6H4-CH2-NH2 (m) | 3,5-dimethylphenyl-* | 4-phenoxyphenethyl-* | 74.0 | 4.99 | 563.34 |

-continued

| # | R1 | R2 | R3 | % | t | M |
|---|---|---|---|---|---|---|
| 2182 | *-NH-CH2-C6H4-CH2-NH2 (meta) | 3,5-dimethylphenyl | isobutyl | 76 | 3.89 | 423.35 |
| 2183 | *-NH-CH2-C6H4-CH2-NH2 (meta) | 3,5-dimethylphenyl | 3,5-dimethylbenzyl | 79.8 | 4.89 | 485.38 |
| 2184 | *-NH-(CH2)5-NH2 | 4-benzyloxyphenyl | benzyl | 80.8 | 4.43 | 501.32 |
| 2185 | *-NH-(CH2)5-NH2 | 4-benzyloxyphenyl | 2-methoxybenzyl | 66.2 | 4.18 | 545.31 |
| 2186 | *-NH-(CH2)5-NH2 | 4-benzyloxyphenyl | 2-trifluoromethylbenzyl | 64.6 | 5.18 | 569.27 |
| 2187 | *-NH-(CH2)5-NH2 | 4-benzyloxyphenyl | (4-nitrophenyl)aminocarbonylmethyl | 57.2 | 4.78 | 589.30 |
| 2188 | *-NH-(CH2)5-NH2 | 4-benzyloxyphenyl | 3-phenylpropyl | 65.7 | 4.41 | 529.36 |
| 2189 | *-NH-(CH2)5-NH2 | 4-benzyloxyphenyl | 4-chlorophenethyl | 65.4 | 4.52 | 549.28 |
| 2190 | *-NH-(CH2)5-NH2 | 4-benzyloxyphenyl | 2-(thiophen-2-yl)ethyl | 65.8 | 4.24 | 521.29 |

| | | | | | | |
|---|---|---|---|---|---|---|
| 2191 | 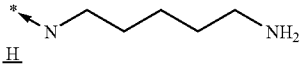 | 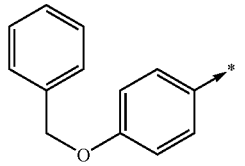 | 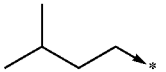 | 71.4 | 4.19 | 481.37 |
| 2192 | 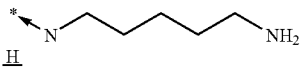 | 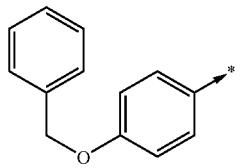 | 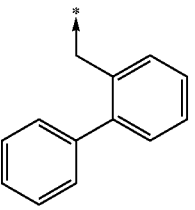 | 83.9 | 4.8 | 577.32 |
| 2193 | 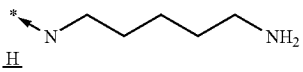 | 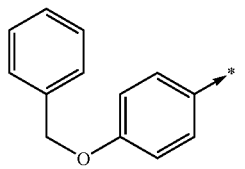 | 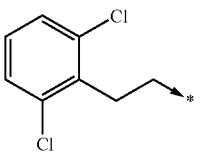 | 76.5 | 4.54 | 583.24 |
| 2194 | 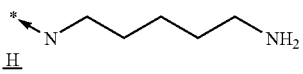 | 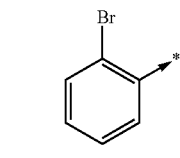 | 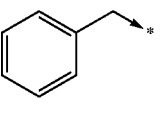 | 67.2 | 4.76 | 473.22 |
| 2195 | 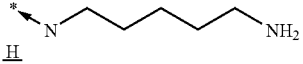 | 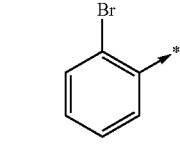 | 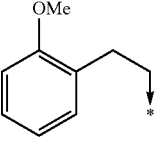 | 66.6 | 4.69 | 517.20 |
| 2196 | 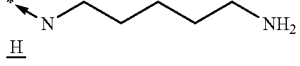 | 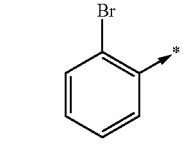 | 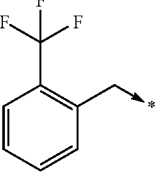 | 71 | 5.2 | 541.18 |
| 2197 | 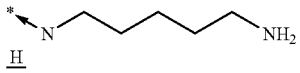 | 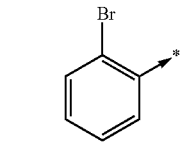 | 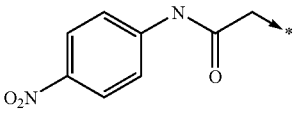 | 69 | 4.73 | 561.15 |
| 2198 | 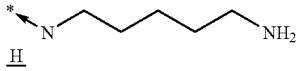 | 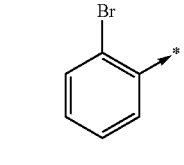 | 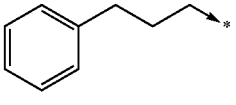 | 74.8 | 5.04 | 501.24 |
| 2199 | 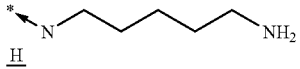 | 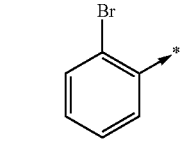 | 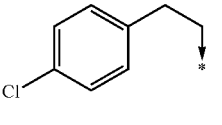 | 69.5 | 5.18 | 521.16 |

-continued

| # | R1 | R2 | R3 | a | b | c |
|---|----|----|----|---|---|---|
| 2200 | *-NH-(CH2)4-NH2 | 2-Br-phenyl | 2-thienyl-ethyl | 79.3 | 4.8 | 493.18 |
| 2201 | *-NH-(CH2)4-NH2 | 2-Br-phenyl | isopentyl | 74.9 | 4.79 | 453.24 |
| 2202 | *-NH-(CH2)4-NH2 | 2-Br-phenyl | 2-biphenyl | 68.9 | 5.41 | 549.20 |
| 2203 | *-NH-(CH2)4-NH2 | 2-Br-phenyl | 2,6-dichlorophenyl-ethyl | 68 | 5.2 | 555.11 |
| 2204 | *-NH-(CH2)4-NH2 | 3-CF3-phenyl | benzyl | 66 | 5.02 | 463.27 |
| 2205 | *-NH-(CH2)4-NH2 | 3-CF3-phenyl | 2-OMe-phenyl-ethyl | 62.2 | 4.83 | 507.28 |
| 2206 | *-NH-(CH2)4-NH2 | 3-CF3-phenyl | 2-CF3-benzyl | 65.2 | 5.48 | 531.24 |
| 2207 | *-NH-(CH2)4-NH2 | 3-CF3-phenyl | (4-nitrophenyl)aminocarbonylmethyl | 66.3 | 4.99 | 551.22 |

| | | | | | | |
|---|---|---|---|---|---|---|
| 2208 | *⃪NH—(CH2)4—NH2 | 3-CF3-C6H4—* | C6H5—(CH2)3—* | 72.9 | 5.22 | 491.31 |
| 2209 | *⃪NH—(CH2)4—NH2 | 3-CF3-C6H4—* | 4-Cl-C6H4—(CH2)2—* | 77.2 | 5.31 | 511.24 |
| 2210 | *⃪NH—(CH2)4—NH2 | 3-CF3-C6H4—* | 2-thienyl—(CH2)2—* | 62.8 | 4.98 | 483.24 |
| 2211 | *⃪HN—(CH2)4—NH2 | 3-CF3-C6H4—* | (CH3)2CH—CH2—CH2—* | 62.4 | 4.98 | 443.31 |
| 2212 | *⃪HN—(CH2)4—NH2 | 3-CF3-C6H4—* | 2-biphenyl—* | 69.6 | 5.55 | 539.29 |
| 2213 | *⃪HN—(CH2)4—NH2 | 3-CF3-C6H4—* | 2,6-Cl2-C6H3—CH2—* | 63.5 | 5.41 | 545.19 |
| 2214 | *⃪HN—(CH2)4—NH2 | 3,5-(MeO)2-C6H3—* | C6H5—CH2—* | 41.2 | 4.09 | 455.28 |

| | | | | | | |
|---|---|---|---|---|---|---|
| 2215 | *↖HN~~~NH₂ | 3,5-dimethoxyphenyl-* | 2-methoxyphenethyl-* | 58.5 | 3.73 | 499.35 |
| 2216 | *↖HN~~~NH₂ | 3,5-dimethoxyphenyl-* | 2-(trifluoromethyl)benzyl-* | 68.8 | 4.78 | 523.28 |
| 2217 | *↖HN~~~NH₂ | 3,5-dimethoxyphenyl-* | N-(4-nitrophenyl)acetamide-* | 36.2 | 4.37 | 543.28 |
| 2218 | *↖HN~~~NH₂ | 3,5-dimethoxyphenyl-* | 3-phenylpropyl-* | 42.9 | 4.1 | 483.36 |
| 2219 | *↖HN~~~NH₂ | 3,5-dimethoxyphenyl-* | 4-methylphenethyl-* | 46.1 | 4.24 | 503.30 |
| 2220 | *↖HN~~~NH₂ | 3,5-dimethoxyphenyl-* | 2-(thiophen-2-yl)ethyl-* | 48.4 | 3.87 | 475.28 |
| 2221 | *↖H̲N~~~NH₂ | 3,5-dimethoxyphenyl-* | isopentyl-* | 39 | 3.8 | 435.34 |

| # | R1 | R2 | R3 | A | B | C |
|---|---|---|---|---|---|---|
| 2222 | *-NH-(CH2)4-NH2 | 3,5-dimethoxyphenyl | 2-biphenyl | 48.3 | 4.55 | 531.30 |
| 2223 | *-NH-(CH2)4-NH2 | 3,5-dimethoxyphenyl | 2,6-dichlorophenethyl | 47 | 4.33 | 537.20 |
| 2224 | *-NH-CH2-(cyclohexane-1,3-diyl)-CH2-NH2 | 4-benzyloxyphenyl | benzyl | 57.4 | 4.64 | 541.34 |
| 2225 | *-NH-CH2-(cyclohexane-1,3-diyl)-CH2-NH2 | 4-benzyloxyphenyl | 2-methoxyphenethyl | 69.1 | 4.34 | 585.37 |
| 2226 | *-NH-CH2-(cyclohexane-1,3-diyl)-CH2-NH2 | 4-benzyloxyphenyl | 2-trifluoromethylbenzyl | 64.6 | 5.36 | 609.35 |
| 2227 | *-NH-CH2-(cyclohexane-1,3-diyl)-CH2-NH2 | 4-benzyloxyphenyl | 4-nitroanilide-CH2 | 40.2 | 4.94 | 629.34 |
| 2228 | *-NH-CH2-(cyclohexane-1,3-diyl)-CH2-NH2 | 4-benzyloxyphenyl | 3-phenylpropyl | 62.6 | 4.57 | 569.3 |
| 2229 | *-NH-CH2-(cyclohexane-1,3-diyl)-CH2-NH2 | 4-benzyloxyphenyl | 4-chlorophenethyl | 68 | 4.72 | 589.31 |

-continued

| # | | | | | | |
|---|---|---|---|---|---|---|
| 2230 | *−NH−CH₂−(cyclohexyl)−CH₂−NH₂ | 4-benzyloxyphenyl | 2-thienylethyl | 61.2 | 4.44 | 561.31 |
| 2231 | *−NH−CH₂−(cyclohexyl)−CH₂−NH₂ | 4-benzyloxyphenyl | isopentyl | 61.2 | 4.37 | 521.36 |
| 2232 | *−NH−CH₂−(cyclohexyl)−CH₂−NH₂ | 4-benzyloxyphenyl | 2-biphenylmethyl | 80.7 | 5.02 | 617.37 |
| 2233 | *−NH−CH₂−(cyclohexyl)−CH₂−NH₂ | 4-benzyloxyphenyl | 2,6-dichlorophenethyl | 74.2 | 4.77 | 623.28 |
| 2234 | *−NH−CH₂−(cyclohexyl)−CH₂−NH₂ | 2-bromophenyl | benzyl | 68.1 | 4.99 | 513.23 |
| 2235 | *−NH−CH₂−(cyclohexyl)−CH₂−NH₂ | 2-bromophenyl | 2-methoxyphenethyl | 66.1 | 4.98 | 557.22 |
| 2236 | *−NH−CH₂−(cyclohexyl)−CH₂−NH₂ | 2-bromophenyl | 2-(trifluoromethyl)benzyl | 68.8 | 5.38 | 581.20 |
| 2237 | *−NH−CH₂−(cyclohexyl)−CH₂−NH₂ | 2-bromophenyl | (4-nitrophenyl)carbamoylmethyl | 69.7 | 4.9 | 601.19 |
| 2238 | *−NH−CH₂−(cyclohexyl)−CH₂−NH₂ | 2-bromophenyl | 3-phenylpropyl | 67.1 | 5.27 | 541.23 |

-continued
| | | | | | | |
|---|---|---|---|---|---|---|
| 2239 | 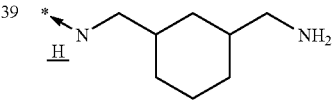 | 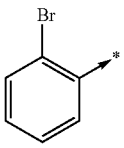 | 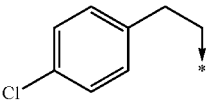 | 72.6 | 5.45 | 561.16 |
| 2240 | 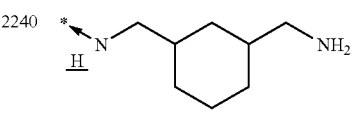 | 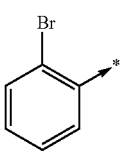 | 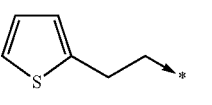 | 75.6 | 5.09 | 533.17 |
| 2241 | 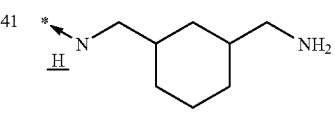 | 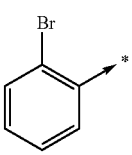 | 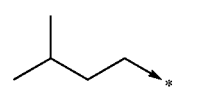 | 74.6 | 5.08 | 493.26 |
| 2242 | 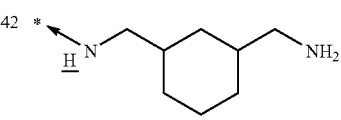 | 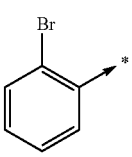 | 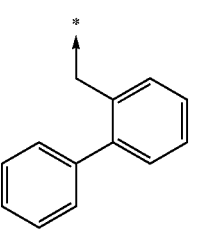 | 74.2 | 5.6 | 589.22 |
| 2243 | 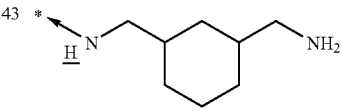 | 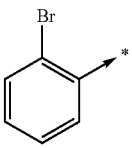 | 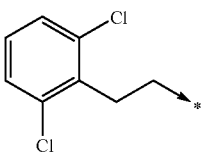 | 70 | 5.48 | 595.14 |
| 2244 | 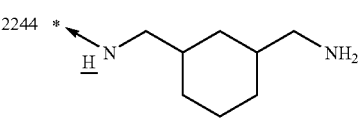 | 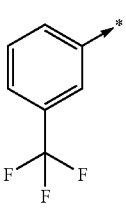 | 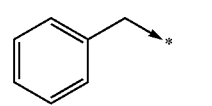 | 63.2 | 5.24 | 503.32 |
| 2245 | 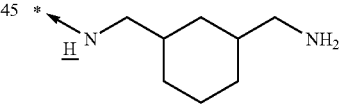 | 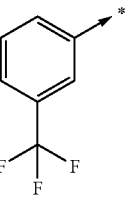 | 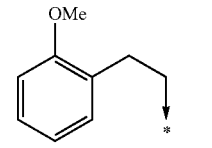 | 61.1 | 5.1 | 547.30 |
| 2246 | 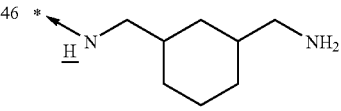 | 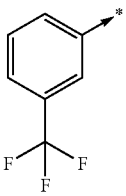 | 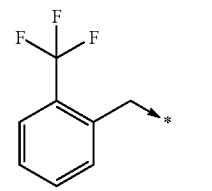 | 63.3 | 5.65 | 571.25 |

-continued
| | | | | | | |
|---|---|---|---|---|---|---|
| 2247 | 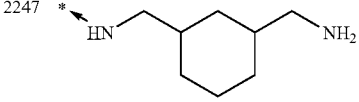 | 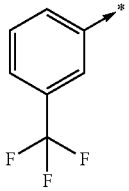 | 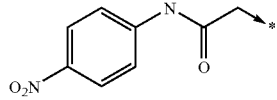 | 63.7 | 5.15 | 591.28 |
| 2248 | 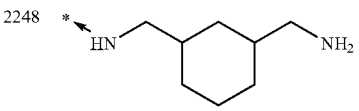 | 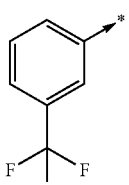 | 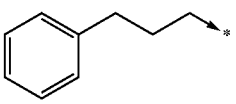 | 67.2 | 5.46 | 531.31 |
| 2249 | 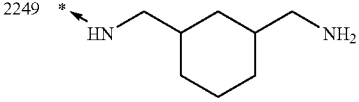 | 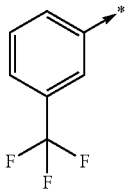 | 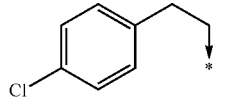 | 76 | 5.58 | 551.24 |
| 2250 | 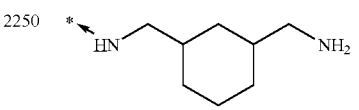 | 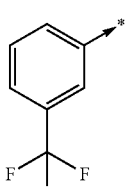 | 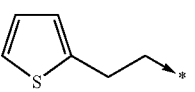 | 60.2 | 5.25 | 523.26 |
| 2251 | 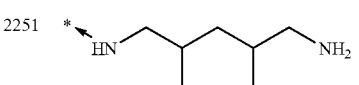 | 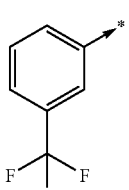 | 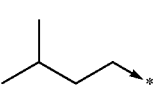 | 58.8 | 5.24 | 483.3 |
| 2252 | 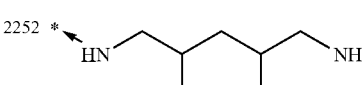 | 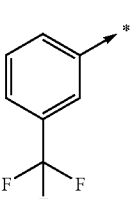 | 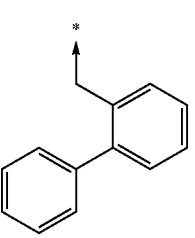 | 72.1 | 5.76 | 579.31 |
| 2253 | 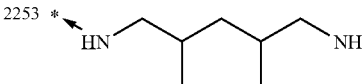 | 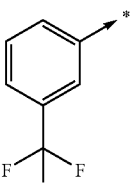 | 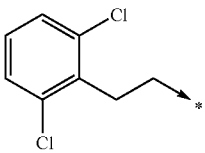 | 65.2 | 5.66 | 585.20 |

-continued
| | | | | | | |
|---|---|---|---|---|---|---|
| 2254 | 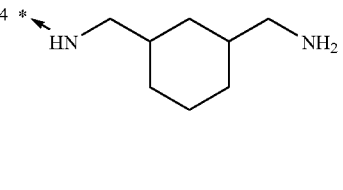 | 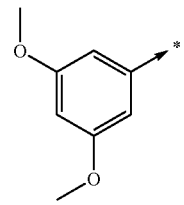 | 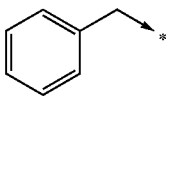 | 36 | 4.36 | 495.33 |
| 2255 | 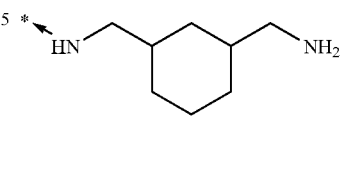 | 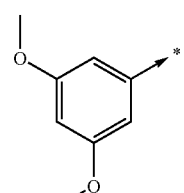 | 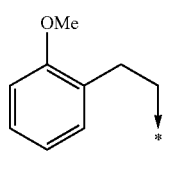 | 58.6 | 3.97 | 539.36 |
| 2256 | 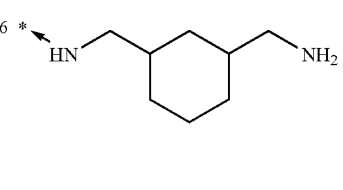 | 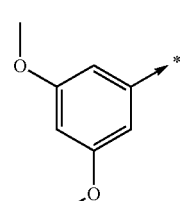 | 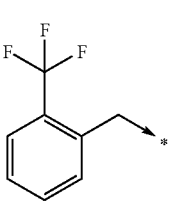 | 70 | 5.0 | 563.28 |
| 2257 | 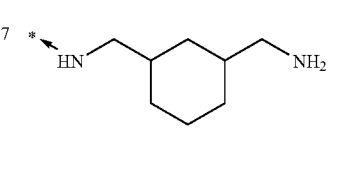 | 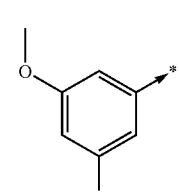 | 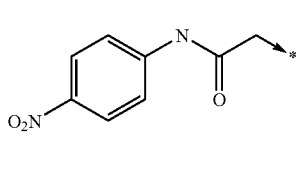 | 50.2 | 4.55 | 583.28 |
| 2258 | 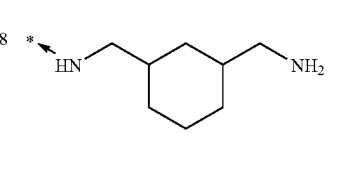 | 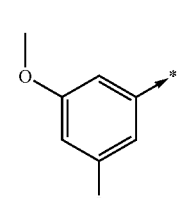 | 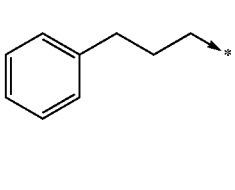 | 43.2 | 4.34 | 523.35 |
| 2259 | 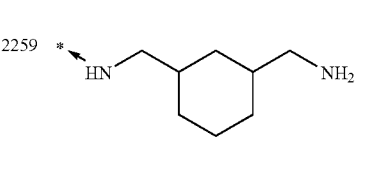 | 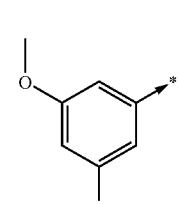 | 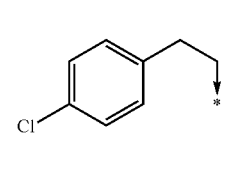 | 52 | 4.53 | 543.29 |
| 2260 | 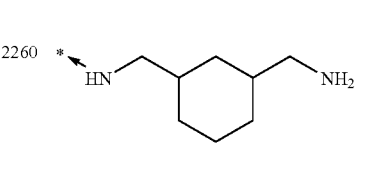 | 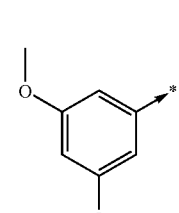 | 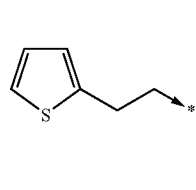 | 52.1 | 4.16 | 515.30 |

-continued

| # | R1 | R2 | R3 | a | b | c |
|---|---|---|---|---|---|---|
| 2261 | cyclohexane-1,3-diyldimethanamine (mono-substituted) | 3,5-dimethoxyphenyl | isopentyl | 46.2 | 4.07 | 475.38 |
| 2262 | cyclohexane-1,3-diyldimethanamine (mono-substituted) | 3,5-dimethoxyphenyl | 2-biphenylmethyl | 55.2 | 4.82 | 571.33 |
| 2263 | cyclohexane-1,3-diyldimethanamine (mono-substituted) | 3,5-dimethoxyphenyl | 2-(2,6-dichlorophenyl)ethyl | 51.5 | 4.63 | 577.22 |
| 2264 | hexane-1,6-diamine | 2-isopropylphenyl | phenethyl | 81.1 | 4.49 | 465.35 |
| 2265 | hexane-1,6-diamine | 2-isopropylphenyl | 2-phenoxyethyl | 84.1 | 4.7 | 481.36 |
| 2266 | hexane-1,6-diamine | 2-isopropylphenyl | 3,3-dimethylbutyl | 65.7 | 4.78 | 445.36 |
| 2267 | hexane-1,6-diamine | 2-isopropylphenyl | 2-propynyl | 63.0 | 4.51 | 399.29 |
| 2268 | hexane-1,6-diamine | 2-isopropylphenyl | 3,3-diphenylpropyl | 77.8 | 5.39 | 555.37 |

-continued

| | 701 | | | 702 | | | |
|---|---|---|---|---|---|---|---|
| 2269 | *HN~~~~~NH | isopropyl-phenyl-* | 2-Cl-benzyl-* | 78.5 | 5.21 | 485.32 |
| 2270 | *HN~~~~~NH | isopropyl-phenyl-* | 2-phenoxy-phenethyl-* | 74.0 | 5.02 | 557.37 |
| 2271 | *HN~~~~~NH | isopropyl-phenyl-* | 2,3-dimethoxy-benzyl-* | 78.1 | 4.38 | 525.37 |
| 2272 | *HN~~~~~NH | isopropyl-phenyl-* | 3-biphenyl-methyl-* | 89.2 | 5.42 | 527.38 |
| 2273 | *HN~~~~~NH | isopropyl-phenyl-* | 3-CF3-5-F-benzyl-* | 83.0 | 5.75 | 537.30 |
| 2274 | *HN~~~~~NH | 2,4,6-trichloro-phenyl-* | phenethyl-* | 67.8 | 5.87 | 525.21 |
| 2275 | *HN~~~~~NH | 2,4,6-trichloro-phenyl-* | 2-phenoxy-ethyl-* | 83.2 | 5.75 | 541.16 |
| 2276 | *HN~~~~~NH | 2,4,6-trichloro-phenyl-* | neopentyl-* | 71.9 | 6.11 | 505.25 |
| 2277 | *HN~~~~~NH | 2,4,6-trichloro-phenyl-* | propargyl-* | 70.5 | 5.14 | 459.15 |

-continued
| | | | | | | |
|---|---|---|---|---|---|---|
| 2278 | 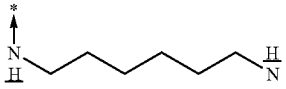 | 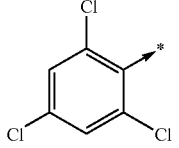 | 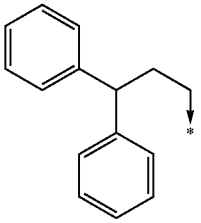 | 74.6 | 6.44 | 615.23 |
| 2279 | 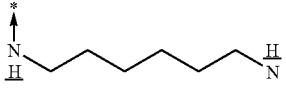 | 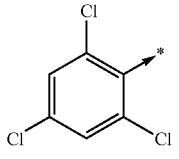 | 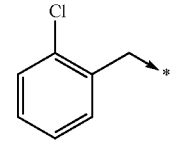 | 71.5 | 5.88 | 545.10 |
| 2280 | 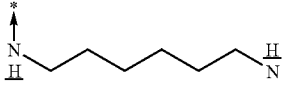 | 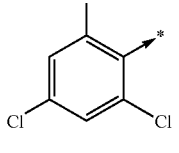 | 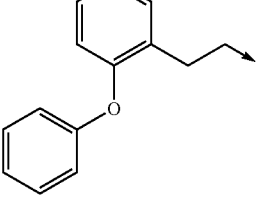 | 80.2 | 6.43 | 617.19 |
| 2281 | 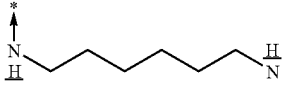 | 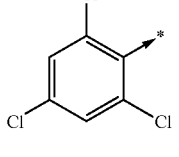 | 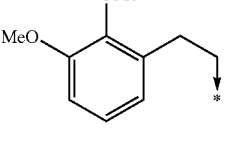 | 93.4 | 5.82 | 585.18 |
| 2282 | 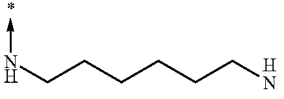 | 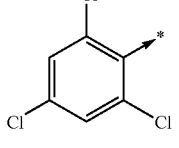 | 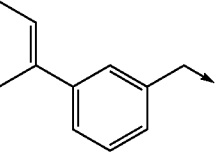 | 74.9 | 6.28 | 587.19 |
| 2283 | 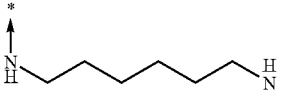 | 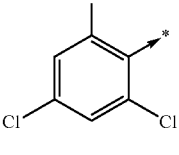 | 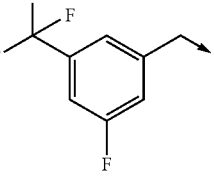 | 68.3 | 6.24 | 597.14 |
| 2284 | 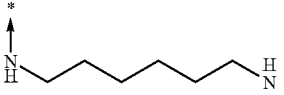 | 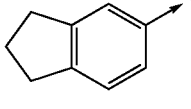 | 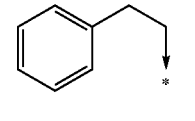 | 65.8 | 4.02 | 463.35 |
| 2285 | 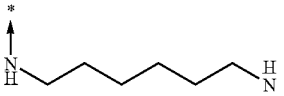 | 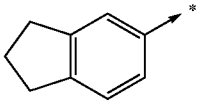 | 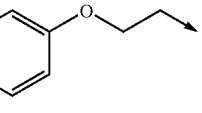 | 75.8 | 4.22 | 479.33 |
| 2286 | 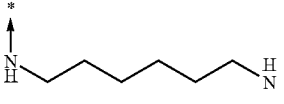 | 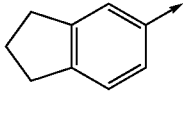 | 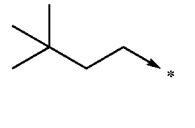 | 69.0 | 4.21 | 443.37 |

-continued

| # | R1 | R2 | R3 | a | b | c |
|---|---|---|---|---|---|---|
| 2287 | *-NH-(CH2)6-NH-* | indanyl-* | HC≡C-CH2-* | 4.2 | 4.36 | 397.33 |
| 2288 | *-NH-(CH2)6-NH-* | indanyl-* | Ph2CH-CH2-CH2-* | 82.7 | 4.74 | 553.37 |
| 2289 | *-NH-(CH2)6-NH-* | indanyl-* | 2-Cl-C6H4-CH2-* | 89.8 | 4.62 | 483.29 |
| 2290 | *-NH-(CH2)6-NH-* | indanyl-* | 2-PhO-C6H4-CH2-CH2-* | 77.2 | 4.52 | 555.33 |
| 2291 | *-NH-(CH2)6-NH-* | indanyl-* | 2,3-(MeO)2-C6H3-CH2-CH2-* | 69.3 | 3.98 | 523.35 |
| 2292 | *-NH-(CH2)6-NH-* | indanyl-* | 3-Ph-C6H4-CH2-* | 73.3 | 4.98 | 525.34 |
| 2293 | *-NH-(CH2)6-NH-* | indanyl-* | 3,5-(F,CF3)-C6H3-CH2-* | 73.1 | 5.44 | 535.29 |
| 2294 | *-NH-(CH2)6-NH-* | 2-Me-4-NO2-C6H3-* | PhCH2CH2-* | 59.4 | 5.14 | 482.30 |

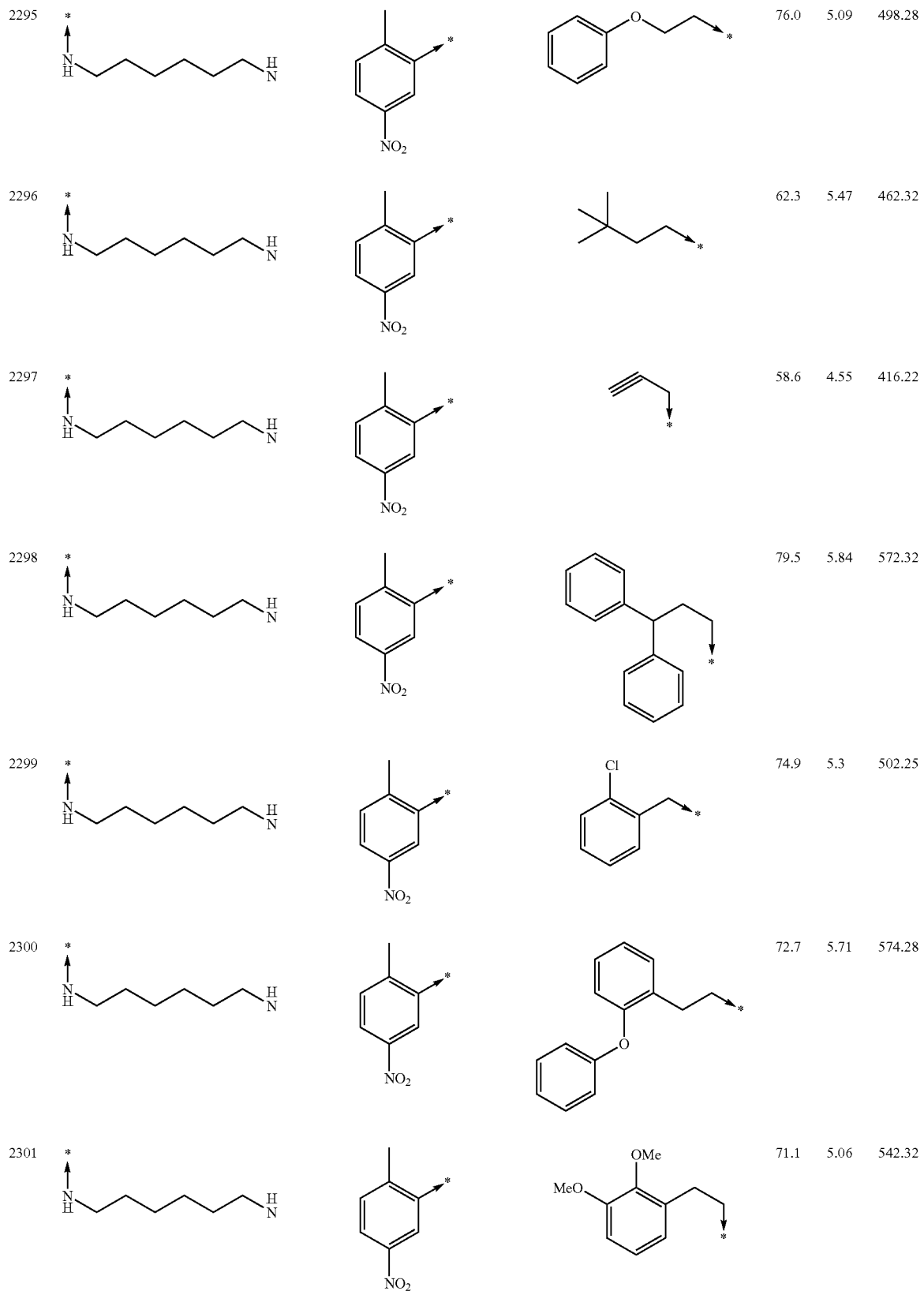

-continued

| | | | | | | |
|---|---|---|---|---|---|---|
| 2302 | *–NH–(CH₂)₆–NH–* | 4-NO₂-2-methylphenyl | 3-biphenylmethyl | 73.0 | 5.66 | 544.29 |
| 2303 | *–NH–(CH₂)₆–NH–* | 4-NO₂-2-methylphenyl | 3-fluoro-5-(trifluoromethyl)benzyl | 64.6 | 5.62 | 554.24 |
| 2304 | piperazinyl–* | 2-isopropylphenyl | phenethyl | 92.2 | 4.62 | 435.30 |
| 2305 | piperazinyl–* | 2-isopropylphenyl | 2-phenoxyethyl | 90.1 | 4.67 | 451.29 |
| 2306 | H-piperazinyl–* | 2-isopropylphenyl | 3,3-dimethylbutyl | 84.3 | 4.76 | 415.32 |
| 2307 | H-piperazinyl–* | 2-isopropylphenyl | 3-butynyl | 43.7 | 4.34 | 369.27 |
| 2308 | H-piperazinyl–* | 2-isopropylphenyl | 3,3-diphenylpropyl | 83.7 | 5.44 | 525.34 |
| 2309 | H-piperazinyl–* | 2-isopropylphenyl | 2-chlorobenzyl | 80.3 | 4.96 | 455.25 |

|  |  |  |  |  |  |  |
|---|---|---|---|---|---|---|
| 2310 | piperazine-NH | isopropylphenyl | 2-phenoxyphenethyl | 83.7 | 5.26 | 527.32 |
| 2311 | piperazine-NH | isopropylphenyl | 2,3-dimethoxyphenethyl | 82.8 | 4.64 | 495.34 |
| 2312 | piperazine-NH | isopropylphenyl | biphenyl-3-ylmethyl | 94.1 | 5.44 | 497.32 |
| 2313 | piperazine-NH | isopropylphenyl | 3-fluoro-5-(trifluoromethyl)benzyl | 90.1 | 5.55 | 507.29 |
| 2314 | piperazine-NH | 2,4,6-trichlorophenyl | phenethyl | 64.7 | 5.62 | 495.16 |
| 2315 | piperazine-NH | 2,4,6-trichlorophenyl | 2-phenoxyethyl | 50.7 | 5.54 | 511.15 |
| 2316 | piperazine-NH | 2,4,6-trichlorophenyl | 3,3-dimethylbutyl | 78.0 | 5.8 | 475.22 |
| 2317 | piperazine-NH | 2,4,6-trichlorophenyl | propargyl | 20.9 | 4.86 | 429.14 |

-continued

| | | | | | | |
|---|---|---|---|---|---|---|
| 2318 | piperazine-NH | 2,4,6-trichlorophenyl | 3,3-diphenylpropyl | 79.2 | 6.27 | 585.15 |
| 2319 | piperazine-NH | 2,4,6-trichlorophenyl | 2-chlorobenzyl | 46.3 | 5.58 | 515.12 |
| 2320 | piperazine-NH | 2,4,6-trichlorophenyl | 2-(2-phenoxyphenyl)ethyl | 84.1 | 6.23 | 587.20 |
| 2321 | piperazine-NH | 2,4,6-trichlorophenyl | 2-(2,3-dimethoxyphenyl)ethyl | 91.1 | 5.64 | 555.18 |
| 2322 | piperazine-NH | 2,4,6-trichlorophenyl | biphenyl-3-ylmethyl | 67.8 | 6.07 | 557.22 |
| 2323 | piperazine-NH | 2,4,6-trichlorophenyl | 3-fluoro-5-(trifluoromethyl)benzyl | 23.9 | 5.96 | 567.17 |
| 2324 | piperazine-NH | indan-5-yl | 2-phenylethyl | 68.1 | 4.02 | 433.40 |
| 2325 | piperazine-NH | indan-5-yl | 2-phenoxyethyl | 65.6 | 4.2 | 449.38 |
| 2326 | piperazine-NH | indan-5-yl | 3,3-dimethylbutyl | 83.5 | 4.14 | 413.39 |

-continued

| | | | | | | |
|---|---|---|---|---|---|---|
| 2327 | piperazine (NH) | indane | propargyl | 36.4 | 3.94 | 367.35 |
| 2328 | piperazine (NH) | indane | 3,3-diphenylpropyl | 87.5 | 4.82 | 523.39 |
| 2329 | piperazine (NH) | indane | 2-chlorobenzyl | 65.1 | 4.42 | 453.33 |
| 2330 | piperazine (NH) | indane | 2-phenoxyphenethyl | 91.7 | 4.59 | 525.37 |
| 2331 | piperazine (NH) | indane | 2,3-dimethoxyphenethyl | 81.5 | 4.01 | 493.40 |
| 2332 | piperazine (NH) | indane | 3-biphenylmethyl | 73.9 | 4.96 | 495.39 |
| 2333 | piperazine (NH) | indane | 3-fluoro-5-(trifluoromethyl)benzyl | 72.7 | 5.3 | 505.33 |
| 2334 | piperazine (NH) | 2-methyl-4-nitrophenyl | phenethyl | 79.9 | 4.93 | 425.35 |

-continued

| # | | | | | | |
|---|---|---|---|---|---|---|
| 2335 | piperazine-NH | 2-methyl-4-nitrophenyl | phenoxyethyl | 81.8 | 4.88 | 468.33 |
| 2336 | piperazine-NH | 2-methyl-4-nitrophenyl | 3,3-dimethylbutyl | 85.9 | 5.17 | 432.36 |
| 2337 | piperazine-NH | 2-methyl-4-nitrophenyl | propargyl | 36.2 | 4.25 | 386.28 |
| 2338 | piperazine-NH | 2-methyl-4-nitrophenyl | 3,3-diphenylpropyl | 93.3 | 5.62 | 542.36 |
| 2339 | piperazine-NH | 2-methyl-4-nitrophenyl | 2-chlorobenzyl | 76.5 | 4.96 | 472.3 |
| 2340 | piperazine-NH | 2-methyl-4-nitrophenyl | 2-(2-phenoxyphenyl)ethyl | 84.9 | 5.53 | 544.34 |
| 2341 | piperazine-NH | 2-methyl-4-nitrophenyl | 2-(2,3-dimethoxyphenyl)ethyl | 80.6 | 4.96 | 512.34 |

-continued
| | | | | | | |
|---|---|---|---|---|---|---|
| 2342 | 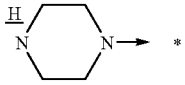 | 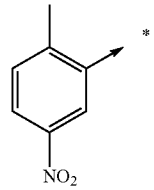 | 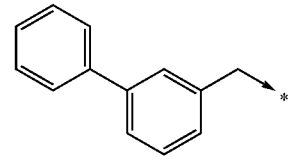 | 79.6 | 5.42 | 514.35 |
| 2343 | 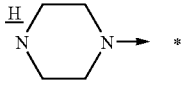 | 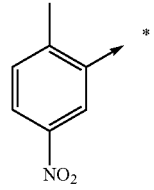 | 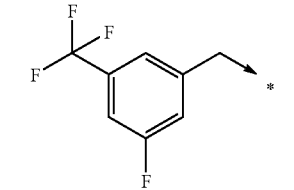 | 64.9 | 5.34 | 524.27 |
| 2344 |  | 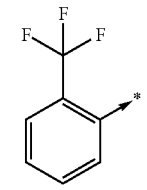 | 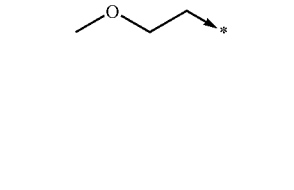 | 76.9 | 4.54 | 431.32 |
| 2345 |  | 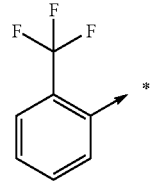 | 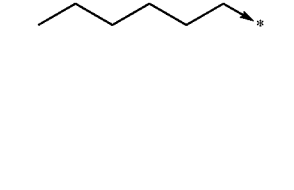 | 80.7 | 5.47 | 457.38 |
| 2346 |  | 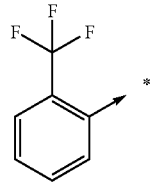 | 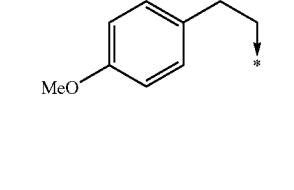 | 82.2 | 5.19 | 507.34 |
| 2347 |  | 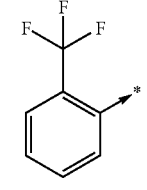 | 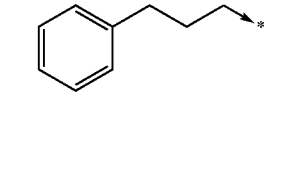 | 82.1 | 5.38 | 491.35 |
| 2348 | 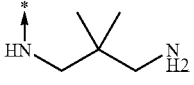 | 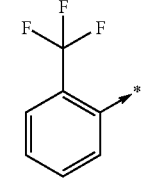 | 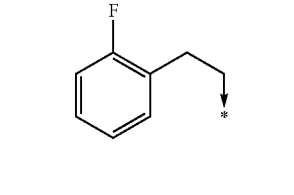 | 76.7 | 5.2 | 495.30 |
| 2349 |  | 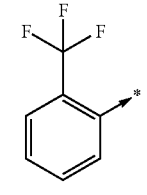 | 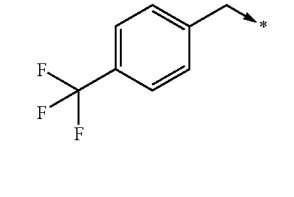 | 83.1 | 5.42 | 531.30 |

-continued
| | | | | | | |
|---|---|---|---|---|---|---|
| 2350 |  | 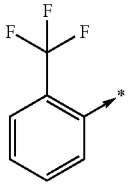 | 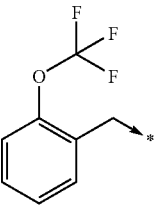 | 78.5 | 5.4 | 547.27 |
| 2351 |  | 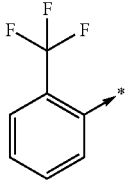 | 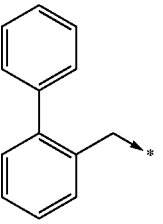 | 86.8 | 5.58 | 539.33 |
| 2352 |  | 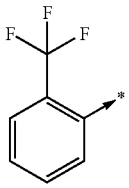 | 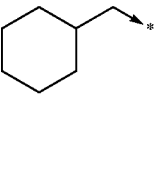 | 79.3 | 5.37 | 469.38 |
| 2353 |  | 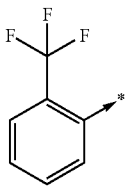 | 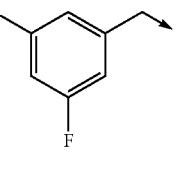 | 83.1 | 5.18 | 499.31 |
| 2354 |  | 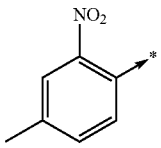 | 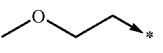 | 82.3 | 4.32 | 422.33 |
| 2355 |  | 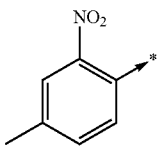 | 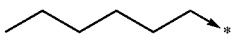 | 78.2 | 5.26 | 448.39 |
| 2356 |  | 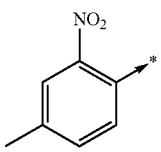 | 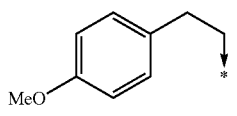 | 79.7 | 4.98 | 498.37 |
| 2357 |  | 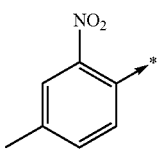 | 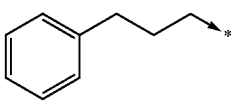 | 80.0 | 5.2 | 482.38 |

-continued
| | | | | | | |
|---|---|---|---|---|---|---|
| 2358 |  | 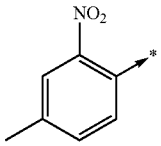 | 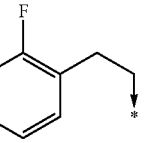 | 75.3 | 5.0 | 486.34 |
| 2359 |  | 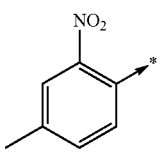 | 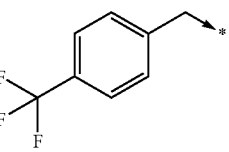 | 81.9 | 5.26 | 522.30 |
| 2360 |  | 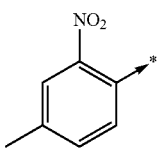 | 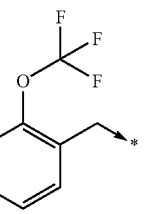 | 77.7 | 5.25 | 538.29 |
| 2361 |  | 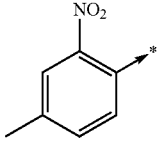 | 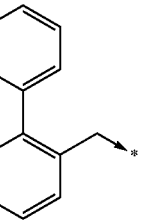 | 83.9 | 5.4 | 530.35 |
| 2362 |  | 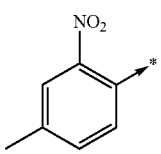 | 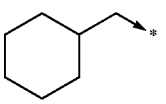 | 81.8 | 5.16 | 460.38 |
| 2363 |  | 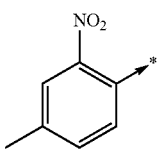 | 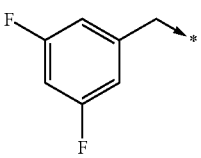 | 79.3 | 5.03 | 490.31 |
| 2364 |  | 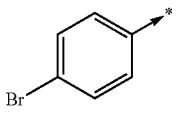 | 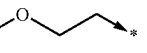 | 82.5 | 4.01 | 441.22 |
| 2365 |  | 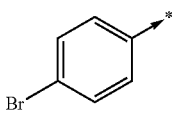 | 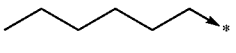 | 80.6 | 4.98 | 467.28 |
| 2366 |  | 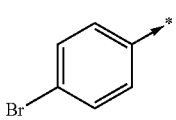 | 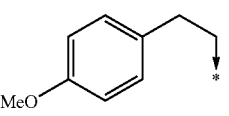 | 82.7 | 4.72 | 517.25 |
| 2367 |  | 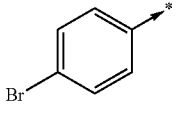 | 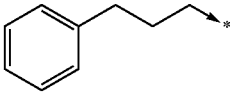 | 83.6 | 5.0 | 501.26 |

-continued

| | | | | | | |
|---|---|---|---|---|---|---|
| 2368 | HN-*  C(CH3)2  NH2 | 4-Br-C6H4-* | 2-F-C6H4-CH2-CH2-* | 84.3 | 4.9 | 505.23 |
| 2369 | HN-*  C(CH3)2  NH2 | 4-Br-C6H4-* | 4-CF3-C6H4-CH2-* | 82.5 | 5.48 | 541.19 |
| 2370 | HN-*  C(CH3)2  NH2 | 4-Br-C6H4-* | 2-(OCF3)-C6H4-CH2-* | 86.6 | 5.5 | 557.19 |
| 2371 | HN-*  C(CH3)2  NH2 | 4-Br-C6H4-* | 2-biphenyl-CH2-* | 85.4 | 5.53 | 549.24 |
| 2372 | HN-*  C(CH3)2  NH2 | 4-Br-C6H4-* | cyclohexyl-CH2-* | 82.3 | 4.9 | 479.30 |
| 2373 | HN-*  C(CH3)2  NH2 | 4-Br-C6H4-* | 3,5-F2-C6H3-CH2-* | 81.5 | 5.26 | 509.21 |
| 2374 | HN-*  C(CH3)2  NH2 | 3-(BnO)-C6H4-* | MeO-CH2-CH2-* | 83.4 | 4.23 | 469.37 |
| 2375 | HN-*  C(CH3)2  NH2 | 3-(BnO)-C6H4-* | n-hexyl-* | 82.3 | 4.94 | 495.40 |
| 2376 | HN-*  C(CH3)2  NH2 | 3-(BnO)-C6H4-* | 4-MeO-C6H4-CH2-CH2-* | 88.1 | 4.73 | 545.36 |

-continued

| | | | | | | |
|---|---|---|---|---|---|---|
| 2377 | H2N-CH2-C(CH3)2-CH2-NH-* | 3-(benzyloxy)phenyl-* | 3-phenylpropyl-* | 90.4 | 4.99 | 529.39 |
| 2378 | H2N-CH2-C(CH3)2-CH2-NH-* | 3-(benzyloxy)phenyl-* | 2-(2-fluorophenyl)ethyl-* | 90.6 | 4.92 | 533.35 |
| 2379 | H2N-CH2-C(CH3)2-CH2-NH-* | 3-(benzyloxy)phenyl-* | 4-(trifluoromethyl)benzyl-* | 85.2 | 5.62 | 569.33 |
| 2380 | H2N-CH2-C(CH3)2-CH2-NH-* | 3-(benzyloxy)phenyl-* | 2-(trifluoromethoxy)benzyl-* | 84.2 | 5.6 | 585.33 |
| 2381 | H2N-CH2-C(CH3)2-CH2-NH-* | 3-(benzyloxy)phenyl-* | biphenyl-2-ylmethyl-* | 85.0 | 5.54 | 577.38 |
| 2382 | H2N-CH2-C(CH3)2-CH2-NH-* | 3-(benzyloxy)phenyl-* | cyclohexylmethyl-* | 80.6 | 4.87 | 507.41 |
| 2383 | H2N-CH2-C(CH3)2-CH2-NH-* | 3-(benzyloxy)phenyl-* | 3,5-difluorobenzyl-* | 85.9 | 5.42 | 537.34 |
| 2384 | 1,4-diazepan-1-yl-* | 2-(trifluoromethyl)phenyl-* | hexyl-* | 74.2 | 5.32 | 455.34 |

-continued
| | | | | | | |
|---|---|---|---|---|---|---|
| 2385 | 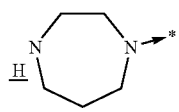 |  | 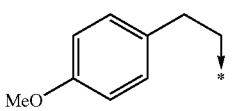 | 92.3 | 5.1 | 505.32 |
| 2386 | 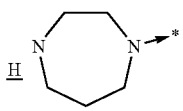 | 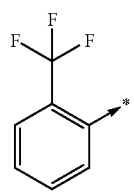 | 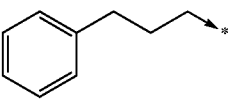 | 78.4 | 5.23 | 489.33 |
| 2387 |  | 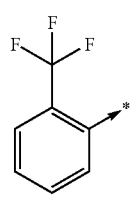 | 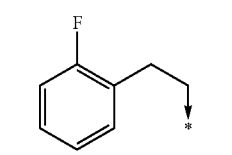 | 71.3 | 5.12 | 493.32 |
| 2388 | 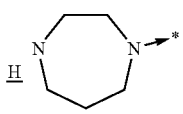 |  | 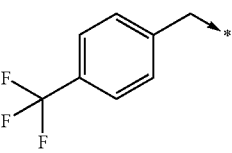 | 74.4 | 5.32 | 529.27 |
| 2389 | 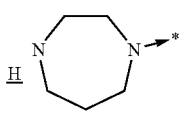 | 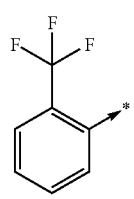 | 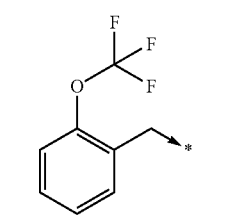 | 68.8 | 5.29 | 545.25 |
| 2390 |  |  | 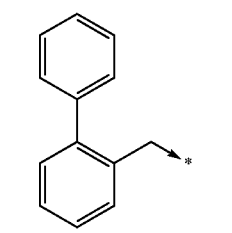 | 77.7 | 5.44 | 537.33 |
| 2391 | 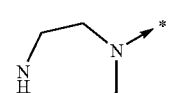 | 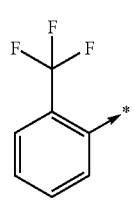 | 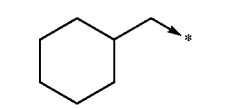 | 80.7 | 5.24 | 467.36 |

-continued

| | | | | | | |
|---|---|---|---|---|---|---|
| 2392 | homopiperazine | 2-(trifluoromethyl)phenyl | 3,5-difluorobenzyl | 63.3 | 5.04 | 497.30 |
| 2393 | homopiperazine | 4-methyl-2-nitrophenyl | 2-methoxyethyl | 87.4 | 4.16 | 420.33 |
| 2394 | homopiperazine | 4-methyl-2-nitrophenyl | n-hexyl | 82.7 | 5.12 | 446.38 |
| 2395 | homopiperazine | 4-methyl-2-nitrophenyl | 4-methoxyphenethyl | 82.4 | 4.88 | 496.35 |
| 2396 | homopiperazine | 4-methyl-2-nitrophenyl | 3-phenylpropyl | 78.0 | 5.04 | 480.37 |
| 2397 | homopiperazine | 4-methyl-2-nitrophenyl | 2-fluorophenethyl | 75.9 | 4.9 | 484.33 |
| 2398 | homopiperazine | 4-methyl-2-nitrophenyl | 4-(trifluoromethyl)benzyl | 71.5 | 5.16 | 520.29 |
| 2399 | homopiperazine | 4-methyl-2-nitrophenyl | 2-(trifluoromethoxy)benzyl | 65.4 | 5.12 | 536.30 |
| 2400 | homopiperazine | 4-methyl-2-nitrophenyl | 2-phenylbenzyl | 76.0 | 5.28 | 528.33 |

-continued

| | | | | | | |
|---|---|---|---|---|---|---|
| 2401 | homopiperazine (NH) | 2-NO₂-4-methylphenyl | cyclohexylmethyl | 93.8 | 5.03 | 458.38 |
| 2402 | homopiperazine (NH) | 2-NO₂-4-methylphenyl | 3,5-difluorobenzyl | 69.2 | 4.88 | 488.30 |
| 2403 | homopiperazine (NH) | 4-bromophenyl | 2-methoxyethyl | 68.3 | 3.88 | 439.23 |
| 2404 | homopiperazine (NH) | 4-bromophenyl | n-hexyl | 70.8 | 4.89 | 465.28 |
| 2405 | homopiperazine (NH) | 4-bromophenyl | 4-methoxyphenethyl | 76.2 | 4.72 | 515.23 |
| 2406 | homopiperazine (NH) | 4-bromophenyl | 3-phenylpropyl | 76.5 | 4.88 | 499.27 |
| 2407 | homopiperazine (NH) | 4-bromophenyl | 2-fluorophenethyl | 90.1 | 4.88 | 503.26 |
| 2408 | homopiperazine (NH) | 4-bromophenyl | 4-trifluoromethylbenzyl | 78.8 | 5.36 | 539.19 |
| 2409 | homopiperazine (NH) | 4-bromophenyl | 2-trifluoromethoxybenzyl | 76.1 | 5.31 | 555.17 |
| 2410 | homopiperazine (NH) | 4-bromophenyl | 2-phenylbenzyl | 80.5 | 5.29 | 547.22 |

-continued

| # | R1 | R2 | R3 | a | b | c |
|---|---|---|---|---|---|---|
| 2411 | homopiperazine-NH | 4-Br-phenyl | cyclohexylmethyl | 68.2 | 4.86 | 477.30 |
| 2412 | homopiperazine-NH | 4-Br-phenyl | 3,5-difluorobenzyl | 55.7 | 5.1 | 507.20 |
| 2413 | homopiperazine-NH | 3-benzyloxyphenyl | 2-methoxyethyl | 69.2 | 4.12 | 467.36 |
| 2414 | homopiperazine-NH | 3-benzyloxyphenyl | n-hexyl | 73.6 | 4.85 | 493.41 |
| 2415 | homopiperazine-NH | 3-benzyloxyphenyl | 4-methoxyphenethyl | 73.9 | 4.72 | 543.36 |
| 2416 | homopiperazine-NH | 3-benzyloxyphenyl | 3-phenylpropyl | 73.4 | 4.87 | 527.39 |
| 2417 | homopiperazine-NH | 3-benzyloxyphenyl | 2-fluorophenethyl | 90.6 | 4.92 | 531.36 |
| 2418 | homopiperazine-NH | 3-benzyloxyphenyl | 4-trifluoromethylbenzyl | 71.6 | 5.5 | 567.32 |
| 2419 | homopiperazine-NH | 3-benzyloxyphenyl | 2-(trifluoromethoxy)benzyl | 60.5 | 5.4 | 583.32 |

-continued

| Ex. | | | | Purity (%) | rt (min.) | [M + H]+ |
|---|---|---|---|---|---|---|
| 2420 | homopiperazine-H | 3-benzyloxyphenyl | 2-biphenylmethyl | 60.8 | 5.29 | 575.36 |
| 2421 | homopiperazine-H | 3-benzyloxyphenyl | cyclohexylmethyl | 58.8 | 4.82 | 505.39 |
| 2422 | homopiperazine-H | 3-benzyloxyphenyl | 3,5-difluorobenzyl | 54.7 | 5.29 | 535.31 |

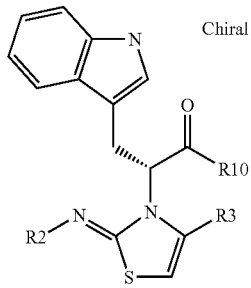

Chiral

| Ex. | R10 | R2 | R3 | Purity (%) | rt (min.) | [M + H]+ |
|---|---|---|---|---|---|---|
| 2423 | $H_2N$-propyl-NH-* | phenyl | t-butyl | 79.8 | 3.66 | 476.30 |
| 2424 | $H_2N$-propyl-NH-* | phenyl | phenyl | 59.3 | 3.68 | 496.26 |
| 2425 | $H_2N$-propyl-NH-* | phenyl | 4-(trifluoromethoxy)phenyl | 60.5 | 4.2 | 580.22 |
| 2426 | $H_2N$-propyl-NH-* | phenyl | 2,3-dihydrobenzo[1,4]dioxin-6-yl | 52.7 | 3.68 | 554.24 |
| 2427 | $H_2N$-propyl-NH-* | 3-methylphenyl | t-butyl | 72.3 | 3.87 | 490.30 |

-continued

| | | | | | | |
|---|---|---|---|---|---|---|
| 2428 | H2N~~~N(H)* | 3-methylphenyl* | phenyl* | 63.8 | 3.85 | 510.26 |
| 2429 | H2N~~~N(H)* | 3-methylphenyl* | 4-(trifluoromethoxy)phenyl* | 63.0 | 4.34 | 594.23 |
| 2430 | H2N~~~N(H)* | 3-methylphenyl* | 2,3-dihydro-1,4-benzodioxin-6-yl* | 54.1 | 3.82 | 568.25 |
| 2431 | H2N~~~~N(H)* | phenyl* | tert-butyl* | 76.9 | 3.72 | 490.30 |
| 2432 | H2N~~~~N(H)* | phenyl* | phenyl* | 70.7 | 3.73 | 510.26 |
| 2433 | H2N~~~~N(H)* | phenyl* | 4-(trifluoromethoxy)phenyl* | 69.1 | 4.23 | 594.24 |
| 2434 | H2N~~~~N(H)* | phenyl* | 2,3-dihydro-1,4-benzodioxin-6-yl* | 52.7 | 3.72 | 568.24 |
| 2435 | H2N~~~~N(H)* | 3-methylphenyl* | tert-butyl* | 76.6 | 3.92 | 504.32 |
| 2436 | H2N~~~~N(H)* | 3-methylphenyl* | phenyl* | 64.8 | 3.9 | 524.28 |
| 2437 | H2N~~~~N(H)* | 3-methylphenyl* | 4-(trifluoromethoxy)phenyl* | 66.2 | 4.37 | 608.24 |
| 2438 | H2N~~~~N(H)* | 3-methylphenyl* | 2,3-dihydro-1,4-benzodioxin-6-yl* | 59.3 | 3.86 | 582.27 |

| | | | | | | |
|---|---|---|---|---|---|---|
| 2439 | NH2-CH2-cyclohexyl-CH2-NH-* | phenyl-* | tert-butyl-* | 74.3 | 3.9 | 544.32 |
| 2440 | NH2-CH2-cyclohexyl-CH2-NH-* | phenyl-* | phenyl-* | 65.4 | 3.91 | 564.29 |
| 2441 | NH2-CH2-cyclohexyl-CH2-NH-* | phenyl-* | 4-(trifluoromethoxy)phenyl-* | 63.8 | 4.41 | 648.30 |
| 2442 | NH2-CH2-cyclohexyl-CH2-NH-* | phenyl-* | 2,3-dihydrobenzo[1,4]dioxin-6-yl-* | 57.6 | 3.92 | 622.31 |
| 2443 | NH2-CH2-cyclohexyl-CH2-NH-* | 3-methylphenyl-* | tert-butyl-* | 77.8 | 4.09 | 558.34 |
| 2444 | NH2-CH2-cyclohexyl-CH2-NH-* | 3-methylphenyl-* | phenyl-* | 65.5 | 4.08 | 578.30 |
| 2445 | NH2-CH2-cyclohexyl-CH2-NH-* | 3-methylphenyl-* | 4-(trifluoromethoxy)phenyl-* | 64.3 | 4.5 | 662.31 |
| 2446 | NH2-CH2-cyclohexyl-CH2-NH-* | 3-methylphenyl-* | 2,3-dihydrobenzo[1,4]dioxin-6-yl-* | 47.6 | 4.04 | 636.36 |
| 2447 | H2N-CH2-(3-phenylene)-CH2-NH-* | phenyl-* | tert-butyl-* | 78.6 | 3.88 | 538.28 |
| 2448 | H2N-CH2-(3-phenylene)-CH2-NH-* | phenyl-* | phenyl-* | 61.2 | 3.9 | 558.24 |

-continued

| # | R1 | R2 | R3 | % | x | MW |
|---|---|---|---|---|---|---|
| 2449 | 3-(aminomethyl)benzyl-NH- | phenyl | 4-(trifluoromethoxy)phenyl | 59.8 | 4.38 | 642.27 |
| 2450 | 3-(aminomethyl)benzyl-NH- | phenyl | 2,3-dihydro-1,4-benzodioxin-6-yl | 48.4 | 3.88 | 616.30 |
| 2451 | 3-(aminomethyl)benzyl-NH- | 3-methylphenyl | tert-butyl | 79.9 | 4.06 | 552.28 |
| 2452 | 3-(aminomethyl)benzyl-NH- | 3-methylphenyl | phenyl | 59.4 | 4.04 | 572.25 |
| 2453 | 3-(aminomethyl)benzyl-NH- | 3-methylphenyl | 4-(trifluoromethoxy)phenyl | 61.4 | 4.52 | 656.29 |
| 2454 | 3-(aminomethyl)benzyl-NH- | 3-methylphenyl | 2,3-dihydro-1,4-benzodioxin-6-yl | 50.0 | 4.02 | 630.31 |
| 2455 | piperazin-1-yl | phenyl | tert-butyl | 76.1 | 3.74 | 488.29 |
| 2456 | piperazin-1-yl | phenyl | phenyl | 88.3 | 3.72 | 508.25 |
| 2457 | piperazin-1-yl | phenyl | 4-(trifluoromethoxy)phenyl | 84.2 | 4.21 | 592.22 |
| 2458 | piperazin-1-yl | phenyl | 2,3-dihydro-1,4-benzodioxin-6-yl | 82.1 | 3.71 | 566.24 |
| 2459 | piperazin-1-yl | 3-methylphenyl | tert-butyl | 72.4 | 3.96 | 502.32 |

-continued
| | | | | | Purity (%) | rt (min.) | [M + H]+ |
|---|---|---|---|---|---|---|---|
| 2460 | 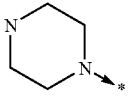 | 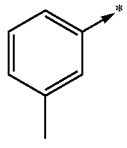 | | 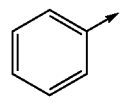 | 88.5 | 3.89 | 522.27 |
| 2461 | 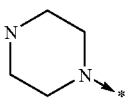 | 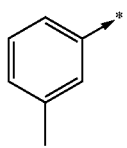 | | 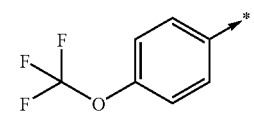 | 86.6 | 4.37 | 606.26 |
| 2462 | 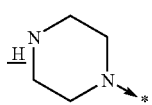 | 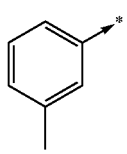 | | 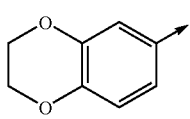 | 77.2 | 3.8 | 580.26 |
Chiral
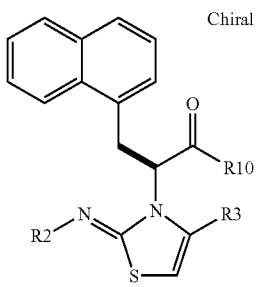
| Ex. | R10 | R2 | R3 | Purity (%) | rt (min.) | [M + H]+ |
|---|---|---|---|---|---|---|
| 2463 | 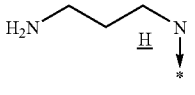 | 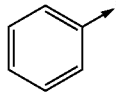 |  | 86.6 | 3.96 | 487.31 |
| 2464 | 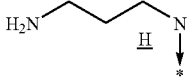 | 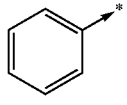 | 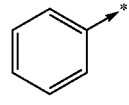 | 58.7 | 4 | 507.27 |
| 2465 | 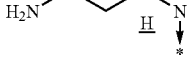 | 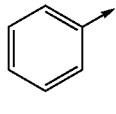 | 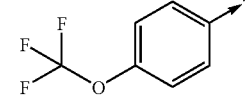 | 64.9 | 4.48 | 591.22 |
| 2466 | 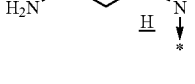 | 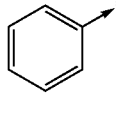 | 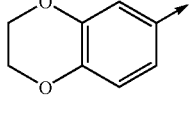 | 40.3 | 4 | 565.25 |
| 2467 |  | 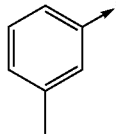 |  | 91.3 | 4.12 | 501.31 |

-continued

| | | | | | | |
|---|---|---|---|---|---|---|
| 2468 | H₂N~~~N(H)→* | 3-methylphenyl* | phenyl* | 61.2 | 4.14 | 521.25 |
| 2469 | H₂N~~~N(H)→* | 3-methylphenyl* | 4-(trifluoromethoxy)phenyl* | 62.4 | 4.62 | 605.25 |
| 2470 | H₂N~~~N(H)→* | 3-methylphenyl* | 2,3-dihydrobenzo[1,4]dioxin-6-yl* | 33.1 | 4.13 | 579.27 |
| 2471 | H₂N~~~~N(H)→* | phenyl* | tert-butyl* | 87.3 | 4.01 | 501.31 |
| 2472 | H₂N~~~~N(H)→* | phenyl* | phenyl* | 54.0 | 4.05 | 521.25 |
| 2473 | H₂N~~~~N(H)→* | phenyl* | 4-(trifluoromethoxy)phenyl* | 69.1 | 4.51 | 605.26 |
| 2474 | H₂N~~~~N(H)→* | phenyl* | 2,3-dihydrobenzo[1,4]dioxin-6-yl* | 35.4 | 4.04 | 579.27 |
| 2475 | H₂N~~~~N(H)→* | 3-methylphenyl* | tert-butyl* | 88.4 | 4.18 | 515.31 |
| 2476 | H₂N~~~~N(H)→* | 3-methylphenyl* | phenyl* | 68.0 | 4.19 | 535.28 |
| 2477 | H₂N~~~~N(H)→* | 3-methylphenyl* | 4-(trifluoromethoxy)phenyl* | 72.9 | 4.64 | 619.25 |
| 2478 | H₂N~~~~N(H)→* | 3-methylphenyl* | 2,3-dihydrobenzo[1,4]dioxin-6-yl* | 32.6 | 4.17 | 593.28 |

-continued

| | | | | | | |
|---|---|---|---|---|---|---|
| 2479 | 4-(aminomethyl)cyclohexyl-CH2-N(H)-* | phenyl-* | tert-butyl-* | 92.7 | 4.18 | 555.33 |
| 2480 | 4-(aminomethyl)cyclohexyl-CH2-N(H)-* | phenyl-* | phenyl-* | 59.4 | 4.24 | 575.29 |
| 2481 | 4-(aminomethyl)cyclohexyl-CH2-N(H)-* | phenyl-* | 4-(trifluoromethoxy)phenyl-* | 71.8 | 4.72 | 659.33 |
| 2482 | 4-(aminomethyl)cyclohexyl-CH2-N(H)-* | phenyl-* | 2,3-dihydro-1,4-benzodioxin-6-yl-* | 36.4 | 4.2 | 633.44 |
| 2483 | 4-(aminomethyl)cyclohexyl-CH2-N(H)-* | 3-methylphenyl-* | tert-butyl-* | 92.4 | 4.36 | 569.34 |
| 2484 | 4-(aminomethyl)cyclohexyl-CH2-N(H)-* | 3-methylphenyl-* | phenyl-* | 62.9 | 4.38 | 589.32 |
| 2485 | 4-(aminomethyl)cyclohexyl-CH2-N(H)-* | 3-methylphenyl-* | 4-(trifluoromethoxy)phenyl-* | 71.9 | 4.82 | 673.33 |
| 2486 | 4-(aminomethyl)cyclohexyl-CH2-N(H)-* | 3-methylphenyl-* | 2,3-dihydro-1,4-benzodioxin-6-yl-* | 32.2 | 4.36 | 647.19 |
| 2487 | 3-(aminomethyl)benzyl-N(H)-* | phenyl-* | tert-butyl-* | 90.2 | 4.14 | 549.28 |
| 2488 | 3-(aminomethyl)benzyl-N(H)-* | phenyl-* | phenyl-* | 59.7 | 4.22 | 569.24 |

-continued

| | | | | | | |
|---|---|---|---|---|---|---|
| 2489 | H₂N-CH₂-C₆H₄-CH₂-N(H)-* (meta) | phenyl | 4-(OCF₃)phenyl | 66.6 | 4.7 | 653.25 |
| 2490 | H₂N-CH₂-C₆H₄-CH₂-N(H)-* (meta) | phenyl | 2,3-dihydro-1,4-benzodioxin-6-yl | 34.5 | 4.22 | 627.27 |
| 2491 | H₂N-CH₂-C₆H₄-CH₂-N(H)-* (meta) | 3-methylphenyl | tert-butyl | 91.3 | 4.32 | 563.30 |
| 2492 | H₂N-CH₂-C₆H₄-CH₂-N(H)-* (meta) | 3-methylphenyl | phenyl | 60.8 | 4.35 | 583.26 |
| 2493 | H₂N-CH₂-C₆H₄-CH₂-N(H)-* (meta) | 3-methylphenyl | 4-(OCF₃)phenyl | 73.3 | 4.8 | 667.27 |
| 2494 | H₂N-CH₂-C₆H₄-CH₂-N(H)-* (meta) | 3-methylphenyl | 2,3-dihydro-1,4-benzodioxin-6-yl | 32.9 | 4.34 | 641.29 |
| 2495 | piperazin-1-yl | phenyl | tert-butyl | 60.4 | 3.94 | 499.30 |
| 2496 | piperazin-1-yl | phenyl | phenyl | 87.0 | 3.92 | 519.24 |
| 2497 | piperazin-1-yl | phenyl | 4-(OCF₃)phenyl | 84.4 | 4.41 | 603.24 |
| 2498 | piperazin-1-yl | phenyl | 2,3-dihydro-1,4-benzodioxin-6-yl | 81.4 | 3.94 | 577.26 |
| 2499 | piperazin-1-yl | 3-methylphenyl | tert-butyl | 73.9 | 4.12 | 513.31 |

-continued

| Ex. | | R2 | R3 | Purity (%) | rt (min.) | [M + H]+ |
|---|---|---|---|---|---|---|
| 2500 | piperazine-N-* | 3-methylphenyl-* | phenyl-* | 91.5 | 4.09 | 533.26 |
| 2501 | piperazine-N-* | 3-methylphenyl-* | 4-(trifluoromethoxy)phenyl-* | 89.6 | 4.54 | 617.26 |
| 2502 | piperazine-N-* | 3-methylphenyl-* | 2,3-dihydro-1,4-benzodioxin-6-yl-* | 85.4 | 4.09 | 591.27 |

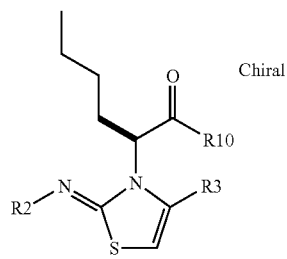

Chiral

| Ex. | R10 | R2 | R3 | Purity (%) | rt (min.) | [M + H]+ |
|---|---|---|---|---|---|---|
| 2503 | H2N-CH2-cyclohexyl-CH2-NH-* | phenyl-* | tert-butyl-* | 77.7 | 3.8 | 471.39 |
| 2504 | H2N-CH2-cyclohexyl-CH2-NH-* | phenyl-* | phenyl-* | 37.7 | 3.82 | 491.34 |
| 2505 | H2N-CH2-cyclohexyl-CH2-NH-* | phenyl-* | 4-chlorophenyl-* | 79.7 | 4.09 | 525.28 |
| 2506 | H2N-CH2-cyclohexyl-CH2-NH-* | phenyl-* | 2-naphthyl-* | 58.5 | 4.23 | 541.33 |
| 2507 | H2N-CH2-cyclohexyl-CH2-NH-* | 3-methylphenyl-* | tert-butyl-* | 84.6 | 4.0 | 485.38 |

-continued

| | | | | | | |
|---|---|---|---|---|---|---|
| 2508 | H2N-CH2-cyclohexyl-CH2-NH-* | 3-methylphenyl-* | phenyl-* | 73.2 | 4.0 | 505.34 |
| 2509 | H2N-CH2-cyclohexyl-CH2-NH-* | 3-methylphenyl-* | 4-chlorophenyl-* | 82.3 | 4.25 | 539.29 |
| 2510 | H2N-CH2-cyclohexyl-CH2-NH-* | 3-methylphenyl-* | 2-naphthyl-* | 74.2 | 4.37 | 555.34 |
| 2511 | H2N-(CH2)4-NH-* | phenyl-* | tert-butyl-* | 57.5 | 3.56 | 417.32 |
| 2512 | H2N-(CH2)4-NH-* | phenyl-* | phenyl-* | 66.9 | 3.56 | 437.27 |
| 2513 | H2N-(CH2)4-NH-* | phenyl-* | 4-chlorophenyl-* | 69.0 | 3.85 | 471.26 |
| 2514 | H2N-(CH2)4-NH-* | phenyl-* | 2-naphthyl-* | 71.1 | 4.0 | 487.33 |
| 2515 | H2N-(CH2)4-NH-* | 3-methylphenyl-* | tert-butyl-* | 76.4 | 3.76 | 431.34 |
| 2516 | H2N-(CH2)4-NH-* | 3-methylphenyl-* | phenyl-* | 67.8 | 3.75 | 451.30 |
| 2517 | H2N-(CH2)4-NH-* | 3-methylphenyl-* | 4-chlorophenyl-* | 75.2 | 4.02 | 485.27 |

-continued

| Ex. | R10 | R2 | R3 | Purity (%) | rt (min.) | [M + H]+ |
|---|---|---|---|---|---|---|
| 2518 | H2N-(CH2)4-NH-* | 3-methylphenyl* | 2-naphthyl* | 70.4 | 4.16 | 501.32 |

Chiral

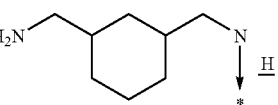

| Ex. | R10 | R2 | R3 | Purity (%) | rt (min.) | [M + H]+ |
|---|---|---|---|---|---|---|
| 2519 | H2N-CH2-(cyclohexyl-1,3)-CH2-NH-* | phenyl* | tert-butyl* | 76.4 | 3.73 | 471.38 |
| 2520 | H2N-CH2-(cyclohexyl-1,3)-CH2-NH-* | phenyl* | phenyl* | 67.9 | 3.76 | 491.33 |
| 2521 | H2N-CH2-(cyclohexyl-1,3)-CH2-NH-* | phenyl* | 4-Cl-phenyl* | 75.0 | 4.04 | 525.28 |
| 2522 | H2N-CH2-(cyclohexyl-1,3)-CH2-NH-* | phenyl* | 2-naphthyl* | 71.2 | 4.17 | 541.34 |
| 2523 | H2N-CH2-(cyclohexyl-1,3)-CH2-NH-* | 3-methylphenyl* | tert-butyl* | 87.9 | 3.94 | 485.39 |
| 2524 | H2N-CH2-(cyclohexyl-1,3)-CH2-NH-* | 3-methylphenyl* | phenyl* | 72.2 | 3.94 | 505.34 |
| 2525 | H2N-CH2-(cyclohexyl-1,3)-CH2-NH-* | 3-methylphenyl* | 4-Cl-phenyl* | 82.1 | 4.2 | 539.30 |
| 2526 | H2N-CH2-(cyclohexyl-1,3)-CH2-NH-* | 3-methylphenyl* | 2-naphthyl* | 80.9 | 4.33 | 555.34 |

-continued
| | | | | | Purity (%) | rt (min.) | [M + H]+ |
|---|---|---|---|---|---|---|---|
| 2527 | H2N~~~NH* | Ph* | tBu* | | 70.7 | 3.51 | 417.32 |
| 2528 | H2N~~~NH* | Ph* | Ph* | | 50.3 | 3.52 | 437.28 |
| 2529 | H2N~~~NH* | Ph* | 4-Cl-Ph* | | 72.4 | 3.8 | 471.26 |
| 2530 | H2N~~~NH* | Ph* | 2-naphthyl* | | 74.5 | 3.96 | 487.32 |
| 2531 | H2N~~~NH* | 3-Me-Ph* | tBu* | | 84.4 | 3.72 | 431.32 |
| 2532 | H2N~~~NH* | 3-Me-Ph* | Ph* | | 68 | 3.71 | 451.29 |
| 2533 | H2N~~~NH* | 3-Me-Ph* | 4-Cl-Ph* | | 89.6 | 3.98 | 485.26 |
| 2534 | H2N~~~NH* | 3-Me-Ph* | 2-naphthyl* | | 77.9 | 4.12 | 501.32 |
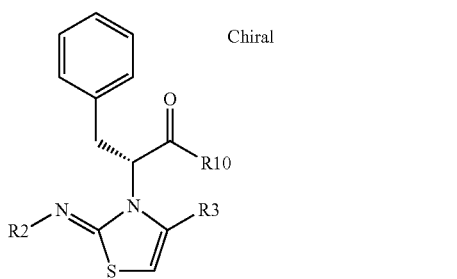
Chiral
| Ex. | R10 | R2 | R3 | Purity (%) | rt (min.) | [M + H]+ |
|---|---|---|---|---|---|---|
| 2535 | H2N-CH2-cyclohexyl-CH2-NH* | Ph* | tBu* | 84.7 | 3.83 | 505.34 |

-continued

| # | Group 1 | Group 2 | Group 3 | | | |
|---|---|---|---|---|---|---|
| 2536 | H₂N-CH₂-cyclohexyl-CH₂-NH-* | phenyl-* | phenyl-* | 75.2 | 3.89 | 525.30 |
| 2537 | H₂N-CH₂-cyclohexyl-CH₂-NH-* | phenyl-* | 4-Cl-phenyl-* | 75.9 | 4.17 | 559.25 |
| 2538 | H₂N-CH₂-cyclohexyl-CH₂-NH-* | phenyl-* | 2-naphthyl-* | 70.4 | 4.29 | 575.30 |
| 2539 | H₂N-CH₂-cyclohexyl-CH₂-NH-* | 3-methylphenyl-* | tert-butyl-* | 90.9 | 4.03 | 519.35 |
| 2540 | H₂N-CH₂-cyclohexyl-CH₂-NH-* | 3-methylphenyl-* | phenyl-* | 71.5 | 4.04 | 539.31 |
| 2541 | H₂N-CH₂-cyclohexyl-CH₂-NH-* | 3-methylphenyl-* | 4-Cl-phenyl-* | 79.2 | 4.31 | 573.25 |
| 2542 | H₂N-CH₂-cyclohexyl-CH₂-NH-* | 3-methylphenyl-* | 2-naphthyl-* | 80.6 | 4.43 | 589.33 |
| 2543 | H₂N-(CH₂)₄-NH-* | phenyl-* | tert-butyl-* | 77.2 | 3.62 | 451.30 |
| 2544 | H₂N-(CH₂)₄-NH-* | phenyl-* | phenyl-* | 69.9 | 3.65 | 471.27 |
| 2545 | H₂N-(CH₂)₄-NH-* | phenyl-* | 4-Cl-phenyl-* | 74.8 | 3.92 | 505.22 |
| 2546 | H₂N-(CH₂)₄-NH-* | phenyl-* | 2-naphthyl-* | 66.7 | 4.06 | 521.26 |

-continued

| Ex. | R10 | R2 | R3 | Purity (%) | rt (min.) | [M + H]+ |
|---|---|---|---|---|---|---|
| 2547 | H2N-(CH2)4-NH-* | 3-methylphenyl* | tert-butyl* | 83.5 | 3.82 | 465.31 |
| 2548 | H2N-(CH2)4-NH-* | 3-methylphenyl* | phenyl* | 72.9 | 3.82 | 485.28 |
| 2549 | H2N-(CH2)4-NH-* | 3-methylphenyl* | 4-chlorophenyl* | 33.1 | 4.1 | 519.23 |
| 2550 | H2N-(CH2)4-NH-* | 3-methylphenyl* | 2-naphthyl* | 51.2 | 4.22 | 535.28 |

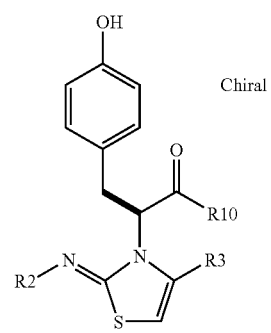

Chiral

| Ex. | R10 | R2 | R3 | Purity (%) | rt (min.) | [M + H]+ |
|---|---|---|---|---|---|---|
| 2551 | H2N-CH2-(1,3-cyclohexylene)-CH2-NH-* | phenyl* | tert-butyl* | 79.8 | 3.45 | 521.33 |
| 2552 | H2N-CH2-(1,3-cyclohexylene)-CH2-NH-* | phenyl* | phenyl* | 72.6 | 4.14 | 541.29 |
| 2553 | H2N-CH2-(1,3-cyclohexylene)-CH2-NH-* | phenyl* | 4-chlorophenyl* | 63.7 | 3.79 | 575.24 |
| 2554 | H2N-CH2-(1,3-cyclohexylene)-CH2-NH-* | phenyl* | 2-naphthyl* | 73.8 | 3.93 | 591.31 |

-continued

| # | R1 | R2 | R3 | % | t | MW |
|---|---|---|---|---|---|---|
| 2555 | H₂N-cyclohexane-CH₂-NH-* | 3-methylphenyl-* | tert-butyl-* | 91.2 | 3.65 | 535.35 |
| 2556 | H₂N-cyclohexane-CH₂-NH-* | 3-methylphenyl-* | phenyl-* | 75.6 | 3.66 | 555.29 |
| 2557 | H₂N-cyclohexane-CH₂-NH-* | 3-methylphenyl-* | 4-Cl-phenyl-* | 78.3 | 3.94 | 589.26 |
| 2558 | H₂N-cyclohexane-CH₂-NH-* | 3-methylphenyl-* | 2-naphthyl-* | 69.7 | 4.06 | 605.35 |
| 2559 | H₂N-(CH₂)₄-NH-* | phenyl-* | tert-butyl-* | 69.1 | 3.22 | 467.29 |
| 2560 | H₂N-(CH₂)₄-NH-* | phenyl-* | phenyl-* | 73.7 | 3.26 | 487.27 |
| 2561 | H₂N-(CH₂)₄-NH-* | phenyl-* | 4-Cl-phenyl-* | 79.6 | 3.56 | 521.20 |
| 2562 | H₂N-(CH₂)₄-NH-* | phenyl-* | 2-naphthyl-* | 73.5 | 3.72 | 537.27 |
| 2563 | H₂N-(CH₂)₄-NH-* | 3-methylphenyl-* | tert-butyl-* | 86.1 | 3.42 | 481.31 |
| 2564 | H₂N-(CH₂)₄-NH-* | 3-methylphenyl-* | phenyl-* | 77.1 | 3.43 | 501.29 |
| 2565 | H₂N-(CH₂)₄-NH-* | 3-methylphenyl-* | 4-Cl-phenyl-* | 83.0 | 3.73 | 535.22 |

-continued

| Ex. | R10 | R2 | R3 | Purity (%) | rt (min.) | [M + H]+ |
|---|---|---|---|---|---|---|
| 2566 | H2N~~~NH-* | 3-methylphenyl-* | 2-naphthyl-* | 71.9 | 3.86 | 551.28 |

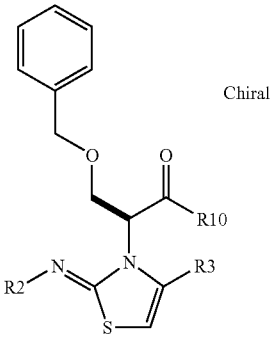

Chiral

| Ex. | R10 | R2 | R3 | Purity (%) | rt (min.) | [M + H]+ |
|---|---|---|---|---|---|---|
| 2567 | H2N-CH2-cyclohexyl-CH2-NH-* | phenyl-* | tert-butyl-* | 82.0 | 3.99 | 535.3 |
| 2568 | H2N-CH2-cyclohexyl-CH2-NH-* | phenyl-* | phenyl-* | 40.6 | 4.04 | 555.31 |
| 2569 | H2N-CH2-cyclohexyl-CH2-NH-* | phenyl-* | 4-chlorophenyl-* | 47.5 | 4.31 | 589.26 |
| 2570 | H2N-CH2-cyclohexyl-CH2-NH-* | phenyl-* | 2-naphthyl-* | 37.4 | 4.43 | 605.33 |
| 2571 | H2N-CH2-cyclohexyl-CH2-NH-* | 3-methylphenyl-* | tert-butyl-* | 79.3 | 4.18 | 549.35 |
| 2572 | H2N-CH2-cyclohexyl-CH2-NH-* | 3-methylphenyl-* | phenyl-* | 38.8 | 4.19 | 569.30 |
| 2573 | H2N-CH2-cyclohexyl-CH2-NH-* | 3-methylphenyl-* | 4-chlorophenyl-* | 51.6 | 4.46 | 603.28 |

-continued
| Ex. | (structure) | (R2) | (R3) | Purity (%) | rt (min.) | [M+H]+ |
|---|---|---|---|---|---|---|
| 2574 | H2N-cyclohexyl-CH2-NH-* | 3-methylphenyl-* | 2-naphthyl-* | 36 | 4.55 | 619.35 |
| 2575 | H2N-(CH2)4-NH-* | phenyl-* | tert-butyl-* | 61.4 | 3.77 | 481.30 |
| 2576 | H2N-(CH2)4-NH-* | phenyl-* | phenyl-* | 37.9 | 3.81 | 501.28 |
| 2577 | H2N-(CH2)4-NH-* | phenyl-* | 4-Cl-phenyl-* | 45.6 | 4.08 | 535.21 |
| 2578 | H2N-(CH2)4-N(H)-* | phenyl-* | 2-naphthyl-* | 34.9 | 4.2 | 551.27 |
| 2579 | H2N-(CH2)4-N(H)-* | 3-methylphenyl-* | tert-butyl-* | 66.2 | 3.95 | 495.31 |
| 2580 | H2N-(CH2)4-N(H)-* | 3-methylphenyl-* | phenyl-* | 44.8 | 3.96 | 515.25 |
| 2581 | H2N-(CH2)4-N(H)-* | 3-methylphenyl-* | 4-Cl-phenyl-* | 54.4 | 4.23 | 549.24 |
| 2582 | H2N-(CH2)4-N(H)-* | 3-methylphenyl-* | 2-naphthyl-* | 36.5 | 4.34 | 565.28 |
Chiral
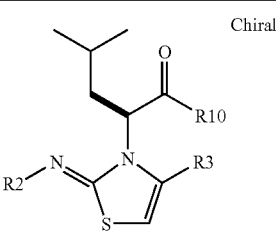
| Ex. | R10 | R2 | R3 | Purity (%) | rt (min.) | [M+H]+ |
|---|---|---|---|---|---|---|

-continued

| # | R1 | R2 | R3 | | | |
|---|---|---|---|---|---|---|
| 2583 | H₂N-(CH₂)₄-NH-* | phenyl-* | 4-methylphenyl-* | 52.2 | 3.91 | 465.24 |
| 2584 | H₂N-(CH₂)₄-NH-* | phenyl-* | 4-bromophenyl-* | 55.9 | 4 | 529.14 |
| 2585 | H₂N-(CH₂)₄-NH-* | 3-methylphenyl-* | tert-butyl-* | 51.3 | 3.9 | 445.29 |
| 2586 | H₂N-(CH₂)₄-NH-* | 3-methylphenyl-* | 3-nitrophenyl-* | 57.4 | 3.9 | 510.24 |
| 2587 | H₂N-(CH₂)₄-NH-* | 3-methylphenyl-* | 4-methylphenyl-* | 54.3 | 4.04 | 479.28 |
| 2588 | H₂N-(CH₂)₄-NH-* | 3-methylphenyl-* | 4-bromophenyl-* | 61.7 | 4.12 | 543.15 |
| 2589 | 4-(aminomethyl)benzyl-NH-* | phenyl-* | tert-butyl-* | 80.0 | 3.82 | 465.25 |
| 2590 | 4-(aminomethyl)benzyl-NH-* | phenyl-* | 3-nitrophenyl-* | 61.6 | 3.85 | 530.20 |
| 2591 | 4-(aminomethyl)benzyl-NH-* | phenyl-* | 4-methylphenyl-* | 61.1 | 3.97 | 499.25 |
| 2592 | 4-(aminomethyl)benzyl-NH-* | phenyl-* | 4-bromophenyl-* | 61.3 | 4.06 | 563.1 |
| 2593 | 4-(aminomethyl)benzyl-NH-* | 3-methylphenyl-* | tert-butyl-* | 84.2 | 3.96 | 479.29 |

-continued
| Ex. | R10 | | Purity (%) | rt (min.) | [M + H]+ |
|---|---|---|---|---|---|
| 2594 | H₂N—⌬—CH₂—N(H)—* | ⌬(m-Me)—* | O₂N—⌬—* | 58.8 | 3.98 | 544.20 |
| 2595 | H₂N—⌬—CH₂—N(H)—* | ⌬(m-Me)—* | Me—⌬—* | 61.5 | 4.1 | 513.26 |
| 2596 | H₂N—⌬—CH₂—N(H)—* | ⌬(m-Me)—* | Br—⌬—* | 65.5 | 4.19 | 577.1 |
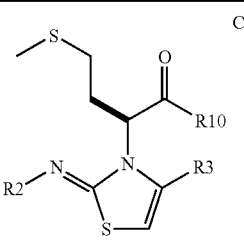
Chiral
| Ex. | R10 | R2 | R3 | Purity (%) | rt (min.) | [M + H]+ |
|---|---|---|---|---|---|---|
| 2597 | H₂N—(CH₂)₅—N(H)—* | Ph—* | O₂N—⌬—* | 28.6 | 3.7 | 514.16 |
| 2598 | H₂N—(CH₂)₅—N(H)—* | Ph—* | Me—⌬—* | 39.0 | 3.83 | 483.24 |
| 2599 | H₂N—(CH₂)₅—N(H)—* | Ph—* | Br—⌬—* | 39.9 | 3.92 | 547.1 |
| 2600 | H₂N—(CH₂)₅—N(H)—* | ⌬(m-Me)—* | tBu—* | 53.5 | 3.8 | 463.26 |
| 2601 | H₂N—(CH₂)₅—N(H)—* | ⌬(m-Me)—* | O₂N—⌬—* | 28.8 | 3.83 | 528.19 |
| 2602 | H₂N—(CH₂)₅—N(H)—* | ⌬(m-Me)—* | Me—⌬—* | 31.0 | 3.96 | 497.24 |

| Ex. | R10 | | R2 | R3 | Purity (%) | rt (min.) | [M+H]+ |
|---|---|---|---|---|---|---|---|
| 2603 | H2N~~~N(H)-* | | 3-methylphenyl | 4-bromophenyl | 34.0 | 4.05 | 561.1 |
| 2604 | 4-(aminomethyl)benzyl-NH- | | phenyl | t-Bu | 64.5 | 3.72 | 483.24 |
| 2605 | 4-(aminomethyl)benzyl-NH- | | phenyl | 3-nitrophenyl | 25.4 | 3.78 | 548.12 |
| 2606 | 4-(aminomethyl)benzyl-NH- | | phenyl | 4-methylphenyl | 36.8 | 3.9 | 517.20 |
| 2607 | 4-(aminomethyl)benzyl-NH- | | phenyl | 4-bromophenyl | 31.2 | 4 | 581.1 |
| 2608 | 4-(aminomethyl)benzyl-NH- | | 3-methylphenyl | t-Bu | 72.8 | 3.86 | 497.24 |
| 2609 | 4-(aminomethyl)benzyl-NH- | | 3-methylphenyl | 3-nitrophenyl | 31.7 | 3.9 | 562.17 |
| 2610 | 4-(aminomethyl)benzyl-NH- | | 3-methylphenyl | 4-methylphenyl | 40.1 | 4.02 | 531.21 |
| 2611 | 4-(aminomethyl)benzyl-NH- | | 3-methylphenyl | 4-bromophenyl | 38.2 | 4.12 | 595.1 |

Chiral

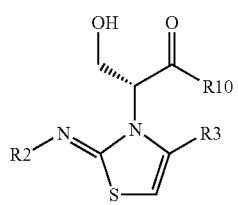

-continued
| Ex. | R10 | R2 | R3 | Purity (%) | rt (min.) | [M + H]+ |
|---|---|---|---|---|---|---|
| 2612 | H2N~~~N(H)-* | 3-methylphenyl-* | t-Bu-* | 45.2 | 3.49 | 419.24 |
| 2613 | H2N-CH2-C6H4-CH2-N(H)-* (para) | phenyl-* | t-Bu-* | 56.6 | 3.39 | 439.21 |
| 2614 | H2N-CH2-C6H4-CH2-N(H)-* (para) | 3-methylphenyl-* | t-Bu-* | 58.6 | 3.56 | 453.23 |
Chiral
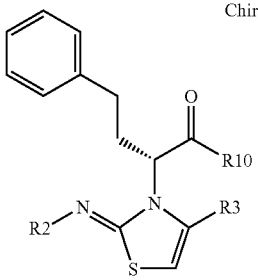
| Ex. | R10 | R2 | R3 | Purity (%) | rt (min.) | [M + H]+ |
|---|---|---|---|---|---|---|
| 2615 | H2N~~~N(H)-* | phenyl-* | t-Bu-* | 65.5 | 3.96 | 479.28 |
| 2616 | H2N~~~N(H)-* | phenyl-* | 3-O2N-phenyl-* | 50.5 | 4 | 544.19 |
| 2617 | H2N~~~N(H)-* | phenyl-* | 4-methylphenyl-* | 55.7 | 4.11 | 513.26 |
| 2618 | H2N~~~N(H)-* | phenyl-* | 4-Br-phenyl-* | 55.5 | 4.2 | 577.13 |
| 2619 | H2N~~~N(H)-* | 3-methylphenyl-* | t-Bu-* | 67.1 | 4.09 | 493.30 |
| 2620 | H2N~~~N(H)-* | 3-methylphenyl-* | 3-O2N-phenyl-* | 53.7 | 4.11 | 558.20 |

| | | | | | | |
|---|---|---|---|---|---|---|
| 2621 | 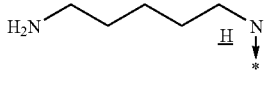 | 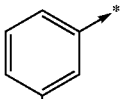 | 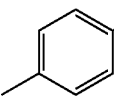 | 55.5 | 4.22 | 527.27 |
| 2622 | 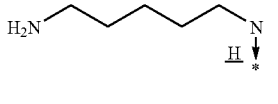 | 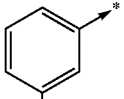 | 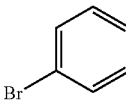 | 72.1 | 4.3 | 591.13 |
| 2623 | 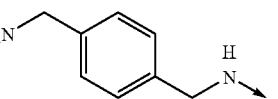 | 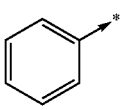 | 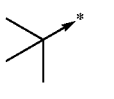 | 81.1 | 4.02 | 513.26 |
| 2624 | 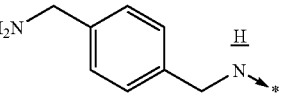 | 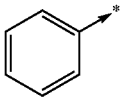 | 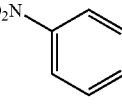 | 51.0 | 4.08 | 578.18 |
| 2625 | 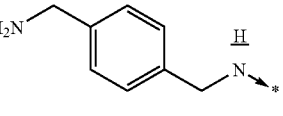 | 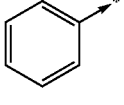 | 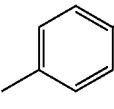 | 54.1 | 4.17 | 547.21 |
| 2626 | 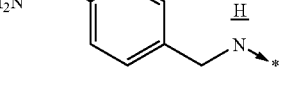 | 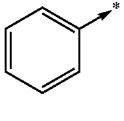 | 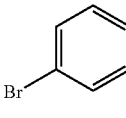 | 65.2 | 4.26 | 611.11 |
| 2627 | 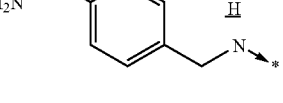 | 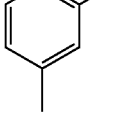 |  | 83.9 | 4.16 | 527.27 |
| 2628 | 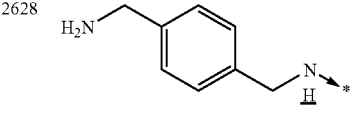 | 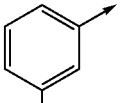 | 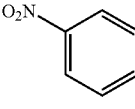 | 60.2 | 4.18 | 592.21 |
| 2629 | 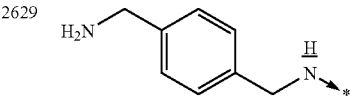 | 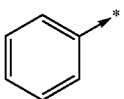 | 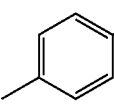 | 63 | 4.3 | 561.21 |
| 2630 | 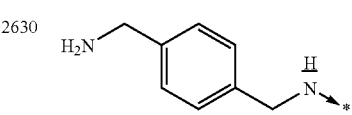 | 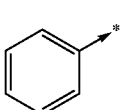 | 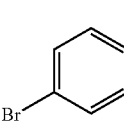 | 74.0 | 4.36 | 625.11 |

-continued
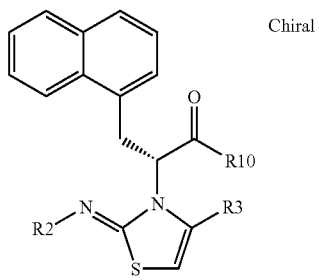
Chiral
| Ex. | R10 | R2 | R3 | Purity (%) | rt (min.) | [M + H]+ |
|---|---|---|---|---|---|---|
| 2631 | H2N-(CH2)5-NH-* | phenyl* | t-butyl* | 83.1 | 4.06 | 515.26 |
| 2632 | H2N-(CH2)5-NH-* | phenyl* | 3-O2N-phenyl* | 57.8 | 4.13 | 580.20 |
| 2633 | H2N-(CH2)5-NH-* | phenyl* | 4-methylphenyl* | 37.4 | 4.22 | 549.23 |
| 2634 | H2N-(CH2)5-NH-* | phenyl* | 4-Br-phenyl* | 43.3 | 4.31 | 613.12 |
| 2635 | H2N-(CH2)5-NH-* | 3-methylphenyl* | t-butyl* | 86.7 | 4.18 | 529.27 |
| 2636 | H2N-(CH2)5-NH-* | 3-methylphenyl* | 3-O2N-phenyl* | 64.3 | 4.22 | 594.19 |
| 2637 | H2N-(CH2)5-NH-* | 3-methylphenyl* | 4-methylphenyl* | 37.0 | 4.32 | 563.25 |
| 2638 | H2N-(CH2)5-NH-* | 3-methylphenyl* | 4-Br-phenyl* | 44.3 | 4.4 | 627.15 |
| 2639 | H2N-CH2-(4-phenylene)-CH2-NH-* | phenyl* | t-butyl* | 86.9 | 4.14 | 549.23 |

-continued
| Ex. | R10 | R2 | R3 | Purity (%) | rt (min.) | [M + H]+ |
|---|---|---|---|---|---|---|
| 2640 | H2N-C6H4-CH2-NH-* | phenyl* | 3-O2N-C6H4* | 53.4 | 4.23 | 614.17 |
| 2641 | H2N-C6H4-CH2-NH-* | phenyl* | 4-Me-C6H4* | 37 | 4.3 | 583.21 |
| 2642 | H2N-C6H4-CH2-NH-* | phenyl* | 4-Br-C6H4* | 45.7 | 4.4 | 647.11 |
| 2643 | H2N-C6H4-CH2-NH-* | 3-Me-C6H4* | t-Bu* | 88.9 | 4.24 | 563.25 |
| 2644 | H2N-C6H4-CH2-NH-* | 3-Me-C6H4* | 3-O2N-C6H4* | 57.3 | 4.3 | 628.19 |
| 2645 | H2N-C6H4-CH2-NH-* | 3-Me-C6H4* | 4-Me-C6H4* | 39.4 | 4.39 | 597.22 |
| 2646 | H2N-C6H4-CH2-NH-* | 3-Me-C6H4* | 4-Br-C6H4* | 44.1 | 4.48 | 661.15 |
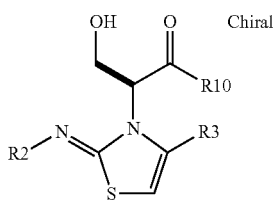
| Ex. | R10 | R2 | R3 | Purity (%) | rt (min.) | [M + H]+ |
|---|---|---|---|---|---|---|
| 2647 | *-HN-CH2-(cyclohexyl)-CH2-NH2 | phenyl* | 2-MeO-C6H4* | 25.6 | 3.18 | 495.23 |
| 2648 | *-HN-CH2-(cyclohexyl)-CH2-NH2 | phenyl* | 3-CF3-C6H4* | 33.1 | 3.59 | 533.15 |

-continued
| | | | | | | |
|---|---|---|---|---|---|---|
| 2649 | 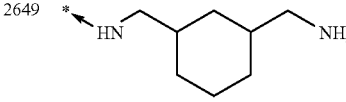 | 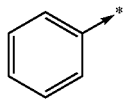 | 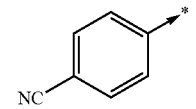 | 27.0 | 3 | 490.2 |
| 2650 | 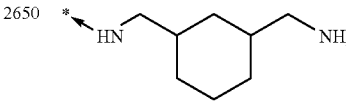 | 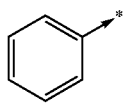 | 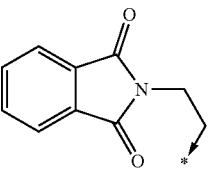 | 33.6 | 3.14 | 562.16 |
| 2651 | 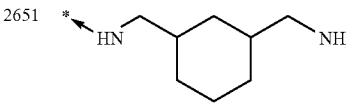 | 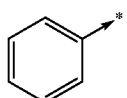 | 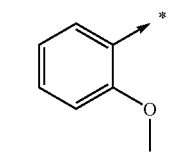 | 27.2 | 3.36 | 509.21 |
| 2652 | 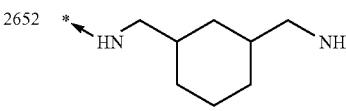 | 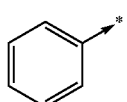 | 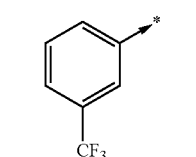 | 32.5 | 3.76 | 547.16 |
| 2653 | 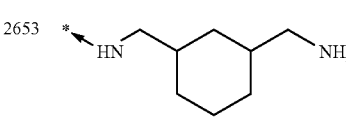 | 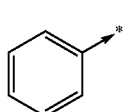 | 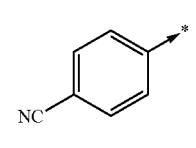 | 29.7 | 3.2 | 504.2 |
| 2654 | 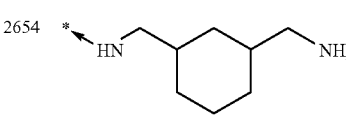 | 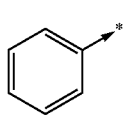 | 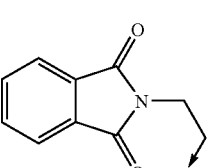 | 34.8 | 3.32 | 576.21 |
| 2655 | 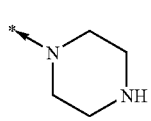 | 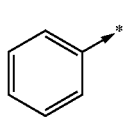 | 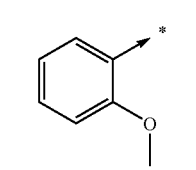 | 73.7 | 2.93 | 439.15 |
| 2656 | 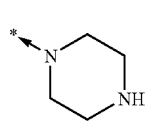 | 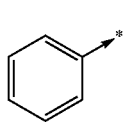 | 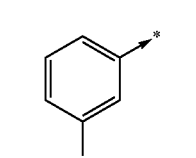 | 60.6 | 3.37 | 477.14 |
| 2657 | 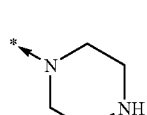 | 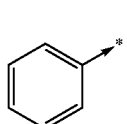 | 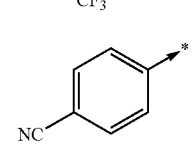 | 65.1 | 2.7 | 434.1 |
| 2658 | 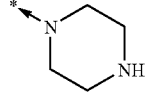 | 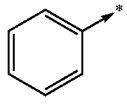 | 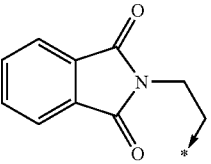 | 69.3 | 2.92 | 506.14 |

-continued
| Ex. | | | | Purity (%) | rt (min.) | [M + H]+ |
|---|---|---|---|---|---|---|
| 2659 | *-N(piperazine)NH | *-(m-tolyl) | *-(2-methoxyphenyl) | 72.5 | 3.14 | 453.17 |
| 2660 | *-N(piperazine)NH | *-(m-tolyl) | *-(3-CF3-phenyl) | 77.2 | 3.55 | 491.14 |
| 2661 | *-N(piperazine)NH | *-(m-tolyl) | *-(4-cyanophenyl) | 66.4 | 2.9 | 448.1 |
| 2662 | *-N(piperazine)NH | *-(m-tolyl) | *-(phthalimido-ethyl) | 65.9 | 3.14 | 520.15 |
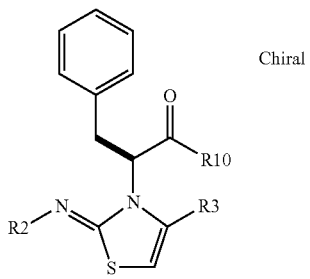
Chiral
| Ex. | R10 | R2 | R3 | Purity (%) | rt (min.) | [M + H]+ |
|---|---|---|---|---|---|---|
| 2663 | *-HN-CH2-(cyclohexane)-CH2-NH2 | *-phenyl | *-(2-methoxyphenyl) | 63.3 | 3.82 | 555.21 |
| 2664 | *-HN-CH2-(cyclohexane)-CH2-NH2 | *-phenyl | *-(3-CF3-phenyl) | 85.8 | 4.24 | 593.19 |
| 2665 | *-HN-CH2-(cyclohexane)-CH2-NH2 | *-phenyl | *-(4-cyanophenyl) | 87.5 | 3.8 | 550.2 |

-continued

| | | | | | | |
|---|---|---|---|---|---|---|
| 2666 | *–HN-cyclohexane-CH2NH2 | phenyl-* | phthalimide-CH2CH2-* | 75.1 | 3.78 | 622.22 |
| 2667 | *–HN-cyclohexane-CH2NH2 | m-tolyl-* | 2-methoxyphenyl-* | 66.1 | 3.98 | 569.21 |
| 2668 | *–HN-cyclohexane-CH2NH2 | m-tolyl-* | 3-CF3-phenyl-* | 87.2 | 4.35 | 607.21 |
| 2669 | *–HN-cyclohexane-CH2NH2 | m-tolyl-* | 4-CN-phenyl-* | 82.9 | 3.9 | 564.2 |
| 2670 | *–HN-cyclohexane-CH2NH2 | m-tolyl-* | phthalimide-CH2CH2-* | 79.1 | 3.94 | 636.25 |
| 2671 | *–N-piperazine-NH | phenyl-* | 2-methoxyphenyl-* | 82.0 | 3.55 | 499.18 |
| 2672 | *–N-piperazine-NH | phenyl-* | 3-CF3-phenyl-* | 82.2 | 3.93 | 537.14 |
| 2673 | *–N-piperazine-NH | phenyl-* | 4-CN-phenyl-* | 86.4 | 3.4 | 494.2 |
| 2674 | *–N-piperazine-NH | phenyl-* | phthalimide-CH2CH2-* | 90.4 | 3.52 | 566.15 |

-continued

| Ex. | R10 | | | Purity (%) | rt (min.) | [M + H]+ |
|---|---|---|---|---|---|---|
| 2675 | piperazine | 3-methylphenyl | 2-methoxyphenyl | 88.0 | 3.72 | 513.19 |
| 2676 | piperazine | 3-methylphenyl | 3-(trifluoromethyl)phenyl | 88.8 | 4.08 | 551.15 |
| 2677 | piperazine | 3-methylphenyl | 4-cyanophenyl | 88.9 | 3.6 | 508.2 |
| 2678 | piperazine | 3-methylphenyl | 2-(phthalimido)ethyl | 93.6 | 3.7 | 580.17 |

Chiral

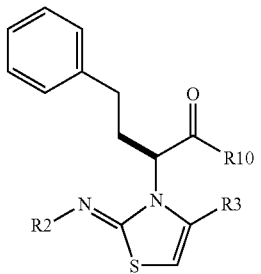

| Ex. | R10 | R2 | R3 | Purity (%) | rt (min.) | [M + H]+ |
|---|---|---|---|---|---|---|
| 2679 | (1,3-cyclohexanediyl)bis(methylene)diamine | phenyl | 2-methoxyphenyl | 59.5 | 4 | 569.20 |
| 2680 | (1,3-cyclohexanediyl)bis(methylene)diamine | phenyl | 3-(trifluoromethyl)phenyl | 82.6 | 4.37 | 607.21 |
| 2681 | (1,3-cyclohexanediyl)bis(methylene)diamine | phenyl | 4-cyanophenyl | 74.9 | 3.9 | 564.2 |

-continued
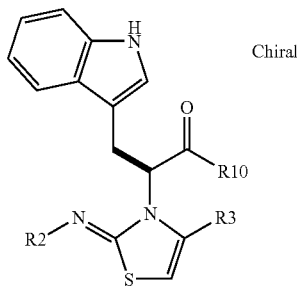
| Ex. | R10 | R2 | R3 | Purity (%) | rt (min.) | [M + H]+ |
|---|---|---|---|---|---|---|
| 2718 | *-HN-cyclohexyl-CH2NH2 | 3-methylphenyl | phthalimido-ethyl-* | 76.9 | 3.92 | 675.26 |
| 2719 | *-piperazinyl-NH | phenyl-* | 2-methoxyphenyl-* | 75.5 | 3.63 | 538.18 |
| 2720 | *-piperazinyl-NH | phenyl-* | 3-CF3-phenyl-* | 79.4 | 3.96 | 576.13 |
| 2721 | *-piperazinyl-NH | phenyl-* | 4-CN-phenyl-* | 73 | 3.5 | 533.2 |
| 2722 | *-piperazinyl-NH | phenyl-* | phthalimido-ethyl-* | 87.0 | 3.56 | 605.17 |
| 2723 | *-piperazinyl-NH | 3-methylphenyl-* | 2-methoxyphenyl-* | 81.8 | 3.8 | 552.18 |
| 2724 | *-piperazinyl-NH | 3-methylphenyl-* | 3-CF3-phenyl-* | 80.1 | 4.11 | 590.15 |

-continued
| Ex. | R2 | | R3 | Purity (%) | rt (min.) | [M + H]+ |
|---|---|---|---|---|---|---|
| 2725 | piperazine | 3-methylphenyl | 4-cyanophenyl | 79.4 | 3.6 | 547.2 |
| 2726 | piperazine | 3-methylphenyl | phthalimidoethyl | 86.3 | 3.73 | 619.18 |
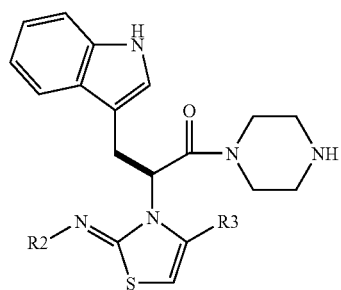
| Ex. | R2 | R3 | Purity (%) | rt (min.) | [M + H]+ |
|---|---|---|---|---|---|
| 2727 | phenyl | tert-butyl | 73.7 | 4.7 | 488.3 |
| 2728 | phenyl | phenyl | 87.1 | 4.2 | 508.2 |
| 2729 | phenyl | benzyl | 90.3 | 4.3 | 522.3 |
| 2730 | phenyl | 3-bromophenyl | 78.2 | 4.5 | 586.1 |
| 2731 | phenyl | 3-cyanophenyl | 73 | 4.1 | 533.2 |
| 2732 | phenyl | 4-chlorophenyl | 86.4 | 4.5 | 542.2 |

-continued

| | R1 | R2 | % | | MW |
|---|---|---|---|---|---|
| 2733 | phenyl* | 4-(CF3)-phenyl* | 77.7 | 4.6 | 576.2 |
| 2734 | phenyl* | 4-(OCF3)-phenyl* | 80 | 4.7 | 592.2 |
| 2735 | phenyl* | 3,5-bis(CF3)-phenyl* | 76.4 | 4.9 | 644.2 |
| 2736 | phenyl* | 2-naphthyl* | 81.4 | 4.6 | 558.2 |
| 2737 | 3-methylphenyl* | tert-butyl* | 79.8 | 4.4 | 502.3 |
| 2738 | 3-methylphenyl* | phenyl* | 87.5 | 4.4 | 522.3 |
| 2739 | 3-methylphenyl* | benzyl* | 91.4 | 4.5 | 536.3 |
| 2740 | 3-methylphenyl* | 3-Br-phenyl* | 83.3 | 4.6 | 600.1 |
| 2741 | 3-methylphenyl* | 3-CN-phenyl* | 82 | 4.3 | 547.2 |
| 2742 | 3-methylphenyl* | 4-Cl-phenyl* | 83.9 | 4.6 | 556.2 |

| | | | | | |
|---|---|---|---|---|---|
| 2743 | 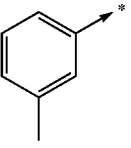 | 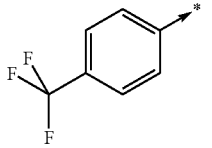 | 85.4 | 4.7 | 590.2 |
| 2744 | 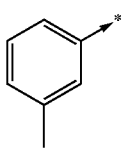 | 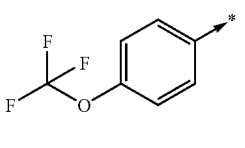 | 85.2 | 4.8 | 606.2 |
| 2745 | 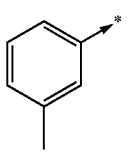 | 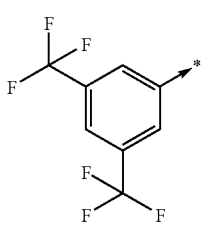 | 82 | 4.3 | 658.2 |
| 2746 | 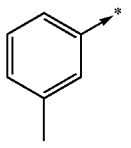 | 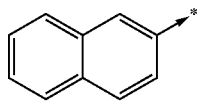 | 86.7 | 4.7 | 572.2 |
| 2747 | 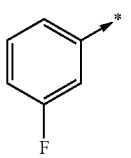 |  | 31.6 | 4.3 | 506.3 |
| 2748 | 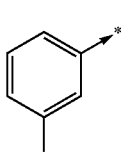 | 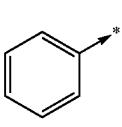 | 71.1 | 4.3 | 526.2 |
| 2749 | 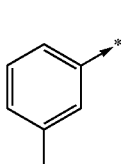 | 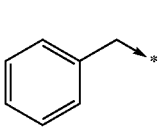 | 89.5 | 4.4 | 540.2 |
| 2750 | 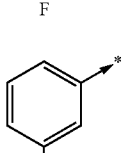 | 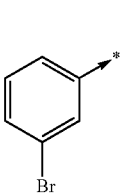 | 59.6 | 4.5 | 604.1 |
| 2751 | 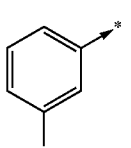 | 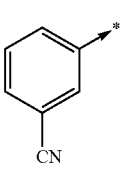 | 51.3 | 4.2 | 551.2 |

| | 801 | 802 | | | |
|---|---|---|---|---|---|
| 2752 | 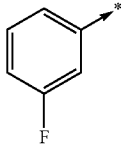 | 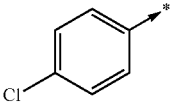 | 62.2 | 4.5 | 560.2 |
| 2753 | 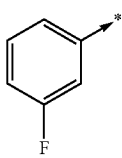 | 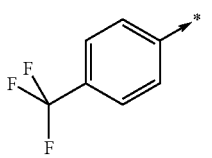 | 59.6 | 4.7 | 594.2 |
| 2754 | 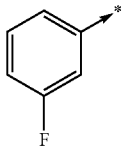 | 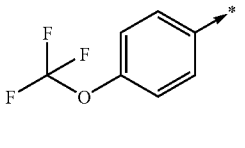 | 63 | 4.7 | 610.2 |
| 2755 | 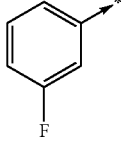 | 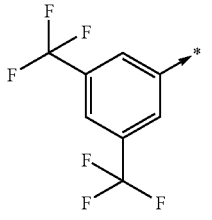 | 52.5 | 4.9 | 662.2 |
| 2756 | 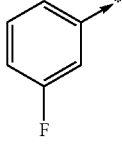 | 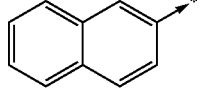 | 67.8 | 4.6 | 576.1 |
| 2757 | 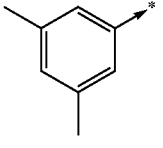 |  | 81.1 | 4.6 | 516.3 |
| 2758 | 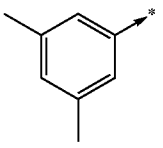 | 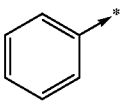 | 85.8 | 4.5 | 536.3 |
| 2759 | 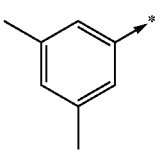 | 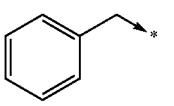 | 85.4 | 4.7 | 550.3 |
| 2760 | 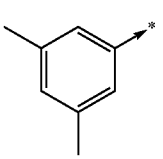 | 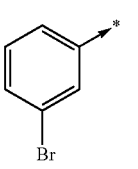 | 76.6 | 4.7 | 614.1 |

-continued
| Ex. | (col2) | (col3) | Purity (%) | rt (min.) | [M + H]⁺ |
|---|---|---|---|---|---|
| 2761 | 3,5-dimethylphenyl* | 3-cyanophenyl* | 77.2 | 4.4 | 561.2 |
| 2762 | 3,5-dimethylphenyl* | 4-chlorophenyl* | 85.4 | 4.7 | 570.2 |
| 2763 | 3,5-dimethylphenyl* | 4-trifluoromethylphenyl* | 79.7 | 4.8 | 604.2 |
| 2764 | 3,5-dimethylphenyl* | 4-trifluoromethoxyphenyl* | 81.1 | 4.9 | 620.2 |
| 2765 | 3,5-dimethylphenyl* | 3,5-bis(trifluoromethyl)phenyl* | 79.2 | 5.1 | 672.2 |
| 2766 | 3,5-dimethylphenyl* | 2-naphthyl* | 82 | 4.8 | 586.3 |
Chiral
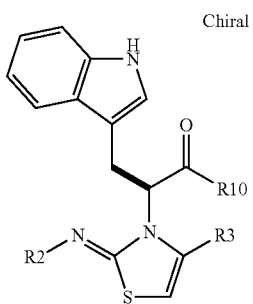
| Ex. | R10 | R2 | R3 | Purity (%) | rt (min.) | [M + H]⁺ |
|---|---|---|---|---|---|---|
| 2767 | 2-methylphenyl* | H₂N-CH₂CH₂-NH-* | 3-chlorophenyl* | 64.3 | 3.91 | 530.20 |

-continued
| | | | | | | |
|---|---|---|---|---|---|---|
| 2768 | 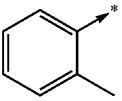 | 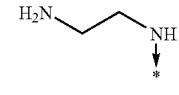 | 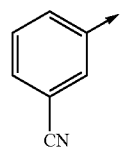 | 58.3 | 3.57 | 521.22 |
| 2769 | 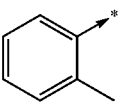 | 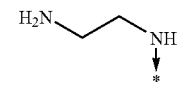 | 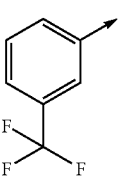 | 66.7 | 4.03 | 564.20 |
| 2770 | 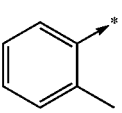 | 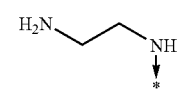 | 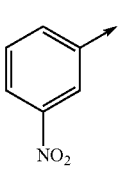 | 65.1 | 3.71 | 541.19 |
| 2771 | 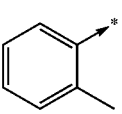 | 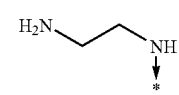 | 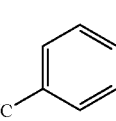 | 56.1 | 3.58 | 521.21 |
| 2772 | 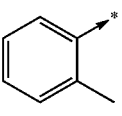 | 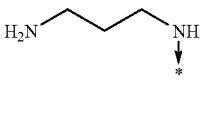 | 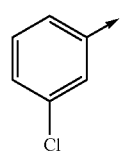 | 42.1 | 3.93 | 544.19 |
| 2773 | 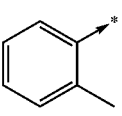 | 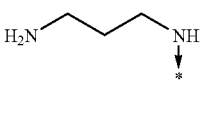 | 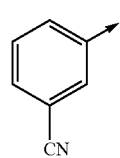 | 34.6 | 3.59 | 535.22 |
| 2774 | 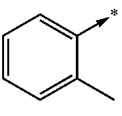 | 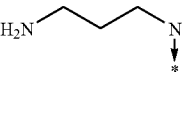 | 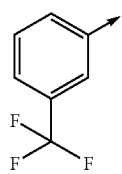 | 46.9 | 4.05 | 578.21 |
| 2775 | 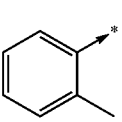 | 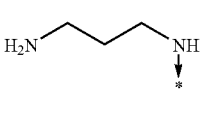 | 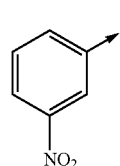 | 33.3 | 3.73 | 555.19 |
| 2776 | 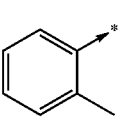 | 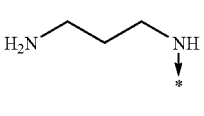 | 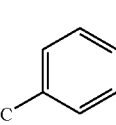 | 33.4 | 3.6 | 535.22 |
| 2777 | 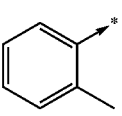 | 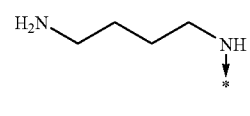 | 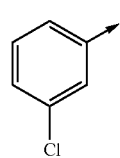 | 39.6 | 3.97 | 558.22 |

-continued
| | | | | | | |
|---|---|---|---|---|---|---|
| 2778 | 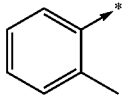 | 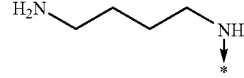 | 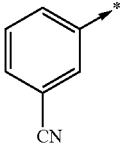 | 47.5 | 3.63 | 549.23 |
| 2779 | 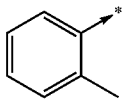 | 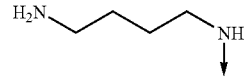 | 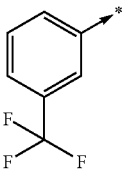 | 50.3 | 4.09 | 592.23 |
| 2780 | 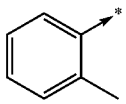 | 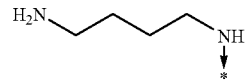 | 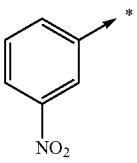 | 40.6 | 3.76 | 569.19 |
| 2781 | 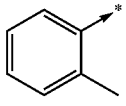 | 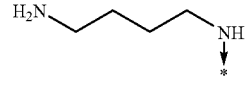 | 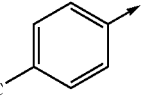 | 42.7 | 3.63 | 549.25 |
| 2782 | 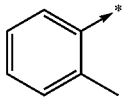 | 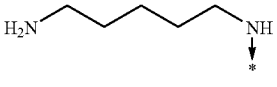 | 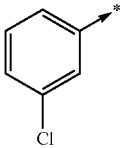 | 35.5 | 4.0 | 572.17 |
| 2783 | 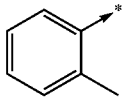 | 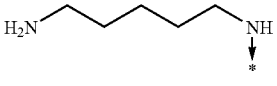 | 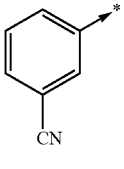 | 33.2 | 3.69 | 563.26 |
| 2784 | 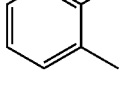 |  | 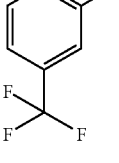 | 45 | 4.1 | 606.27 |
| 2785 | 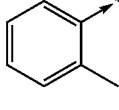 | 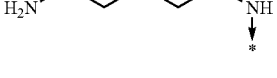 | 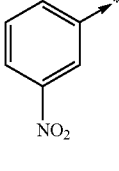 | 36.0 | 3.82 | 583.23 |
| 2786 | 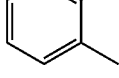 |  | 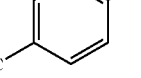 | 27.1 | 3.7 | 563.26 |

-continued

| # | Ar1 | Linker | Ar2 | a | b | c |
|---|---|---|---|---|---|---|
| 2787 | 3-methylphenyl | H2N-CH2CH2-NH- | 3-chlorophenyl | 73.6 | 3.98 | 530.19 |
| 2788 | 3-methylphenyl | H2N-CH2CH2-NH- | 3-cyanophenyl | 62.5 | 3.64 | 521.21 |
| 2789 | 3-methylphenyl | H2N-CH2CH2-NH- | 3-(trifluoromethyl)phenyl | 74.8 | 4.09 | 564.2 |
| 2790 | 3-methylphenyl | H2N-CH2CH2-NH- | 3-nitrophenyl | 67.7 | 3.77 | 541.20 |
| 2791 | 3-methylphenyl | H2N-CH2CH2-NH- | 4-cyanophenyl | 71.3 | 3.65 | 521.21 |
| 2792 | 3-methylphenyl | H2N-CH2CH2CH2-NH- | 3-chlorophenyl | 52.4 | 4.0 | 544.18 |
| 2793 | 3-methylphenyl | H2N-CH2CH2CH2-NH- | 3-cyanophenyl | 47.0 | 3.65 | 535.22 |
| 2794 | 3-methylphenyl | H2N-CH2CH2CH2-NH- | 3-(trifluoromethyl)phenyl | 54.7 | 4.11 | 578.22 |
| 2795 | 3-methylphenyl | H2N-CH2CH2CH2-NH- | 3-nitrophenyl | 43.7 | 3.79 | 555.20 |

| | | | | | | |
|---|---|---|---|---|---|---|
| 2796 | 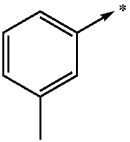 | 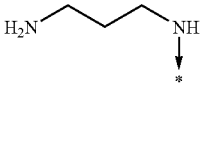 | 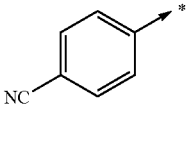 | 44.6 | 3.67 | 535.22 |
| 2797 | 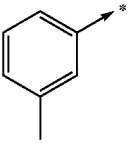 | 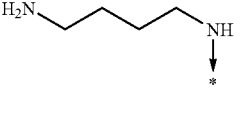 | 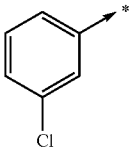 | 53.7 | 4.03 | 558.20 |
| 2798 | 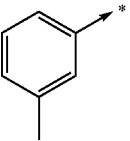 | 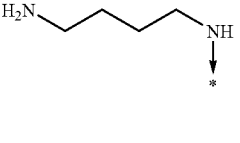 | 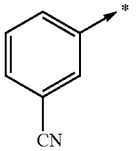 | 51.0 | 3.69 | 549.23 |
| 2799 | 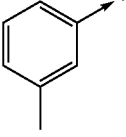 | 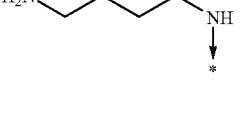 | 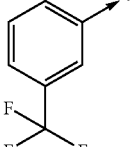 | 56.5 | 4.15 | 592.23 |
| 2800 | 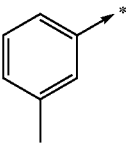 | 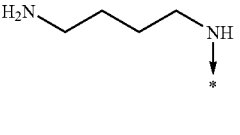 | 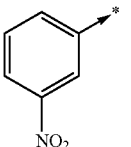 | 48.9 | 3.83 | 569.20 |
| 2801 | 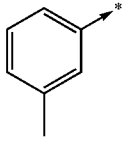 | 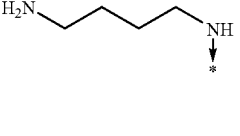 | 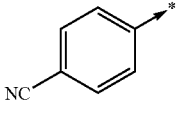 | 46.0 | 3.7 | 549.24 |
| 2802 | 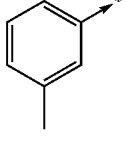 | 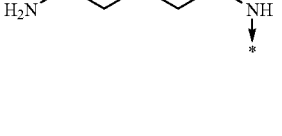 | 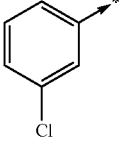 | 41.2 | 4.1 | 572.21 |
| 2803 | 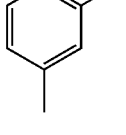 |  | 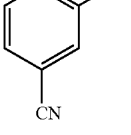 | 36.7 | 3.76 | 563.26 |
| 2804 | 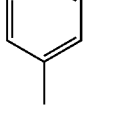 |  | 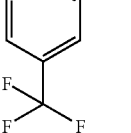 | 47.4 | 4.2 | 606.26 |

-continued

| Ex. | (col2) | (col3) | (col4) | Purity | rt (min.) | [M + H]+ |
|---|---|---|---|---|---|---|
| 2805 | 3-methylphenyl | H₂N-(CH₂)₅-NH- | 3-nitrophenyl | 37.0 | 3.89 | 583.22 |
| 2806 | 3-methylphenyl | H₂N-(CH₂)₅-NH- | 4-cyanophenyl | 37.3 | 3.76 | 563.26 |

Chiral

Structure: indol-3-yl-CH₂-C*H(-C(=O)-N(piperazinyl-NH))-N(thiazoline with R3 at 4-position and =N-R2 at 2-position, S in ring)

| Ex. | R3 | R2 | Purity (%) | rt (min.) | [M + H]+ |
|---|---|---|---|---|---|
| 2807 | 3-cyanophenyl | 2-methylphenyl | 52.1 | 3.65 | 547.22 |
| 2808 | 3-cyanophenyl | 2-methoxyphenyl | 61.7 | 3.61 | 563.24 |
| 2809 | 3-cyanophenyl | 3-ethylphenyl | 54.1 | 3.91 | 561.26 |
| 2810 | 3-cyanophenyl | 3-methoxyphenyl | 56.7 | 3.69 | 563.23 |
| 2811 | 3-cyanophenyl | 4-methylphenyl | 54.7 | 3.65 | 547.23 |

-continued
| | | | | | |
|---|---|---|---|---|---|
| 2812 | 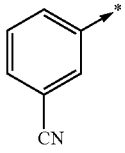 | 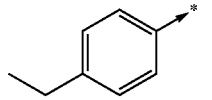 | 63.6 | 3.96 | 561.25 |
| 2813 | 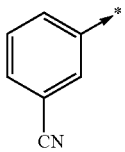 | 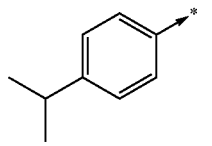 | 66.1 | 4.13 | 575.26 |
| 2814 | 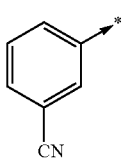 | 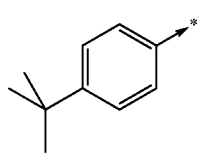 | 34.9 | 4.29 | 589.29 |
| 2815 | 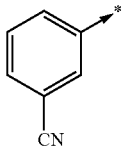 | 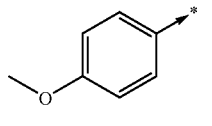 | 69.3 | 3.66 | 563.24 |
| 2816 | 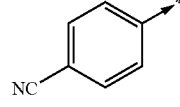 | 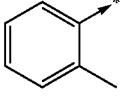 | 47.6 | 3.66 | 547.23 |
| 2817 | 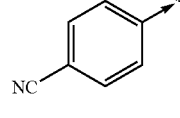 | 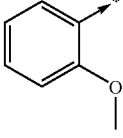 | 41.4 | 3.61 | 563.23 |
| 2818 | 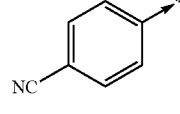 | 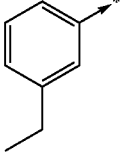 | 28.5 | 3.97 | 561.24 |
| 2819 | 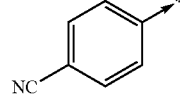 | 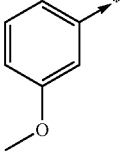 | 56.4 | 3.71 | 563.23 |
| 2820 | 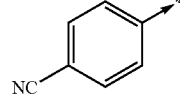 | 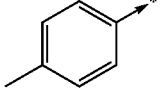 | 45.6 | 3.65 | 547.22 |
| 2821 | 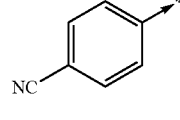 | 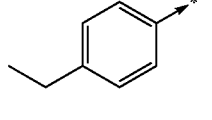 | 62.6 | 3.99 | 561.24 |

-continued

| | | | | | |
|---|---|---|---|---|---|
| 2822 | NC-C6H4-* | iPr-C6H4-* | 42.0 | 4.17 | 575.26 |
| 2823 | NC-C6H4-* | tBu-C6H4-* | 45.7 | 4.32 | 589.28 |
| 2824 | NC-C6H4-* | F-C6H4-* | 23.5 | 3.65 | 551.21 |
| 2825 | NC-C6H4-* | MeO-C6H4-* | 70.9 | 3.67 | 563.22 |

Some compounds according to the invention can be obtained according to method G described hereafter.

Method G

Synthesis in solution of 2-iminothiazole-4-carboxamide derivatives from monoprotected symmetrical diamines (Boc)

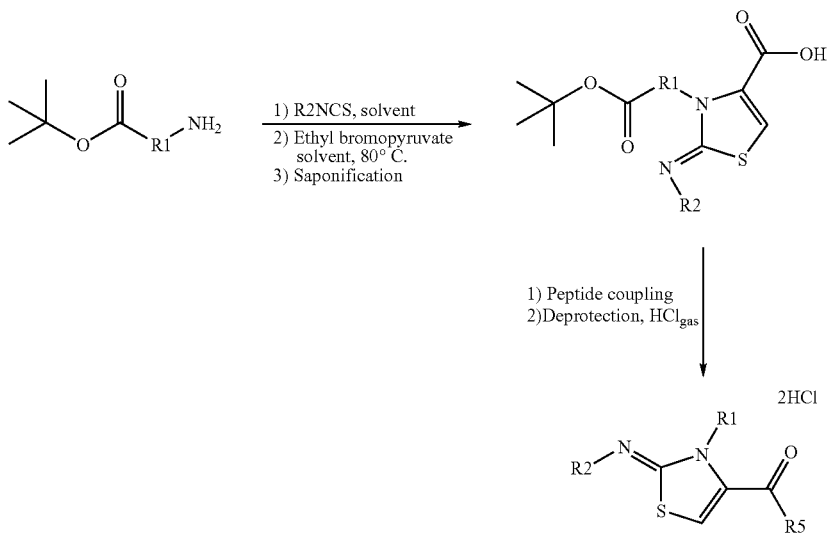

General Procedure:

The monoprotected symmetrical diamine (Boc) (1 equiv) is agitated overnight with an aromatic isothiocyanate (1 equiv) at ambient temperature in an anhydrous solvent such as dioxane, dimethylformamide or chloroform, 1 equivalent of an inorganic base such as sodium or potassium hydrogen carbonate and 1 equivalent of ethyl bromopyruvate dissolved beforehand in an anhydrous solvent such as dioxane or dimethylformamide is successively added to the crude isothiourea intermediate. The mixture is then heated at 80° C. for 1 to 3 hours and the inorganic salts are eliminated by filtration. The solvents are evaporated off under vacuum and the residue is purified by flash chromatography on silica gel using an ethyl acetate/heptane gradient. Saponification of the ester intermediate is carried out in a solvent such as tetrahydrofuran using a 1N solution of KOH, LiOH or NaOH. The mixture is agitated vigorously for 6 to 20 hours at ambient temperature then acidified with a 1N aqueous solution of hydrochloric acid to pH 2.5.

The organic phase is extracted several times with dichloromethane then the organic phase is washed with water until neutral pH and dried over sodium sulphate. A primary or secondary amine (1.1 to 2 equiv.) pre-dissolved in a anhydrous solvent such as dimethylformamide is added under argon to a solution of carboxylic acid intermediate (1 equiv.) and a peptide coupling agent such as DIC, DIC/HOBt, HATU or TBTU (1.1 to 2 equiv.), dissolved beforehand in an anhydrous solvent such as dimethylformamide. The mixture is agitated overnight at ambient temperature. The solvent is evaporated off under vacuum and the residue purified by flash chromatography on silica gel using an ethyl acetate/heptane gradient. The carboxamide intermediate is diluted in a solvent such as dichloromethane or ethyl acetate and deprotected after passage through the solution of a current of dry hydrogen chloride for 1 to 6 hours at ambient temperature. The corresponding dihydrochloride is isolated either by filtration of the precipitate or, after evaporation under vacuum of the solvent, by adding diethylether for better crystallisation.

Preparation 25 ethyl(2Z)-3-{5-[(tert-butoxycarbonyl)amino]pentyl}-2-[(3,5-dimethylphenyl)imino]-2,3-dihydro-1,3-thiazole-4-carboxylate ($C_{14}H_{25}N_3O_4S$; MM=461.63)

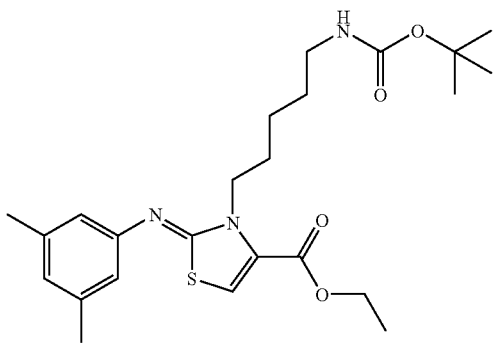

N-Boc-1,5-diaminopentane (1.04 g; 5 mmol) is agitated with 3,5-dimethylisothiocyanate (824 mg; 5 mmol) in 10 ml anhydrous dioxane. 420 mg (5 mmol) of sodium hydrogen carbonate and 1.08 g (5 mmol) of ethyl bromopyruvate dissolved beforehand in 2 ml of anhydrous dioxane are successively added to the, crude isothiourea intermediate. The mixture is then heated at 80° C. for one hour and the inorganic salts are eliminated by filtration. The dioxane is evaporated off under vacuum and the yellow residue is purified by flash chromatography on silica gel (eluent:ethyl acetate/heptane 2:8 then 3:7). A yellow oil (1.8 g; yield of 77.9%) corresponding to the expected compound is then isolated.

NMR $^1$H (DMSO-$d_6$, 400 MHz) δ: 7.23 (s, 1H); 6.71 (broad s, 1H); 6.65 (s, 1H); 6.54 (s, 2H); 4.26 (q, 2H, J=6.4 Hz); 4.13 (t, 2H, J=6.4 Hz); 2.9 (q, 2H, J=6 Hz); 2.22 (s, 6H); 1.63 (m, 2H); 1.4 (m, 2H); 1.36 (s, 9H); 1.29–1.23 (m, 2H+3H). MS/LC: m/z=462.3 (M+H)$^+$.

Preparation 26

(2Z)-3-{5-[(ten-buroxycarbonyl)amino]pentyl}-2-[(3,5-dimethylphenyl)imino]=2,3-dihydro-1,3-thiazole-4-carboxylic acid ($C_{22}H_{31}N_3O_4S$; MM=433.57)

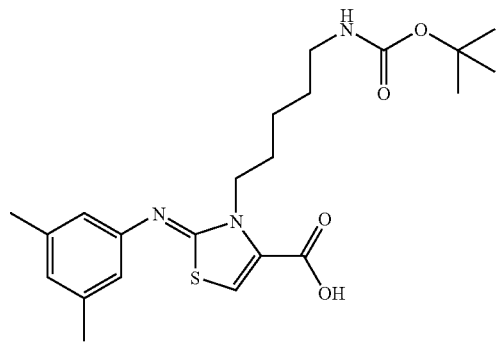

The compound of Preparation 25 (1.77; 3.83 mmol) is dissolved in 20 ml of tetrahydrofuran and treated with 15 ml of a 1N aqueous solution of NaOH. The mixture is agitated vigorously for 6 hours at ambient temperature. The carboxylate is then acidified with a 1N aqueous solution of hydrochloric acid to pH 2.5. The aqueous phase is extracted with dichloromethane (4×50 ml) and the organic phases are washed with water until neutral pH and dried over sodium sulphate. A pale yellow solid is isolated (1.51 g; yield of 90.9%) after evaporation under vacuum of the solvents.

NMR $^1$H (DMSO-$d_6$, 400 MHz) δ: 13.28 (broad s, 1H); 7.16 (s, 1H); 6.69 (broad s, 1H); 6.65 (s, 1H); 6.54 (s, 2H); 4.17 (t, 2H, J=7.2 Hz); 2.89 (q, 2H, J=6.4 Hz); 2.22 (s, 6H); 1.63 (q, 2H, J=6.8 Hz); 1.41 (m, 2H); 1.36 (s, 9H); 1.25 (m, 2H). MS/LC: m/z=434.27 (M+H)$^+$ Preparation 27 tert-butyl 5-[(2Z)-2-[(3,5-dimethylphenyl)imino]-4-{[(1-phenylpropyl)amino]carbonyl}-1,3-thiazol-3(2H)-yl]pentylcarbamate ($C_{31}H_{42}N_4O_3S$; MM=550.76)

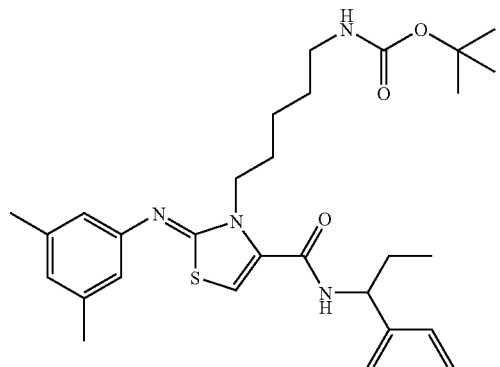

600 mg (1.38 mmol) of carboxylic acid of Preparation 26 are activated beforehand with 888 mg (2.76 mmol; 2 equiv.) of TBTU in 10 ml of anhydrous dimethylformamide for one hour. 410 μl (2.76 mmol; 2 equiv.) of α-ethylbenzylamine is then added and the mixture is agitated at ambient temperature overnight. After evaporation of the dimethylformamide, the crude residue is purified by flash chromatography on silica gel (eluent: ethyl acetate/heptane 4:6) in order to produce a white solid (498 mg; yield of 65.5%).

NMR $^1$H (DMSO-$d_6$, 400 MHz)*: 9.00 (d, 1H, J=8.4 Hz); 7.36–7.30 (m, 4H); 7.25–7.21 (m, 1H); 6.72 (t, 1H, J=5.4 Hz); 6.67 (s, 1H); 6.63 (s, 1H); 6.53 (s, 2H); 4.77 (q, 1H, J=8.8 Hz); 3.95 (m, 2H); 2.84 (q, 2H, J=6 Hz); 2.21 (s, 6H); 1.74 (m, 2H); 151 (m, 2H); 1.36 (s, 9H); 1.31 (q, 2H, J=7.2 Hz); 1.13 (m, 2H); 0.89 (t, 3H, J=7.2 Hz). MS/LC: m/z=551.44 (M+H)$^+$.

EXAMPLE 2826
(2Z)-3-(5-aminopentyl)-2-[(3,5-dimethylphenyl)imino]-N-(1-phenylpropyl)-2,3-dihydro-1,3-thiazole-4-carboxamide dihydrochloride ($C_{26}H_{34}N_4OS.2HCl$; MM=523.57)

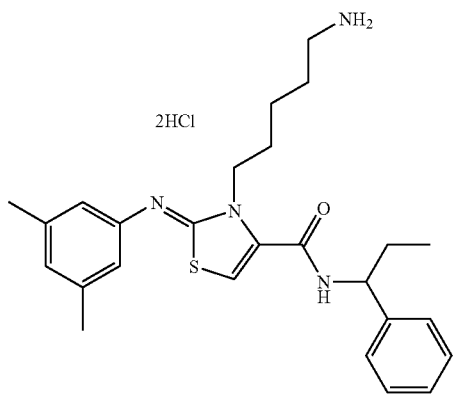

300 mg (0.54 mmol) of tert-butyl 5-[(2Z)-2-[(3,5-dimethylphenyl)imino]-4-{[(1-phenylpropyl)amino]carbonyl}-1,3-thiazol-3(2H)-yl]pentylcarbamate is dissolved in 15 ml of ethyl acetate. After bubbling anhydrous hydrogen chloride through the reaction medium for one hour at ambient temperature, the corresponding dihydrochloride salt precipitates. It is recovered by filtration and washed with diethyl ether in order to produce a white solid (268 mg; yield of 94.8%).

NMR $^1$H (DMSO-$d_6$, 400 MHz)*: 9.48 (broad s, 1H); 8.03 (broad s, 3H); 7.39–7.32 (m, 5H); 7.25 (t, 1H, J=7.2 Hz); 7.00 (m, 3H); 4.80 (q, 1H, J=8.4 Hz); 4.33 (broad s, 2H); 2.70 (q, 2H, J=6.8 Hz); 2.29 (s, 6H); 1.77 (m, 2H); 1.65 (m, 2H); 1.52 (m, 2H); 1.27 (m, 2H); 0.89 (t, 3H, J=7.2 Hz).

MS/LC: m/z=451.35 (M+M)$^+$.

According to method G, a series of compounds can be synthesized which include:

the R1 and R2 groups already described for method A; and the R5 groups already described for method C.

In particular, the compounds shown in the table below have been synthesised using method G.

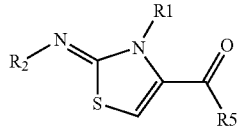

| Ex. | R1 | R2 | R5 | Purity (%) | rt (min) | [M + H]$^+$ |
|---|---|---|---|---|---|---|
| 2827 | ![H2N-cyclohexyl-CH2] | ![3,5-dimethylphenyl] | ![CH(CH3)-phenyl] | 69 + 27 | 4.57 + 4.73 | 477.33 |
| 2828 | ![H2N-(CH2)5] | ![3,5-dimethylphenyl] | ![CH(CH3)-phenyl] | 98 | 4.36 | 437.29 |

-continued
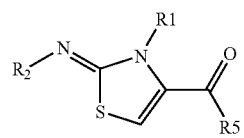
| Ex. | R1 | R2 | R5 | Purity (%) | rt (min) | [M + H]+ |
|---|---|---|---|---|---|---|
| 2829 | H2N-(CH2)5-* | 3,5-dimethylphenyl-* | *-HN-CH(CH3)-phenyl | 98 | 4.37 | 437.33 |
| 2830 | H2N-(CH2)4-* | 3,5-dimethylphenyl-* | *-HN-CH(CH3)-phenyl | 98 | 3.72 | 423.37 |
| 2831 | H2N-(CH2)4-* | 3,5-dimethylphenyl-* | *-HN-CH(CH3)-phenyl | 99 | 3.73 | 423.37 |
| 2832 | H2N-(CH2)5-* | 3,5-dimethylphenyl-* | *-HN-CH(CH3)-(4-F-phenyl) | 99 | 4.07 | 455.32 |
| 2833 | H2N-(CH2)5-* | 3,5-dimethylphenyl-* | *-HN-CH(CH3)-(4-Cl-phenyl) | 99 | 4.29 | 471.32 |
| 2834 | H2N-(CH2)5-* | 3,5-dimethylphenyl-* | *-HN-CH(CH3)-(4-Br-phenyl) | 98 | 4.33 | 515.24 |
| 2835 | H2N-(CH2)5-* | 3,5-dimethylphenyl-* | *-HN-CH(C2H5)-phenyl | 99 | 3.87 | 451.34 |
| 2836 | H2N-(CH2)5-* | 3,5-dimethylphenyl-* | *-HN-CH(C2H5)-phenyl | 99 | 3.88 | 451.34 |

Pharmacological Properties of the Products of the Invention

The compounds of the present invention can and have been tested as regards their affinity for different sub-types of somatostatin receptors according to the procedures described below.

Study of the Affinity for the Sub-Types of Human Somatostatin Receptors:

The affinity of a compound of the invention on sub-types of human somatostatin receptors 1 to 5 ($sst_1$, $sst_2$, $sst_3$, $sst_4$ and $sst_5$, respectively) is determined by measurement of the inhibition of the bond of [$^{125}$I-Tyr$^{11}$]SRIF-14 to transfected CHO-K1 cells.

The gene of the $sst_1$ receptor of human somatostatin was cloned in the form of a genomic fragment. A segment PstI-XmnI of 1.5 Kb containing 100 bp of the non transcribed 5' region, 1.17 Kb of the coding region in totality, and 230 bp of the non transcribed 3' region is modified by the addition of the linker BglII. The resulting DNA fragment is subcloned in the BamHI site of a pCMV-81 in order to produce the expression plasmid in mammals (provided by Dr. Graeme Bell, Univ. Chicago). A cloned cell line expressing in a stable fashion the $sst_1$ receptor is obtained by transfection in CHO-K1 cells (ATCC) using the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The gene of the $sst_2$ receptor of human somatostatin, isolated in the form of a genomic fragment of DNA of 1.7 Kb BamHI-HindIII and subcloned in a plasmid vector pGEM3Z (Promega), was provided by Dr. G. Bell (Univ. of Chicago). The expression vector of the mammalian cells is constructed by inserting the BamHI-HindII fragment of 1.7 Kb in endonuclease restriction sites compatible with the plasmid pCMV5. A cloned cell line is obtained by transfection in CHO-K1 cells using the calcium phosphate co-precipitation method. The plasmid pRSV-neo is included as selection marker.

The $sst_3$ receptor is isolated as a genomic fragment, and the complete coding sequence is contained in a BamHI/HindIII fragment of 2.4 Kb. The expression plasmid in mammals, pCMV-h3, is constructed by insertion of the NcoI-HindIII fragment of 2.0 Kb in the EcoRI site of the vector pCMV after modification of the terminations and addition of EcoRI linkers. A cloned cell line expressing in a stable fashion the $sst_3$ receptor is obtained by transfection in CHO-K1 cells (ATCC) by the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The expression plasmid of the human $sst_4$ receptor, pCMV-HX, was provided by Dr. Graeme Bell (Univ. Chicago). This vector contains the genomic fragment coding for the human $sst_4$ receptor of 1.4 Kb NheI—NheI, 456 bp of the non transcribed 5' region, and 200 bp of the non transcribed 3' region, cloned in the XbaI/EcoRI sites of PCMV-HX. A cloned cell line expressing in a stable fashion the $sst_4$ receptor is obtained by transfection in CHO-K1 (ATCC) cells by the calcium phosphate co-precipitation method. The plasmid pRSV-neo (ATCC) is included as selection marker. Cloned cell lines were selected in an RPMI. 1640 medium containing 0.5 mg/ml of G418 (Gibco), followed by circular cloning and multiplication in culture.

The gene corresponding to the human $sst_5$ receptor, obtained by the PCR method using a genomic λ clone as probe was provided by Dr. Graeme Bell (Univ. Chicago). The resulting PCR fragment of 1.2 Kb contains 21 base pairs of the non transcribe 5' region, the coding region in totality, and 55 bp of the non transcribed 3' region. The clone is inserted in an EcoRI site of the plasmid pBSSK(+). The insert is recovered in the form of a HindIII-XbaI fragment of 1.2 Kb for subcloning in an expression vector in mammals, pCVM5. A cloned cell line expressing in a stable fashion the $sst_5$ receptor is obtained by transfection in CHO-K1 cells (ATCC) by the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The CHO-K1 cells which express in a stable fashion the human sst receptors are cultured in an RPMI 1640 medium containing 10% of foetal calf serum and 0.4 mg/ml of geneticin. The cells are collected with EDTA at 0.5 mM and centrifuged at 500 g for approximately 5 minutes at approximately 4° C. The pellet is resuspended in a Tris 50 mM buffer at pH 7.4 and centrifuged twice at 500 g for approximately 5 minutes at approximately 4° C. The cells are lysed by sonication then centrifuged at 39000 g for approximately 10 minutes at 4° C. The pellet is resuspended in the same buffer and centrifuged at 50000 g for approximately 10 minutes at approximately 4° C. and the membranes in the pellet obtained are stored at −80° C.

The competitive inhibition experiments of the bond with [$^{125}$I-Tyr$^{11}$]SRIF-14 are carried out in duplicate in 96-well polypropylene plates. The cell membranes (10 μg protein/well) are incubated with [$^{125}$I-Tyr$^{11}$]SRIF-14 (0.05 nM) for approximately 60 min. at approximately 37° C. in a HEPES 50 mM buffer (pH 7.4) containing BSA 0.2%, $MgCl_2$ 5 mM, Trasylol '200 KIU/ml, bacitricin 0.02 mg/ml and phenylmethylsulphonyl fluoride 0.02 mg/ml.

The bound [$^{125}$I-Tyr$^{11}$]SRIF-14 is separated from the free [$^{125}$-Tyr$^{11}$]SRIF-14 by immediate filtration, through GF/C glass fibre filter plates (Unifilter, Packard) pre-impregnated with 0.1% of polyethylenimine (P.E.I.), using a Filternate 196 (Packard). The filters are washed with 50 mM HEPES buffer at approximately 0–4° C. for approximately 4 seconds and their radioactivity is determined using a counter (Packard Top Count).

The specific bond is obtained by subtracting the non-specific bond (determined in the presence of 0.1 μM of SRIF-14) from the total bond. The data relative to the bond is analyzed by computer-aided non-linear regression analysis (MDL) and the values of the inhibition constants (Ki) are determined.

Determination of the agonist or antagonist character of a compound of the present invention is carried out using the test described below.

Functional Test: Inhibition of Production of Intracellular cAMP:

CHO-K1 cells expressing the sub-types of human somatostatin receptors (SRIF-14) are cultured in 24-well plates in an RPMI 1640 medium with 10% of foetal calf serum and 0.4 mg/ml of geneticin. The medium is changed the day preceding the experiment.

The cells at a rate of $10^5$ cells/well are washed twice with 0.5 ml of new RPMI medium comprising 0.2% BSA completed by 0.5 mM of 3-isobutyl-1-methylxanthine (IBMX) and incubated for approximately 5 minutes at approximately 37° C.

The production of cyclic AMP is stimulated by the addition of 1 mM of forskolin (ASK) for 15–30 minutes at approximately 37° C., The inhibitory effect of the somatostatin of an agonist compound is measured by the simultaneous addition of FSK (1 µM), SRIF-14 ($10^{-12}$ M to $10^{-6}$ M) and of the compound to be tested ($10^{-10}$ M to $10^{-5}$ M).

The antagonist effect of a compound is measured by the simultaneous addition of FSK (1 µM), SRIF-14 (1 to 10 mM) and of the compound to be tested ($10^{-10}$ M to $10^{-5}$ M).

The reaction medium is eliminated and 200 ml of 0.1 N HCl is added. The quantity of cAMP is measured by a radioimmunological test (FlashPlate SMP001A kit, New England Nuclear).

RESULTS

The tests carried out according to the protocols described above have demonstrated that the products of general formula (I) defined in the present Application have a good affinity for at least one of the sub-types of somatostatin receptors, the inhibition constant $K_i$ being lower than micromolar for certain exemplified compounds, and in particular for the products shown in the table below.

| Formula of compound | $K_i$ (nM) |
|---|---|
| 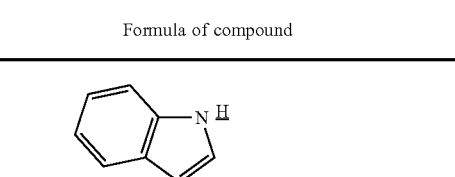 | <200 |
In addition to the compounds in the above tables, each of the compounds of Examples 2827 to 2836 also has a $K_i$ constant lower than 200 nM.
The invention claimed is:
1. A compound of the formula:
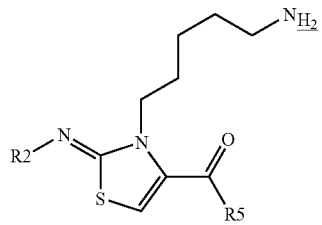
(i)
wherein
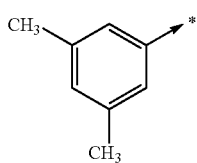
and $R_5$ is
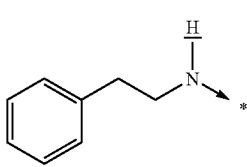
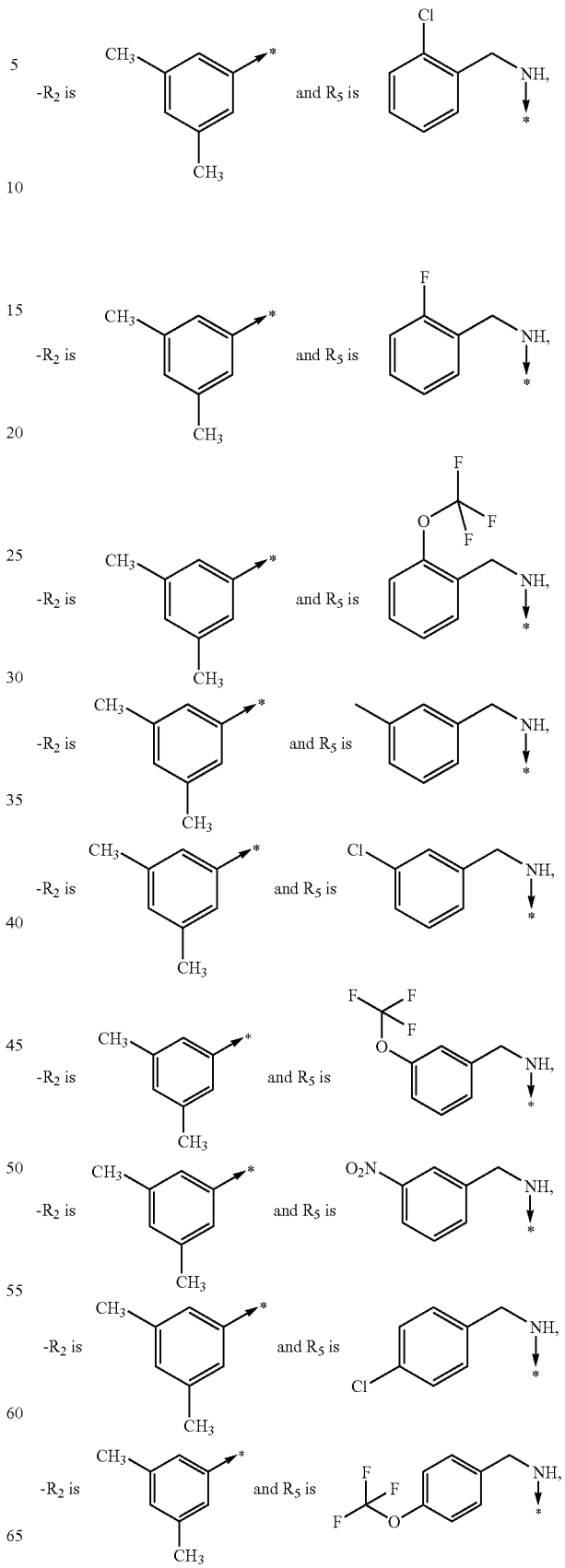

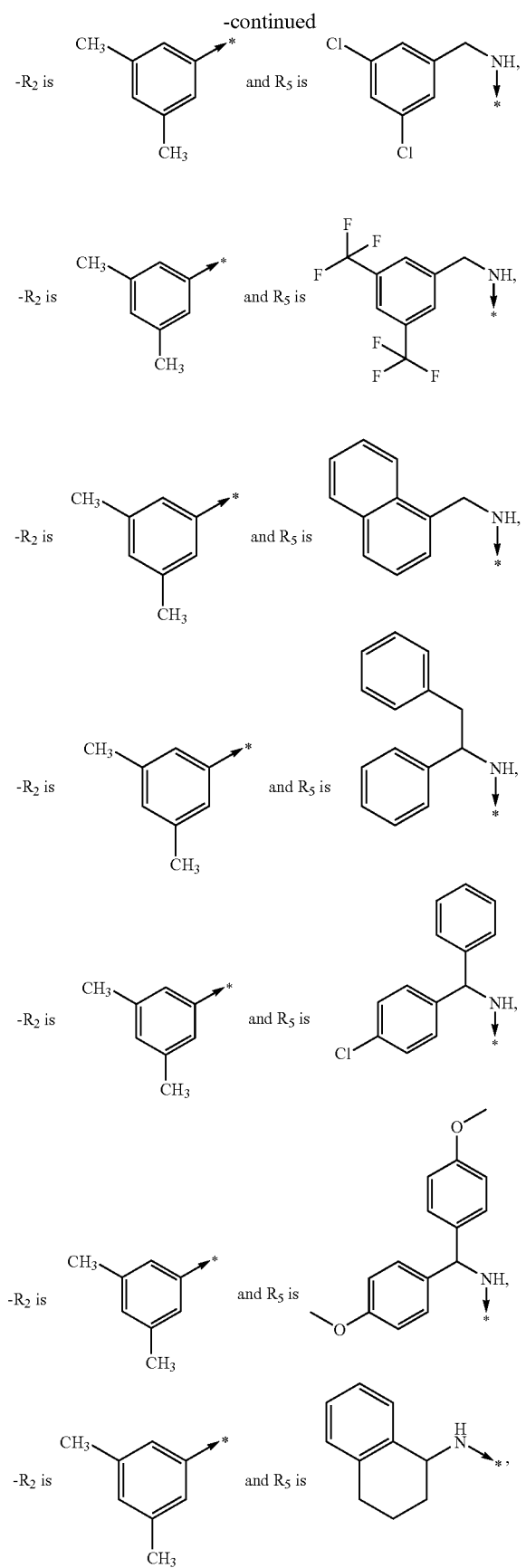
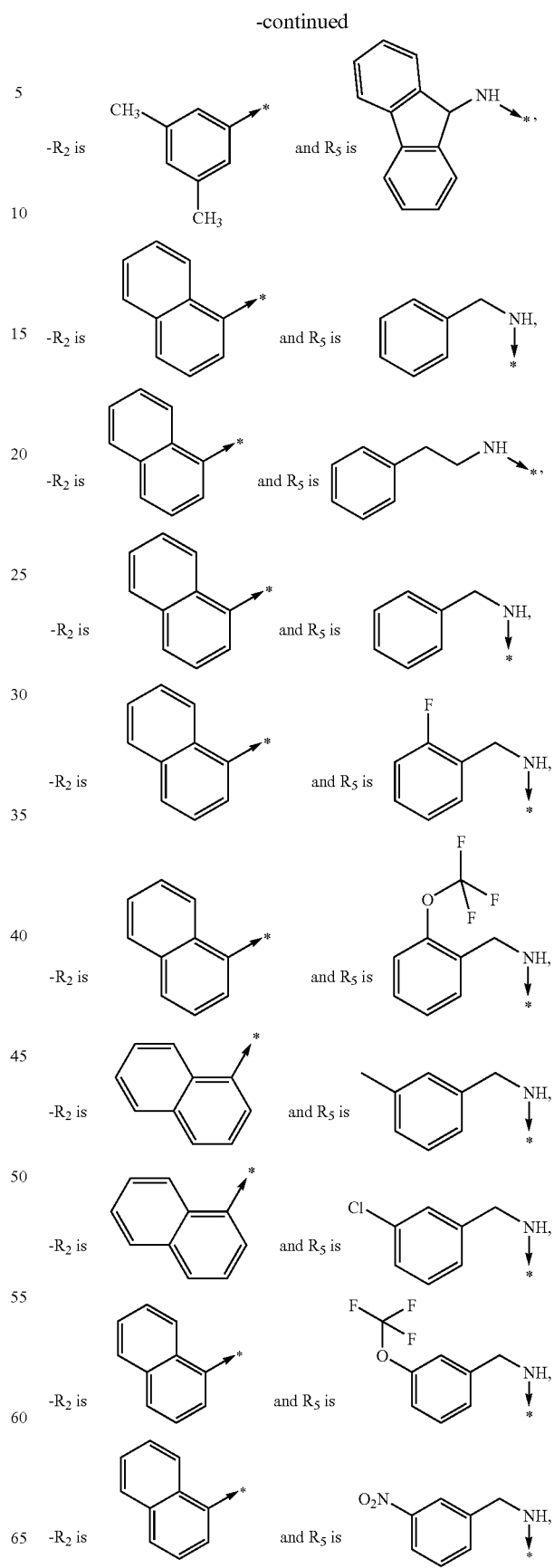

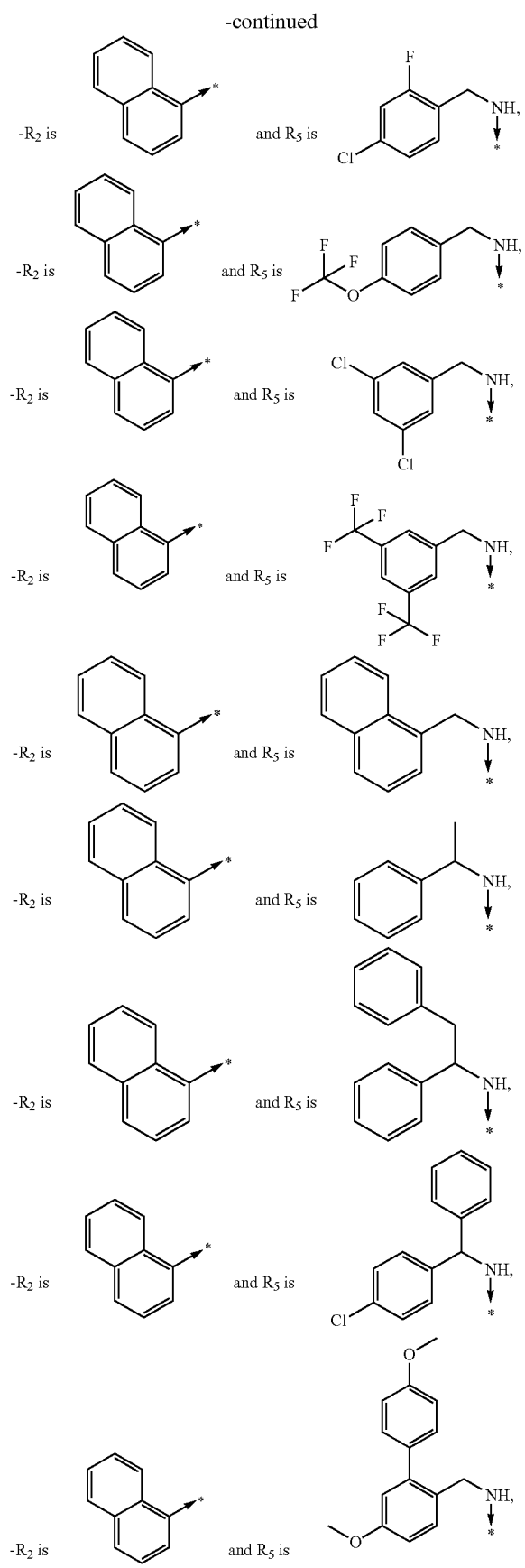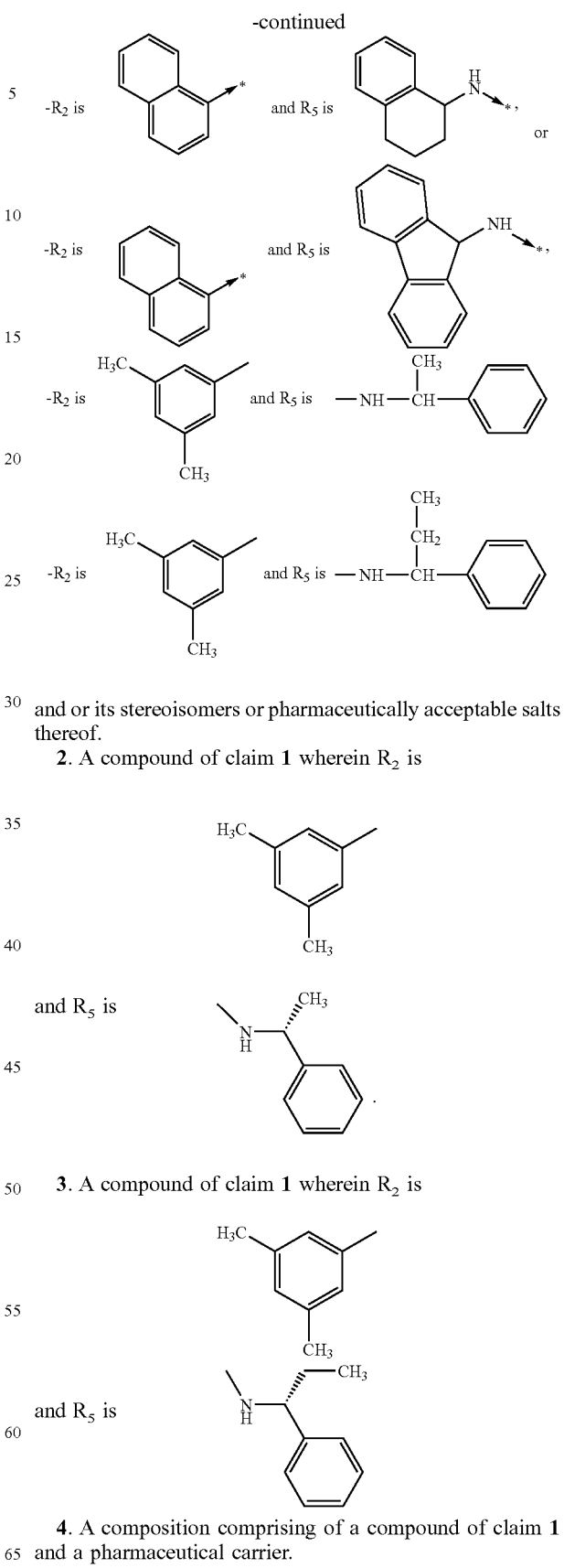
and or its stereoisomers or pharmaceutically acceptable salts thereof.
2. A compound of claim 1 wherein $R_2$ is
and $R_5$ is
3. A compound of claim 1 wherein $R_2$ is
and $R_5$ is
4. A composition comprising of a compound of claim 1 and a pharmaceutical carrier.
* * * * *